US007914990B2

(12) United States Patent
Buela et al.

(10) Patent No.: US 7,914,990 B2
(45) Date of Patent: Mar. 29, 2011

(54) METHODS AND PRODUCTS FOR IN VITRO GENOTYPING

(75) Inventors: Laureano Simon Buela, Vizcaya (ES); Antonio Martinez Martinez, Vizcaya (ES); Diego Tejedor Hernandez, Vizcaya (ES); Elisa Jimenez Uribe, Vizcaya (ES); Monica Lopez Martinez, Vizcaya (ES); Marta Artieda Osenalde, Vizcaya (ES); Lorena Hernandez Garcia, Vizcaya (ES)

(73) Assignee: Progenika Biopharma, S.A. (ES)

( * ) Notice: Subject to any disclaimer, the term of this patent is extended or adjusted under 35 U.S.C. 154(b) by 425 days.

(21) Appl. No.: 11/813,646

(22) PCT Filed: Jan. 12, 2006

(86) PCT No.: PCT/IB2006/000796

§ 371 (c)(1),
(2), (4) Date: Jul. 10, 2007

(87) PCT Pub. No.: WO2006/075254

PCT Pub. Date: Jul. 20, 2006

(65) Prior Publication Data

US 2008/0070253 A1 Mar. 20, 2008

Related U.S. Application Data

(60) Provisional application No. 60/758,192, filed on Jan. 12, 2006.

(30) Foreign Application Priority Data

Jan. 13, 2005 (ES) .................................. 200500089
Oct. 5, 2005 (ES) .................................. 200502423

(51) Int. Cl.
*C12Q 1/68* (2006.01)

(52) U.S. Cl. .......................................................... 435/6

(58) Field of Classification Search ........................ None
See application file for complete search history.

(56) References Cited

U.S. PATENT DOCUMENTS

2004/0126782 A1 * 7/2004 Holden et al. .................... 435/6

FOREIGN PATENT DOCUMENTS

WO 01/29268 A2 4/2001

OTHER PUBLICATIONS

Kozal, et al. "Extensive Polymorphisms Observed in HIV-1 Clade B Protease Gene using High-Density Oligonucleotide Arrays." Natural Medicine. vol. 2, No. 7, pp. 753-759 (1996).
Hacia, et al. "Detection of Heterozygous Mutations in BRCA1 using High Density Oligonucleotide Arrays and Two-Colour Fluorescence Analysis." Nature Genetics. vol. 14, No. 4, pp. 441-447 (1996).
Chee, et al. "Accessing Genetic Information with High Density DNA Arrays." Science. vol. 274, 25 pp. 610-614 (1996).
Sapolsky, et al. "High-Throughput Polymorphism Screening and Genotyping with High-Density Oligonucleotide Arrays." Genetic Analysis. vol. 14, No. 5-6 pp. 187-192, (1999).
Cutler, et al. "High-Throughput Variation Detection and Genotyping using Microarrays." Genome Research. vol. 11, No. 11, pp. 1913-1925 (2001).

* cited by examiner

*Primary Examiner* — Christopher M. Babic
(74) *Attorney, Agent, or Firm* — Klarquist Sparkman, LLP

(57) ABSTRACT

An in vitro method for genotyping genetic variations in a individual, and products for use in the method.

11 Claims, 13 Drawing Sheets

METHODS AND PRODUCTS FOR IN VITRO GENOTYPING

RELATED APPLICATIONS

This application is a continuation of, and claims priority to, PCT Patent Application no. PCT/IB2006/000796, filed Jan. 12, 2006, which claims priority to: Spanish patent application P200500089 filed 13 Jan. 2005; Spanish patent application P200502423 filed 5 Oct. 2005; and U.S. Provisional Application No. 60/758,192, filed Jan. 12, 2006, the contents of all of which are incorporated herein by reference in their entirety.

FIELD OF THE INVENTION

The invention relates to methods and products for in vitro genotyping by analysis of biological samples. In particular the invention relates to DNA-chips and the use of the chips to detect genetic variations, e.g., polymorphisms or genetic mutations associated with disease, or connected to genotyping of antigens of interest, or associated with resistance to pharmaceutical treatment. The invention further relates to methods for analysing chip data and to computer software based on the methods.

BACKGROUND OF THE INVENTION

DNA-chips

In 2001, the Consortium for the Human Genome Project and the private company Celera presented the first complete example of the human genome with 30,000 genes. From this moment on, the possibility of studying the complete genome or large scale (high-throughput) studies began. So-called "DNA-chips", also named "micro-arrays", "DNA-arrays" or "DNA bio-chips" are apparatus that functional genomics can use for large scale studies. Functional genomics studies changes in the expression of genes due to environmental factors and to genetic characteristics of an individual. Gene sequences present small interindividual variations at one unique nucleotide called an SNP ("single nucleotide polymorphism"), which in a small percentage are involved in changes in the expression and/or function of genes that cause certain pathologies. The majority of studies which apply DNA-chips study gene expression, although chips are also used in the detection of SNPs.

The first DNA-chip was the "Southern blot" where labelled nucleic acid molecules were used to examine nucleic acid molecules attached to a solid support. The support was typically a nylon membrane.

Two breakthroughs marked the definitive beginning of DNA-chip. The use of a solid non-porous support, such as glass, enabled miniaturisation of arrays thereby allowing a large number of individual probe features to be incorporated onto the surface of the support at a density of >1,000 probes per $cm^2$. The adaptation of semiconductor photolithographic techniques enabled the production of DNA-chips containing more than 400,000 different oligonucleotides in a region of approximately 20 $\mu m^2$, so-called high density DNA-chips.

In general, a DNA-chip comprises a solid support, which contains hundreds of fragments of sequences of different genes represented in the form of DNA, cDNA or fixed oligonucleotides, attached to the solid surface in fixed positions. The supports are generally glass slides for the microscope, nylon membranes or silicon "chips". It is important that the nucleotide sequences or probes are attached to the support in fixed positions as the robotized localisation of each probe determines the gene whose expression is being measured. DNA-chips can be classified as:

- high density DNA-chips: the oligonucleotides found on the surface of the support, e.g. glass slides, have been synthesized "in situ", by a method called photolithography.
- low density DNA-chips: the oligonucleotides, cDNA or PCR amplification fragments are deposited in the form of nanodrops on the surface of the support, e.g. glass, by means of a robot that prints those DNA sequences on the support. There are very few examples of low density DNA-chips which exist: a DNA-chip to detect 5 mutations in the tyrosinase gene; a DNA-chip to detect mutations in p53 and k-ras; a DNA-chip to detect 12 mutations which cause hypertrophic cardiomypathy; a DNA-chip for genotyping of *Escherichia coli* strains; or DNA-chips to detect pathogens such as *Cryptosporidium parvum* or *rotavirus*.

For genetic expression studies, probes deposited on the solid surface, e.g. glass, are hybridized to cDNAs synthesized from mRNAs extracted from a given sample. In general the cDNA has been labelled with a fluorophore. The larger the number of cDNA molecules joined to their complementary sequence in the DNA-chip, the greater the intensity of the fluorescent signal detected, typically measured with a laser. This measure is therefore a reflection of the number of mRNA molecules in the analyzed sample and consequently, a reflection of the level of expression of each gene represented in the DNA-chip.

Gene expression DNA-chips typically also contain probes for detection of expression of control genes, often referred to as "house-keeping genes", which allow experimental results to be standardized and multiple experiments to be compared in a quantitive manner. With the DNA-chip, the levels of expression of hundreds or thousands of genes in one cell can be determined in one single experiment. cDNA of a test sample and that of a control sample can be labelled with two different fluorophores so that the same DNA-chip can be used to study differences in gene expression. DNA-chips for detection of genetic polymorphisms, changes or mutations (in general, genetic variations) in the DNA sequence, comprise a solid surface, typically glass, on which a high number of genetic sequences are deposited (the probes), complementary to the genetic variations to be studied. Using standard robotic printers to apply probes to the array a high density of individual probe features can be obtained, for example probe densities of 600 features per $cm^2$ or more can be typically achieved. The positioning of probes on an array is precisely controlled by the printing device (robot, inkjet printer, photolithographic mask etc) and probes are aligned in a grid. The organisation of probes on the array facilitates the subsequent identification of specific probe-target interactions. Additionally it is common, but not necessary to divide the array features into smaller sectors, also grid-shaped, that are subsequently referred to as sub-arrays. Sub-arrays typically comprise 32 individual probe features although lower (e.g. 16) or higher (e.g. 64 or more) features can comprise each subarray.

One strategy used to detect genetic variations involves hybridization to sequences which specifically recognize the normal and the mutant allele in a fragment of DNA derived from a test sample. Typically, the fragment has been amplified, e.g. by using the polymerase chain reaction (PCR), and labelled e.g. with a fluorescent molecule. A laser can be used to detect bound labelled fragments on the chip and thus an individual who is homozygous for the normal allele can be specifically distinguished from heterozygous individuals (in the case of autosomal dominant conditions then these individuals are referred to as carriers) or those who are homozygous for the mutant allele.

Another strategy to detect genetic variations comprises carrying out an amplification reaction or extension reaction on the DNA-chip itself.

For differential hybridisation based methods there are a number of methods for analysing hybridization data for genotyping:

- Increase in hybridization level: The hybridization level of complementary probes to the normal and mutant alleles are compared.
- Decrease in hybridization level: Differences in the sequence between a control sample and a test sample can be identified by a fall in the hybridization level of the totally complementary oligonucleotides with a reference sequence. A complete loss is produced in mutant homozygous individuals while there is only 50% loss in heterozygotes. In DNA-chips for examining all the bases of a sequence of "n" nucleotides ("oligonucleotide") of length in both strands, a minimum of "2n" oligonucleotides that overlap with the previous oligonucleotide in all the sequence except in the nucleotide are necessary. Typically the size of the oligonucleotides is about 25 nucleotides. The increased number of oligonucleotides used to reconstruct the sequence reduces errors derived from fluctuation of the hybridization level. However, the exact change in sequence cannot be identified with this method; sequencing is later necessary in order to identify the mutation.

Where amplification or extension is carried out on the DNA-chip itself, three methods are presented by way of example:

In the Minisequencing strategy, a mutation specific primer is fixed on the slide and after an extension reaction with fluorescent dideoxynucleotides, the image of the DNA-chip is captured with a scanner.

In the Primer extension strategy, two oligonucleotides are designed for detection of the wild type and mutant sequences respectively. The extension reaction is subsequently carried out with one fluorescently labelled nucleotide and the remaining nucleotides unlabelled. In either case the starting material can be either an RNA sample or a DNA product amplified by PCR.

In the Tag arrays strategy, an extension reaction is carried out in solution with specific primers, which carry a determined 5' sequence or "tag". The use of DNA-chips with oligonucleotides complementary to these sequences or "tags" allows the capture of the resultant products of the extension. Examples of this include the high density DNA-chip "Flexflex" (Affymetrix).

For genetic diagnosis, simplicity must be taken into account. The need for amplification and purification reactions presents disadvantages for the on-chip extension/amplification methods compared to the differential hybridization based methods.

Typically, DNA-chip analysis is carried out using differential hybridization techniques. However, differential hybridization does not produce as high specificity or sensitivity as methods associated with amplification on glass slides. For this reason the development of mathematical algorithms, which increase specificity and sensitivity of the hybridization methodology, are needed (Cutler D J, Zwick M E, Carrasquillo M N, Yohn C T, Tobi K P, Kashuk C, Mathews D J, Shah N, Eichler E E, Warrington J A, Chakravarti A. Geneome Research; 11:1913-1925 (2001).

The problems of existing DNA-chips in simultaneously detecting the presence or absence of a high number of genetic variations in a sensitive, specific and reproducible manner has prevented the application of DNA-chips for routine use in clinical diagnosis, of human disease. The inventors have developed a sequential method of processing and interpreting the experimental data generated by genotyping DNA-chips based on an increase in hybridization signal. The method produces high levels of specificity, sensitivity and reproducibility, which allow the DNA-chips developed on the basis of this method to be used for example, for reliable clinical genetic diagnosis.

Inflammatory Bowel Disease

Inflammatory Bowel Disease (IBD) is characterized by chronic inflammation of the intestine. This pathology presents two clinical forms, Crohns Disease (CD) and Ulcerative Colitis (UC). CD can affect any area of the intestinal tract and is associated with irregular internal injuries of the intestinal wall, while in the case of UC the inflammation is limited to the rectum and colonic mucosa and the injuries are continuous and superficial. The annual rate of UC and CD in Spain is from 4 to 5 and from 1.8 to 2.5 cases per 100,000 people, respectively. In the United States the prevalence of these diseases can reach numbers of 200 to 300 in every 100,000. The disease has a severe effect on quality of life, in particular given its chronic progress, evolution in outbreaks and frequent need for surgery. Patients of both suffer inflammation of the skin, eyes and joints.

Treatments for IBD include immunosuppressants, anti-inflammatory agents, such as antibodies targeted against tumour necrosis factor $\alpha$ (TNF-$\alpha$) and surgery. The molecular biology of the pathogenesis of IBD is still not clear, but causative factors appear to include bacterial infection in the intestinal wall and an imbalance in the regulation of the bowel immune response.

CD and UC are classified as autoimmune diseases, both being more prevalent in individuals who have previously had another autoimmune condition. There is a predominance of CD in the female population and of UC in the male, predominantly in the older age bracket with distal proctitis or colitis.

Epidemiologic and genetic studies have provided evidence of the presence of genetic susceptibility factors for IBD, increasing expectations that the identification of genes related to IBD could bring a better understanding of the pathogenesis, diagnosis, location, and prognosis and appropriate treatment. Starting from informal studies to evaluate the risk of contracting the disease, such as segregation analysis, evidence has been provided of a genetic origin. Between 10-20% of the relatives of patients affected by CD or UC also suffered from these diseases. However, the tendency to CD and UC is complex and includes various genes as well as environmental factors. IBD is considered to be a complex genetic disease in which inheritance is not considered to be a simple Mendelian trait. Numerous studies of the association between genome and disease susceptibility have recently identified several genes in which one or more genetic variations results in a higher or lower risk of contracting the disease, a better or worse response to drugs or a better or worse prognosis.

For this reason, the clinical application of a DNA-chip to characterize the genetic variations associated with IBD will provide benefits for diagnosis and treatment. From a clinical point of view, the early diagnosis, prognosis and location of the disease would influence therapeutic decisions as to treatment of IBD. At least two different groups would benefit from this development:

- relatives of IBD patients who are interested in knowing their likelihood of developing the disease; and patients who have IBD, in order to be able to choose a personalised therapy, depending on the risk of inflammation or fistulae. The higher the risk of contracting a severe form of IBD, the greater the need for more aggressive therapy.

Apart from the contribution to diagnosis and treatment of IBD and the development of new therapeutic strategies, progress in the physiopathology of the inflammatory reaction in IBD will also be of interest in the study of a wide range of autoimmune diseases including several neurodegenerative diseases, rheumatoid arthritis and dermatological conditions such as psoriasis.

A DNA-chip, which allows the simultaneous, sensitive, specific and reproducible detection of genetic variations associated with IBD, could be used clinically in diagnosing IBD.

Erythrocyte Antigens

The blood of each person is so characteristic that it can serve as a means of identification that is nearly as precise as fingerprints; only identical twins have exactly the same blood characteristics. Blood group determination is particularly useful in medical fields such as blood transfusions, haemolytic diseases in fetuses and the new born, medical-legal applications and organ transplantation.

The majority of transfusions can be considered safe. However, sometimes they produce slight reactions or possibly a serious and even fatal reaction. Temperature and allergic (hypersensitivity) reactions, occur in 1-2% of transfusions, but more serious incompatibilities do exist which cause the destruction of red cells, (a haemolytic intravascular reaction).

Foetal and new born haemolytic disease (HDNF) is a well known immunological condition, in which the potential for survival of the fetus or new born is compromised due to the action of maternal antibodies that pass through the placenta and specifically target antigens of paternal origin present in the red cells of the fetus or new born. It has been determined that EHPN is not only due to antibodies against the D antigen, but that antigens of the RH system, the ABO system and others are also involved.

Correct genotyping of blood groups therefore has importance in transfusions (including the detection of rare or infrequent alleles).

Blood groups are composed of alloantigens present on the surface of the erythrocyte membrane and red cells, which are transmitted from parents to children according to the laws of Mendelian genetics.

The International Society of Blood Transfusions has classified more than 26 different human blood groups. The majority have been defined at a genetic level and include polymorphisms at one unique nucleotide (SNPs), genetic deletions, conversions and other events, which result in genetic variation. The blood group antigens can be classified in two large groups:

A. Antigens determined by carbohydrates.

B. Antigens determined by proteins.

A. Antigens Determined by Carbohydrates

Group ABO

This blood group is of clinical importance because it causes the majority of incompatibility reactions in transfusions and organ transplants. The biochemical basis of group ABO depends on the activity of an N-acetylgalactosamine transferase in individuals of blood group A and a galactosyl transferase in blood group B; whilst individuals belonging to group O lack an active transferase enzyme. The genetic basis of the ABO phenotypes is the substitution of amino acids in the ABO gene of glycosyltransferase. This gene is 19,514 bases in size and encodes a membrane bound enzyme that uses GalNAc or UDP-Gal as a substrate. Four amino acid changes in exons 6 and 7 of the ABO gene are responsible for substrate specificity of the transferases A and B respectively, within them the changes Gly235Ser and Leu266Met are vital. The majority of individuals of group O present deletion of one single nucleotide (A261G) which gives rise to a change in the reading frame and results in the production of an inactive transferase protein. Nonetheless, a growing number of O alleles (about 20) exist that result in nonexpression of the transferases A or B. Rare alleles of the subgroup ABO, like A3, Ax, Ael, B3Bx and Bel have been described. These alleles have arisen from genetic recombinations from different alleles of the ABO group.

B. Antigens Determined by Proteins.

B.1. Antigens Dependent on Expression of Erythrocyte Transferase Molecules.

Rh (RH)

Incompatibility of RH occurs in a large portion of transfusion reactions and is the main cause of hemolytic disease in newborn and fetuses (HDNF). The RH antigens come from two proteins (RH CcEe and RH D) encoded by the RH locus (1p34-36.2) that contains the genes RHD and RHCE (70 Kb). Possibly the positive D haplotypes present ay configuration of the genes RHD-RHCE of the same orientation, while the negative D haplotypes present a reverse orientation. The negative D phenotype, common in old European populations, is caused by a deletion of the gene RHD. This seems to have been generated by an unequal crossing over between the genes RHCE and RHD. In the African population a pseudogene of RHD is the predominant D negative allele but its frequency diminishes amongst Afro-Americans and Afro-Caribbeans. Recombinations between the genes RHCE and RHD cause rare hybrids that lead to a partial expression of the D antigen. These uncommon antigens on some occasions have been identified as clinically significant.

The proteins RH CcEe and RH D co-express themselves with an equivalent glycoprotein (36% identity), the associated glycoprotein RH (RHAG). This erythrocyte specific complex is possibly a hetero tetramer implicated in bidirectional ammonia transport. The mutations in RHAG are the causes of RH null syndrome, associated with defects in transport across the erythrocyte membrane, deficiencies in CD47 and a total absence of ICAM-4. Furthermore, genes related to RHAG, RHBG and RHCG have been found in the regions 1q21.3 and 15q25 respectively. These genes are expressed in different forms in different human tissue.

Kidd (JK)

The Kidd (JK) antigens occur in the urea transporter hUT-B1 of red cells. The significance of the Kidd antigen has been known for two decades when it was discovered that JK ($a^-b^-$) red cells were resistant to lysis in 2M urea. The molecular basis of the expression of the Kidd antigen is a SNP in nucleotide 838 (G-A) causing a change Asp280Asn (JK*A-JK*B). The Kidd null phenotype, JK ($a^-b^-$) is due to mutations causing fame-shift mutations, premature termination of translation, inappropriate gene splicing and partial deletions in the gene SLC14A1.

Diego (DI)

The antigens of the blood group Diego (DI) are the most abundant proteins on the surface of red cells (1.1 million copies per cell), and are crucial for carrying $CO_2$ and acid-base homeostasis. It is thought that Di antigens vary due to multiple SNPs present in the gene SLC4A1.

Colton (CO)

The CO antigens (COa, COb and CO3) are expressed by the carrier molecule AQP-1. The (COa-COb) antigens are produced by a SNP in AQP-1 that produces a change in codon 45 from alanine to valine.

B.2 Antigens Determined by Expression of Red Cell Membrane Enzymes.

Kell (KEL)

The antigens of the KEL system are very important in transfusions; the k antigen is the second main cause of haemolytic disease in the new born. The glycoprotein KEL is a type II membrane protein. The C-terminal catalytic regions process large endothelins that are potent vasocontrictors. Cysteine 72 of the glycoprotein KEL forms a disulphide bridge with the protein Kx, which might explain why erythrocytes null for KEL (Ko) show activation of levels of the Kx antigen. The antigen of this system with most clinical importance, K (KEL1), is associated with a change Met193Thr that allows Asn-X.ThrN-glycosylation to occur.

Dombrock (DO)

The variants DOa/DOb are due to an SNP in the gene DOK1, which encodes an enzyme ADP ribosyltransferase, that affects codon 265 (Asn-Asp). The ADP ribosyltransferase of red cells could help eliminate the NAD+ of serum, but it has been noted that it also takes part in the post-transcriptional modification of other proteins. The RGD motif and DOb take part in cellular adhesion. Oddly the allelic variant DO*B is more common in African and Asian populations and could be an evolutionary advantage against the invasion of Plasmodium falciparum which expresses RGD proteins during its infection process.

B.3. Antigens Determined by Expression of Membrane Receptors of Red Cells.

Duffy (FY)

The function of the glycoprotein FY as a cytokine receptor of red cells is to accelerate proinflammatory cytokine signalling. The FY glycoprotein is the erythrocyte receptor for the malarial parasite Plasmodium vivax and as a consequence FY negative individuals (FY a-b-) are very common in populations where this parasite is found (Western Africa). Three main alleles of FY exist: FY*A, FY*B and FY*A and B which differ due to an SNP which alters codon 42, while phenotype FY (a⁻b⁻) in Africans is caused by a SNP (C-T) in the FY gene promoter that results in an absence of FY glycoprotein in the erythrocytes.

MNSs (MNS)

The MNS antigens are generated against glycoporin A, while the Ss antigens are against glycoporin B. The genes GYPA and GYPB line up in tandem in the locus 4q28-31 but there is no relationship between glycoporins C and D. Two amino acid changes in the N-terminal region of GPA are responsible for the blood group M-N and a change in amino acid in GPB determines the blood group S-s. A large number of MNS alleles exist due to genetic recombinations, genetic conversions or SNPs.

Human blood groups have been defined at a genetic level for the majority of antigens with clinical significance. Nevertheless, genotyping of red cells is still only performed rarely, mainly in prenatal determination of blood groups in cases of haemolytic diseases in newborns and fetuses.

The compatibility of blood transfusions between donors and recipients is generally evaluated by serological techniques (antibody-antigen reactions). The use of these techniques can give incorrect results, which could lead to a potential adverse immune reaction in the recipient (patient). No serological tests exist for a high number of the so-called 'weak' genes and on various occasions the antibodies used have not been sufficiently specific. The only process capable of preventing problems of this type is that based on complete molecular genotyping of both the donor and the recipient.

SNP genotyping will allow both these determinations to be carried out on a large scale and also the genotyping of rare alleles in blood groups that with existing techniques cannot be determined.

The appearance of new alleles in certain blood groups (e.g. RH) will continue and will therefore require technology capable of progressing and being constantly monitored. The Human Genome project has identified new SNPs in many proteins in the blood groups concerned, although it still needs to be serologically determined if these SNPs are in antigens related to blood groups.

Nowadays genetic molecular analysis is common in transfusions. For example, detection of viral contamination, such as the hepatitis C virus (HCV), the human immunodeficiency virus (HIV) or the hepatitis B virus (HBV), by PCR methodology from small volumes of plasma has been common practice in the European Union (EU) since 1999. Diagnosis based on PCR has practically taken the place of serology in the determination of HLA (human leukocyte antigen); and is routinely used in transfusion centres involved in bone marrow transplants.

One of the discoveries of the Human Genome project was the high frequency of polymorphisms in a single nucleotide (SNPs) found in human DNA. Approximately one SNP was found for every kilobase. This discovery has pushed forward the technical development of rapid diagnosis of SNP genotyping, for example by using DNA-chips. This new technology can be applied to developing a rapid method of genotyping of blood groups.

Diverse methods of diagnosis for different blood groups have been described. As an illustrative example, U.S. Pat. No. 5,80,4379 relates to a molecular method of diagnosis and a kit to determine the genotypes of the blood group KEL. U.S. Pat. No. 5,723,293 relates to a method and kit to determine the genotypes of the blood group RH. Furthermore a serological diagnostic test to classify blood groups from blood or serum has been described. Likewise new genetic variations of the blood group Duffy have been described as a method of genotyping this blood group.

However, no method has been described based on DNA-chip technology capable of being an open platform for genotyping of all the allelic variants of the blood groups with major clinical relevance (including rare variants) that can be used as a method of diagnosis on a huge scale in the population.

A DNA-chip which allows the simultaneous, sensitive, specific and reproducible detection of genetic variations associated with determined erythrocyte antigens could be used clinically for genotyping antigens of blood erythrocytes on a large scale in the population and therefore for determining blood groups in humans.

Adverse Reactions to Medicine

Any medicine is developed with the intention of curing, relieving, preventing or diagnosing an illness or disease but unfortunately these can also produce adverse effects with a risk, which, depending on the specific case, could range from minimal to severe. Although difficult to calculate, the risk of the treatment should not be ignored and the order of magnitude should be known by the doctor and also the patient and accepted, with the understanding that the potential benefit of the medicine compensates any of these risks.

An adverse reaction is any harmful or unwanted effect that happens after the administration of the dose usually prescribed to a human being for the prophylaxis, diagnosis or treatment of a disease. Present consensus allows this definition, which was created by the World Health Association in 1972, to be understood in the following manner: "It is any unwanted effect that appears on administering a medicine of adequate dose, for the prophylaxis, diagnosis or treatment of a disease or for the modification of a physiological function."

Developed countries count on systems of drug vigilance to centralize the supervision of security and efficiency of drugs used, which are responsible for collecting and analyzing details of adverse reactions suspected of being produced by the drug used on the market.

In Spain the first steps in creating a system of pharmacovigilance were started in the 70s and in 1983, Spain incorporated the International Programme of Pharmacovigilance of Health. In 1992 a computerized database called FEDRA (Spanish Pharmacovigilance of Data of Adverse Reactions) was created. The pharmaceutical industry actively collaborates with this system, and moreover as established by The 1986 General Health Act, and also The 1990 Medicine Act, all public health personnel, including doctors, pharmacists, vets and nurses, are obliged to notify health authorities of any suspicion of adverse reactions to drugs known to them and to collaborate with the Spanish system of pharmacovigilance. Spain also collaborates with the European Medical Evaluation Agency which came into operation in 1995. From the information collected by FEDRA it appears that Spain is within the group of countries with the highest rate of notification, with an average similar to Germany and France although lower than countries such as the USA, Ireland, Norway, New Zealand, The UK or Sweden.

Nowadays, in countries like Spain, where the older population is growing and more medicine is being administered, particularly to this age group and also with increasing self-medication, it is only to be expected that the problem of adverse reactions may be important. The Centre for Drug Evaluation and Research of the FDA (U.S. Food and Drug Administration), confirms that more than two million adverse reactions occur annually in the USA, which cause about 100,000 deaths a year, being the fourth cause of death ahead of lung disease, diabetes, AIDS, pneumonia and traffic accidents. The number of patients that die in England and Wales due to errors in prescription of medicines or adverse reactions is growing and the difficulty is that the extent of the problem is not known. In Spain, five out of every hundred casualty cases in public hospitals are due to adverse reactions to drugs and between 10-20% of those hospitalized suffered this medical mishap on receiving medication. Of those affected, 1% die as a consequence.

Until May 2000 about 80,000 notifications of adverse reactions to registered drugs had been recorded in the database at the Centre for Pharmaceutical Vigilance in Catalunya. Of these, two thirds were spontaneous and came from primary care. Of those reactions notified most were minor or moderate, whilst 12% were serious and 1% fatal. 50% of reactions were skin, digestive or neurological. The majority of decisions to withdraw drugs are related to hepatic/liver and haematological reactions. What causes concern is that these types of reactions, which represent a small percentage of the total, are those where the majority of drugs are withdrawn. Antibiotics are the main cause of adverse effects, followed by anti-rheumatic drugs and painkillers and drugs to prevent cardiovascular disease. The detection of adverse effects can provoke not only the withdrawal but also the decision to change the use of the drug, or the reformulation or introduction of new directions for specific patients.

A DNA-chip, which allows the simultaneous, sensitive, specific and reproducible detection of genetic variations associated with adverse reactions to medicine, could be clinically useful to prevent or reduce the aforementioned reactions in patients receiving medical treatment.

SUMMARY OF THE INVENTION

The present inventors have developed a sensitive, specific and reproducible method for simultaneously detecting and characterising genetic variations which is useful for the development of products for genotyping. The method is based on a combination of an original trial design for genotyping DNA-chips and the development of a sequential system (algorithm) for processing and interpreting the trial data generated by the chips (based on an increase in hybridization signal), which guarantees high levels of specificity, sensitivity and reproducibility of results and in turn allows the chips to be used, for example, as reliable apparatus in clinical genetic diagnosis.

Accordingly the invention provides an in vitro method for genotyping genetic variations in an individual, the method comprising:

(a) providing a sample containing nucleic acid which comprises the genetic variations to be genotyped (the target DNA);

(b) providing, for each genetic variation to be genotyped, at least 2 oligonucleotide probe pairs, wherein:

(i) one pair consists of probes 1 and 2, and the other pair consists of probes 3 and 4;

(ii) one probe in each pair is capable of hybridising to genetic variation A and the other probe in each pair is capable of hybridising to genetic variation B;

(iii) each probe is provided in replicates; and (iv) the probe replicates are deposited at positions on a solid support according to a known uniform distribution;

(c) contacting the target DNA with the probes under conditions which allow hybridisation to occur, thereby forming nucleic acid-probe hybridisation complexes, wherein each complex is detectably labelled;

(d) determining the intensity of detectable label at each probe replica position, thereby obtaining a raw intensity value;

(e) optionally amending the raw intensity value to take account of background noise, thereby obtaining a clean intensity value for each replica; and (e) applying a suitable algorithm to the intensity data from (d) or (e), thereby determining the genotype with respect to each genetic variation, wherein application of the algorithm comprises calculating an average intensity value from the intensity values for each of the replicas of each probe and wherein the algorithm uses three linear functions that characterise each of the three possible genotypes AA, AB or BB for the genetic variation.

For genotyping of each of the allelic variant subjected to study, an algorithm has been developed which allows each one of the mutations to be detected with such a sensitivity, specificity and reproducibility that allows the clinical application of the method, on the basis of obtaining the three Fisher Linear Functions, which characterize each of the three possible genotypes.

$$AA \quad a1 \text{ ratio } 1 + b1 \text{ ratio } 2 + c1 \text{ Function 1}$$

$$AB \quad a2 \text{ ratio } 1 + b2 \text{ ratio } 2 + c2 \text{ Function 2}$$

$$BB \quad a3 \text{ ratio } 1 + b3 \text{ ratio } 2 + c3 \text{ Function 3}$$

Wherein

AA represents the genotype of a homozygote subject for the allelic variant 1;

AB represents the genotype of a homozygote subject for the allelic variants 1 and 2;

BB represents the genotype of a homozygote subject for the allelic variant 2;

a1 is the coefficient which accompanies the X in the Fisher Linear Function for the genotype AA; this coefficient is obtained by applying the discriminate analysis to ratios 1 and 2 obtained from analysing 10 patients for the genotype AA, 10 for BB and 10 for AB;

b1 is the coefficient which accompanies the Y in the Fisher Linear Function for the genotype AA; this coefficient is obtained by applying the discriminate analysis to ratios 1 and 2 obtained from analysing 10 patients for the genotype AA, 10 for BB and 10 for AB;

c1 is the independent term of the first Fisher Linear Function;

a2 is the coefficient which accompanies the X in the in the Fisher Linear Function for the genotype AB; this coefficient is obtained by applying the discriminate analysis to ratios 1 and 2 obtained from analysing 10 patients for the genotype AA, 10 for BB and 10 for AB;

b2 is the coefficient which accompanies the Y in the Fisher Linear Function for the genotype AB; this coefficient is obtained by applying the discriminate analysis to ratios 1 and 2 obtained from analysing 10 patients for the genotype AA, 10 for BB and 10 for AB;

c2 is the independent term of the second Fisher Linear Function;

a3 is the coefficient which accompanies the X in the Fisher Linear Function for the genotype BB; this coefficient is obtained by applying the discriminate analysis to ratios 1 and 2 obtained from analysing 10 patients for the genotype AA, 10 for BB and 10 for AB;

b3 is the coefficient which accompanies the Y in the Fisher Linear Function for the genotype BB; this coefficient is obtained by applying the discriminate analysis to ratios 1 and 2 obtained from analysing 10 patients for the genotype AA, 10 for BB and 10 for AB;

c3 is the independent term of the third linear function;

Function 1 is the Fisher Linear Function, which characterizes patients with genotype AA; this function is obtained the same as 2 and 3 when discriminate analysis is applied to the discrimination of 10 patients AA, 10 BB and 10 AB whose ratios 1 and 2 are known;

Function 2 is the Fisher Linear Function for genotype AB;

Function 3 is the Fisher Linear Function for genotype BB;

Ratio 1 is the proportion of the average collected from the intensities of the 10 replicas of the oligo normal 1 which detects the normal allele divided by the average collected from the 10 replicas of the oligo 1 plus the average collected from the 10 replicas from mutant oligo 1 (detects the mutant allele) and can be calculated by the equation:

$$\text{ratio } 1 = \frac{\text{Average oligo intensity normal 1}}{\text{Average oligo intensity normal 1} + \text{average oligo intensity mutant 1}}$$

Ratio 2 is the proportion of the average collected from the intensities of the 10 replicas of the oligo normal 2 which detects the normal allele divided by the average collected from the 10 replicas of the oligo 2 plus the average collected from the 10 replicas from mutant oligo 2 (detecta at mutant allele) and can be calculated by the equation:

$$\text{ratio } 2 = \frac{\text{Average oligo intensity normal 2}}{\text{Average oligo intensity normal 2} + \text{average oligo intensity mutant 2}}.$$

The invention additionally provides:

- a DNA chip comprising a plurality of probes deposited on a solid support, the chip being suitable for use in a method of the invention;
- a computational method for obtaining a genotype from DNA-chip hybridisation intensity data wherein the method comprises using ratios 1 and 2 in each of three linear functions which characterise each of the three possible genotypes, AA, AB and BB, for a genetic variation wherein:

Function 1 is the linear function that characterises individuals with the genotype AA and consists of a linear combination of ratios 1 and 2;

Function 2 is the linear function that characterises individuals with the genotype AB and consists of a linear combination of ratios 1 and 2;

Function 3 is the linear function that characterises individuals with the genotype BB and consists of a linear combination of ratios 1 and 2; and the linear functions are formed by coefficients which accompany the variables ratio 1 and 2;

and wherein:

$$\text{ratio } 1 = \frac{\text{average intensity value for probe 1}}{\text{average intensity value for probe 1} + \text{average intensity value for probe 2}}$$

and $$\text{ratio } 2 = \frac{\text{average intensity value for probe 3}}{\text{average intensity value for probe 3} + \text{average intensity value for probe 4}}$$

and wherein:

probes 1 and 3 detect genetic variation A and probes 2 and 4 detect genetic variation B; and the average intensity values are obtainable by a method of the invention;

- a method of deriving linear functions for use in a method of the invention, the method comprising, for each of n individuals having genotype AA, n individuals having genotype AB and n individuals having genotype BB with respect to a genetic variation:

(a) providing a sample containing nucleic acid which comprises the genetic variation (the target DNA);

(b) providing, for the genetic variation, at least 2 oligonucleotide probe pairs (probes 1+2, and probes 3+4), wherein:

(i) one pair consists of probes 1 and 2 and the other pair consists of probes 3 and 4;

(ii) one probe in each pair is capable of hybridising to genetic variation A and the other probe in each pair is capable of hybridising to genetic variation B;

(iii) each probe is provided in replicates; and (iv) the probes are deposited at positions on a solid support which comprises additional deposited probes, and the probes are deposited according to a known uniform distribution;

(c) contacting the nucleic acid sample with the probes under conditions which allow hybridisation to occur, thereby forming nucleic acid-probe hybridisation complexes, wherein each complex is detectably labelled;

(d) determining the intensity of detectable label at each probe replica position thereby obtaining a raw intensity value;

(e) optionally amending the raw intensity value to take account of background noise thereby obtaining a clean intensity value for each replica;

(f) applying a suitable algorithm to the intensity data from (d) or (e), wherein application of the algorithm comprises calculating an average intensity value from the intensity values for each of the replicas of each probe and wherein the algorithm uses three linear functions intended to characterise each of the three possible genotypes AA, AB or BB for the genetic variation; and (g) deriving linear functions which maximise discrimination between the three genotype groups AA, AB and BB in a discriminatory analysis;

a computational method of deriving linear functions for use in a method of the invention using ratios 1 and 2 obtained for each of n individuals having genotype AA,n individuals having genotype AB and n individuals having genotype BB with respect to a genetic variation, which comprises:

(a) applying a suitable algorithm, wherein the algorithm uses three linear functions (Functions 1, 2 and 3) intended to characterise each of the three possible genotypes AA, AB or BB for the genetic variation and wherein:

Function 1 is the linear function that characterises individuals with the genotype AA and consists of a linear combination of ratios 1 and 2;

Function 2 is the linear function that characterises individuals with the genotype AB and consists of a linear combination of ratios 1 and 2;

Function 3 is the linear function that characterises individuals with the genotype BB and consists of a linear combination of ratios 1 and 2; and the linear functions are formed by coefficients which accompany the variables ratio 1 and 2;

and wherein:

$$\text{ratio } 1 = \frac{\text{average intensity value for probe 1}}{\text{average intensity value for probe 1} + \text{average intensity value for probe 2}}$$

and $$\text{ratio } 2 = \frac{\text{average intensity value for probe 3}}{\text{average intensity value for probe 3} + \text{average intensity value for probe 4}}$$

and wherein:

probes 1 and 3 detect genetic variation A and probes 2 and 4 detect genetic variation B;

and (b) deriving linear functions which maximise discrimination between the three genotype groups AA, AB and BB in a discriminatory analysis, thereby obtaining coefficients for each of the three functions;

wherein ratios 1 and 2 are obtainable by a method of the invention;

a computer system comprising a processor and means for controlling the processor to carry out a computational method of the invention;

a computer program comprising computer program code which when run on a computer or computer network causes the computer or computer network to carry out a computational method of the invention;

at least one oligonucleotide selected from:

the oligonucleotides listed in SEQ ID NOS 255-630;

the oligonucleotides listed in SEQ ID NOS 631-960 and 1429-1652;

the oligonucleotides listed in SEQ ID NOS 961-1316; and the oligonucleotides of SEQ ID NOs 1-254 and 1317-1428;

a pair of PCR primers selected from the pairs of PCR primers in SEQ ID NOs 1-254 and 1317-1428;

a PCR amplification kit comprising at least one pair of primers of the invention;

a pair of oligonucleotide probes for identification of a genetic variation, the pair being selected from the probe pairs in SEQ ID NOS 255-1316 and 1429-1652;

a set of at least 4 oligonucleotide probes, comprising at least 2 pairs of probes according to the invention wherein each pair is for identification of the same genetic variation;

a diagnostic kit comprising a DNA-chip of the invention;

a method of diagnosing IBD or susceptibility to IBD in an individual comprising genotyping an individual with respect to one or more genetic variations by a method of the invention wherein the genetic variations are associated with IBD;

a method of selecting a treatment for an individual having IBD comprising:

(a) genotyping an individual with respect to one or more genetic variations by a method of the invention wherein the genetic variations are associated with IBD; and (b) selecting a suitable treatment based on the genotype determined in (a).

a method of treating an individual having IBD comprising:

(a) genotyping an individual with respect to one or more genetic variations by a method of the invention wherein the genetic variations are associated with IBD; and (b) selecting a suitable treatment based on the genotype determined in (a); and (c) administering said treatment to the individual.

a method of determining blood group in an individual comprising genotyping an individual with respect to one or more genetic variations by a method of the invention wherein the genetic variations are associated with erythrocyte antigens;

a method of determining susceptibility to adverse reactions to pharmaceuticals in an individual comprising genotyping an individual with respect to one or more genetic variations by a method of the invention wherein the genetic variations are associated with adverse reactions to pharmaceuticals;

a method of selecting a pharmaceutical treatment for an individual comprising:

(a) genotyping an individual with respect to one or more genetic variations by a method of the invention wherein the genetic variations are associated with adverse reactions to pharmaceuticals; and (b) selecting a suitable treatment based on the genotype determined in (a);

a method of treating an individual with a pharmaceutical comprising:

(a) genotyping an individual with respect to one or more genetic variations by a method of the invention wherein the genetic variations are associated with adverse reactions to pharmaceuticals;
(b) selecting a suitable treatment based on the genotype determined in (a); and
(c) administering said treatment to the individual;
a method of identifying genetic variations predictive of a particular IBD phenotype the method comprising:
(a) genotyping a plurality of individuals with respect to one or more genetic variations by a method of the invention, wherein the genetic variations are associated with IBD and wherein the IBD phenotype of the individuals is known;
(b) comparing the genotypes of the individuals tested for one or more genetic variations with the known phenotypes of the individuals; and
(c) identifying any genetic variations for which there is a statistically significant association between the genetic variation and the phenotype;
a method of predicting the likely development of the IBD phenotype of an individual by determining the genotype of the individual with respect to one more genetic variations which have been identified as predictive of development of a particular IBD phenotype by the method of the invention;
a nucleic acid selected from SEQ ID NOS: 1-1652 for use in medicine.

BRIEF DESCRIPTION OF THE FIGURES

FIGS. 3-7 show probabilities for development of phenotypes associated with Crohns disease and FIGS. 8-10 show probabilities associated with the development of phenotypes associated with ulcerative colitis.

BRIEF DESCRIPTION OF THE SEQUENCES

Figure 1:
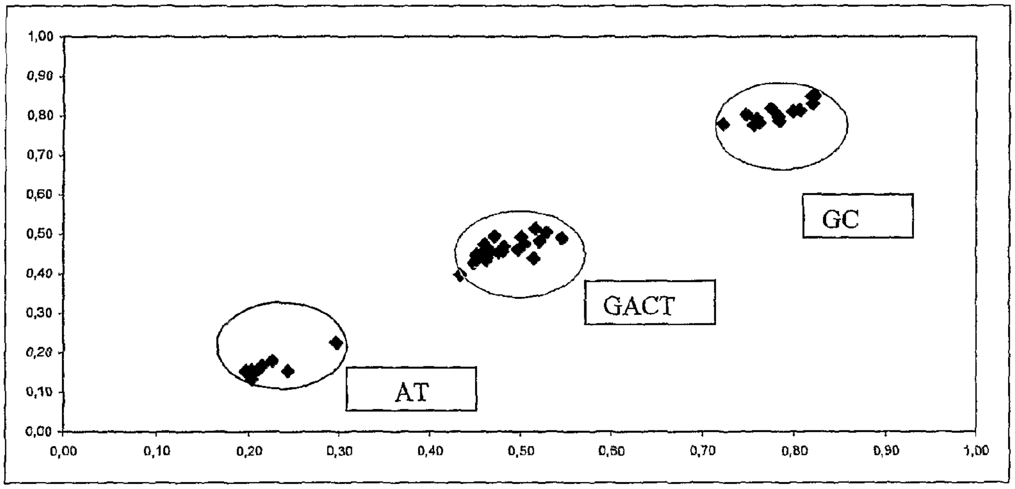
FIG. 1 shows a representation of ratios 1 and 2 in a study of 15 blood donors, five of genotype 188G189C, five of genotype 188GA189CT and five of genotype 188A1189T (Example 2).

SEQ ID NOS 1-124 and 1317-1428 are PCR primers suitable for amplifying target DNA regions comprising genetic variations associated with IBD.
SEQ ID NOS 125-254 are PCR primers suitable for amplifying target DNA regions comprising genetic variations associated with adverse reactions to pharmaceuticals.
SEQ ID NOS 255-630 are probes suitable for detection of genetic variations associated with known erythrocyte antigens, and useful for genotyping for blood groups.
SEQ ID NOS 631-960 and 1429-1652 are probes suitable for detection of genetic variations associated with IBD.
SEQ ID NOS 961-1316 are probes suitable for detection of genetic variations associated with adverse reactions to pharmaceuticals.
SEQ ID NO 1653 is an external control nucleic acid.
SEQ ID NOS 1654-1655 are probes suitable for detection of the external control nucleic acid of SEQ ID NO: 1653.

DETAILED DESCRIPTION OF THE INVENTION

The present invention relates to a method of genotyping genetic variations in an individual, which is sufficiently sensitive, specific and reproducible as to allow its use in a clinical setting. The inventors have developed DNA-chips with specifically designed probes for use in the method, and a computational method or algorithm for interpreting and processing the data generated by the chips.

Thus in one aspect, the invention comprises an in vitro method for genotyping genetic variations in an individual. The in vitro, extracorporeal method is for simultaneous sensitive, specific and reproducible genotyping of multiple human genetic variations present in one or more genes of a subject. The method of the invention allows identification of nucleotide changes, such as, insertions, duplications and deletions and the determination of the genotype of a subject for a given genetic variation.

The terms "genetic variation" or "genetic variant", as they are used in the present description include mutations, polymorphisms and allelic variants. A variation or genetic variant is found amongst individuals within the population and amongst populations within the species.

The term "polymorphism" refers to a variation in the sequence of nucleotides of nucleic acid where every possible sequence is present in a proportion of equal to or greater than 1% of a population; in a particular case, when the said variation occurs in just one nucleotide (A, C, T or G) it is called a single nucleotide polymorphism (SNP).

The term "genetic mutation" refers to a variation in the sequence of nucleotides in a nucleic acid where every possible sequence is present in less than 1% of a population The terms "allelic variant" or "allele" are used without distinction in the present description and refer to a polymorphism that appears in the same locus in the same population.

Thus a genetic variation may comprise a deletion, substitution or insertion of one or more nucleotides. In one aspect the genetic variations to be genotyped according to the present methods comprise SNPs.

A given gene may comprise one or more genetic variations. Thus the present methods may be used for genotyping of one or more genetic variations in one or more genes.

Typically the individual is a human.

Typically, for a given genetic variation there are three possible genotypes:
AA the individual is homozygous for genetic variation A (e.g homozygous for a wild type allele)
BB the individual is homozygous for genetic variation B (e.g. homozygous for a mutant allele)
AB the individual is heterozygous for genetic variations A and B (e.g. one wild type and one mutant allele)

In one aspect the genetic variations, such as SNPs, to be analysed according to the present methods, are associated with a particular phenotype or disease condition. For example, the variations may be associated with particular erythrocyte antigens (and thus often a particular blood group); or with IBD; or with adverse reactions to pharmaceuticals in an individual.

Examples of genetic variations associated with IBD which may be assessed by the present methods include those in Table 1 below.

TABLE 1

| Genetic variations associated with IBD |
|---|
| The polymorphism G2677T/A/C Ala893Ser/Thr/Pro of the gene Multidrug resistance protein 1 (MDR1); |
| The polymorphism C3435T of the gene Multidrug resistance protein 1 (MDR1); |
| The polymorphisms R702W, G908R, 1007insC in the gene Caspase recruitment domain-containing protein 15 (CARD15); |
| The polymorphism T612C Y113H in the gene Microsomal epoxide hydrolase (EPXH1); |
| The polymorphism (−2518) G/A of the gene Monocyte chemotactic protein 1 (MCP1); |
| The polymorphisms (−1082) G/A and G43A (G15R) in the gene Interleukin 10 (IL10); |
| The polymorphism (−295) T/C in the gene Interleukin 16 (IL16); |
| The polymorphism (−843) C/T in the gene Fas ligand; |
| The polymorphisms 94delATTG and −263A/G in the gene Nuclear factor kappa-B 1(NFKB1); |
| The polymorphism in 3'UTR (G/A) of the gene Nuclear factor kappa-B inhibitor alpha (NFKBIA); |
| The polymorphism G2964A in the gene Signal transducer and activator of transcription 6 (STAT6); |
| The polymorphism TCA/TCC of codon 35 in the gene Interleukin 18 (IL18); |
| The polymorphisms E474E, Q476Q, D510D, P588P, −177A/G, A165A, R202Q in the gene Mediterranean fever gene (MEFV); |
| The polymorphism 113G/A (R30Q) in the gene Discslarge, *Drosophila*, homolog of, 5 (DLG5); |
| The polymorphism A2033T in the gene Colony stimulating factor receptor 1 (CSFR1); |
| The polymorphism 1672C/T (L503F) in the gene Organic cation transporter (OCTN1, SLC22A4); |
| The polymorphism (−207G/C) in the Organic cation transporter (OCTN2, SLC22A5); |
| The polymorphisms Asp299Gly and Thr399Ile in the gene Toll-like receptor 4 (TLR4); |
| The polymorphisms (−511) A/C and 3954 TaqI RFLP in the gene Interleukin 1 beta (IL1β); |
| The polymorphism Ala16Val in the gene Superoxide dismutase 2 (SOD2); |
| The polymorphism Pro12Ala in the gene Peroxisome proliferator-activated receptor gamma (PPARG); |
| The polymorphisms K469E, R241G in the gene Intercellular adhesion molecule 1 (ICAM1); |
| The polymorphisms IGR2060a_1, IGR2198a_1, IGR3096a_1 in the locus Inflammatory Bowel Disease 5 (IBD5); |
| The polymorphism 1267A/G (Gln351Gln) in the gene Heat shock protein 70 (HSP70-2); |
| The polymorphism 1237C/T in the gene Toll-like receptor 9 (TLR9); |
| The polymorphism C677T (V222A) in the gene Methylinetetrahydrofolate reductase (MTFHR); |
| The polymorphisms (−590) C/T, (−34) C/T in the gene Interleukin 4 (IL4); |
| The polymorphisms Gly54Asp (A/G), Gly57Glu (A/G), Arg52Cys (C/T) in the gene Mannose-binding lectin (MBL); |
| The polymorphism (−6) A/T in the gene Angiotensinogen precursor (AGT); |
| The polymorphism 4G/5G in the gene Plasminogen activator inhibitor (PAI); |
| The polymorphisms (−857C/T), (−308G/A), (−238 G/A) in the gene Tumor necrosis factor alpha (TNF-α); |
| The polymorphisms G238C, G460A, A719G in the gene TPMT; |
| The polymorphisms Trp14Gly, Thr24Ala, Met129Val, Lys173Glu, Gly175Ser of the gene Major histocompatibility complex class I chain-realted-gene A (MICA) that discriminates the alleles MICA*007 and MICA*008; |
| The polymorphism of the promoter region (−377 to −222) characteristic of allele 7 of the gene Solute carrier family 11, member 1 (SLC11A1 = NRAMP1); |
| The polymorphism (−159) T/C of the gene CD14; |
| The polymorphism G4985T (Val158Phe) of the gene CD16A = FCGR3A; |
| The polymorphism −25385C/T of the gene Nuclear receptor subfamily 1, group I, member 2 (NR1I2); |
| The polymorphism (T/A) (Cys10Stop) of the gene Caspase recruitment domain-containing protein 8 (TUCAN/CARD8/CARDINAL); |
| The polymorphism 738T/C (Cys224Arg) of the gene Inhibitor of kappa light chain gene enhancer in B cells-like (IKBL); |
| The polymorphisms G593A and T620C of the gene Tumor necrosis factor receptor subfamily, member 1B (TNFRSF1B = TNFR2); |
| The polymorphism Asp643Asn of the gene Mitogen-Activated kinase kinase kinase 1 (MEKK1); |
| The polymorphisms 159G/A/C and 282C/T of the gene Major Histocompatibility complex, class II, DQ Alpha-1 (HLA-DQ) for the identification of the alleles DQB1*0401 and DQB1*0402; |
| The polymorphisms 109T/C, 119T/C/G/A, 122A/C/G/T, 129A/G, 161G/A/T, 175A/T/C/G, 184A/C/delA, 286C/A/T, 305C/G for the identification of alleles DR2, DR9, DRB1*0103, DR4, DR7, DRB3*0301 and DR3 of the gene Major histocompatibility complex, class II, DR Beta-1 (HLA-DRB1); |
| The polymorphisms 2018T/C and 2073C/T of the gene Interleukin 1 receptor antagonist (IL1RN); |
| The polymorphism 3954 C/T (TAQI) of the gene Interleukin 1 receptor, type II (IL1RB); |
| The polymorphism (−670) G/A of the gene Fas Antigen; |
| The polymorphism 93 C/T of the gene Caspase 9 (CASP9); |
| The polymorphism G/C (R80T) of the gene Toll-like receptor 1 (TLR1); |
| The polymorphism A/G (R753G) of the gene Toll-like receptor 2 (TLR2); |
| The polymorphism T/C (S249P) of the gene Toll-like receptor 6 (TLR6); |
| The polymorphism 5A/6A of the gene Matrix metalloproteinase 3 (MMP3); |
| The polymorphism indel +32656 of the gene NOD-1 protein (NOD1 = CARD4); |
| The polymorphism DLG5_e26 in the gene Discslarge, *Drosophila*, homolog of, 5 (DLG5); |
| The polymorphism with rs20752817 of the gene NOD-1 protein (NOD1 = CARD4); |
| The polymorphism with rs2975632 of the gene NOD-1 protein (NOD1 = CARD4); |
| The polymorphism with rs3020207 of the gene NOD-1 protein (NOD1 = CARD4); |
| The polymorphism with rs2075818 of the gene NOD-1 protein (NOD1 = CARD4); |
| The polymorphism with rs2235099 of the gene NOD-1 protein (NOD1 = CARD4); |
| The polymorphism with rs2075821 of the gene NOD-1 protein (NOD1 = CARD4); |
| The polymorphism with rs2075822 of the gene NOD-1 protein (NOD1 = CARD4); |
| The polymorphism with rs2907748 of the gene NOD-1 protein (NOD1 = CARD4); |
| The polymorphism with rs5743368 of the gene NOD-1 protein (NOD1 = CARD4); |
| The polymorphism with rs2289311 of the gene NOD-1 protein (NOD1 = CARD4); |
| The polymorphism A1298C in the gene Methylinetetrahydrofolate reductase (MTFHR); |
| The polymorphism Ile114Thr in the gene N-Acetyl tranferase 2 (NAT2); |
| The polymorphism (A/G) Lys268Arg in the gene N-Acetyl tranferase 2 (NAT2); |
| The polymorphism with rs9340799 of the gene Estrogen receptor 1 (ESR1); |
| The polymorphism with rs2234693 of the gene Estrogen receptor 1 (ESR1); |
| The polymorphism C/T V726A in the gene Mediterranean fever gene (MEFV); |
| The polymorphism with rs10735810 in the Vitamin D receptor (VDR); |
| The polymorphism (C/G) E127Q in EGF-like module-contining, mucin-like hormone receptor 3 (EMR3); |
| The polymorphism (G/T) Q496K in EGF-like module-contining, mucin-like hormone receptor 1 (EMR3); |
| The polymorphism R653Q in the Methylenetetrahydrofate dehydrogenase 1 (MTHFD1); |
| The polymorphism 1420 (C/T) in the Serine hydroxymethyltransferase (SHMT1); |
| The polymorphism Gly286Glu in the gene N-Acetyl tranferase 2 (NAT2); |
| The polymorphism Arg197Gln in the gene N-Acetyl tranferase 2 (NAT2); |

TABLE 1-continued

| Genetic variations associated with IBD |
|---|
| The polymorphism 191 (G/A) in the gene N-Acetyl tranferase 2 (NAT2); |
| The polymorphism Arg392Stop of the gene Toll-like receptor 5 (TLR5); |
| The polymorphism A49G of the gene cytotoxic T lymphocyte-associated 4 (CTLA4); |
| The polymorphism D132H of the gene MutL, *E. coli,* homolog of, 1 (MLH1); |
| The polymorphism 66A/G of the gene Methionine synthase reductase (MTRR); |
| The polymorphism 94C/A of the gene Inosine Triphosphatase (ITPA); |
| The polymorphism E148Q in the gene Mediterranean fever gene (MEFV); |
| The polymorphism R620W in the protein tyrosine phosphatase, nonreceptor-type, 22 (PTPN22); |
| The polymorphism 3357 A/G in the Low density lipoprotein receptor-related protein 5 (LRP-5); |
| The polymorphism C318T of the gene cytotoxic T lymphocyte-associated 4 (CTLA4); |
| The polymorphism rs333 32bpdel of the gene chemokine, CC motif, receptor 5 (CCR5); |
| The polymorphism −174G/C of the gene interleukin-6(IL6); |
| The polymorphism with rs6190 of the gene glucocorticoid receptor (GR ER22/23EK); |
| The polymorphism Arg72Pro of the gene p53; |
| The polymorphism P1371Q in the gene Discslarge, *Drosophila*, homolog of, 5 (DLG5); |
| The polymorphism with rs6189 of the gene glucocorticoid receptor (GR ER22/23EK); |
| The polymorphism C135242T in the Low density lipoprotein receptor-related protein 5 (LRP-5); |
| The polymorphism G121513A in the gene Low density lipoprotein receptor-related protein 5 (LRP-5); |
| The polymorphism C141759T in the gene Low density lipoprotein receptor-related protein 5 (LRP-5); |
| The polymorphism G138351A in the gene Low density lipoprotein receptor-related protein 5 (LRP-5); |
| The polymorphism (−298) C/T in the gene Purinergic receptor P2X, ligand-gated ion chanel, 7 (P2RX7); |
| The polymorphism (−838) G/T in the gene Purinergic receptor P2X, ligand-gated ion chanel, 7 (P2RX7); |
| The polymorphism E1317Q in the gene Adenomatous polyposis of the colon (APC); |
| And the polymorphism T64C in the gene CD97 (CD97); |

Examples of genetic variations associated with particular erythrocyte antigens which may be assessed by the present methods include those in Table 2 below.

TABLE 2

| Genetic variations associated with erythrocyte antigens |
|---|
| The polymorphism GG87_88insG (Genotype O4) (BC008) in exon 2 of the gene ABO, |
| The polymorphism G188A + C189T (Genotype O1v) (BC012) in exon 4 of the gene ABO, |
| The polymorphisms 261delG (Genotype O1/O1v) (BC001), C322T (Genotype O5) (BC009) in exon 6 of the gene ABO, |
| The polymorphisms C467T (P156L) (Genotype A2) (BC014), G542A (Genotype O8) (BC013), T646A (Genotype Ax/O1v) (BC015), G703A (Genotype G235S) (B) (BC002), C796A (Genotype L266M) (B) (BC003), G802A (Genotype O2) (BC004), G803C (Genotype G268A) (B, cisAB-1) (BC005), 798-804insG (Genotype O3, Ael) (BC007), C893T (Genotype O6) (BC010), C927A (Genotype O7) (BC011), 1059-1061delC (D FS354 + 21aa) (Genotype A2) (BC006) in exon 7 of the gene ABO, |
| The polymorphisms C8G (S3C) (Genotype weak D type 3) (BC040), G48A (W16X) (Genotype RHD W16X) (BC046), C121T (Q41X) (Genotype RHD Q41X) (BC047) in exon 1 of the gene RHD, |
| The polymorphisms A178C, G203A, T307C (exon scanning) (BC016, BC017, BC018), T161C (L54P) (Genotype DMH) (BC033), G270A (W90X) (Genotype RHD W90X) (BC047), T329C (L110P) (Genotype DVII) (BC028) in exon 2 of the gene RHD, |

TABLE 2-continued

| Genetic variations associated with erythrocyte antigens |
|---|
| The polymorphisms C340T (Genotype weak D type 17) (BC043), C410T (Genotype DIIIiv) (BC059), C446A (A149D) (Genotype weak D type 5) (BC041), A455C (Genotype DIIIa, DIIIiv, DIVa) (BC060), IVS3 + 1G > A (Genotype negative allele) (BC049) in exon 3 of the gene RHD, |
| The polymorphisms 488del4 negative genotype allele (BC050), A497C (H166P) (Genotype DFW) (BC030), T509C (M170T) (Genotype DOL) (BC027), A514T (Genotype DFRI) (BC065), T544A, G577A, A594T (Genotype DVI-I weak D type 4) (exon scanning), (BC019, BC020, BC021) in exon 4 of the gene RHD, |
| The polymorphisms G635T (G212V) (Genotype RHD G212V) (BC051), T667G (Genotype DIIIa, weak D type 4, Dva, DAR, DOL, DCS) (BC061), G676C (Genotype DCS, G686A (Genotype DHR) (BC031), G697C (E233Q), (Genotype G712A (M238V) (DVI I, weak D type 4, DV, DCS) (BC022, BC023), A712G (genotype negative allele) (BC023) in exon 5 of the gene RHD, |
| The polymorphisms T807G (Genotype pseudogene) (BC044), T809G (Genotype weak D type 1) (BC038), G845A (G282D) (Genotype weak D type 15, DIM) (BC037), C848T (T283I) (Genotype DHMI) (BC029), G854A (C285Y) (Genotype DIM) (BC032), G885T (M295I) (Genotype negative allele M295I) (BC053), 906insGGCT (Genotype negative allele) (BC054), G916A, A932G (consensus exon scanning) (BC062, BC063), IVS6 + 1del4 (Genotype allele negative) (BC055) in exon 6 the gene RHD, polymorphisms G941T (G314V) (Genotype negative allele) (BC056), C990G (Y330X) (Genotype negative allele) (BC057), G1016A (G339E) (Genotype weak D type 7) (BC042), T1025C (I342T) (exon scanning) (BC024), G1048C (Genotype DIVa, DIVb) (BC094), G1057A (G353R) (Genotype DNU) (BC034), C1061A (A354N) (Genotype DII) (BC036), G1063A (G355S) (Genotype DNB) (BC026), T1073C (Genotype DWI) (BC035) in exon 7 the gene RHD, |
| The polymorphism IV8 + 1G > A (Genotype negative allele) (BC058) in exon 8 of the gene RHD, |
| The polymorphisms G1154C (G385A) (Genotype weak D type 2) (BC039), A1193T (Genotype DIVb) (BC064), G1227A (K409K) (Genotype K409K) (BC045) in exon 9 of the gene RHD, |
| The polymorphisms G106A (A36T) (Genotype Cx) (BC068), A122G (Q41R) (Genotype Cw) (BC067) in exon 1 of the gene RHCE, |
| The polymorphism T307C (S103P) (Genotype RHc) (BC066) in exon 2 of the gene RHCE, |
| The polymorphism C410T (A137V) (BC059) in exon 3 of the gene RHCE, |
| The polymorphisms C676G (P226A) (Genotype Ee) (BC025, BC069), C733G (L245V) (Genotype VS) (BC070) in exon 5 of the gene RHCE, |
| The polymorphism G1006T (G336C) (Genotype VS−/VS+) (BC071) in exon 7 of the gene RHCE, |
| The polymorphisms A697T (Genotype Kk) (BC073), C698T (T193M) (Genotype Kk) (BC072) in exon 6 of the gene KEL, |
| The polymorphisms T961C (R281W) (Genotype KpaKpb) (BC074), G962A (R281Q) (Genotype KpbKpc) (BC075) in exon 8 of the gene KEL, |
| The polymorphism G1208A (S363N) (Genotype Kmod-1) (BC077) in exon 10 of the gene KEL, |
| The polymorphism C1910T (L597P) (Genotype JsaJsb) (BC076) in exon 17 of the gene KEL, |
| The polymorphism I5AG > AA (Genotype Jknull) (BC079) in exon 6 of the gene SLC14A1 (blood group KIDD), |
| The polymorphisms G838A (D280N) (Genotype JkaJkb) (BC078), T871C (S291P) (Genotype Jknull) (BC080) in exon 9 of the gene SLC14A1 (blood group KIDD), |
| The polymorphisms T-33C (Genotype FYGATA) (BC082), G125A (D42G) (Genotype FYaFYb) (BC081), C265T (R89C) (Genotype FYx) (BC083) in the gene DARC (blood group DUFFY), |
| The polymorphisms C59T, G71A, T72G (S20L, G42E, G42E) (Genotype MN) (BC084, BC085) in exon 2 of the gene GYPA, |
| The polymorphism T143C (M48T) (Genotype Ss) (BC086) in exon 4 of the gene GYPB, |
| The polymorphisms C790A (Genotype GpMUR MiIII) (BC089), C850G (Genotype GpMUR MiIII) (BC090) in exon 3 of the gene GYPE, |
| The polymorphisms C230T (Genotype U) (BC087), I5 + 5GT (Genotype U) (BC088) in exon 5 of the gene GYPB, |
| The polymorphism T2561C (P854L) (Genotype DiaDib) (BC091) in exon 19 of the gene SLC4A1 (blood group DIEGO), |
| The polymorphism A793G (Genotype DoaDob) (BC092) in exon 2 of the gene DOMBROCK, |

TABLE 2-continued

| Genetic variations associated with erythrocyte antigens |
|---|
| The polymorphism C134T (A45V) (Genotype CoaCob) (BC093) in exon 1 of the gene COLTON. |

Examples of genetic variations associated with adverse reactions to pharmaceuticals which may be assessed by the present methods include those in Table 3 below.

TABLE 3

| Genetic variations associated with adverse reactions to pharmaceuticals |
|---|
| The polymorphism Arg389Gly in the adrenergic beta 1 receptor (ADRB1) |
| The polymorphisms Arg16Gly and Gln27Glu in the adrenergic beta 2 receptor (ADRB2), |
| The polymorphism Ser9Gly of the dopamine receptor D3 (DRD3), |
| The polymorphisms His452Tyr and T102C of the serotonin receptor 2A (HTR2A), |
| The polymorphism Val108Met of Catechol-O-methyltransferase (COMT), |
| The polymorphism Ile105Val of Glutathione S transferase class 1 (GSTP1), |
| The polymorphism Gly460Trp of Adducin 1 (ADD1), |
| The polymorphism Arg399Gln of the DNA repair protein XRCC1, |
| The polymorphism Ile462Val of the cytochrome P450 1A1 (CYP1A1), |
| The polymorphism A1166C of the angiotensin II, type 1 receptor (AGTR1), |
| The polymorphism C-58T of the receptor B2 of bradykinin (BDKRB2), |
| The polymorphism Met235Thr of angiotensinogen (AGT), |
| The polymorphisms C430T, A1075C, 818delA, T1076C and C1080G of the cytochrome P450 2C9 (CYP2C9), |
| The polymorphisms H324P, V136V, V11M, C882G, C1038T, G4180C, A1847G, C-1584G, C100T, 138insT, C1023T, G1659A, 1707T/del, G1758A/T, 1863ins9bp, 1973insG, 2539delAACT, 2549A/del, 2613delAGA, C2850T, G3183A, C3198G, T3277C, G4042A and 4125insGTGCCCACT of the cytochrome P450 2D6 (CYP2D6), |
| The polymorphisms A805T, G416A, A1196G and C792G of the cytochrome P450 2C8 (CYP2C8), |
| The polymorphisms T341C, C481T, A803G, C282T, G590A, G857A and G191A of N-acetyltransferase 2 (NAT2), |
| The polymorphisms G636A, G681A, C680T, A1G, IVS5 + 2T > A, T358C, G431A and C1297T of the cytochrome P450 2C19 (CYP2C19), |
| The polymorphism C2664T of the glutamate receptor ionotropic, N-methyl D-asparate (NMDA) 2B (GRIN2B), |
| The polymorphism C3435T of glycoprotein P (ABCB1), |
| The polymorphisms A719G and G238C of thiopurine S-methyltransferase (TPMT), |
| The polymorphism C677T of 5,10-methylenetetrahydrofolatereductase (MTHFR) |
| The polymorphisms Asp70Gly and Ala539Thr of butyrylcholinesterase (BCHE), |
| The polymorphism A-392G of the cytochrome P450 3A4 (CYP3A4), |
| The polymorphisms A-163C, A-3860G, G3534A and C558A of the cytochrome P450 1A2 (CYP1A2), |
| The polymorphisms G14690A, C3699T, G19386A, T29753C and G6986A of the cytochrome P450 3A5 (CYP3A5), |
| The polymorphism 44 bp deletion of the promotor of the serotonin transporter (SLC6A4), |
| The polymorphism delAGA (allele*B) of Glutathione S-transferase M3 (GSTM3), |
| The polymorphism null allele of Glutathione S-transferase M1 (GSTM1), |
| The polymorphism null allele of Glutathione S-transferase n1 (GSTT1), |
| The polymorphisms Cys112Arg and Arg158Cys of apolipoprotein E (APOE), |
| The polymorphism G-308A of Tumor necrosis factor (TNF), and |
| The polymorphism G-1082A of Interleukin 10 (IL10) |

The sequences of all the genes mentioned in Tables 1-3 are known and recognized on the following websites: GeneBank (NCBI), GeneCard (Weizmann Institute of Sciences) and Snpper.chip.org (Innate Immunity PGA).

By permitting clinical genotyping of one or more of the above genetic variations, the present method has use in for example, diagnosing susceptibility to or the presence of IBD or adverse reactions to pharmaceuticals. The methods also allow reliable determination of erythrocyte antigens and are useful in blood grouping or typing.

At least one genetic variation is analysed in the present methods. The present methods allow simultaneous genotyping of multiple variations in an individual and typically multiple variations are analysed, in general, at least 10, 12, 14, 16, 18 or 20 genetic variations. For example, 30, 40, 50, 60, 70, 80 or 100 variations or up to 200, 300, 400, 500, or 600 variations may be tested, such as 250, 350 or 450 variations.

Thus the present methods may be used for genotyping an individual with respect to all of the variations in any one of Tables 1 to 3, or a selection of the variations in any one of the Tables, as described herein. Thus the variations to be detected may comprise or be selected from any one of Tables 1 to 3.

According to the present methods, a sample is provided, containing nucleic acid which comprises at least one of the genetic variations to be tested (the target DNA). The nucleic acid comprises one or more target regions comprising the genetic variation(s) which are to be characterised.

The nucleic acid may be obtained from any appropriate biological sample which contains nucleic acid. The sample may be taken from a fluid or tissue, secretion, cell or cell line derived from the human body.

For example, samples may be taken from blood, including serum, lymphocytes, lymphoblastoid cells, fibroblasts, platelets, mononuclear cells or other blood cells, from saliva, liver, kidney, pancreas or heart, urine or from any other tissue, fluid, cell or cell line derived from the human body. For example, a suitable sample may be a sample of cells from the buccal cavity. Preferably nucleic acid is obtained from a blood sample.

In general, nucleic acid is extracted from the biological sample using conventional techniques. The nucleic acid to be extracted from the biological sample may be DNA, or RNA, typically total RNA. Typically RNA is extracted if the genetic variation to be studied is situated in the coding sequence of a gene. Where RNA is extracted from the biological sample, the methods further comprise a step of obtaining cDNA from the RNA. This may be carried out using conventional methods, such as reverse transcription using suitable primers. Subsequent procedures are then carried out on the extracted DNA or the cDNA obtained from extracted RNA. The term DNA, as used herein, may include both DNA and cDNA.

In general the genetic variations to be tested are known and characterised, e.g. in terms of sequence. Therefore nucleic acid regions comprising the genetic variations may be obtained using methods known in the art.

In one aspect, DNA regions which contain the genetic variations to be identified (target DNA regions) are subjected to an amplification reaction in order to obtain amplification products which contain the genetic variations to be identified. Any suitable technique or method may be used for amplification. In general, the technique allows the (simultaneous) amplification of all the DNA sequences containing the genetic variations to be identified. In other words, where multiple genetic variations are to be analysed, it is preferable to simultaneously amplify all of the corresponding target DNA regions (comprising the variations). Carrying out the amplification in a single step (or as few steps as possible) simplifies the method.

For example, multiplex PCR may be carried out, using appropriate pairs of oligonucleotide PCR primers which are capable of amplifying the target regions containing the genetic variations to be identified. Any suitable pair of primers which allow specific amplification of a target DNA region may be used. In one aspect, the primers allow amplification in the least possible number of PCR reactions. Thus, by using appropriate pairs of oligonucleotide primers and appropriate conditions, all of the target DNA regions necessary for genotyping the genetic variations can be amplified for genotyping (e.g. DNA-chip) analysis with the minimum number of reactions. Suitable PCR primers for amplification of target DNA regions comprising genetic variations associated with erythrocyte antigens, IBD, or adverse reaction to pharmaceuticals, are described herein. In particular, PCR primers for amplification of target DNA regions comprising the genetic variations associated with IBD in Table 1 are listed in SEQ ID NOS 1-124 and 1317-1428. PCR primers for amplification of target DNA regions comprising the genetic variations associated with adverse reaction to drugs in Table 3 are listed in SEQ ID NOS 125-254. The present method may comprise the use of one or more of these primers or one or more of the listed primer pairs.

In one instance, the amplification products can be labelled during the amplification reaction with a detectable label. The aim is to be able to later detect hybridisation between the fragments of target DNA containing the genetic variations being analysed and probes fixed on a solid support. The greater the extent of hybridisation of labelled target DNA to a probe, the greater the intensity of detectable label at that probe position.

The amplification products may be labelled by conventional methods. For example, a labelled nucleotide may be incorporated during the amplification reaction or labelled primers may be used for amplification.

Labelling may be direct using for example, fluorescent or radioactive markers or any other marker known by persons skilled in the art. Examples of fluorophores which can be used, include for example, Cy3 or Cy5. Alternatively enzymes may be used for sample labelling, for example alkaline phosphatase or peroxidase. Examples of radioactive isotopes which can be used include for example $^{33}P$, $^{125}I$, or any other marker known by persons skilled in the art. In one instance, labelling of amplification products is carried out using a nucleotide which has been labelled directly or indirectly with one or more fluorophores. In another example, labelling of amplification products is carried out using primers labelled directly or indirectly with one or more fluorophores.

Labelling may also be indirect, using, for example, chemical or enzymatic methods. For example, an amplification product may incorporate one member of a specific binding pair, for example avidin or streptavidin, conjugated with a fluorescent marker and the probe to which it will hybridise may be joined to the other member of the specific binding pair, for example biotin (indicator), allowing the probe/target binding signal to be measured by fluorimetry. In another example, an amplification product may incorporate one member of a specific binding pair, for example, an anti-dioxigenin antibody combined with an enzyme (marker) and the probe to which it will hybridise may be joined to the other member of the specific binding pair, for example dioxigenin (indicator). On hybridization of amplification product to probe the enzyme substrate is converted into a luminous or fluorescent product and the signal can be read by, for example, chemiluminescence or fluorometry.

The nucleic acid comprising the genetic variation(s) to be tested, e.g. the (optionally labelled) amplification products, may further undergo a fragmentation reaction, thereby obtaining some fragmentation products which comprise or contain the genetic variations to be identified or analysed. Typically fragmentation increases the efficiency of the hybridisation reaction. Fragmentation may be carried out by any suitable method known in the art, for example, by contacting the nucleic acid, e.g. the amplification products with a suitable enzyme such as a DNase.

If the nucleic acid has not been previously labelled, e.g. during the amplification reaction, (and, typically, where no posthybridisation amplification or ligation is carried out on the solid support) then labelling with a detectable label may be carried out prehybridisation by labelling the fragmentation products. Suitable labelling techniques are known in the art and may be direct or indirect as described herein. Direct labelling may comprise the use of, for example, fluorophores, enzymes or radioactive isotopes. Indirect labelling may comprise the use of, for example, specific binding pairs that incorporate e.g. fluorophores, enzymes, etc. For example, if amplification products have not been labelled during the amplification reaction the fragmentation products may undergo a direct or indirect labelling with one or various markers, for example one or various fluorophores, although other known markers can be used by those skilled in the art.

According to the present methods the nucleic acid, e.g. the amplification or fragmentation products, comprising the genetic variation(s) to be detected (target DNA), is contacted with oligonucleotide probes which are capable of detecting the corresponding genetic variations by hybridisation under suitable conditions.

Typically the hybridisation conditions allow specific hybridisation between probes and corresponding target nucleic acids to form specific probe/target hybridisation complexes while minimising hybridisation between probes carrying one or more mismatches to the DNA. Such conditions may be determined empirically, for example by varying the time and/or temperature of hybridisation and/or the number and stringency of the array washing steps that are performed following hybridisation and are designed to eliminate all probe-DNA interactions that are inspecific.

In the method, the probes are provided deposited on a solid support or surface. The probes are deposited at positions on the solid support according to a predetermined pattern, forming a "DNA-chip". It has been found that the chips should comply with a number of requirements in order to be used in the present methods, for example in terms of the design of the probes, the number of probes provided for each genetic variation to be detected and the distribution of probes on the support. These are described in detail herein. The inventors have developed suitable genotyping chips for use in the present methods and accordingly in one aspect the invention provides a DNA-chip or (micro)array comprising a plurality of probes deposited or immobilised on a solid support as described herein.

In general the solid support or phase comprises oligonucleotide probes suitable for detection of each genetic variation to be tested. The number and type of genetic variations to be tested using a chip may be selected as described herein.

Typically there will be at least one probe which is capable of hybridising specifically to genetic variation A (e.g. a wild-type or normal allele) (probe 1) and one probe which is capable of hybridising specifically to genetic variation B (e.g. a mutant allele) (probe 2) under the selected hybridisation conditions. These probes form a probe pair. Probe 1 is for detection of genetic variation A and probe 2 for detection of genetic variation B. Typically the probes can be used to discriminate between A and B (e.g. the wildtype and mutant alleles).

The probes may examine either the sense or the antisense strand. Typically, probes 1 and 2 examine the same nucleic acid strand (e.g. the sense strand or antisense strand) although in some cases the probes may examine different strands. In one aspect probes 1 and 2 have the same sequence except for the site of the genetic variation.

In one instance, the probes in a probe pair have the same length. In some aspects, where two or more pairs of probes are provided for analysis of a genetic variation, the probes may all have the same length.

Preferably more than one probe pair is provided for detection of each genetic variation. Thus, at least 2, 3, 4, 5, 6, 7, 8, 9, 10 or more probe pairs may be provided per genetic variation. In one aspect, (at least) 2 probe pairs are provided. The aim is to reduce the rate of false positives and negatives in the present methods.

For example, for a given genetic variation there may be:

Probe 1 which is capable of hybridising to genetic variation A (e.g. a normal allele)

Probe 2 which is capable of hybridising to genetic variation B (e.g. a mutant allele)

Probe 3 which is capable of hybridising to genetic variation A (e.g. a normal allele)

Probe 4 which is capable of hybridising to genetic variation B (e.g. a mutant allele).

The probes may examine the same or different strands. Thus in one embodiment, probes 3 and 4 are the complementary probes of probes 1 and 2 respectively and are designed to examine the complementary strand. In one aspect it is preferred that the probes provided for detection of each genetic variation examine both strands.

More than 2 pairs of probes may be provided for analysis of a genetic variation as above. For example, where a genetic variation exists as any one of 4 bases in the same strand (e.g. there are three mutant possibilities), at least one pair of probes may be provided to detect each possibility. Preferably, at least 2 pairs of probes are provided for each possibility.

Thus, for example, for the SNP G2677T/A/C, at least one pair of probes may be provided for detection of G2677T, one pair for detection of G2677/A, and one pair for detection of G2677C. Preferably at least two pairs of probes are provided for each of these substitutions.

A number of methods are known in the art for designing oligonucleotide probes suitable for use in DNA-chips.

A "standard tiling" method may be used. In this method, 4 oligonucleotides are designed that are totally complementary to the reference sequence except in the central position where, typically the 4 possible nucleotides A, C, G and T are examined. An illustrative example of this strategy is the DNA-chip for genotyping of HIV-1 (Affymetrix).

In "alternative tiling" 5 oligonucleotides are designed, so that the fifth examines a possible deletion in the sequence. An example of this strategy is the DNA-chip to detect mutations in p53 (Affymetrix).

In "block tiling" 4 oligonucleotides are designed that are totally complementary to the normal sequence and another 4 totally complementary to the mutant sequence. The nucleotide which changes is placed in the central position, but a mismatch of one of the 4 bases (A, C, T or G) is placed 2 nucleotides before or after the nucleotide position that it is wished to interrogate. An example of this strategy is the DNA-chip for the detection of mutations in cytochrome p450 (Roche and Affymetrix).

A further example is "alternative block tiling" where the "mismatch" is used to increase the specificity of the hybrid not only in one position but also in the positions −4, −1, 0, +1 and +4 to identify the change produced in the central position or 0. An example is the DNA-chip to detect 1,500 SNPs (Affymetrix).

Any one or more of these strategies may be used to design probes for the present invention. Preferably standard tiling is used, in particular with 2 pairs of probes e.g. 2 pairs of complementary probes as above. Thus it is preferable that the oligonucleotide sequence is complementary to the target DNA or sequence in the regions flanking the variable nucleotide(s). However, in some cases, one or more mismatches may be introduced, as described above.

The oligonucleotide probes for use in the present invention typically present the base to be examined (the site of the genetic variation) at the centre of the oligonucleotide. This is particularly the case where differential hybridisation methods are used, as in general this allows the best discrimination between matched and mismatched probes. In these methods, typically there is formation of specific detectable hybridisation complexes without post-hybridisation on-chip amplification. For example, for precise (single base) mutations, the base which differs between the normal and the mutant allele is typically placed in the central position of the probe. In the case of insertions, deletions and duplications, the first nucleotide which differs between the normal and the mutant sequence is placed in the central position. It is believed that placing the mutation at the centre of the probe maximises specificity.

Where post-hybridisation on-chip amplification (e.g. ligation or primer extension methods) is employed, oligonucleotide probes typically present the variable base(s) at the 3' end of the probe. Where OLA methodology is used, oligonucleotides (labelled directly or indirectly) are also designed which hybridise to probe-target complexes to allow ligation.

In general the probes for use in the present invention comprise or in some embodiments consist (essentially) of 17 to 27 nucleotides, for example, 19, 21, 23, or 25 nucleotides or 18, 20, 22, 24 or 26 nucleotides.

Preferably the individual probes provided for detection of a genetic variation are capable of hybridising specifically to the normal and mutant alleles respectively under the selected hybridisation conditions. For example, the melting temperature of the probe/target complexes may occur at 75-85 degrees C. and hybridisation may be for one hour, although higher and lower temperatures and longer or shorter hybridisations may also suffice.

The probes provided for detection of each genetic variation (as described above) are typically capable of discriminating between genetic variation A and B (e.g. the normal and mutant alleles) under the given hybridisation conditions as above. Preferably the discrimination capacity of the probes is substantially 100%. If the discrimination capacity is not 100%, the probes are preferably redesigned. Preferably the melting temperature of the probe/target complexes occurs at 75-85 degrees C. Methods for testing discrimination capacity are described herein.

In one example, the probes provided for detection of a genetic variation examine both strands and have lengths ranging from 19-27 nucleotides. Preferably the probes have 100% discrimination capacity and the melting temperature of probe/target complexes is 75-85 degrees C.

Typically in order to obtain probes for use in the present methods, a number of probes are designed and tested experimentally for, e.g. hybridisation specificity and ability to discriminate between genetic variants (e.g. a normal and a mutant allele). Candidate oligonucleotide probe sequences may be designed as described above. These may vary for example in length, strand specificity, position of the genetic variation and degree of complementarity to the sequence flanking the genetic variation in the target DNA. Once probe pairs have been designed, these can be tested for hybridisation specificity and discrimination capacity. The capacity of specific probes to discriminate between the genetic variations A and B (e.g. normal and mutant alleles) depends on hybridisation conditions, the sequence flanking the mutation and the secondary structure of the sequence in the region of the mutation. By using stable hybridisation conditions, appropriate parameters such as strand specificities and lengths can be established in order to maximise discrimination. Preferably, the genetic variation is maintained at the central position in the tested probes.

Methods for testing discrimination capacity of probes are described herein. Typically a number of candidate probe pairs are provided and used in a training method as described below. In general two pairs of probes (probes 1 and 2, and probes 3 and 4) are tested in the method. For example, two pairs of probes examining both strands (complementary to each other) may be tested. If it is not possible to obtain 100% discrimination between the three genotyping groups using the probes, the probes are typically redesigned. Hybridisation conditions in the training method are generally maintained stably. Typically the melting temperature of probe/target complexes is 75-85 degrees C.

For example, starting from probes of 25 nucleotides which detect a genetic variation (e.g. the normal allele) and another genetic variation (e.g. a mutant allele) in both strands (sense and antisense), in general an average of 8 probes may be experimentally tested to identify two definite pairs.

Probes are chosen to have maximum hybridisation specificity and discrimination capacity between genetic variants (e.g. a normal and a mutant allele) under suitable hybridisation conditions. For example, the probes for detection of a given genetic variation, e.g. two probe pairs, typically have substantially 100% discrimination capacity. Typically the melting temperature of probe/target complexes is at 75-85° C.

Using the methods herein the inventors have developed oligonucleotide probes suitable for detection of the IBD-associated genetic variations in Table 1. These probes are presented as SEQ ID NOS 631-960 and 1429-1652. The probes are listed in probe sets (133 sets in total), each set being for detection of a given genetic variation. At least two pairs of probes are listed in each set.

The inventors have also developed oligonucleotide probes suitable for detection of the erythrocyte antigen-associated genetic variations in Table 2. These probes are presented as SEQ ID NOS 255-630. The probes are listed in probe sets (94 sets in total), each set being for detection of a given genetic variation. At least two pairs of probes are listed in each set.

The inventors have also developed oligonucleotide probes suitable for detection of the genetic variations associated with adverse reactions to drugs in Table 3. These probes are presented as SEQ ID NOS 961-1316. The probes are listed in probe sets (89 sets in total), each set being for detection of a given genetic variation. At least two pairs of probes are listed in each set.

In one aspect the invention relates to any one or more of the oligonucleotide probes, pairs of probes or sets of probes set out in SEQ ID NOS 255-630, 631-960, 961-1316 or 1429-1652, and to their use in the genotyping, diagnostic or therapeutic methods of the invention. The invention further relates to any one or more of the oligonucleotide probes, pairs of probes or sets of probes set out in SEQ ID NOS 255-630, 631-960, 961-1316 or 1429-1652 for use in medicine, for example in a diagnostic or therapeutic method described herein. A chip of the invention may comprise one or more of the listed probe pairs or sets.

In general probes are provided on the support in replicate. Typically, at least 4, 6, 8, 10, 12, 14, 16, 18 or 20 replicates are provided of each probe, in particular, 6, 8 or 10 replicates. Thus for example, the support (or DNA-chip) may comprise or include 10 replicates for each of (at least) 4 probes used to detect each genetic variation (i.e. 40 probes). Alternatively the support (or DNA-chip) may comprise or include 8 replicates for each of (at least) 4 probes used to detect each genetic variation (i.e. 32 probes). Still further the support (or DNA-chip) may comprise or include 6 replicates for each of (at least) 4 probes used to detect each genetic variation (i.e. 24 probes). Using probe replicates helps to minimise distortions in data interpretation from the chip and improves reliability of the methods.

In general the support also comprises one or more control oligonucleotide probes. These are also provided in replicate as above. Thus the support (or DNA-chip) may additionally comprise one or more oligonucleotides deposited on the support which are useful as positive and/or negative controls of the hybridisation reactions. If post-hybridisation amplification or ligation reactions are carried out on the chip, there may also be one or more positive or negative controls of these reactions.

Typically the chip or array will include positive control probes, e.g., probes known to be complementary and hybridisable to sequences in the target polynucleotide molecules, probes known to hybridise to an external control DNA, and negative control probes, e.g., probes known to not be complementary and hybridizable to sequences in the target polynucleotide molecules. The chip may have one or more controls specific for each target, for example, 2, 3, or more controls. There may also be at least one control for the array.

Positive controls may for example be synthesized along the perimeter of the array or in diagonal stripes across the array. The reverse complement for each probe may be synthesized next to the position of the probe to serve as a negative control. In yet another example, sequences from other species of organism may be used as negative controls in order to help determine background (non-specific) hybridisation.

As above, the support (or DNA-chip) may include some (one or more) oligonucleotides deposited on the support which are useful as positive and negative controls of the hybridization reactions. In general, each one of the sub-arrays, for example 16, which typically constitute a DNA-chip, is flanked by some external hybridization controls, which serve as reference points allowing allow the points within the grid to be located more easily.

In one instance, the nucleotide sequence of an external control DNA is the following (5'→3'):

```
CEH:
GTCGTCAAGATGCTACCGTTCAGGAGTCGTCAAG    SEQ ID NO:1653
ATGCTACCGTTCAGGA
```

and the sequences of the oligonucleotides for its detection are the following:

```
ON1:
CTTGACGACTCCTGAACGG                   SEQ ID NO:1654

ON2:
CTTGACGACACCTGAACGG                   SEQ ID NO:1655
```

Positive control probes are generally designed to hybridise equally to all target DNA samples and provide a reference signal intensity against which hybridisation of the target DNA (sample) to the test probes can be compared. Negative controls comprise either "blanks" where only solvent (DMSO) has been applied to the support or control oligonucleotides that have been selected to show no, or only minimal, hybridisation to the target, e.g. human, DNA (the test DNA). The intensity of any signal detected at either blank or negative control oligonucleotide features is an indication of non-specific interactions between the sample DNA and the array and is thus a measure of the background signal against which the signal from real probe-sample interactions must be discriminated.

Desirably, the number of sequences in the array will be such that where the number of nucleic acids suitable for detection of genetic variations is n, the number of positive and negative control nucleic acids is n', where n' is typically from 0.01 to 0.4n.

In general, the support or chip is suitable for genotyping, in particular, genotyping according to the present methods. The chip typically comprises probes suitable for detection of at least one but preferably multiple, genetic variation(s), typically at least 10, 12, 14, 16, 18 or 20 genetic variations. For example, 30, 40, 50, 60, 70, 80 or 100 variations or up to 200, 300, 400, 500, or 600 variations may be tested, such as 250, 350 or 450 variations.

The genetic variations may be those in any one of Tables 1 to 3. Thus an array may comprise probes suitable for genotyping an individual with respect to all of the variations in any one of Tables 1 to 3, or a selection of the variations in any one of the Tables, as described above.

The present DNA-chips can be used, in combination with the present methods, to detect practically any human genetic variation of interest, for example, human genetic variations associated with diseases or antigens of interest. Suitable probes will be used for those genetic variations to be detected. As genetic variations associated with the diseases or antigens of interest are identified, suitable probes for their detection can be incorporated in the chips. Probes and DNA-chips for this purpose can be designed in accordance with the teaching of the present invention.

The inventors have designed, produced and validated the clinical use of the invention in detection of genetic variations associated with IBD, with known human erythrocyte antigens and with adverse reactions to medicine by developing (designing and producing) corresponding DNA-chips.

Therefore, in one particular embodiment, the invention relates to a chip for genotyping of genetic variations associated with IBD (an "IBD-chip"). Typically the DNA-chip allows simultaneous, sensitive, specific and reproducible detection of genetic variations associated with IBD. Non-limiting examples of such variations are given in Table 1. Nevertheless, the number of genetic variations contained in the Table can be increased as other genetic variations are subsequently identified and are associated with IBD. Thus the genetic variations detectable by the chip may comprise, or consist (essentially) of those listed in Table 1 or a selection of these. The chip will comprise probes suitable for detection of these genetic variations as described herein. In one aspect the chip comprises probes selected from those in SEQ ID NOS 631-960 and 1429-1652. The probes are listed in probe sets (133 sets in total), each set being for detection of a given genetic variation. At least two pairs of probes are provided in each set. A chip may comprise at least one probe pair or at least one probe set, or a selection of the probe sets, for example, at least 5, 10, 20, 30, 40, 50, 60, 70, 80, 90, 100, 110, 120, 130 or all 133 sets, according to the genetic variations being tested. A chip may comprise other probes for detection of variations in Table 1 or other variations associated with IBD instead of or in addition to those specifically listed.

In another embodiment the chip is for genotyping of genetic variations associated with erythrocyte antigens (the "blood chip"). Typically the DNA-chip allows the simultaneous, sensitive, specific and reproducible detection of genetic variations associated with determined erythrocyte antigens. Non-limiting examples of such variations are given in Table 2. Nonetheless the number of genetic variations contained in the table can be increased as other genetic variations are subsequently identified and are associated with erythrocyte antigens. Thus the genetic variations detectable by the chip may comprise, or consist (essentially) of those listed in Table 2 or a selection of these. The chip will comprise probes suitable for detection of these genetic variations as described herein. In one aspect the chip comprises probes selected from those in SEQ ID NOS 255-630. The probes are listed in probe sets (94 sets in total), each set being for detection of a given genetic variation. At least two pairs of probes are provided in each set. A chip may comprise at least one probe pair or at least one probe set, or a selection of the probe sets, for example, at least 5, 10, 20, 30, 40, 50, 60, 70, 80, 90, or all 94 sets, according to the genetic variations being tested. A chip may comprise other probes for detection of variations in Table 2 or other variations associated with erythrocyte antigens instead of or in addition to those specifically listed.

In another embodiment the chip is for genotyping of genetic variations associated with adverse reactions to pharmaceuticals (the "drug chip"). Typically the chip allows the simultaneous, sensitive, specific and reproducible detection of genetic variations associated with adverse reactions to medicine. Non-limiting examples are given in Table 3. Nevertheless, the number of genetic variations contained in the table can be increased as other genetic variations are subsequently identified and are associated with these adverse reactions. Thus the genetic variations detectable by the chip may comprise, or consist (essentially) of those listed in Table 3 or a selection of these. The chip will comprise probes suitable for detection of these genetic variations as described herein. In one aspect the chip comprises probes selected from those in SEQ ID NOS 961-1316. The probes are listed in probe sets (89 sets in total), each set being for detection of a given genetic variation. At least two pairs of probes are provided in each set. A chip may comprise at least one probe pair or at least one probe set, or a selection of the probe sets, for example, at least 5, 10, 20, 30, 40, 50, 60, 70, 80, or all 89 sets, according to the genetic variations being tested. A chip may comprise other probes for detection of variations in Table 3 or other variations associated with adverse reactions to drugs instead of or in addition to those specifically listed.

An IBD chip, blood chip or drug chip may additionally comprise oligonucleotide probes for detection of genetic variations not associated with IBD, erythrocyte antigens or adverse reactions to drugs respectively. For example, the chips may comprise probes for detection of genetic variations such as SNPs associated with another (related) condition or other (related) antigen(s). Typically, in an IBD chip, blood chip or drug chip, the number of nucleic acids suitable for detection of genetic variations associated with IBD, erythrocyte antigens or adverse reactions to drugs respectively (e.g. those in Tables 1, 2, or 3) represent at least 50%, 60%, 70%, 75%, 80%, 85%, 90%, 95%, 97%, 98%, 99% or more of the nucleic acids in the array.

In general the support or chip has from 300 to 40000 nucleic acids (probes), for example, from 400 to 30000 or 400 to 20000. The chip may have from 1000 to 20000 probes, such as 1000 to 15000 or 1000 to 10000, or 1000 to 5000. A suitable chip may have from 2000 to 20000, 2000 to 10000 or 2000 to 5000 probes. For example, a chip may have 1000, 2000, 3000, 4000, 5000, 6000, 7000, 8000, 9000, 10000, 12000, 14000, 16000, 18000 or 20000 probes. Smaller chips 400 to 1000 probes, such as 400, 500, 600, 700, 800, 900 or 950 probes are also envisaged.

In general the array or chip of the invention comprises a support or surface with an ordered array of binding (e.g. hybridisation) sites or probes. Thus the arrangement of probes on the support is predetermined. Each probe (i.e each probe replicate) is located at a known predetermined position on the solid support such that the identity (i.e. the sequence) of each probe can be determined from its position in the array. Typically the probes are uniformly distributed in a predetermined pattern.

Preferably, the probes deposited on the support, although they maintain a predetermined arrangement, are not grouped by genetic variation but have a random distribution. Typically they are also not grouped within the same genetic variation. If desired, this random distribution can be always the same. Therefore, typically the probes are deposited on the solid support (in an array) following a predetermined pattern so that they are uniformly distributed, for example, between the two areas that may constitute a DNA-chip, but not grouped according to the genetic variation to be characterised. Distributing probe replicates across the array in this way helps to reduce or eliminate any distortion of signal and data interpretation, e.g. arising from a non-uniform distribution of background noise across the array.

As explained above, probes may be arranged on the support in subarrays.

The support, on which the plurality of probes is deposited, can be any solid support to which oligonucleotides can be attached. Practically any support, to which an oligonucleotide can be joined or immobilized, and which may be used in the production of DNA-chips, can be used in the invention. For example, the said support can be of a non-porous material, for example, glass, silicone, plastic, or a porous material such as a membrane or filter (for example, nylon, nitrocelullose) or a gel. In one embodiment, the said support is a glass support, such as a glass slide.

Microarrays are in general prepared by selecting probes which comprise a given polynucleotide sequence, and then immobilizing such probes to a solid support or surface. Probes may be designed, tested and selected as described herein. In general the probes may comprise DNA sequences. In some embodiments the probes may comprise RNA sequences, or copolymer sequences of DNA and RNA. The polynucleotide sequences of the probes may also comprise DNA and/or RNA analogues, or combinations thereof. For example, the polynucleotide sequences of the probes may be full or partial fragments of genomic DNA. The polynucleotide sequences of the probes may also be synthesized nucleotide sequences, such as synthetic oligonucleotide sequences. The probe sequences can be synthesized either enzymatically in vivo, enzymatically in vitro (e.g., by PCR), or non-enzymatically in vitro.

Microarrays or chips can be made in a number of ways. However produced, microarrays typically share certain characteristics. The arrays are reproducible, allowing multiple copies of a given array to be produced and easily compared with each other. Preferably, microarrays are made from materials that are stable under binding (e.g., nucleic acid hybridization) conditions. The microarrays are preferably small, e.g., between 0.25 to 25 or 0.5 to 20 $cm^2$, such 0.5 to 20 $cm^2$ or 0.5 to 15 $cm^2$, for example, 1 to 15 $cm^2$ or 1 to 10 $cm^2$, such as 2, 4, 6 or 9 $cm^2$.

Probes may be attached to the present support using conventional techniques for immobilization of oligonucleotides on the surface of the supports. The techniques used depend, amongst other factors, on the nature of the support used [porous (membranes, micro-particles, etc.) or non-porous (glass, plastic, silicone, etc.)] In general, the probes can be immobilized on the support either by using non-covalent immobilization techniques or by using immobilization techniques based on the covalent binding of the probes to the support by chemical processes.

Preparation of non-porous supports (e.g., glass, silicone, plastic) requires, in general, either pre-treatment with reactive groups (e.g., amino, aldehyde) or covering the surface of the support with a member of a specific binding pair (e.g. avidin, streptavidin). Likewise, in general, it is advisable to pre-activate the probes to be immobilized by means of corresponding groups such as thiol, amino or biotin, in order to achieve a specific immobilization of the probes on the support.

The immobilization of the probes on the support can be carried out by conventional methods, for example, by means of techniques based on the synthesis in situ of probes on the support (e.g., photolithography, direct chemical synthesis, etc.) or by techniques based on, for example, robotic arms which deposit the corresponding pre-synthesized probe (e.g. printing without contact, printing by contact).

In one embodiment, the support is a glass slide and in this case, the probes, in the number of established replicates (for example, 6, 8 or 10) are printed on pre-treated glass slides, for example coated with aminosilanes, using equipment for automated production of DNA-chips by deposition of the oligonucleotides on the glass slides ("micro-arrayer"). Deposition is carried out under appropriate conditions, for example, by means of crosslinking with ultraviolet radiation and heating (80° C.), maintaining the humidity and controlling the temperature during the process of deposition, typically at a relative humidity of between 40-50% and typically at a temperature of 20° C.

The replicate probes are distributed uniformly amongst the areas or sectors (sub-arrays), which typically constitute a DNA-chip. The number of replicas and their uniform distribution across the DNA-chip minimizes the variability arising from the printing process that can affect experimental results. Likewise, positive and negative hybridisation controls (as described herein) may be printed.

To control the quality of the manufacturing process of the DNA-chip, in terms of hybridization signal, background noise, specificity, sensitivity and reproducibility of each replica as well as differences caused by variations in the morphology of the spotted probe features after printing, a commercial DNA can be used. For example, as a quality control of the printing of the DNA-chips, hybridization may be carried out with a commercial DNA (e.g. k562 DNA High Molecular Weight, Promega)

In the first place, the morphology and size of the printed spots are analyzed. In the hybridization with control DNA the parameters described below for determining reliability of genotype determination, are adhered to; specifically the relationship between the signal intensity and background noise, average specificity and sensitivity and reproducibility between replicated copies of the same probe. This method allows the correct genotype of the control DNA to be determined.

As above, in accordance with the present method, a nucleic acid sample, e.g. amplification or fragmentation products, comprising the genetic variation(s) to be detected (target DNA) is contacted with a probe array as described herein, under conditions which allow hybridisation to occur between target DNA and the corresponding probes. Specific hybridisation complexes are thus formed between target nucleic acid and corresponding probes.

The hybridization of e.g. fragmentation products, with probes capable of detecting corresponding genetic variations deposited on a support may be carried out using conventional methods and devices. In one instance, hybridization is carried out using an automated hybridisation station. For hybridization to occur, the e.g. fragmentation products, are placed in contact with the probes under conditions which allow hybridization to take place. Using stable hybridization conditions allows the length and sequence of the probes to be optimised in order to maximize the discrimination between genetic variations A and B, e.g. between wild type and mutant sequences, as described herein.

In one instance, the method relies on differential hybridisation, in particular an increase in hybridisation signal. The method involves formation of specific hybridisation complexes between target DNA and corresponding probes. Thus target DNA bearing the wild type sequence will hybridise to the probes designed to detect the wild type sequence, whereas target DNA bearing a mutant sequence will hybridise to the probes designed to detect that mutant sequence. The hybridisation complexes are detectably labelled by means described herein (e.g. the target DNA is directly labelled, or both target and probe are labelled in such a way that the label is only detectable on hybridisation). By detecting the intensity of detectable label (if any) at the predetermined probe positions it is possible to determine the nature of the target DNA in the sample. In this instance the probes (also referred to as allele specific oligonucleotides, ASOs) preferably have the variable nucleotide(s) at the central position, as described herein.

In another instance, hybridisation of target DNA to probes on the solid support (chip) may be followed by on-chip amplification, for example, using primer extension or ligation, e.g. oligonucleotide ligation assay (OLA) technologies (Eggerding F A, Iovannisci D M, Brinson E., Grossman P., Winn-Deen E. S. 1995 Human Mutation, 5:153-65). In this case, the probes on the support typically comprise the variable nucleotide(s) at the 3' end of the probe.

Labelling can be carried out during post hybridisation amplification. The labelling can be by direct labelling using, for example, fluorophores, enzymes, radioactive isotopes, etc. or by indirect labelling using, for example, specific binding pairs which incorporate fluorophores, enzymes etc., by using conventional methods, such as those previously mentioned in relation to labelling amplification or fragmentation products.

Post-hybridization amplification may be carried out, for example, using the "primer extension" methodology. Typically, after hybridization, an extension reaction of the hybrid oligonucleotides is carried out on the support (e.g. a glass slide). Extension may be carried out with directly or indirectly labelled nucleotides and will only happen if the extreme 3' of the oligonucleotide hybridizes perfectly with the amplification product.

Primer extension is a known method for genotype discrimination (Pastinen T, Raitio M, Lindroos K, Tainola P, Peltonen L, Syvanen AC. 2000 *Genome Research* 10:1031-42.) and can be performed in a number of different ways. In a commonly used approach a set of allele specific oligonucleotide probes are designed to hybridise to the target sequences. The probes differ from one another in their extreme 3' nucleotide, which for each probe is designed to complement one of the possible polymorphic nucleotides at a given position.

When the 3' nucleotide of the probe complements the sequence under test then the ensuing base pairing allows a DNA polymerase to extend the oligonucleotide primer by incorporation of additional nucleotides that can be directly or indirectly labelled thereby allowing the subsequent identification of those probes that have been extended and those that have not. Probes that are successfully extended carry the complementary nucleotide to the SNP at their 3' end thus allowing the genotype of the test sample to be determined. Similar approaches, for example the Amplification Refractory Mutation System (ARMS) have also been developed.

Alternatively, a post hybridization ligation reaction may be carried out, for example using OLA methodology. After hybridization, a ligation reaction of the hybridised oligonucleotides is carried out on the support (e.g. glass slide) with labelled oligonucleotides. A ligation will only take place if the extreme 3' end of the probe deposited on the support hybridizes perfectly with the target DNA (e.g. amplification product).

The oligonucleotide ligation assay (OLA) is another method for interrogating SNPs (Eggerding F A, Iovannisci D M, Brinson E., Grossman P., Winn-Deen E. S. 1995 Human Mutation, 5:153-65). OLA uses a pair of oligonucleotide probes that hybridize to adjacent segments of target DNA including the variable base. The probe designed to hybridise to the 5' side of the polymorphic nucleotide is an allele-specific oligonucleotide (ASO) to one of the target alleles. The last base at the 3' end of this ASO is positioned at the site of the target DNA's polymorphism; the ASO typically also has a biotin molecule at its 5' end that functions as a "hook" that can subsequently be used to recover the oligonucleotide by virtue of the highly specific interaction that biotin undergoes with streptavidin.

The oligomer on the 3' or right-hand side of the pair is the common oligomer (the sequence is the same for the two or more different alleles it is wished to test.) The common oligomer is positioned at an invariable site next to the target DNA's polymorphism and is fluorescently labelled at its 3' end.

If the ASO is perfectly complementary to the target sequence the ASO hybridizes completely when annealed and will lie flat against that target allowing DNA ligase to covalently join the ASO to the common oligomer. After the ligation reaction the biotin hook is used to remove the ASO and the e.g. fluorescently labeled common oligomer will also be removed, producing detectable fluorescence.

When the ASO is not a perfect match to the target sequence hybridization is incomplete and the 3' base of the oligomer will not be base-paired to the target DNA thus preventing ligation. Under these circumstances when the biotin hook is used to remove the ASO, the common oligonucleotide will not be removed and therefore there is no detectable label, e.g. fluorescence, in the molecule removed.

To distinguish between two known alleles that differ by a single base, three oligonucleotides are necessary: Two are allele-specific oligonucleotides (ASOs) that differ from each other only in the single 3' terminal base; the first is complementary to one allele and the second is complementary to the second allele. The third oligonucleotide is complementary to the invariable sequence adjacent to the variant base.

Once hybridisation (and optionally post-hybridisation amplification) has taken place, the intensity of detectable label at each probe position (including control probes) can be determined. The intensity of the signal (the raw intensity value) is a measure of hybridisation at each probe.

The intensity of detectable label at each probe position (each probe replica) may be determined using any suitable means. The means chosen will depend upon the nature of the label. In general an appropriate device, for example, a scanner, collects the image of the hybridized and developed DNA-chip. An image is captured and quantified.

In one instance, e.g. where fluorescent labelling is used, after hybridization, (optionally after post-hybridization amplification or ligation) the hybridized and developed DNA-chip is placed in a scanner in order to quantify the intensity of labelling at the points where hybridization has taken place. Although practically any scanner can be used, in one embodiment a fluorescence confocal scanner is used. In this case, the DNA-chip is placed in the said apparatus and the signal emitted by the fluorpohore due to excitation by a laser is scanned in order to quantify the signal intensity at the points where hybridization has taken place. Non-limiting examples of scanners which can be used according to the present invention, include scanners marketed by the following companies: Axon, Agilent, Perkin Elmer, etc.

Typically, in determining the intensity of detectable label at each probe position (i.e for each probe replica), account is taken of background noise, which is eliminated. Background noise arises because of non-specific binding to the probe array and may be determined by means of controls included in the array. Once the intensity of the background signal has been determined, this can be subtracted from the raw intensity value for each probe replica in order to obtain a clean intensity value. Typically the local background, based on the signal intensity detected in the vicinity of each individual feature is subtracted from the raw signal intensity value. This background is determined from the signal intensity in a predetermined area surrounding each feature (e.g. an area of X, Y or Z μm2 centred on the position of the probe). The background signal is typically determined from the local signal of "blank" controls (solvent only). In many instances the device, e.g. scanner, which is used to determine signal intensities will provide means for determining background signal.

Thus, for example, where the label is a fluorescent label, absolute fluorescence values (raw intensity values) may be gathered for each probe replica and the background noise associated with each probe replica can also be assessed in order to produce "clean" values for signal intensity at each probe position.

Once the target DNA has been hybridised to the chip and the intensity of detectable label has been determined at the probe replica positions on the chip (the raw intensity values), it is necessary to provide a method (model) which can relate the intensity data from the chip to the genotype of the individual.

The inventors have found that this can be done by applying a suitable algorithm to the intensity data. The algorithm and computer software developed by the inventors allows analysis of the genetic variations with sufficient sensitivity and reproducibility as to allow use in a clinical setting. The algorithm uses three linear functions which characterise each of the three genotypes AA, AB and BB for a given genetic variation. The method generally involves collating the intensity values for all of the replicas of each probe, to calculate an average intensity value for each probe. Optionally, the raw intensity values for each replica may be amended to take account of background noise (to obtain a clean intensity value) before the intensity values for each of the replicas are collated.

In general, for a given genetic variation, analysis and interpretation of a chip comprises the following steps:

(a) providing the intensity of detectable label at each replica for each of at least four probes (probes 1, 2, 3 and 4) provided for detection of the genetic variation (the raw intensity value), wherein:
 probe 1 detects (is capable of specifically hybridising to) genetic variation A (e.g. a normal allele), and probe 2 detects (is capable of specifically hybridising to) genetic variation B (e.g. a mutant allele);
 probe 3 detects (is capable of specifically hybridising to) genetic variation A (e.g. a normal allele)and probe 4 detects (is capable of specifically hybridising to) genetic variation B (e.g. a mutant allele); and
 probes 1 and 2 form a first probe pair and probes 3 and 4 form a second probe pair;
(b) optionally amending the raw intensity value for each replica to take account of background noise, thus obtaining a clean intensity value;
(c) collating the (optionally clean) intensity values for each of the replicas of each probe and determining an average intensity value for each probe;
(d) calculating ratios 1 and 2 wherein:

$$\text{Ratio } 1 = \frac{\text{average intensity value for probe 1}}{\text{average intensity value for probe 1} + \text{average intensity value for probe 2}}$$

and $$\text{Ratio } 2 = \frac{\text{average intensity value for probe 3}}{\text{average intensity value for probe 3} + \text{average intensity value for probe 4}}$$

(e) inputting ratios 1 and 2 into each of three linear functions which characterise each of the three possible genotypes, AA, AB and BB, wherein:
Function 1 is the linear function that characterises individuals with the genotype AA and consists of a linear combination of ratios 1 and 2;
Function 2 is the linear function that characterises individuals with the genotype AB and consists of a linear combination of ratios 1 and 2;
Function 3 is the linear function that characterises individuals with the genotype BB and consists of a linear combination of ratios 1 and 2;
the linear functions are formed by coefficients which accompany the variables ratio 1 and 2;
(f) determining which of the three linear functions has the highest value; and
(g) thereby determining the genotype of the individual for the genetic variation.

Thus the linear function corresponding to the genotype of that individual will have the highest absolute value.

The inventors have found that the use of replicas and averages calculated from replicas is important for reliable working of the invention. Use of the functions speeds up analysis and allows better discrimination.

Preferably the discrimination capacity between the three genotypes is (approximately) 100%. If the discrimination is less than 100% the probes are preferably redesigned.

The raw intensity value for each probe replica may be determined according to the methods described above. Thus probe sequences and replicas can be selected as described herein. In one example, 4 probes are used per genetic variation and 6, 8 or 10 replicas are used per probe.

Typically, amending the raw intensity value to obtain the clean intensity value for each probe replica comprises subtracting background noise from the raw value. Background noise is typically determined using appropriate controls as described herein.

Typically calculating the average intensity value comprises eliminating extreme values or outliers. Thus, when the (optionally clean) intensity values from each of the probe replicas are collated, outlying values can be identified and excluded from further consideration. In one embodiment outliers make up between 10% and 50%, for example, 15, 20, 25, 30, 35, 40 or 45% of the values obtained. In one embodiment, 40% of values are eliminated. In one embodiment, 4 probes are used with 6, 8 or 10 replicas per probe and extreme values or outliers make up between 10% and 50% of the values obtained.

A number of suitable linear functions are known in the art. These functions may be used in a linear discriminant analysis for the purposes of the present invention.

In one aspect the invention thus relates to a computational method or model (algorithm) for determining genotype with respect to a given genetic variation using ratios 1 and 2 in the three linear functions as defined above (steps e and f). The method can thus in one embodiment produce an output of genotype (AA, AB or BB) from an input of ratios 1 and 2. The method may also include calculating one or both of ratios 1 and 2 (step d). In some embodiments the method additionally comprises calculating an average intensity value for each probe (step c) and/or calculating a clean intensity value for each probe replica (step b). Thus the input to the model may comprise one or more of the average intensity values, clean replica intensity values or raw replica intensity values. The method may additionally comprise determining the raw intensity value for each probe replica (step a). The method may comprise one or more of the above steps.

In order to carry out the above methods, the coefficients for the linear functions must first be determined in a training process using data from control individuals whose genotype for the genetic variation is already known. Methods for training are known in the art. Typically in such methods, input data (in this case, typically ratios 1 and 2) is used for which the output (in the present case, genotype) is already known. Coefficients are substituted in the three linear equations at random and the output is calculated. Based on that output, one or more coefficients are altered and the input data is entered again to produce another output. The process is continued until coefficients are obtained which optimise the desired output. These optimised coefficients are then used in the linear functions when the method is applied to test data (where the output is as yet unknown).

In order to train the present model, ratios 1 and 2 are obtained for n control individuals having genotype AA (for example, homozygous wild type), n control individuals having genotype AB (heterozygous) and n control individuals having genotype BB (for example, homozygous mutant). The ratios may be obtained using the methods described above. The ratios are inputted as above and the coefficients altered in a discriminatory analysis until three linear functions are obtained which maximise discrimination between the AA, AB and BB groups. These coefficients are then used in the three functions when the model is used on unknown test samples (where the genotype is not predetermined)

Thus in one aspect the invention provides a method of deriving linear functions for use in the present genotyping methods. The method typically comprises carrying out the steps of the genotyping methods as described, for n control individuals having genotype AA (for example, homozygous wild type), n control individuals having genotype AB (heterozygous) and n control individuals having genotype BB (for example, homozygous mutant) with respect to a genetic variation. The intensity values obtained for each of the probe replicas are gathered as described and an algorithm is applied.

As described for the genotyping methods, application of the algorithm comprises calculating an average intensity value for each probe and the algorithm uses three linear functions intended to characterise each of the three possible genotypes, AA, AB and BB for the given genetic variation. Coefficients are inserted in the functions in a repetitive way until functions are derived which maximise discrimination between the genotypes in a discriminatory analysis. This provides the coefficients for use in the linear functions when the method or algorithm is in operational use (i.e. to determine the genotype of test individuals).

The algorithm or method which uses the three linear functions for analysing the intensity data may be as described above.

In some cases, the training method allows feedback optimisation. Thus, as intensity values and ratios are obtained for test individuals and these are genotyped, the intensity data, e.g. the ratios, and genotype are inputted and coefficients recalculated for the linear functions.

In one aspect the invention relates to a computational method for training. The method can be used to derive linear functions for use in the present genotyping methods by using ratios 1 and 2 obtained for each of n individuals having genotype AA, n individuals having genotype AB and n individuals having genotype BB with respect to a genetic variation. The ratios can be obtained by the methods described above. The method typically comprises applying the algorithm which uses the three linear functions (Functions 1, 2 and 3) intended to characterise each of the three possible genotypes AA, AB or BB for the genetic variation such that:

Function 1 is the linear function that characterises individuals with the genotype AA and consists of a linear combination of ratios 1 and 2;

Function 2 is the linear function that characterises individuals with the genotype AB and consists of a linear combination of ratios 1 and 2;

Function 3 is the linear function that characterises individuals with the genotype BB and consists of a linear combination of ratios 1 and 2; and the linear functions are formed by coefficients which accompany the variables ratio 1 and 2;

and deriving linear functions which maximise discrimination between the three genotype groups AA, AB and BB in a discriminatory analysis, so as to obtain the coefficients which can be used in the linear functions when the algorithm is used in a test method (i.e. is in operational use for determining genotype).

The algorithm or method which uses the three linear functions for analysing the intensity data may be as described above.

The computational training method may additionally involve calculating ratios 1 and 2 from average intensity value provided for each of the probes, and/or collating intensity values from probe replicas to determine an average intensity value for each probe and/or amending a raw intensity value for a probe replica to take account of background noise thereby obtaining clean intensity values for the replica.

In some aspects the computational method also allows a feedback optimisation step as described.

Typically in training n is $\geqq 3$, for example, 3, 4, 5, 6, 7, 8, 9 or 10. In one aspect, n is $\geqq 5$. In some cases n may be from 10 to 50 or more, for example, 15 to 40, or 25 to 35, such as 20 or 30.

Probes and probe replicas for the training method are selected as described herein. In one embodiment 4 probes are used for each genetic variation, with 6, 8 or 10 replicas of each probe. Once selected, the probes used in training are also used when the model is in operational use (to determine unknown genotype). If the probes are altered, typically the model must be retrained to optimise discrimination with the new probes.

Preferably the coefficients are such that the discrimination between the three genotype groups (both in training and in operational use) is substantially 100%. If the discrimination is not 100%, the probes are preferably redesigned.

As above, the model may also undergo feedback optimisation when it is in operational use. In that case, the model is first used to determine the genotype of an individual (AA, AB or BB). The ratios 1 and 2 for that individual are then inputted into the model and the coefficients in the linear functions altered as necessary in order to optimise discrimination between the three genotype groups. In this way, the additional data gathered as the model is in use can be used to optimise the discrimination capacity of the linear functions.

There are a number of parameters which can be determined and optimised in order to optimise performance and reliability of the analytical model or method.

(i) In one aspect ratios 1 and 2 determined for an individual fall within the range of ratios 1 and 2 used to train the model (i.e. to optimise the three linear functions). If desired this can thus provide a double test for the genotype of an individual.

(ii) In one aspect the average fluorescence intensity of 4n replicas (where "n" is the number of replicas for each probe, e.g. 6, 8 or 10), for example, 40 replicas, with regard to the background noise is greater than 5.

(iii) In one aspect the variation between intensity values (raw or clean) for replicas of the same probe is a minimum. For example, the coefficient of variation between the intensity values for the replicas of a given probe is preferably less than 0.25

(iv) In one aspect the ratio of the sum of the raw intensity values for all probe replicas on a chip to the intensity of the background noise is greater than 15 when a fluorescence scanner is used.

(v) In one aspect the raw signal intensity value obtained for the negative controls is $\leqq 3$ times greater than the intensity value of the background noise. For example, negative controls may include the DMSO "blank" and the non-hybridising oligonucleotides referred to above. The background noise is the signal derived from the regions of the array where no probe has been spotted and may be determined as above.

Preferably any one or more of (i) to (v) applies when intensity is fluorescence intensity of a fluorescent label, in particular where the intensity is determined by means of a confocal fluorescent scanner.

Ensuring that the model meets one or more of the above helps to provide reliability and reproducibility. Any one or more of (i) to (v) may be true for the model. Preferably the model meets (i) above. In one example, (i), (ii) and (iii) are true. In another example, (iii), (iv), (v) are true. Preferably, all of the above are true for the model. This applies both to training and to operational use.

As above, the experimentally derived ratios obtained for a test sample may be compared to the ratios previously obtained for the (n) control samples obtained from individuals of known genotype, where n is as above, usually >5, or >10, or >20. The reference ratios derived from analysis of the control samples permits a genotype to be assigned to the test sample. This can therefore be a double test.

In one instance the analytical method or algorithm of the invention comprises a sequence of the following steps: using 4 probes (2 pairs of probes) in replicate (6, 8 or 10 replicas), calculating the average intensity of each probe from the collated intensities of the replicas; calculating ratios 1 and 2 as above for the 2 pairs of probes (to detect the genetic variations A and B); substituting ratios 1 and 2 obtained in three linear equations which have been derived in a discriminatory analysis using ratios 1 and 2 calculated for "n" control patients with genotype AA, "n" control patients with genotype AB and "n" control patients with genotype BB (with respect to the genetic variation) (in one experiment "n" is 5); and determining the genotype of a patient for the genetic variation (for each genetic variation included in the DNA-chip) based on which linear function has the greatest absolute value. The test ratios may also be compared to the ratios of the "n" control patients to determine each genotype.

In one aspect a genotyping method of the invention comprises:

- extracting DNA from a biological sample provided by a subject;
- amplifying the regions of the said nucleic acid which contain the genetic variations to be identified and as an option, labelling these products during the reaction of amplification in order to obtain several products of amplification, optionally labelled, which contain the genetic variations to be identified;
- fragmenting the products of amplification to obtain several products of fragmentation which contain the genetic variations and if the said products have not been previously labelled during the amplification stage, labelling the products of fragmentation which contain the genetic variations to be identified;
- hybridising the fragmentation products which contain the genetic variations to be identified with probes capable of identifying the genetic variations under conditions which allow hybridization to take place, wherein said probes are deposited on a support and for every genetic variation to be characterized, 4 probes are used following a determined pattern so that they are uniformly distributed but not grouped by genetic variation to be characterized, wherein of the 4 probes, 2 detect one genetic variation and the other two detect another and wherein the number of replicas of each one of the probes is 10, 8 or 6;
- introducing the solid support into a scanner and quantifying the intensity of the points where hybridisation has occurred and;
- genotyping each one of the genetic variants from the average of the collated intensities of the 10, 8 or 6 replicates of each one of the 4 probes, wherein extreme values are eliminated, by an algorithm developed for such a purpose that permits the detection of each one of the mutations with a sensitivity, specificity and reproducibility that permits this method to be used for clinical applications, based on the fact that it leads to obtaining three linear functions which characterize each one of the possible genotypes.

The analysis and interpretation above has been described with respect to one genetic variation. However, it is to be understood that the present chip generally includes probes for detection of multiple genetic variations which can be analysed at the same time. Thus the present methods include analysis of multiple genetic variations, as described herein, in parallel.

In a further aspect the invention relates to a computer system comprising a processor and means for controlling the processor to carry out a computational method of the invention.

The invention additionally relates to a computer program comprising computer program code which when run on a computer or computer network causes the computer or computer network to carry out a computational method of the invention. The computer program may be stored on a computer readable medium.

In addition to the probes and chips described herein, the inventors have also designed and validated oligonucleotide primers which are capable of amplifying, e.g. by means of multiplex PCR, the target DNA regions which contain human genetic variations associated with IBD, or adverse reactions to drugs. These primers are therefore useful in preparing nucleic acid for use in the present genotyping, diagnostic and therapeutic methods.

Example 3 lists pairs of primers which amplify target DNA regions that contain human genetic variations associated with IBD (SEQ ID NOS 1-124 and 1317-1428) and the corresponding genetic variation. In particular, these primers are useful for amplification of target DNA regions containing the genetic variations in Table 1.

Example 5 lists pairs of primers which amplify target DNA regions that contain human genetic variations associated with adverse reactions to drugs (SEQ ID NOS 125-254) and the corresponding genetic variations. In particular, these primers are useful for amplification of target DNA regions containing the genetic variations in Table 3.

The listed oligonucleotide primers have the advantage of allowing specific amplification of the said target DNA regions in a very low number of PCR reactions. For example, in the case of detection of genetic variations associated with IBD, the listed primers allow, in a minimum number of multiplex PCR reactions, amplification of all the fragments necessary for genotyping of the genetic variations in Table 1, and which may be analyzed on an IBD-chip as in Example 3. In the case of the detection of genetic variations associated with adverse reactions to drugs the listed primers allow, in only 4 multiplex PCR reactions, amplification of 65 fragments necessary for genotyping of the 89 genetic variations in Table 3 which may be analyzed on a drug-chip as in Example 5.

In a further aspect, the present invention relates to each of the PCR primers listed in Examples 3 and 5 (SEQ ID NOS 1-254 and 1317-1428), and in particular to each of the listed pairs of PCR primers and their use in PCR amplification, e.g. in a multiplex PCR reaction, of a target DNA region containing the corresponding genetic variation. The invention in one aspect provides any one of these primers or pairs of primers for use in medicine, in particular for use in the present genotyping, diagnostic or therapeutic methods.

The invention further relates to a PCR amplification kit comprising at least one pair of listed PCR primers. The kit may additionally include, for example, a (thermostable) polymerase, dNTPs, a suitable buffer, additional primers, and/or instructions for use, e.g. to amplify a target DNA region containing the corresponding genetic variation. The kit may be used for amplification of target DNA regions from nucleic acid samples, for use in the present methods.

In another aspect the present invention relates to a genotyping or diagnostic (preferably in vitro) kit comprising a DNA-chip or array according to the invention. The kit may additionally comprise instructions for use of the chip in a genotyping method of the invention, for example instructions for use in the present analytical method or algorithm. Further components of a kit may include:

computer software, a computer program or a computer system according to the invention;

one or more PCR primers or pairs of PCR primers according to the invention; and/or a PCR amplification kit according to the invention.

The probes for the chip or PCR primers may be selected as above depending on the genetic variations to be detected or the diagnostic purpose of the kit.

The kit may contain one or more positive and/or negative controls of the hybridisation reaction.

The kit may be used to detect and analyse genetic variations associated with diseases or antigens of interest. Suitable probes may be designed accordingly.

In one aspect the kit is for detection or genotyping of genetic variations associated with known erythrocyte antigens, such as those described herein. The kit may therefore be useful in determining blood group type of an individual.

In another aspect the kit is for detection or genotyping of genetic variations associated with IBD, such as those described herein. The kit may therefore be useful in diagnosing IBD or susceptibility to IBD as described herein.

In a further aspect the genotyping kit is for detection or genotyping of genetic variations associated with adverse reactions to pharmaceuticals, such as those described herein. The kit may therefore be useful in diagnosing or predicting susceptibility to adverse reactions as described herein.

The invention further relates to the use of the kit in a genotyping, diagnostic or therapeutic method of the invention.

As described herein, the present methods are useful for diagnosing IBD in a patient or susceptibility to IBD in a patient. The present methods may be used to genotype an individual with respect to one or more genetic variations associated with IBD (e.g. those in Table 1). The results may be used to diagnose IBD or for prognosis and may be useful in determining the appropriate treatment for IBD (e.g. by predicting response to therapy).

IBD presents a number of phenotypes. For example, phenotypes observed in sufferers from Crohns disease include the development of fistulae, perianal disease and clinically relevant extraintestinal manifestations, in addition some sufferers require surgical intervention (intestinal resection). Examples of disease phenotypes observed in sufferers from ulcerative colitis include pancolitis and clinically relevant extraintestinal manifestations, in addition surgical intervention may be required (colectomy).

Genetic data obtained from a Spanish trial of IBDchip (579 patients) has demonstrated a clear ability to predict the probability (high, moderate, low or minimal) of developing the abovementioned disease phenotypes in individuals suffering from Crohns disease and ulcerative colitis respectively based on their specific genetic profiles (FIGS. 3-10—Example 6).

Because of the aggressive nature of IBD, successful treatment often depends on individualising treatment regimens to fit each person's needs. Treatment typically includes controlling the active inflammation of the disease and maintaining remission through medication. The IBDchip is a genotyping tool that allows clinicians to evaluate the likely course of disease progression based on the individual genetic profiles of their patients as well as providing an indication of the most appropriate therapeutic interventions. A genotype predictive of a rapidly progressing and/or aggressive development of the disease will indicate the need for earlier and more closely monitored treatment regimes as well as indicating the probable need for surgical intervention. Conversely a genotype predictive of less severe disease progression may prevent the use of unnecessary treatment and/or surgery.

Figure 11:
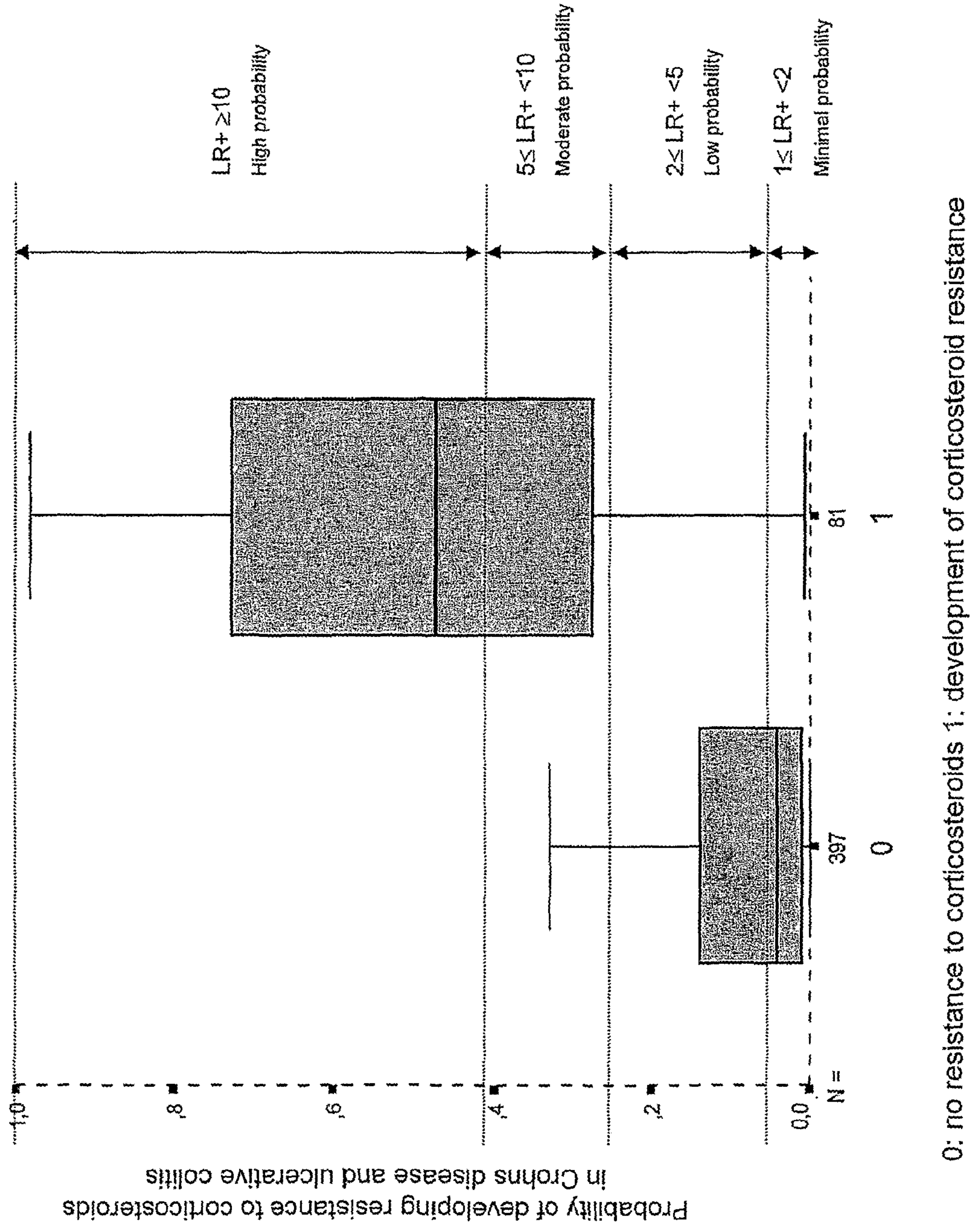
FIGS. 11-13 (Example 6) indicate the probabilities associated with the risk of developing resistance to corticosteroid treatment in individuals suffering from IBD.
Figure 12:
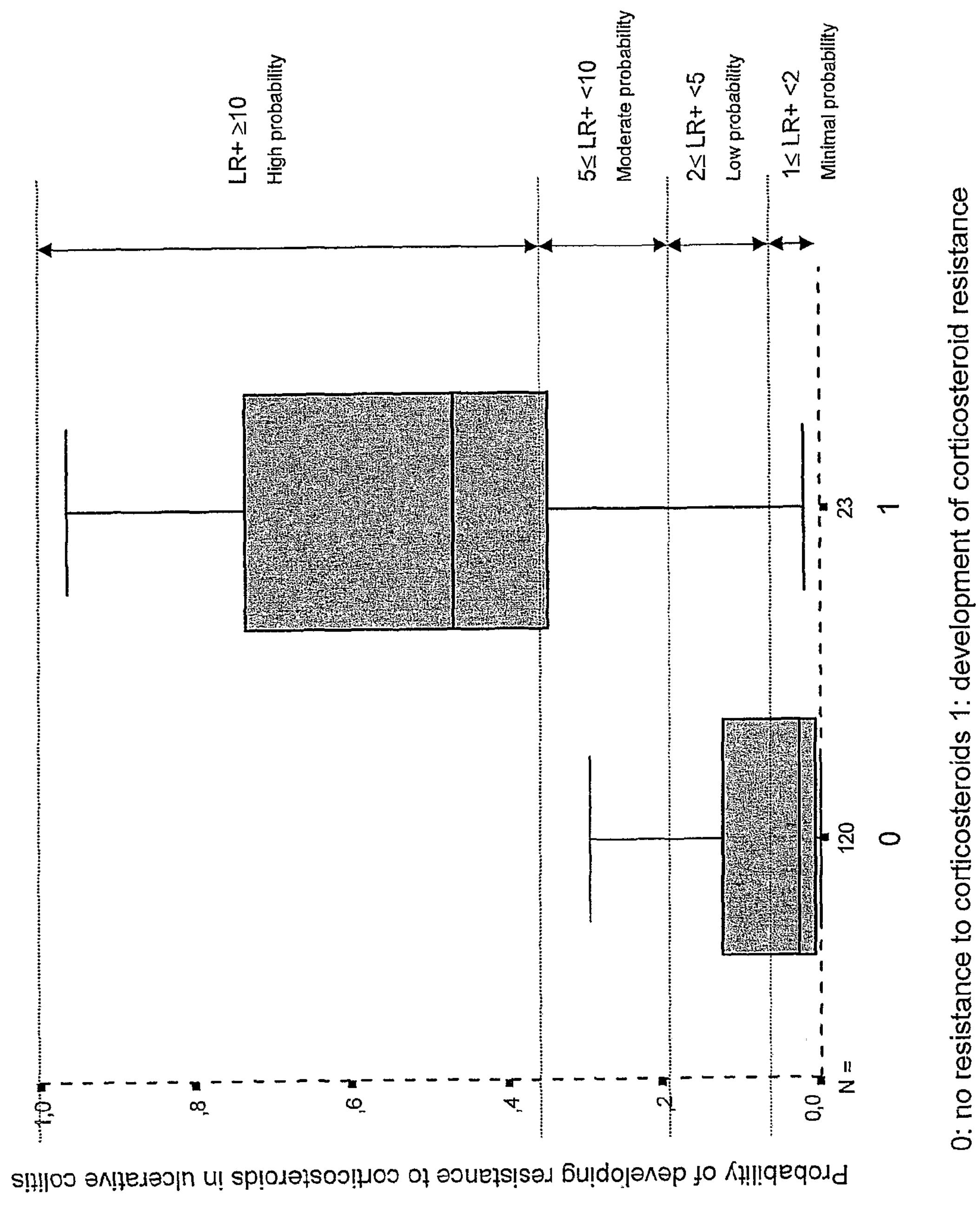
Figure 13:
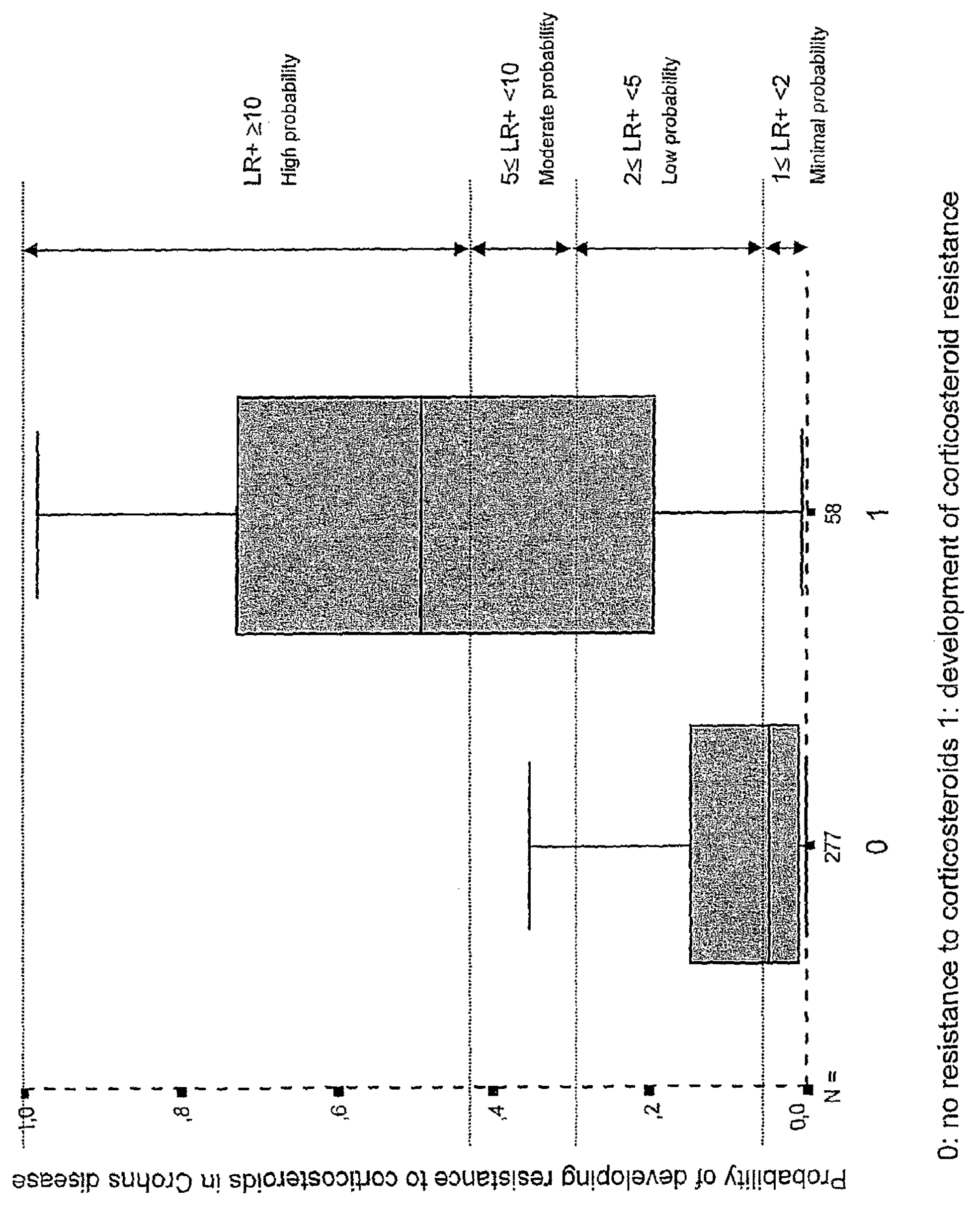

A wide range of drugs are been used to treat IBD sufferers including: aminosalysilates (e.g. sulfasalazine, olsalazine); antimetabolites (e.g. mercaptopurine, methotrexate); anti-rheumatics (e.g. azathioprine, 6-mercaptopurine) antibiotics (ciprofloxacin), biologics (e.g. infliximab); as well as a wide range of corticosteroid drugs. However, as discussed above the response of individual patient to these treatments can vary enormously and there is a clear clinical need for better methods of selecting the best therapeutic approach for IBD sufferers. Use of genetic data obtained from the use of IBDchip allowed the identification of individuals with varying probabilities (high, moderate, low and minimal) of developing resistance to corticosteroid treatment (FIGS. 11-13—Example 6). The genotyping methodology described herein can be used to determine similar patterns relating to the genetic influence on drug response in similar clinical trials.

The present arrays and methods thus provide a means for clinicians to predict the likely course of disease progression in individual patients and also aid in the selection of the most suitable treatment regime including the likelihood of the need for surgical intervention. They are therefore useful prognostic tools. Genotype information obtained according to the present invention may aid in clinical decision making or diagnosis in cases where symptoms (disease phenotype) are ambiguous. Genetic information provided by IBDchip or other methods could also help in determining the likelihood of disease development in asymptomatic individuals (e.g. immediate family members of IBD sufferers) allowing for example guidance on lifestyle and diet to be provided and indicating the need for continued monitoring of individuals who have a genetic constitution that indicates possible susceptibility to disease development.

In one aspect the invention therefore relates to a method of diagnosing IBD or susceptibility to IBD in an individual, or determining the likely course of disease progression in an individual as above. Preferably the method is in vitro. The invention further relates to a method of selecting a treatment, e.g. determining the need for surgical intervention for an individual having IBD, in some cases where the individual has been diagnosed or tested according to the methods of the invention. Still further the invention in some aspects relates to methods of treating an individual suffering from IBD, wherein, after the treatment is selected, the treatment is administered to the individual.

Particular genetic variations associated with IBD may be predictive of particular phenotypes or development of particular phenotypes and hence disease progession. In other words, it may be that there is a statistically significant association between e.g. the mutant allele B, of a given genetic variation and the occurrence/development of a particular phenotype.

Since the present genotyping methods allow reliable genotyping of multiple genetic variations in a clinical setting, these can be used to genotype individuals of known IBD phenotype, and to thus identify genetic variations predictive of particular IBD phenotypes.

In one aspect the invention therefore relates to a method of identifying genetic variations predictive of a particular IBD phenotype, such as the phenotypes listed above. The method involves genotyping a plurality of individuals with respect to one or more genetic variations using a method of the invention, in which the genetic variations are associated with IBD. Typically 300-1000 individuals are genotyped, for example 400, 500 or 600 individuals may be genotyped. The IBD phenotype of each individual is already known. IBD phenotype may be determined by any appropriate method, e.g. the Vienna Classification (Gasche C, Scholmerich J, Brynskov J, et al. A simple classification of Crohn's disease: report of the Working Party for the World Congresses of Gastroenterology, Vienna 1998. Inflamm Bowel Dis 2000; 6: 8-15) or the Montreal Classification (Silverberg M S, Satsangi J, Ahmad T, Arnott I D, Bernstein C N, Brant S R, Caprilli R, Colombel J F, Gasche C, Geboes K, Jewell D P, Karban A, Loftus Jr E V, Pena A S, Riddell R H, Sachar D B, Schreiber S, Steinhart A H, Targan S R, Vermeire S, Warren B F. Toward an integrated clinical, molecular and serological classification of inflammatory bowel disease: Report of a Working Party of the 2005 Montreal World Congress of Gastroenterology. *Can J Gastroenterol.* 2005 September;19 Suppl A:5-36)

Once the genotypes are obtained, this data is compared with the phenotype data and statistically significant associations between particular genotypes and particular phenotypes are identified. Methods for determining statistical significance are known in the art.

The genetic variations identified as predictive of particular phenotypes/disease course can then be used to diagnose these phenotypes/disease courses in test individuals, by genotyping the individuals with respect to the predictive genetic variation (s). Thus it is possible to determine the likely course of disease progression in the individual. Genotyping can be done by any appropriate method, depending on the number of variations to be tested. For example, a genotyping method of the invention may be used. Alternatively, sequence based or other chip-based methods may be appropriate.

Thus in one aspect the invention further relates to a method of diagnosing IBD phenotype or predicting the likely course of disease progression in an individual by determining the genotype of the individual with respect to one or more genetic variations which have been identified as predictive (of the particular IBD phenotype or disease course) by the methods described herein.

Once the prediction has been made, it will then be possible to select the most suitable therapeutic approach, e.g. to determine the need for surgical intervention.

The invention is also useful in determining the blood group of an individual by determining genotype with respect to one or more particular erythrocyte associated antigens (e.g. those in Table 2) Therefore in a further aspect the invention relates to a method (in one aspect in vitro) of determining blood group or type in an individual. Such methods may be useful in for example, blood transfusions, organ transplantation, medical-legal applications ot treatment of haemolytic disease of the fetus and new born.

The invention is further useful in determining the likelihood of an adverse reaction to pharmaceuticals in an individual. Therefore in a further aspect the invention relates to a method (in one aspect in vitro) of diagnosing or predicting susceptibility to adverse reaction to pharmaceuticals in an individual. The method comprises determining the genotype of an individual with respect to one or more genetic variations associated with adverse reaction to pharmaceuticals (e.g. those in Table 3) by the present genotyping methods. The genotyping results may be used to select a treatment for the individual which can then be administered. Thus in some aspects the invention further relates to methods of selecting a pharmaceutical treatment for an individual, and methods of treating an individual with the selected pharmaceutical.

The diagnostic, predictive and therapeutic methods comprise carrying out a genotyping method of the invention as described herein. Any of the methods may involve carrying out a training method of the invention as described herein in order to derive linear functions for use in determining genotype. Further the methods may comprise the use of a chip, computer system, computer program, oligonucleotide probes or pair or set of probes, oligonucleotide primer or pair of primers, PCR amplification kit or diagnostic kit of the invention as described herein.

EXAMPLES

Although in general, the techniques mentioned herein are well known in the art, reference may be made in particular to Sambrook et al, 1989, Molecular Cloning: a laboratory manual.

Example 1

Detection of Human Genetic Variations Associated with Human Erythrocyte Antigens, Using a DNA-Chip for the Identification of Human Blood Groups 1.1 Design of the DNA-Chip for Genotyping Blood Groups A DNA-chip was designed and produced to detect human genetic variations associated with several erythrocyte antigens, which permits the simultaneous, sensitive, specific and reproducible detection of the genetic variations. Illustrative examples of the variations which can be determined using the DNA-chip are listed in Table 2.

In this case, the DNA-chip designed and produced consists of a support (a glass slide), which comprises a plurality of probes on its surface, which permit the detection of the genetic variations. These probes are capable of hybridizing with (amplified) target gene sequences that encode the erythrocyte antigens to be studied. The DNA sequences of the probes used are listed below. In general, the name of the gene, the mutation (nucleotide change, “ins”: insertion “del”: deletion), the genotype and the exon are indicated.

```
ABO G261delG GENOTYPE: ABO O1/O1v [probes to detect the
polymorphism G261delG (Genotype ABO O1/O1v) in exon 6 of
the ABO gene]
EXON 6
BC001OV01   CAGCCAAGGGGTCACCACGAGGACA       25  SEQ ID NO:255
BC001OV02   CCAGCCAAGGGGTACCACGAGGACA       25  SEQ ID NO:256
BC001OV03   CCAGCCAAGGGGTCACCACGAGGACAT     27  SEQ ID NO:257
BC001OV04   GCCAGCCAAGGGGTACCACGAGGACAT     27  SEQ ID NO:258

ABO G703A GENOTYPE: ABO B
EXON 7
BC002OV01   ACCCTGCACCCCGGCTTCTACGGAA       25  SEQ ID NO:259
BC002OV02   ACCCTGCACCCCAGCTTCTACGGAA       25  SEQ ID NO:260
BC002OV03   CACCCTGCACCCCGGCTTCTACGGAAG     27  SEQ ID NO:261
BC002OV04   CACCCTGCACCCCAGCTTCTACGGAAG     27  SEQ ID NO:262

ABO C796A GENOTYPE: ABO B
EXON7
BC003OV01   AGAACCCCCCCAGGTAGTAGAAATC       25  SEQ ID NO:263
BC003OV02   AGAACCCCCCCATGTAGTAGAAATC       25  SEQ ID NO:264
BC003OV03   AAGAACCCCCCCAGGTAGTAGAAATCG     27  SEQ ID NO:265
BC003OV04   AAGAACCCCCCCATGTAGTAGAAATCG     27  SEQ ID NO:266

ABO G802A GENOTYPE: ABO O2
EXON7
BC004OV01   CCCCGAAGAACCCCCCCAGGTAGTA       25  SEQ ID NO:267
BC004OV02   CCCCGAAGAACCTCCCCAGGTAGTA       25  SEQ ID NO:268
BC004OV03   CCCGAAGAACCCCCCCAGGTAGT         23  SEQ ID NO:269
BC004OV04   CCCGAAGAACCTCCCCAGGTAGT         23  SEQ ID NO:270

ABO G803C GENOTYPE: ABO B2, cisAB-1
EXON7
BC005OV01   CCCCCGAAGAACCCCCCCAGGTAGT       25  SEQ ID NO:271
BC005OV02   CCCCCGAAGAACGCCCCCAGGTAGT       25  SEQ ID NO:272
BC005OV03   ACCCCCGAAGAACCCCCCCAGGTAGTA     27  SEQ ID NO:273
BC005OV04   ACCCCCGAAGAACGCCCCCAGGTAGTA     27  SEQ ID NO:274

ABO CCC1059-1061 GENOTYPE: ABO A2
EXON7
BC006OV01   CGGTCCGGAACCCGTGAGCGGCTGC       25  SEQ ID NO:275
BC006OV02   CGGTCCGGAACCGTGAGCGGCTGCC       25  SEQ ID NO:276
BC006OV03   GCGGTCCGGAACCCGTGAGCGGCTGCC     27  SEQ ID NO:277
BC006OV04   GCGGTCCGGAACCGTGAGCGGCTGCCA     27  SEQ ID NO:273

ABO GGGGGGG G798_804insG GENOTYPE: ABO O3, Ael
EXON7
BC007OV01   CCCCGAAGAACCCCCCCAG             19  SEQ ID NO:279
BC007OV02   CCCGAAGAACCCCCCCCAG             19  SEQ ID NO:280
BC007OV03   CCCCCGAAGAACCCCCCCAGG           21  SEQ ID NO:231
BC007OV04   CCCCGAAGAACCCCCCCCAGG           21  SEQ ID NO:232

ABO GG87_88insG GENOTYPE: ABO O4
EXON2
BC008OV01   TGCTTGTCTTGGTCTTGTTTGGGTA       25  SEQ ID NO:283
BC008OV02   TGCTTGTCTTGGGTCTTGTTTGGGT       25  SEQ ID NO:284
BC008OV03   GCTTGTCTTGGTCTTGTTTGGGT         23  SEQ ID NO:285
BC008OV04   GCTTGTCTTGGGTCTTGTTTGGG         23  SEQ ID NO:286

ABO C322T GENOTYPE: ABO O5
EXON6
```

-continued

BC009OV01 GGAGCCTGAACTGCTCGTTGAGGAT 25 SEQ ID NO:287
BC009OV02 GGAGCCTGAACTACTCGTTGAGGAT 25 SEQ ID NO:288
BC009OV03 TGGAGCCTGAACTGCTCGTTGAGGATG 27 SEQ ID NO:289
BC009OV04 TGGAGCCTGAACTACTCGTTGAGGATG 27 SEQ ID NO:290

ABO C893T GENOTYPE: ABO O6
EXON7
BC010OV01 TCGTGCCACACGGCCTCGATGCCGT 25 SEQ ID NO:291
BC010OV02 TCGTGCCACACGACCTCGATGCCGT 25 SEQ ID NO:292
BC010OV03 CGTGCCACACGGCCTCGATGCCG 23 SEQ ID NO:293
BC010OV04 CGTGCCACACGACCTCGATGCCG 23 SEQ ID NO:294

ABO C927A GENOTYPE: ABO O7
EXON7
BC011OV01 CCTGAACAAGTACCTGCTGCGCCAC 25 SEQ ID NO:295
BC011OV02 CCTGAACAAGTAACTGCTGCGCCAC 25 SEQ ID NO:296
BC011OV03 ACCTGAACAAGTACCTGCTGCGCCACA 27 SEQ ID NO:297
BC011OV04 ACCTGAACAAGTAACTGCTGCGCCACA 27 SEQ ID NO:298

ABO G188A/C189T GENOTYPE: ABO O1v
EXON4
BC012OV01 ACCATCTGCAGCGCGTCTCGTTGCC 25 SEQ ID NO:299
BC012OV02 ACCATCTGCAGCATGTCTCGTTGCC 25 SEQ ID NO:300
BC012OV03 CCATCTGCAGCGCGTCTCGTTGC 23 SEQ ID NO:301
BC012OV04 CCATCTGCAGCATGTCTCGTTGC 23 SEQ ID NO:302

ABO G542A GENOTYPE: ABO O8
EXON7
BC013OV01 GACACGTCCTGCCAGCGCTTGTAGG 25 SEQ ID NO:303
BC013OV02 GACACGTCCTGCTAGCGCTTGTAGG 25 SEQ ID NO:304
BC013OV03 ACACGTCCTGCCAGCGCTTGTAG 23 SEQ ID NO:305
BC013OV04 ACACGTCCTGCTAGCGCTTGTAG 23 SEQ ID NO:306

ABO C467T GENOTYPE: ABO A2
EXON7
BC014OV01 GGCACCGCGGCCGGCTGGTCGGTGA 25 SEQ ID NO:307
BC014OV02 GGCACCGCGGCCAGCTGGTCGGTGA 25 SEQ ID NO:308
BC014OV03 GGGCACCGCGGCCGGCTGGTCGGTGAA 27 SEQ ID NO:309
BC014OV04 GGGCACCGCGGCCAGCTGGTCGGTGAA 27 SEQ ID NO:310

ABO T646A GENOTYPE: ABO Ax/O1v
EXON7
BC015OV01 GTGGACATGGAGTTCCGCGACCACG 25 SEQ ID NO:311
BC015OV02 GTGGACATGGAGATCCGCGACCACG 25 SEQ ID NO:312
BC015OV03 CGTGGACATGGAGTTCCGCGACCACGT 27 SEQ ID NO:313
BC015OV04 CGTGGACATGGAGATCCGCGACCACGT 27 SEQ ID NO:314

RHD A178C GENOTYPE: RHD DIIIb
EXON2
BC016OV01 GTGATGGCGGCCATTGGCTTGGGCT 25 SEQ ID NO:315
BC016OV02 GTGATGGCGGCCCTTGGCTTGGGCT 25 SEQ ID NO:316
BC016OV03 TGATGGCGGCCATTGGCTTGGGC 23 SEQ ID NO:317
BC016OV04 TGATGGCGGCCCTTGGCTTGGGC 23 SEQ ID NO:318

RHD G203A GENOTYPE: RHD DIIIb
EXON2
BC017OV01 TCCTCACCTCGAGTTTCCGGAGACA 25 SEQ ID NO:319
BC017OV02 TCCTCACCTCGAATTTCCGGAGACA 25 SEQ ID NO:320
BC017OV03 TTCCTCACCTCGAGTTTCCGGAGACAC 27 SEQ ID NO:321
BC017OV04 TTCCTCACCTCGAATTTCCGGAGACAC 27 SEQ ID NO:322

RHD T307C GENOTYPE: RHD DIIIb
EXON 2
BC018OV01 AGCCAGTTCCCTTCTGGGAAGGTGG 25 SEQ ID NO:323
BC018OV02 AGCCAGTTCCCTCCTGGGAAGGTGG 25 SEQ ID NO:324
BC018OV03 GAGCCAGTTCCCTTCTGGGAAGGTGGT 27 SEQ ID NO:325
BC018OV04 GAGCCAGTTCCCTCCTGGGAAGGTGGT 27 SEQ ID NO:326

RHD T544A GENOTYPE: RHD EXON SCANNING
EXON4
BC019OV01 TATTTTGGGCTGTCTGTGGCCTGGT 25 SEQ ID NO:327
BC019OV02 TATTTTGGGCTGACTGTGGCCTGGT 25 SEQ ID NO:328
BC019OV03 TTTTGGGCTGTCTGTGGCCTG 21 SEQ ID NO:329
BC019OV04 TTTTGGGCTGACTGTGGCCTG 21 SEQ ID NO:330

RHD G577A GENOTYPE: RHD EXON SCANNING
EXON4
BC020OV01 AGCCTCTACCCGAGGGAACGGAG 23 SEQ ID NO:331
BC020OV02 AGCCTCTACCCAAGGGAACGGAG 23 SEQ ID NO:332
BC020OV03 GCCTCTACCCGAGGGAACGGA 21 SEQ ID NO:333
BC020OV04 GCCTCTACCCAAGGGAACGGA 21 SEQ ID NO:334

-continued

RHD A594T GENOTYPE: RHD EXON SCANNING
EXON4

| | | | |
|---|---|---|---|
| BC021OV01 | ACGGAGGATAAAGATCAGACAGC | 23 | SEQ ID NO:335 |
| BC021OV02 | ACGGAGGATAATGATCAGACAGC | 23 | SEQ ID NO:336 |
| BC021OV03 | CGGAGGATAAAGATCAGACAG | 21 | SEQ ID NO:337 |
| BC021OV04 | CGGAGGATAATGATCAGACAG | 21 | SEQ ID NO:338 |

RHD G697C GENOTYPE: RHD Dva (kou, to, yh, sm)
EXON5

| | | | |
|---|---|---|---|
| BC022OV01 | AGAAGTCCAATCGAAAGGAAGAATG | 25 | SEQ ID NO:339 |
| BC022OV02 | AGAAGTCCAATCCAAAGGAAGAATG | 25 | SEQ ID NO:340 |
| BC022OV03 | GAAGTCCAATCGAAAGGAAGAAT | 23 | SEQ ID NO:341 |
| BC022OV04 | GAAGTCCAATCCAAAGGAAGAAT | 23 | SEQ ID NO:342 |

RHD G712A GENOTYPE: RHD Dva (to, yh)
EXON5

| | | | |
|---|---|---|---|
| BC023OV01 | GGAAGAATGCCGTGTTCAACACC | 23 | SEQ ID NO:343 |
| BC023OV02 | GGAAGAATGCCATGTTCAACACC | 23 | SEQ ID NO:344 |
| BC023OV03 | GAAGAATGCCGTGTTCAACAC | 21 | SEQ ID NO:345 |
| BC023OV04 | GAAGAATGCCATGTTCAACAC | 21 | SEQ ID NO:346 |

RHD T1025C GENOTYPE: RHD DAR (weakDtype4.2)
EXON7

| | | | |
|---|---|---|---|
| BC024OV01 | TGGAGAGATCATCTACATTGTGC | 23 | SEQ ID NO:347 |
| BC024OV02 | TGGAGAGATCACCTACATTGTGC | 23 | SEQ ID NO:348 |
| BC024OV03 | GGAGAGATCATCTACATTGTG | 21 | SEQ ID NO:349 |
| BC024OV04 | GGAGAGATCACCTACATTGTG | 21 | SEQ ID NO:350 |

RHD G676C GENOTYPE: RHD DCS, Dva (kou, yh)
EXON5

| | | | |
|---|---|---|---|
| BC025OV01 | AGTTTCAACTCTGCTCTGCTGAGAA | 25 | SEQ ID NO:351 |
| BC025OV02 | AGTTTCAACTCTCCTCTGCTGAGAA | 25 | SEQ ID NO:352 |
| BC025OV03 | AATTTTCAACTCTGCTCTGCTGAGAAG | 27 | SEQ ID NO:353 |
| BC025OV04 | AAGTTTCAACTCTCCTCTGCTGAGAAG | 27 | SEQ ID NO:354 |

RHD G1063A GENOTYPE: RHD DNB
EXON7

| | | | |
|---|---|---|---|
| BC026OV01 | ACCGTCGGAGCCGGCAATGGCATGT | 25 | SEQ ID NO:355 |
| BC026OV02 | ACCGTCGGAGCCAGCAATGGCATGT | 25 | SEQ ID NO:356 |
| BC026OV03 | TACCGTCGGAGCCGGCAATGGCATGTG | 27 | SEQ ID NO:357 |
| BC026OV04 | TACCGTCGGAGCCAGCAATGGCATGTG | 27 | SEQ ID NO:358 |

RHD T509C GENOTYPE: RHD DFRI, DOL
EXON4

| | | | |
|---|---|---|---|
| BC027OV01 | ACATGAACATGATGCACATCTACGT | 25 | SEQ ID NO:359 |
| BC027OV02 | ACATGAACATGACGCACATCTACGT | 25 | SEQ ID NO:360 |
| BC027OV03 | CACATGAACATGATGCACATCTACGTG | 27 | SEQ ID NO:361 |
| BC027OV04 | CACATGAACATGACGCACATCTACGTG | 27 | SEQ ID NO:362 |

RHD T329C GENOTYPE: RHD DVII
EXON2

| | | | |
|---|---|---|---|
| BC028OV01 | TGGTCATCACACTGTTCAGGTATTG | 25 | SEQ ID NO:363 |
| BC028OV02 | TGGTCATCACACCGTTCAGGTATTG | 25 | SEQ ID NO:364 |
| BC028OV03 | GGTCATCACACTGTTCAGGTATT | 23 | SEQ ID NO:365 |
| BC028OV04 | GGTCATCACACCGTTCAGGTATT | 23 | SEQ ID NO:366 |

RHD C848T GENOTYPE: RHD DHMi
EXON6

| | | | |
|---|---|---|---|
| BC029OV01 | GCTGTGGGTACCTCGTGTCAC | 21 | SEQ ID NO:367 |
| BC029OV02 | GCTGTGGGTATCTCGTGTCAC | 21 | SEQ ID NO:368 |
| BC029OV03 | GGCTGTGGGTACCTCGTGTCACC | 23 | SEQ ID NO:369 |
| BC029OV04 | GGCTGTGGGTATCTCGTGTCACC | 23 | SEQ ID NO:370 |

RHD A497C GENOTYPE: RHD DFW
EXON4

| | | | |
|---|---|---|---|
| BC030OV01 | AGACAGACTACCACATGAACATGAT | 25 | SEQ ID NO:371 |
| BC030OV02 | AGACAGACTACCCCATGAACATGAT | 25 | SEQ ID NO:372 |
| BC030OV03 | GACAGACTACCACATGAACATGA | 23 | SEQ ID NO:373 |
| BC030OV04 | GACAGACTACCCCATGAACATGA | 23 | SEQ ID NO:374 |

RHD G686A GENOTYPE: RHD DHR
EXON5

| | | | |
|---|---|---|---|
| BC031OV01 | CTGCTCTGCTGAGAAGTCCAATCGA | 25 | SEQ ID NO:375 |
| BC031OV02 | CTGCTCTGCTGAAAAGTCCAATCGA | 25 | SEQ ID NO:376 |
| BC031OV03 | TGCTCTGCTGAGAAGTCCAATCG | 23 | SEQ ID NO:377 |
| BC031OV04 | TGCTCTGCTGAAAAGTCCAATCG | 23 | SEQ ID NO:378 |

RHD G854A GENOTYPE: RHD DIM
EXON6

| | | | |
|---|---|---|---|
| BC032OV01 | TGGGTACCTCGTGTCACCTGATCCC | 25 | SEQ ID NO:379 |

-continued

```
BC032OV02   TGGGTACCTCGTATCACCTGATCCC       25  SEQ ID NO:380
BC032OV03   GGGTACCTCGTGTCACCTGATCC         23  SEQ ID NO:331
BC032OV04   GGGTACCTCGTATCACCTGATCC         23  SEQ ID NO:382

RHD T161C GENOTYPE: RHD DMH
EXON2
BC033OV01   TTGGCCAAGATCTGACCGTGATGGC       25  SEQ ID NO:383
BC033OV02   TTGGCCAAGATCCGACCGTGATGGC       25  SEQ ID NO:384
BC033OV03   GTTGGCCAAGATCTGACCGTGATGGCG     27  SEQ ID NO:385
BC033OV04   GTTGGCCAAGATCCGACCGTGATGGCG     27  SEQ ID NO:386

RHD G1057A GENOTYPE: RHD DNU
EXON7
BC034OV01   CTTGATACCGTCGGAGCCGGCAATG       25  SEQ ID NO:387
BC034OV02   CTTGATACCGTCAGAGCCGGCAATG       25  SEQ ID NO:388
BC034OV03   GCTTGATACCGTCGGAGCCGGCAATGG     27  SEQ ID NO:389
BC034OV04   GCTTGATACCGTCAGAGCCGGCAATGG     27  SEQ ID NO:390

RHD T1073C GENOTYPE: RHD DWI
EXON7
BC035OV01   CCGGCAATGGCATGTGGGTCACTGG       25  SEQ ID NO:391
BC035OV02   CCGGCAATGGCACGTGGGTCACTGG       25  SEQ ID NO:392
BC035OV03   CGGCAATGGCATGTGGGTCACTG         23  SEQ ID NO:393
BC035OV04   CGGCAATGGCACGTGGGTCACTG         23  SEQ ID NO:394

RHD C1061A GENOTYPE: RHD DII, DIV IV
EXON7
BC036OV01   ATACCGTCGGAGCCGGCAATGGCAT       25  SEQ ID NO:395
BC036OV02   ATACCGTCGGAGACGGCAATGGCAT       25  SEQ ID NO:396
BC036OV03   GCCGGCAATGGCATGTGGGTCACTGGG     27  SEQ ID NO:397
BC036OV04   GCCGGCAATGGCACGTGGGTCACTGGG     27  SEQ ID NO:398

RHD G845A GENOTYPE: RHD weak D type 15
EXON6
BC037OV01   GCGTGGCTGTGGGTACCTCGTGTCA       25  SEQ ID NO:399
BC037OV02   GCGTGGCTGTGGATACCTCGTGTCA       25  SEQ ID NO:400
BC037OV03   GATACCGTCGGAGCCGGCAATGGCATG     27  SEQ ID NO:401
BC037OV04   GATACCGTCGGAGACGGCAATGGCATG     27  SEQ ID NO:402

RHD T809G GENOTYPE: RHD weak D type 1, psi
EXON6
BC038OV01   TGCAGACTTATGTGCACAGTGCGGT       25  SEQ ID NO:403
BC038OV02   TGCAGACTTATGGGCACAGTGCGGT       25  SEQ ID NO:404
BC038OV03   GCAGACTTATGTGCACAGTGCGG         23  SEQ ID NO:405
BC038OV04   GCAGACTTATGGGCACAGTGCGG         23  SEQ ID NO:406

RHD G1154C GENOTYPE: RHD weak D type 2
EX0N9
BC039OV01   GCATTTAAACAGGTTTGCTCCTAAA       25  SEQ ID NO:407
BC039OV02   GCATTTAAACAGCTTTGCTCCTAAA       25  SEQ ID NO:408
BC039OV03   TGCATTTAAACAGGTTTGCTCCTAAAT     27  SEQ ID NO:409
BC039OV04   TGCATTTAAACAGCTTTGCTCCTAAAT     27  SEQ ID NO:410

RHD C8G GENOTYPE: RHD weak D type 3
EXON1
BC040OV01   ACAGGATGAGCTCTAAGTACCCGCG       25  SEQ ID NO:411
BC040OV02   ACAGGATGAGCTGTAAGTACCCGCG       25  SEQ ID NO:412
BC040OV03   CACAGGATGAGCTCTAAGTACCCGCGG     27  SEQ ID NO:413
BC040OV04   CACAGGATGAGCTGTAAGTACCCGCGG     27  SEQ ID NO:414

RHD C446A GENOTYPE: RHD weak D type 5
EXON3
BC041OV01   TGGAGGTGACAGCTTTAGGCAACCT       25  SEQ ID NO:415
BC041OV02   TGGAGGTGACAGATTTAGGCAACCT       25  SEQ ID NO:416
BC041OV03   GGAGGTGACAGCTTTAGGCAACC         23  SEQ ID NO:417
BC041OV04   GGAGGTGACAGATTTAGGCAACC         23  SEQ ID NO:418

RHD G1016A GENOTYPE: RHD weak D type 7
EXON7
BC042OV01   TGGGTCTGCTTGGAGAGATCATCTA       25  SEQ ID NO:419
BC042OV02   TGGGTCTGCTTGAAGAGATCATCTA       25  SEQ ID NO:420
BC042OV03   GGGTCTGCTTGGAGAGATCATCT         23  SEQ ID NO:421
BC042OV04   GGGTCTGCTTGAAGAGATCATCT         23  SEQ ID NO:422

RHD C340T GENOTYPE: RHD weak D type 17
EXON3
BC043OV01   TCCCCCAGTATTCGGCTGGCCACCA       25  SEQ ID NO:423
BC043OV02   TCCCCCAGTATTTGGCTGGCCACCA       25  SEQ ID NO:424
BC043OV03   CTCCCCCAGTATTCGGCTGGCCACCAT     27  SEQ ID NO:425
BC043OV04   CTCCCCCAGTATTTGGCTGGCCACCAT     27  SEQ ID NO:426
```

-continued

RHD T807G GENOTYPE: RHD PSI
EXON6

| | | | |
|---|---|---|---|
| BC044OV01 | TTTGCAGACTTATGTGCACAGTGCG | 25 | SEQ ID NO:427 |
| BC044OV02 | TTTGCAGACTTAGGTGCACAGTGCG | 25 | SEQ ID NO:428 |
| BC044OV03 | TTGCAGACTTATGTGCACAGTGC | 23 | SEQ ID NO:429 |
| BC044OV04 | TTGCAGACTTAGGTGCACAGTGC | 23 | SEQ ID NO:430 |

RHD G1227A GENOTYPE: RHD K409K Dnull
EXON9

| | | | |
|---|---|---|---|
| BC045OV01 | AGTTTTCTGGAAGGTAAGATTTTTC | 25 | SEQ ID NO:431 |
| BC045OV02 | AGTTTTCTGGAAAGTAAGATTTTTC | 25 | SEQ ID NO:432 |
| BC045OV03 | AAGTTTTCTGGAAGGTAAGATTTTTCA | 27 | SEQ ID NO:433 |
| BC045OV04 | AAGTTTTCTGGAAAGTAAGATTTTTCA | 27 | SEQ ID NO:434 |

RHD G48A GENOTYPE: RHD W16X Dnull
EXON1

| | | | |
|---|---|---|---|
| BC046OV01 | CCTGCCCCTCTGGGCCCTAACACTG | 25 | SEQ ID NO:435 |
| BC046OV02 | CCTGCCCCTCTGAGCCCTAACACTG | 25 | SEQ ID NO:436 |
| BC046OV03 | CTGCCCCTCTGGGCCCTAACACT | 23 | SEQ ID NO:437 |
| BC046OV04 | CTGCCCCTCTGAGCCCTAACACT | 23 | SEQ ID NO:438 |

RHD C121T GENOTYPE: RHD Q41X Dnull
EXON1

| | | | |
|---|---|---|---|
| BC047OV01 | TCCTTAGAGGATCAAAAGGGGCTCG | 25 | SEQ ID NO:439 |
| BC047OV02 | TCCTTAGAGGATTAAAAGGGGCTCG | 25 | SEQ ID NO:440 |
| BC047OV03 | CCTTAGAGGATCAAAAGGGGCTC | 23 | SEQ ID NO:441 |
| BC047OV04 | CCTTAGAGGATTAAAAGGGGCTC | 23 | SEQ ID NO:442 |

RHD G270A GENOTYPE: RHD W90X Dnull
EXON2

| | | | |
|---|---|---|---|
| BC048OV01 | TGGTGTGCAGTGGGCAATCCTGCTG | 25 | SEQ ID NO:443 |
| BC048OV02 | TGGTGTGCAGTGAGCAATCCTGCTG | 25 | SEQ ID NO:444 |
| BC048OV03 | GGTGTGCAGTGGGCAATCCTGCT | 23 | SEQ ID NO:445 |
| BC048OV04 | GGTGTGCAGTGAGCAATCCTGCT | 23 | SEQ ID NO:446 |

RHD IVS3 + 1G > A GENOTYPE: RHD IVS3 + 1G > A Dneg
EXON3

| | | | |
|---|---|---|---|
| BC049OV01 | AATATCTTCAACGTGAGTCATGGTG | 25 | SEQ ID NO:447 |
| BC049OV02 | AATATCTTCAACATGAGTCATGGTG | 25 | SEQ ID NO:448 |
| BC049OV03 | ATATCTTCAACGTGAGTCATGGT | 23 | SEQ ID NO:449 |
| BC049OV04 | ATATCTTCAACATGAGTCATGGT | 23 | SEQ ID NO:450 |

RHD 488del4 GENOTYPE: RHD 488del4 Dnull
EXON4

| | | | |
|---|---|---|---|
| BC050OV01 | TTTATTGCAGACAGACTACCACATG | 25 | SEQ ID NO:451 |
| BC050OV02 | TTTATTGCAGACTACCACATGAACA | 25 | SEQ ID NO:452 |
| BC050OV03 | TTATTGCAGACAGACTACCACAT | 23 | SEQ ID NO:453 |
| BC050OV04 | TTATTGCAGACTACCACATGAAC | 23 | SEQ ID NO:454 |

RHD G635T GENOTYPE: RHD G212V Dnull
EXON5

| | | | |
|---|---|---|---|
| BC051OV01 | CTGGCCCCCAGGCGCCCTCTTCT | 23 | SEQ ID NO:455 |
| BC051OV02 | CTGGCCCCCAGTCGCCCTCTTCT | 23 | SEQ ID NO:456 |
| BC051OV03 | TGGCCCCCAGGCGCCCTCTTC | 21 | SEQ ID NO:457 |
| BC051OV04 | TGGGCCCCAGTCGCCCTCTTC | 21 | SEQ ID NO:458 |

RHD del711 GENOTYPE: RHD del711 Dnull
EXON5

| | | | |
|---|---|---|---|
| BC052OV01 | AAGGAAGAATGCCGTGTTCAACACC | 25 | SEQ ID NO:459 |
| BC052OV02 | AAGGAAGAATGCGTGTTCAACACCT | 25 | SEQ ID NO:460 |
| BC052OV03 | AGGAAGAATGCCGTGTTCAACAC | 23 | SEQ ID NO:461 |
| BC052OV04 | AGGAAGAATGCGTGTTCAACACC | 23 | SEQ ID NO:462 |

RHD G885T GENOTYPE: RHD M295I Dnull, weak D type11
EXON5

| | | | |
|---|---|---|---|
| BC053OV01 | GCTTGCCATGGTGCTGGGT | 19 | SEQ ID NO:463 |
| BC053OV02 | GCTTGCCATTGTGCTGGGT | 19 | SEQ ID NO:464 |
| BC053OV03 | GGCTTGCCATGGTGCTGGGTC | 21 | SEQ ID NO:465 |
| BC053OV04 | GGCTTGCCATTGTGCTGGGTC | 21 | SEQ ID NO:466 |

RHD 906insTGGCT GENOTYPE: RHD 906insTGGCT Dnull
EXON6

| | | | |
|---|---|---|---|
| BC054OV01 | CTTGTGGCTGGGCTGATCTCCGTCG | 25 | SEQ ID NO:467 |
| BC054OV02 | CTTGTGGCTGGGGGCTCTGATCTCC | 25 | SEQ ID NO:468 |
| BC054OV03 | TTGTGGCTGGGCTGATCTCCGTC | 23 | SEQ ID NO:469 |
| BC054OV04 | TTGTGGCTGGGGGCTCTGATCTC | 23 | SEQ ID NO:470 |

RHD IVS6 + 1del4 GENOTYPE: RHD IVS6 + 1del4 Dnull
EXON6

| | | | |
|---|---|---|---|
| BC055OV01 | AGTACCTGCCGGTAAGAAACTAGAC | 25 | SEQ ID NO:471 |
| BC055OV02 | AGTACCTGCCGGAAACTAGACAACT | 25 | SEQ ID NO:472 |

-continued

| | | | |
|---|---|---|---|
| BC055OV03 | GTACCTGCCGGTAAGAAACTAGA | 23 | SEQ ID NO:473 |
| BC055OV04 | GTACCTGCCGGAAACTAGACAAC | 23 | SEQ ID NO:474 |

RHD G941T GENOTYPE: RHD G314V Dnull
EXON7

| | | | |
|---|---|---|---|
| BC056OV01 | CTTGTCCACAGGGGTGTTGTAACCG | 25 | SEQ ID NO:475 |
| BC056OV02 | CTTGTCCACAGGTGTGTTGTAACCG | 25 | SEQ ID NO:476 |
| BC056OV03 | TTGTCCACAGGGGTGTTGTAACC | 23 | SEQ ID NO:477 |
| BC056OV04 | TTGTCCACAGGTGTGTTGTAACC | 23 | SEQ ID NO:478 |

RHD C990G GENOTYPE: RHD Y330X Dnull
EXON7

| | | | |
|---|---|---|---|
| BC057OV01 | CATCATGGGCTACAACTTCAGCTTG | 25 | SEQ ID NO:479 |
| BC057OV02 | CATCATGGGCTAGAACTTCAGCTTG | 25 | SEQ ID NO:480 |
| BC057OV03 | ATCATGGGCTACAACTTCAGCTT | 23 | SEQ ID NO:481 |
| BC057OV04 | ATCATGGGCTAGAACTTCAGCTT | 23 | SEQ ID NO:482 |

RHD IVS8 + 1G > A GENOTYPE: RHD IVS8 + 1G > A Dnull
EXON8

| | | | |
|---|---|---|---|
| BC058OV01 | GTCTCCTGACAGGTCAGTGTGAGGC | 25 | SEQ ID NO:483 |
| BC058OV02 | GTCTCCTGACAGATCAGTGTGAGGC | 25 | SEQ ID NO:484 |
| BC058OV03 | TCTCCTGACAGGTCAGTGTGAGG | 23 | SEQ ID NO:485 |
| BC058OV04 | TCTCCTGACAGATCAGTGTGAGG | 23 | SEQ ID NO:486 |

RHD C410T GENOTYPE: RHD DIII IV
EXON3

| | | | |
|---|---|---|---|
| BC059OV01 | GGTCAACTTGGCGCAGTTGGTGG | 23 | SEQ ID NO:487 |
| BC059OV02 | GGTCAACTTGGTGCAGTTGGTGG | 23 | SEQ ID NO:488 |
| BC059OV03 | GTCAACTTGGCGCAGTTGGTG | 21 | SEQ ID NO:489 |
| BC059OV04 | GTCAACTTGGTGCAGTTGGTG | 21 | SEQ ID NO:490 |

RHD A455C GENOTYPE: RHD DIIIa, DIIIc, DIII IV, DIVa
EXON3

| | | | |
|---|---|---|---|
| BC060OV01 | CAGCTTTAGGCAACCTGAGGATGGT | 25 | SEQ ID NO:491 |
| BC060OV02 | CAGCTTTAGGCACCCTGAGGATGGT | 25 | SEQ ID NO:492 |
| BC060OV03 | ACAGCTTTAGGCAACCTGAGGATGGTC | 27 | SEQ ID NO:493 |
| BC060OV04 | ACAGCTTTAGGCACCCTGAGGATGGTC | 27 | SEQ ID NO:494 |

RHD T667G GENOTYPE: RHD DIIIa, DVa (kou, yh), DCS, DAR (weak D type 4.2), weak D type4, weak D type 4.1, weak D type 29, DIII V, DOL
EXON5

| | | | |
|---|---|---|---|
| BC061OV01 | CTGGCCAAGTTTCAACTCTGC | 21 | SEQ ID NO:495 |
| BC061OV02 | CTGGCCAAGTGTCAACTCTGC | 21 | SEQ ID NO:496 |
| BC061OV03 | TGGCCAAGTTTCAACTCTG | 19 | SEQ ID NO:497 |
| BC061OV04 | TGGCCAAGTGTCAACTCTG | 19 | SEQ ID NO:498 |

RHD G916A RHD [consensus strand] exon scanning
EXON6

| | | | |
|---|---|---|---|
| BC062OV01 | GGCTGATCTCCGTCGGGGGAGCC | 23 | SEQ ID NO:499 |
| BC062OV02 | GGCTGATCTCCATCGGGGGAGCC | 23 | SEQ ID NO:500 |
| BC062OV03 | GCTGATCTCCGTCGGGGGAGC | 21 | SEQ ID NO:501 |
| BC062OV04 | GCTGATCTCCATCGGGGGAGC | 21 | SEQ ID NO:502 |

RHD A932G RHD [consensus strand] exon scanning
EXON6

| | | | |
|---|---|---|---|
| BC063OV01 | GGGGAGCCAAGTACCTGCCGGTAAG | 25 | SEQ ID NO:503 |
| BC063OV02 | GGGGAGCCAAGTGCCTGCCGGTAAG | 25 | SEQ ID NO:504 |
| BC063OV03 | GGGAGCCAAGTACCTGCCGGTAA | 23 | SEQ ID NO:505 |
| BC063OV04 | GGGAGCCAAGTGCCTGCCGGTAA | 23 | SEQ ID NO:506 |

RHD A1193T GENOTYPE: RHD DIVb
EXON9

| | | | |
|---|---|---|---|
| BC064OV01 | GCACCTCATGAGGCTAAATAT | 21 | SEQ ID NO:507 |
| BC064OV02 | GCACCTCATGTGGCTAAATAT | 21 | SEQ ID NO:508 |
| BC064OV03 | AGCACCTCATGAGGCTAAATATT | 23 | SEQ ID NO:509 |
| BC064OV04 | AGCACCTCATGTGGCTAAATATT | 23 | SEQ ID NO:510 |

RHD A514T GENOTYPE: RHD DFRI
EXON4

| | | | |
|---|---|---|---|
| BC065OV01 | AACATGATGCACATCTACGTGTTCG | 25 | SEQ ID NO:511 |
| BC065OV02 | AACCTGAGGCACTTCTACGTGTTCG | 25 | SEQ ID NO:512 |
| BC065OV03 | ACATGATGCACATCTACGTGTTC | 23 | SEQ ID NO:513 |
| BC065OV04 | ACCTGAGGCACTTCTACGTGTTC | 23 | SEQ ID NO:514 |

RHCE T307C GENOTYPE: RHCE RHc
EXON2

| | | | |
|---|---|---|---|
| BC066OV01 | AGCCAGTTCCCTTCTGGGAAGGTGG | 25 | SEQ ID NO:515 |
| BC066OV02 | AGCCAGTTCCCTCCTGGGAAGGTGG | 25 | SEQ ID NO:516 |
| BC066OV03 | GAGCCAGTTCCCTTCTGGGAAGGTGGT | 27 | SEQ ID NO:517 |

-continued

BC066OV04 GAGCCAGTTCCCTCCTGGGAAGGTGGT 27 SEQ ID NO:518

RHCE A122G GENOTYPE: RHCE Cw
EXON1
BC067OV01 CTTAGAGGATCAAAAGGGGCTCG 23 SEQ ID NO:519
BC067OV02 CTTAGAGGATCGAAAGGGGCTCG 23 SEQ ID NO:520
BC067OV03 TTAGAGGATCAAAAGGGGCTC 21 SEQ ID NO:521
BC067OV04 TTAGAGGATCGAAAGGGGCTC 21 SEQ ID NO:522

RHCE G106A GENOTYPE: RHCE Cx
EXON1
BC068OV01 ACCCACTATGACGCTTCCTTAGAGG 25 SEQ ID NO:523
BC068OV02 ACCCACTATGACACTTCCTTAGAGG 25 SEQ ID NO:524
BC068OV03 TACCCACTATGACGCTTCCTTAGAGGA 27 SEQ ID NO:525
BC068OV04 TACCCACTATGACACTTCCTTAGAGGA 27 SEQ ID NO:526

RHCE C676G GENOTYPE: RHCE E/e
EXON5
BC069OV01 AGTGTCAACTCTCCTCTGCTGAGAA 25 SEQ ID NO:527
BC069OV02 AGTGTCAACTCTGCTCTGCTGAGAA 25 SEQ ID NO:528
BC069OV03 AAGTGTCAACTCTCCTCTGCTGAGAAG 27 SEQ ID NO:529
BC069OV04 AAGTGTCAACTCTGCTCTGCTGAGAAG 27 SEQ ID NO:530

RHCE C733G GENOTYPE: RHCE VS
EXON5
BC070OV01 ACCTACTATGCTCTAGCAGTCAGTG 25 SEQ ID NO:531
BC070OV02 ACCTACTATGCTGTAGCAGTCAGTG 25 SEQ ID NO:532
BC070OV03 CACCTACTATGCTCTAGCAGTCAGTGT 27 SEQ ID NO:533
BC070OV04 CACCTACTATGCTGTAGCAGTCAGTGT 27 SEQ ID NO:534

RHCE G1006T GENOTYPE: RHCE VS/V-
EXON7
BC071OV01 TTCAGCTTGCTGGGTCTTGCTTGGA 25 SEQ ID NO:535
BC071OV02 TTCAGCTTGCTGTGTCTTGCTTGGA 25 SEQ ID NO:536
BC071OV03 CTTCAGCTTGCTGGGTCTTGCTTGGAG 27 SEQ ID NO:537
BC071OV04 CTTCAGCTTGCTGTGTCTTGCTTGGAG 27 SEQ ID NO:538

KEL T698C GENOTYPE: KEL K/k
EXON6
BC072OV01 AGAAGTCTCAGCATTCGGTTAAAGT 25 SEQ ID NO:539
BC072OV02 AGAAGTCTCAGCGTTCGGTTAAAGT 25 SEQ ID NO:540
BC072OV03 CAGAAGTCTCAGCATTCGGTTAAAGTT 27 SEQ ID NO:541
BC072OV04 CAGAAGTCTCAGCGTTCGGTTAAAGTT 27 SEQ ID NO:542

KEL A697T GENOTYPE: KEL K
EXON6
BC073OV01 AACTTTAACCGAACGCTGAGACTTC 25 SEQ ID NO:543
BC073OV02 AACTTTAACCGATCGCTGAGACTTC 25 SEQ ID NO:544
BC073OV03 AAACTTTAACCGAACGCTGAGACTTCT 27 SEQ ID NO:545
BC073OV04 AAACTTTAACCGATCGCTGAGACTTCT 27 SEQ ID NO:546

KEL T961C GENOTYPE: KEL Kpa/Kpb
EXON8
BC074OV01 ACTGGAACAGCCATGAAGTGATGGA 25 SEQ ID NO:547
BC074OV02 ACTGGAACAGCCGTGAAGTGATGGA 25 SEQ ID NO:548
BC074OV03 AACTGGAACAGCCATGAAGTGATGGAG 27 SEQ ID NO:549
BC074OV04 AACTGGAACAGCCGTGAAGTGATGGAG 27 SEQ ID NO:550

KEL G962A GENOTYPE: KEL Kpc
EXON8
BC075OV01 AACTGGAACAGCCGTGAAGTGATGG 25 SEQ ID NO:551
BC075OV02 AACTGGAACAGCTGTGAAGTGATGG 25 SEQ ID NO:552
BC075OV03 AAACTGGAACAGCCGTGAAGTGATGGA 27 SEQ ID NO:553
BC075OV04 AAACTGGAACAGCTGTGAAGTGATGGA 27 SEQ ID NO:554

KEL C1910T GENOTYPE: KEL Jsa/Jsb
EXON17
BC076OV01 TGGGGGCTGCCCCGCCTGTGACA 23 SEQ ID NO:555
BC076OV02 TGGGGGCTGCCTCGCCTGTGACA 23 SEQ ID NO:556
BC076OV03 GGGGGCTGCCCCGCCTGTGAC 21 SEQ ID NO:557
BC076OV04 GGGGGCTGCCTCGCCTGTGAC 21 SEQ ID NO:558

KEL G1208A GENOTYPE: KEL Kmod-1
EXON10
BC077OV01 AAGATCATGTGGCTCTGCAGAAAGT 25 SEQ ID NO:559
BC077OV02 AAGATCATGTGGTTCTGCAGAAAGT 25 SEQ ID NO:560
BC077OV03 TAAGATCATGTGGCTCTGCAGAAAGTC 27 SEQ ID NO:561
BC077OV04 TAAGATCATGTGGTTCTGCAGAAAGTC 27 SEQ ID NO:562

KIDD G838A GENOTYPE: KIDD Jka/Jkb
EXON9

-continued

```
BC078OV01  GCCCCATTTGAGGACATCTACTTTG    25  SEQ ID NO:563
BC078OV02  GCCCCATTTGAGAACATCTACTTTG    25  SEQ ID NO:564
BC078OV03  CCCCATTTGAGGACATCTACTTT      23  SEQ ID NO:565
BC078OV04  CCCCATTTGAGAACATCTACTTT      23  SEQ ID NO:566

KIDD Intron5G > A GENOTYPE: KIDD Jknull
EXON6
BC079OV01  TCTTGCCCCACAGGTCATTAATAGC    25  SEQ ID NO:567
BC079OV02  TCTTGCCCCACAAGTCATTAATAGC    25  SEQ ID NO:568
BC079OV03  GCTATTAATGACCTGTGGGGCAAGA    25  SEQ ID NO:569
BC079OV04  GCTATTAATGACTTGTGGGGCAAGA    25  SEQ ID NO:570

KIDD T871C GENOTYPE: KIDD Jknull
EXON9
BC080OV01  GGTTTCAACAGCTCTCTGGCCTGCA    25  SEQ ID NO:571
BC080OV02  GGTTTCAACAGCCCTCTGGCCTGCA    25  SEQ ID NO:572
BC080OV03  GGGTTTCAACAGCTCTCTGGCCTGCAT  27  SEQ ID NO:573
BC080OV04  GGGTTTCAACAGCCCTCTGGCCTGCAT  27  SEQ ID NO:574

DUFFY G125A GENOTYPE: DUFFY FYa/FYb
BC081OV01  ATGGAGACTATGGTGCCAACCTGGA    25  SEQ ID NO:575
BC081OV02  ATGGAGACTATGATGCCAACCTGGA    25  SEQ ID NO:576
BC081OV03  GATGGAGACTATGGTGCCAACCTGGAA  27  SEQ ID NO:577
BC081OV04  GATGGAGACTATGATGCCAACCTGGAA  27  SEQ ID NO:578

DUFFY T-33C GENOTYPE: DUFFY FYGATA-1
PROMOTER
BC082OV01  CCTTGGCTCTTATCTTGGAAGCACA    25  SEQ ID NO:579
BC082OV02  CCTTGGCTCTTACCTTGGAAGCACA    25  SEQ ID NO:580
BC082OV03  CTTGGCTCTTATCTTGGAAGCAC      23  SEQ ID NO:581
BC082OV04  CTTGGCTCTTACCTTGGAAGCAC      23  SEQ ID NO:582

DUFFY C265T GENOTYPE: DUFFY FYx
BC083OV01  CCTCTCTTCCGCTGGCAGC          19  SEQ ID NO:583
BC083OV02  CCTCTCTTCCGCTGGCAGC          19  SEQ ID NO:584
BC083OV03  ACCTCTCTTCCGCTGGCAGCT        21  SEQ ID NO:585
BC083OV04  ACCTCTCTTCCGCTGGCAGCT        21  SEQ ID NO:586

MNS C59T GENOTYPE: MNS MN
EXON2GYPA
BC084OV01  GCATATCAGCATCAAGTACCACTGG    25  SEQ ID NO:587
BC084OV02  GCATATCAGCATTAAGTACCACTGA    25  SEQ ID NO:588
BC084OV03  CATATCAGCATCAAGTACCACTG      23  SEQ ID NO:589
BC084OV04  CATATCAGCATTAAGTACCACTG      23  SEQ ID NO:590

MNS G71A T72G GENOTYPE: MNS MN
EXON2GYPA
BC085OV01  CAAGTACCACTGGTGTGGCAATGCA    25  SEQ ID NO:591
BC085OV02  TAAGTACCACTGAGGTGGCAATGCA    25  SEQ ID NO:592
BC085OV03  TCAAGTACCACTGGTGTGGCAATGCAC  27  SEQ ID NO:593
BC085OV04  TTAAGTACCACTGAGGTGGCAATGCAC  27  SEQ ID NO:594

MNS T143C GENOTYPE: MNS S/s
EXON4GYPB
BC086OV01  TTATAGGAGAAATGGGACAACTTGT    25  SEQ ID NO:595
BC086OV02  TTATAGGAGAAACGGGACAACTTGT    25  SEQ ID NO:596
BC086OV03  TTTATAGGAGAAATGGGACAACTTGTC  27  SEQ ID NO:597
BC086OV04  TTTATAGGAGAAACGGGACAACTTGTC  27  SEQ ID NO:598

MNS C230T GENOTYPE: MNS U
EXON5GYPB
BC087OV01  GTATTATTGGAACGATCCTCTTAAT    25  SEQ ID NO:599
BC087OV02  GTATTATTGGAATGATCCTCTTAAT    25  SEQ ID NO:600
BC087OV03  GGTATTATTGGAACGATCCTCTTAATT  27  SEQ ID NO:601
BC087OV04  GGTATTATTGGAATGATCCTGTTAATT  27  SEQ ID NO:602

MNS INTRON5 + 5GT GENOTYPE: MNS U
EXON5GYPB
BC088OV01  TGATAAAGGTGAGAATTCAGTTTTT    25  SEQ ID NO:603
BC088OV02  TGATAAAGGTGATAATTCAGTTTTT    25  SEQ ID NO:604
BC088OV03  AAAAACTGAATTCTCACCTTTATCA    25  SEQ ID NO:605
BC088OV04  AAAAACTGAATTATCACCTTTATCA    25  SEQ ID NO:606

MNS C790A GENOTYPE: MNS GP.Mur (Mi.III)
EXON3
BC089OV01  TATATGCAGATACGCACAAACGGGA    25  SEQ ID NO:607
BC089OV02  TATATGCAGATAAGCACAAACGGGA    25  SEQ ID NO:608
BC089OV03  TTATATGCAGATACGCACAAACGGGAC  27  SEQ ID NO:609
BC089OV04  TTATATGCAGATAAGCACAAACGGGAC  27  SEQ ID NO:610

MNS C850G GENOTYPE: MNS MNS GP.Mur (Mi.III)
```

-continued

| | | | |
|---|---|---|---|
| EXON3 | | | |
| BC090OV01 | GGGGAAACAGTTGTAACAGAAATTT | 25 | SEQ ID NO:611 |
| BC090OV02 | GGGCAAACAGTTCTAACAGAAATTT | 25 | SEQ ID NO:612 |
| BC090OV03 | AGGGGAAACAGTTGTAACAGAAATTTC | 27 | SEQ ID NO:613 |
| BC090OV04 | AGGGCAAACAGTTCTAACAGAAATTTC | 27 | SEQ ID NO:614 |
| DIEGO T2561C GENOTYPE: DIEGO DIa/DIb | | | |
| EXON19 | | | |
| BC091OV01 | GCCAGGGAGGCCAGCGTGGACTTCA | 25 | SEQ ID NO:615 |
| BC091OV02 | GCCAGGGAGGCCGGCGTGGACTTCA | 25 | SEQ ID NO:616 |
| BC091OV03 | CCAGGGAGGCCAGCGTGGACTTC | 23 | SEQ ID NO:617 |
| BC091OV04 | CCAGGGAGGCCGGCGTGGACTTC | 23 | SEQ ID NO:618 |
| DOMBROCK A793G GENOTYPE: DOMBROCK DOa/DOb | | | |
| EXON2 | | | |
| BC092OV01 | ACTGCAACCAGTTTCCTCTTGGGTG | 25 | SEQ ID NO:619 |
| BC092OV02 | ACTGCAACCAGTCTCCTCTTGGGTG | 25 | SEQ ID NO:620 |
| BC092OV03 | AACTGCAACCAGTTTCCTCTTGGGTGG | 27 | SEQ ID NO:621 |
| BC092OV04 | AACTGCAACCAGTCTCCTCTTGGGTGG | 27 | SEQ ID NO:622 |
| COLTON C134T GENOTYPE: COLTON COa/COb | | | |
| EXON1 | | | |
| BC093OV01 | TTGTCCTGGACCGCCGTCTGGTTGT | 25 | SEQ ID NO:623 |
| BC093OV02 | TTGTCCTGGACCACCGTCTGGTTGT | 25 | SEQ ID NO:624 |
| BC093OV03 | TGTCCTGGACCGCCGTCTGGTTG | 23 | SEQ ID NO:625 |
| BC093OV04 | TGTCCTGGACCACCGTCTGGTTG | 23 | SEQ ID NO:626 |
| RHD G1048C GENOTYPE: RHD DIVa/DIVb | | | |
| EXON7 | | | |
| BC094OV01 | GCTGGTGCTTGATACCGTCGG | 21 | SEQ ID NO:627 |
| BC094OV02 | GCTGGTGCTTCATACCGTCGG | 21 | SEQ ID NO:628 |
| BC094OV03 | TGCTGGTGCTTGATACCGTCGGA | 23 | SEQ ID NO:629 |
| BC094OV04 | TGCTGGTGCTTCATACCGTCGGA | 23 | SEQ ID NO:630 |

1.2 Production of the DNA-chip for Genotyping Blood Groups Printing and Processing of the Glass Slides The probes capable of detecting the genetic variations previously identified are printed onto aminosilane coated supports (glass slides) using DMSO as a solvent. The printing is carried out using a spotter or printer of oligonucleotides (probes) while controlling the temperature and relative humidity.

The joining of the probes to the support (glass slides) is carried out by means of crosslinking with ultraviolet radiation and heating as described in the documentation provided by the manufacturer (for example, Corning Lifesciences; available on the World Wide Web at corning.com). The relative humidity during the deposition process is maintained between 40-50% and the temperature around 20° C.

1.3 Validation of the Clinical Usefulness of the DNA-chip to Identify Human Blood Groups: Simultaneous, Sensitive, Specific and Reproducible Detection of Human Genetic Variations Associated with Erythrocyte Antigens 1.3.1 Preparation of the Sample to be Hybridized The DNA of the individual is extracted from a blood sample by a standard protocol of filtration. (For example, commercial kits from Macherey Nagel, Qiagene etc).

All the exons and introns of interest are amplified by multiplex PCR using appropriate pairs of oligonucleotide primers. Oligonucleotide primers useful for carrying out PCR multiplex for the detection of genetic variations associated with human erythrocyte antigens can be designed by those skilled in the art using the corresponding gene sequences as described in GenBank with, for example, the software: Primer 3 (available on the World Wide Web at frodo.wi.mit-edu/cgi-bin/primer3/primer3) or Web Primer (available on the World Wide Web at seq.yeastgenome.org/cgi-bin/web-primer). Practically any pair of oligonucleotide primers can be used that permit the specific amplification of genetic fragments where a genetic variation to be detected may exist. Where possible, those pairs of oligonucleotide primers which permit the said amplifications to be performed in the least possible number of PCR reactions are used.

In this case, primers were selected which permitted, in only 3 PCR reactions, amplification of the 36 fragments necessary for genotyping the (94) genetic variations previously mentioned using the DNA-chip for detection of genetic variations associated with erythrocyte antigens.

The PCR multiplex reactions are carried out simultaneously under the same conditions of time and temperature which permit specific amplification of the gene fragments in which the genetic variations to be detected can exist. Once the PCR multiplex has finished, agarose gel analysis is used to check that the amplification reaction has taken place.

Next, the sample to be hybridized (products of amplification) is subjected to fragmentation with a DNase and the resulting fragmentation products subjected to indirect labelling. A terminal transferase adds a nucleotide, covalently joined to one member of a pair of molecules that show specific binding to one another e.g. biotin, to the end of these small DNA fragments.

Before applying the sample to the DNA-chip, the sample is denatured by heating to 95° C. for 5 minutes and then, the "ChipMap Kit Hybridization Buffer" (Ventana Medical System) is added.

1.3.2 Hybridization

Hybridization is carried out automatically in a hybridisation station such as the Ventana Discovery (Ventana Medical Systems) that has been specifically developed for such a use. Alternatively hybridisation can be performed manually.

The prehybridization and blocking of the slides is carried out with BSA. Next, the hybridization solution {ChipMap Kit Hybridization Buffer, Ventana Medical System) is applied to the surface of the DNA-chip which is maintained at 45° C. for 1 hour following the protocol of Ventana 9.0 Europe (Ventana Medical System). Finally the slides are subjected to different cleaning solutions (ChipMap hybridisation Kit Buffers, Ventana Medical System). Once the process of hybridization has finished, the final cleaning and drying of the slides begins.

When hybridization has taken place, the DNA chip is developed by incubation with a fluorescently labelled molecule that is able to specifically bind to the molecule incorporated into the amplification product by terminal transferase (e.g. in the case of biotin incorporation a fluorophore coupled to streptavidin such as streptavidin-Cy3 can be used) to label the probe positions where hybridization has occured.

1.3.3. Scanning the Slides

The slides are placed in a fluorescent confocal scanner, for example Axon 4100$^{a}$, and the signal emitted by the fluorophore is scanned when stimulated by the laser.

1.3.4 Quantification of the Image

The scanner's own software allows quantification of the image obtained from the signal at the points where hybridization has taken place.

1.3.5 Interpretation of the Results: Determination of the Genotype of the Individual, Regarding the Human Genetic Variations Associated with Human Erythrocyte Antigens and the Identification of the Blood Group of the Individual.

From the signal obtained with the probes which detect the different genetic variations, the genotype of the individual is established. In the first instance the scanner software executes a function to subtract the local background noise from the absolute signal intensity value obtained for each probe. Next, the replicates for each of the 4 probes that are used to characterize each genetic variation are grouped. The average intensity value for each of 4 probes is calculated using the average collated from the replicates in order to identify abnormal values (outliers) that can be excluded from further consideration. Once the average intensity value for each of the probes is known then two ratios are calculated (ratio 1 and ratio 2):

$$\text{Ratio 1} = \frac{\text{Average intensity value for probe 1}}{\text{Average intensity value for probe 1} + \text{Average intensity value for probe 2}}$$

$$\text{Ratio 2} = \frac{\text{Average intensity value for probe 3}}{\text{Average intensity value for probe 3} + \text{Average intensity value for probe 4}}$$

wherein probe 1 detects (is capable of specifically hybridising to) genetic variation A (e.g. a normal allele), probe 2 detects (is capable of specifically hybridising to) genetic variation B (e.g. a mutant allele), probe 3 detects (is capable of specifically hybridising to) genetic variation A (e.g. a normal allele) and probe 4 detects (is capable of specifically hybridising to) genetic variation B (e.g. a mutant allele).

These ratios are substituted in three linear functions which characterize each one of the three possible genotypes:

| | |
|---|---|
| AA | Function 1 |
| AB | Function 2 |
| BB | Function 3 |

The function which presents the highest absolute value determines the genotype of the patient.

In this case, the linear functions are obtained by analyzing 5 subjects for each of the three possible genotypes of the genetic variation (AA, AB, BB). With the results, ratios 1 and 2 are calculated for the 15 subjects. These ratios are classification variables for the three groups to create the linear functions, with which the discriminatory capacity of the two pairs of designed probes are evaluated. If the discriminatory capacity is not 100%, the probes are redesigned. New subjects characterized for each of the three genotypes make up new ratios 1 and 2 to perfect the linear functions and in short, to improve the discriminatory capacity of the algorithm based on these three functions.

When using a confocal fluorescent scanner, to obtain reliable results it is preferable that ratios 1 and 2 are within the range of the ratios used to build the groups, the average fluorescence intensity of the 4n (for example 40) replicates with regard to background noise is greater than 5 and the coefficient of variation of all of the DNA-chip replicates is below 0.25.

Again when a fluorescent confocal scanner is used in the experiment, for a complete hybridization to be considered reliable preferably the ratio of probe fluorescence intensity to background noise of all the DNA-chip probes is above 15. Likewise, the average of all the ratios is preferably above 0.6 and the negative control is preferably less than or equal to 3 times the background noise To sum up, in this case 4 probes (repeated 10 times) are presented on the slide for detection of each mutation. Two of the probes detect one genetic variation (A) and the other two the other genetic variation (B). The examined base is located in the central position of the probes.

A subject homozygous for the genetic variation A will not show genetic variation B. Consequently, in the image obtained from the glass support the probes which detect genetic variation B will show a hybridization signal significantly less than that shown by variation A and vice versa. In this case the ratios 1 and 2 will show 1 and the subjects will be assigned as homozygous AA by the software analysis.

On the other hand, a heterozygous subject for the determined genetic variation shows both the genetic variations. Therefore, the probes which detect them show an equivalent hybridization signal. The ratios 1 and 2 will show 0.5 and the subject will be assigned as heterozygous AB by the software analysis.

Example 2

Identification of the Blood Group of 15 Individual Blood Donors, Using the DNA-chip for the Genotyping of Blood Groups 2.1 DNA Extraction DNA was extracted from 15 blood donors who responded to serological groups A and 0 by conventional methods. Genetic analysis by sequencing of the region of interest confirmed that 5 of the donors had genotype 188G189C (serological determination A), another 5 donors had genotype 188GA189CT (serological determination 0) and the remaining 5 188A189T (serological determination 0)

2.2 Probe Design 4 probes were designed for the detection of the polymorphism ABO G188A/C189T genotype ABO O1v as previously described (Example 1):

```
BC012OV01
ACCATCTGCAGCGCGTCTCGTTGCC        25    SEQ ID NO:299

BC012OV02
ACCATCTGCAGCATGTCTCGTTGCC        25    SEQ ID NO:300

BC012OV03
CCATCTGCAGCGCGTCTCGTTGC          23    SEQ ID NO:301

BC012OV04
CCATCTGCAGCATGTCTCGTTGC          23    SEQ ID NO:302
```

2.3 Production of the DNA Chip for the Detection of Human Genetic Variations Associated with Determined Human Erythrocyte Antigens The designed probes were printed onto glass slides with a micro-arrayer as described in Example 1.2.

2.4 PCR and Labelling the Sample

The region of the ABO gene for the analysis of the genetic variation of interest (ABO G188A/C189T genotype ABO O1v) was amplified by means of PCR multiplex using specific primers. The product of the amplification was fragmented and labelled as described in Example 1.3.1.

2.5 Hybridization of the Samples

Hybridization was carried out in an automated hybridisation station, as described in Example 1.3.2.

2.6 Analysis of the Results

The slides were placed in the scanner. The signal emitted by the bound flurophore on excitation by the laser was measured (Example 1.3.3) and the image obtained from the signal at the points where hybridization had taken place was quantified (Example 1.3.4).

The analysis of the results was carried out using the algorithm previously described in Example 1.3.5. The algorithm allowed characterization of this genetic variation for the 15 subjects with a coincidence of 100% compared to serological methods and sequencing.

FIG. 1 shows the representation of ratios 1 and 2 and allows characterization of the 15 patients.

Table 5 shows the linear functions for the three genotype groups, when the number of replicates of the 4 probes used was 10. “X” is ratio 1; “Y” is ratio 2; “0” corresponds to the genotype 188A189T; “1” corresponds to the genotype 188GA189CT; and “2” corresponds to the genotype 188G189C.

TABLE 5

| Coefficients of the functions used for genotyping | | | |
|---|---|---|---|
| CLASS | 0 | 1 | 2 |
| X | 7.338994 | 101.6024 | 176.7265 |
| Y | 1227.301 | 603.8602 | 81.12664 |
| (Constant) | −499.132 | −163.927 | −27.3071 |

A donor with genotype 188G189C had ratios 1 and 2 of 0.77 and 0.82 respectively. On substituting these ratios for linear functions, it is observed that function 2 shows a greater absolute value. From this we can see how the algorithm of the invention classifies perfectly classifies donors when 10 replicates are used for each one of the 4 probes.

Table 6 shows the linear functions obtained when 8 replicates of each of the 4 probes are used.

TABLE 6

| Coefficients of the functions used for genotyping | | | |
|---|---|---|---|
| CLASS | 0 | 1 | 2 |
| X | 178.1139 | 272.6293 | 417.9721 |
| Y | −42.2919 | 59.0597 | 132.0375 |
| (Constant) | −16.0985 | −82.5103 | −225.228 |

The same donor with genotype 188G189C had the same ratios 1 and 2 of 0.77 and 0.82, respectively. On substituting these ratios for linear functions, it is observed that function 2 shows a greater absolute value. From this, we can see that the algorithm of the invention perfectly classifies patients when 8 replicates are used for each one of the 4 probes.

Table 7 shows the linear functions obtained when 6 replicates of each of the 4 probes are used.

TABLE 7

| Coefficients of the functions used for genotyping | | | |
|---|---|---|---|
| CLASS | 0 | 1 | 2 |
| X | 181.8305 | 307.0291 | 477.2833 |
| Y | −51.0987 | 15.33189 | 57.86783 |
| (Constant) | −15.1285 | −79.8083 | −218.298 |

The same donor with genotype 188G189C had the same ratios 1 and 2 of 0.77 and 0.82, respectively. On substituting these ratios for linear functions, it is observed that function 2 shows a greater absolute value. From this, we can see that the algorithm of the invention perfectly classifies patients when 6 replicates are used for each one of the 4 probes.

Example 3

Detection of Human Genetic Variations Associated with Inflammatory Bowel Disease (IBD), Using a DNA-chip for the Diagnosis, Prognosis and Prediction of Response to Treatment of IBD 3.1 Design of the DNA-chip for Genotyping of Genetic Variations Associated with IBD A DNA-chip which permits the simultaneous, sensitive, specific and reproducible detection of human genetic variations associated with IBD was designed and manufactured. The genetic variations are related to a greater or lesser risk of suffering from IBD, a better or worse response to treatment and also a better or worse prognosis of the disease. Table 1 lists illustrative examples of human genetic variations associated with BED which can be determined using this DNA-chip.

The DNA-chip designed and produced consists of a support (glass slide) which comprises a plurality of probes on its surface that permit the detection of the genetic variations. These probes are capable of hybridizing with the (amplified) target sequences of the genes related to IBD. The DNA sequences of the probes used are listed below. In general, the name of the gene and the mutation is indicated (change of nucleotide, “ins”: insertion “del” deletion or change of amino acid):

```
1. - Multidrug resistance protein (MDR-1)
G2677T/A/C Ala893Ser/Thr/Pro) The probes detect
the polymorphisms G2677T (Ala893Ser), G2677A
(Ala893Thr) and G2677C (Ala893Pro) of the gene
Multidrug resistance protein MDR-1)
TCACCTTCCCAGCACCTTCTAGTTC       SEQ ID NO:631
GAACTAGAAGGTGCTGGGAAGGTGA       SEQ ID NO:632
TCACCTTCCCAGGACCTTCTAGTTC       SEQ ID NO:633
GAACTAGAAGGTCCTGGGAAGGTGA       SEQ ID NO:634
TCACCTTCCCAGAACCTTCTAGTTC       SEQ ID NO:635
GAACTAGAAGGTTCTGGGAAGGTGA       SEQ ID NO:636
TCACCTTCCCAGTACCTTCTAGTTC       SEQ ID NO:637
GAACTAGAAGGTACTGGGAAGGTGA       SEQ ID NO:638

2. - Multidrug resistance protein (MDR-1) C3435T
TGCTGCCCTCACAATCTCTTCCTGT       SEQ ID NO:639
ACAGGAAGAGATTGTGAGGGCAGCA       SEQ ID NO:640
TGCTGCCCTCACGATCTCTTCCTGT       SEQ ID NO:641
ACAGGAAGAGATCGTGAGGGCAGCA       SEQ ID NO:642
```

-continued

3. - CARD15 R702W
AAGGCCCTGCTCCGGCGCCAGGCCT SEQ ID NO:643
AGGCCTGGCGCCGGAGCAGGGCCTT SEQ ID NO:644
AAGGCCCTGCTCTGGCGCCAGGCCT SEQ ID NO:645
AGGCCTGGCGCCAGAGCAGGGCCTT SEQ ID NO:646

4. - CARD15 G908R
TTCAGATTCTGGGGCAACAGAGTGG SEQ ID NO:647
CCACTCTGTTGCCCCAGAATCTGAA SEQ ID NO:648
TTCAGATTCTGGCGCAACAGAGTGG SEQ ID NO:649
CCACTCTGTTGCGCCAGAATCTGAA SEQ ID NO:650

5. - CARD15 1007insC
TCCTGCAGGCCCCTTGAAAGGAATG SEQ ID NO:651
CATTCCTTTCAAGGGGCCTGCAGGA SEQ ID NO:652
TCCTGCAGGCCCTTGAAAGGAATGA SEQ ID NO:653
TCATTCCTTTCAAGGGCCTGCAGGA SEQ ID NO:654

6. - Microsomal epoxide hydrolase (EPXH1) T612C (Y113H)
ATTCTCAACAGATACCCTCACTTCA SEQ ID NO:655
TGAAGTGAGGGTATCTGTTGAGAAT SEQ ID NO:656
ATTCTCAACAGACACCCTCACTTCA SEQ ID NO:657
TGAAGTGAGGGTGTCTGTTGAGAAT SEQ ID NO:658

7. - Monocyte chemotactic protein 1 (MCP1) (-2518) G/A
AGGCAGACAGCTGTCACTTTCCAGA SEQ ID NO:659
TCTGGAAAGTGACAGCTGTCTGCCT SEQ ID NO:660
AGGCAGACAGCTATCACTTTCCAGA SEQ ID NO:661
TCTGGAAAGTGATAGCTGTCTGCCT SEQ ID NO:662

8. - Interleukin 10 (IL10) (-1082) G/A
GCTTCTTTGGGAAGGGGAAGTAGGG SEQ ID NO:663
CCCTACTTCCCCTTCCCAAAGAAGC SEQ ID NO:664
GCTTCTTTGGGAGGGGGAAGTAGGG SEQ ID NO:665
CCCTACTTCCCCCTCCCAAAGAAGC SEQ ID NO:666

9. - Interleukin 10 (IL10) G15R G43A
GTCCTCCTGACTGGGGTGAGGGCCA SEQ ID NO:667
GTCCTCCTGACTAGGGTGAGGGCCA SEQ ID NO:668
TGGCCCTCACCCCAGTCAGGAGGAC SEQ ID NO:669
TGGCCCTCACCCTAGTCAGGAGGAC SEQ ID NO:670

10. - Interleukin 16 (IL16) (-295) T/C
TTGTTCCTATCATAAAGAGTCAGGG SEQ ID NO:671
CCCTGACTCTTTATGATAGGAACAA SEQ ID NO:672
TTGTTCCTATCACAAAGAGTCAGGG SEQ ID NO:673
CCCTGACTCTTTGTGATAGGAACAA SEQ ID NO:674

11. - Fas ligand (-843) C/T
ATGAAAACATTGTGAAATACAAAGC SEQ ID NO:675
GCTTTGTATTTCACAATGTTTTCAT SEQ ID NO:676
ATGAAAACATTGCGAAATACAAAGC SEQ ID NO:677
GCTTTGTATTTCGCAATGTTTTCAT SEQ ID NO:678

12. - Nuclear factor kappa-B (NFκB1) 94delATTG
CCCCGACCATTGGGCCCGGCAGGCG SEQ ID NO:679
CGCCTGCCGGGCCCAATGGTCGGGG SEQ ID NO:680
CCCCGACCATTGATTGGGCCCGGCA SEQ ID NO:681
TGCCGGGCCCAATCAATGGTCGGGG SEQ ID NO:682

13. - Nuclear factor kappa-B inhibitor alpha (NFκKBIA) SNP in the 3'UTR (G/A)
TGCACACTGCCTGGCCCAAAACGTC SEQ ID NO:683
TGCACACTGCCTAGCCCAAAACGTC SEQ ID NO:684
GACGTTTTGGGCCAGGCAGTGTGCA SEQ ID NO:685
GACGTTTTGGGCTAGGCAGTGTGCA SEQ ID NO:686

14. - Signal transducer and activator of transcription 6 (STAT6) G2964A
GCTCTGAGACACGCCCCAACATGCC SEQ ID NO:687
GGCATGTTGGGGCGTGTCTCAGAGC SEQ ID NO:688
GCTCTGAGACACACCCCAACATGCC SEQ ID NO:689
GGCATGTTGGGGTGTGTCTCAGAGC SEQ ID NO:690

15. - Interleukin 18 (IL18) TCA/TCC in the codon 35
GCCAAAGTAATCGGATTCCAGGTTT SEQ ID NO:691
AAACCTGGAATCCGATTACTTTGGC SEQ ID NO:692
GCCAAAGTAATCTGATTCCAGGTTT SEQ ID NO:693
AAACCTGGAATCAGATTACTTTGGC SEQ ID NO:694

16. - Mediterranean fever gene (MEFV) E474E
CTACTTCCTGGAGCAGCAAGAGCAT SEQ ID NO:695
ATGCTCTTGCTGCTCCAGGAAGTAG SEQ ID NO:696
CTACTTCCTGGAACAGCAAGAGCAT SEQ ID NO:697
ATGCTCTTGCTGTTCCAGGAAGTAG SEQ ID NO:698

17. - Mediterranean fever gene (MEFV) Q476Q
CCTGGAGCAGCAGGAGCATTTCTTT SEQ ID NO:699
AAAGAAATGCTCCTGCTGCTCCAGG SEQ ID NO:700
CCTGGAGCAGCAAGAGCATTTCTTT SEQ ID NO:701
AAAGAAATGCTCTTGCTGCTCCAGG SEQ ID NO:702

18. - Mediterranean fever gene (MEFV) D510D
CGCCCTGCTCGACGCGCTGATTGGG SEQ ID NO:703
CCCAATCAGCGCGTCGAGCAGGGCG SEQ ID NO:704
CGCCCTGCTCGATGCGCTGATTGGG SEQ ID NO:705
CCCAATCAGCGCATCGAGCAGGGCG SEQ ID NO:706

19. - Mediterranean fever gene (MEFV) P588P
GCCAATCAGCTCCGGAACTACGGAG SEQ ID NO:707
CTCCGTAGTTCCGGAGCTGATTGGC SEQ ID NO:708
GCCAATCAGCTCTGGAACTACGGAG SEQ ID NO:709
CTCCGTAGTTCCAGAGCTGATTGGC SEQ ID NO:710

20. - Discs, large homolog 5 (DLG5) 113G/A (R30Q)
TCATTCACTTGCCGGTCAGTGAGGA SEQ ID NO:711
TCCTCACTGACCGGCAAGTGAATGA SEQ ID NO:712
TCATTCACTTGCTGGTCAGTGAGGA SEQ ID NO:713
TCCTCACTGACCAGCAAGTGAATGA SEQ ID NO:714

21. - Colony stimulating factor receptor 1 (CSFR1) A2033T
AAACCCTTATTCACCTAATCACAGC SEQ ID NO:715
GCTGTGATTAGGTGAATAAGGGTTT SEQ ID NO:716
AAACCCTTATTCTCCTAATCACAGC SEQ ID NO:717
GCTGTGATTAGGAGAATAAGGGTTT SEQ ID NO:718

22. - Organic cation transporter (OCTN1, SLC22A4) 1672C/T (L503F)
CTGATTGGAATCCTCACCCTTTTTT SEQ ID NO:719
AAAAAAGGGTGAGGATTCCAATCAG SEQ ID NO:720
CTGATTGGAATCTTCACCCTTTTTT SEQ ID NO:721
AAAAAAGGGTGAAGATTCCAATCAG SEQ ID NO:722

23. - Organic cation transporter (OCTN2, SLC22A5) (-207) G/C
CCAGGGAAGGTTGCGGGCCTGGGCC SEQ ID NO:723
GGCCCAGGCCCGCAACCTTCCCTGG SEQ ID NO:724
CCAGGGAAGGTTCCGGGCCTGGGCC SEQ ID NO:725
GGCCCAGGCCCGGAACCTTCCCTGG SEQ ID NO:726

24. - Toll-like receptor 4 (TLR4) (A/G) Asp299Gly
ACTACCTCGATGATATTATTGACTT SEQ ID NO:727
AAGTCAATAATATCATCGAGGTAGT SEQ ID NO:728
ACTACCTCGATGGTATTATTGACTT SEQ ID NO:729
AAGTCAATAATACCATCGAGGTAGT SEQ ID NO:730

25. - Toll-like receptor 4 (TLR4) (C/T) Thr399Ile
ATTTTGGGACAACCAGCCTAAAGTA SEQ ID NO:731
TACTTTAGGCTGGTTGTCCCAAAAT SEQ ID NO:732
ATTTTGGGACAATCAGCCTAAAGTA SEQ ID NO:733
TACTTTAGGCTGATTGTCCCAAAAT SEQ ID NO:734

26. - Interleukin 1 beta (IL1β) (-511) A/C
GAAGAGAATCCCAGAGCAGCCTGTT SEQ ID NO:735
AACAGGCTGCTCTGGGATTCTCTTC SEQ ID NO:736
GAAGAGAATCCCCGAGCAGCCTGTT SEQ ID NO:737
AACAGGCTGCTCGGGGATTCTCTTC SEQ ID NO:738

27. - Superoxide dismutase 2 (SOD2) (C/T) Ala16Val
AGCTGGCTCCGGCTTTGGGGTATCT SEQ ID NO:739
AGATACCCCAAAGCCGGAGCCAGCT SEQ ID NO:740
AGCTGGCTCCGGTTTTGGGGTATCT SEQ ID NO:741
AGATACCCCAAAACCGGAGCCAGCT SEQ ID NO:742

28. - Peroxisome proliferator-activated receptor gamma (PPARG) (C/G) Pro12Ala
TCTCCTATTGACCCAGAAAGCGATT SEQ ID NO:743
AATCGCTTTCTGGGTCAATAGGAGA SEQ ID NO:744

-continued

TCTCCTATTGACGCAGAAAGCGATT SEQ ID NO:745
AATCGCTTTCTGCGTCAATAGGAGA SEQ ID NO:746

29. - Intercellular adhesion molecule 1 (ICAM1) (A/G) K469E
GAGGTCACCCGCAAGGTGACCGTGA SEQ ID NO:747
TCACGGTCACCTTGCGGGTGACCTC SEQ ID NO:748
GAGGTCACCCGCGAGGTGACCGTGA SEQ ID NO:749
TCACGGTCACCTCGCGGGTGACCTC SEQ ID NO:750

30. - Intercellular adhesion molecule 1 ICAM1 R241G
TGTTCCCTGGACAGGCTGTTCCCAG SEQ ID NO:751
CTGGGAACAGCCTGTCCAGGGAACA SEQ ID NO:752
TGTTCCCTGGACGGGCTGTTCCCAG SEQ ID NO:753
CTGGGAACAGCCCGTCCAGGGAACA SEQ ID NO:754

31. - IBD5 locus IGR2060a_1
CCTTGCAACCCTGGCAAAGGTAATG SEQ ID NO:755
CATTACCTTTGCCAGGGTTGCAAGG SEQ ID NO:756
CCTTGCAACCCTCGCAAAGGTAATG SEQ ID NO:757
CATTACCTTTGCGAGGGTTGCAAGG SEQ ID NO:758

32. - IBD5 locus IGR2198a_1
CAGTAGACGAACGATGCAAAATACC SEQ ID NO:759
GGTATTTTGCATCGTTCGTCTACTG SEQ ID NO:760
CAGTAGACGAACCATGCAAAATACC SEQ ID NO:761
GGTATTTTGCATGGTTCGTCTACTG SEQ ID NO:762

33. - IBD5 locus IGR3096a_1
CATCCTGGAGAATAGCTGAGAACCT SEQ ID NO:763
AGGTTCTCAGCTATTCTCCAGGATG SEQ ID NO:764
CATCCTGGAGAACAGCTGAGAACCT SEQ ID NO:765
AGGTTCTCAGCTGTTCTCCAGGATG SEQ ID NO:766

34. - Heat shock protein 70 (HSP70-2) 1267A/G Gln351Gln
GAAGCTGCTGCAAGACTTCTTCAAC SEQ ID NO:767
GTTGAAGAAGTCTTGCAGCAGCTTC SEQ ID NO:768
GAAGCTGCTGCAGGACTTCTTCAAC SEQ ID NO:769
GTTGAAGAAGTCCTGCAGCAGCTTC SEQ ID NO:770

35. - Toll-like receptor (TLR9) 1237C/T
TCCCTCTGCCTGAAAACTCCCCCAA SEQ ID NO:771
TTGGGGGAGTTTTCAGGCAGAGGGA SEQ ID NO:772
TCCCTCTGCCTGGAAACTCCCCCAA SEQ ID NO:773
TTGGGGGAGTTTCCAGGCAGAGGGA SEQ ID NO:774

36. - Methylenetetrahydrofolate reductase (MTFHR) C677T Val222Ala
TGTCTGCGGGAGCCGATTTCATCAT SEQ ID NO:775
ATGATGAAATCGGCTCCCGCAGACA SEQ ID NO:776
TGTCTGCGGGAGTCGATTTCATCAT SEQ ID NO:777
ATGATGAAATCGACTCCCGCAGACA SEQ ID NO:778

37. - Interleukin 4 (IL4) (-590) C/T
GGAGAACATTGTCCCCCAGTGCTGG SEQ ID NO:779
CCAGCACTGGGGGACAATGTTCTCC SEQ ID NO:780
GGAGAACATTGTTCCCCAGTGCTGG SEQ ID NO:781
CCAGCACTGGGGAACAATGTTCTCC SEQ ID NO:782

38. - Interleukin 4 (IL4) (-34) C/T
ATAAACTAATTGCCTCACATTGTCA SEQ ID NO:783
TGACAATGTGAGGCAATTAGTTTAT SEQ ID NO:784
ATAAACTAATTGTCTCACATTGTCA SEQ ID NO:785
TGACAATGTGAGACAATTAGTTTAT SEQ ID NO:786

39. - Mannose-binding lectin (MBL) (A/G) Gly54Asp
ATGGGCGTGATGACACCAAGGGAGA SEQ ID NO:787
TCTCCCTTGGTGTCATCACGCCCAT SEQ ID NO:788
ATGGGCGTGATGGCACCAAGGGAGA SEQ ID NO:789
TCTCCCTTGGTGCCATCACGCCCAT SEQ ID NO:790

40. - Mannose-binding lectin (MBL) (A/G) Gly57Glu
ATGGCACCAAGGAAGAAAAGGGGGA SEQ ID NO:791
TCCCCCTTTTCTTCCTTGGTGCCAT SEQ ID NO:792
ATGGCACCAAGGGAGAAAAGGGGGA SEQ ID NO:793
TCCCCCTTTTCTCCCTTGGTGCCAT SEQ ID NO:794

41. - Mannose-binding lectin (MBL) (C/T) Arg52Cys
GGCAAAGATGGGCGTGATGGCACCA SEQ ID NO:795
TGGTGCCATCACGCCCATCTTTGCC SEQ ID NO:796
GGCAAAGATGGGTGTGATGGCACCA SEQ ID NO:797
TGGTGCCATCACACCCATCTTTGCC SEQ ID NO:798

42. - Angiotensinogen precursor (AGT) (-6) A/T
CGTGACCCGGCCAGGGGAAGAAGCT SEQ ID NO:799
CGTGACCCGGCCGGGGGAAGAAGCT SEQ ID NO:800
AGCTTCTTCCCCTGGCCGGGTCACG SEQ ID NO:801
AGCTTCTTCCCCCGGCCGGGTCACG SEQ ID NO:802

43. - Plasminogen activator inhibitor (PAI1) 4G/5G
GGACACGTGGGGGAGTCAGCCGTGT SEQ ID NO:803
ACACGGCTGACTCCCCCACGTGTCC SEQ ID NO:804
GGACACGTGGGGAGTCAGCCGTGTA SEQ ID NO:805
TACACGGCTGACTCCCCACGTGTCC SEQ ID NO:806

44. - Tumor necrosis factor alpha (TNF α) (-857) C/T
CCCCCCCCTTAACGAAGACAGGGCC SEQ ID NO:807
GGCCCTGTCTTCGTTAAGGGGGGGG SEQ ID NO:808
CCCCCCCCTTAATGAAGACAGGGCC SEQ ID NO:809
GGCCCTGTCTTCATTAAGGGGGGGG SEQ ID NO:810

45. - Tumor necrosis factor alpha (TNF α) (-308) G/A
TTGAGGGGCATGGGGACGGGGTTCA SEQ ID NO:811
TGAACCCCGTCCCCATGCCCCTCAA SEQ ID NO:812
TTGAGGGGCATGAGGACGGGGTTCA SEQ ID NO:813
TGAACCCCGTCCTCATGCCCCTCAA SEQ ID NO:814

46. - Tumor necrosis factor alpha (TNF α) (-238) G/A
CCCCTCGGAATCGGAGCAGGGAGGA SEQ ID NO:815
TCCTCCCTGCTCCGATTCCGAGGGG SEQ ID NO:816
CCCCTCGGAATCAGAGCAGGGAGGA SEQ ID NO:817
TCCTCCCTGCTCTGATTCCGAGGGG SEQ ID NO:818

47. - TPMT G238C
GTCCCCGGTCTGCAAACCTGCATAA SEQ ID NO:819
TTATGCAGGTTTGCAGACCGGGGAC SEQ ID NO:820
GTCCCCGGTCTGGAAACCTGCATAA SEQ ID NO:821
TTATGCAGGTTTCCAGACCGGGGAC SEQ ID NO:822

48. - TPMT G460A
TGGGATAGAGGAGCATTAGTTGCCA SEQ ID NO:823
TGGGATAGAGGAACATTAGTTGCCA SEQ ID NO:824
TGGCAACTAATGCTCCTCTATCCCA SEQ ID NO:825
TGGCAACTAATGTTCCTCTATCCCA SEQ ID NO:826

49. - TPMT A719G
TCTGTAAGTAGATATAACTTTTCAA SEQ ID NO:827
TTGAAAAGTTATATCTACTTACAGA SEQ ID NO:828
TCTGTAAGTAGACATAACTTTTCAA SEQ ID NO:829
TTGAAAAGTTATGTCTACTTACAGA SEQ ID NO:830

50. - MICA Trp14Gly
ACGGTGCTGTCCTGGGATGGATCTG SEQ ID NO:831
ACGGTGCTGTCCGGGGATGGATCTG SEQ ID NO:832
CAGATCCATCCCAGGACAGCACCGT SEQ ID NO:833
CAGATCCATCCCCGGACAGCACCGT SEQ ID NO:834

51. - MICA Thr24Ala
TCAGGGTTTCTCGCTGAGGTACATC SEQ ID NO:835
TCAGGGTTTCTCACTGAGGTACATC SEQ ID NO:836
GATGTACCTCAGCGAGAAACCCTGA SEQ ID NO:837
GATGTACCTCAGTGAGAAACCCTGA SEQ ID NO:838

52. - MICA Met129Val
GAGGAATGGACAATGCCCCAGTCCT SEQ ID NO:839
GAGGAATGGACAGTGCCCCAGTCCT SEQ ID NO:840
AGGACTGGGGCATTGTCCATTCCTC SEQ ID NO:841
AGGACTGGGGCACTGTCCATTCCTC SEQ ID NO:842

53. - MICA Lys173Glu
CGGCGATATCTAAAATCCGGCGTAG SEQ ID NO:843
CGGCGATATCTAGAATCCGGCGTAG SEQ ID NO:844
CTACGCCGGATTTTAGATATCGCCG SEQ ID NO:845
CTACGCCGGATTCTAGATATCGCCG SEQ ID NO:846

54. - MICA Gly175Ser
TATCTAAAATCCGGCGTAGTCCTGA SEQ ID NO:847
TATCTAAAATCCAGCGTAGTCCTGA SEQ ID NO:848

-continued

TCAGGACTACGCCGGATTTTAGATA SEQ ID NO:849
TCAGGACTACGCTGGATTTTAGATA SEQ ID NO:850

55. - SLC11A1 = NRAMP1 in the promoter region (-377 to -222): allele7
CGTGTGTGTGTATGTGTGTGTGTGT SEQ ID NO:851
CGTGTGTGTGTACGTGTGTGTGTGT SEQ ID NO:852
ACACACACACACATACACACACACG SEQ ID NO:853
ACACACACACACGTACACACACACG SEQ ID NO:854

56. - CD14 (-159) T/C
TTCCTGTTACGGTCCCCCTCCCTGA SEQ ID NO:858
TTCCTGTTACGGCCCCCCTCCCTGA SEQ ID NO:856
TCAGGGAGGGGGACCGTAACAGGAA SEQ ID NO:857
TCAGGGAGGGGGGCCGTAACAGGAA SEQ ID NO:858

57. - CD16A = FCGR3A G4985T Val158Phe
TGCAGGGGGCTTGTTGGGAGTAAAA SEQ ID NO:859
TGCAGGGGGCTTTTTGGGAGTAAAA SEQ ID NO:860
TTTTACTCCCAACAAGCCCCCTGCA SEQ ID NO:861
TTTTACTCCCAAAAAGCCCCCTGCA SEQ ID NO:862

58. - NR1I2 (-25385) C/T
CAATCCCAGGTTCTCTTTTCTACCT SEQ ID NO:863
CAATCCCAGGTTTTCTTTTCTACCT SEQ ID NO:864
AGGTAGAAAAGAGAACCTGGGATTG SEQ ID NO:865
AGGTAGAAAAGAAAACCTGGGATTG SEQ ID NO:866

59. - TUCAN/CARD8/CARDINAL (T/A) Cys10Stop
GAGCCATTATTGTTCCGTGCTGTTC SEQ ID NO:867
GAGCCATTATTGATCCGTGCTGTTC SEQ ID NO:868
GAACAGCACGGAACAATAATGGCTC SEQ ID NO:869
GAACAGCACGGATCAATAATGGCTC SEQ ID NO:870

60. - IKBL +738T/C Cys224Arg
GCAGAGGGATCCTGTCGACCCCCAC SEQ ID NO:871
GCAGAGGGATCCCGTCGACCCCCAC SEQ ID NO:872
GTGGGGGTCGACAGGATCCCTCTGC SEQ ID NO:873
GTGGGGGTCGACGGGATCCCTCTGC SEQ ID NO:874

61. - TNFRSF1B = TNFR2 G593A
GCAGAGGCAGCGGGTTGTGGAAAGC SEQ ID NO:875
GCAGAGGCAGCGAGTTGTGGAAAGC SEQ ID NO:876
GCTTTCCACAACCCGCTGCCTCTGC SEQ ID NO:877
GCTTTCCACAACTCGCTGCCTCTGC SEQ ID NO:878

62. - TNFRSF1B = TNFR2 T620C
CTGCTGCCATGGCGTGTCCCTCTCG SEQ ID NO:879
CTGCTGCCATGGTGTGTCCCTCTCG SEQ ID NO:880
CGAGAGGGACACGCCATGGCAGCAG SEQ ID NO:881
CGAGAGGGACACACCATGGCAGCAG SEQ ID NO:882

63. - MEKK1 Asp643Asn
AGTGGGAATTATCAATGGACTGCAA SEQ ID NO:883
AGTGGGAATTATTAATGGACTGCAA SEQ ID NO:884
TTGCAGTCCATTGATAATTCCCACT SEQ ID NO:885
TTGCAGTCCATTAATAATTCCCACT SEQ ID NO:886

64. - HLA-DQ4 159G/A/C
CACCAACGGGACGGAGCGCGTGCGG SEQ ID NO:887
CACCAACGGGACAGAGCGCGTGCGG SEQ ID NO:888
CACCAACGGGACCGAGCGCGTGCGG SEQ ID NO:889
CCGCACGCGCTCCGTCCCGTTGGTG SEQ ID NO:890
CCGCACGCGCTCTGTCCCGTTGGTG SEQ ID NO:891
CCGCACGCGCTCGGTCCCGTTGGTG SEQ ID NO:892

65. - HLA-DQ4 282C/T
CGAGTACTGGAACAGCCAGAAGGAA SEQ ID NO:893
CGAGTACTGGAATAGCCAGAAGGAA SEQ ID NO:894
TTCCTTCTGGCTGTTCCAGTACTCG SEQ ID NO:895
TTCCTTCTGGCTATTCCAGTACTCG SEQ ID NO:896

66. - HLA-DRB 109T/C
CGACCACGTTTCTTGTGGCAGCTTA SEQ ID NO:897
TAAGCTGCCACAAGAAACGTGGTCG SEQ ID NO:898
CGACCACGTTTCCTGTGGCAGCTTA SEQ ID NO:899
TAAGCTGCCACAGGAAACGTGGTCG SEQ ID NO:900

67. - HLA-DRB 119T/C/G/A
TCTTCTGGCAGCTTAAGTTTGAATG SEQ ID NO:901
CATTCAAACTTAAGCTGCCACAAGA SEQ ID NO:902
TCTTGTGGCAGCCTAAGTTTGAATG SEQ ID NO:903
CATTCAAACTTAGGCTGCCACAAGA SEQ ID NO:904
TCTTGTGGCAGCGTAAGTTTGAATG SEQ ID NO:905
CATTCAAACTTACGCTGCCACAAGA SEQ ID NO:906
TCTTGTGGCAGCATAAGTTTGAATG SEQ ID NO:907
CATTCAAACTTATGCTGCCACAAGA SEQ ID NO:908

68. - HLA-DRB 122A/C/G/T
TGTGGCAGCTTAAGTTTGAATGTCA SEQ ID NO:909
TGACATTCAAACTTAAGCTGCCACA SEQ ID NO:910
TGTGGCAGCTTACGTTTGAATGTCA SEQ ID NO:911
TGACATTCAAACGTAAGCTGCCACA SEQ ID NO:912
TGTGGCAGCTTAGGTTTGAATGTCA SEQ ID NO:913
TGACATTCAAACCTAAGCTGCCACA SEQ ID NO:914
TGTGGCAGCTTATGTTTGAATGTCA SEQ ID NO:915
TGACATTCAAACATAAGCTGCCACA SEQ ID NO:916

69. - HLA-DRB 129A/G
GCTTAAGTTTGAATGTCATTTCTTC SEQ ID NO:917
GAAGAAATGACATTCAAACTTAAGC SEQ ID NO:918
GCTTAAGTTTGAGTGTCATTTCTTC SEQ ID NO:919
GAAGAAATGACACTCAAACTTAAGC SEQ ID NO:920

70. - HLA-DRB 161G/A/T
CGGAGCGGGTGCGGTTGCTGGAAAG SEQ ID NO:921
CTTTCCAGCAACCGCACCCGCTCCG SEQ ID NO:922
CGGAGCGGGTGCAGTTGCTGGAAAG SEQ ID NO:923
CTTTCCAGCAACTGCACCCGCTCCG SEQ ID NO:924
CGGAGCGGGTGCTGTTGCTGGAAAG SEQ ID NO:925
CTTTCCAGCAACAGCACCCGCTCCG SEQ ID NO:926

71. - HLA-DRB 175 T/C/G
TTGCTGGAAAGATGCATCTATAACC SEQ ID NO:927
GGTTATAGATGCATCTTTCCAGCAA SEQ ID NO:928
TTGCTGGAAAGACGCATCTATAACC SEQ ID NO:929
GGTTATAGATGCGTCTTTCCAGCAA SEQ ID NO:930
TTGCTGGAAAGAGGCATCTATAACC SEQ ID NO:931
GGTTATAGATGCCTCTTTCCAGCAA SEQ ID NO:932

72. - HLA-DRB 184A/C/delA
AGATGCATCTATAACCAAGAGGAGT SEQ ID NO:933
ACTCCTCTTGGTTATAGATGCATCT SEQ ID NO:934
AGATGCATCTATCACCAAGAGGAGT SEQ ID NO:935
ACTCCTCTTGGTGATAGATGCATCT SEQ ID NO:936
AGATGCATCTATACCAAGAGGAGTC SEQ ID NO:937
GACTCCTCTTGGTATAGATGCATCT SEQ ID NO:938

73. - HLA-DRB 286C/A/T
AGCCAGAAGGACCTCCTGGAGCAGA SEQ ID NO:939
TCTGCTCCAGGAGGTCCTTCTGGCT SEQ ID NO:940
AGCCAGAAGGACATCCTGGAGCAGA SEQ ID NO:941
TCTGCTCCAGGATGTCCTTCTGGCT SEQ ID NO:942
AGCCAGAAGGACTTCCTGGAGCAGA SEQ ID NO:943
TCTGCTCCAGGAAGTCCTTCTGGCT SEQ ID NO:944

74. - HLA-DRB 305C/G
AGCAGAGGCGGGCCGCGGTGGACAC SEQ ID NO:945
GTGTCCACCGCGGCCCGCCTCTGCT SEQ ID NO:946
AGCAGAGGCGGGGCGCGGTGGACAC SEQ ID NO:947
GTGTCCACCGCGCCCCGCCTCTGCT SEQ ID NO:948

75. - IL1RN 2018 T/C EXON2
CCAACTAGTTGCTGGATACTTGCAA SEQ ID NO:949
CCAACTAGTTGCCGGATACTTGCAA SEQ ID NO:950
TTGCAAGTATCCAGCAACTAGTTGG SEQ ID NO:951
TTGCAAGTATCCGGCAACTAGTTGG SEQ ID NO:952

76. - IL1RN 2073 C/T INTRON 2
TTGCCAGGAAAGCCAATGTATGTGG SEQ ID NO:953
TTGCCAGGAAAGTCAATGTATGTGG SEQ ID NO:954
CCACATACATTGGCTTTCCTGGCAA SEQ ID NO:955
CCACATACATTGACTTTCCTGGCAA SEQ ID NO:956

77. - IL1B 3954 C/T TAQI
ACCTATCTTCTTCGACACATGGGAT SEQ ID NO:957
ACCTATCTTCTTTGACACATGGGAT SEQ ID NO:958
ATCCCATGTGTCGAAGAAGATAGGT SEQ ID NO:959
ATCCCATGTGTCAAAGAAGATAGGT SEQ ID NO:960

78. - Fas -670 G/A
TCACAGACGTTCCTGGAATGGAC SEQ ID NO:1429

-continued

| | |
|---|---|
| TCACAGACGTTTCTGGAATGGAC | SEQ ID NO:1430 |
| GTCCATTCCAGGAACGTCTGTGA | SEQ ID NO:1431 |
| GTCCATTCCAGAAACGTCTGTGA | SEQ ID NO:1432 |

79. - Caspase 9 C93T

| | |
|---|---|
| GTCCTGCTGAGCCGCGAGCTGTT | SEQ ID NO:1433 |
| GTCCTGCTGAGTCGCGAGCTGTT | SEQ ID NO:1434 |
| AACAGCTCGCGGCTCAGCAGGAC | SEQ ID NO:1435 |
| AACAGCTCGCGACTCAGCAGGAC | SEQ ID NO:1436 |

80. - TLR1 R80T (G/C)

| | |
|---|---|
| TTCTCATAATAGAATCCAGTATC | SEQ ID NO:1437 |
| TTCTCATAATACAATCCAGTATC | SEQ ID NO:1438 |
| GATACTGGATTCTATTATGAGAA | SEQ ID NO:1439 |
| GATACTGGATTGTATTATGAGAA | SEQ ID NO:1440 |

81. - TLR2 R753G (A/G)

| | |
|---|---|
| CTGCAAGCTGCGGAAGATAATGA | SEQ ID NO:1441 |
| CTGCAAGCTGCAGAAGATAATGA | SEQ ID NO:1442 |
| TCATTATCTTCCGCAGCTTGCAG | SEQ ID NO:1443 |
| TCATTATCTTCTGCAGCTTGCAG | SEQ ID NO:1444 |

82. - TLR6 S249P (T/C)

| | |
|---|---|
| TCACCAGAGGTCCAACCTTACTG | SEQ ID NO:1445 |
| TCACCAGAGGTTCAACCTTACTG | SEQ ID NO:1446 |
| CAGTAAGGTTGGACCTCTGGTGA | SEQ ID NO:1447 |
| CAGTAAGGTTGAACCTCTGGTGA | SEQ ID NO:1448 |

83. - MMP3 5A/6A

| | |
|---|---|
| GATGGGGGGAAAAACCATGTCTT | SEQ ID NO:1449 |
| GATGGGGGGAAAAAACCATGTCT | SEQ ID NO:1450 |
| AAGACATGGTTTTTCCCCCCATC | SEQ ID NO:1451 |
| AGACATGGTTTTTTCCCCCCATC | SEQ ID NO:1452 |

84. - NOD1 (CARD4) indel +32656

| | |
|---|---|
| GCCCGCCCCCCCCCACACACAGC | SEQ ID NO:1453 |
| GCCCGCCCCCCACACACACAGCA | SEQ ID NO:1454 |
| GCTGTGTGTGGGGGGGGGCGGGC | SEQ ID NO:1455 |
| TGCTGTGTGTGTGGGGGGCGGGC | SEQ ID NO:1456 |

85. - DLG5 DLG5_e26

| | |
|---|---|
| TGGGGTGGGGCAGGGGTCGCCGA | SEQ ID NO:1457 |
| TGGGGTGGGGCGGGGTCGCCGAG | SEQ ID NO:1458 |
| TCGGCGACCCCTGCCCCACCCCA | SEQ ID NO:1459 |
| CTCGGCGACCCCGCCCCACCCCA | SEQ ID NO:1460 |

86. - NOD1 rs2075817 C/T

| | |
|---|---|
| GGAGGCGGGATCTGCGTGCGGGC | SEQ ID NO:1461 |
| GGAGGCGGGATTTGCGTGCGGGC | SEQ ID NO:1462 |
| GCCCGCACGCAGATCCCGCCTCC | SEQ ID NO:1463 |
| GCCCGCACGCAAATCCCGCCTCC | SEQ ID NO:1464 |

87. - NOD 1 rs2975632 C/T

| | |
|---|---|
| GAAGGAAGCTGCGCAACACCCCT | SEQ ID NO:1465 |
| GAAGGAAGCTGTGCAACACCCCT | SEQ ID NO:1466 |
| AGGGGTGTTGCGCAGCTTCCTTC | SEQ ID NO:1467 |
| AGGGGTGTTGCACAGCTTCCTTC | SEQ ID NO:1468 |

88. - NOD1 rs3020207 A/G

| | |
|---|---|
| GAGGTGGGGTGAGCTCTTTCTGT | SEQ ID NO:1469 |
| GAGGTGGGGTGGGCTCTTTCTGT | SEQ ID NO:1470 |
| ACAGAAAGAGCTCACCCCACCTC | SEQ ID NO:1471 |
| ACAGAAAGAGCCCACCCCACCTC | SEQ ID NO:1472 |

89. - NOD1 rs2075818 C/G

| | |
|---|---|
| TACTTCTCGGCGGAAGATGCGGA | SEQ ID NO:1473 |
| TACTTCTCGGCCGAAGATGCGGA | SEQ ID NO:1474 |
| TCCGCATCTTCCGCCGAGAAGTA | SEQ ID NO:1475 |
| TCCGCATCTTCGGCCGAGAAGTA | SEQ ID NO:1476 |

90. - NOD1 rs2235099 C/T

| | |
|---|---|
| ATCTACATGGACACCATCATGGA | SEQ ID NO:1477 |
| ATCTACATGGATACCATCATGGA | SEQ ID NO:1478 |
| TCCATGATGGTGTCCATGTAGAT | SEQ ID NO:1479 |
| TCCATGATGGTATCCATGTAGAT | SEQ ID NO:1480 |

91. - NOD1 rs2075821 A/G

| | |
|---|---|
| AGTGGTCCGGCACGGGAAGACCT | SEQ ID NO:1481 |
| AGTGGTCCGGCGCGGGAAGACCT | SEQ ID NO:1482 |
| AGGTCTTCCCGTGCCGGACCACT | SEQ ID NO:1483 |
| AGGTCTTCCCGCGCCGGACCACT | SEQ ID NO:1484 |

-continued

92. - NOD1 rs2075822 C/T

| | |
|---|---|
| CGGGAATGGCACCATGGACCAGG | SEQ ID NO:1485 |
| CGGGAATGGCATCATGGACCAGG | SEQ ID NO:1486 |
| CCTGGTCCATGGTGCCATTCCCG | SEQ ID NO:1487 |
| CCTGGTCCATGATGCCATTCCCG | SEQ ID NO:1488 |

93. - NOD1 rs2907748 C/T

| | |
|---|---|
| ATTTCTTAGCCCAGCTACCTGTA | SEQ ID NO:1489 |
| ATTTCTTAGCCTAGCTACCTGTA | SEQ ID NO:1490 |
| TACAGGTAGCTGGGCTAAGAAAT | SEQ ID NO:1491 |
| TACAGGTAGCTAGGCTAAGAAAT | SEQ ID NO:1492 |

94. - NOD1 rs5743368 A/G

| | |
|---|---|
| AGAACTTGTTTAGAACTTGTCAT | SEQ ID NO:1493 |
| AGAACTTGTTTGGAACTTGTCAT | SEQ ID NO:1494 |
| ATGACAAGTTCTAAACAAGTTCT | SEQ ID NO:1495 |
| ATGACAAGTTCCAAACAAGTTCT | SEQ ID NO:1496 |

95. - DLG5 haplotype A rs2289311 C/T

| | |
|---|---|
| CAGCAGGGTCTCGATGGCCCTGC | SEQ ID NO:1497 |
| CAGCAGGGTCTTGATGGCCCTGC | SEQ ID NO:1498 |
| GCAGGGCCATCGAGACCCTGCTG | SEQ ID NO:1499 |
| GCAGGGCCATCAAGACCCTGCTG | SEQ ID NO:1500 |

96. - MTHFR A1298C

| | |
|---|---|
| GACCAGTGAAGAAAGTGTCTTTG | SEQ ID NO:1501 |
| GACCAGTGAAGCAAGTGTCTTTG | SEQ ID NO:1502 |
| CAAAGACACTTTCTTCACTGGTC | SEQ ID NO:1503 |
| CAAAGACACTTGCTTCACTGGTC | SEQ ID NO:1504 |

97. - NAT2 Ile114Thr

| | |
|---|---|
| GCAGGTGACCACTGACGGCAGGA | SEQ ID NO:1505 |
| GCAGGTGACCATTGACGGCAGGA | SEQ ID NO:1506 |
| TCCTGCCGTCAGTGGTCACCTGC | SEQ ID NO:1507 |
| TCCTGCCGTCAATGGTCACCTGC | SEQ ID NO:1508 |

98. - NAT2 Lys268Arg A/G

| | |
|---|---|
| AGAAGTGCTGAAAAATATATTTA | SEQ ID NO:1509 |
| AGAAGTGCTGAGAAATATATTTA | SEQ ID NO:1510 |
| TAAATATATTTTTCAGCACTTCT | SEQ ID NO:1511 |
| TAAATATATTTCTCAGCACTTCT | SEQ ID NO:1512 |

99. - ESR1 rs9340799 A/G

| | |
|---|---|
| GAGTGTGGTCTAGAGTTGGGATG | SEQ ID NO:1513 |
| GAGTGTGGTCTGGAGTTGGGATG | SEQ ID NO:1514 |
| CATCCCAACTCTAGACCACACTC | SEQ ID NO:1515 |
| CATCCCAACTCCAGACCACACTC | SEQ ID NO:1516 |

100. - ESR1 rs2234693 C/T

| | |
|---|---|
| AATGTCCCAGCCGTTTTATGCTT | SEQ ID NO:1517 |
| AATGTCCCAGCTGTTTTATGCTT | SEQ ID NO:1518 |
| AAGCATAAAACGGCTGGGACATT | SEQ ID NO:1519 |
| AAGCATAAAACAGCTGGGACATT | SEQ ID NO:1520 |

101. - MEFV V726A C/T

| | |
|---|---|
| GGACTACAGAGCTGGAAGCATCT | SEQ ID NO:1521 |
| GGACTACAGAGTTGGAAGCATCT | SEQ ID NO:1522 |
| AGATGCTTCCAGCTCTGTAGTCC | SEQ ID NO:1523 |
| AGATGCTTCCAACTCTGTAGTCC | SEQ ID NO:1524 |

102. - Vit D receptor (VDR) rs10735810 A/G

| | |
|---|---|
| CCATTGCCTCCATCCCTGTAAGA | SEQ ID NO:1525 |
| CCATTGCCTCCGTCCCTGTAAGA | SEQ ID NO:1526 |
| TCTTACAGGGATGGAGGCAATGG | SEQ ID NO:1527 |
| TCTTACAGGGACGGAGGCAATGG | SEQ ID NO:1528 |

103. - EMR3 E127Q C/G

| | |
|---|---|
| TTTCCTGCCCTCGGTTGTCTTTG | SEQ ID NO:1529 |
| TTTCCTGCCCTGGGTTGTCTTTG | SEQ ID NO:1530 |
| CAAAGACAACCGAGGGCAGGAAA | SEQ ID NO:1531 |
| CAAAGACAACCCAGGGCAGGAAA | SEQ ID NO:1532 |

104. - EMR1 Q496K G/T

| | |
|---|---|
| CTGGTGGTCTTGGAAGAAGCGCT | SEQ ID NO:1533 |
| CTGGTGGTCTTTGAAGAAGCGCT | SEQ ID NO:1534 |
| AGCGCTTCTTCCAAGACCACCAG | SEQ ID NO:1535 |
| AGCGCTTCTTCAAAGACCACCAG | SEQ ID NO:1536 |

105. - MTHFD1 R653Q A/G

| | |
|---|---|
| CATTGCAGACCAGATCGCACTCA | SEQ ID NO:1537 |

-continued

CATTGCAGACCGGATCGCACTCA SEQ ID NO:1538
TGAGTGCGATCTGGTCTGCAATG SEQ ID NO:1539
TGAGTGCGATCCGGTCTGCAATG SEQ ID NO:1540

106. - SHMT1 1420C/T
CAGAGGGAAGAAAGAGGCGAAGC SEQ ID NO:1541
CAGAGGGAAGAGAGAGGCGAAGC SEQ ID NO:1542
GCTTCGCCTCTTTCTTCCCTCTG SEQ ID NO:1543
GCTTCGCCTCTCTCTTCCCTCTG SEQ ID NO:1544

107. - NAT2 857G/A Gly286Glu
ACCTGGTGATGAATCCCTTACTA SEQ ID NO:1545
ACCTGGTGATGGATCCCTTACTA SEQ ID NO:1545
TAGTAAGGGATTCATCACCAGGT SEQ ID NO:1547
TAGTAAGGGATCCATCACCAGGT SEQ ID NO:1548

108. - NAT2 Arg197Gln R197Q A/G
GCTTGAACCTCAAACAATTGAAG SEQ ID NO:1549
GCTTGAACCTCGAACAATTGAAG SEQ ID NO:1550
CTTCAATTGTTTGAGGTTCAAGC SEQ ID NO:1551
CTTCAATTGTTCGAGGTTCAAGC SEQ ID NO:1552

109. - NAT2 rs1801279 191 G/A
AAGAAGAAACCAGGGTGGGTGGT SEQ ID NO:1553
AAGAAGAAACCGGGGTGGGTGGT SEQ ID NO:1554
ACCACCCACCCTGGTTTCTTCTT SEQ ID NO:1555
ACCACCCACCCCGGTTTCTTCTT SEQ ID NO:1556

110. - TLR5 Arg392Stop C/T
CCTTGGATCTCCGAGACAATGCT SEQ ID NO:1557
CCTTGGATCTCTGAGACAATGCT SEQ ID NO:1558
AGCATTGTCTCGGAGATCCAAGG SEQ ID NO:1559
AGCATTGTCTCAGAGATCCAAGG SEQ ID NO:1560

111. - CTLA4 A49G
TGAACCTGGCTACCAGGACCTGG SEQ ID NO:1561
TGAACCTGGCTGCCAGGACCTGG SEQ ID NO:1562
CCAGGTCCTGGTAGCCAGGTTCA SEQ ID NO:1563
CCAGGTCCTGGCAGCCAGGTTCA SEQ ID NO:1564

112. - MLH1 D132H C/G
CAAGTTACTCACATGGAAAACTG SEQ ID NO:1565
CAAGTTACTCAGATGGAAAACTG SEQ ID NO:1566
CAGTTTTCCATGTGAGTAACTTG SEQ ID NO:1567
CAGTTTTCCATCTGAGTAACTTG SEQ ID NO:1568

113. - MTRR 66A/G
GCAGAAGAAATATGTGAGCAAGC SEQ ID NO:1569
GCAGAAGAAATGTGTGAGCAAGC SEQ ID NO:1570
GCTTGCTCACATATTTCTTCTGC SEQ ID NO:1571
GCTTGCTCACACATTTCTTCTGC SEQ ID NO:1572

114. - ITPA 94C/A
GAGATAAGTTTACATGCACTTTG SEQ ID NO:1573
GAGATAAGTTTCCATGCACTTTG SEQ ID NO:1574
CAAAGTGCATGTAAACTTATCTC SEQ ID NO:1575
CAAAGTGCATGGAAACTTATCTC SEQ ID NO:1576

115. - MEFV E148Q C/G
GCAGCCAGCCCCAGGCCGGGAGG SEQ ID NO:1577
GCAGCCAGCCCGAGGCCGGGAGG SEQ ID NO:1578
CCTCCCGGCCTGGGGCTGGCTGC SEQ ID NO:1579
CCTCCCGGCCTCGGGCTGGCTGC SEQ ID NO:1580

116. - PTPN22 R620W C/T
TTCAGGTGTCCATACAGGAAGTG SEQ ID NO:1581
TTCAGGTGTCCGTACAGGAAGTG SEQ ID NO:1582
CACTTCCTGTATGGACACCTGAA SEQ ID NO:1583
CACTTCCTGTACGGACACCTGAA SEQ ID NO:1584

117. - LDL-receptor LRP-5 3357A/G
GCCCTGGTGGTAGACAACACACT SEQ ID NO:1585
GCCCTGGTGGTGGACAACACACT SEQ ID NO:1586
AGTGTGTTGTCTACCACCAGGGC SEQ ID NO:1587
AGTGTGTTGTCCACCACCAGGGC SEQ ID NO:1588

118. - CTLA4-C318T
ATCCAGATCCTCAAAGTGAACAT SEQ ID NO:1589
ATCCAGATCCTTAAAGTGAACAT SEQ ID NO:1590
ATGTTCACTTTGAGGATCTGGAT SEQ ID NO:1591
ATGTTCACTTTAAGGATCTGGAT SEQ ID NO:1592

-continued

119. - CCR5 rs333 32bpdel
TTTTCCATACATTAAAGATAGTC SEQ ID NO:1593
TTTTCCATACATGGTCCTGCCGC SEQ ID NO:1594
GACTATCTTTAATGTATGGAAAA SEQ ID NO:1595
GCGGCAGGACCATGTATGGAAAA SEQ ID NO:1596

120. - IL6 -174 G/C
TTGTGTCTTGCCATGCTAAAGGA SEQ ID NO:1597
TTGTGTCTTGCGATGCTAAAGGA SEQ ID NO:1598
TCCTTTAGCATGGCAAGACACAA SEQ ID NO:1599
TCCTTTAGCATCGCAAGACACAA SEQ ID NO:1600

121. - GR ER22/23EK rs6190
TGCTCAGGAGAAGGGAGATGTGA SEQ ID NO:1601
TGCTCAGGAGAGGGGAGATGTGA SEQ ID NO:1602
TCACATCTCCCTTCTCCTGAGCA SEQ ID NO:1603
TCACATCTCCCCTCTCCTGAGCA SEQ ID NO:1604

122. - P53 Arg72Pro C/G
GGCTGCTCCCCCCGTGGCCCCTG SEQ ID NO:1605
GGCTGCTCCCCGCGTGGCCCCTG SEQ ID NO:1606
CAGGGGCCACGGGGGGAGCAGCC SEQ ID NO:1607
CAGGGGCCACGGGGGGAGCAGCC SEQ ID NO:1608

123. - DLG5 P1371Q A/C
TAGCACCCCCCAAGCCAAGCAGA SEQ ID NO:1609
TAGCACCCCCCCAGCCAAGCAGA SEQ ID NO:1610
TCTGCTTGGCTTGGGGGGTGCTA SEQ ID NO:1611
TCTGCTTGGCTGGGGGGGTGCTA SEQ ID NO:1612

124. - GR ER22/23EK rs6189
CTTGCTCAGGAAAGGGGAGATGT SEQ ID NO:1613
CTTGCTCAGGAGAGGGGAGATGT SEQ ID NO:1614
ACATCTCCCCTTTCCTGAGCAAG SEQ ID NO:1615
ACATCTCCCCTCTCCTGAGCAAG SEQ ID NO:1616

125. - GR ER22/23EK rs6190
TGCTCAGGAGAAGGGAGATGTGA SEQ ID NO:1617
TGCTCAGGAGAGGGGAGATGTGA SEQ ID NO:1618
TCACATCTCCCTTCTCCTGAGCA SEQ ID NO:1619
TCACATCTCCCCTCTCCTGAGCA SEQ ID NO:1620

126. - LDL-receptor LRP-5 C135242T
AGCGTGAACCCAAAAATGTGCGG SEQ ID NO:1621
AGCGTGAACCCGAAAATGTGCGG SEQ ID NO:1622
CCGCACATTTTTGGGTTCACGCT SEQ ID NO:1623
CCGCACATTTTCGGGTTCACGCT SEQ ID NO:1624

127. - LDL-receptor LRP-5 G121513A
CTGGGGATGCTACAGAGACCAGA SEQ ID NO:1625
CTGGGGATGCTGCAGAGACCAGA SEQ ID NO:1626
TCTGGTCTCTGTAGCATCCCCAG SEQ ID NO:1627
TCTGGTCTCTGCAGCATCCCCAG SEQ ID NO:1628

128. - LDL-receptor LRP-5 C141759T
ACTGGGACCAACAGAATCGAAGT SEQ ID NO:1629
ACTGGGACCAATAGAATCGAAGT SEQ ID NO:1630
ACTTCGATTCTGTTGGTCCCAGT SEQ ID NO:1631
ACTTCGATTCTATTGGTCCCAGT SEQ ID NO:1632

129. - LDL-receptor LRP-5 G138351A
ACCAAGAAGGCCTCAGGCACGAT SEQ ID NO:1633
ACCAAGAAGGCTTCAGGCACGAT SEQ ID NO:1634
ATCGTGCCTGAGGCCTTCTTGGT SEQ ID NO:1635
ATCGTGCCTGAAGCCTTCTTGGT SEQ ID NO:1636

130. - P2X7 -298 C/T
ATGGGCATTTTCAGAATTCTCCC SEQ ID NO:1637
ATGGGCATTTTTAGAATTCTCCC SEQ ID NO:1638
GGGAGAATTCTGAAAATGCCCAT SEQ ID NO:1639
GGGAGAATTCTAAAAATGCCCAT SEQ ID NO:1640

131. - P2X7 -838 G/T
ACAGCAATTTAGTATAGGATTCC SEQ ID NO:1641
ACAGCAATTTATTATAGGATTCC SEQ ID NO:1642
GGAATCCTATACTAAATTGCTGT SEQ ID NO:1643
GGAATCCTATAATAAATTGCTGT SEQ ID NO:1644

132. - APC E1317Q C/G
CTAGGTCAGCTCAAGATCCTGTG SEQ ID NO:1645

-continued

| | |
|---|---|
| CTAGGTCAGCTGAAGATCCTGTG | SEQ ID NO:1646 |
| CACAGGATCTTGAGCTGACCTAG | SEQ ID NO:1647 |
| CACAGGATCTTCAGCTGACCTAG | SEQ ID NO:1648 |

133. - CD97-T64C A/G

| | |
|---|---|
| GTCCCGTCTCCACAGGCTAGGCA | SEQ ID NO:1649 |
| GTCCCGTCTCCGCAGGCTAGGCA | SEQ ID NO:1650 |
| TGCCTAGCCTGTGGAGACGGGAC | SEQ ID NO:1651 |
| TGCCTAGCCTGCGGAGACGGGAC | SEQ ID NO:1652 |

3.2 Production of the DNA-chip for Genotyping of Genetic Variations Associated with IBD Probes are attached to the glass slide by means of crosslinking with ultraviolet radiation and heat as previously described (Example 1.2) maintaining the relative humidity during the deposition process between 40-50% and the temperature around 20° C.

3.3 Validation of the Clinical Utility of the DNA-chip for the Diagnosis of IBD: Simultaneous, Sensitive, Specific and Reproducible Detection of Human Genetic Variations Associated with IBD Using a DNA-chip 3.3.1 Preparation of the Sample to be Hybridized The DNA of the individual is extracted from a blood sample by a filtration protocol.

All the exons and introns of interest are amplified by PCR mutliplex using pairs of oligonucleotide primers. Any suitable pair of oligonucleotides can be used which allow specific amplification of genetic fragments where a genetic variation to be detected might exist. Advantageously, those pairs which permit the said amplification in the least possible number of PCR reactions are used.

The oligonucleotide primers used to PCR amplify fragments of the genes to be detected are listed below (with corresponding genetic variations associated with IBD). The oligonucleotide primers represent an additional aspect to the present invention.

1. - Multidrug resistance protein (MDR-1) G2677T/A/C Ala893Ser/Thr/Pro (oligonucleotides to amplify the fragment of the gene "Multidrug resistance protein MDR-1" in which may exist the polymorphism G2677T/C Ala893Ser/Thr)
SEQ ID NO 1: GCATAGTAAGCAGTAGGGAGTAACA
SEQ ID NO 2: TGCAATAGCAGGAGTTGTTGA 2. - Multidrug resistance protein (MDR-1) C3435T
SEQ ID NO 3: TGCTCCCAGGCTGTTTATTT
SEQ ID NO 4: TGTTTTCAGCTGCTTGATGG 3. - CARD15 R702W
SEQ ID NO 5: AGATCACAGCAGCCTTCCTG
SEQ ID NO 6: GGATGGAGTGGAAGTGCTTG 4. - CARD15 G908R
SEQ ID NO 7: ACTGCAGAGGGAGGAGGACT
SEQ ID NO 8: CCACCTCAAGCTCTGGTGAT 5. - CARD15 1007insC
SEQ ID NO 9: ACTGGCTAACTCCTGCAGTC
SEQ ID NO 10: GAAAAACTGAGGTTCGGAGA 6. - Microsomal epoxide hydrolase (EPXH1) T612C Y113H
SEQ ID NO 11: CTCTCAACTTGGGGTCCTGA
SEQ ID NO 12: GGCGTTTTGCAAACATACCT 7. - Monocyte chemotactic protein 1 (MCP1) (-2518) G/A
SEQ ID NO 13: CCAGCCAAATGCATTCTCTT
SEQ ID NO 14: CACAGGGAAGGTGAAGGGTA -continued 8. - Interleukin 10 (IL10) (-1082) G/A
SEQ ID NO 15: CAACTGGCTCCCCTTACCTT
SEQ ID NO 16: ATGGAGGCTGGATAGGAGGT 9. - Interleukin 10 (IL10) G15R G43A
SEQ ID NO 17: AGAGGCCTCCCTGAGCTTAC
SEQ ID NO 18: TCTCGGAGATCTCGAAGCAT 10. - Interleukin 16 (IL16) (-295) T/C
SEQ ID NO 19: AACTGAAGCAATGCCAGTCC
SEQ ID NO 20: CAGAGCCAGCACCTCCTAGA 11.- Fas ligand (-843) C/T
SEQ ID NO 21: CTTGAGCCCAGGAGTTTGAG
SEQ ID NO 22: ATCAGAGGCTGCAAACCAGT 12.- Nuclear factor kappa-B (NFKB1) 94dtheATTG
SEQ ID NO 23: TGGACCGCATGACTCTATCA
SEQ ID NO 24: GGCTCTGGCTTCCTAGCAG 13.- Nuclear factor kappa-B inhibitor alpha (NFKBIA) SNP in the 3'UTR (G/A)
SEQ ID NO 25: CCAGCCATCATTTCCACTCT
SEQ ID NO 26: CCTGCACCCTGTAATCCTGT 14. - Signal transducer and activator of transcription 6 (STAT6) G2964A
SEQ ID NO 27: AGCCAATCCACTCCTTCCTT
SEQ ID NO 28: CATGCCCTAACCTGTGCTCT 15. - Interleukin 18 (IL18) TCA/TCC in the codon 35
SEQ ID NO 29: ATAGAGGCCGATTTCCTTGG
SEQ ID NO 30: TTCTGGAACAGAAGATTGTCATT 16. - Mediterranean fever gene (MEFV) E474E
SEQ ID NO 31: GCTCCCCAGAAACAAACTGA
SEQ ID NO 32: CACCTGCAGAAGTTCCCATT 17. - Mediterranean fever gene (MEFV) Q476Q
SEQ ID NO 33: GCTCCCCAGAAACAAACTGA
SEQ ID NO 34: CACCTGCAGAAGTTCCCATT 18. - Mediterranean fever gene (MEFV) D510D
SEQ ID NO 35: AGGAAGCTGGAGCAGGTGTA
SEQ ID NO 36: CCATTCTGACTGGCACTCCT 19. - Mediterranean fever gene (MEFV) P588P
SEQ ID NO 37: TCTTCTGGAACGTGGTAGGG
SEQ ID NO 38: CTAAGCAGGGGGTTCCTTGT 20. - Discs large homolog 5 (DLG5) 113G/A (R30Q)
SEQ ID NO 39: CGGCGCAATTACTACCTCTT
SEQ ID NO 40: CGTGAATGCCAGATGAACAC 21. - Colony stimulating factor receptor 1 (CSFR1) A2033T
SEQ ID NO 41: CTCCTTGCTTGCTTTCCTTG
SEQ ID NO 42: AGTAGGGATGGGATGGATGG 22. - Organic cation transporter (OCTN1, SLC22A4) 1672C/T (L503F)
SEQ ID NO 43: CAAGAGTGCCCAGAGAGTCC
SEQ ID NO 44: TTCTCCCTAAGGCATTTTGGT 23. - Organic cation transporter (OCTN2, SLC22A5) (-207G/C)
SEQ ID NO 45: CTTACATAGGGCGCACGAC
SEQ ID NO 46: AGTCCCGCTGCCTTCCTA 24. - Toll-like receptor 4 (TLR4) Asp299Gly (A/G)
SEQ ID NO 47: CTCTAGAGGGCCTGTGCAAT
SEQ ID NO 48: TCAATGTGGGAAACTGTCCA 25. - Toll-like receptor 4 (TLR4) Thr399Ile (C/T)
SEQ ID NO 49: CAACAAAGGTGGGAATGCTT
SEQ ID NO 50: TTTCAAATTGGAATGCTGGA 26. - Interleukin 1 beta -(IL1β) (-511) A/C
SEQ ID NO 51: AGGCAGAGAGGGAAGGAGAG
SEQ ID NO 52: AAACAGCGAGGGAGAAACTG -continued 27. - Superoxide dismutase 2 (SOD2) Ala16Val C/T
SEQ ID NO 53: GGCTGTGCTTTCTCGTCTTC
SEQ ID NO 54: GGTGACGTTCAGGTTGTTCA 28. - Peroxisome proliferator-activated receptor gamma (PPARG) Pro12Ala C/G
SEQ ID NO 55: AGCAAACCCCTATTCCATGC
SEQ ID NO 56: TACATAAATGCCCCCACGTC 29. - Intercellular adhesion molecule 1 (ICAM1) K469E (A/G)
SEQ ID NO 57: CTTGAGGGCACCTACCTCTG
SEQ ID ND 58: CATTATGACTGCGGCTGCTA 30. - Intercellular adhesion molecule 1 ICAM1 R241G
SEQ ID NO 59: GAATGAAATGCCCCAGAGAA
SEQ ID NO 60: ACTGTGGGGTTCAACCTCTG 31. - IBD5 locus IGR2060a_1
SEQ ID NO 61: CATACAGCACCTTCGGGTCT
SEQ ID NO 62: GGGCAGACTTTGGAACTCAG 32. - IBD5 locus IGR2198a_1
SEQ ID NO 63: CATAATCAGGGGTTGCATGA
SEQ ID NO 64: CCAGAGACACTGGGACATCA 33. - IBD5 locus IGR3096a_1
SEQ ID NO 65: CCAAGGCCATGGTGTATAGC
SEQ ID NO 66: GTGCCACCTCCCATCTCTAA 34. - Heat shock protein 70 (HSP70-2) 1267A/G Gln351Gln
SEQ ID NO 67: CTGTTTGAGGGCATCGACTT
SEQ ID NO 68: GGGGTTGATGCTCTTGTTCA 35. - Toll-like receptor (TLR9) 1237C/T
SEQ ID NO 69: AGTCAAAGCCACAGTCCACA
SEQ ID NO 70: CCCTGTTGAGAGGGTGACAT 36. - Methylenetetrahydrofolate reductase (MTFHR) C677T Val222Ala
SEQ ID NO 71: GCCTCTCCTGACTGTCATCC
SEQ ID NO 72: TCACAAAGCGGAAGAATGTG 37. - Interleukin 4 (IL4) (-590) C/T
SEQ ID NO 73: ACCCAAACTAGGCCTCACCT
SEQ ID NO 74: ACAGGTGGCATCTTGGAAAC 38. - Interleukin 4 (IL4) (-34) C/T
SEQ ID NO 75: TCATTTTCCCTCGGTTTCAG
SEQ ID NO 76: AGAACAGAGGGGGAAGCAGT 39. - Mannose-binding lectin (MBL) (A/G) Gly54Asp
SEQ ID NO 77: TGGCAGCGTCTTACTCAGAA
SEQ ID NO 78: AGAACAGCCCAACACGTACC 40. - Mannose-binding lectin (MBL) (A/G) Gly57Glu
SEQ ID NO 79: GTTCCCCTTGCACGTTCC
SEQ ID NO 80: TTGTTGGAAGAAAAGAATTGTCC 41. - Mannose-binding lectin (MBL) (C/T) Arg52Cys
SEQ ID NO 81: CAACCTCAGCCAGACAAGGT
SEQ ID NO 82: CAGCCACGTGATTGTCTAGG 42. - Angiotensinogen precursor (AGT) (-6) A/T
SEQ ID NO 83: GCTTCTGGCATCTGTCCTTC
SEQ ID NO 84: CCGGCTTACCTTCTGCTGTA 43. - Plasminogen activator inhibitor (PAI1) 4G/5G
SEQ ID NO 85: ACCTGGTCCCCAAAAGAAAT
SEQ ID NO 86: AAAGTTGGGGACACACAAGC 44. - Tumor necrosis factor alpha (TNF α) (-857) C/T
SEQ ID NO 87: ACCACAGCAATGGGTAGGAG
SEQ ID NO 88: TGGTTTCAGTCTTGGCTTCC 45. - Tumor necrosis factor alpha (TNF α) (-308) G/A y (-238) G/A
SEQ ID NO 89: ACCTGGTCCCCAAAAGAAAT -continued

SEQ ID NO 90: AAAGTTGGGGACACACAAGC

46. - TPMT G238C
SEQ ID NO 91: AAAACTTTTGTGGGGATATGGA
SEQ ID NO 92: CCCTCTATTTAGTCATTTGAAAACA

47. - TPMT G460A
SEQ ID NO 93: CCAGGTCCACACATTCCTCT
SEQ ID NO 94: TTACCATTTGCGATCACCTG

48. - TPMT A719G
SEQ ID NO 95: CATCCATTACATTTTCAGGCTTT
SEQ ID NO 96: GGTTGATGCTTTTGAAGAACG

49. - MICA Trp14Gly and Thr24Ala
SEQ ID NO 97: GAGCCCCACAGTCTTCGTTA
SEQ ID NO 98: TTTCCGTTCCCTGTCAAGTC 50. - MICA Met129Val, Lys173Glu and Gly175Ser
SEQ ID NO 99: GCTCTTCCTCTCCCAAAACC
SEQ ID NO 100: CACCATGGGGGGCACTGTTC 51. - SLC11A1 = NRAMP1 in the promoter region (-377 to -222): allele 7
SEQ ID NO 101: AACGAGGGGTCTTGGAACTC
SEQ ID NO 102: GTGTTCTGTGCCTCCCAAGT 52. - CD14 (-159)T/C
SEQ ID NO 103: CACCCACCAGAGAAGGCTTA
SEQ ID NO 104: ATCACCTCCCCACCTCTCTT 53. - CD16A = FCGR3A G4985T Val158Phe
SEQ ID NO 105: CCAAAAGCCACACTCAAAGAC
SEQ ID NO 106: CTTGAGTGATGGTGATGTTCA 54. - NR1I2 (-25385)C/T
SEQ ID NO 107: TCACCAGGGCTGGATTAAAG
SEQ ID NO 108: GCCTCTGGCAACAGTAAAGC 55. - TUCAN/CARD8/CARDINAL (T/A) Cys10Stop
SEQ ID NO 109: CTGCCGAGACGGGTATACAG
SEQ ID NO 110: GCAAATGTCTCCTGGGAATG 56. - IKBL +738T/C Cys224Arg
SEQ ID NO 111: TGAGTCCTTCTCAGCCTGGT
SEQ ID NO 112: CTCTCACGCAGCTCTTCCTC 57. - TNFRSF1B = TNFR2 G593A y T620C
SEQ ID NO 113: TTCTGGGCCAAGTTCCTCTA
SEQ ID NO 114: GGGGCAGGTCACAGAGAGT 58. - MEKK1 Asp643Asn
SEQ ID NO 115: CTGGAAAGTTTGCCAACCA
SEQ ID NO 116: ACCCAAAGTCTGGGCTCTTT 59. - HLA-DQ4 159G/A/C and 282C/T (DQB1*0401 and DQB1*0402)
SEQ ID NO 117: GTTTAAGGGCATGTGCTAC
SEQ ID NO 118: AGCTCCAACTGGTAGTTGTG 60. - HLA-DRB 109T/C, 119T/C/G/A, 122A/C/G/T, 129A/G, 161G/A/T, 175A/T/C/G, 184A/C/dtheA, 286C/A/T, 305C/G
SEQ ID NO 119: GCGCTTCGACAGCGACGTGGG
SEQ ID NO 120: CTCGCCGCTGCACTGTGAAG 61. - IL1RN 2018 T/C EXON 2 AND 2073 C/T INTRON 2
SEQ ID NO 121: ACAAGTTCTGGGGGACACAG
SEQ ID NO 122: ATTGCACCTAGGGTTTGTGC 62. - IL1B 3954 C/T TAQI
SEQ ID NO 123: TGTTCTTAGCCACCCCACTC
SEQ ID NO 124: GTGATCGTACAGGTGCATCG 63. - Fas -670 G/A
SEQ ID NO 1317: AGTTGGGGAGGTCTTGAAGG
SEQ ID NO 1318: CCTATGGCGCAACATCTGTA 64. - Caspase 9 C93T
SEQ ID NO 1319: GGAAGAGCTGCAGGTGGAC
SEQ ID NO 1320: GAATCGCTTTAGCGAACACC -continued 65. - TLR1 R80T (G/C)
SEQ ID NO 1321: TCTGAGCTTTGGACTTCTGACA
SEQ ID NO 1322: AGGGTGGCAAGAAATCTTCA 66. - TLR2 R753G (A/G)
SEQ ID NO 1323: TCCCATTTCCGTCTTTTTGA
SEQ ID NO 1324: CAAAATCCTTCCCGCTGAG 67. - TLR6 S249P (T/C)
SEQ ID NO 1325: ACTTTAGGGTGCTTACAACTGACT
SEQ ID NO 1326: GACTCTGACCAGGCATTTCC 68. - MMP3 5A/6A
SEQ ID NO 1327: GCCTCAACCTCTCAAAGTGC
SEQ ID NO 1328: AATTCACATCACTGCCACCA 69. - NOD1 (CARD4) indel +32656
SEQ ID NO 1329: CACTATCTCTCCCCGACAGC
SEQ ID NO 1330: TGGCTGTGAAGAACAGCAAA 70. - DLG5 DLG5_e26
SEQ ID NO 1331: GAGAATGCCCAGAAGATCCA
SEQ ID NO 1332: AAGCAGAATCCCTCCTCCAG 71. - NOD1 rs2075817 C/T
SEQ ID NO 1333: GGCTGCGAAGTCTGTAAACC
SEQ ID NO 1334: CGCTACATGCTTCAAACTCG 72. - NOD 1 rs2975632 C/T
SEQ ID NO 1335: GCGGCGATTACAGAAAACAT
SEQ ID NO 1336: AATGCCATGCTCCATTCTTT 73. - NOD1 rs3020207 A/G
SEQ ID NO 1337: GAGAAACCCCACAACCAGTG
SEQ ID NO 1338: AGCGGCTACTTTTCCCAAAT 74. - NOD1 rs2075818 C/G
SEQ ID NO 1339: CAGAGTCTCACCCCCACATT
SEQ ID NO 1340: CTCAGATCAGCAGGGAGAGG 75. - NOD1 rs2235099 C/T
SEQ ID NO 1341: TCCCTCCAGTGAGCAGGTAT
SEQ ID NO 1342: GCATCACCCAGGATGAAGAT 76. - NOD1 rs2075821 A/G
SEQ ID NO 1343: TCAGGTTCTTCCAGGAGTGG
SEQ ID NO 1344: CTGTTTGGCTTTGGACAACA 77. - NOD1 rs2075822 C/T
SEQ ID NO 1345: CGCCTCACTGTTCTCAGGT
SEQ ID NO 1346: AAGCTTTGCACCTTGACCTC 78. - NOD1 rs2907748 C/T
SEQ ID NO 1347: TCACTTGCTGAGAACCCAGA
SEQ ID NO 1348: GGACCCTGGGACTAGAGGAG 79. - NOD1 rs5743368 A/G
SEQ ID NO 1349: ACTTAATTGCCTGGGTGACG
SEQ ID NO 1350: GCAATTCACCAAACTGATCG 80. - DLG5 haplotype A rs2289311 C/T
SEQ ID NO 1351: CCACCTTTGCTTTTCTCACC
SEQ ID NO 1352: CTGCGTTTGTGCTTGTGTTT 81. - MTHFR A1298C
SEQ ID NO 1353: TTTGGGGAGCTGAAGGACTA
SEQ ID NO 1354: CTTTGTGACCATTCCGGTTT 82. - NAT2 Ile114Thr
SEQ ID NO 1355: TGGTGTCTCCAGGTCAATCA
SEQ ID NO 1356: GGCTGATCCTTCCCAGAAAT 83. - NAT2 Lys268Arg A/G
SEQ ID NO 1357: ACTGTTTGGTGGGCTTCATC
SEQ ID NO 1358: AGGGATCCATCACCAGGTTT 84. - ESR1 rs9340799 A/G
SEQ ID NO 1359: AGGGTTATGTGGCAATGACG
SEQ ID NO 1360: ACCAATGCTCATCCCAACTC -continued 85. - ESR1 rs2234693 C/T
SEQ ID NO 1361: CATGAACCACCATGCTCAGT
SEQ ID NO 1362: ACCACACTCAGGGTCTCTGG 86. - MEFV V726A C/T
SEQ ID NO 1363: AGAATGGCTACTGGGTGGTG
SEQ ID NO 1364: AGAGCAGCTGGCGAATGTAT 87. - Vit D receptor (VDR) rs10735810 A/G
SEQ ID NO 1365: TCAAAGTCTCCAGGGTCAGG
SEQ ID NO 1366: AGGGCGAATCATGTATGAGG 88. - EMR3 E127Q C/G
SEQ ID NO 1367: CATCCCCATTTGCTCACTTT
SEQ ID NO 1368: GCCTGGTCACTCTCAGTTCC 89. - EMR1 Q496K G/T
SEQ ID NO 1369: CGAGGAGTTCCCAACAGGTA
SEQ ID NO 1370: GGCTTTTGTCTCCTTTGTGG 90. - MTHFD1 R653Q A/G
SEQ ID NO 1371: TCCAGTGTTTGTCCATGCTG
SEQ ID NO 1372: TTCCCCTGATGTTAAAAGAAACA 91. - SHMT1 1420C/T
SEQ ID NO 1373: GTCAACAGTTCCCCTTTGGA
SEQ ID NO 1374: TGGCAGGGGATAAGTACCAG 92. - NAT2 857G/A Gly286Glu
SEQ ID NO 1375: ACTGTTTGGTGGGCTTCATC
SEQ ID NO 1376: GGGTGATACATACACAAGGGTTT 93. - NAT2 Arg197Gln R197Q A/G
SEQ ID NO 1377: CCTGCCAAAGAAGAAACACC
SEQ ID NO 1378: GATGAAGCCCACCAAACAGT 94. - NAT2 rs1801279 191 G/A
SEQ ID NO 1379: GGGGATCATGGACATTGAAG
SEQ ID NO 1380: TGTGGTCAGAGCCCAGTACA 95. - TLR5 Arg392Stop C/T
SEQ ID NO 1381: CCTTCTGGGGGAACTTTACA
SEQ ID NO 1382: CGCTGTAAGGTTGATCTTTGG 96. - CTLA4 A49G
SEQ ID NO 1383: CTGAACACCGCTCCCATAAA
SEQ ID NO 1384: CCTCCTCCATCTTCATGCTC 97. - MLH1 D132N C/G
SEQ ID NO 1385: CCGGGATCAGGAAAGAAGAT
SEQ ID NO 1386: AGGGGCTTTCAGTTTTCCAT 98. - MTRR 66A/G
SEQ ID NO 1387: TGTGTGGGTATTGTTGCATTG
SEQ ID NO 1388: CCATGTACCACAGCTTGCTC 99. - ITPA 94C/A
SEQ ID NO 1389: CTCATTGGTGGGGAAGAAGA
SEQ ID NO 1390: CGAACTGCCTCCTGACATTT 100. - MEFV E148Q C/G
SEQ ID NO 1391: GCCCAGGAGCCTGAAGAC
SEQ ID NO 1392: CCTTCTCTCTGCGTTTGCTC 101. - PTPN22 R620W C/T
SEQ ID NO 1393: GGCCTCAATGAACTCCTCAA
SEQ ID NO 1394: GGATAGCAACTGCTCCAAGG 102. - LDL-receptor LRP-5 3357A/G
SEQ ID NO 1395: ACTTCACCAACATGCAGGAC
SEQ ID NO 1396: CAGGTCACAGCTCTCAATGC 103. - CTLA4 -C318T
SEQ ID NO 1397: TGGTTAAGGATGCCCAGAAG
SEQ ID NO 1398: CGAAAAGACAACCTCAAGCAC 104. - CCR5 rs333 32bpdel
SEQ ID NO 1399: CTGTCGTCCATGCTGTGTTT
SEQ ID NO 1400: GACCAGCCCCAAGATGACTA -continued

```
105. - IL6 -174 G/C
SEQ ID NO 1401:       GCCTCAATGACGACCTAAGC
SEQ ID NO 1402:       TCATGGGAAAATCCCACATT

106. - GR ER22/23EK rs6190
SEQ ID NO 1403:       AAGAAAACCCCAGCAGTGTG
SEQ ID NO 1404:       GCCTTTTGGAAAATCAACCA

107. - P53 Arg72Pro C/G
SEQ ID NO 1405:       GAAGACCCAGGTCCAGATGA
SEQ ID NO 1406:       ACTGACCGTGCAAGTCACAG

108. - DLG5 P1371Q A/C
SEQ ID NO 1407:       CTGTCATCGACCCACTGATG
SEQ ID NO 1408:       GACACAGGGAAGGCTCACA

109. - GR ER22/23EK rs6189
SEQ ID NO 1409:       AAGAAAACCCCAGCAGTGTG
SEQ ID NO 1410:       GCCTTTTGGAAAATCAACCA

110. - GR ER22/23EK rs6190
SEQ ID NO 1411:       AAGAAAACCCCAGCAGTGTG
SEQ ID NO 1412:       GCCTTTTGGAAAATCAACCA

111. - LDL-receptor LRP-5 C135242T
SEQ ID NO 1413:       GTAGATGAAGTCCCCCAGCA
SEQ ID NO 1414:       GCATTGAACCCGTCTTGTTT

112. - LDL-receptor LRP-5 G121513A
SEQ ID NO 1415:       GCACCGACATTTACTGACACC
SEQ ID NO 1416:       ATGAGGCTGGAGAAGAAGCA

113. - LDL-receptor LRP-5 C141759T
SEQ ID NO 1417:       GAGCACGTGGTGGAGTTTG
SEQ ID NO 1418:       TTGTCCAAGTCCCTCCACAC

114. - LDL-receptor LRP-5 G138351A
SEQ ID NO 1419:       ATGGCCACGTCGTTGTTATT
SEQ ID NO 1420:       AGCCACCTGTGCTTCTTCAC

115. - P2X7 -298 C/T
SEQ ID NO 1421:       GTGTTCAGAGGATGGGCATT
SEQ ID NO 1422:       GGGGCTGAATAAAGGGTTGT

116. - P2X7 -838 G/T
SEQ ID NO 1423:       GAGCTACGCACATCACCAAA
SEQ ID NO 1424:       GGTCCTCTTTGCAATCCAGA

117. - APC E1317Q C/G
SEQ ID NO 1425:       CAGACGACACAGGAAGCAGA
SEQ ID NO 1426:       TGTCTGAGCACCACTTTTGG

118. - CD97 -T64C A/G
SEQ ID NO 1427:       GGGAAAGAGTGAGTGGGACA
SEQ ID NO 1428:       CCCCTGGGTCTGTGTTTTTA
```

The multiplex PCRs are carried out simultaneously under the same time and temperature conditions which permit specific amplification of the gene fragments where the genetic variation to be detected might exist. Once the PCR multiplex has finished, agarose gel analysis is used to check that amplification has taken place Next, the sample to be hybridized (product of the amplification) is subjected to fragmentation with a DNase and the resulting fragmentation products are then subjected to indirect labelling. A terminal transferase adds a nucleotide, joined to one member of a pair of molecules that specifically bind to one another (e.g. biotin allowing subsequent binding to streptavidin) to the ends of these small DNA fragments.

Before applying the sample to the DNA-chip, the sample is denatured by heating to 95° C. for 5 minutes and, the "ChipMap Kit Hybridization Buffer" (Ventana Medical System) is added.

Next, the stages of hybridization are performed, scanning the slide, quantification of the image and interpretation of the results, following the procedure described in the sections 1.3.2, 1.3.3, 1.3.4 and 1.3.5 of Example 1.

Example 4

Identification of the Genotype of 9 Individuals for the Human Genetic Variations Associated with IBD Using a DNA-chip 4.1 DNA Extraction DNA was extracted from 9 individuals (patients) by conventional methods to characterize the genetic variations found in these individuals with regard to the genetic variation A2033T of the gene CSFR1 associated with the development of Crohn's Disease. Genetic analysis of the region of interest by sequencing determined that 3 of the patients had genotype AA, another 3 genotype AT (heterozygotes) and the other 3 genotype TT.

4.2 Design of the Probes 4 probes were designed for the detection of the genetic variation A2033T CSFR1S:

```
AAACCCTTATTCACCTAATCACAGC     SEQ ID NO: 715

GCTGTGATTAGGTGAATAAGGGTTT     SEQ ID NO: 716

AAACCCTTATTCTCCTAATCACAGC     SEQ ID NO: 717

GCTGTGATTAGGAGAATAAGGGTTT     SEQ ID NO: 718
```

4.3 Production of the DNA-chip for the Detection of Human Genetic Variations Associated with IBD The designed oligonucleotides were printed onto the slide with a microarrayer as described in Example 3.2.

4.4 PCR and Labelling the Sample

The region of the gene CSFR1 which permitted the analysis of the genetic variation of interest was amplified by means of PCR multiplex using specific primers (SEQ ID NO 41 and SEQ ID NO 42). The product of the amplification was fragmented and labelled as indicated in Example 1.3.1.

4.5 Hybridization of the Samples

Hybridization was carried out in an automatic hybridization station as described in Example 1.3.2.

4.6 Analysis of the Results

The slides were placed in the scanner. The signal emitted by the bound fluorophore on being stimulated by the laser was scanned (Example 1.3.3) and the image obtained from the signal at the points where hybridization had taken place was quantified (Example 1.3.4).

The analysis of the results was carried out using the algorithm described in Example 1.3.5. Using this algorithm allowed the characterization of the genotypes for each of the 9 subjects tested with complete correspondence to the genotypes obtained by nucleotide sequence analysis of the subjects' samples.

Figure 2:
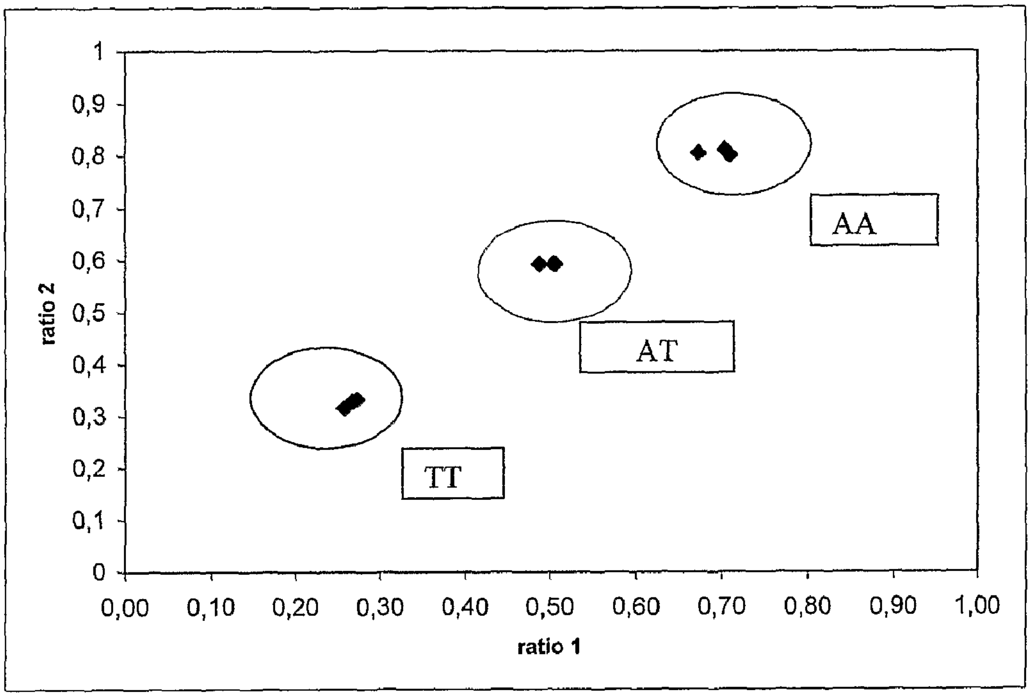
FIG. 2 shows a representation of ratios 1 and 2 in a study of 9 patients, 3 of genotype AA, 3 of genotype AT and 3 of genotype TT at genetic variation A2033T in the CSFR1 gene (Example 4).
Figure 3:
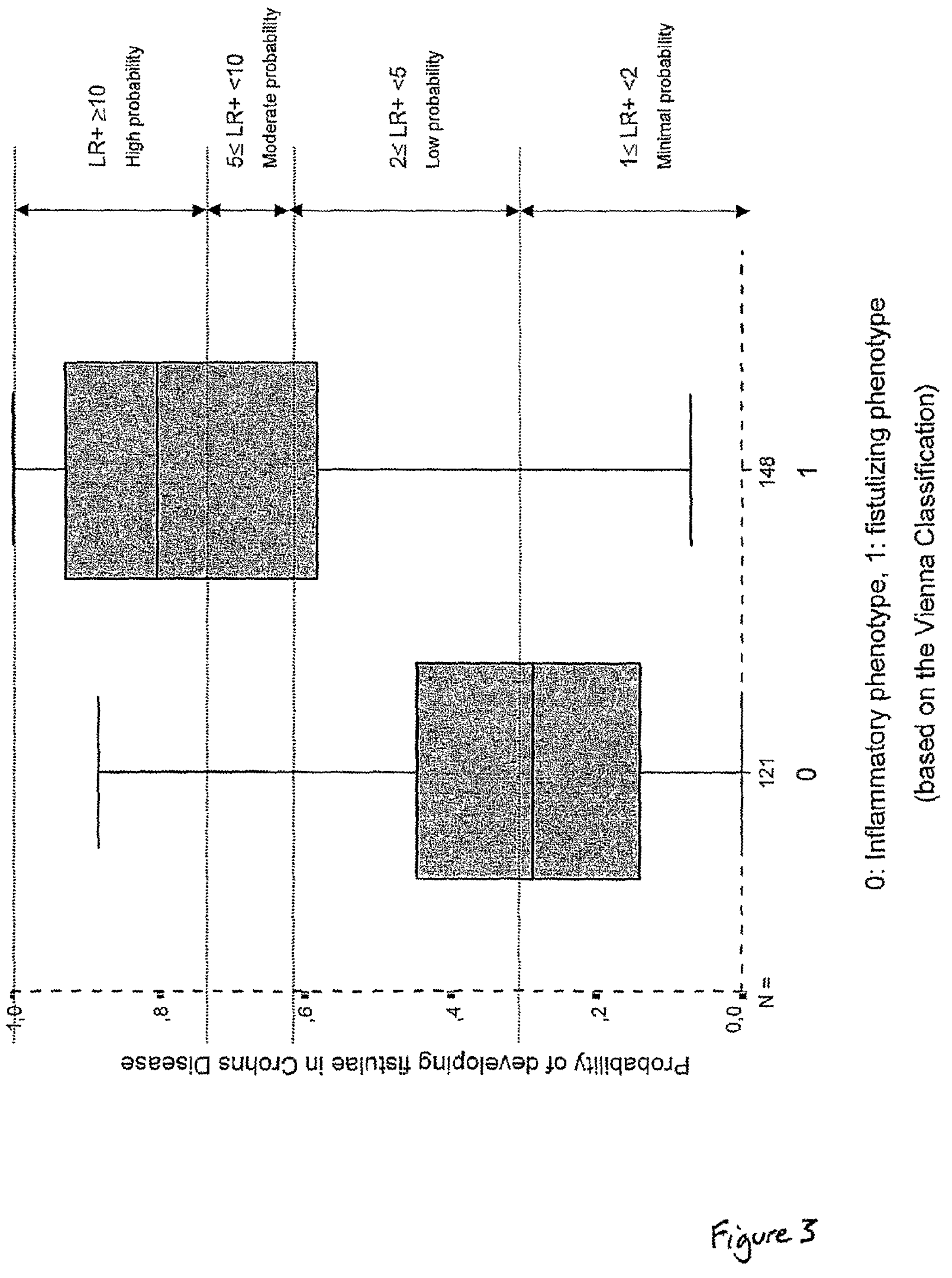
FIGS. 3-10 (Example 6) demonstrate the respective probabilities associated with the development of determined phenotypes (disease prognosis), based on genotypic data obtained with a DNA-chip according to the invention, for each of the eight IBD phenotypes analysed.
Figure 4:
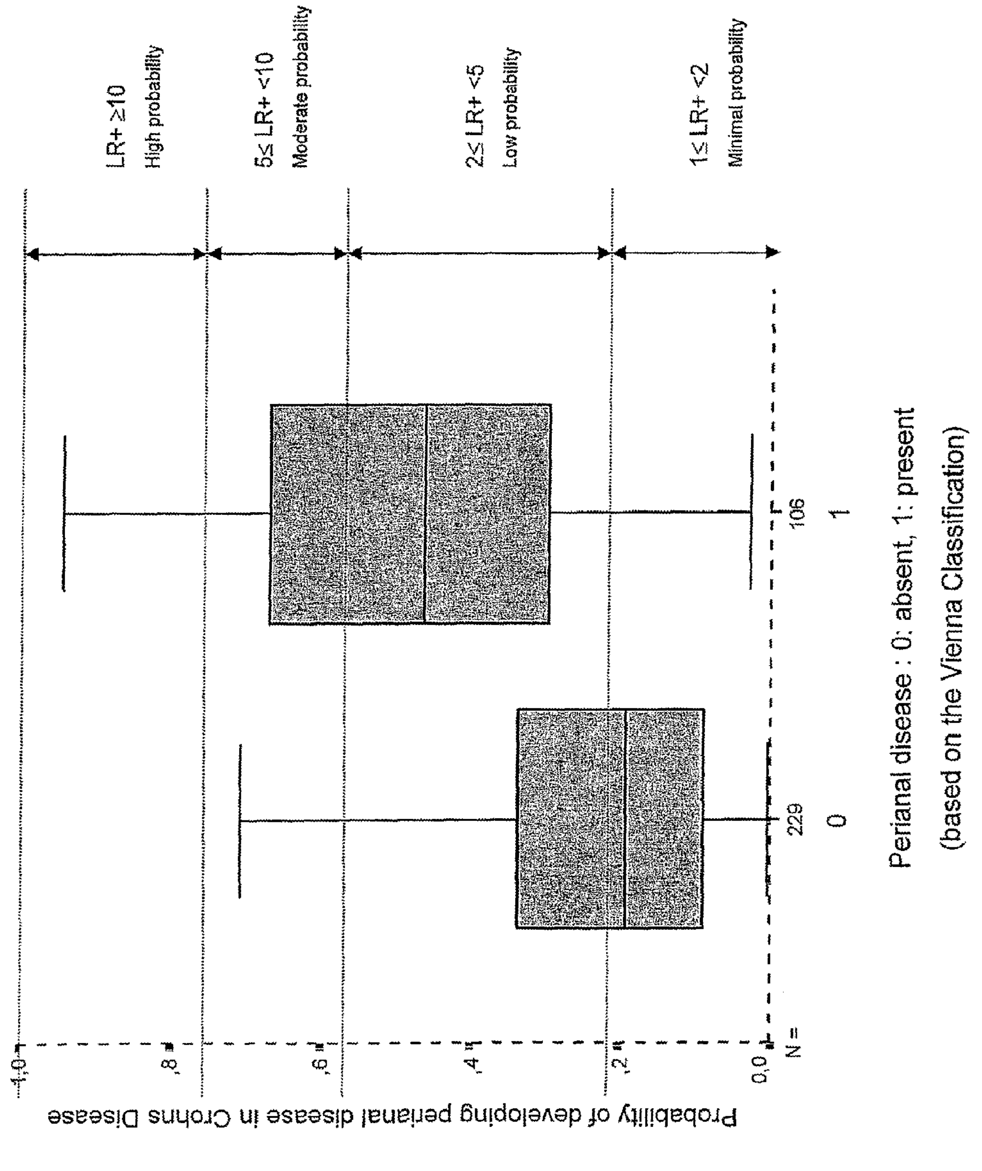
Figure 5:
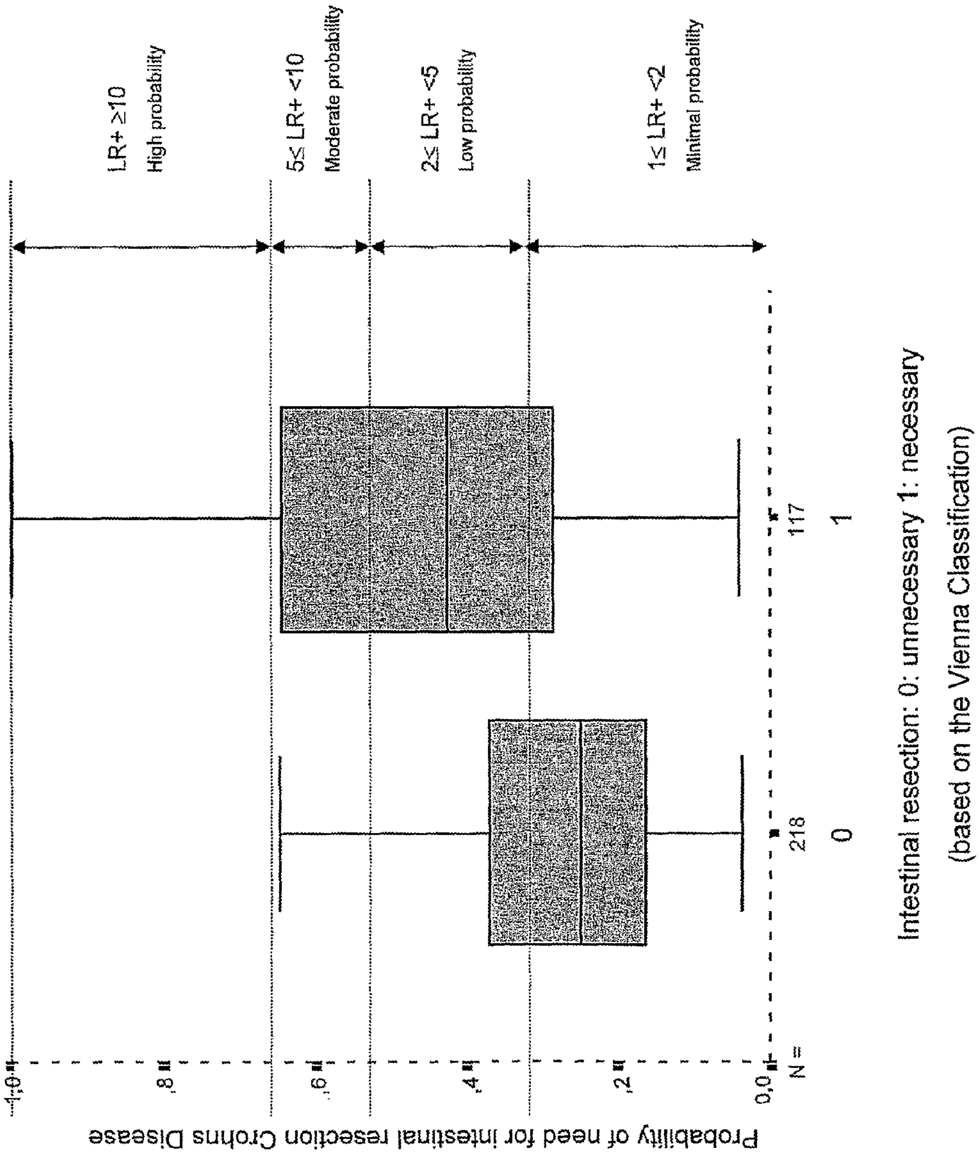
Figure 6:
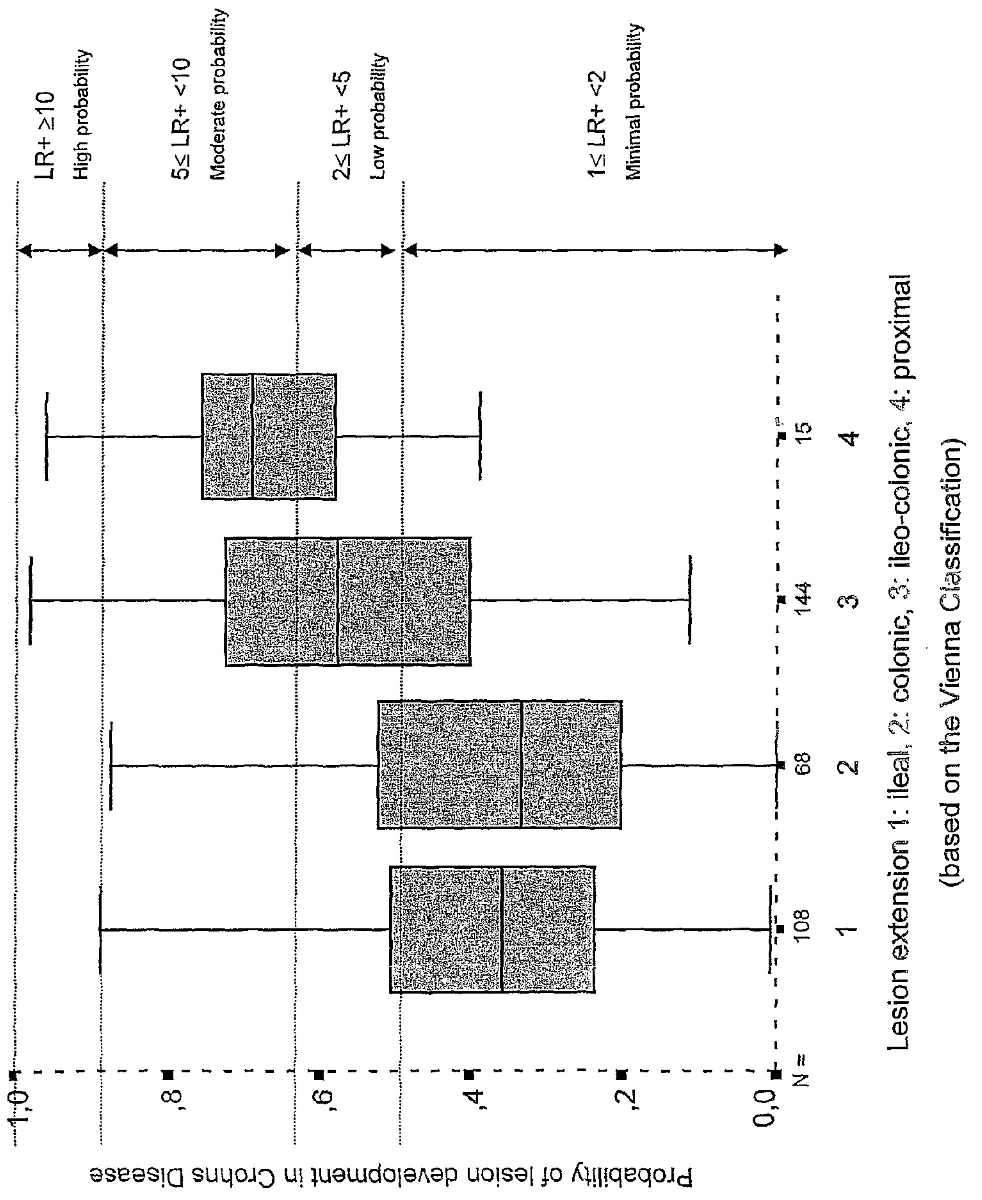
Figure 7:
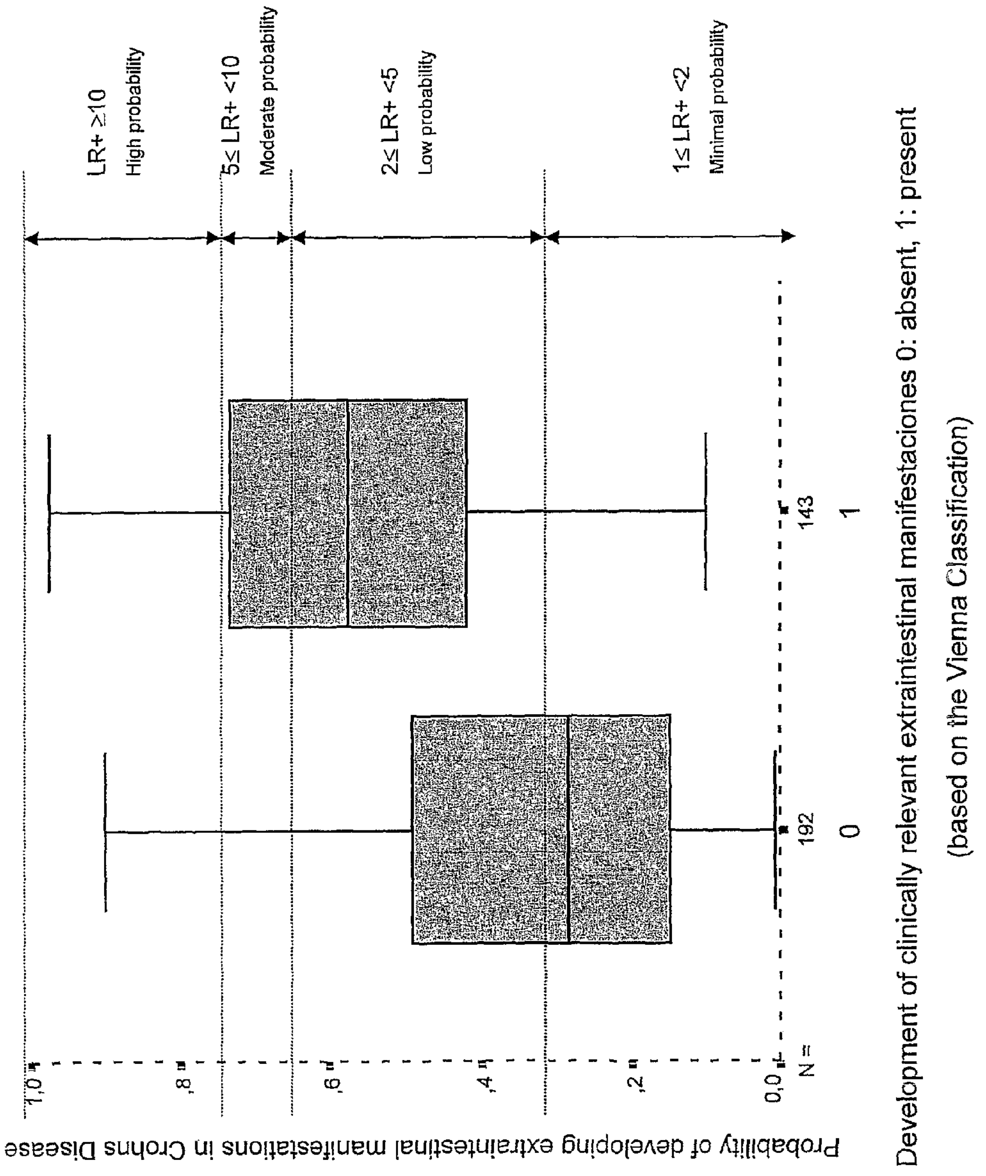

FIG. 2 shows the representation of ratios 1 and 2 and allows the genotypes of the 9 patients to be characterised.

Table 8 shows the linear functions obtained for the three genotype groups where 10 replicates of each of the 4 probes were used; "X" is ratio 1; "Y" is ratio 2; "0" corresponds to the genotype TT; "1" corresponds to the genotype AT; and "2" corresponds to the genotype AA.

TABLE 8

| Coefficients of the functions used for genotyping | | | |
|---|---|---|---|
| CLASS | 0 | 1 | 2 |
| X | 427.052 | 863.0399 | 1270.836 |
| Y | 8937.156 | 16216.35 | 21969.05 |
| (Constant) | −1514.27 | −5026.28 | −9293.69 |

A donor with genotype AA had ratios 1 and 2 of 0.26 and 0.32 respectively. On substituting these ratios in the linear functions, it is observed that function 2 shows a greater absolute value. From this we can see how the algorithm of the invention perfectly classifies donors when 10 replicates of each of the 4 probes are used.

Table 9 shows the linear functions obtained when 8 replicates of each of the 4 probes were used.

TABLE 9

| Coefficients of the functions used for genotyping | | | |
|---|---|---|---|
| CLASS | 0 | 1 | 2 |
| X | 751.6869 | 1446.046 | 2065.363 |
| Y | 10369.47 | 18620.87 | 25204.48 |
| (Constant) | −1813.36 | −5892.27 | −10868.5 |

The same donor with genotype AA had the same ratios 1 and 2 of 0.26 and 0.32, respectively. On substituting these ratios in the linear functions, it is observed that function 2 shows a greater absolute value. From this, we can see the algorithm of the invention perfectly classifies patients when 8 replicates of each of the 4 probes are used.

Table 10 shows the linear functions obtained when 6 replicates of each of the 4 probes are used.

TABLE 10

| Coefficients of the functions used for genotyping | | | |
|---|---|---|---|
| CLASS | 0 | 1 | 2 |
| X | 227.5676 | 531.6475 | 798.1821 |
| Y | 11864.89 | 21269.96 | 28789.95 |
| (Constant) | −1992.22 | −6460.62 | −11889.5 |

The same donor with genotype AA had the same ratios 1 and 2 of 0.26 and 0.32, respectively. On substituting these ratios in the linear functions, it is observed that function 2 shows a greater absolute value. From this, we can see the algorithm of the invention perfectly classifies patients when 6 replicates are used for each of the 4 probes.

Example 5

Detection of Human Genetic Variations Associated with Adverse Reactions to Drugs, Using a DNA-chip 5.1 Design of the DNA-chip for the Detection of Human Genetic Variations Associated with Adverse Reactions to Drugs A DNA-chip was designed and produced to detect adverse pharmaceutical reactions. The chip permits the simultaneous, sensitive, specific and reproducible detection of genetic variations associated with adverse reactions to drugs. Illustrative examples of these human genetic variations are listed in Table 3.

In this case, the DNA-chip consists of a support which comprises a plurality of probes on its surface which permit the detection of the genetic variations. These probes are capable of hybridizing with (amplified) target sequences of genes associated with the adverse reactions to be studied. The DNA sequences of each of the probes used are listed below. In general, the name of the gene and the genetic variation (change of amino acid, change of nucleotide, "ins": insertion, "del": deletion)] are given.

```
1. - Beta-1-adrenergic receptor (ADRB1) Arg389 Gly
(probes to detect the polymorphism Arg389 Gly in
the gene of the Beta-1 adrenergic receptor)
AAGGCCTTCCAGCGACTGCTCTGCT       SEQ ID NO: 961
AAGGCCTTCCAGGGACTGCTCTGCT       SEQ ID NO: 962
AGCAGAGCAGTCGCTGGAAGGCCTT       SEQ ID NO: 963
AGCAGAGCAGTCCCTGGAAGGCCTT       SEQ ID NO: 964

2. - Beta-2-adrenergic receptor (ADRB2) Arg16Gly
CTGGCACCCAATGGAAGCCATGCGC       SEQ ID NO: 965
CTGGCACCCAATAGAAGCCATGCGC       SEQ ID NO: 966
GCGCATGGCTTCCATTGGGTGCCAG       SEQ ID NO: 967
GCGCATGGCTTCTATTGGGTGCCAG       SEQ ID NO: 968

3. - Beta-2-adrenergic receptor (ADRB2) Gln27Glu
GACGTCACGCAGCAAAGGGACGAGG       SEQ ID NO: 969
GACGTCACGCAGGAAAGGGACGAGG       SEQ ID NO: 970
CCTCGTCCCTTTGCTGCGTGACGTC       SEQ ID NO: 971
CCTCGTCCCTTTCCTGCGTGACGTC       SEQ ID NO: 972

4. - Dopamine D3 receptor (DRD3) Ser9Gly
AGTTCAGGTGGCCACTCAGCTGGCT       SEQ ID NO: 973
AGTTCAGGTGGCTACTCAGCTGGCT       SEQ ID NO: 974
AGCCAGCTGAGTGGCCACCTGAACT       SEQ ID NO: 975
AGCCAGCTGAGTAGCCACCTGAACT       SEQ ID NO: 976

5. - Serotonin 2A receptor (HTR2A) His452Tyr
CTAGGAAAGCAGCATTCTGAAGAGG       SEQ ID NO: 977
CTAGGAAAGCAGTATTCTGAAGAGG       SEQ ID NO: 978
CCTCTTCAGAATGCTGCTTTCCTAG       SEQ ID NO: 979
CCTCTTCAGAATACTGCTTTCCTAG       SEQ ID NO: 980

6. - Serotonin 2A receptor (HTR2A) T102C
GTTAGCTTCTCCGGAGTTAAAGTCA       SEQ ID NO: 981
GTTAGCTTCTCCAGAGTTAAAGTCA       SEQ ID NO: 982
TGACTTTAACTCCGGAGAAGCTAAC       SEQ ID NO: 983
TGACTTTAACTCTGGAGAAGCTAAC       SEQ ID NO: 984

7. - Catechol-O-methyltransferase (COMT) Val108Met
GATTTCGCTGGCGTGAAGGACAAGG       SEQ ID NO: 985
GATTTCGCTGGCATGAAGGACAAGG       SEQ ID NO: 986
CCTTGTCCTTCACGCCAGCGAAATC       SEQ ID NO: 987
CCTTGTCCTTCATGCCAGCGAAATC       SEQ ID NO: 988

8. - Glutathione S transferase class 1 (GSTP1)
Ile105Val
CGCTGCAAATACATCTCCCTCATCT       SEQ ID NO: 989
CGCTGCAAATACGTCTCCCTCATCT       SEQ ID NO: 990
AGATGAGGGAGATGTATTTGCAGCG       SEQ ID NO: 991
AGATGAGGGAGACGTATTTGCAGCG       SEQ ID NO: 992

9. - Adducin 1 (ADD1) Gly460Trp
GCTTCCGAGGAAGGGCAGAATGGAA       SEQ ID NO: 993
GCTTCCGAGGAATGGCAGAATGGAA       SEQ ID NO: 994
TTCCATTCTGCCCTTCCTCGGAAGC       SEQ ID NO: 995
TTCCATTCTGCCATTCCTCGGAAGC       SEQ ID NO: 996

10. - DNA Repair Enzyme XRCC1 Arg399Gln
GGCTGCCCTCCCGGAGGTAAGGCCT       SEQ ID NO: 997
GGCTGCCCTCCCAGAGGTAAGGCCT       SEQ ID NO: 998
AGGCCTTACCTCCGGGAGGGCAGCC       SEQ ID NO: 999
AGGCCTTACCTCTGGGAGGGCAGCC       SEQ ID NO: 1000

11. - Cytochrome P450 1A1 (CYP1A1) Ile462Val
ATCGGTGAGACCATTGCCCGCTGGG       SEQ ID NO: 1001
ATCGGTGAGACCGTTGCCCGCTGGG       SEQ ID NO: 1002
CCCAGCGGGCAATGGTCTCACCGAT       SEQ ID NO: 1003
CCCAGCGGGCAACGGTCTCACCGAT       SEQ ID NO: 1004
```

-continued

12. - Angiotensin II receptor, type 1 (AGTR1) A1166C
TACCAAATGAGCATTAGCTACTTTT SEQ ID NO: 1005
TACCAAATGAGCCTTAGCTACTTTT SEQ ID NO: 1006
AAAAGTAGCTAATGCTCATTTGGTA SEQ ID NO: 1007
AAAAGTAGCTAAGGCTCATTTGGTA SEQ ID NO: 1008

13. - Bradykinin receptor B2 (BDKRB2) C-58T
TGCCATCTAACCATCTTTTCTTCTC SEQ ID NO: 1009
TGCCATCTAACCGTCTTTTCTTCTC SEQ ID NO: 1010
GAGAAGAAAAGATGGTTAGATGGCA SEQ ID NO: 1011
GAGAAGAAAAGACGGTTAGATGGCA SEQ ID NO: 1012

14. - Angiotensinogen (AGT) Met235Thr
GCTGCTCCCTGACGGGAGCCAGTGT SEQ ID NO: 1013
GCTGCTCCCTGATGGGAGCCAGTGT SEQ ID NO: 1014
ACACTGGCTCCCGTCAGGGAGCAGC SEQ ID NO: 1015
ACACTGGCTCCCATCAGGGAGCAGC SEQ ID NO: 1016

15. - Cytochrome P450 2C9 (CYP2C9) C430T
AGCATTGAGGACCGTGTTCAAGAGG SEQ ID NO: 1017
AGCATTGAGGACTGTGTTCAAGAGG SEQ ID NO: 1018
CCTCTTGAACACGGTCCTCAATGCT SEQ ID NO: 1019
CCTCTTGAACACAGTCCTCAATGCT SEQ ID NO: 1020

16. - Cytochrome P450 2C9 (CYP2C9) A1075C
GTCCAGAGATACATTGACCTTCTCC SEQ ID NO: 1021
GTCCAGAGATACCTTGACCTTCTCC SEQ ID NO: 1022
GGAGAAGGTCAATGTATCTCTGGAC SEQ ID NO: 1023
GGAGAAGGTCAAGGTATCTCTGGAC SEQ ID NO: 1024

17. - Cytochrome P450 2C9 (CYP2C9) 818delA
TGAAAATGGAGAAGGTAAAATGTAA SEQ ID NO: 1025
TGAAAATGGAGAGGTAAAATGTAAA SEQ ID NO: 1026
TTACATTTTACCTTCTCCATTTTCA SEQ ID NO: 1027
TTTACATTTTACCTCTCCATTTTCA SEQ ID NO: 1028

18. - Cytochrome P450 2C9 (CYP2C9) T1076C
TCCAGAGATACATTGACCTTCTCCC SEQ ID NO: 1029
TCCAGAGATACACTGACCTTCTCCC SEQ ID NO: 1030
GGGAGAAGGTCAATGTATCTCTGGA SEQ ID NO: 1031
GGGAGAAGGTCAGTGTATCTCTGGA SEQ ID NO: 1032

19. - Cytochrome P450 2C9 (CYP2C9) C1080G
GAGATACATTGACCTTCTCCCCACC SEQ ID NO: 1033
GAGATACATTGAGCTTCTCCCCACC SEQ ID NO: 1034
GGTGGGGAGAAGGTCAATGTATCTC SEQ ID NO: 1035
GGTGGGGAGAAGCTCAATGTATCTC SEQ ID NO: 1036

20. - Cytochrome P450 2D6 (CY2D6) H324P
TGCACATCCGGAGGTAGGATCATGA SEQ ID NO: 1037
TGCACATCCGGATGTAGGATCATGA SEQ ID NO: 1038
TCATGATCCTACCTCCGGATGTGCA SEQ ID NO: 1039
TCATGATCCTACATCCGGATGTGCA SEQ ID NO: 1040

21. - Cytochrome P450 2D6 (CYP2D6) V136V
GCGCTTCTCCGTGTCCACCTTGCGC SEQ ID NO: 1041
GCGCTTCTCCGTCTCCACCTTGCGC SEQ ID NO: 1042
GCGCAAGGTGGACACGGAGAAGCGC SEQ ID NO: 1043
GCGCAAGGTGGAGACGGAGAAGCGC SEQ ID NO: 1044

22. - Cytochrome P450 2D6 (CYP2D6) V11M
GTGCCCCTGGCCGTGATAGTGGCCA SEQ ID NO: 1045
GTGCCCCTGGCCATGATAGTGGCCA SEQ ID NO: 1046
TGGCCACTATCACGGCCAGGGGCAC SEQ ID NO: 1047
TGGCCACTATCATGGCCAGGGGCAC SEQ ID NO: 1048

23. - Cytochrome P450 2D6 (CYP2D6) C882G
GCGGCGCCGCAACTGCAGAGGGAGG SEQ ID NO: 1049
GCGGCGCCGCAAGTGCAGAGGGAGG SEQ ID NO: 1050
CCTCCCTCTGCAGTTGCGGCGCCGC SEQ ID NO: 1051
CCTCCCTCTGCACTTGCGGCGCCGC SEQ ID NO: 1052

24. - Cytochrome P450 2D6 (CYP2D6) C1038T
GATCCTGGGTTTCGGGCCGCGTTCC SEQ ID NO: 1053
GATCCTGGGTTTTGGGCCGCGTTCC SEQ ID NO: 1054
GGAACGCGGCCCGAAACCCAGGATC SEQ ID NO: 1055
GGAACGCGGCCCAAAACCCAGGATC SEQ ID NO: 1056

-continued

25. - Cytochrome P450 2D6 (CYP2D6) G4180C
CTTTCCTGGTGAGCCCATCCCCCTA SEQ ID NO: 1057
CTTTCCTGGTGACCCCATCCCCCTA SEQ ID NO: 1058
TAGGGGGATGGGCTCACCAGGAAAG SEQ ID NO: 1059
TAGGGGGATGGGGTCACCAGGAAAG SEQ ID NO: 1060

26. - Cytochrome P450 2D6 (CYP2D6) A1847G
CTCCCACCCCCAGGACGCCCCTTTC SEQ ID NO: 1061
CTCCCACCCCCAAGACGCCCCTTTC SEQ ID NO: 1062
GAAAGGGGCGTCCTGGGGGTGGGAG SEQ ID NO: 1063
GAAAGGGGCGTCTTGGGGGTGGGAG SEQ ID NO: 1064

27. - Cytochrome P450 2D6 (CYP2D6) C-1584G
CTTGGAAGAACCCGGTCTCTACAAA SEQ ID NO: 1065
CTTGGAAGAACCGGGTCTCTACAAA SEQ ID NO: 1066
TTTGTAGAGACCGGGTTCTTCCAAG SEQ ID NO: 1067
TTTGTAGAGACCCGGTTCTTCCAAG SEQ ID NO: 1068

28. - Cytochrome P450 2D6 (CYP2D6) C100T
GCTGCACGCTACCCACCAGGCCCCC SEQ ID NO: 1069
GCTGCACGCTACTCACCAGGCCCCC SEQ ID NO: 1070
GGGGGCCTGGTGGGTAGCGTGCAGC SEQ ID NO: 1071
GGGGGCCTGGTGAGTAGCGTGCAGC SEQ ID NO: 1072

29. - Cytochrome P450 2D6 (CYP2D6) 138insT
GCTGGGCAACCTGCTGCATGTGGAC SEQ ID NO: 1073
GCTGGGCAACCTTGCTGCATGTGGA SEQ ID NO: 1074
GTCCACATGCAGCAGGTTGCCCAGC SEQ ID NO: 1075
TCCACATGCAGCAAGGTTGCCCAGC SEQ ID NO: 1076

30. - Cytochrome P450 2D6 (CYP2D6) C1023T
CTGTGCCCATCACCCAGATCCTGGG SEQ ID NO: 1077
CTGTGCCCATCATCCAGATCCTGGG SEQ ID NO: 1078
CCCAGGATCTGGGTGATGGGCACAG SEQ ID NO: 1079
CCCAGGATCTGGATGATGGGCACAG SEQ ID NO: 1080

31. - Cytochrome P450 2D6 (CYP2D6) G1659A
AGGCGCTTCTCCGTGTCCACCTTGC SEQ ID NO: 1081
AGGCGCTTCTCCATGTCCACCTTGC SEQ ID NO: 1082
GCAAGGTGGACACGGAGAAGCGCCT SEQ ID NO: 1083
GCAAGGTGGACATGGAGAAGCGCCT SEQ ID NO: 1084

32. - Cytochrome P450 2D6 (CYP2D6) 1707T/del
TCGCTGGAGCAGTGGGTGACCGAGG SEQ ID NO: 1085
TCGCTGGAGCAGGGGTGACCGAGGA SEQ ID NO: 1086
CCTCGGTCACCCACTGCTCCAGCGA SEQ ID NO: 1087
TCCTCGGTCACCCCTGCTCCAGCGA SEQ ID NO: 1088

33. - Cytochrome P450 2D6 (CYP2D6) G1758A
GCCAACCACTCCGGTGGGTGATGGG SEQ ID NO: 1089
GCCAACCACTCCAGTGGGTGATGGG SEQ ID NO: 1090
CCCATCACCCACCGGAGTGGTTGGC SEQ ID NO: 1091
CCCATCACCCACTGGAGTGGTTGGC SEQ ID NO: 1092

34. - Cytochrome P450 2D6 (CYP2D6) G1758T
GCCAACCACTCCGGTGGGTGATGGG SEQ ID NO: 1093
GCCAACCACTCCTGTGGGTGATGGG SEQ ID NO: 1094
CCCATCACCCACCGGAGTGGTTGGC SEQ ID NO: 1095
CCCATCACCCACAGGAGTGGTTGGC SEQ ID NO: 1096

35. - Cytochrome P450 2D6 (CYP2D6) 1863ins9bp
CCCTTTCGCCCCAACGGTCTCTTGG SEQ ID NO: 1197
CCCTTTCGCCCCTTTCGCCCCAACG SEQ ID NO: 1198
CCAAGAGACCGTTGGGGCGAAAGGG SEQ ID NO: 1199
CGTTGGGGCGAAAGGGGCGAAAGGG SEQ ID NO: 1100

36. - Cytochrome P450 2D6 (CYP2D6) 1973insG
ACCTAGCTCAGGAGGGACTGAAGGA SEQ ID NO: 1101
ACCTAGCTCAGGGAGGGACTGAAGG SEQ ID NO: 1102
TCCTTCAGTCCCTCCTGAGCTAGGT SEQ ID NO: 1103
CCTTCAGTCCCTCCCTGAGCTAGGT SEQ ID NO: 1104

37. - Cytochrome P450 2D6 (CYP2D6) 2539delAACT
GGATGAGCTGCTAACTGAGCACAGG SEQ ID NO: 1105
GGATGAGCTGCTGAGCACAGGATGA SEQ ID NO: 1106
CCTGTGCTCAGTTAGCAGCTCATCC SEQ ID NO: 1107
TCATCCTGTGCTCAGCAGCTCATCC SEQ ID NO: 1108

38. - Cytochrome P450 2D6 (CYP2D6) 2549A/del
CTAACTGAGCACAGGATGACCTGGG SEQ ID NO: 1109

-continued

CTAACTGAGCACGGATGACCTGGGA SEQ ID NO: 1110
CCCAGGTCATCCTGTGCTCAGTTAG SEQ ID NO: 1111
TCCCAGGTCATCCGTGCTCAGTTAG SEQ ID NO: 1112

39. - Cytochrome P450 2D6 (CYP2D6) 2613delAGA
TGGCAGAGATGGAGAAGGTGAGAGT SEQ ID NO: 1113
TGGCAGAGATGGAGGTGAGAGTGGC SEQ ID NO: 1114
ACTCTCACCTTCTCCATCTCTGCCA SEQ ID NO: 1115
GCCACTCTCACCTCCATCTCTGCCA SEQ ID NO: 1116

40. - Cytochrome P450 2D6 (CYP2D6) C2850T
GATGAGAACCTGCGCATAGTGGTGG SEQ ID NO: 1117
GATGAGAACCTGTGCATAGTGGTGG SEQ ID NO: 1118
CCACCACTATGCGCAGGTTCTCATC SEQ ID NO: 1119
CCACCACTATGCACAGGTTCTCATC SEQ ID NO: 1120

41. - Cytochrome P450 2D6 (CYP2D6) G3183A
GAGATCGACGACGTGATAGGGCAGG SEQ ID NO: 1121
GAGATCGACGACATGATAGGGCAGG SEQ ID NO: 1122
CCTGCCCTATCACGTCGTCGATCTC SEQ ID NO: 1123
CCTGCCCTATCATGTCGTCGATCTC SEQ ID NO: 1124

42.- Cytochrome P450 2D6 (CYP2D6) C3198G
ATAGGGCAGGTGCGGCGACCAGAGA SEQ ID NO: 1125
ATAGGGCAGGTGGGGCGACCAGAGA SEQ ID NO: 1126
TCTCTGGTCGCCGCACCTGCCCTAT SEQ ID NO: 1127
TCTCTGGTCGCCCCACCTGCCCTAT SEQ ID NO: 1128

43. - Cytochrome P450 2D6 (CYP2D6) T3277C
GCTTTGGGGACATCGTCCCCCTGGG SEQ ID NO: 1129
GCTTTGGGGACACCGTCCCCCTGGG SEQ ID NO: 1130
CCCAGGGGGACGATGTCCCCAAAGC SEQ ID NO: 1131
CCCAGGGGGACGGTGTCCCCAAAGC SEQ ID NO: 1132

44. - Cytochrome P450 2D6 (CYP2D6) G4042A
TCCCCACAGGCCGCCGTGCATGCCT SEQ ID NO: 1133
TCCCCACAGGCCACCGTGCATGCCT SEQ ID NO: 1134
AGGCATGCACGGCGGCCTGTGGGGA SEQ ID NO: 1135
AGGCATGCACGGTGGCCTGTGGGGA SEQ ID NO: 1136

45. - Cytochrome P450 2D6 (CYP2D6) 4125ins GTGCCCACT
TCGGTGCCCACTGGACAGCCCCGGC SEQ ID NO: 1137
TCGGTGCCCACTGTGCCCACTGGAC SEQ ID NO: 1138
GCCGGGGCTGTCCAGTGGGCACCGA SEQ ID NO: 1139
GTCCAGTGGGCACAGTGGGCACCGA SEQ ID NO: 1140

46. - Cytochrome P450 2C8 (CYP2C8) A805T
GATTGCTTCCTGATCAAAATGGAGC SEQ ID NO: 1141
GATTGCTTCCTGTTCAAAATGGAGC SEQ ID NO: 1142
GCTCCATTTTGATCAGGAAGCAATC SEQ ID NO: 1143
GCTCCATTTTGAACAGGAAGCAATC SEQ ID NO: 1144

47. - Cytochrome P450 2C8 (CYP2C8) G416A
GGATGGGGAAGAGGAGCATTGAGGA SEQ ID NO: 1145
GGATGGGGAAGAAGAGCATTGAGGA SEQ ID NO: 1146
TCCTCAATGCTCCTCTTCCCCATCC SEQ ID NO: 1147
TCCTCAATGCTCTTCTTCCCCATCC SEQ ID NO: 1148

48. - Cytochrome P450 2C8 (CYP2C8) A1196G
TTAGGAAATTCTTTGTCATCATGTA SEQ ID NO: 1149
TTAGGAAATTCTCTGTCATCATGTA SEQ ID NO: 1150
TACATGATGACAAAGAATTTCCTAA SEQ ID NO: 1151
TACATGATGACAGAGAATTTCCTAA SEQ ID NO: 1152

49. - Cytochrome P450 2C8 (CYP2C8) C792G
TCGGGACTTTATCGATTGCTTCCTG SEQ ID NO: 1153
TCGGGACTTTATGGATTGCTTCCTG SEQ ID NO: 1154
CAGGAAGCAATCGATAAAGTCCCGA SEQ ID NO: 1155
CAGGAAGCAATCCATAAAGTCCCGA SEQ ID NO: 1156

50. - N-acetyltransferase 2 (NAT2) T341C
TGCAGGTGACCATTGACGGCAGGAA SEQ ID NO: 1157
TGCAGGTGACCACTGACGGCAGGAA SEQ ID NO: 1158
TTCCTGCCGTCAATGGTCACCTGCA SEQ ID NO: 1159
TTCCTGCCGTCAGTGGTCACCTGCA SEQ ID NO: 1160

51. - N-acetyltransferase 2 (NAT2) C481T
GGAATCTGGTACCTGGACCAAATCA SEQ ID NO: 1161
GGAATCTGGTACTTGGACCAAATCA SEQ ID NO: 1162
TGATTTGGTCCAGGTACCAGATTCC SEQ ID NO: 1163

-continued

TGATTTGGTCCAAGTACCAGATTCC SEQ ID NO: 1164

52. - N-acetyltransferase 2 (NAT2) A803G
AAGAAGTGCTGAAAAATATATTTAA SEQ ID NO: 1165
AAGAAGTGCTGAGAAATATATTTAA SEQ ID NO: 1166
TTAAATATATTTTTCAGCACTTCTT SEQ ID NO: 1167
TTAAATATATTTCTCAGCACTTCTT SEQ ID NO: 1168

53. - N-acetyltransferase 2 (NAT2) C282T
AGGGTATTTTTACATCCCTCCAGTT SEQ ID NO: 1169
AGGGTATTTTTATATCCCTCCAGTT SEQ ID NO: 1170
AACTGGAGGGATGTAAAAATACCCT SEQ ID NO: 1171
AACTGGAGGGATATAAAAATACCCT SEQ ID NO: 1172

54. - N-acetyltransferase 2 (NAT2) G590A
CGCTTGAACCTCGAACAATTGAAGA SEQ ID NO: 1173
CGCTTGAACCTCAAACAATTGAAGA SEQ ID NO: 1174
TCTTCAATTGTTCGAGGTTCAAGCG SEQ ID NO: 1175
TCTTCAATTGTTTGAGGTTCAAGCG SEQ ID NO: 1176

55. - N-acetyltransferase 2 (NAT2) G857A
AACCTGGTGATGGATCCCTTACTAT SEQ ID NO: 1177
AACCTGGTGATGAATCCCTTACTAT SEQ ID NO: 1178
ATAGTAAGGGATCCATCACCAGGTT SEQ ID NO: 1179
ATAGTAAGGGATTCATCACCAGGTT SEQ ID NO: 1180

56. - N-acetyltransferase 2 (NAT2) G191A
TAAGAAGAAACCGGGGTGGGTGGTG SEQ ID NO: 1181
TAAGAAGAAACCAGGGTGGGTGGTG SEQ ID NO: 1182
CACCACCCACCCCGGTTTCTTCTTA SEQ ID NO: 1183
CACCACCCACCCTGGTTTCTTCTTA SEQ ID NO: 1184

57. - Cytochrome P450 2C19 (CYP2C19) G636A
AAGCACCCCCTGGATCCAGGTAAGG SEQ ID NO: 1185
AAGCACCCCCTGAATCCAGGTAAGG SEQ ID NO: 1186
CCTTACCTGGATCCAGGGGGTGCTT SEQ ID NO: 1187
CCTTACCTGGATTCAGGGGGTGCTT SEQ ID NO: 1188

58. - Cytochrome P450 2C19 (CYP2C19) G681A
TGATTATTTCCCGGGAACCCATAAC SEQ ID NO: 1189
TGATTATTTCCCAGGAACCCATAAC SEQ ID NO: 1190
GTTATGGGTTCCCGGGAAATAATCA SEQ ID NO: 1191
GTTATGGGTTCCTGGGAAATAATCA SEQ ID NO: 1192

59. - Cytochrome P450 2C19 (CYP2C19) C680T
TTGATTATTTCCCGGGAACCCATAA SEQ ID NO: 1193
TTGATTATTTCCTGGGAACCCATAA SEQ ID NO: 1194
TTATGGGTTCCCGGGAAATAATCAA SEQ ID NO: 1195
TTATGGGTTCCCAGGAAATAATCAA SEQ ID NO: 1196

60. - Cytochrome P450 2C19 (CYP2C19) A1G
GAGAAGGCTTCAATGGATCCTTTTG SEQ ID NO: 1197
GAGAAGGCTTCAGTGGATCCTTTTG SEQ ID NO: 1198
CAAAAGGATCCATTGAAGCCTTCTC SEQ ID NO: 1199
CAAAAGGATCCACTGAAGCCTTCTC SEQ ID NO: 1200

61. - Cytochrome P450 2C19 (CYP2C19) IVS5 + 2T > A
AAATGGAGAAGGTAAAATGTTAACA SEQ ID NO: 1201
AAATGGAGAAGGAAAAATGTTAACA SEQ ID NO: 1202
TGTTAACATTTTACCTTCTCCATTT SEQ ID NO: 1203
TGTTAACATTTTTCCTTCTCCATTT SEQ ID NO: 1204

62. - Cytochrome P450 2C19 (CYP2C19) T358C
AATGGAAAGAGATGGAAGGAGATCC SEQ ID NO: 1205
AATGGAAAGAGACGGAAGGAGATCC SEQ ID NO: 1206
GGATCTCCTTCCATCTCTTTCCATT SEQ ID NO: 1207
GGATCTCCTTCCGTCTCTTTCCATT SEQ ID NO: 1208

63. - Cytochrome P450 2C19 (CYP2C19) G431A
GCATTGAGGACCGTGTTCAAGAGGA SEQ ID NO: 1209
GCATTGAGGACCATGTTCAAGAGGA SEQ ID NO: 1210
TCCTCTTGAACACGGTCCTCAATGC SEQ ID NO: 1211
TCCTCTTGAACATGGTCCTCAATGC SEQ ID NO: 1212

64. - Cytochrome P450 2C19 (CYP2C19) C1297T
TTTTCAGGAAAACGGATTTGTGTGG SEQ ID NO: 1213
TTTTCAGGAAAATGGATTTGTGTGG SEQ ID NO: 1214
CCACACAAATCCGTTTTCCTGAAAA SEQ ID NO: 1215
CCACACAAATCCATTTTCCTGAAAA SEQ ID NO: 1216

-continued

65. - Glutamate receptor, ionotropic, N-methyl D-asparate (NMDA) 2B(GRIN2B) C2664T

| | |
|---|---|
| GTTCATGGTTGCGGTGGGGGAGTTC | SEQ ID NO: 1217 |
| GTTCATGGTTGCAGTGGGGGAGTTC | SEQ ID NO: 1218 |
| GAACTCCCCCACCGCAACCATGAAC | SEQ ID NO: 1219 |
| GAACTCCCCCACTGCAACCATGAAC | SEQ ID NO: 1220 |

66. - Glycoprotein P (ABCB1) C3435T

| | |
|---|---|
| TGCTGCCCTCACAATCTCTTCCTGT | SEQ ID NO: 1221 |
| TGCTGCCCTCACGATCTCTTCCTGT | SEQ ID NO: 1222 |
| ACAGGAAGAGATTGTGAGGGCAGCA | SEQ ID NO: 1223 |
| ACAGGAAGAGATCGTGAGGGCAGCA | SEQ ID NO: 1224 |

67. - Thiopurine methyltransferase (TPMT) A719G

| | |
|---|---|
| TTGAAAAGTTATATCTACTTACAGA | SEQ ID NO: 1225 |
| TTGAAAAGTTATGTCTACTTACAGA | SEQ ID NO: 1226 |
| TCTGTAAGTAGATATAACTTTTCAA | SEQ ID NO: 1227 |
| TCTGTAAGTAGACATAACTTTTCAA | SEQ ID NO: 1228 |

67. - Thiopurine methyltransferase (TPMT) G238C

| | |
|---|---|
| GTCCCCGGTCTGGAAACCTGCATAA | SEQ ID NO: 1229 |
| GTCCCCGGTCTGCAAACCTGCATAA | SEQ ID NO: 1230 |
| TTATGCAGGTTTCCAGACCGGGGAC | SEQ ID NO: 1231 |
| TTATGCAGGTTTGCAGACCGGGGAC | SEQ ID NO: 1232 |

69. - 5,10-methylenetetrahydrofolate reductase (MTHFR) C677T

| | |
|---|---|
| TGTCTGCGGGAGCCGATTTCATCAT | SEQ ID NO: 1233 |
| TGTCTGCGGGAGTCGATTTCATCAT | SEQ ID NO: 1234 |
| ATGATGAAATCGGCTCCCGCAGACA | SEQ ID NO: 1235 |
| ATGATGAAATCGACTCCCGCAGACA | SEQ ID NO: 1236 |

70. - Butyrylcholinesterase (BCHE) Asp70Gly

| | |
|---|---|
| GTCAGAACATAGATCAAAGTTTTCC | SEQ ID NO: 1237 |
| GTCAGAACATAGGTCAAAGTTTTCC | SEQ ID NO: 1238 |
| GGAAAACTTTGATCTATGTTCTGAC | SEQ ID NO: 1239 |
| GGAAAACTTTGACCTATGTTCTGAC | SEQ ID NO: 1240 |

71. - Butyrylcolinesterase (BCHE) Ala539Thr

| | |
|---|---|
| AATATTGATGAAGCAGAATGGGAGT | SEQ ID NO: 1241 |
| AATATTGATGAAACAGAATGGGAGT | SEQ ID NO: 1242 |
| ACTCCCATTCTGCTTCATCAATATT | SEQ ID NO: 1243 |
| ACTCCCATTCTGTTTCATCAATATT | SEQ ID NO: 1244 |

72. - Cytochrome P450 3A4 (CYP3A4) A-392G

| | |
|---|---|
| GAGACAAGGGCAAGAGAGAGGCGAT | SEQ ID NO: 1245 |
| GAGACAAGGGCAGGAGAGAGGCGAT | SEQ ID NO: 1246 |
| ATCGCCTCTCTCTTGCCCTTGTCTC | SEQ ID NO: 1247 |
| ATCGCCTCTCTCCTGCCCTTGTCTC | SEQ ID NO: 1248 |

73. - Cytochrome P450 1A2 (CYP1A2) A-163C

| | |
|---|---|
| AGCTCTGTGGGCACAGGACGCATGG | SEQ ID NO: 1249 |
| AGCTCTGTGGGCCCAGGACGCATGG | SEQ ID NO: 1250 |
| CCATGCGTCCTGTGCCCACAGAGCT | SEQ ID NO: 1251 |
| CCATGCGTCCTGGGCCCACAGAGCT | SEQ ID NO: 1252 |

74. - Cytochrome P450 1A2 (CYP1A2) A-3860G

| | |
|---|---|
| CCTCCGCCTCTCGGATTCAAGCAAT | SEQ ID NO: 1253 |
| CCTCCGCCTCTCAGATTCAAGCAAT | SEQ ID NO: 1254 |
| ATTGCTTGAATCCGAGAGGCGGAGG | SEQ ID NO: 1255 |
| ATTGCTTGAATCTGAGAGGCGGAGG | SEQ ID NO: 1256 |

75. - Cytochrome P450 1A2 (CYP1A2) G3534A

| | |
|---|---|
| CAACCATGACCCGTGAGTACATACC | SEQ ID NO: 1257 |
| CAACCATGACCCATGAGTACATACC | SEQ ID NO: 1258 |
| GGTATGTACTCACGGGTCATGGTTG | SEQ ID NO: 1259 |
| GGTATGTACTCATGGGTCATGGTTG | SEQ ID NO: 1260 |

76. - Cytochrome P450 1A2 (CYP1A2) C558A

| | |
|---|---|
| GCCTGGGCACTTCGACCCTTACAAT | SEQ ID NO: 1261 |
| GCCTGGGCACTTAGACCCTTACAAT | SEQ ID NO: 1262 |
| ATTGTAAGGGTCGAAGTGCCCAGGC | SEQ ID NO: 1263 |
| ATTGTAAGGGTCTAAGTGCCCAGGC | SEQ ID NO: 1264 |

77. - Cytochrome P450 3A5 (CYP3A5) G14690A

| | |
|---|---|
| GGAGAGCACTAAGAAGTTCCTAAAA | SEQ ID NO: 1265 |
| GGAGAGCACTAAAAAGTTCCTAAAA | SEQ ID NO: 1266 |
| TTTTAGGAACTTCTTAGTGCTCTCC | SEQ ID NO: 1267 |
| TTTTAGGAACTTTTTAGTGCTCTCC | SEQ ID NO: 1268 |

-continued

78. - Cytochrome P450 3A5 (CYP3A5) C3699T

| | |
|---|---|
| AGATATGGGACCCGTACACATGGAC | SEQ ID NO: 1269 |
| AGATATGGGACCTGTACACATGGAC | SEQ ID NO: 1270 |
| GTCCATGTGTACGGGTCCCATATCT | SEQ ID NO: 1271 |
| GTCCATGTGTACAGGTCCCATATCT | SEQ ID NO: 1272 |

79. - Cytochrome P450 3A5 (CYP3A5) G19386A

| | |
|---|---|
| AAGGAGATTGATGCAGTTTTGCCCA | SEQ ID NO: 1273 |
| AAGGAGATTGATACAGTTTTGCCCA | SEQ ID NO: 1274 |
| TGGGCAAAACTGCATCAATCTCCTT | SEQ ID NO: 1275 |
| TGGGCAAAACTGTATCAATCTCCTT | SEQ ID NO: 1276 |

80. - Cytochrome P450 3A5 (CYP3A5) T29753C

| | |
|---|---|
| TTGGCATGAGGTTTGCTCTCATGAA | SEQ ID NO: 1277 |
| TTGGCATGAGGTCTGCTCTCATCAA | SEQ ID NO: 1278 |
| TTCATGAGAGCAAACCTCATGCCAA | SEQ ID NO: 1279 |
| TTCATGAGAGCAGACCTCATGCCAA | SEQ ID NO: 1280 |

81. - Cytochrome P450 3A5 (CYP3A5) G6986A

| | |
|---|---|
| TTTTGTCTTTCAGTATCTCTTCCCT | SEQ ID NO: 1281 |
| TTTTGTCTTTCAATATCTCTTCCCT | SEQ ID NO: 1282 |
| AGGGAAGAGATACTGAAAGACAAAA | SEQ ID NO: 1283 |
| AGGGAAGAGATATTGAAAGACAAAA | SEQ ID NO: 1284 |

82. - Serotonin transporter (SLC6A4) promoter 44bp deletion

| | |
|---|---|
| ATCCCCCCTGCACCCCCCAGCATCC | SEQ ID NO: 1285 |
| ATCCCCCCTGCACCCCCAGCATCCC | SEQ ID NO: 1286 |
| GGATGCTGGGGGGTGCAGGGGGGAT | SEQ ID NO: 1287 |
| GGGATGCTGGGGGTGCAGGGGGGAT | SEQ ID NO: 1288 |

83. - Gluthatione S-transferase M3 (GSTM3) delAGA (allele*B)

| | |
|---|---|
| AGGGAAAAGAAGAGGATACTTCTCT | SEQ ID NO: 1289 |
| AGGGAAAAGAAGATACTTCTCTATC | SEQ ID NO: 1290 |
| AGAGAAGTATCCTCTTCTTTTCCCT | SEQ ID NO: 1291 |
| GATAGAGAAGTATCTTCTTTTCCCT | SEQ ID NO: 1292 |

84. - Gluthatione S-transferase M1 (GSTM1) allele [nulo?]

| | |
|---|---|
| CACACATTCTTGGCCTTCTGCAGAT | SEQ ID NO: 1293 |
| CACACATTCTTGACCTTCTGCAGAT | SEQ ID NO: 1294 |
| ATCTGCAGAAGGCCAAGAATGTGTG | SEQ ID NO: 1295 |
| ATCTGCAGAAGGTCAAGAATGTGTG | SEQ ID NO: 1296 |

85. - Gluthathione S-transferase n1 (GSTT1) null allele

| | |
|---|---|
| CTGCCTAGTGGGTTCACCTGCCCAC | SEQ ID NO: 1297 |
| CTGCCTAGTGGGGTCACCTGCCCAC | SEQ ID NO: 1298 |
| GTGGGCAGGTGAACCCACTAGGCAG | SEQ ID NO: 1299 |
| GTGGGCAGGTGACCCCACTAGGCAG | SEQ ID NO: 1300 |

86. - Apolipoprotein E (APOE) Arg158Cys

| | |
|---|---|
| GACCTGCAGAAGCGCCTGGCAGTGT | SEQ ID NO: 1301 |
| ACACTGCCAGGCGCTTCTGCAGGTC | SEQ ID NO: 1302 |
| GACCTGCAGAAGTGCCTGGCAGTGT | SEQ ID NO: 1303 |
| ACACTGCCAGGCACTTCTGCAGGTC | SEQ ID NO: 1304 |

87. - Apolipoprotein E (APOE) Cys112Arg

| | |
|---|---|
| ATGGAGGACGTGTGCGGCCGCCTGG | SEQ ID NO: 1305 |
| CCAGGCGGCCGCACACGTCCTCCAT | SEQ ID NO: 1306 |
| ATGGAGGACGTGCGCGGCCGCCTGG | SEQ ID NO: 1307 |
| CCAGGCGGCCGCGCACGTCCTCCAT | SEQ ID NO: 1308 |

88. - Tumor necrosis factor (TNF) G-308A

| | |
|---|---|
| TTGAGGGGCATGGGGACGGGGTTCA | SEQ ID NO: 1309 |
| TTGAGGGGCATGAGGACGGGGTTCA | SEQ ID NO: 1310 |
| TGAACCCCGTCCCCATGCCCCTCAA | SEQ ID NO: 1311 |
| TGAACCCCGTCCTCATGCCCCTCAA | SEQ ID NO: 1312 |

89. - Interleukin 10 (IL10) G-1082A

| | |
|---|---|
| GCTTCTTTGGGAAGGGGAAGTAGGG | SEQ ID NO: 1313 |
| GCTTCTTTGGGAGGGGGAAGTAGGG | SEQ ID NO: 1314 |
| CCCTACTTCCCCTTCCCAAAGAAGC | SEQ ID NO: 1315 |
| CCCTACTTCCCCCTCCCAAAGAAGC | SEQ ID NO: 1316 |

5.2 Production of the DNA-chip for Genotyping Genetic Variations Associated with Adverse Reactions to Drugs

5.2.1 Printing of the Glass Slides

The probes capable of detecting the genetic variations of interest are printed or deposited on the support (glass slides)

using DMSO as solvent. The printing is carried out with a spotter or printer of oligonucleotides while controlling the temperature and relative humidity.

5.2.2 Processing of the Glass Slides

Probes are attached to the support (glass slides) by means of crosslinking with ultraviolet radiation and heating as previously described (Example 1.2) maintaining the relative humidity during the deposition process between 40-50% and the temperature around 20° C.

5.3 Validation of the Clinical Utility of the DNA-chip for the Simultaneous, Sensitive, Specific and Reproducible Detection of Human Genetic Variations Associated with Adverse Reactions to Pharmaceutical Drugs 5.3.1 Preparation of the Sample to be Hybridized DNA is extracted from a blood sample of an individual by means of a filtration protocol.

All the exons and introns of interest are amplified by multiplex PCR using appropriate pairs of oligonucleotide primers. Any suitable pair of oligonucleotides can be used that allows specific amplification of genetic fragments where a genetic variation to be detected might exist. Advantageously, those pairs which permit the said amplification in the least possible number of PCR reactions are used.

The oligonucleotide primers used to PCR amplify the fragments of the genes to be detected are listed below with corresponding genetic variations associated with adverse reactions to pharmaceutical drugs.

1. - Beta-1-adrenergic receptor (ADRB1) Arg3B9Gly (oligonucleotides to amplify the fragment where the polymorphism Arg389Gly might exist in the Beta-1-adrenergic receptor gene (ADRB1)
SEQ ID NO 125: GCCTTCAACCCCATCATCTA
SEQ ID NO 126: CAGGCTCGAGTCGCTGTC 2. - Beta-2-adrenergic receptor (ADRB2) Arg16Gly and Gln27Glu (oligonucleotides to amplify the fragment where the polymorphism Arg389Gly might exist in the Beta-2-adrenergic receptor gene (ADRB2)
SEQ ID NO 227: GCTCACCTGCCAGACTGC
SEQ ID NO 128: GCCAGGACGATGAGAGACAT 3. - Dopamine D3 receptor (DRD3) Ser9Gly
SEQ ID NO 129: CGCAGTAGGAGAGGGCATAG
SEQ ID NO 130: CAAGCCCCAAAGAGTCTGAT 4. - Serotonin 2A receptor (HTR2A) His452Tyr
SEQ ID NO 131: AGCAAGATGCCAAGACAACA
SEQ ID NO 132: CAGTGTGCCTTCCACAGTTG 5. - Serotonin 2A receptor (HTR2A) T102C
SEQ ID NO 133: AGGAGAGACACGACGGTGAG
SEQ ID NO 134: CAAGTTCTGGCTTAGACATGGA 6. - Catechol-Q-methyltransferase (COMT) Val108Met
SEQ ID NO 135: GGGCCTACTGTGGCTACTCA
SEQ ID NO 136: CCCTTTTTCCAGGTCTGACA 7. - Glutathione S transferase class 1 (GSTP1) Ile105Val
SEQ ID NO 137: TGGTGGACATGGTGAATGAC
SEQ ID NO 138: GTGCAGGTTGTGTCTTGTCC 8. - Adducin-1 (ADD1) Gly460Trp
SEQ ID NO 139: TTGCTAGTGACGGTGATTCG
SEQ ID NO 140: GAGACTGCAGCAAGGGTTTC 9. - DNA repair enzyme XRCC1 Arg399Gln
SEQ ID NO 141: TGTCTCCCCTGTCTCATTCC
SEQ ID NO 142: ATTGCCCAGCACAGGATAAG -continued 10. - Cytochrome P450 1A1 (CYP1A1) Ile462Val
SEQ ID NO 143: CTCACCCCTGATGGTGCTAT
SEQ ID NO 144: TTTGGAAGTGCTCACAGCAG 11. - Angiotensin II receptor, type 1 (AGTR1) A1166C
SEQ ID NO 145: GAGAACATTCCTCTGCAGCAC
SEQ ID NO 146: TGTGGCTTTGCTTTGTCTTG 12. - Bradykinin receptor (BDKRB2) C-58T
SEQ ID NO 147: GAGCAATGTCTGGCTTCTCC
SEQ ID NO 148: CCAGGGAGAGAACATTTGGA 13. - Angiotensinogen (AGT) Met235Thr
SEQ ID NO 149: AGGCTGTGACAGGATGGAAG
SEQ ID NO 150: GGTGGTCACCAGGTATGTCC 14. - Cytochrome P450 2C9 (CYP2C9) C430T
SEQ ID NO 151: CCTGGGATCTCCCTCCTAGT
SEQ ID NO 152: CCACCCTTGGTTTTTCTCAA 15. - Cytochrome P450 2C9 (CYP2C9) A1075C, T1076C and C1080G
SEQ ID NO 153: CCACATGCCCTACACAGATG
SEQ ID NO 154: TCGAAAACATGGAGTTGCAG 16. - Cytochrome P450 2C9 (CYP2C9) 818delA
SEQ ID NO 155: CCGGGAACTCACAACAAATTA
SEQ ID NO 156: CACAAATTCACAAGCAGTCACA 17. - Cytochrome P450 2D6 31G > A, 100C > T and 138insT
SEQ ID NO 157: CAGGTATGGGGCTAGAAGCA
SEQ ID NO 158: ACCTGGTCGAAGCAGTATGG 18. - Cytochrome P450 2D6 883G > C, 1023C > T, 1039C > T
SEQ ID NO 159: GATCCTGGCTTGACAAGAGG
SEQ ID NO 160: TCCCACGGAAATCTGTCTCT 19. - Cytochrome P450 2D6 1659G > A, 1661G > C, 1707T > del, 1758G > A and 1758G > T
SEQ ID NO 161: GTGGGGCTAATGCCTTCAT
SEQ ID NO 162: CTTCCCAGTTCCCGCTTT 20. - Cytochrome P450 2D6 1846G > A and 1863ins9 bp
SEQ ID NO 163: GTGGGTGATGGGCAGAAG
SEQ ID NO 164: *GAGGGTCGTCGTACTCGAAG*

21. - Cytochrome P450 2D6 1973insG
SEQ ID NO 165: AGCCGTGAGCAACGTGAT
SEQ ID NO 166: CTGCAGAGACTCCTCGGTCT 22. - Cytochrome P450 2D6 2539delAACT, 2549A > del, 2613delAGA
SEQ ID NO 167: CAAGGTCCTACGCTTCCAAA
SEQ ID NO 168: GATGCACTGGTCCAACCTTT 23. - Cytochrome P450 2D6 2850C > T and 2935A > C
SEQ ID NO 169: GGAACCCTGAGAGCAGCTT

SEQ ID NO 170: GGTGTCCCAGCAAAGTTCAT

24. - Cytochrome P450 2D6 3183G > A, 3198C > G and 3277T > C
SEQ ID NO 171: GGAGGCAAGAAGGAGTGTCA
SEQ ID NO 172: CGATGTCACGGGATGTCATA 25. - Cytochrome P450 2D6 4042G > A and 4125insGTGCCCACT
SEQ ID NO 173: GGAGTCTTGCAGGGGTATCA
SEQ ID NO 174: TCACCAGGAAAGCAAAGACA 26. - Cytochrome P450 2C8 (CYP2C8) C792G and A805T
SEQ ID NO 175: GAACACCAAGCATCACTGGA
SEQ ID NO 176: GATGTTTAGTGCAGGCCCATA 27. - Cytochrome P450 2C8 (CYP2C8) G416A
SEQ ID NO 177: CTCACAACCTTGCGGAATTT
SEQ ID NO 178: CTTCAAATCTCCCTCCACCA -continued 28. - Cytochrome P450 2C8 (CYP2C8) A1196G
SEQ ID NO 179: ACCTGCTGAGAAAGGCATGA
SEQ ID NO 180: TTCCAGGGCACAACCATAAT 29. - N-acetyltransferase 2 (NAT2) 191G > A and 282C > T
SEQ ID NO 181: CCATGGAGTTGGGCTTAGAG
SEQ ID NO 182: CCATGCCAGTGCTGTATTTG 30. - N-acetyltransferase 2 (NAT2) T341C
SEQ ID NO 183: TGGTGTCTCCAGGTCAATCA
SEQ ID NO 184: GGCTGATCCTTCCCAGAAAT 31. - N-acetyltransferase 2 (NAT2) C481T
SEQ ID NO 185: TGACGGCAGGAATTACATTG
SEQ ID NO 186: TGTTTCTTCTTTGGCAGGAGA 32. - N-acetyltransferase 2 (NAT2) A803G
SEQ ID NO 187: ACTGTTTGGTGGGCTTCATC
SEQ ID NO 188: AGGTTTGGGCACGAGATTT 33. - N-acetyltransferase 2 (NAT2) G590A
SEQ ID NO 189: CCTGCCAAAGAAGAAACACC
SEQ ID NO 190: GATGAAGCCCACCAAACAGT 34. - N-acetyltransferase 2 (NAT2) G857A
SEQ ID NO 191: ACTGTTTGGTGGGCTTCATC
SEQ ID NO 192: GGGTGATACATACACAAGGGTTT 35. - Cytochrome P450 2C19 (CYP2C19) G636A
SEQ ID NO 193: ACCCTGTGATCCCACTTTCA
SEQ ID NO 194: TGTACTTCAGGGCTTGGTCA 36. - Cytochrome P450 2C19 (CYP2C19) C680T and G681A
SEQ ID NO 195: CAACCAGAGCTTGGCATATTG
SEQ ID NO 196: TAAAGTCCCGAGGGTTGTTG 37. - Cytochrome P450 2C19 (CYP2C19) A1G
SEQ ID NO 197: TAGTGGGCCTAGGTGATTGG
SEQ ID NO 198: TTTCCAATCACTGGGAGAGG 38. - Cytochrome P450 2C19 (CYP2C19) IVS5 + 2T > A
SEQ ID NO 199: CAACCCTCGGGACTTTATTG
SEQ ID NO 200: CAAGCATTACTCCTTGACCTGTT 39. - Cytochrome P450 2C19 (CYP2C19) T358C
SEQ ID NO 201: CCCAGTGTCAGCTTCCTCTT
SEQ ID NO 202: GTCCTCAATGCTCCTCTTCC 40. - Cytochrome P450 2C19 (CYP2C19) G431A
SEQ ID NO 203: GAATCGTTTTCAGCAATGGAA
SEQ ID NO 204: GTATGTTCACCCACCCTTGG 41. - Cytochrome P450 2C19 (CYP2C19) C1297T
SEQ ID NO 205: TCACCGAACAGTTCTTGCAT
SEQ ID NO 206: GTCAAGGTCCTTTGGGTCAA 42. - Glutamate receptor, ionotropic, N-methyl D-aspartate (NMDA) 2B (GRIN2B) C2664T
SEQ ID NO 207: GCAGGATGTTGGAGTGTGTG
SEQ ID NO 208: GCAATTATTGGTGGGAGAGTG 43. - Glycoprotein P (ABCB1) C3435T
SEQ ID NO 209: TGCTCCCAGGCTGTTTATTT
SEQ ID NO 210: TGTTTTCAGCTGCTTGATGG 44. - Thiopurine methyltransferase (TPMT) A719G
SEQ ID NO 211: GGTTGATGCTTTTGAAGAACG
SEQ ID NO 212: CATCCATTACATTTTCAGGCTTT 45. - Thiopurine methyltransferase (TPMT) G238C
SEQ ID NO 213: AAAACTTTTGTGGGGATATGGA
SEQ ID NO 214: AACCCTCTATTTAGTCATTTGAAAACA 46. - 5,10-methylenetetra hydrofolate reductase (MTHFR) C677T
SEQ ID NO 215: TCCCTGTGGTCTCTTCATCC
SEQ ID NO 216: CAAAGCGGAAGAATGTGTCA -continued 47. - Butyrylcholinesterase (BCHE) Asp70Gly
SEQ ID NO 217: AAAGCCACAGTCTCTGACCAA
SEQ ID NO 218: GGTGCTGGAATCCATACATTT 48. - Butyrylcholinesterase (BCHE) Ala539Thr
SEQ ID NO 219: GAGAAAATGGCTTTTGTATTCG
SEQ ID NO 220: TGATTTTTCCAGTCCATCATGT 49. - Cytochrome P450 3A4 (CYP3A4) A-392G
SEQ ID NO 221: CAGGGGAGGAAATGGTTACA
SEQ ID NO 222: TGGAGCCATTGGCATAAAAT 50. - Cytochrome P450 1A2 (CYP1A2) A-163C
SEQ ID NO 223: AGAGAGCCAGCGTTCATGTT
SEQ ID NO 224: CTGATGCGTGTTCTGTGCTT 51. - Cytochrome P450 1A2 (CYP1A2) A-3860G
SEQ ID NO 225: GAGTGCAGTGGTGCGATCT
SEQ ID NO 226: TGAGGCCAGGAGTTCAAGAC 52. - Cytochrome P450 1A2 (CYP1A2) G3534A
SEQ ID NO 227: GGTGGAGGTAGGAGCAACAC
SEQ ID NO 228: CTGCTGAACCTGCACACATT 53. - Cytochrome P450 1A2 (CYP1A2) C558A
SEQ ID NO 229: CCTCATCCTCCTGCTACCTG
SEQ ID NO 230: GAGGCAGTCTCCACGAACTC 54. - Cytochrome P450 3A5 (CYP3A5) G14690A
SEQ ID NO 231: GCCTACAGCATGGATGTGA
SEQ ID NO 232: TGGAATTGTACCTTTTAAGTGGA 55. - Cytochrome P450 3A5 (CYP3A5) C3699T
SEQ ID NO 233: TCACAATCCCTGTGACCTGA
SEQ ID NO 234: GGGGCATTTTTACTGATGGA 56. - Cytochrome P450 3A5 (CYP3A5) G19386A
SEQ ID NO 235: TGAAACCACCAGCAGTGTTC
SEQ ID NO 236: AAAATTCTCCTGGGGAGTGG 57. - Cytochrome P450 3A5 (CYP3A5) T29753C
SEQ ID NO 237: ACCCCTAACATGTAACTCTGTGG
SEQ ID NO 238: TTTGAAGGAGAAGTTCTGAAGGA 58. - Cytochrozne P450 3A5 (CYP3A5) G6986A
SEQ ID NO 239: CACCCAGCTTAACGAATGCT
SEQ ID NO 240: CCAGGAAGCCAGACTTTGAT 59. - Serotonin transporter (SLC6A4) promoter 44 bp deletion
SEQ ID NO 241: ACCCCTAATGTCCCTACTGC
SEQ ID NO 242: GGAGATCCTGGGAGAGGTG 60. - Glutathione S-transferase M3 (GSTM3) delAGA (allele*B)
SEQ ID NO 243: TTCTGGGGAAATTCTCATGG
SEQ ID NO 244: TCAGGTTTGGGAACTCATCC 61. - Glutathione S-transferase M1 (GSTM1) null allele
SEQ ID NO 245: ATGGTTTGCAGGAAACAAGG
SEQ ID NO 246: AAAGCGGGAGATGAAGTCCT 62. - Glutathione S-transferase n1 (GSTT1) null allele
SEQ ID NO 247: GGCAGCATAAGCAGGACTTC
SEQ ID NO 248: GTTGCTCGAGGACAAGTTCC 63. - Apolipoprotein E (APOE) Arg158Cys and Cys112Arg
SEQ ID NO 249: GCACGGCTGTCCAAGGA
SEQ ID NO 250: GCGGGCCCCGGCCTGGT 64. - Tumor necrosis factor (TNF) G-308A
SEQ ID NO 251: ACCTGGTCCCCAAAAGAAAT
SEQ ID NO 252: AAAGTTGGGGACACACAAGC 65. - Interleukin 10 (IL10) G-1082A
SEQ ID NO 253: CACACACACACACAAATCCAAG
SEQ ID NO 254: *GATGGGGTGGAAGAAGTTGA*

The multiplex PCR is carried out simultaneously under the same conditions of time and temperature that permit specific amplification of the gene fragments in which the genetic variations to be detected are located. Following the multiplex PCR agarose gel analysis of the reactions is performed to determine if the amplification reaction has been successful.

Next, the sample to be hybridized (products of amplification) is subjected to fragmentation with a DNase and the resulting fragmentation products subjected to indirect labelling. A terminal transferase adds a nucleotide, joined to one member of a pair of specifically interacting molecules, (e.g. biotin for subsequent binding to a chemically labelled streptavidin molecule) to the end of these small DNA fragments.

Before applying the sample to the DNA-chip, it is denatured by heating to 95° C. for 5 minutes and then, ChipMap Kit Hybridization Buffer (Ventana Medical System) is added.

Next, the stages of hybridization are performed, scanning the slide, quantification of the image and interpretation of the results, following the procedure described in the sections 1.3.2, 1.3.3, 1.3.4 and 1.3.5 of Example 1.

Example 6

Application of the IBDchip for Prognosis of Disease Progression and Response to Therapy in Individuals Suffering from Inflammatory Bowel Disease The value of the IBDchip in predicting disease progression and response to corticosteroid treatment was assessed based on the results of a clinical validation using blood samples obtained from 579 individuals with inflammatory bowel disease (IBD), of which 335 suffered from Crohns disease and 244 from ulcerative colitis. All samples were from individuals with at least a five year history of IBD.

Prognosis of disease progression is based on the positive likelihood ratio (LR+, measured as sensitivity/[1-specificity]), which defines the probability of developing a given disease phenotype or response to therapy. An LR+ value of ≧10 indicates a high probability of developing a defined phenotype; an LR+ value≧5 but <10 indicates a moderate probability of developing a defined phenotype; a value≧2 but <5 indicates a low probability of developing a defined phenotype; a value ≧1 but <2 indicates a minimal chance of developing a given phenotype.

Figure 8:
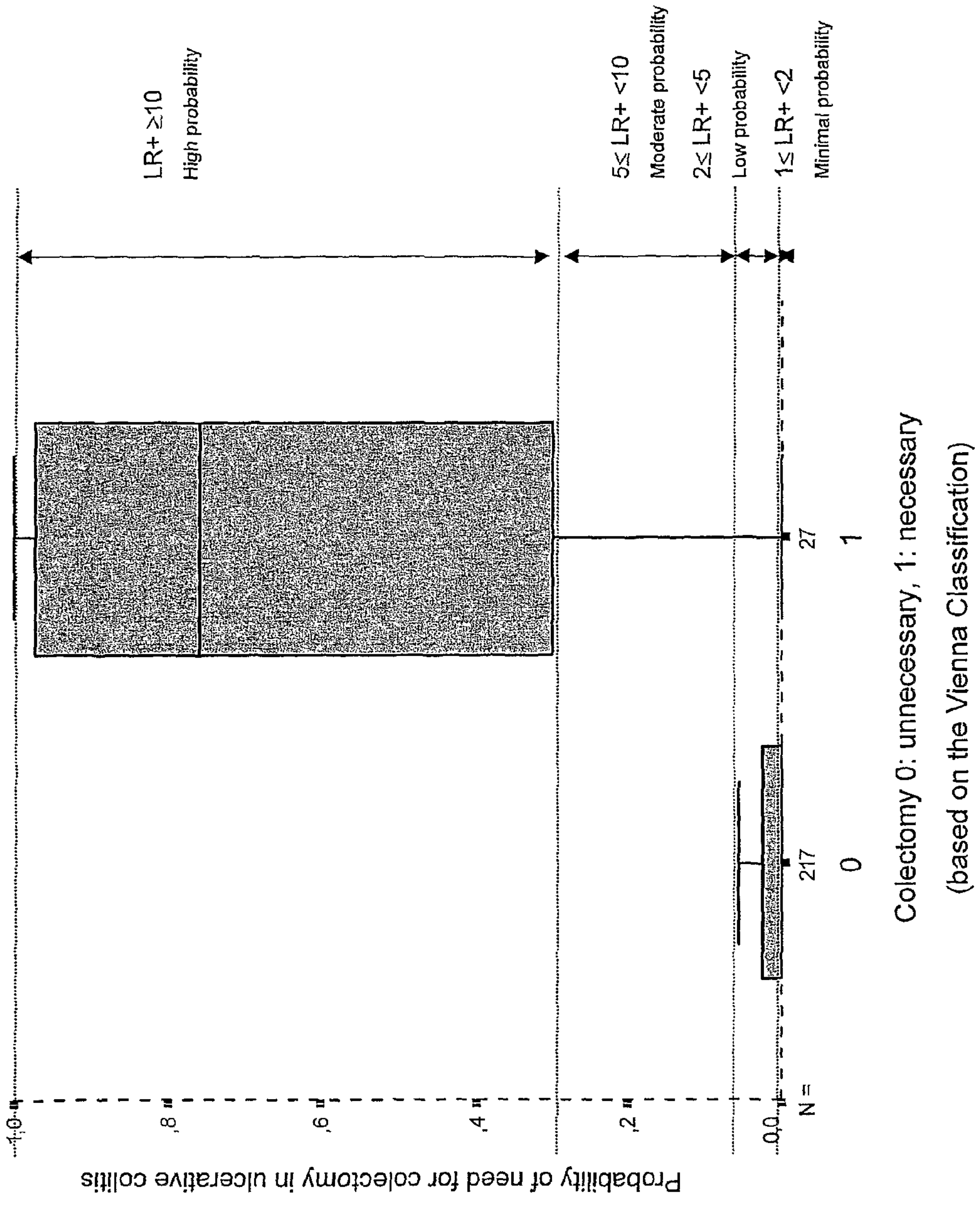
Figure 9:
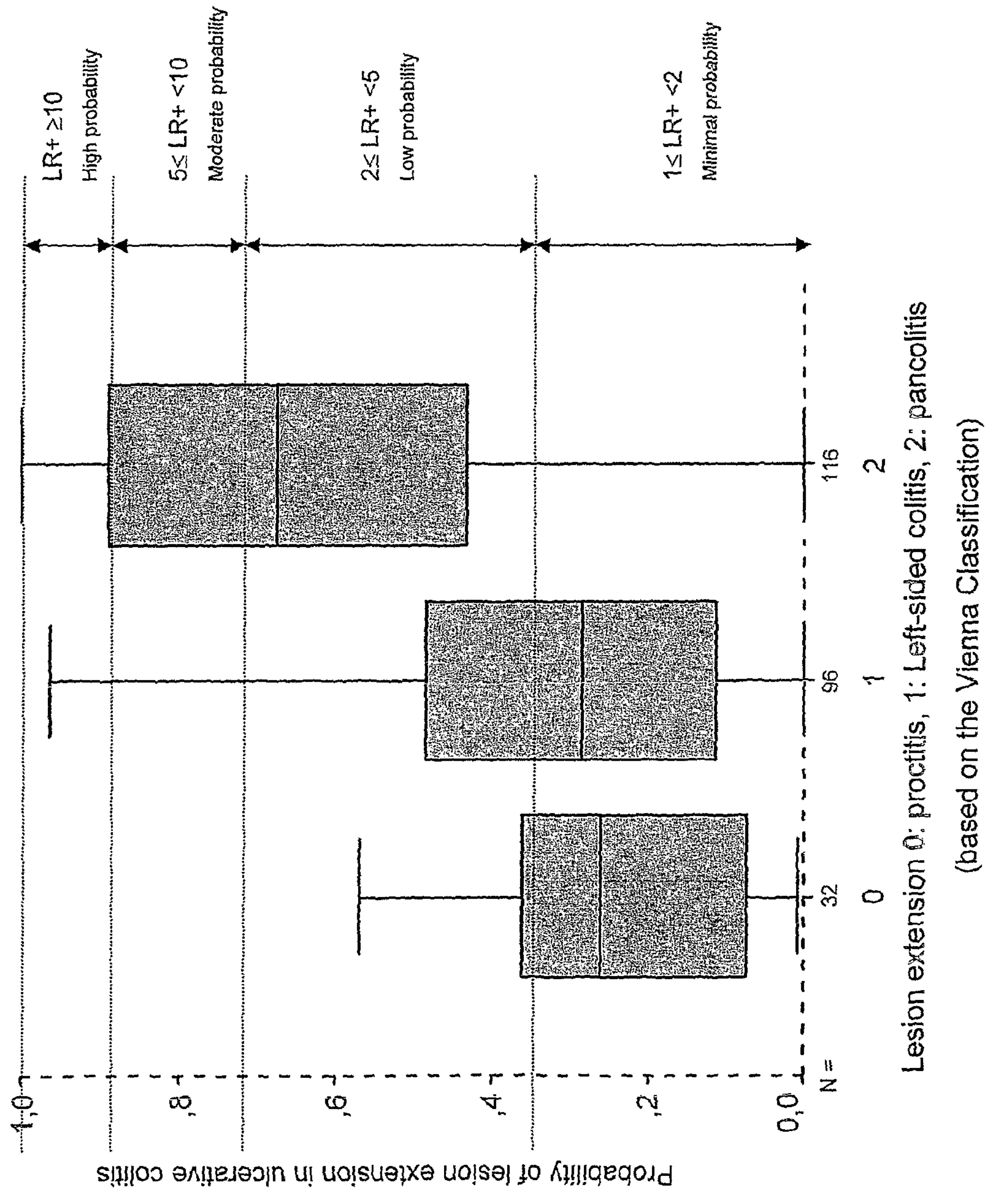
Figure 10:
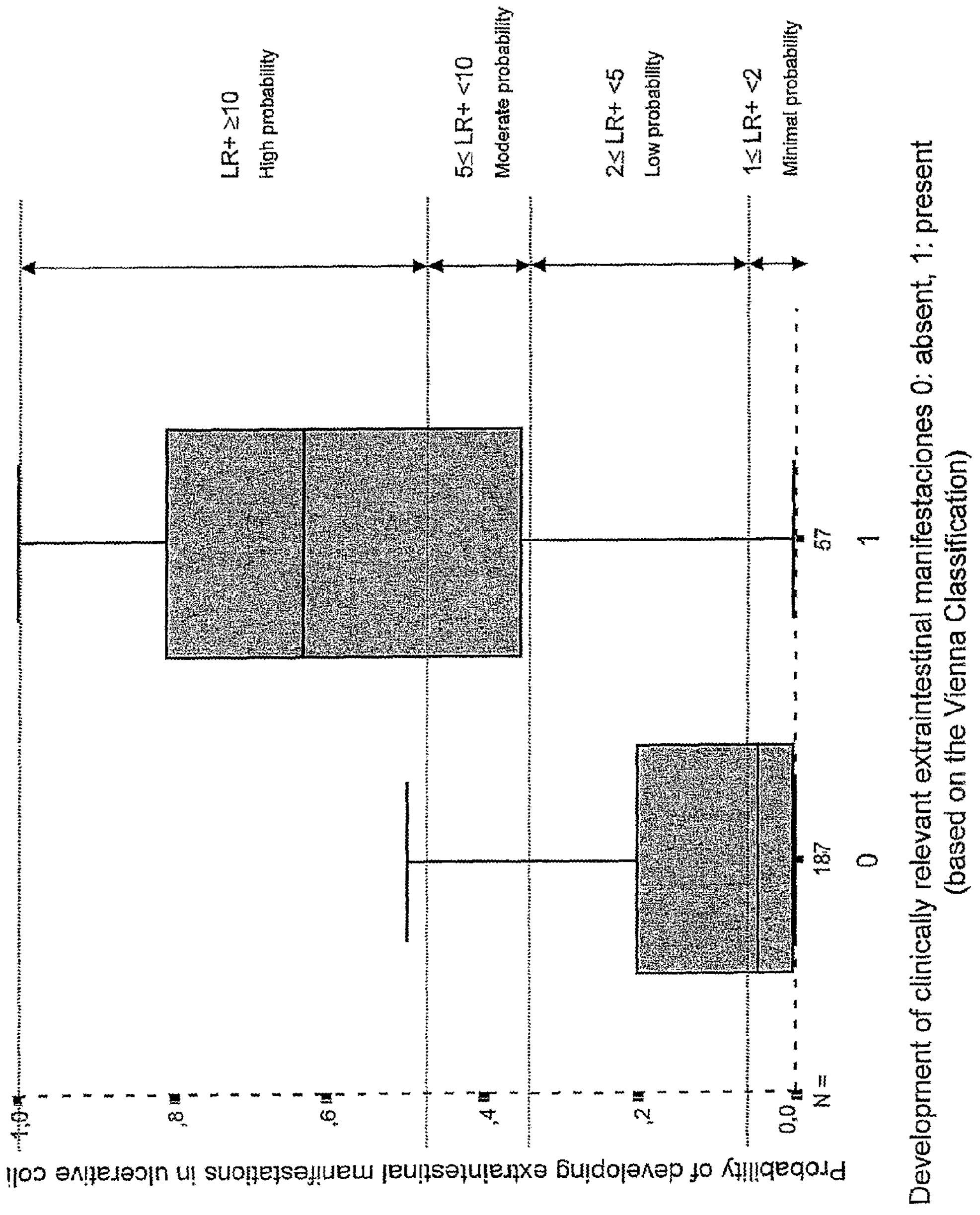

FIGS. 3-10 demonstrate the respective probabilities associated with the development of determined phenotypes (disease prognosis), based on genotypic data obtained with a DNA-chip, for each of the eight phenotypes analysed. FIGS. 3-7 show probabilities for development of phenotypes associated with Crohns disease and FIGS. 8-10 show probabilities associated with the development of phenotypes associated with ulcerative colitis. FIGS. 11-13 indicate the probabilities associated with the risk of developing resistance to corticosteroid treatment in individuals suffering from IBD.

The invention claimed is:

1. An in vitro method for genotyping genetic variations in an individual, the method comprising:

(a) providing a sample containing nucleic acid which comprises the genetic variations to be genotyped (the target DNA);

(b) providing, for each genetic variation to be genotyped, at least 2 oligonucleotide probe pairs, wherein:

(i) one pair consists of probes 1 and 2, and the other pair consists of probes 3 and 4;

(ii) probes 1 and 3 are capable of hybridising to genetic variation A and probes 2 and 4 are capable of hybridising to genetic variation B;

(iii) each probe is provided in replicates; and (iv) the probe replicates are deposited at positions on a solid support according to a known uniform distribution;

(c) contacting the target DNA with the probes under conditions which allow hybridisation to occur, thereby forming nucleic acid-probe hybridisation complexes, wherein each complex is detectably labelled;

(d) determining the intensity of detectable label at each probe replica position, thereby obtaining a raw intensity value;

(e) optionally amending the raw intensity value to take account of background noise, thereby obtaining a clean intensity value for each replica; and (f) applying an algorithm to the intensity data from (d) or (e), thereby determining the genotype with respect to each genetic variation, wherein application of the algorithm comprises calculating an average intensity value from the intensity values for each of the replicas of each probe and wherein the algorithm comprises deriving:

a first Fisher linear function: a1ratio1+b1ratio2+c1 that characterises the genotype AA;

a second Fisher linear function: a2ratio1+b2ratio2+c2 that characterises the genotype AB; and BB, wherein:

AA represents the genotype of a homozygote subject for the variant A;

AB represents the genotype of a heterozygote subject for the variants A and B;

BB represents the genotype of a homozygote subject for the variant B;

a1 is the coefficient which accompanies the X in the first linear function, a1 being obtained by applying a discriminate analysis to ratios 1 and 2 obtained from analysing n subjects for each of the genotypes AA, BB and AB;

b1 is the coefficient which accompanies the Y in the first linear function, b1 being obtained by applying a discriminate analysis to ratios 1 and 2 obtained from analysing n subjects for each of the genotypes AA, BB and AB;

c1 is the independent term of the first linear function;

a2 is the coefficient which accompanies the X in the second linear function, a2 being obtained by applying a discriminate analysis to ratios 1 and 2 obtained from analysing n subjects for each of the genotypes AA, BB and AB;

b2 is the coefficient which accompanies the Y in the second linear function, b2 being obtained by applying a discriminate analysis to ratios 1 and 2 obtained from analysing n subjects for each of the genotypes AA, BB and AB;

c2 is the independent term of the second linear function;

a3 is the coefficient which accompanies the X in the third linear function, a3 being obtained by applying a discriminate analysis to ratios 1 and 2 obtained from analysing n subjects for each of the genotypes AA, BB and AB;

b3 is the coefficient which accompanies the Y in the third linear function, b3 being obtained by applying a discriminate analysis to ratios 1 and 2 obtained from analysing n subjects for each the genotypes AA, BB and AB;

c3 is the independent term of the third linear function;

n is a number which is at least 3;

$$\text{ratio 1} = \frac{\text{average intensity value for probe 1}}{\text{average intensity value for probe 1} + \text{average intensity value for probe 2}};$$

and $$\text{ratio 2} = \frac{\text{average intensity value for probe 3}}{\text{average intensity value for probe 3} + \text{average intensity value for probe 4}}.$$

2. A method of deriving linear functions for use in a method according to claim 1, the method comprising, for each of n individuals having genotype AA, n individuals having genotype AB and n individuals having genotype BB with respect to a genetic variation:

(a) providing a sample containing nucleic acid which comprises the genetic variation (the target DNA);

(b) providing, for the genetic variation, at least 2 oligonucleotide probe pairs, wherein:
(i) one pair consists of probes 1 and 2 and the other pair consists of probes 3 and 4;
(ii) probes 1 and 3 are capable of hybridising to genetic variation A and probes 2 and 4 are capable of hybridising to genetic variation B;
(iii) each probe is provided in replicates; and
(iv) the probes are deposited at positions on a solid support which comprises additional deposited probes, and the probes are deposited according to a known uniform distribution;
(c) contacting the nucleic acid sample with the probes under conditions which allow hybridisation to occur, thereby forming nucleic acid-probe hybridisation complexes, wherein each complex is detectably labelled;
(d) determining the intensity of detectable label at each probe replica position thereby obtaining a raw intensity value;
(e) optionally amending the raw intensity value to take account of background noise thereby obtaining a clean intensity value for each replica;
(f) applying a suitable algorithm to the intensity data from (d) or (e), wherein application of the algorithm comprises calculating an average intensity value from the intensity values for each of the replicas of each probe and wherein the algorithm comprises deriving:
a first Fisher linear function: a1ratio1+b1ratio2+c1 that characterises the genotype AA;
a second Fisher linear function: a2ratiol+b2ratio2+c2 that characterises the genotype AB; and
a third Fisher linear function: a3ratiol+b3ratio2+c3 that characterises the genotype BB.
wherein:
AA represents the genotype of a homozygote subject for the variant A;
AB represents the genotype of a heterozygote subject for the variants A and B;
BB represents the genotype of a homozygote subject for the variant B;
a1 is the coefficient which accompanies the X in the first linear function, a1 being obtained by applying a discriminate analysis to ratios 1 and 2 obtained from analysing n subjects for each of the genotypes AA, BB and AB;
b1 is the coefficient which accompanies the Yin the first linear function, b1 being obtained by applying a discriminate analysis to ratios 1 and 2 obtained from analysing n subjects for each of the genotypes AA, BB and AB;
c1 is the independent term of the first linear function;
a2 is the coefficient which accompanies the X in the second linear function, a2 being obtained by applying a discriminate analysis to ratios 1 and 2 obtained from analysing n subjects for each of the genotypes AA, BB and AB;
b2 is the coefficient which accompanies the Y in the second linear function, b2 being obtained by applying a discriminate analysis to ratios 1 and 2 obtained from analysing n subjects for each of the genotypes AA, BB and AB:
c2 is the independent term of the second linear function;
a3 is the coefficient which accompanies the X in the third linear function, a3 being obtained by applying a discriminate analysis to ratios 1 and 2 obtained from analysing n subjects for each of the genotypes AA, BB and AB;
b3 is the coefficient which accompanies the Y in the third linear function, b3 being obtained by applying a discriminate analysis to ratios 1 and 2 obtained from analysing n subjects for each the genotypes AA, BB and AB;
c3 is the independent term of the third linear function;
n is a number which is at least 3;

$$\text{ratio } 1 = \frac{\text{average intensity value for probe 1}}{\text{average intensity value for probe 1} + \text{average intensity value for probe 2}};$$

and $$\text{ratio } 2 = \frac{\text{average intensity value for probe 3}}{\text{average intensity value for probe 3} + \text{average intensity value for probe 4}}.$$

3. A method of diagnosing IBD or susceptibility to IBD in an individual, the method comprising:
(a) genotyping an individual with respect to one or more genetic variations by a method according to claim 1 wherein the genetic variations are associated with IBD; and
(b) diagnosing IBD or susceptibility to IBD based on the genotype determined in (a).

4. A method of selecting a treatment for an individual having IBD comprising:
(a) genotyping an individual with respect to one or more genetic variations by a method according to claim 1 wherein the genetic variations are associated with IBD; and
(b) selecting a suitable treatment based on the genotype determined in (a).

5. A method of treating an individual having IBD comprising:
(a) genotyping an individual with respect to one or more genetic variations by a method according to claim 1 wherein the genetic variations are associated with IBD; and
(b) selecting a suitable treatment based on the genotype determined in (a); and
(c) administering said treatment to the individual.

6. A method of determining blood group in an individual, the method comprising:
(a) genotyping an individual with respect to one or more genetic variations by a method according to claim 1 wherein the genetic variations are associated with erythrocyte antigens; and
(b) determining the blood group of the individual based on the genotype determined in (a).

7. A method of determining susceptibility to adverse reactions to pharmaceuticals in an individual, the method comprising:
(a) genotyping an individual with respect to one or more genetic variations by a method according to claim 1 wherein the genetic variations are associated with adverse reactions to pharmaceuticals; and
(b) determining the susceptibility of the individual to adverse reactions to pharmaceuticals based on the genotype determined in (a).

8. A method of selecting a pharmaceutical treatment for an individual comprising:
(a) genotyping an individual with respect to one or more genetic variations by a method according to claim 1 wherein the genetic variations are associated with adverse reactions to pharmaceuticals; and (b) selecting a suitable treatment based on the genotype determined in (a).

9. A method of treating an individual with a pharmaceutical comprising:

(a) genotyping an individual with respect to one or more genetic variations by a method according to claim 1 wherein the genetic variations are associated with adverse reactions to pharmaceuticals;

(b) selecting a suitable treatment based on the genotype determined in (a); and (c) administering said treatment to the individual.

10. A method of identifying genetic variations predictive of a particular IBD phenotype the method comprising:

(a) genotyping a plurality of individuals with respect to one or more genetic variations by a method according to claim 1, wherein the genetic variations are associated with IBD and wherein the IBD phenotype of the individuals is known;

(b) comparing the genotypes of the individuals tested for one or more genetic variations with the known phenotypes of the individuals; and (c) identifying any genetic variations for which there is a statistically significant association between the genetic variation and the phenotype.

11. A method of predicting the likely development of the IBD phenotype of an individual, the method comprising:

(a) determining the genotype of the individual with respect to one more genetic variations which have been identified as predictive of development of a particular IBD phenotype by the method of claim 10; and (b) predicting the development of the particular IBD phenotype based on the genotype determined in (a).

* * * * *

UNITED STATES PATENT AND TRADEMARK OFFICE

CERTIFICATE OF CORRECTION

PATENT NO. : 7,914,990 B2
APPLICATION NO. : 11/813646
DATED : March 29, 2011
INVENTOR(S) : Buela et al.

It is certified that error appears in the above-identified patent and that said Letters Patent is hereby corrected as shown below:

On the Title Page Item (56):

Under the heading FOREIGN PATENT DOCUMENTS, "WO 01/29268" should read --WO 01/29269--.

Column 6, Line 22, "ay" should read --a--.

Column 8, Line 32, "5,80,4379" should read --5,804,379--.

Column 9, Lines 40-41, "due to errors in prescription" should read --due to errors in prescription--.

Column 10, Line 62, "*a*1 ratio 1 + *b*1 ratio 2" should read --a1ratio1 + b1ratio2--.

Column 10, Line 63, "*a*2 ratio 1 + *b*2 ratio 2" should read --a2ratio1 + b2ratio2--.

Column 10, Line 64, "*a*3 ratio 1 + *b*3 ratio 2" should read --*a*3ratio1 + *b*3ratio2--.

Column 663, Line 55, "AB; and BB," should read --AB; and a third Fisher linear function: a3ratio1 + b3ratio2 + c3 that characterises the genotype BB--.

Column 665, Line 46, "Yin" should read --Y in--.

Signed and Sealed this
Thirteenth Day of March, 2012

David J. Kappos
*Director of the United States Patent and Trademark Office*

SEQUENCE LISTING

```
<160> NUMBER OF SEQ ID NOS: 1655

<210> SEQ ID NO 1
<211> LENGTH: 25
<212> TYPE: DNA
<213> ORGANISM: Artificial sequence
<220> FEATURE:
<223> OTHER INFORMATION: Synthetic sequence: PCR primer suitable for
      amplifying target DNA regions comprising genetic variations
      associated with IBD

<400> SEQUENCE: 1

gcatagtaag cagtagggag taaca                                 25


<210> SEQ ID NO 2
<211> LENGTH: 21
<212> TYPE: DNA
<213> ORGANISM: Artificial sequence
<220> FEATURE:
<223> OTHER INFORMATION: Synthetic sequence: PCR primer suitable for
      amplifying target DNA regions comprising genetic variations
      associated with IBD

<400> SEQUENCE: 2

tgcaatagca ggagttgttg a                                     21


<210> SEQ ID NO 3
<211> LENGTH: 20
<212> TYPE: DNA
<213> ORGANISM: Artificial sequence
<220> FEATURE:
<223> OTHER INFORMATION: Synthetic sequence: PCR primer suitable for
      amplifying target DNA regions comprising genetic variations
      associated with IBD

<400> SEQUENCE: 3

tgctcccagg ctgtttattt                                       20
```

<210> SEQ ID NO 4
<211> LENGTH: 20
<212> TYPE: DNA
<213> ORGANISM: Artificial sequence
<220> FEATURE:
<223> OTHER INFORMATION: Synthetic sequence: PCR primer suitable for amplifying target DNA regions comprising genetic variations associated with IBD

<400> SEQUENCE: 4
tgttttcagc tgcttgatgg 20

<210> SEQ ID NO 5
<211> LENGTH: 20
<212> TYPE: DNA
<213> ORGANISM: Artificial sequence
<220> FEATURE:
<223> OTHER INFORMATION: Synthetic sequence: PCR primer suitable for amplifying target DNA regions comprising genetic variations associated with IBD

<400> SEQUENCE: 5
agatcacagc agccttcctg 20

<210> SEQ ID NO 6
<211> LENGTH: 20
<212> TYPE: DNA
<213> ORGANISM: Artificial sequence
<220> FEATURE:
<223> OTHER INFORMATION: Synthetic sequence: PCR primer suitable for amplifying target DNA regions comprising genetic variations associated with IBD

<400> SEQUENCE: 6
ggatggagtg gaagtgcttg 20

<210> SEQ ID NO 7
<211> LENGTH: 20
<212> TYPE: DNA
<213> ORGANISM: Artificial sequence
<220> FEATURE:
<223> OTHER INFORMATION: Synthetic sequence: PCR primer suitable for amplifying target DNA regions comprising genetic variations associated with IBD

<400> SEQUENCE: 7
actgcagagg gaggaggact 20

<210> SEQ ID NO 8
<211> LENGTH: 20
<212> TYPE: DNA
<213> ORGANISM: Artificial sequence
<220> FEATURE:
<223> OTHER INFORMATION: Synthetic sequence: PCR primer suitable for amplifying target DNA regions comprising genetic variations associated with IBD

<400> SEQUENCE: 8
ccacctcaag ctctggtgat 20

<210> SEQ ID NO 9
<211> LENGTH: 20
<212> TYPE: DNA
<213> ORGANISM: Artificial sequence
<220> FEATURE:
<223> OTHER INFORMATION: Synthetic sequence: PCR primer suitable for amplifying target DNA regions comprising genetic variations associated with IBD

```
<400> SEQUENCE: 9

actggctaac tcctgcagtc                                                 20


<210> SEQ ID NO 10
<211> LENGTH: 20
<212> TYPE: DNA
<213> ORGANISM: Artificial sequence
<220> FEATURE:
<223> OTHER INFORMATION: Synthetic sequence: PCR primer suitable for
      amplifying target DNA regions comprising genetic variations
      associated with IBD

<400> SEQUENCE: 10

gaaaaactga ggttcggaga                                                 20


<210> SEQ ID NO 11
<211> LENGTH: 20
<212> TYPE: DNA
<213> ORGANISM: Artificial sequence
<220> FEATURE:
<223> OTHER INFORMATION: Synthetic sequence: PCR primer suitable for
      amplifying target DNA regions comprising genetic variations
      associated with IBD

<400> SEQUENCE: 11

ctctcaactt ggggtcctga                                                 20


<210> SEQ ID NO 12
<211> LENGTH: 20
<212> TYPE: DNA
<213> ORGANISM: Artificial sequence
<220> FEATURE:
<223> OTHER INFORMATION: Synthetic sequence: PCR primer suitable for
      amplifying target DNA regions comprising genetic variations
      associated with IBD

<400> SEQUENCE: 12

ggcgttttgc aaacatacct                                                 20


<210> SEQ ID NO 13
<211> LENGTH: 20
<212> TYPE: DNA
<213> ORGANISM: Artificial sequence
<220> FEATURE:
<223> OTHER INFORMATION: Synthetic sequence: PCR primer suitable for
      amplifying target DNA regions comprising genetic variations
      associated with IBD

<400> SEQUENCE: 13

ccagccaaat gcattctctt                                                 20


<210> SEQ ID NO 14
<211> LENGTH: 20
<212> TYPE: DNA
<213> ORGANISM: Artificial sequence
<220> FEATURE:
<223> OTHER INFORMATION: Synthetic sequence: PCR primer suitable for
      amplifying target DNA regions comprising genetic variations
      associated with IBD

<400> SEQUENCE: 14

cacagggaag gtgaagggta                                                 20


<210> SEQ ID NO 15
<211> LENGTH: 20
<212> TYPE: DNA
<213> ORGANISM: Artificial sequence
```

<220> FEATURE:
<223> OTHER INFORMATION: Synthetic sequence: PCR primer suitable for amplifying target DNA regions comprising genetic variations associated with IBD

<400> SEQUENCE: 15
caactggctc cccttacctt 20

<210> SEQ ID NO 16
<211> LENGTH: 20
<212> TYPE: DNA
<213> ORGANISM: Artificial sequence
<220> FEATURE:
<223> OTHER INFORMATION: Synthetic sequence: PCR primer suitable for amplifying target DNA regions comprising genetic variations associated with IBD

<400> SEQUENCE: 16
atggaggctg gataggaggt 20

<210> SEQ ID NO 17
<211> LENGTH: 20
<212> TYPE: DNA
<213> ORGANISM: Artificial sequence
<220> FEATURE:
<223> OTHER INFORMATION: Synthetic sequence: PCR primer suitable for amplifying target DNA regions comprising genetic variations associated with IBD

<400> SEQUENCE: 17
agaggcctcc ctgagcttac 20

<210> SEQ ID NO 18
<211> LENGTH: 20
<212> TYPE: DNA
<213> ORGANISM: Artificial sequence
<220> FEATURE:
<223> OTHER INFORMATION: Synthetic sequence: PCR primer suitable for amplifying target DNA regions comprising genetic variations associated with IBD

<400> SEQUENCE: 18
tctcggagat ctcgaagcat 20

<210> SEQ ID NO 19
<211> LENGTH: 20
<212> TYPE: DNA
<213> ORGANISM: Artificial sequence
<220> FEATURE:
<223> OTHER INFORMATION: Synthetic sequence: PCR primer suitable for amplifying target DNA regions comprising genetic variations associated with IBD

<400> SEQUENCE: 19
aactgaagca atgccagtcc 20

<210> SEQ ID NO 20
<211> LENGTH: 20
<212> TYPE: DNA
<213> ORGANISM: Artificial sequence
<220> FEATURE:
<223> OTHER INFORMATION: Synthetic sequence: PCR primer suitable for amplifying target DNA regions comprising genetic variations associated with IBD

<400> SEQUENCE: 20
cagagccagc acctcctaga 20

<210> SEQ ID NO 21
<211> LENGTH: 20
<212> TYPE: DNA
<213> ORGANISM: Artificial sequence
<220> FEATURE:
<223> OTHER INFORMATION: Synthetic sequence: PCR primer suitable for amplifying target DNA regions comprising genetic variations associated with IBD

<400> SEQUENCE: 21
cttgagccca ggagtttgag 20

<210> SEQ ID NO 22
<211> LENGTH: 20
<212> TYPE: DNA
<213> ORGANISM: Artificial sequence
<220> FEATURE:
<223> OTHER INFORMATION: Synthetic sequence: PCR primer suitable for amplifying target DNA regions comprising genetic variations associated with IBD

<400> SEQUENCE: 22
atcagaggct gcaaaccagt 20

<210> SEQ ID NO 23
<211> LENGTH: 20
<212> TYPE: DNA
<213> ORGANISM: Artificial sequence
<220> FEATURE:
<223> OTHER INFORMATION: Synthetic sequence: PCR primer suitable for amplifying target DNA regions comprising genetic variations associated with IBD

<400> SEQUENCE: 23
tggaccgcat gactctatca 20

<210> SEQ ID NO 24
<211> LENGTH: 19
<212> TYPE: DNA
<213> ORGANISM: Artificial sequence
<220> FEATURE:
<223> OTHER INFORMATION: Synthetic sequence: PCR primer suitable for amplifying target DNA regions comprising genetic variations associated with IBD

<400> SEQUENCE: 24
ggctctggct tcctagcag 19

<210> SEQ ID NO 25
<211> LENGTH: 20
<212> TYPE: DNA
<213> ORGANISM: Artificial sequence
<220> FEATURE:
<223> OTHER INFORMATION: Synthetic sequence: PCR primer suitable for amplifying target DNA regions comprising genetic variations associated with IBD

<400> SEQUENCE: 25
ccagccatca tttccactct 20

<210> SEQ ID NO 26
<211> LENGTH: 20
<212> TYPE: DNA
<213> ORGANISM: Artificial sequence
<220> FEATURE:
<223> OTHER INFORMATION: Synthetic sequence: PCR primer suitable for amplifying target DNA regions comprising genetic variations associated with IBD

<400> SEQUENCE: 26
cctgcaccct gtaatcctgt 20

<210> SEQ ID NO 27
<211> LENGTH: 20
<212> TYPE: DNA
<213> ORGANISM: Artificial sequence
<220> FEATURE:
<223> OTHER INFORMATION: Synthetic sequence: PCR primer suitable for amplifying target DNA regions comprising genetic variations associated with IBD

<400> SEQUENCE: 27
agccaatcca ctccttcctt 20

<210> SEQ ID NO 28
<211> LENGTH: 20
<212> TYPE: DNA
<213> ORGANISM: Artificial sequence
<220> FEATURE:
<223> OTHER INFORMATION: Synthetic sequence: PCR primer suitable for amplifying target DNA regions comprising genetic variations associated with IBD

<400> SEQUENCE: 28
catgccctaa cctgtgctct 20

<210> SEQ ID NO 29
<211> LENGTH: 20
<212> TYPE: DNA
<213> ORGANISM: Artificial sequence
<220> FEATURE:
<223> OTHER INFORMATION: Synthetic sequence: PCR primer suitable for amplifying target DNA regions comprising genetic variations associated with IBD

<400> SEQUENCE: 29
atagaggccg atttccttgg 20

<210> SEQ ID NO 30
<211> LENGTH: 23
<212> TYPE: DNA
<213> ORGANISM: Artificial sequence
<220> FEATURE:
<223> OTHER INFORMATION: Synthetic sequence: PCR primer suitable for amplifying target DNA regions comprising genetic variations associated with IBD

<400> SEQUENCE: 30
ttctggaaca gaagattgtc att 23

<210> SEQ ID NO 31
<211> LENGTH: 20
<212> TYPE: DNA
<213> ORGANISM: Artificial sequence
<220> FEATURE:
<223> OTHER INFORMATION: Synthetic sequence: PCR primer suitable for amplifying target DNA regions comprising genetic variations associated with IBD

<400> SEQUENCE: 31
gctccccaga aacaaactga 20

<210> SEQ ID NO 32
<211> LENGTH: 20
<212> TYPE: DNA
<213> ORGANISM: Artificial sequence
<220> FEATURE:
<223> OTHER INFORMATION: Synthetic sequence: PCR primer suitable for amplifying target DNA regions comprising genetic variations
associated with IBD

<400> SEQUENCE: 32
cacctgcaga agttcccatt 20

<210> SEQ ID NO 33
<211> LENGTH: 20
<212> TYPE: DNA
<213> ORGANISM: Artificial sequence
<220> FEATURE:
<223> OTHER INFORMATION: Synthetic sequence: PCR primer suitable for
amplifying target DNA regions comprising genetic variations
associated with IBD

<400> SEQUENCE: 33
gctccccaga aacaaactga 20

<210> SEQ ID NO 34
<211> LENGTH: 20
<212> TYPE: DNA
<213> ORGANISM: Artificial sequence
<220> FEATURE:
<223> OTHER INFORMATION: Synthetic sequence: PCR primer suitable for
amplifying target DNA regions comprising genetic variations
associated with IBD

<400> SEQUENCE: 34
cacctgcaga agttcccatt 20

<210> SEQ ID NO 35
<211> LENGTH: 20
<212> TYPE: DNA
<213> ORGANISM: Artificial sequence
<220> FEATURE:
<223> OTHER INFORMATION: Synthetic sequence: PCR primer suitable for
amplifying target DNA regions comprising genetic variations
associated with IBD

<400> SEQUENCE: 35
aggaagctgg agcaggtgta 20

<210> SEQ ID NO 36
<211> LENGTH: 20
<212> TYPE: DNA
<213> ORGANISM: Artificial sequence
<220> FEATURE:
<223> OTHER INFORMATION: Synthetic sequence: PCR primer suitable for
amplifying target DNA regions comprising genetic variations
associated with IBD

<400> SEQUENCE: 36
ccattctgac tggcactcct 20

<210> SEQ ID NO 37
<211> LENGTH: 20
<212> TYPE: DNA
<213> ORGANISM: Artificial sequence
<220> FEATURE:
<223> OTHER INFORMATION: Synthetic sequence: PCR primer suitable for
amplifying target DNA regions comprising genetic variations
associated with IBD

<400> SEQUENCE: 37
tcttctggaa cgtggtaggg 20

<210> SEQ ID NO 38
<211> LENGTH: 20

<212> TYPE: DNA
<213> ORGANISM: Artificial sequence
<220> FEATURE:
<223> OTHER INFORMATION: Synthetic sequence: PCR primer suitable for amplifying target DNA regions comprising genetic variations associated with IBD

<400> SEQUENCE: 38
ctaagcaggg ggttccttgt 20

<210> SEQ ID NO 39
<211> LENGTH: 20
<212> TYPE: DNA
<213> ORGANISM: Artificial sequence
<220> FEATURE:
<223> OTHER INFORMATION: Synthetic sequence: PCR primer suitable for amplifying target DNA regions comprising genetic variations associated with IBD

<400> SEQUENCE: 39
cggcgcaatt actacctctt 20

<210> SEQ ID NO 40
<211> LENGTH: 20
<212> TYPE: DNA
<213> ORGANISM: Artificial sequence
<220> FEATURE:
<223> OTHER INFORMATION: Synthetic sequence: PCR primer suitable for amplifying target DNA regions comprising genetic variations associated with IBD

<400> SEQUENCE: 40
cgtgaatgcc agatgaacac 20

<210> SEQ ID NO 41
<211> LENGTH: 20
<212> TYPE: DNA
<213> ORGANISM: Artificial sequence
<220> FEATURE:
<223> OTHER INFORMATION: Synthetic sequence: PCR primer suitable for amplifying target DNA regions comprising genetic variations associated with IBD

<400> SEQUENCE: 41
ctccttgctt gctttccttg 20

<210> SEQ ID NO 42
<211> LENGTH: 20
<212> TYPE: DNA
<213> ORGANISM: Artificial sequence
<220> FEATURE:
<223> OTHER INFORMATION: Synthetic sequence: PCR primer suitable for amplifying target DNA regions comprising genetic variations associated with IBD

<400> SEQUENCE: 42
agtagggatg ggatggatgg 20

<210> SEQ ID NO 43
<211> LENGTH: 20
<212> TYPE: DNA
<213> ORGANISM: Artificial sequence
<220> FEATURE:
<223> OTHER INFORMATION: Synthetic sequence: PCR primer suitable for amplifying target DNA regions comprising genetic variations associated with IBD

<400> SEQUENCE: 43
caagagtgcc cagagagtcc 20

<210> SEQ ID NO 44
<211> LENGTH: 21
<212> TYPE: DNA
<213> ORGANISM: Artificial sequence
<220> FEATURE:
<223> OTHER INFORMATION: Synthetic sequence: PCR primer suitable for amplifying target DNA regions comprising genetic variations associated with IBD

<400> SEQUENCE: 44
ttctccctaa ggcattttgg t 21

<210> SEQ ID NO 45
<211> LENGTH: 19
<212> TYPE: DNA
<213> ORGANISM: Artificial sequence
<220> FEATURE:
<223> OTHER INFORMATION: Synthetic sequence: PCR primer suitable for amplifying target DNA regions comprising genetic variations associated with IBD

<400> SEQUENCE: 45
cttacatagg gcgcacgac 19

<210> SEQ ID NO 46
<211> LENGTH: 18
<212> TYPE: DNA
<213> ORGANISM: Artificial sequence
<220> FEATURE:
<223> OTHER INFORMATION: Synthetic sequence: PCR primer suitable for amplifying target DNA regions comprising genetic variations associated with IBD

<400> SEQUENCE: 46
agtcccgctg ccttccta 18

<210> SEQ ID NO 47
<211> LENGTH: 20
<212> TYPE: DNA
<213> ORGANISM: Artificial sequence
<220> FEATURE:
<223> OTHER INFORMATION: Synthetic sequence: PCR primer suitable for amplifying target DNA regions comprising genetic variations associated with IBD

<400> SEQUENCE: 47
ctctagaggg cctgtgcaat 20

<210> SEQ ID NO 48
<211> LENGTH: 20
<212> TYPE: DNA
<213> ORGANISM: Artificial sequence
<220> FEATURE:
<223> OTHER INFORMATION: Synthetic sequence: PCR primer suitable for amplifying target DNA regions comprising genetic variations associated with IBD

<400> SEQUENCE: 48
tcaatgtggg aaactgtcca 20

<210> SEQ ID NO 49
<211> LENGTH: 20
<212> TYPE: DNA
<213> ORGANISM: Artificial sequence
<220> FEATURE:
<223> OTHER INFORMATION: Synthetic sequence: PCR primer suitable for amplifying target DNA regions comprising genetic variations associated with IBD

<400> SEQUENCE: 49
caacaaaggt gggaatgctt 20

<210> SEQ ID NO 50
<211> LENGTH: 20
<212> TYPE: DNA
<213> ORGANISM: Artificial sequence
<220> FEATURE:
<223> OTHER INFORMATION: Synthetic sequence: PCR primer suitable for amplifying target DNA regions comprising genetic variations associated with IBD

<400> SEQUENCE: 50
tttcaaattg gaatgctgga 20

<210> SEQ ID NO 51
<211> LENGTH: 20
<212> TYPE: DNA
<213> ORGANISM: Artificial sequence
<220> FEATURE:
<223> OTHER INFORMATION: Synthetic sequence: PCR primer suitable for amplifying target DNA regions comprising genetic variations associated with IBD

<400> SEQUENCE: 51
aggcagagag ggaaggagag 20

<210> SEQ ID NO 52
<211> LENGTH: 20
<212> TYPE: DNA
<213> ORGANISM: Artificial sequence
<220> FEATURE:
<223> OTHER INFORMATION: Synthetic sequence: PCR primer suitable for amplifying target DNA regions comprising genetic variations associated with IBD

<400> SEQUENCE: 52
aaacagcgag ggagaaactg 20

<210> SEQ ID NO 53
<211> LENGTH: 20
<212> TYPE: DNA
<213> ORGANISM: Artificial sequence
<220> FEATURE:
<223> OTHER INFORMATION: Synthetic sequence: PCR primer suitable for amplifying target DNA regions comprising genetic variations associated with IBD

<400> SEQUENCE: 53
ggctgtgctt tctcgtcttc 20

<210> SEQ ID NO 54
<211> LENGTH: 20
<212> TYPE: DNA
<213> ORGANISM: Artificial sequence
<220> FEATURE:
<223> OTHER INFORMATION: Synthetic sequence: PCR primer suitable for amplifying target DNA regions comprising genetic variations associated with IBD

<400> SEQUENCE: 54
ggtgacgttc aggttgttca 20

<210> SEQ ID NO 55
<211> LENGTH: 20
<212> TYPE: DNA
<213> ORGANISM: Artificial sequence
<220> FEATURE:
<223> OTHER INFORMATION: Synthetic sequence: PCR primer suitable for amplifying target DNA regions comprising genetic variations associated with IBD

<400> SEQUENCE: 55
agcaaacccc tattccatgc 20

<210> SEQ ID NO 56
<211> LENGTH: 20
<212> TYPE: DNA
<213> ORGANISM: Artificial sequence
<220> FEATURE:
<223> OTHER INFORMATION: Synthetic sequence: PCR primer suitable for amplifying target DNA regions comprising genetic variations associated with IBD

<400> SEQUENCE: 56
tacataaatg cccccacgtc 20

<210> SEQ ID NO 57
<211> LENGTH: 20
<212> TYPE: DNA
<213> ORGANISM: Artificial sequence
<220> FEATURE:
<223> OTHER INFORMATION: Synthetic sequence: PCR primer suitable for amplifying target DNA regions comprising genetic variations associated with IBD

<400> SEQUENCE: 57
cttgagggca cctacctctg 20

<210> SEQ ID NO 58
<211> LENGTH: 20
<212> TYPE: DNA
<213> ORGANISM: Artificial sequence
<220> FEATURE:
<223> OTHER INFORMATION: Synthetic sequence: PCR primer suitable for amplifying target DNA regions comprising genetic variations associated with IBD

<400> SEQUENCE: 58
cattatgact gcggctgcta 20

<210> SEQ ID NO 59
<211> LENGTH: 20
<212> TYPE: DNA
<213> ORGANISM: Artificial sequence
<220> FEATURE:
<223> OTHER INFORMATION: Synthetic sequence: PCR primer suitable for amplifying target DNA regions comprising genetic variations associated with IBD

<400> SEQUENCE: 59
gaatgaaatg ccccagagaa 20

<210> SEQ ID NO 60
<211> LENGTH: 20
<212> TYPE: DNA
<213> ORGANISM: Artificial sequence
<220> FEATURE:
<223> OTHER INFORMATION: Synthetic sequence: PCR primer suitable for amplifying target DNA regions comprising genetic variations associated with IBD

<400> SEQUENCE: 60
actgtggggt tcaacctctg 20

<210> SEQ ID NO 61
<211> LENGTH: 20
<212> TYPE: DNA
<213> ORGANISM: Artificial sequence
<220> FEATURE:
<223> OTHER INFORMATION: Synthetic sequence: PCR primer suitable for amplifying target DNA regions comprising genetic variations associated with IBD

<400> SEQUENCE: 61
catacagcac cttcgggtct 20

<210> SEQ ID NO 62
<211> LENGTH: 20
<212> TYPE: DNA
<213> ORGANISM: Artificial sequence
<220> FEATURE:
<223> OTHER INFORMATION: Synthetic sequence: PCR primer suitable for amplifying target DNA regions comprising genetic variations associated with IBD

<400> SEQUENCE: 62
gggcagactt tggaactcag 20

<210> SEQ ID NO 63
<211> LENGTH: 20
<212> TYPE: DNA
<213> ORGANISM: Artificial sequence
<220> FEATURE:
<223> OTHER INFORMATION: Synthetic sequence: PCR primer suitable for amplifying target DNA regions comprising genetic variations associated with IBD

<400> SEQUENCE: 63
cataatcagg ggttgcatga 20

<210> SEQ ID NO 64
<211> LENGTH: 20
<212> TYPE: DNA
<213> ORGANISM: Artificial sequence
<220> FEATURE:
<223> OTHER INFORMATION: Synthetic sequence: PCR primer suitable for amplifying target DNA regions comprising genetic variations associated with IBD

<400> SEQUENCE: 64
ccagagacac tgggacatca 20

<210> SEQ ID NO 65
<211> LENGTH: 20
<212> TYPE: DNA
<213> ORGANISM: Artificial sequence
<220> FEATURE:
<223> OTHER INFORMATION: Synthetic sequence: PCR primer suitable for amplifying target DNA regions comprising genetic variations associated with IBD

<400> SEQUENCE: 65
ccaaggccat ggtgtatagc 20

<210> SEQ ID NO 66
<211> LENGTH: 20
<212> TYPE: DNA
<213> ORGANISM: Artificial sequence
<220> FEATURE:
<223> OTHER INFORMATION: Synthetic sequence: PCR primer suitable for amplifying target DNA regions comprising genetic variations associated with IBD

<400> SEQUENCE: 66
gtgccacctc ccatctctaa 20

<210> SEQ ID NO 67
<211> LENGTH: 20
<212> TYPE: DNA
<213> ORGANISM: Artificial sequence
<220> FEATURE:
<223> OTHER INFORMATION: Synthetic sequence: PCR primer suitable for amplifying target DNA regions comprising genetic variations associated with IBD

<400> SEQUENCE: 67
ctgtttgagg gcatcgactt 20

<210> SEQ ID NO 68
<211> LENGTH: 20
<212> TYPE: DNA
<213> ORGANISM: Artificial sequence
<220> FEATURE:
<223> OTHER INFORMATION: Synthetic sequence: PCR primer suitable for amplifying target DNA regions comprising genetic variations associated with IBD

<400> SEQUENCE: 68
ggggttgatg ctcttgttca 20

<210> SEQ ID NO 69
<211> LENGTH: 20
<212> TYPE: DNA
<213> ORGANISM: Artificial sequence
<220> FEATURE:
<223> OTHER INFORMATION: Synthetic sequence: PCR primer suitable for amplifying target DNA regions comprising genetic variations associated with IBD

<400> SEQUENCE: 69
agtcaaagcc acagtccaca 20

<210> SEQ ID NO 70
<211> LENGTH: 20
<212> TYPE: DNA
<213> ORGANISM: Artificial sequence
<220> FEATURE:
<223> OTHER INFORMATION: Synthetic sequence: PCR primer suitable for amplifying target DNA regions comprising genetic variations associated with IBD

<400> SEQUENCE: 70
ccctgttgag agggtgacat 20

<210> SEQ ID NO 71
<211> LENGTH: 20
<212> TYPE: DNA
<213> ORGANISM: Artificial sequence
<220> FEATURE:
<223> OTHER INFORMATION: Synthetic sequence: PCR primer suitable for amplifying target DNA regions comprising genetic variations associated with IBD

<400> SEQUENCE: 71
gcctctcctg actgtcatcc 20

<210> SEQ ID NO 72
<211> LENGTH: 20
<212> TYPE: DNA
<213> ORGANISM: Artificial sequence
<220> FEATURE:
<223> OTHER INFORMATION: Synthetic sequence: PCR primer suitable for amplifying target DNA regions comprising genetic variations associated with IBD

<400> SEQUENCE: 72
tcacaaagcg gaagaatgtg 20

<210> SEQ ID NO 73
<211> LENGTH: 20
<212> TYPE: DNA
<213> ORGANISM: Artificial sequence
<220> FEATURE:
<223> OTHER INFORMATION: Synthetic sequence: PCR primer suitable for amplifying target DNA regions comprising genetic variations associated with IBD

<400> SEQUENCE: 73
acccaaacta ggcctcacct 20

<210> SEQ ID NO 74
<211> LENGTH: 20
<212> TYPE: DNA
<213> ORGANISM: Artificial sequence
<220> FEATURE:
<223> OTHER INFORMATION: Synthetic sequence: PCR primer suitable for amplifying target DNA regions comprising genetic variations associated with IBD

<400> SEQUENCE: 74
acaggtggca tcttggaaac 20

<210> SEQ ID NO 75
<211> LENGTH: 20
<212> TYPE: DNA
<213> ORGANISM: Artificial sequence
<220> FEATURE:
<223> OTHER INFORMATION: Synthetic sequence: PCR primer suitable for amplifying target DNA regions comprising genetic variations associated with IBD

<400> SEQUENCE: 75
tcattttccc tcggtttcag 20

<210> SEQ ID NO 76
<211> LENGTH: 20
<212> TYPE: DNA
<213> ORGANISM: Artificial sequence
<220> FEATURE:
<223> OTHER INFORMATION: Synthetic sequence: PCR primer suitable for amplifying target DNA regions comprising genetic variations associated with IBD

<400> SEQUENCE: 76
agaacagagg gggaagcagt 20

<210> SEQ ID NO 77
<211> LENGTH: 20
<212> TYPE: DNA
<213> ORGANISM: Artificial sequence
<220> FEATURE:
<223> OTHER INFORMATION: Synthetic sequence: PCR primer suitable for amplifying target DNA regions comprising genetic variations associated with IBD

<400> SEQUENCE: 77
tggcagcgtc ttactcagaa 20

<210> SEQ ID NO 78
<211> LENGTH: 20

```
<212> TYPE: DNA
<213> ORGANISM: Artificial sequence
<220> FEATURE:
<223> OTHER INFORMATION: Synthetic sequence: PCR primer suitable for
      amplifying target DNA regions comprising genetic variations
      associated with IBD

<400> SEQUENCE: 78

agaacagccc aacacgtacc                                              20

<210> SEQ ID NO 79
<211> LENGTH: 18
<212> TYPE: DNA
<213> ORGANISM: Artificial sequence
<220> FEATURE:
<223> OTHER INFORMATION: Synthetic sequence: PCR primer suitable for
      amplifying target DNA regions comprising genetic variations
      associated with IBD

<400> SEQUENCE: 79

gttccccttg cacgttcc                                                18

<210> SEQ ID NO 80
<211> LENGTH: 23
<212> TYPE: DNA
<213> ORGANISM: Artificial sequence
<220> FEATURE:
<223> OTHER INFORMATION: Synthetic sequence: PCR primer suitable for
      amplifying target DNA regions comprising genetic variations
      associated with IBD

<400> SEQUENCE: 80

ttgttggaag aaaagaattg tcc                                          23

<210> SEQ ID NO 81
<211> LENGTH: 20
<212> TYPE: DNA
<213> ORGANISM: Artificial sequence
<220> FEATURE:
<223> OTHER INFORMATION: Synthetic sequence: PCR primer suitable for
      amplifying target DNA regions comprising genetic variations
      associated with IBD

<400> SEQUENCE: 81

caacctcagc cagacaaggt                                              20

<210> SEQ ID NO 82
<211> LENGTH: 20
<212> TYPE: DNA
<213> ORGANISM: Artificial sequence
<220> FEATURE:
<223> OTHER INFORMATION: Synthetic sequence: PCR primer suitable for
      amplifying target DNA regions comprising genetic variations
      associated with IBD

<400> SEQUENCE: 82

cagccacgtg attgtctagg                                              20

<210> SEQ ID NO 83
<211> LENGTH: 20
<212> TYPE: DNA
<213> ORGANISM: Artificial sequence
<220> FEATURE:
<223> OTHER INFORMATION: Synthetic sequence: PCR primer suitable for
      amplifying target DNA regions comprising genetic variations
      associated with IBD

<400> SEQUENCE: 83

gcttctggca tctgtccttc                                              20
```

<210> SEQ ID NO 84
<211> LENGTH: 20
<212> TYPE: DNA
<213> ORGANISM: Artificial sequence
<220> FEATURE:
<223> OTHER INFORMATION: Synthetic sequence: PCR primer suitable for amplifying target DNA regions comprising genetic variations associated with IBD

<400> SEQUENCE: 84
ccggcttacc ttctgctgta 20

<210> SEQ ID NO 85
<211> LENGTH: 20
<212> TYPE: DNA
<213> ORGANISM: Artificial sequence
<220> FEATURE:
<223> OTHER INFORMATION: Synthetic sequence: PCR primer suitable for amplifying target DNA regions comprising genetic variations associated with IBD

<400> SEQUENCE: 85
acctggtccc caaaagaaat 20

<210> SEQ ID NO 86
<211> LENGTH: 20
<212> TYPE: DNA
<213> ORGANISM: Artificial sequence
<220> FEATURE:
<223> OTHER INFORMATION: Synthetic sequence: PCR primer suitable for amplifying target DNA regions comprising genetic variations associated with IBD

<400> SEQUENCE: 86
aaagttgggg acacacaagc 20

<210> SEQ ID NO 87
<211> LENGTH: 20
<212> TYPE: DNA
<213> ORGANISM: Artificial sequence
<220> FEATURE:
<223> OTHER INFORMATION: Synthetic sequence: PCR primer suitable for amplifying target DNA regions comprising genetic variations associated with IBD

<400> SEQUENCE: 87
accacagcaa tgggtaggag 20

<210> SEQ ID NO 88
<211> LENGTH: 20
<212> TYPE: DNA
<213> ORGANISM: Artificial sequence
<220> FEATURE:
<223> OTHER INFORMATION: Synthetic sequence: PCR primer suitable for amplifying target DNA regions comprising genetic variations associated with IBD

<400> SEQUENCE: 88
tggtttcagt cttggcttcc 20

<210> SEQ ID NO 89
<211> LENGTH: 20
<212> TYPE: DNA
<213> ORGANISM: Artificial sequence
<220> FEATURE:
<223> OTHER INFORMATION: Synthetic sequence: PCR primer suitable for amplifying target DNA regions comprising genetic variations associated with IBD

<400> SEQUENCE: 89
acctggtccc caaaagaaat 20

<210> SEQ ID NO 90
<211> LENGTH: 20
<212> TYPE: DNA
<213> ORGANISM: Artificial sequence
<220> FEATURE:
<223> OTHER INFORMATION: Synthetic sequence: PCR primer suitable for amplifying target DNA regions comprising genetic variations associated with IBD

<400> SEQUENCE: 90
aaagttgggg acacacaagc 20

<210> SEQ ID NO 91
<211> LENGTH: 22
<212> TYPE: DNA
<213> ORGANISM: Artificial sequence
<220> FEATURE:
<223> OTHER INFORMATION: Synthetic sequence: PCR primer suitable for amplifying target DNA regions comprising genetic variations associated with IBD

<400> SEQUENCE: 91
aaaacttttg tggggatatg ga 22

<210> SEQ ID NO 92
<211> LENGTH: 25
<212> TYPE: DNA
<213> ORGANISM: Artificial sequence
<220> FEATURE:
<223> OTHER INFORMATION: Synthetic sequence: PCR primer suitable for amplifying target DNA regions comprising genetic variations associated with IBD

<400> SEQUENCE: 92
ccctctattt agtcatttga aaaca 25

<210> SEQ ID NO 93
<211> LENGTH: 20
<212> TYPE: DNA
<213> ORGANISM: Artificial sequence
<220> FEATURE:
<223> OTHER INFORMATION: Synthetic sequence: PCR primer suitable for amplifying target DNA regions comprising genetic variations associated with IBD

<400> SEQUENCE: 93
ccaggtccac acattcctct 20

<210> SEQ ID NO 94
<211> LENGTH: 20
<212> TYPE: DNA
<213> ORGANISM: Artificial sequence
<220> FEATURE:
<223> OTHER INFORMATION: Synthetic sequence: PCR primer suitable for amplifying target DNA regions comprising genetic variations associated with IBD

<400> SEQUENCE: 94
ttaccatttg cgatcacctg 20

<210> SEQ ID NO 95
<211> LENGTH: 23
<212> TYPE: DNA
<213> ORGANISM: Artificial sequence
<220> FEATURE:
<223> OTHER INFORMATION: Synthetic sequence: PCR primer suitable for amplifying target DNA regions comprising genetic variations associated with IBD

<400> SEQUENCE: 95
catccattac attttcaggc ttt 23

<210> SEQ ID NO 96
<211> LENGTH: 21
<212> TYPE: DNA
<213> ORGANISM: Artificial sequence
<220> FEATURE:
<223> OTHER INFORMATION: Synthetic sequence: PCR primer suitable for amplifying target DNA regions comprising genetic variations associated with IBD

<400> SEQUENCE: 96
ggttgatgct tttgaagaac g 21

<210> SEQ ID NO 97
<211> LENGTH: 20
<212> TYPE: DNA
<213> ORGANISM: Artificial sequence
<220> FEATURE:
<223> OTHER INFORMATION: Synthetic sequence: PCR primer suitable for amplifying target DNA regions comprising genetic variations associated with IBD

<400> SEQUENCE: 97
gagccccaca gtcttcgtta 20

<210> SEQ ID NO 98
<211> LENGTH: 20
<212> TYPE: DNA
<213> ORGANISM: Artificial sequence
<220> FEATURE:
<223> OTHER INFORMATION: Synthetic sequence: PCR primer suitable for amplifying target DNA regions comprising genetic variations associated with IBD

<400> SEQUENCE: 98
tttccgttcc ctgtcaagtc 20

<210> SEQ ID NO 99
<211> LENGTH: 20
<212> TYPE: DNA
<213> ORGANISM: Artificial sequence
<220> FEATURE:
<223> OTHER INFORMATION: Synthetic sequence: PCR primer suitable for amplifying target DNA regions comprising genetic variations associated with IBD

<400> SEQUENCE: 99
gctcttcctc tcccaaaacc 20

<210> SEQ ID NO 100
<211> LENGTH: 20
<212> TYPE: DNA
<213> ORGANISM: Artificial sequence
<220> FEATURE:
<223> OTHER INFORMATION: Synthetic sequence: PCR primer suitable for amplifying target DNA regions comprising genetic variations associated with IBD

<400> SEQUENCE: 100
caccatgggg ggcactgttc 20

<210> SEQ ID NO 101
<211> LENGTH: 20
<212> TYPE: DNA
<213> ORGANISM: Artificial sequence
<220> FEATURE:
<223> OTHER INFORMATION: Synthetic sequence: PCR primer suitable for amplifying target DNA regions comprising genetic variations associated with IBD

<400> SEQUENCE: 101
aacgaggggt cttggaactc 20

<210> SEQ ID NO 102
<211> LENGTH: 20
<212> TYPE: DNA
<213> ORGANISM: Artificial sequence
<220> FEATURE:
<223> OTHER INFORMATION: Synthetic sequence: PCR primer suitable for amplifying target DNA regions comprising genetic variations associated with IBD

<400> SEQUENCE: 102
gtgttctgtg cctcccaagt 20

<210> SEQ ID NO 103
<211> LENGTH: 20
<212> TYPE: DNA
<213> ORGANISM: Artificial sequence
<220> FEATURE:
<223> OTHER INFORMATION: Synthetic sequence: PCR primer suitable for amplifying target DNA regions comprising genetic variations associated with IBD

<400> SEQUENCE: 103
cacccaccag agaaggctta 20

<210> SEQ ID NO 104
<211> LENGTH: 20
<212> TYPE: DNA
<213> ORGANISM: Artificial sequence
<220> FEATURE:
<223> OTHER INFORMATION: Synthetic sequence: PCR primer suitable for amplifying target DNA regions comprising genetic variations associated with IBD

<400> SEQUENCE: 104
atcacctccc cacctctctt 20

<210> SEQ ID NO 105
<211> LENGTH: 21
<212> TYPE: DNA
<213> ORGANISM: Artificial sequence
<220> FEATURE:
<223> OTHER INFORMATION: Synthetic sequence: PCR primer suitable for amplifying target DNA regions comprising genetic variations associated with IBD

<400> SEQUENCE: 105
ccaaaagcca cactcaaaga c 21

<210> SEQ ID NO 106
<211> LENGTH: 21
<212> TYPE: DNA
<213> ORGANISM: Artificial sequence
<220> FEATURE:
<223> OTHER INFORMATION: Synthetic sequence: PCR primer suitable for amplifying target DNA regions comprising genetic variations associated with IBD

<400> SEQUENCE: 106
cttgagtgat ggtgatgttc a 21

<210> SEQ ID NO 107
<211> LENGTH: 20
<212> TYPE: DNA
<213> ORGANISM: Artificial sequence
<220> FEATURE:
<223> OTHER INFORMATION: Synthetic sequence: PCR primer suitable for amplifying target DNA regions comprising genetic variations associated with IBD

<400> SEQUENCE: 107
tcaccagggc tggattaaag 20

<210> SEQ ID NO 108
<211> LENGTH: 20
<212> TYPE: DNA
<213> ORGANISM: Artificial sequence
<220> FEATURE:
<223> OTHER INFORMATION: Synthetic sequence: PCR primer suitable for amplifying target DNA regions comprising genetic variations associated with IBD

<400> SEQUENCE: 108
gcctctggca acagtaaagc 20

<210> SEQ ID NO 109
<211> LENGTH: 20
<212> TYPE: DNA
<213> ORGANISM: Artificial sequence
<220> FEATURE:
<223> OTHER INFORMATION: Synthetic sequence: PCR primer suitable for amplifying target DNA regions comprising genetic variations associated with IBD

<400> SEQUENCE: 109
ctgccgagac gggtatacag 20

<210> SEQ ID NO 110
<211> LENGTH: 20
<212> TYPE: DNA
<213> ORGANISM: Artificial sequence
<220> FEATURE:
<223> OTHER INFORMATION: Synthetic sequence: PCR primer suitable for amplifying target DNA regions comprising genetic variations associated with IBD

<400> SEQUENCE: 110
gcaaatgtct cctgggaatg 20

<210> SEQ ID NO 111
<211> LENGTH: 20
<212> TYPE: DNA
<213> ORGANISM: Artificial sequence
<220> FEATURE:
<223> OTHER INFORMATION: Synthetic sequence: PCR primer suitable for amplifying target DNA regions comprising genetic variations associated with IBD

<400> SEQUENCE: 111
tgagtccttc tcagcctggt 20

<210> SEQ ID NO 112
<211> LENGTH: 20
<212> TYPE: DNA
<213> ORGANISM: Artificial sequence
<220> FEATURE:
<223> OTHER INFORMATION: Synthetic sequence: PCR primer suitable for amplifying target DNA regions comprising genetic variations associated with IBD

<400> SEQUENCE: 112
ctctcacgca gctcttcctc 20

<210> SEQ ID NO 113
<211> LENGTH: 20
<212> TYPE: DNA
<213> ORGANISM: Artificial sequence
<220> FEATURE:
<223> OTHER INFORMATION: Synthetic sequence: PCR primer suitable for amplifying target DNA regions comprising genetic variations associated with IBD

<400> SEQUENCE: 113
ttctgggcca agttcctcta 20

<210> SEQ ID NO 114
<211> LENGTH: 19
<212> TYPE: DNA
<213> ORGANISM: Artificial sequence
<220> FEATURE:
<223> OTHER INFORMATION: Synthetic sequence: PCR primer suitable for amplifying target DNA regions comprising genetic variations associated with IBD

<400> SEQUENCE: 114
ggggcaggtc acagagagt 19

<210> SEQ ID NO 115
<211> LENGTH: 19
<212> TYPE: DNA
<213> ORGANISM: Artificial sequence
<220> FEATURE:
<223> OTHER INFORMATION: Synthetic sequence: PCR primer suitable for amplifying target DNA regions comprising genetic variations associated with IBD

<400> SEQUENCE: 115
ctggaaagtt tgccaacca 19

<210> SEQ ID NO 116
<211> LENGTH: 20
<212> TYPE: DNA
<213> ORGANISM: Artificial sequence
<220> FEATURE:
<223> OTHER INFORMATION: Synthetic sequence: PCR primer suitable for amplifying target DNA regions comprising genetic variations associated with IBD

<400> SEQUENCE: 116
acccaaagtc tgggctcttt 20

<210> SEQ ID NO 117
<211> LENGTH: 19
<212> TYPE: DNA
<213> ORGANISM: Artificial sequence
<220> FEATURE:
<223> OTHER INFORMATION: Synthetic sequence: PCR primer suitable for amplifying target DNA regions comprising genetic variations associated with IBD

<400> SEQUENCE: 117
gtttaagggc atgtgctac 19

<210> SEQ ID NO 118
<211> LENGTH: 20

<212> TYPE: DNA
<213> ORGANISM: Artificial sequence
<220> FEATURE:
<223> OTHER INFORMATION: Synthetic sequence: PCR primer suitable for amplifying target DNA regions comprising genetic variations associated with IBD

<400> SEQUENCE: 118
agctccaact ggtagttgtg 20

<210> SEQ ID NO 119
<211> LENGTH: 21
<212> TYPE: DNA
<213> ORGANISM: Artificial sequence
<220> FEATURE:
<223> OTHER INFORMATION: Synthetic sequence: PCR primer suitable for amplifying target DNA regions comprising genetic variations associated with IBD

<400> SEQUENCE: 119
gcgcttcgac agcgacgtgg g 21

<210> SEQ ID NO 120
<211> LENGTH: 20
<212> TYPE: DNA
<213> ORGANISM: Artificial sequence
<220> FEATURE:
<223> OTHER INFORMATION: Synthetic sequence: PCR primer suitable for amplifying target DNA regions comprising genetic variations associated with IBD

<400> SEQUENCE: 120
ctcgccgctg cactgtgaag 20

<210> SEQ ID NO 121
<211> LENGTH: 20
<212> TYPE: DNA
<213> ORGANISM: Artificial sequence
<220> FEATURE:
<223> OTHER INFORMATION: Synthetic sequence: PCR primer suitable for amplifying target DNA regions comprising genetic variations associated with IBD

<400> SEQUENCE: 121
acaagttctg ggggacacag 20

<210> SEQ ID NO 122
<211> LENGTH: 20
<212> TYPE: DNA
<213> ORGANISM: Artificial sequence
<220> FEATURE:
<223> OTHER INFORMATION: Synthetic sequence: PCR primer suitable for amplifying target DNA regions comprising genetic variations associated with IBD

<400> SEQUENCE: 122
attgcaccta gggtttgtgc 20

<210> SEQ ID NO 123
<211> LENGTH: 20
<212> TYPE: DNA
<213> ORGANISM: Artificial sequence
<220> FEATURE:
<223> OTHER INFORMATION: Synthetic sequence: PCR primer suitable for amplifying target DNA regions comprising genetic variations associated with IBD

<400> SEQUENCE: 123
tgttcttagc caccccactc 20

<210> SEQ ID NO 124
<211> LENGTH: 20
<212> TYPE: DNA
<213> ORGANISM: Artificial sequence
<220> FEATURE:
<223> OTHER INFORMATION: Synthetic sequence: PCR primer suitable for amplifying target DNA regions comprising genetic variations associated with IBD

<400> SEQUENCE: 124
gtgatcgtac aggtgcatcg 20

<210> SEQ ID NO 125
<211> LENGTH: 20
<212> TYPE: DNA
<213> ORGANISM: Artificial sequence
<220> FEATURE:
<223> OTHER INFORMATION: Synthetic sequence: PCR primer suitable for amplifying target DNA regions comprising genetic variations associated with adverse reactions to pharmaceuticals

<400> SEQUENCE: 125
gccttcaacc ccatcatcta 20

<210> SEQ ID NO 126
<211> LENGTH: 18
<212> TYPE: DNA
<213> ORGANISM: Artificial sequence
<220> FEATURE:
<223> OTHER INFORMATION: Synthetic sequence: PCR primer suitable for amplifying target DNA regions comprising genetic variations associated with adverse reactions to pharmaceuticals

<400> SEQUENCE: 126
caggctcgag tcgctgtc 18

<210> SEQ ID NO 127
<211> LENGTH: 18
<212> TYPE: DNA
<213> ORGANISM: Artificial sequence
<220> FEATURE:
<223> OTHER INFORMATION: Synthetic sequence: PCR primer suitable for amplifying target DNA regions comprising genetic variations associated with adverse reactions to pharmaceuticals

<400> SEQUENCE: 127
gctcacctgc cagactgc 18

<210> SEQ ID NO 128
<211> LENGTH: 20
<212> TYPE: DNA
<213> ORGANISM: Artificial sequence
<220> FEATURE:
<223> OTHER INFORMATION: Synthetic sequence: PCR primer suitable for amplifying target DNA regions comprising genetic variations associated with adverse reactions to pharmaceuticals

<400> SEQUENCE: 128
gccaggacga tgagagacat 20

<210> SEQ ID NO 129
<211> LENGTH: 20
<212> TYPE: DNA
<213> ORGANISM: Artificial sequence
<220> FEATURE:
<223> OTHER INFORMATION: Synthetic sequence: PCR primer suitable for amplifying target DNA regions comprising genetic variations associated with adverse reactions to pharmaceuticals

<400> SEQUENCE: 129
cgcagtagga gagggcatag 20

<210> SEQ ID NO 130
<211> LENGTH: 20
<212> TYPE: DNA
<213> ORGANISM: Artificial sequence
<220> FEATURE:
<223> OTHER INFORMATION: Synthetic sequence: PCR primer suitable for amplifying target DNA regions comprising genetic variations associated with adverse reactions to pharmaceuticals

<400> SEQUENCE: 130
caagccccaa agagtctgat 20

<210> SEQ ID NO 131
<211> LENGTH: 20
<212> TYPE: DNA
<213> ORGANISM: Artificial sequence
<220> FEATURE:
<223> OTHER INFORMATION: Synthetic sequence: PCR primer suitable for amplifying target DNA regions comprising genetic variations associated with adverse reactions to pharmaceuticals

<400> SEQUENCE: 131
agcaagatgc caagacaaca 20

<210> SEQ ID NO 132
<211> LENGTH: 20
<212> TYPE: DNA
<213> ORGANISM: Artificial sequence
<220> FEATURE:
<223> OTHER INFORMATION: Synthetic sequence: PCR primer suitable for amplifying target DNA regions comprising genetic variations associated with adverse reactions to pharmaceuticals

<400> SEQUENCE: 132
cagtgtgcct tccacagttg 20

<210> SEQ ID NO 133
<211> LENGTH: 20
<212> TYPE: DNA
<213> ORGANISM: Artificial sequence
<220> FEATURE:
<223> OTHER INFORMATION: Synthetic sequence: PCR primer suitable for amplifying target DNA regions comprising genetic variations associated with adverse reactions to pharmaceuticals

<400> SEQUENCE: 133
aggagagaca cgacggtgag 20

<210> SEQ ID NO 134
<211> LENGTH: 22
<212> TYPE: DNA
<213> ORGANISM: Artificial sequence
<220> FEATURE:
<223> OTHER INFORMATION: Synthetic sequence: PCR primer suitable for amplifying target DNA regions comprising genetic variations associated with adverse reactions to pharmaceuticals

<400> SEQUENCE: 134
caagttctgg cttagacatg ga 22

<210> SEQ ID NO 135
<211> LENGTH: 20
<212> TYPE: DNA
<213> ORGANISM: Artificial sequence
<220> FEATURE:
<223> OTHER INFORMATION: Synthetic sequence: PCR primer suitable for amplifying target DNA regions comprising genetic variations associated with adverse reactions to pharmaceuticals

<400> SEQUENCE: 135
gggcctactg tggctactca 20

<210> SEQ ID NO 136
<211> LENGTH: 20
<212> TYPE: DNA
<213> ORGANISM: Artificial sequence
<220> FEATURE:
<223> OTHER INFORMATION: Synthetic sequence: PCR primer suitable for amplifying target DNA regions comprising genetic variations associated with adverse reactions to pharmaceuticals

<400> SEQUENCE: 136 cccttttcc aggtctgaca 20

<210> SEQ ID NO 137
<211> LENGTH: 20
<212> TYPE: DNA
<213> ORGANISM: Artificial sequence
<220> FEATURE:
<223> OTHER INFORMATION: Synthetic sequence: PCR primer suitable for amplifying target DNA regions comprising genetic variations associated with adverse reactions to pharmaceuticals

<400> SEQUENCE: 137
tggtggacat ggtgaatgac 20

<210> SEQ ID NO 138
<211> LENGTH: 20
<212> TYPE: DNA
<213> ORGANISM: Artificial sequence
<220> FEATURE:
<223> OTHER INFORMATION: Synthetic sequence: PCR primer suitable for amplifying target DNA regions comprising genetic variations associated with adverse reactions to pharmaceuticals

<400> SEQUENCE: 138
gtgcaggttg tgtcttgtcc 20

<210> SEQ ID NO 139
<211> LENGTH: 20
<212> TYPE: DNA
<213> ORGANISM: Artificial sequence
<220> FEATURE:
<223> OTHER INFORMATION: Synthetic sequence: PCR primer suitable for amplifying target DNA regions comprising genetic variations associated with adverse reactions to pharmaceuticals

<400> SEQUENCE: 139
ttgctagtga cggtgattcg 20

<210> SEQ ID NO 140
<211> LENGTH: 20
<212> TYPE: DNA
<213> ORGANISM: Artificial sequence
<220> FEATURE:
<223> OTHER INFORMATION: Synthetic sequence: PCR primer suitable for amplifying target DNA regions comprising genetic variations associated with adverse reactions to pharmaceuticals

<400> SEQUENCE: 140
gagactgcag caagggtttc 20

<210> SEQ ID NO 141
<211> LENGTH: 20
<212> TYPE: DNA
<213> ORGANISM: Artificial sequence
<220> FEATURE:
<223> OTHER INFORMATION: Synthetic sequence: PCR primer suitable for amplifying target DNA regions comprising genetic variations associated with adverse reactions to pharmaceuticals

<400> SEQUENCE: 141
tgtctcccct gtctcattcc 20

<210> SEQ ID NO 142
<211> LENGTH: 20
<212> TYPE: DNA
<213> ORGANISM: Artificial sequence
<220> FEATURE:
<223> OTHER INFORMATION: Synthetic sequence: PCR primer suitable for amplifying target DNA regions comprising genetic variations associated with adverse reactions to pharmaceuticals

<400> SEQUENCE: 142
attgcccagc acaggataag 20

<210> SEQ ID NO 143
<211> LENGTH: 20
<212> TYPE: DNA
<213> ORGANISM: Artificial sequence
<220> FEATURE:
<223> OTHER INFORMATION: Synthetic sequence: PCR primer suitable for amplifying target DNA regions comprising genetic variations associated with adverse reactions to pharmaceuticals

<400> SEQUENCE: 143
ctcacccctg atggtgctat 20

<210> SEQ ID NO 144
<211> LENGTH: 20
<212> TYPE: DNA
<213> ORGANISM: Artificial sequence
<220> FEATURE:
<223> OTHER INFORMATION: Synthetic sequence: PCR primer suitable for amplifying target DNA regions comprising genetic variations associated with adverse reactions to pharmaceuticals

<400> SEQUENCE: 144
tttggaagtg ctcacagcag 20

<210> SEQ ID NO 145
<211> LENGTH: 21
<212> TYPE: DNA
<213> ORGANISM: Artificial sequence
<220> FEATURE:
<223> OTHER INFORMATION: Synthetic sequence: PCR primer suitable for amplifying target DNA regions comprising genetic variations associated with adverse reactions to pharmaceuticals

<400> SEQUENCE: 145
gagaacattc ctctgcagca c 21

<210> SEQ ID NO 146
<211> LENGTH: 20
<212> TYPE: DNA
<213> ORGANISM: Artificial sequence
<220> FEATURE:
<223> OTHER INFORMATION: Synthetic sequence: PCR primer suitable for amplifying target DNA regions comprising genetic variations associated with adverse reactions to pharmaceuticals

<400> SEQUENCE: 146
tgtggctttg ctttgtcttg 20

<210> SEQ ID NO 147
<211> LENGTH: 20
<212> TYPE: DNA
<213> ORGANISM: Artificial sequence
<220> FEATURE:
<223> OTHER INFORMATION: Synthetic sequence: PCR primer suitable for amplifying target DNA regions comprising genetic variations associated with adverse reactions to pharmaceuticals

<400> SEQUENCE: 147
gagcaatgtc tggcttctcc 20

<210> SEQ ID NO 148
<211> LENGTH: 20
<212> TYPE: DNA
<213> ORGANISM: Artificial sequence
<220> FEATURE:
<223> OTHER INFORMATION: Synthetic sequence: PCR primer suitable for amplifying target DNA regions comprising genetic variations associated with adverse reactions to pharmaceuticals

<400> SEQUENCE: 148
ccagggagag aacatttgga 20

<210> SEQ ID NO 149
<211> LENGTH: 20
<212> TYPE: DNA
<213> ORGANISM: Artificial sequence
<220> FEATURE:
<223> OTHER INFORMATION: Synthetic sequence: PCR primer suitable for amplifying target DNA regions comprising genetic variations associated with adverse reactions to pharmaceuticals

<400> SEQUENCE: 149
aggctgtgac aggatggaag 20

<210> SEQ ID NO 150
<211> LENGTH: 20
<212> TYPE: DNA
<213> ORGANISM: Artificial sequence
<220> FEATURE:
<223> OTHER INFORMATION: Synthetic sequence: PCR primer suitable for amplifying target DNA regions comprising genetic variations associated with adverse reactions to pharmaceuticals

<400> SEQUENCE: 150
ggtggtcacc aggtatgtcc 20

<210> SEQ ID NO 151
<211> LENGTH: 20
<212> TYPE: DNA
<213> ORGANISM: Artificial sequence
<220> FEATURE:
<223> OTHER INFORMATION: Synthetic sequence: PCR primer suitable for amplifying target DNA regions comprising genetic variations associated with adverse reactions to pharmaceuticals

<400> SEQUENCE: 151
cctgggatct ccctcctagt 20

<210> SEQ ID NO 152
<211> LENGTH: 20

<212> TYPE: DNA
<213> ORGANISM: Artificial sequence
<220> FEATURE:
<223> OTHER INFORMATION: Synthetic sequence: PCR primer suitable for amplifying target DNA regions comprising genetic variations associated with adverse reactions to pharmaceuticals

<400> SEQUENCE: 152
ccacccttgg tttttctcaa 20

<210> SEQ ID NO 153
<211> LENGTH: 20
<212> TYPE: DNA
<213> ORGANISM: Artificial sequence
<220> FEATURE:
<223> OTHER INFORMATION: Synthetic sequence: PCR primer suitable for amplifying target DNA regions comprising genetic variations associated with adverse reactions to pharmaceuticals

<400> SEQUENCE: 153
ccacatgccc tacacagatg 20

<210> SEQ ID NO 154
<211> LENGTH: 20
<212> TYPE: DNA
<213> ORGANISM: Artificial sequence
<220> FEATURE:
<223> OTHER INFORMATION: Synthetic sequence: PCR primer suitable for amplifying target DNA regions comprising genetic variations associated with adverse reactions to pharmaceuticals

<400> SEQUENCE: 154
tcgaaaacat ggagttgcag 20

<210> SEQ ID NO 155
<211> LENGTH: 21
<212> TYPE: DNA
<213> ORGANISM: Artificial sequence
<220> FEATURE:
<223> OTHER INFORMATION: Synthetic sequence: PCR primer suitable for amplifying target DNA regions comprising genetic variations associated with adverse reactions to pharmaceuticals

<400> SEQUENCE: 155
ccgggaactc acaacaaatt a 21

<210> SEQ ID NO 156
<211> LENGTH: 22
<212> TYPE: DNA
<213> ORGANISM: Artificial sequence
<220> FEATURE:
<223> OTHER INFORMATION: Synthetic sequence: PCR primer suitable for amplifying target DNA regions comprising genetic variations associated with adverse reactions to pharmaceuticals

<400> SEQUENCE: 156
cacaaattca caagcagtca ca 22

<210> SEQ ID NO 157
<211> LENGTH: 20
<212> TYPE: DNA
<213> ORGANISM: Artificial sequence
<220> FEATURE:
<223> OTHER INFORMATION: Synthetic sequence: PCR primer suitable for amplifying target DNA regions comprising genetic variations associated with adverse reactions to pharmaceuticals

<400> SEQUENCE: 157
caggtatggg gctagaagca 20

<210> SEQ ID NO 158
<211> LENGTH: 20
<212> TYPE: DNA
<213> ORGANISM: Artificial sequence
<220> FEATURE:
<223> OTHER INFORMATION: Synthetic sequence: PCR primer suitable for amplifying target DNA regions comprising genetic variations associated with adverse reactions to pharmaceuticals

<400> SEQUENCE: 158
acctggtcga agcagtatgg 20

<210> SEQ ID NO 159
<211> LENGTH: 20
<212> TYPE: DNA
<213> ORGANISM: Artificial sequence
<220> FEATURE:
<223> OTHER INFORMATION: Synthetic sequence: PCR primer suitable for amplifying target DNA regions comprising genetic variations associated with adverse reactions to pharmaceuticals

<400> SEQUENCE: 159
gatcctggct tgacaagagg 20

<210> SEQ ID NO 160
<211> LENGTH: 20
<212> TYPE: DNA
<213> ORGANISM: Artificial sequence
<220> FEATURE:
<223> OTHER INFORMATION: Synthetic sequence: PCR primer suitable for amplifying target DNA regions comprising genetic variations associated with adverse reactions to pharmaceuticals

<400> SEQUENCE: 160
tcccacggaa atctgtctct 20

<210> SEQ ID NO 161
<211> LENGTH: 19
<212> TYPE: DNA
<213> ORGANISM: Artificial sequence
<220> FEATURE:
<223> OTHER INFORMATION: Synthetic sequence: PCR primer suitable for amplifying target DNA regions comprising genetic variations associated with adverse reactions to pharmaceuticals

<400> SEQUENCE: 161
gtggggctaa tgccttcat 19

<210> SEQ ID NO 162
<211> LENGTH: 18
<212> TYPE: DNA
<213> ORGANISM: Artificial sequence
<220> FEATURE:
<223> OTHER INFORMATION: Synthetic sequence: PCR primer suitable for amplifying target DNA regions comprising genetic variations associated with adverse reactions to pharmaceuticals

<400> SEQUENCE: 162
cttcccagtt cccgcttt 18

<210> SEQ ID NO 163
<211> LENGTH: 18
<212> TYPE: DNA
<213> ORGANISM: Artificial sequence
<220> FEATURE:
<223> OTHER INFORMATION: Synthetic sequence: PCR primer suitable for amplifying target DNA regions comprising genetic variations associated with adverse reactions to pharmaceuticals

<400> SEQUENCE: 163
gtgggtgatg ggcagaag 18

<210> SEQ ID NO 164
<211> LENGTH: 20
<212> TYPE: DNA
<213> ORGANISM: Artificial sequence
<220> FEATURE:
<223> OTHER INFORMATION: Synthetic sequence: PCR primer suitable for amplifying target DNA regions comprising genetic variations associated with adverse reactions to pharmaceuticals

<400> SEQUENCE: 164
gagggtcgtc gtactcgaag 20

<210> SEQ ID NO 165
<211> LENGTH: 18
<212> TYPE: DNA
<213> ORGANISM: Artificial sequence
<220> FEATURE:
<223> OTHER INFORMATION: Synthetic sequence: PCR primer suitable for amplifying target DNA regions comprising genetic variations associated with adverse reactions to pharmaceuticals

<400> SEQUENCE: 165
agccgtgagc aacgtgat 18

<210> SEQ ID NO 166
<211> LENGTH: 20
<212> TYPE: DNA
<213> ORGANISM: Artificial sequence
<220> FEATURE:
<223> OTHER INFORMATION: Synthetic sequence: PCR primer suitable for amplifying target DNA regions comprising genetic variations associated with adverse reactions to pharmaceuticals

<400> SEQUENCE: 166
ctgcagagac tcctcggtct 20

<210> SEQ ID NO 167
<211> LENGTH: 20
<212> TYPE: DNA
<213> ORGANISM: Artificial sequence
<220> FEATURE:
<223> OTHER INFORMATION: Synthetic sequence: PCR primer suitable for amplifying target DNA regions comprising genetic variations associated with adverse reactions to pharmaceuticals

<400> SEQUENCE: 167
caaggtccta cgcttccaaa 20

<210> SEQ ID NO 168
<211> LENGTH: 20
<212> TYPE: DNA
<213> ORGANISM: Artificial sequence
<220> FEATURE:
<223> OTHER INFORMATION: Synthetic sequence: PCR primer suitable for amplifying target DNA regions comprising genetic variations associated with adverse reactions to pharmaceuticals

<400> SEQUENCE: 168
gatgcactgg tccaaccttt 20

<210> SEQ ID NO 169
<211> LENGTH: 19
<212> TYPE: DNA
<213> ORGANISM: Artificial sequence
<220> FEATURE:
<223> OTHER INFORMATION: Synthetic sequence: PCR primer suitable for amplifying target DNA regions comprising genetic variations associated with adverse reactions to pharmaceuticals

<400> SEQUENCE: 169
ggaaccctga gagcagctt 19

<210> SEQ ID NO 170
<211> LENGTH: 20
<212> TYPE: DNA
<213> ORGANISM: Artificial sequence
<220> FEATURE:
<223> OTHER INFORMATION: Synthetic sequence: PCR primer suitable for amplifying target DNA regions comprising genetic variations associated with adverse reactions to pharmaceuticals

<400> SEQUENCE: 170
ggtgtcccag caaagttcat 20

<210> SEQ ID NO 171
<211> LENGTH: 20
<212> TYPE: DNA
<213> ORGANISM: Artificial sequence
<220> FEATURE:
<223> OTHER INFORMATION: Synthetic sequence: PCR primer suitable for amplifying target DNA regions comprising genetic variations associated with adverse reactions to pharmaceuticals

<400> SEQUENCE: 171
ggaggcaaga aggagtgtca 20

<210> SEQ ID NO 172
<211> LENGTH: 20
<212> TYPE: DNA
<213> ORGANISM: Artificial sequence
<220> FEATURE:
<223> OTHER INFORMATION: Synthetic sequence: PCR primer suitable for amplifying target DNA regions comprising genetic variations associated with adverse reactions to pharmaceuticals

<400> SEQUENCE: 172
cgatgtcacg ggatgtcata 20

<210> SEQ ID NO 173
<211> LENGTH: 20
<212> TYPE: DNA
<213> ORGANISM: Artificial sequence
<220> FEATURE:
<223> OTHER INFORMATION: Synthetic sequence: PCR primer suitable for amplifying target DNA regions comprising genetic variations associated with adverse reactions to pharmaceuticals

<400> SEQUENCE: 173
ggagtcttgc aggggtatca 20

<210> SEQ ID NO 174
<211> LENGTH: 20
<212> TYPE: DNA
<213> ORGANISM: Artificial sequence
<220> FEATURE:
<223> OTHER INFORMATION: Synthetic sequence: PCR primer suitable for amplifying target DNA regions comprising genetic variations associated with adverse reactions to pharmaceuticals

<400> SEQUENCE: 174
tcaccaggaa agcaaagaca 20

<210> SEQ ID NO 175
<211> LENGTH: 20
<212> TYPE: DNA
<213> ORGANISM: Artificial sequence
<220> FEATURE:
<223> OTHER INFORMATION: Synthetic sequence: PCR primer suitable for amplifying target DNA regions comprising genetic variations associated with adverse reactions to pharmaceuticals

<400> SEQUENCE: 175
gaacaccaag catcactgga 20

<210> SEQ ID NO 176
<211> LENGTH: 21
<212> TYPE: DNA
<213> ORGANISM: Artificial sequence
<220> FEATURE:
<223> OTHER INFORMATION: Synthetic sequence: PCR primer suitable for amplifying target DNA regions comprising genetic variations associated with adverse reactions to pharmaceuticals

<400> SEQUENCE: 176
gatgtttagt gcaggcccat a 21

<210> SEQ ID NO 177
<211> LENGTH: 20
<212> TYPE: DNA
<213> ORGANISM: Artificial sequence
<220> FEATURE:
<223> OTHER INFORMATION: Synthetic sequence: PCR primer suitable for amplifying target DNA regions comprising genetic variations associated with adverse reactions to pharmaceuticals

<400> SEQUENCE: 177
ctcacaacct tgcggaattt 20

<210> SEQ ID NO 178
<211> LENGTH: 20
<212> TYPE: DNA
<213> ORGANISM: Artificial sequence
<220> FEATURE:
<223> OTHER INFORMATION: Synthetic sequence: PCR primer suitable for amplifying target DNA regions comprising genetic variations associated with adverse reactions to pharmaceuticals

<400> SEQUENCE: 178
cttcaaatct ccctccacca 20

<210> SEQ ID NO 179
<211> LENGTH: 20
<212> TYPE: DNA
<213> ORGANISM: Artificial sequence
<220> FEATURE:
<223> OTHER INFORMATION: Synthetic sequence: PCR primer suitable for amplifying target DNA regions comprising genetic variations associated with adverse reactions to pharmaceuticals

<400> SEQUENCE: 179
acctgctgag aaaggcatga 20

<210> SEQ ID NO 180
<211> LENGTH: 20
<212> TYPE: DNA
<213> ORGANISM: Artificial sequence
<220> FEATURE:
<223> OTHER INFORMATION: Synthetic sequence: PCR primer suitable for amplifying target DNA regions comprising genetic variations associated with adverse reactions to pharmaceuticals

<400> SEQUENCE: 180
ttccagggca caaccataat 20

<210> SEQ ID NO 181
<211> LENGTH: 20
<212> TYPE: DNA
<213> ORGANISM: Artificial sequence
<220> FEATURE:
<223> OTHER INFORMATION: Synthetic sequence: PCR primer suitable for amplifying target DNA regions comprising genetic variations associated with adverse reactions to pharmaceuticals

<400> SEQUENCE: 181
ccatggagtt gggcttagag 20

<210> SEQ ID NO 182
<211> LENGTH: 20
<212> TYPE: DNA
<213> ORGANISM: Artificial sequence
<220> FEATURE:
<223> OTHER INFORMATION: Synthetic sequence: PCR primer suitable for amplifying target DNA regions comprising genetic variations associated with adverse reactions to pharmaceuticals

<400> SEQUENCE: 182
ccatgccagt gctgtatttg 20

<210> SEQ ID NO 183
<211> LENGTH: 20
<212> TYPE: DNA
<213> ORGANISM: Artificial sequence
<220> FEATURE:
<223> OTHER INFORMATION: Synthetic sequence: PCR primer suitable for amplifying target DNA regions comprising genetic variations associated with adverse reactions to pharmaceuticals

<400> SEQUENCE: 183
tggtgtctcc aggtcaatca 20

<210> SEQ ID NO 184
<211> LENGTH: 20
<212> TYPE: DNA
<213> ORGANISM: Artificial sequence
<220> FEATURE:
<223> OTHER INFORMATION: Synthetic sequence: PCR primer suitable for amplifying target DNA regions comprising genetic variations associated with adverse reactions to pharmaceuticals

<400> SEQUENCE: 184
ggctgatcct tcccagaaat 20

<210> SEQ ID NO 185
<211> LENGTH: 20
<212> TYPE: DNA
<213> ORGANISM: Artificial sequence
<220> FEATURE:
<223> OTHER INFORMATION: Synthetic sequence: PCR primer suitable for amplifying target DNA regions comprising genetic variations associated with adverse reactions to pharmaceuticals

<400> SEQUENCE: 185
tgacggcagg aattacattg 20

<210> SEQ ID NO 186
<211> LENGTH: 21
<212> TYPE: DNA
<213> ORGANISM: Artificial sequence
<220> FEATURE:
<223> OTHER INFORMATION: Synthetic sequence: PCR primer suitable for amplifying target DNA regions comprising genetic variations associated with adverse reactions to pharmaceuticals

<400> SEQUENCE: 186
tgtttcttct ttggcaggag a 21

<210> SEQ ID NO 187
<211> LENGTH: 20
<212> TYPE: DNA
<213> ORGANISM: Artificial sequence
<220> FEATURE:
<223> OTHER INFORMATION: Synthetic sequence: PCR primer suitable for amplifying target DNA regions comprising genetic variations associated with adverse reactions to pharmaceuticals

<400> SEQUENCE: 187
actgtttggt gggcttcatc 20

<210> SEQ ID NO 188
<211> LENGTH: 19
<212> TYPE: DNA
<213> ORGANISM: Artificial sequence
<220> FEATURE:
<223> OTHER INFORMATION: Synthetic sequence: PCR primer suitable for amplifying target DNA regions comprising genetic variations associated with adverse reactions to pharmaceuticals

<400> SEQUENCE: 188
aggtttgggc acgagattt 19

<210> SEQ ID NO 189
<211> LENGTH: 20
<212> TYPE: DNA
<213> ORGANISM: Artificial sequence
<220> FEATURE:
<223> OTHER INFORMATION: Synthetic sequence: PCR primer suitable for amplifying target DNA regions comprising genetic variations associated with adverse reactions to pharmaceuticals

<400> SEQUENCE: 189
cctgccaaag aagaaacacc 20

<210> SEQ ID NO 190
<211> LENGTH: 20
<212> TYPE: DNA
<213> ORGANISM: Artificial sequence
<220> FEATURE:
<223> OTHER INFORMATION: Synthetic sequence: PCR primer suitable for amplifying target DNA regions comprising genetic variations associated with adverse reactions to pharmaceuticals

<400> SEQUENCE: 190
gatgaagccc accaaacagt 20

<210> SEQ ID NO 191
<211> LENGTH: 20
<212> TYPE: DNA
<213> ORGANISM: Artificial sequence
<220> FEATURE:
<223> OTHER INFORMATION: Synthetic sequence: PCR primer suitable for amplifying target DNA regions comprising genetic variations associated with adverse reactions to pharmaceuticals

<400> SEQUENCE: 191
actgtttggt gggcttcatc 20

<210> SEQ ID NO 192
<211> LENGTH: 23

<212> TYPE: DNA
<213> ORGANISM: Artificial sequence
<220> FEATURE:
<223> OTHER INFORMATION: Synthetic sequence: PCR primer suitable for amplifying target DNA regions comprising genetic variations associated with adverse reactions to pharmaceuticals

<400> SEQUENCE: 192
gggtgataca tacacaaggg ttt 23

<210> SEQ ID NO 193
<211> LENGTH: 20
<212> TYPE: DNA
<213> ORGANISM: Artificial sequence
<220> FEATURE:
<223> OTHER INFORMATION: Synthetic sequence: PCR primer suitable for amplifying target DNA regions comprising genetic variations associated with adverse reactions to pharmaceuticals

<400> SEQUENCE: 193
accctgtgat cccactttca 20

<210> SEQ ID NO 194
<211> LENGTH: 20
<212> TYPE: DNA
<213> ORGANISM: Artificial sequence
<220> FEATURE:
<223> OTHER INFORMATION: Synthetic sequence: PCR primer suitable for amplifying target DNA regions comprising genetic variations associated with adverse reactions to pharmaceuticals

<400> SEQUENCE: 194
tgtacttcag ggcttggtca 20

<210> SEQ ID NO 195
<211> LENGTH: 21
<212> TYPE: DNA
<213> ORGANISM: Artificial sequence
<220> FEATURE:
<223> OTHER INFORMATION: Synthetic sequence: PCR primer suitable for amplifying target DNA regions comprising genetic variations associated with adverse reactions to pharmaceuticals

<400> SEQUENCE: 195
caaccagagc ttggcatatt g 21

<210> SEQ ID NO 196
<211> LENGTH: 20
<212> TYPE: DNA
<213> ORGANISM: Artificial sequence
<220> FEATURE:
<223> OTHER INFORMATION: Synthetic sequence: PCR primer suitable for amplifying target DNA regions comprising genetic variations associated with adverse reactions to pharmaceuticals

<400> SEQUENCE: 196
taaagtcccg agggttgttg 20

<210> SEQ ID NO 197
<211> LENGTH: 20
<212> TYPE: DNA
<213> ORGANISM: Artificial sequence
<220> FEATURE:
<223> OTHER INFORMATION: Synthetic sequence: PCR primer suitable for amplifying target DNA regions comprising genetic variations associated with adverse reactions to pharmaceuticals

<400> SEQUENCE: 197
tagtgggcct aggtgattgg 20

<210> SEQ ID NO 198
<211> LENGTH: 20
<212> TYPE: DNA
<213> ORGANISM: Artificial sequence
<220> FEATURE:
<223> OTHER INFORMATION: Synthetic sequence: PCR primer suitable for amplifying target DNA regions comprising genetic variations associated with adverse reactions to pharmaceuticals

<400> SEQUENCE: 198
tttccaatca ctgggagagg 20

<210> SEQ ID NO 199
<211> LENGTH: 20
<212> TYPE: DNA
<213> ORGANISM: Artificial sequence
<220> FEATURE:
<223> OTHER INFORMATION: Synthetic sequence: PCR primer suitable for amplifying target DNA regions comprising genetic variations associated with adverse reactions to pharmaceuticals

<400> SEQUENCE: 199
caaccctcgg gactttattg 20

<210> SEQ ID NO 200
<211> LENGTH: 23
<212> TYPE: DNA
<213> ORGANISM: Artificial sequence
<220> FEATURE:
<223> OTHER INFORMATION: Synthetic sequence: PCR primer suitable for amplifying target DNA regions comprising genetic variations associated with adverse reactions to pharmaceuticals

<400> SEQUENCE: 200
caagcattac tccttgacct gtt 23

<210> SEQ ID NO 201
<211> LENGTH: 20
<212> TYPE: DNA
<213> ORGANISM: Artificial sequence
<220> FEATURE:
<223> OTHER INFORMATION: Synthetic sequence: PCR primer suitable for amplifying target DNA regions comprising genetic variations associated with adverse reactions to pharmaceuticals

<400> SEQUENCE: 201
cccagtgtca gcttcctctt 20

<210> SEQ ID NO 202
<211> LENGTH: 20
<212> TYPE: DNA
<213> ORGANISM: Artificial sequence
<220> FEATURE:
<223> OTHER INFORMATION: Synthetic sequence: PCR primer suitable for amplifying target DNA regions comprising genetic variations associated with adverse reactions to pharmaceuticals

<400> SEQUENCE: 202
gtcctcaatg ctcctcttcc 20

<210> SEQ ID NO 203
<211> LENGTH: 21
<212> TYPE: DNA
<213> ORGANISM: Artificial sequence
<220> FEATURE:
<223> OTHER INFORMATION: Synthetic sequence: PCR primer suitable for amplifying target DNA regions comprising genetic variations associated with adverse reactions to pharmaceuticals

<400> SEQUENCE: 203
gaatcgtttt cagcaatgga a 21

<210> SEQ ID NO 204
<211> LENGTH: 20
<212> TYPE: DNA
<213> ORGANISM: Artificial sequence
<220> FEATURE:
<223> OTHER INFORMATION: Synthetic sequence: PCR primer suitable for amplifying target DNA regions comprising genetic variations associated with adverse reactions to pharmaceuticals

<400> SEQUENCE: 204
gtatgttcac ccacccttgg 20

<210> SEQ ID NO 205
<211> LENGTH: 20
<212> TYPE: DNA
<213> ORGANISM: Artificial sequence
<220> FEATURE:
<223> OTHER INFORMATION: Synthetic sequence: PCR primer suitable for amplifying target DNA regions comprising genetic variations associated with adverse reactions to pharmaceuticals

<400> SEQUENCE: 205
tcaccgaaca gttcttgcat 20

<210> SEQ ID NO 206
<211> LENGTH: 20
<212> TYPE: DNA
<213> ORGANISM: Artificial sequence
<220> FEATURE:
<223> OTHER INFORMATION: Synthetic sequence: PCR primer suitable for amplifying target DNA regions comprising genetic variations associated with adverse reactions to pharmaceuticals

<400> SEQUENCE: 206
gtcaaggtcc tttgggtcaa 20

<210> SEQ ID NO 207
<211> LENGTH: 20
<212> TYPE: DNA
<213> ORGANISM: Artificial sequence
<220> FEATURE:
<223> OTHER INFORMATION: Synthetic sequence: PCR primer suitable for amplifying target DNA regions comprising genetic variations associated with adverse reactions to pharmaceuticals

<400> SEQUENCE: 207
gcaggatgtt ggagtgtgtg 20

<210> SEQ ID NO 208
<211> LENGTH: 21
<212> TYPE: DNA
<213> ORGANISM: Artificial sequence
<220> FEATURE:
<223> OTHER INFORMATION: Synthetic sequence: PCR primer suitable for amplifying target DNA regions comprising genetic variations associated with adverse reactions to pharmaceuticals

<400> SEQUENCE: 208
gcaattattg gtgggagagt g 21

<210> SEQ ID NO 209
<211> LENGTH: 20
<212> TYPE: DNA
<213> ORGANISM: Artificial sequence
<220> FEATURE:
<223> OTHER INFORMATION: Synthetic sequence: PCR primer suitable for amplifying target DNA regions comprising genetic variations associated with adverse reactions to pharmaceuticals

<400> SEQUENCE: 209
tgctcccagg ctgtttattt 20

<210> SEQ ID NO 210
<211> LENGTH: 20
<212> TYPE: DNA
<213> ORGANISM: Artificial sequence
<220> FEATURE:
<223> OTHER INFORMATION: Synthetic sequence: PCR primer suitable for amplifying target DNA regions comprising genetic variations associated with adverse reactions to pharmaceuticals

<400> SEQUENCE: 210
tgttttcagc tgcttgatgg 20

<210> SEQ ID NO 211
<211> LENGTH: 21
<212> TYPE: DNA
<213> ORGANISM: Artificial sequence
<220> FEATURE:
<223> OTHER INFORMATION: Synthetic sequence: PCR primer suitable for amplifying target DNA regions comprising genetic variations associated with adverse reactions to pharmaceuticals

<400> SEQUENCE: 211
ggttgatgct tttgaagaac g 21

<210> SEQ ID NO 212
<211> LENGTH: 23
<212> TYPE: DNA
<213> ORGANISM: Artificial sequence
<220> FEATURE:
<223> OTHER INFORMATION: Synthetic sequence: PCR primer suitable for amplifying target DNA regions comprising genetic variations associated with adverse reactions to pharmaceuticals

<400> SEQUENCE: 212
catccattac attttcaggc ttt 23

<210> SEQ ID NO 213
<211> LENGTH: 22
<212> TYPE: DNA
<213> ORGANISM: Artificial sequence
<220> FEATURE:
<223> OTHER INFORMATION: Synthetic sequence: PCR primer suitable for amplifying target DNA regions comprising genetic variations associated with adverse reactions to pharmaceuticals

<400> SEQUENCE: 213
aaaacttttg tggggatatg ga 22

<210> SEQ ID NO 214
<211> LENGTH: 27
<212> TYPE: DNA
<213> ORGANISM: Artificial sequence
<220> FEATURE:
<223> OTHER INFORMATION: Synthetic sequence: PCR primer suitable for amplifying target DNA regions comprising genetic variations associated with adverse reactions to pharmaceuticals

<400> SEQUENCE: 214
aaccctctat ttagtcattt gaaaaca 27

<210> SEQ ID NO 215
<211> LENGTH: 20
<212> TYPE: DNA
<213> ORGANISM: Artificial sequence
<220> FEATURE:
<223> OTHER INFORMATION: Synthetic sequence: PCR primer suitable for amplifying target DNA regions comprising genetic variations associated with adverse reactions to pharmaceuticals

<400> SEQUENCE: 215
tccctgtggt ctcttcatcc 20

<210> SEQ ID NO 216
<211> LENGTH: 20
<212> TYPE: DNA
<213> ORGANISM: Artificial sequence
<220> FEATURE:
<223> OTHER INFORMATION: Synthetic sequence: PCR primer suitable for amplifying target DNA regions comprising genetic variations associated with adverse reactions to pharmaceuticals

<400> SEQUENCE: 216
caaagcggaa gaatgtgtca 20

<210> SEQ ID NO 217
<211> LENGTH: 21
<212> TYPE: DNA
<213> ORGANISM: Artificial sequence
<220> FEATURE:
<223> OTHER INFORMATION: Synthetic sequence: PCR primer suitable for amplifying target DNA regions comprising genetic variations associated with adverse reactions to pharmaceuticals

<400> SEQUENCE: 217
aaagccacag tctctgacca a 21

<210> SEQ ID NO 218
<211> LENGTH: 21
<212> TYPE: DNA
<213> ORGANISM: Artificial sequence
<220> FEATURE:
<223> OTHER INFORMATION: Synthetic sequence: PCR primer suitable for amplifying target DNA regions comprising genetic variations associated with adverse reactions to pharmaceuticals

<400> SEQUENCE: 218
ggtgctggaa tccatacatt t 21

<210> SEQ ID NO 219
<211> LENGTH: 22
<212> TYPE: DNA
<213> ORGANISM: Artificial sequence
<220> FEATURE:
<223> OTHER INFORMATION: Synthetic sequence: PCR primer suitable for amplifying target DNA regions comprising genetic variations associated with adverse reactions to pharmaceuticals

<400> SEQUENCE: 219
gagaaaatgg cttttgtatt cg 22

<210> SEQ ID NO 220
<211> LENGTH: 22
<212> TYPE: DNA
<213> ORGANISM: Artificial sequence
<220> FEATURE:
<223> OTHER INFORMATION: Synthetic sequence: PCR primer suitable for amplifying target DNA regions comprising genetic variations associated with adverse reactions to pharmaceuticals

<400> SEQUENCE: 220
tgatttttcc agtccatcat gt 22

<210> SEQ ID NO 221
<211> LENGTH: 20
<212> TYPE: DNA
<213> ORGANISM: Artificial sequence
<220> FEATURE:
<223> OTHER INFORMATION: Synthetic sequence: PCR primer suitable for amplifying target DNA regions comprising genetic variations associated with adverse reactions to pharmaceuticals

<400> SEQUENCE: 221
caggggagga aatggttaca 20

<210> SEQ ID NO 222
<211> LENGTH: 20
<212> TYPE: DNA
<213> ORGANISM: Artificial sequence
<220> FEATURE:
<223> OTHER INFORMATION: Synthetic sequence: PCR primer suitable for amplifying target DNA regions comprising genetic variations associated with adverse reactions to pharmaceuticals

<400> SEQUENCE: 222
tggagccatt ggcataaaat 20

<210> SEQ ID NO 223
<211> LENGTH: 20
<212> TYPE: DNA
<213> ORGANISM: Artificial sequence
<220> FEATURE:
<223> OTHER INFORMATION: Synthetic sequence: PCR primer suitable for amplifying target DNA regions comprising genetic variations associated with adverse reactions to pharmaceuticals

<400> SEQUENCE: 223
agagagccag cgttcatgtt 20

<210> SEQ ID NO 224
<211> LENGTH: 20
<212> TYPE: DNA
<213> ORGANISM: Artificial sequence
<220> FEATURE:
<223> OTHER INFORMATION: Synthetic sequence: PCR primer suitable for amplifying target DNA regions comprising genetic variations associated with adverse reactions to pharmaceuticals

<400> SEQUENCE: 224
ctgatgcgtg ttctgtgctt 20

<210> SEQ ID NO 225
<211> LENGTH: 19
<212> TYPE: DNA
<213> ORGANISM: Artificial sequence
<220> FEATURE:
<223> OTHER INFORMATION: Synthetic sequence: PCR primer suitable for amplifying target DNA regions comprising genetic variations associated with adverse reactions to pharmaceuticals

<400> SEQUENCE: 225
gagtgcagtg gtgcgatct 19

<210> SEQ ID NO 226
<211> LENGTH: 20
<212> TYPE: DNA
<213> ORGANISM: Artificial sequence
<220> FEATURE:
<223> OTHER INFORMATION: Synthetic sequence: PCR primer suitable for amplifying target DNA regions comprising genetic variations
associated with adverse reactions to pharmaceuticals

<400> SEQUENCE: 226
tgaggccagg agttcaagac 20

<210> SEQ ID NO 227
<211> LENGTH: 20
<212> TYPE: DNA
<213> ORGANISM: Artificial sequence
<220> FEATURE:
<223> OTHER INFORMATION: Synthetic sequence: PCR primer suitable for
amplifying target DNA regions comprising genetic variations
associated with adverse reactions to pharmaceuticals

<400> SEQUENCE: 227
ggtggaggta ggagcaacac 20

<210> SEQ ID NO 228
<211> LENGTH: 20
<212> TYPE: DNA
<213> ORGANISM: Artificial sequence
<220> FEATURE:
<223> OTHER INFORMATION: Synthetic sequence: PCR primer suitable for
amplifying target DNA regions comprising genetic variations
associated with adverse reactions to pharmaceuticals

<400> SEQUENCE: 228
ctgctgaacc tgcacacatt 20

<210> SEQ ID NO 229
<211> LENGTH: 20
<212> TYPE: DNA
<213> ORGANISM: Artificial sequence
<220> FEATURE:
<223> OTHER INFORMATION: Synthetic sequence: PCR primer suitable for
amplifying target DNA regions comprising genetic variations
associated with adverse reactions to pharmaceuticals

<400> SEQUENCE: 229
cctcatcctc ctgctacctg 20

<210> SEQ ID NO 230
<211> LENGTH: 20
<212> TYPE: DNA
<213> ORGANISM: Artificial sequence
<220> FEATURE:
<223> OTHER INFORMATION: Synthetic sequence: PCR primer suitable for
amplifying target DNA regions comprising genetic variations
associated with adverse reactions to pharmaceuticals

<400> SEQUENCE: 230
gaggcagtct ccacgaactc 20

<210> SEQ ID NO 231
<211> LENGTH: 19
<212> TYPE: DNA
<213> ORGANISM: Artificial sequence
<220> FEATURE:
<223> OTHER INFORMATION: Synthetic sequence: PCR primer suitable for
amplifying target DNA regions comprising genetic variations
associated with adverse reactions to pharmaceuticals

<400> SEQUENCE: 231
gcctacagca tggatgtga 19

<210> SEQ ID NO 232
<211> LENGTH: 23

<212> TYPE: DNA
<213> ORGANISM: Artificial sequence
<220> FEATURE:
<223> OTHER INFORMATION: Synthetic sequence: PCR primer suitable for amplifying target DNA regions comprising genetic variations associated with adverse reactions to pharmaceuticals

<400> SEQUENCE: 232
tggaattgta ccttttaagt gga 23

<210> SEQ ID NO 233
<211> LENGTH: 20
<212> TYPE: DNA
<213> ORGANISM: Artificial sequence
<220> FEATURE:
<223> OTHER INFORMATION: Synthetic sequence: PCR primer suitable for amplifying target DNA regions comprising genetic variations associated with adverse reactions to pharmaceuticals

<400> SEQUENCE: 233
tcacaatccc tgtgacctga 20

<210> SEQ ID NO 234
<211> LENGTH: 20
<212> TYPE: DNA
<213> ORGANISM: Artificial sequence
<220> FEATURE:
<223> OTHER INFORMATION: Synthetic sequence: PCR primer suitable for amplifying target DNA regions comprising genetic variations associated with adverse reactions to pharmaceuticals

<400> SEQUENCE: 234
ggggcatttt tactgatgga 20

<210> SEQ ID NO 235
<211> LENGTH: 20
<212> TYPE: DNA
<213> ORGANISM: Artificial sequence
<220> FEATURE:
<223> OTHER INFORMATION: Synthetic sequence: PCR primer suitable for amplifying target DNA regions comprising genetic variations associated with adverse reactions to pharmaceuticals

<400> SEQUENCE: 235
tgaaaccacc agcagtgttc 20

<210> SEQ ID NO 236
<211> LENGTH: 20
<212> TYPE: DNA
<213> ORGANISM: Artificial sequence
<220> FEATURE:
<223> OTHER INFORMATION: Synthetic sequence: PCR primer suitable for amplifying target DNA regions comprising genetic variations associated with adverse reactions to pharmaceuticals

<400> SEQUENCE: 236
aaaattctcc tggggagtgg 20

<210> SEQ ID NO 237
<211> LENGTH: 23
<212> TYPE: DNA
<213> ORGANISM: Artificial sequence
<220> FEATURE:
<223> OTHER INFORMATION: Synthetic sequence: PCR primer suitable for amplifying target DNA regions comprising genetic variations associated with adverse reactions to pharmaceuticals

<400> SEQUENCE: 237
acccctaaca tgtaactctg tgg 23

<210> SEQ ID NO 238
<211> LENGTH: 23
<212> TYPE: DNA
<213> ORGANISM: Artificial sequence
<220> FEATURE:
<223> OTHER INFORMATION: Synthetic sequence: PCR primer suitable for amplifying target DNA regions comprising genetic variations associated with adverse reactions to pharmaceuticals

<400> SEQUENCE: 238
tttgaaggag aagttctgaa gga 23

<210> SEQ ID NO 239
<211> LENGTH: 20
<212> TYPE: DNA
<213> ORGANISM: Artificial sequence
<220> FEATURE:
<223> OTHER INFORMATION: Synthetic sequence: PCR primer suitable for amplifying target DNA regions comprising genetic variations associated with adverse reactions to pharmaceuticals

<400> SEQUENCE: 239
cacccagctt aacgaatgct 20

<210> SEQ ID NO 240
<211> LENGTH: 20
<212> TYPE: DNA
<213> ORGANISM: Artificial sequence
<220> FEATURE:
<223> OTHER INFORMATION: Synthetic sequence: PCR primer suitable for amplifying target DNA regions comprising genetic variations associated with adverse reactions to pharmaceuticals

<400> SEQUENCE: 240
ccaggaagcc agactttgat 20

<210> SEQ ID NO 241
<211> LENGTH: 20
<212> TYPE: DNA
<213> ORGANISM: Artificial sequence
<220> FEATURE:
<223> OTHER INFORMATION: Synthetic sequence: PCR primer suitable for amplifying target DNA regions comprising genetic variations associated with adverse reactions to pharmaceuticals

<400> SEQUENCE: 241
acccctaatg tccctactgc 20

<210> SEQ ID NO 242
<211> LENGTH: 19
<212> TYPE: DNA
<213> ORGANISM: Artificial sequence
<220> FEATURE:
<223> OTHER INFORMATION: Synthetic sequence: PCR primer suitable for amplifying target DNA regions comprising genetic variations associated with adverse reactions to pharmaceuticals

<400> SEQUENCE: 242
ggagatcctg ggagaggtg 19

<210> SEQ ID NO 243
<211> LENGTH: 20
<212> TYPE: DNA
<213> ORGANISM: Artificial sequence
<220> FEATURE:
<223> OTHER INFORMATION: Synthetic sequence: PCR primer suitable for amplifying target DNA regions comprising genetic variations associated with adverse reactions to pharmaceuticals

<400> SEQUENCE: 243
ttctggggaa attctcatgg 20

<210> SEQ ID NO 244
<211> LENGTH: 20
<212> TYPE: DNA
<213> ORGANISM: Artificial sequence
<220> FEATURE:
<223> OTHER INFORMATION: Synthetic sequence: PCR primer suitable for amplifying target DNA regions comprising genetic variations associated with adverse reactions to pharmaceuticals

<400> SEQUENCE: 244
tcaggtttgg gaactcatcc 20

<210> SEQ ID NO 245
<211> LENGTH: 20
<212> TYPE: DNA
<213> ORGANISM: Artificial sequence
<220> FEATURE:
<223> OTHER INFORMATION: Synthetic sequence: PCR primer suitable for amplifying target DNA regions comprising genetic variations associated with adverse reactions to pharmaceuticals

<400> SEQUENCE: 245
atggtttgca ggaaacaagg 20

<210> SEQ ID NO 246
<211> LENGTH: 20
<212> TYPE: DNA
<213> ORGANISM: Artificial sequence
<220> FEATURE:
<223> OTHER INFORMATION: Synthetic sequence: PCR primer suitable for amplifying target DNA regions comprising genetic variations associated with adverse reactions to pharmaceuticals

<400> SEQUENCE: 246
aaagcgggag atgaagtcct 20

<210> SEQ ID NO 247
<211> LENGTH: 20
<212> TYPE: DNA
<213> ORGANISM: Artificial sequence
<220> FEATURE:
<223> OTHER INFORMATION: Synthetic sequence: PCR primer suitable for amplifying target DNA regions comprising genetic variations associated with adverse reactions to pharmaceuticals

<400> SEQUENCE: 247
ggcagcataa gcaggacttc 20

<210> SEQ ID NO 248
<211> LENGTH: 20
<212> TYPE: DNA
<213> ORGANISM: Artificial sequence
<220> FEATURE:
<223> OTHER INFORMATION: Synthetic sequence: PCR primer suitable for amplifying target DNA regions comprising genetic variations associated with adverse reactions to pharmaceuticals

<400> SEQUENCE: 248
gttgctcgag gacaagttcc 20

<210> SEQ ID NO 249
<211> LENGTH: 17
<212> TYPE: DNA
<213> ORGANISM: Artificial sequence
<220> FEATURE:
<223> OTHER INFORMATION: Synthetic sequence: PCR primer suitable for amplifying target DNA regions comprising genetic variations associated with adverse reactions to pharmaceuticals

<400> SEQUENCE: 249
gcacggctgt ccaagga 17

<210> SEQ ID NO 250
<211> LENGTH: 17
<212> TYPE: DNA
<213> ORGANISM: Artificial sequence
<220> FEATURE:
<223> OTHER INFORMATION: Synthetic sequence: PCR primer suitable for amplifying target DNA regions comprising genetic variations associated with adverse reactions to pharmaceuticals

<400> SEQUENCE: 250
gcgggccccg gcctggt 17

<210> SEQ ID NO 251
<211> LENGTH: 20
<212> TYPE: DNA
<213> ORGANISM: Artificial sequence
<220> FEATURE:
<223> OTHER INFORMATION: Synthetic sequence: PCR primer suitable for amplifying target DNA regions comprising genetic variations associated with adverse reactions to pharmaceuticals

<400> SEQUENCE: 251
acctggtccc caaaagaaat 20

<210> SEQ ID NO 252
<211> LENGTH: 20
<212> TYPE: DNA
<213> ORGANISM: Artificial sequence
<220> FEATURE:
<223> OTHER INFORMATION: Synthetic sequence: PCR primer suitable for amplifying target DNA regions comprising genetic variations associated with adverse reactions to pharmaceuticals

<400> SEQUENCE: 252
aaagttgggg acacacaagc 20

<210> SEQ ID NO 253
<211> LENGTH: 22
<212> TYPE: DNA
<213> ORGANISM: Artificial sequence
<220> FEATURE:
<223> OTHER INFORMATION: Synthetic sequence: PCR primer suitable for amplifying target DNA regions comprising genetic variations associated with adverse reactions to pharmaceuticals

<400> SEQUENCE: 253
cacacacaca cacaaatcca ag 22

<210> SEQ ID NO 254
<211> LENGTH: 20
<212> TYPE: DNA
<213> ORGANISM: Artificial sequence
<220> FEATURE:
<223> OTHER INFORMATION: Synthetic sequence: PCR primer suitable for amplifying target DNA regions comprising genetic variations associated with adverse reactions to pharmaceuticals

<400> SEQUENCE: 254
gatggggtgg aagaagttga 20

<210> SEQ ID NO 255
<211> LENGTH: 25
<212> TYPE: DNA
<213> ORGANISM: Artificial sequence
<220> FEATURE:
<223> OTHER INFORMATION: Synthetic sequence: Probe suitable for detection of genetic variations associated with known erythrocyte antigens, and useful for genotyping for blood groups

<400> SEQUENCE: 255
cagccaaggg gtcaccacga ggaca 25

<210> SEQ ID NO 256
<211> LENGTH: 25
<212> TYPE: DNA
<213> ORGANISM: Artificial sequence
<220> FEATURE:
<223> OTHER INFORMATION: Synthetic sequence: Probe suitable for detection of genetic variations associated with known erythrocyte antigens, and useful for genotyping for blood groups

<400> SEQUENCE: 256
ccagccaagg ggtaccacga ggaca 25

<210> SEQ ID NO 257
<211> LENGTH: 27
<212> TYPE: DNA
<213> ORGANISM: Artificial sequence
<220> FEATURE:
<223> OTHER INFORMATION: Synthetic sequence: Probe suitable for detection of genetic variations associated with known erythrocyte antigens, and useful for genotyping for blood groups

<400> SEQUENCE: 257
ccagccaagg ggtcaccacg aggacat 27

<210> SEQ ID NO 258
<211> LENGTH: 27
<212> TYPE: DNA
<213> ORGANISM: Artificial sequence
<220> FEATURE:
<223> OTHER INFORMATION: Synthetic sequence: Probe suitable for detection of genetic variations associated with known erythrocyte antigens, and useful for genotyping for blood groups

<400> SEQUENCE: 258
gccagccaag gggtaccacg aggacat 27

<210> SEQ ID NO 259
<211> LENGTH: 25
<212> TYPE: DNA
<213> ORGANISM: Artificial sequence
<220> FEATURE:
<223> OTHER INFORMATION: Synthetic sequence: Probe suitable for detection of genetic variations associated with known erythrocyte antigens, and useful for genotyping for blood groups

<400> SEQUENCE: 259
accctgcacc ccggcttcta cggaa 25

<210> SEQ ID NO 260
<211> LENGTH: 25
<212> TYPE: DNA
<213> ORGANISM: Artificial sequence
<220> FEATURE:
<223> OTHER INFORMATION: Synthetic sequence: Probe suitable for detection of genetic variations associated with known erythrocyte antigens, and useful for genotyping for blood groups

<400> SEQUENCE: 260
accctgcacc ccagcttcta cggaa 25

<210> SEQ ID NO 261
<211> LENGTH: 27
<212> TYPE: DNA
<213> ORGANISM: Artificial sequence
<220> FEATURE:
<223> OTHER INFORMATION: Synthetic sequence: Probe suitable for detection of genetic variations associated with known erythrocyte antigens, and useful for genotyping for blood groups

<400> SEQUENCE: 261
caccctgcac cccggcttct acggaag 27

<210> SEQ ID NO 262
<211> LENGTH: 27
<212> TYPE: DNA
<213> ORGANISM: Artificial sequence
<220> FEATURE:
<223> OTHER INFORMATION: Synthetic sequence: Probe suitable for detection of genetic variations associated with known erythrocyte antigens, and useful for genotyping for blood groups

<400> SEQUENCE: 262
caccctgcac cccagcttct acggaag 27

<210> SEQ ID NO 263
<211> LENGTH: 25
<212> TYPE: DNA
<213> ORGANISM: Artificial sequence
<220> FEATURE:
<223> OTHER INFORMATION: Synthetic sequence: Probe suitable for detection of genetic variations associated with known erythrocyte antigens, and useful for genotyping for blood groups

<400> SEQUENCE: 263 agaaccccc caggtagtag aaatc 25

<210> SEQ ID NO 264
<211> LENGTH: 25
<212> TYPE: DNA
<213> ORGANISM: Artificial sequence
<220> FEATURE:
<223> OTHER INFORMATION: Synthetic sequence: Probe suitable for detection of genetic variations associated with known erythrocyte antigens, and useful for genotyping for blood groups

<400> SEQUENCE: 264 agaaccccc catgtagtag aaatc 25

<210> SEQ ID NO 265
<211> LENGTH: 27
<212> TYPE: DNA
<213> ORGANISM: Artificial sequence
<220> FEATURE:
<223> OTHER INFORMATION: Synthetic sequence: Probe suitable for detection of genetic variations associated with known erythrocyte antigens, and useful for genotyping for blood groups

<400> SEQUENCE: 265
aagaaccccc ccaggtagta gaaatcg 27

<210> SEQ ID NO 266
<211> LENGTH: 27
<212> TYPE: DNA
<213> ORGANISM: Artificial sequence
<220> FEATURE:
<223> OTHER INFORMATION: Synthetic sequence: Probe suitable for detection of genetic variations associated with known erythrocyte antigens, and useful for genotyping for blood groups

<400> SEQUENCE: 266
aagaaccccc ccatgtagta gaaatcg 27

<210> SEQ ID NO 267
<211> LENGTH: 25
<212> TYPE: DNA
<213> ORGANISM: Artificial sequence
<220> FEATURE:
<223> OTHER INFORMATION: Synthetic sequence: Probe suitable for detection of genetic variations associated with known erythrocyte antigens, and useful for genotyping for blood groups

<400> SEQUENCE: 267
ccccgaagaa cccccccagg tagta 25

<210> SEQ ID NO 268
<211> LENGTH: 25
<212> TYPE: DNA
<213> ORGANISM: Artificial sequence
<220> FEATURE:
<223> OTHER INFORMATION: Synthetic sequence: Probe suitable for detection of genetic variations associated with known erythrocyte antigens, and useful for genotyping for blood groups

<400> SEQUENCE: 268
ccccgaagaa cctccccagg tagta 25

<210> SEQ ID NO 269
<211> LENGTH: 23
<212> TYPE: DNA
<213> ORGANISM: Artificial sequence
<220> FEATURE:
<223> OTHER INFORMATION: Synthetic sequence: Probe suitable for detection of genetic variations associated with known erythrocyte antigens, and useful for genotyping for blood groups

<400> SEQUENCE: 269
cccgaagaac ccccccaggt agt 23

<210> SEQ ID NO 270
<211> LENGTH: 23
<212> TYPE: DNA
<213> ORGANISM: Artificial sequence
<220> FEATURE:
<223> OTHER INFORMATION: Synthetic sequence: Probe suitable for detection of genetic variations associated with known erythrocyte antigens, and useful for genotyping for blood groups

<400> SEQUENCE: 270
cccgaagaac ctccccaggt agt 23

<210> SEQ ID NO 271
<211> LENGTH: 25
<212> TYPE: DNA
<213> ORGANISM: Artificial sequence
<220> FEATURE:
<223> OTHER INFORMATION: Synthetic sequence: Probe suitable for detection of genetic variations associated with known erythrocyte antigens, and useful for genotyping for blood groups

<400> SEQUENCE: 271
cccccgaaga acccccccag gtagt 25

<210> SEQ ID NO 272
<211> LENGTH: 25

<212> TYPE: DNA
<213> ORGANISM: Artificial sequence
<220> FEATURE:
<223> OTHER INFORMATION: Synthetic sequence: Probe suitable for detection of genetic variations associated with known erythrocyte antigens, and useful for genotyping for blood groups

<400> SEQUENCE: 272
cccccgaaga acgcccccag gtagt 25

<210> SEQ ID NO 273
<211> LENGTH: 27
<212> TYPE: DNA
<213> ORGANISM: Artificial sequence
<220> FEATURE:
<223> OTHER INFORMATION: Synthetic sequence: Probe suitable for detection of genetic variations associated with known erythrocyte antigens, and useful for genotyping for blood groups

<400> SEQUENCE: 273
acccccgaag aacccccccca ggtagta 27

<210> SEQ ID NO 274
<211> LENGTH: 27
<212> TYPE: DNA
<213> ORGANISM: Artificial sequence
<220> FEATURE:
<223> OTHER INFORMATION: Synthetic sequence: Probe suitable for detection of genetic variations associated with known erythrocyte antigens, and useful for genotyping for blood groups

<400> SEQUENCE: 274
acccccgaag aacgccccca ggtagta 27

<210> SEQ ID NO 275
<211> LENGTH: 25
<212> TYPE: DNA
<213> ORGANISM: Artificial sequence
<220> FEATURE:
<223> OTHER INFORMATION: Synthetic sequence: Probe suitable for detection of genetic variations associated with known erythrocyte antigens, and useful for genotyping for blood groups

<400> SEQUENCE: 275
cggtccggaa cccgtgagcg gctgc 25

<210> SEQ ID NO 276
<211> LENGTH: 25
<212> TYPE: DNA
<213> ORGANISM: Artificial sequence
<220> FEATURE:
<223> OTHER INFORMATION: Synthetic sequence: Probe suitable for detection of genetic variations associated with known erythrocyte antigens, and useful for genotyping for blood groups

<400> SEQUENCE: 276
cggtccggaa ccgtgagcgg ctgcc 25

<210> SEQ ID NO 277
<211> LENGTH: 27
<212> TYPE: DNA
<213> ORGANISM: Artificial sequence
<220> FEATURE:
<223> OTHER INFORMATION: Synthetic sequence: Probe suitable for detection of genetic variations associated with known erythrocyte antigens, and useful for genotyping for blood groups

<400> SEQUENCE: 277
gcggtccgga acccgtgagc ggctgcc 27

-continued

```
<210> SEQ ID NO 278
<211> LENGTH: 27
<212> TYPE: DNA
<213> ORGANISM: Artificial sequence
<220> FEATURE:
<223> OTHER INFORMATION: Synthetic sequence: Probe suitable for
      detection of genetic variations associated with known erythrocyte
      antigens, and useful for genotyping for blood groups

<400> SEQUENCE: 278

gcggtccgga accgtgagcg gctgcca                                          27

<210> SEQ ID NO 279
<211> LENGTH: 19
<212> TYPE: DNA
<213> ORGANISM: Artificial sequence
<220> FEATURE:
<223> OTHER INFORMATION: Synthetic sequence: Probe suitable for
      detection of genetic variations associated with known erythrocyte
      antigens, and useful for genotyping for blood groups

<400> SEQUENCE: 279

ccccgaagaa ccccccccag                                                  19

<210> SEQ ID NO 280
<211> LENGTH: 19
<212> TYPE: DNA
<213> ORGANISM: Artificial sequence
<220> FEATURE:
<223> OTHER INFORMATION: Synthetic sequence: Probe suitable for
      detection of genetic variations associated with known erythrocyte
      antigens, and useful for genotyping for blood groups

<400> SEQUENCE: 280

cccgaagaac ccccccag                                                    19

<210> SEQ ID NO 281
<211> LENGTH: 21
<212> TYPE: DNA
<213> ORGANISM: Artificial sequence
<220> FEATURE:
<223> OTHER INFORMATION: Synthetic sequence: Probe suitable for
      detection of genetic variations associated with known erythrocyte
      antigens, and useful for genotyping for blood groups

<400> SEQUENCE: 281

cccccgaaga accccccag g                                                 21

<210> SEQ ID NO 282
<211> LENGTH: 21
<212> TYPE: DNA
<213> ORGANISM: Artificial sequence
<220> FEATURE:
<223> OTHER INFORMATION: Synthetic sequence: Probe suitable for
      detection of genetic variations associated with known erythrocyte
      antigens, and useful for genotyping for blood groups

<400> SEQUENCE: 282

ccccgaagaa ccccccccag g                                                21

<210> SEQ ID NO 283
<211> LENGTH: 25
<212> TYPE: DNA
<213> ORGANISM: Artificial sequence
<220> FEATURE:
<223> OTHER INFORMATION: Synthetic sequence: Probe suitable for
      detection of genetic variations associated with known erythrocyte
      antigens, and useful for genotyping for blood groups
```

<400> SEQUENCE: 283
tgcttgtctt ggtcttgttt gggta 25

<210> SEQ ID NO 284
<211> LENGTH: 25
<212> TYPE: DNA
<213> ORGANISM: Artificial sequence
<220> FEATURE:
<223> OTHER INFORMATION: Synthetic sequence: Probe suitable for detection of genetic variations associated with known erythrocyte antigens, and useful for genotyping for blood groups

<400> SEQUENCE: 284
tgcttgtctt gggtcttgtt tgggt 25

<210> SEQ ID NO 285
<211> LENGTH: 23
<212> TYPE: DNA
<213> ORGANISM: Artificial sequence
<220> FEATURE:
<223> OTHER INFORMATION: Synthetic sequence: Probe suitable for detection of genetic variations associated with known erythrocyte antigens, and useful for genotyping for blood groups

<400> SEQUENCE: 285
gcttgtcttg gtcttgtttg ggt 23

<210> SEQ ID NO 286
<211> LENGTH: 23
<212> TYPE: DNA
<213> ORGANISM: Artificial sequence
<220> FEATURE:
<223> OTHER INFORMATION: Synthetic sequence: Probe suitable for detection of genetic variations associated with known erythrocyte antigens, and useful for genotyping for blood groups

<400> SEQUENCE: 286
gcttgtcttg ggtcttgttt ggg 23

<210> SEQ ID NO 287
<211> LENGTH: 25
<212> TYPE: DNA
<213> ORGANISM: Artificial sequence
<220> FEATURE:
<223> OTHER INFORMATION: Synthetic sequence: Probe suitable for detection of genetic variations associated with known erythrocyte antigens, and useful for genotyping for blood groups

<400> SEQUENCE: 287
ggagcctgaa ctgctcgttg aggat 25

<210> SEQ ID NO 288
<211> LENGTH: 25
<212> TYPE: DNA
<213> ORGANISM: Artificial sequence
<220> FEATURE:
<223> OTHER INFORMATION: Synthetic sequence: Probe suitable for detection of genetic variations associated with known erythrocyte antigens, and useful for genotyping for blood groups

<400> SEQUENCE: 288
ggagcctgaa ctactcgttg aggat 25

<210> SEQ ID NO 289
<211> LENGTH: 27
<212> TYPE: DNA
<213> ORGANISM: Artificial sequence
<220> FEATURE:
<223> OTHER INFORMATION: Synthetic sequence: Probe suitable for detection of genetic variations associated with known erythrocyte antigens, and useful for genotyping for blood groups

<400> SEQUENCE: 289
tggagcctga actgctcgtt gaggatg 27

<210> SEQ ID NO 290
<211> LENGTH: 27
<212> TYPE: DNA
<213> ORGANISM: Artificial sequence
<220> FEATURE:
<223> OTHER INFORMATION: Synthetic sequence: Probe suitable for detection of genetic variations associated with known erythrocyte antigens, and useful for genotyping for blood groups

<400> SEQUENCE: 290
tggagcctga actactcgtt gaggatg 27

<210> SEQ ID NO 291
<211> LENGTH: 25
<212> TYPE: DNA
<213> ORGANISM: Artificial sequence
<220> FEATURE:
<223> OTHER INFORMATION: Synthetic sequence: Probe suitable for detection of genetic variations associated with known erythrocyte antigens, and useful for genotyping for blood groups

<400> SEQUENCE: 291
tcgtgccaca cggcctcgat gccgt 25

<210> SEQ ID NO 292
<211> LENGTH: 25
<212> TYPE: DNA
<213> ORGANISM: Artificial sequence
<220> FEATURE:
<223> OTHER INFORMATION: Synthetic sequence: Probe suitable for detection of genetic variations associated with known erythrocyte antigens, and useful for genotyping for blood groups

<400> SEQUENCE: 292
tcgtgccaca cgacctcgat gccgt 25

<210> SEQ ID NO 293
<211> LENGTH: 23
<212> TYPE: DNA
<213> ORGANISM: Artificial sequence
<220> FEATURE:
<223> OTHER INFORMATION: Synthetic sequence: Probe suitable for detection of genetic variations associated with known erythrocyte antigens, and useful for genotyping for blood groups

<400> SEQUENCE: 293
cgtgccacac ggcctcgatg ccg 23

<210> SEQ ID NO 294
<211> LENGTH: 23
<212> TYPE: DNA
<213> ORGANISM: Artificial sequence
<220> FEATURE:
<223> OTHER INFORMATION: Synthetic sequence: Probe suitable for detection of genetic variations associated with known erythrocyte antigens, and useful for genotyping for blood groups

<400> SEQUENCE: 294
cgtgccacac gacctcgatg ccg 23

<210> SEQ ID NO 295
<211> LENGTH: 25
<212> TYPE: DNA
<213> ORGANISM: Artificial sequence
<220> FEATURE:
<223> OTHER INFORMATION: Synthetic sequence: Probe suitable for detection of genetic variations associated with known erythrocyte antigens, and useful for genotyping for blood groups

<400> SEQUENCE: 295
cctgaacaag tacctgctgc gccac 25

<210> SEQ ID NO 296
<211> LENGTH: 25
<212> TYPE: DNA
<213> ORGANISM: Artificial sequence
<220> FEATURE:
<223> OTHER INFORMATION: Synthetic sequence: Probe suitable for detection of genetic variations associated with known erythrocyte antigens, and useful for genotyping for blood groups

<400> SEQUENCE: 296
cctgaacaag taactgctgc gccac 25

<210> SEQ ID NO 297
<211> LENGTH: 27
<212> TYPE: DNA
<213> ORGANISM: Artificial sequence
<220> FEATURE:
<223> OTHER INFORMATION: Synthetic sequence: Probe suitable for detection of genetic variations associated with known erythrocyte antigens, and useful for genotyping for blood groups

<400> SEQUENCE: 297
acctgaacaa gtacctgctg cgccaca 27

<210> SEQ ID NO 298
<211> LENGTH: 27
<212> TYPE: DNA
<213> ORGANISM: Artificial sequence
<220> FEATURE:
<223> OTHER INFORMATION: Synthetic sequence: Probe suitable for detection of genetic variations associated with known erythrocyte antigens, and useful for genotyping for blood groups

<400> SEQUENCE: 298
acctgaacaa gtaactgctg cgccaca 27

<210> SEQ ID NO 299
<211> LENGTH: 25
<212> TYPE: DNA
<213> ORGANISM: Artificial sequence
<220> FEATURE:
<223> OTHER INFORMATION: Synthetic sequence: Probe suitable for detection of genetic variations associated with known erythrocyte antigens, and useful for genotyping for blood groups

<400> SEQUENCE: 299
accatctgca gcgcgtctcg ttgcc 25

<210> SEQ ID NO 300
<211> LENGTH: 25
<212> TYPE: DNA
<213> ORGANISM: Artificial sequence
<220> FEATURE:
<223> OTHER INFORMATION: Synthetic sequence: Probe suitable for detection of genetic variations associated with known erythrocyte antigens, and useful for genotyping for blood groups

<400> SEQUENCE: 300
accatctgca gcatgtctcg ttgcc 25

<210> SEQ ID NO 301
<211> LENGTH: 23
<212> TYPE: DNA
<213> ORGANISM: Artificial sequence
<220> FEATURE:
<223> OTHER INFORMATION: Synthetic sequence: Probe suitable for detection of genetic variations associated with known erythrocyte antigens, and useful for genotyping for blood groups

<400> SEQUENCE: 301
ccatctgcag cgcgtctcgt tgc 23

<210> SEQ ID NO 302
<211> LENGTH: 23
<212> TYPE: DNA
<213> ORGANISM: Artificial sequence
<220> FEATURE:
<223> OTHER INFORMATION: Synthetic sequence: Probe suitable for detection of genetic variations associated with known erythrocyte antigens, and useful for genotyping for blood groups

<400> SEQUENCE: 302
ccatctgcag catgtctcgt tgc 23

<210> SEQ ID NO 303
<211> LENGTH: 25
<212> TYPE: DNA
<213> ORGANISM: Artificial sequence
<220> FEATURE:
<223> OTHER INFORMATION: Synthetic sequence: Probe suitable for detection of genetic variations associated with known erythrocyte antigens, and useful for genotyping for blood groups

<400> SEQUENCE: 303
gacacgtcct gccagcgctt gtagg 25

<210> SEQ ID NO 304
<211> LENGTH: 25
<212> TYPE: DNA
<213> ORGANISM: Artificial sequence
<220> FEATURE:
<223> OTHER INFORMATION: Synthetic sequence: Probe suitable for detection of genetic variations associated with known erythrocyte antigens, and useful for genotyping for blood groups

<400> SEQUENCE: 304
gacacgtcct gctagcgctt gtagg 25

<210> SEQ ID NO 305
<211> LENGTH: 23
<212> TYPE: DNA
<213> ORGANISM: Artificial sequence
<220> FEATURE:
<223> OTHER INFORMATION: Synthetic sequence: Probe suitable for detection of genetic variations associated with known erythrocyte antigens, and useful for genotyping for blood groups

<400> SEQUENCE: 305
acacgtcctg ccagcgcttg tag 23

<210> SEQ ID NO 306
<211> LENGTH: 23
<212> TYPE: DNA
<213> ORGANISM: Artificial sequence
<220> FEATURE:
<223> OTHER INFORMATION: Synthetic sequence: Probe suitable for detection of genetic variations associated with known erythrocyte antigens, and useful for genotyping for blood groups

<400> SEQUENCE: 306
acacgtcctg ctagcgcttg tag 23

<210> SEQ ID NO 307
<211> LENGTH: 25
<212> TYPE: DNA
<213> ORGANISM: Artificial sequence
<220> FEATURE:
<223> OTHER INFORMATION: Synthetic sequence: Probe suitable for detection of genetic variations associated with known erythrocyte antigens, and useful for genotyping for blood groups

<400> SEQUENCE: 307
ggcaccgcgg ccggctggtc ggtga 25

<210> SEQ ID NO 308
<211> LENGTH: 25
<212> TYPE: DNA
<213> ORGANISM: Artificial sequence
<220> FEATURE:
<223> OTHER INFORMATION: Synthetic sequence: Probe suitable for detection of genetic variations associated with known erythrocyte antigens, and useful for genotyping for blood groups

<400> SEQUENCE: 308
ggcaccgcgg ccagctggtc ggtga 25

<210> SEQ ID NO 309
<211> LENGTH: 27
<212> TYPE: DNA
<213> ORGANISM: Artificial sequence
<220> FEATURE:
<223> OTHER INFORMATION: Synthetic sequence: Probe suitable for detection of genetic variations associated with known erythrocyte antigens, and useful for genotyping for blood groups

<400> SEQUENCE: 309
gggcaccgcg gccggctggt cggtgaa 27

<210> SEQ ID NO 310
<211> LENGTH: 27
<212> TYPE: DNA
<213> ORGANISM: Artificial sequence
<220> FEATURE:
<223> OTHER INFORMATION: Synthetic sequence: Probe suitable for detection of genetic variations associated with known erythrocyte antigens, and useful for genotyping for blood groups

<400> SEQUENCE: 310
gggcaccgcg gccagctggt cggtgaa 27

<210> SEQ ID NO 311
<211> LENGTH: 25
<212> TYPE: DNA
<213> ORGANISM: Artificial sequence
<220> FEATURE:
<223> OTHER INFORMATION: Synthetic sequence: Probe suitable for detection of genetic variations associated with known erythrocyte antigens, and useful for genotyping for blood groups

<400> SEQUENCE: 311
gtggacatgg agttccgcga ccacg 25

<210> SEQ ID NO 312
<211> LENGTH: 25

<212> TYPE: DNA
<213> ORGANISM: Artificial sequence
<220> FEATURE:
<223> OTHER INFORMATION: Synthetic sequence: Probe suitable for detection of genetic variations associated with known erythrocyte antigens, and useful for genotyping for blood groups

<400> SEQUENCE: 312
gtggacatgg agatccgcga ccacg 25

<210> SEQ ID NO 313
<211> LENGTH: 27
<212> TYPE: DNA
<213> ORGANISM: Artificial sequence
<220> FEATURE:
<223> OTHER INFORMATION: Synthetic sequence: Probe suitable for detection of genetic variations associated with known erythrocyte antigens, and useful for genotyping for blood groups

<400> SEQUENCE: 313
cgtggacatg gagttccgcg accacgt 27

<210> SEQ ID NO 314
<211> LENGTH: 27
<212> TYPE: DNA
<213> ORGANISM: Artificial sequence
<220> FEATURE:
<223> OTHER INFORMATION: Synthetic sequence: Probe suitable for detection of genetic variations associated with known erythrocyte antigens, and useful for genotyping for blood groups

<400> SEQUENCE: 314
cgtggacatg gagatccgcg accacgt 27

<210> SEQ ID NO 315
<211> LENGTH: 25
<212> TYPE: DNA
<213> ORGANISM: Artificial sequence
<220> FEATURE:
<223> OTHER INFORMATION: Synthetic sequence: Probe suitable for detection of genetic variations associated with known erythrocyte antigens, and useful for genotyping for blood groups

<400> SEQUENCE: 315
gtgatggcgg ccattggctt gggct 25

<210> SEQ ID NO 316
<211> LENGTH: 25
<212> TYPE: DNA
<213> ORGANISM: Artificial sequence
<220> FEATURE:
<223> OTHER INFORMATION: Synthetic sequence: Probe suitable for detection of genetic variations associated with known erythrocyte antigens, and useful for genotyping for blood groups

<400> SEQUENCE: 316
gtgatggcgg cccttggctt gggct 25

<210> SEQ ID NO 317
<211> LENGTH: 23
<212> TYPE: DNA
<213> ORGANISM: Artificial sequence
<220> FEATURE:
<223> OTHER INFORMATION: Synthetic sequence: Probe suitable for detection of genetic variations associated with known erythrocyte antigens, and useful for genotyping for blood groups

<400> SEQUENCE: 317
tgatggcggc cattggcttg ggc 23

<210> SEQ ID NO 318
<211> LENGTH: 23
<212> TYPE: DNA
<213> ORGANISM: Artificial sequence
<220> FEATURE:
<223> OTHER INFORMATION: Synthetic sequence: Probe suitable for detection of genetic variations associated with known erythrocyte antigens, and useful for genotyping for blood groups

<400> SEQUENCE: 318
tgatggcggc ccttggcttg ggc 23

<210> SEQ ID NO 319
<211> LENGTH: 25
<212> TYPE: DNA
<213> ORGANISM: Artificial sequence
<220> FEATURE:
<223> OTHER INFORMATION: Synthetic sequence: Probe suitable for detection of genetic variations associated with known erythrocyte antigens, and useful for genotyping for blood groups

<400> SEQUENCE: 319
tcctcacctc gagtttccgg agaca 25

<210> SEQ ID NO 320
<211> LENGTH: 25
<212> TYPE: DNA
<213> ORGANISM: Artificial sequence
<220> FEATURE:
<223> OTHER INFORMATION: Synthetic sequence: Probe suitable for detection of genetic variations associated with known erythrocyte antigens, and useful for genotyping for blood groups

<400> SEQUENCE: 320
tcctcacctc gaatttccgg agaca 25

<210> SEQ ID NO 321
<211> LENGTH: 27
<212> TYPE: DNA
<213> ORGANISM: Artificial sequence
<220> FEATURE:
<223> OTHER INFORMATION: Synthetic sequence: Probe suitable for detection of genetic variations associated with known erythrocyte antigens, and useful for genotyping for blood groups

<400> SEQUENCE: 321
ttcctcacct cgagtttccg gagacac 27

<210> SEQ ID NO 322
<211> LENGTH: 27
<212> TYPE: DNA
<213> ORGANISM: Artificial sequence
<220> FEATURE:
<223> OTHER INFORMATION: Synthetic sequence: Probe suitable for detection of genetic variations associated with known erythrocyte antigens, and useful for genotyping for blood groups

<400> SEQUENCE: 322
ttcctcacct cgaatttccg gagacac 27

<210> SEQ ID NO 323
<211> LENGTH: 25
<212> TYPE: DNA
<213> ORGANISM: Artificial sequence
<220> FEATURE:
<223> OTHER INFORMATION: Synthetic sequence: Probe suitable for detection of genetic variations associated with known erythrocyte antigens, and useful for genotyping for blood groups

<400> SEQUENCE: 323
agccagttcc cttctgggaa ggtgg 25

<210> SEQ ID NO 324
<211> LENGTH: 25
<212> TYPE: DNA
<213> ORGANISM: Artificial sequence
<220> FEATURE:
<223> OTHER INFORMATION: Synthetic sequence: Probe suitable for detection of genetic variations associated with known erythrocyte antigens, and useful for genotyping for blood groups

<400> SEQUENCE: 324
agccagttcc ctcctgggaa ggtgg 25

<210> SEQ ID NO 325
<211> LENGTH: 27
<212> TYPE: DNA
<213> ORGANISM: Artificial sequence
<220> FEATURE:
<223> OTHER INFORMATION: Synthetic sequence: Probe suitable for detection of genetic variations associated with known erythrocyte antigens, and useful for genotyping for blood groups

<400> SEQUENCE: 325
gagccagttc ccttctggga aggtggt 27

<210> SEQ ID NO 326
<211> LENGTH: 27
<212> TYPE: DNA
<213> ORGANISM: Artificial sequence
<220> FEATURE:
<223> OTHER INFORMATION: Synthetic sequence: Probe suitable for detection of genetic variations associated with known erythrocyte antigens, and useful for genotyping for blood groups

<400> SEQUENCE: 326
gagccagttc cctcctggga aggtggt 27

<210> SEQ ID NO 327
<211> LENGTH: 25
<212> TYPE: DNA
<213> ORGANISM: Artificial sequence
<220> FEATURE:
<223> OTHER INFORMATION: Synthetic sequence: Probe suitable for detection of genetic variations associated with known erythrocyte antigens, and useful for genotyping for blood groups

<400> SEQUENCE: 327
tattttgggc tgtctgtggc ctggt 25

<210> SEQ ID NO 328
<211> LENGTH: 25
<212> TYPE: DNA
<213> ORGANISM: Artificial sequence
<220> FEATURE:
<223> OTHER INFORMATION: Synthetic sequence: Probe suitable for detection of genetic variations associated with known erythrocyte antigens, and useful for genotyping for blood groups

<400> SEQUENCE: 328
tattttgggc tgactgtggc ctggt 25

<210> SEQ ID NO 329
<211> LENGTH: 21
<212> TYPE: DNA
<213> ORGANISM: Artificial sequence
<220> FEATURE:
<223> OTHER INFORMATION: Synthetic sequence: Probe suitable for
detection of genetic variations associated with known erythrocyte
antigens, and useful for genotyping for blood groups

<400> SEQUENCE: 329
ttttgggctg tctgtggcct g 21

<210> SEQ ID NO 330
<211> LENGTH: 21
<212> TYPE: DNA
<213> ORGANISM: Artificial sequence
<220> FEATURE:
<223> OTHER INFORMATION: Synthetic sequence: Probe suitable for
detection of genetic variations associated with known erythrocyte
antigens, and useful for genotyping for blood groups

<400> SEQUENCE: 330
ttttgggctg actgtggcct g 21

<210> SEQ ID NO 331
<211> LENGTH: 23
<212> TYPE: DNA
<213> ORGANISM: Artificial sequence
<220> FEATURE:
<223> OTHER INFORMATION: Synthetic sequence: Probe suitable for
detection of genetic variations associated with known erythrocyte
antigens, and useful for genotyping for blood groups

<400> SEQUENCE: 331
agcctctacc cgagggaacg gag 23

<210> SEQ ID NO 332
<211> LENGTH: 23
<212> TYPE: DNA
<213> ORGANISM: Artificial sequence
<220> FEATURE:
<223> OTHER INFORMATION: Synthetic sequence: Probe suitable for
detection of genetic variations associated with known erythrocyte
antigens, and useful for genotyping for blood groups

<400> SEQUENCE: 332
agcctctacc caagggaacg gag 23

<210> SEQ ID NO 333
<211> LENGTH: 21
<212> TYPE: DNA
<213> ORGANISM: Artificial sequence
<220> FEATURE:
<223> OTHER INFORMATION: Synthetic sequence: Probe suitable for
detection of genetic variations associated with known erythrocyte
antigens, and useful for genotyping for blood groups

<400> SEQUENCE: 333
gcctctaccc gagggaacgg a 21

<210> SEQ ID NO 334
<211> LENGTH: 21
<212> TYPE: DNA
<213> ORGANISM: Artificial sequence
<220> FEATURE:
<223> OTHER INFORMATION: Synthetic sequence: Probe suitable for
detection of genetic variations associated with known erythrocyte
antigens, and useful for genotyping for blood groups

<400> SEQUENCE: 334
gcctctaccc aagggaacgg a 21

<210> SEQ ID NO 335
<211> LENGTH: 23
<212> TYPE: DNA
<213> ORGANISM: Artificial sequence
<220> FEATURE:
<223> OTHER INFORMATION: Synthetic sequence: Probe suitable for detection of genetic variations associated with known erythrocyte antigens, and useful for genotyping for blood groups

<400> SEQUENCE: 335
acggaggata aagatcagac agc 23

<210> SEQ ID NO 336
<211> LENGTH: 23
<212> TYPE: DNA
<213> ORGANISM: Artificial sequence
<220> FEATURE:
<223> OTHER INFORMATION: Synthetic sequence: Probe suitable for detection of genetic variations associated with known erythrocyte antigens, and useful for genotyping for blood groups

<400> SEQUENCE: 336
acggaggata atgatcagac agc 23

<210> SEQ ID NO 337
<211> LENGTH: 21
<212> TYPE: DNA
<213> ORGANISM: Artificial sequence
<220> FEATURE:
<223> OTHER INFORMATION: Synthetic sequence: Probe suitable for detection of genetic variations associated with known erythrocyte antigens, and useful for genotyping for blood groups

<400> SEQUENCE: 337
cggaggataa agatcagaca g 21

<210> SEQ ID NO 338
<211> LENGTH: 21
<212> TYPE: DNA
<213> ORGANISM: Artificial sequence
<220> FEATURE:
<223> OTHER INFORMATION: Synthetic sequence: Probe suitable for detection of genetic variations associated with known erythrocyte antigens, and useful for genotyping for blood groups

<400> SEQUENCE: 338
cggaggataa tgatcagaca g 21

<210> SEQ ID NO 339
<211> LENGTH: 25
<212> TYPE: DNA
<213> ORGANISM: Artificial sequence
<220> FEATURE:
<223> OTHER INFORMATION: Synthetic sequence: Probe suitable for detection of genetic variations associated with known erythrocyte antigens, and useful for genotyping for blood groups

<400> SEQUENCE: 339
agaagtccaa tcgaaaggaa gaatg 25

<210> SEQ ID NO 340
<211> LENGTH: 25
<212> TYPE: DNA
<213> ORGANISM: Artificial sequence
<220> FEATURE:
<223> OTHER INFORMATION: Synthetic sequence: Probe suitable for detection of genetic variations associated with known erythrocyte antigens, and useful for genotyping for blood groups

<400> SEQUENCE: 340
agaagtccaa tccaaaggaa gaatg 25

<210> SEQ ID NO 341
<211> LENGTH: 23
<212> TYPE: DNA
<213> ORGANISM: Artificial sequence
<220> FEATURE:
<223> OTHER INFORMATION: Synthetic sequence: Probe suitable for detection of genetic variations associated with known erythrocyte antigens, and useful for genotyping for blood groups

<400> SEQUENCE: 341
gaagtccaat cgaaaggaag aat 23

<210> SEQ ID NO 342
<211> LENGTH: 23
<212> TYPE: DNA
<213> ORGANISM: Artificial sequence
<220> FEATURE:
<223> OTHER INFORMATION: Synthetic sequence: Probe suitable for detection of genetic variations associated with known erythrocyte antigens, and useful for genotyping for blood groups

<400> SEQUENCE: 342
gaagtccaat ccaaaggaag aat 23

<210> SEQ ID NO 343
<211> LENGTH: 23
<212> TYPE: DNA
<213> ORGANISM: Artificial sequence
<220> FEATURE:
<223> OTHER INFORMATION: Synthetic sequence: Probe suitable for detection of genetic variations associated with known erythrocyte antigens, and useful for genotyping for blood groups

<400> SEQUENCE: 343
ggaagaatgc cgtgttcaac acc 23

<210> SEQ ID NO 344
<211> LENGTH: 23
<212> TYPE: DNA
<213> ORGANISM: Artificial sequence
<220> FEATURE:
<223> OTHER INFORMATION: Synthetic sequence: Probe suitable for detection of genetic variations associated with known erythrocyte antigens, and useful for genotyping for blood groups

<400> SEQUENCE: 344
ggaagaatgc catgttcaac acc 23

<210> SEQ ID NO 345
<211> LENGTH: 21
<212> TYPE: DNA
<213> ORGANISM: Artificial sequence
<220> FEATURE:
<223> OTHER INFORMATION: Synthetic sequence: Probe suitable for detection of genetic variations associated with known erythrocyte antigens, and useful for genotyping for blood groups

<400> SEQUENCE: 345
gaagaatgcc gtgttcaaca c 21

<210> SEQ ID NO 346
<211> LENGTH: 21
<212> TYPE: DNA
<213> ORGANISM: Artificial sequence
<220> FEATURE:
<223> OTHER INFORMATION: Synthetic sequence: Probe suitable for detection of genetic variations associated with known erythrocyte antigens, and useful for genotyping for blood groups

<400> SEQUENCE: 346
gaagaatgcc atgttcaaca c 21

<210> SEQ ID NO 347
<211> LENGTH: 23
<212> TYPE: DNA
<213> ORGANISM: Artificial sequence
<220> FEATURE:
<223> OTHER INFORMATION: Synthetic sequence: Probe suitable for detection of genetic variations associated with known erythrocyte antigens, and useful for genotyping for blood groups

<400> SEQUENCE: 347
tggagagatc atctacattg tgc 23

<210> SEQ ID NO 348
<211> LENGTH: 23
<212> TYPE: DNA
<213> ORGANISM: Artificial sequence
<220> FEATURE:
<223> OTHER INFORMATION: Synthetic sequence: Probe suitable for detection of genetic variations associated with known erythrocyte antigens, and useful for genotyping for blood groups

<400> SEQUENCE: 348
tggagagatc acctacattg tgc 23

<210> SEQ ID NO 349
<211> LENGTH: 21
<212> TYPE: DNA
<213> ORGANISM: Artificial sequence
<220> FEATURE:
<223> OTHER INFORMATION: Synthetic sequence: Probe suitable for detection of genetic variations associated with known erythrocyte antigens, and useful for genotyping for blood groups

<400> SEQUENCE: 349
ggagagatca tctacattgt g 21

<210> SEQ ID NO 350
<211> LENGTH: 21
<212> TYPE: DNA
<213> ORGANISM: Artificial sequence
<220> FEATURE:
<223> OTHER INFORMATION: Synthetic sequence: Probe suitable for detection of genetic variations associated with known erythrocyte antigens, and useful for genotyping for blood groups

<400> SEQUENCE: 350
ggagagatca cctacattgt g 21

<210> SEQ ID NO 351
<211> LENGTH: 25
<212> TYPE: DNA
<213> ORGANISM: Artificial sequence
<220> FEATURE:
<223> OTHER INFORMATION: Synthetic sequence: Probe suitable for detection of genetic variations associated with known erythrocyte antigens, and useful for genotyping for blood groups

<400> SEQUENCE: 351
agtttcaact ctgctctgct gagaa 25

<210> SEQ ID NO 352
<211> LENGTH: 25

<212> TYPE: DNA
<213> ORGANISM: Artificial sequence
<220> FEATURE:
<223> OTHER INFORMATION: Synthetic sequence: Probe suitable for detection of genetic variations associated with known erythrocyte antigens, and useful for genotyping for blood groups

<400> SEQUENCE: 352
agtttcaact ctcctctgct gagaa 25

<210> SEQ ID NO 353
<211> LENGTH: 27
<212> TYPE: DNA
<213> ORGANISM: Artificial sequence
<220> FEATURE:
<223> OTHER INFORMATION: Synthetic sequence: Probe suitable for detection of genetic variations associated with known erythrocyte antigens, and useful for genotyping for blood groups

<400> SEQUENCE: 353
aattttcaac tctgctctgc tgagaag 27

<210> SEQ ID NO 354
<211> LENGTH: 27
<212> TYPE: DNA
<213> ORGANISM: Artificial sequence
<220> FEATURE:
<223> OTHER INFORMATION: Synthetic sequence: Probe suitable for detection of genetic variations associated with known erythrocyte antigens, and useful for genotyping for blood groups

<400> SEQUENCE: 354
aagtttcaac tctcctctgc tgagaag 27

<210> SEQ ID NO 355
<211> LENGTH: 25
<212> TYPE: DNA
<213> ORGANISM: Artificial sequence
<220> FEATURE:
<223> OTHER INFORMATION: Synthetic sequence: Probe suitable for detection of genetic variations associated with known erythrocyte antigens, and useful for genotyping for blood groups

<400> SEQUENCE: 355
accgtcggag ccggcaatgg catgt 25

<210> SEQ ID NO 356
<211> LENGTH: 25
<212> TYPE: DNA
<213> ORGANISM: Artificial sequence
<220> FEATURE:
<223> OTHER INFORMATION: Synthetic sequence: Probe suitable for detection of genetic variations associated with known erythrocyte antigens, and useful for genotyping for blood groups

<400> SEQUENCE: 356
accgtcggag ccagcaatgg catgt 25

<210> SEQ ID NO 357
<211> LENGTH: 27
<212> TYPE: DNA
<213> ORGANISM: Artificial sequence
<220> FEATURE:
<223> OTHER INFORMATION: Synthetic sequence: Probe suitable for detection of genetic variations associated with known erythrocyte antigens, and useful for genotyping for blood groups

<400> SEQUENCE: 357
taccgtcgga gccggcaatg gcatgtg 27

<210> SEQ ID NO 358
<211> LENGTH: 27
<212> TYPE: DNA
<213> ORGANISM: Artificial sequence
<220> FEATURE:
<223> OTHER INFORMATION: Synthetic sequence: Probe suitable for detection of genetic variations associated with known erythrocyte antigens, and useful for genotyping for blood groups

<400> SEQUENCE: 358
taccgtcgga gccagcaatg gcatgtg 27

<210> SEQ ID NO 359
<211> LENGTH: 25
<212> TYPE: DNA
<213> ORGANISM: Artificial sequence
<220> FEATURE:
<223> OTHER INFORMATION: Synthetic sequence: Probe suitable for detection of genetic variations associated with known erythrocyte antigens, and useful for genotyping for blood groups

<400> SEQUENCE: 359
acatgaacat gatgcacatc tacgt 25

<210> SEQ ID NO 360
<211> LENGTH: 25
<212> TYPE: DNA
<213> ORGANISM: Artificial sequence
<220> FEATURE:
<223> OTHER INFORMATION: Synthetic sequence: Probe suitable for detection of genetic variations associated with known erythrocyte antigens, and useful for genotyping for blood groups

<400> SEQUENCE: 360
acatgaacat gacgcacatc tacgt 25

<210> SEQ ID NO 361
<211> LENGTH: 27
<212> TYPE: DNA
<213> ORGANISM: Artificial sequence
<220> FEATURE:
<223> OTHER INFORMATION: Synthetic sequence: Probe suitable for detection of genetic variations associated with known erythrocyte antigens, and useful for genotyping for blood groups

<400> SEQUENCE: 361
cacatgaaca tgatgcacat ctacgtg 27

<210> SEQ ID NO 362
<211> LENGTH: 27
<212> TYPE: DNA
<213> ORGANISM: Artificial sequence
<220> FEATURE:
<223> OTHER INFORMATION: Synthetic sequence: Probe suitable for detection of genetic variations associated with known erythrocyte antigens, and useful for genotyping for blood groups

<400> SEQUENCE: 362
cacatgaaca tgacgcacat ctacgtg 27

<210> SEQ ID NO 363
<211> LENGTH: 25
<212> TYPE: DNA
<213> ORGANISM: Artificial sequence
<220> FEATURE:
<223> OTHER INFORMATION: Synthetic sequence: Probe suitable for detection of genetic variations associated with known erythrocyte antigens, and useful for genotyping for blood groups

<400> SEQUENCE: 363
tggtcatcac actgttcagg tattg 25

<210> SEQ ID NO 364
<211> LENGTH: 25
<212> TYPE: DNA
<213> ORGANISM: Artificial sequence
<220> FEATURE:
<223> OTHER INFORMATION: Synthetic sequence: Probe suitable for detection of genetic variations associated with known erythrocyte antigens, and useful for genotyping for blood groups

<400> SEQUENCE: 364
tggtcatcac accgttcagg tattg 25

<210> SEQ ID NO 365
<211> LENGTH: 23
<212> TYPE: DNA
<213> ORGANISM: Artificial sequence
<220> FEATURE:
<223> OTHER INFORMATION: Synthetic sequence: Probe suitable for detection of genetic variations associated with known erythrocyte antigens, and useful for genotyping for blood groups

<400> SEQUENCE: 365
ggtcatcaca ctgttcaggt att 23

<210> SEQ ID NO 366
<211> LENGTH: 23
<212> TYPE: DNA
<213> ORGANISM: Artificial sequence
<220> FEATURE:
<223> OTHER INFORMATION: Synthetic sequence: Probe suitable for detection of genetic variations associated with known erythrocyte antigens, and useful for genotyping for blood groups

<400> SEQUENCE: 366
ggtcatcaca ccgttcaggt att 23

<210> SEQ ID NO 367
<211> LENGTH: 21
<212> TYPE: DNA
<213> ORGANISM: Artificial sequence
<220> FEATURE:
<223> OTHER INFORMATION: Synthetic sequence: Probe suitable for detection of genetic variations associated with known erythrocyte antigens, and useful for genotyping for blood groups

<400> SEQUENCE: 367
gctgtgggta cctcgtgtca c 21

<210> SEQ ID NO 368
<211> LENGTH: 21
<212> TYPE: DNA
<213> ORGANISM: Artificial sequence
<220> FEATURE:
<223> OTHER INFORMATION: Synthetic sequence: Probe suitable for detection of genetic variations associated with known erythrocyte antigens, and useful for genotyping for blood groups

<400> SEQUENCE: 368
gctgtgggta tctcgtgtca c 21

<210> SEQ ID NO 369
<211> LENGTH: 23
<212> TYPE: DNA
<213> ORGANISM: Artificial sequence
<220> FEATURE:
<223> OTHER INFORMATION: Synthetic sequence: Probe suitable for detection of genetic variations associated with known erythrocyte antigens, and useful for genotyping for blood groups

<400> SEQUENCE: 369
ggctgtgggt acctcgtgtc acc 23

<210> SEQ ID NO 370
<211> LENGTH: 23
<212> TYPE: DNA
<213> ORGANISM: Artificial sequence
<220> FEATURE:
<223> OTHER INFORMATION: Synthetic sequence: Probe suitable for detection of genetic variations associated with known erythrocyte antigens, and useful for genotyping for blood groups

<400> SEQUENCE: 370
ggctgtgggt atctcgtgtc acc 23

<210> SEQ ID NO 371
<211> LENGTH: 25
<212> TYPE: DNA
<213> ORGANISM: Artificial sequence
<220> FEATURE:
<223> OTHER INFORMATION: Synthetic sequence: Probe suitable for detection of genetic variations associated with known erythrocyte antigens, and useful for genotyping for blood groups

<400> SEQUENCE: 371
agacagacta ccacatgaac atgat 25

<210> SEQ ID NO 372
<211> LENGTH: 25
<212> TYPE: DNA
<213> ORGANISM: Artificial sequence
<220> FEATURE:
<223> OTHER INFORMATION: Synthetic sequence: Probe suitable for detection of genetic variations associated with known erythrocyte antigens, and useful for genotyping for blood groups

<400> SEQUENCE: 372
agacagacta ccccatgaac atgat 25

<210> SEQ ID NO 373
<211> LENGTH: 23
<212> TYPE: DNA
<213> ORGANISM: Artificial sequence
<220> FEATURE:
<223> OTHER INFORMATION: Synthetic sequence: Probe suitable for detection of genetic variations associated with known erythrocyte antigens, and useful for genotyping for blood groups

<400> SEQUENCE: 373
gacagactac cacatgaaca tga 23

<210> SEQ ID NO 374
<211> LENGTH: 23
<212> TYPE: DNA
<213> ORGANISM: Artificial sequence
<220> FEATURE:
<223> OTHER INFORMATION: Synthetic sequence: Probe suitable for detection of genetic variations associated with known erythrocyte antigens, and useful for genotyping for blood groups

<400> SEQUENCE: 374
gacagactac cccatgaaca tga 23

<210> SEQ ID NO 375
<211> LENGTH: 25
<212> TYPE: DNA
<213> ORGANISM: Artificial sequence
<220> FEATURE:
<223> OTHER INFORMATION: Synthetic sequence: Probe suitable for detection of genetic variations associated with known erythrocyte antigens, and useful for genotyping for blood groups

<400> SEQUENCE: 375
ctgctctgct gagaagtcca atcga 25

<210> SEQ ID NO 376
<211> LENGTH: 25
<212> TYPE: DNA
<213> ORGANISM: Artificial sequence
<220> FEATURE:
<223> OTHER INFORMATION: Synthetic sequence: Probe suitable for detection of genetic variations associated with known erythrocyte antigens, and useful for genotyping for blood groups

<400> SEQUENCE: 376
ctgctctgct gaaaagtcca atcga 25

<210> SEQ ID NO 377
<211> LENGTH: 23
<212> TYPE: DNA
<213> ORGANISM: Artificial sequence
<220> FEATURE:
<223> OTHER INFORMATION: Synthetic sequence: Probe suitable for detection of genetic variations associated with known erythrocyte antigens, and useful for genotyping for blood groups

<400> SEQUENCE: 377
tgctctgctg agaagtccaa tcg 23

<210> SEQ ID NO 378
<211> LENGTH: 23
<212> TYPE: DNA
<213> ORGANISM: Artificial sequence
<220> FEATURE:
<223> OTHER INFORMATION: Synthetic sequence: Probe suitable for detection of genetic variations associated with known erythrocyte antigens, and useful for genotyping for blood groups

<400> SEQUENCE: 378
tgctctgctg aaaagtccaa tcg 23

<210> SEQ ID NO 379
<211> LENGTH: 25
<212> TYPE: DNA
<213> ORGANISM: Artificial sequence
<220> FEATURE:
<223> OTHER INFORMATION: Synthetic sequence: Probe suitable for detection of genetic variations associated with known erythrocyte antigens, and useful for genotyping for blood groups

<400> SEQUENCE: 379
tgggtacctc gtgtcacctg atccc 25

<210> SEQ ID NO 380
<211> LENGTH: 25
<212> TYPE: DNA
<213> ORGANISM: Artificial sequence
<220> FEATURE:
<223> OTHER INFORMATION: Synthetic sequence: Probe suitable for detection of genetic variations associated with known erythrocyte antigens, and useful for genotyping for blood groups

<400> SEQUENCE: 380
tgggtacctc gtatcacctg atccc 25

<210> SEQ ID NO 381
<211> LENGTH: 23
<212> TYPE: DNA
<213> ORGANISM: Artificial sequence
<220> FEATURE:
<223> OTHER INFORMATION: Synthetic sequence: Probe suitable for detection of genetic variations associated with known erythrocyte antigens, and useful for genotyping for blood groups

<400> SEQUENCE: 381
gggtacctcg tgtcacctga tcc 23

<210> SEQ ID NO 382
<211> LENGTH: 23
<212> TYPE: DNA
<213> ORGANISM: Artificial sequence
<220> FEATURE:
<223> OTHER INFORMATION: Synthetic sequence: Probe suitable for detection of genetic variations associated with known erythrocyte antigens, and useful for genotyping for blood groups

<400> SEQUENCE: 382
gggtacctcg tatcacctga tcc 23

<210> SEQ ID NO 383
<211> LENGTH: 25
<212> TYPE: DNA
<213> ORGANISM: Artificial sequence
<220> FEATURE:
<223> OTHER INFORMATION: Synthetic sequence: Probe suitable for detection of genetic variations associated with known erythrocyte antigens, and useful for genotyping for blood groups

<400> SEQUENCE: 383
ttggccaaga tctgaccgtg atggc 25

<210> SEQ ID NO 384
<211> LENGTH: 25
<212> TYPE: DNA
<213> ORGANISM: Artificial sequence
<220> FEATURE:
<223> OTHER INFORMATION: Synthetic sequence: Probe suitable for detection of genetic variations associated with known erythrocyte antigens, and useful for genotyping for blood groups

<400> SEQUENCE: 384
ttggccaaga tccgaccgtg atggc 25

<210> SEQ ID NO 385
<211> LENGTH: 27
<212> TYPE: DNA
<213> ORGANISM: Artificial sequence
<220> FEATURE:
<223> OTHER INFORMATION: Synthetic sequence: Probe suitable for detection of genetic variations associated with known erythrocyte antigens, and useful for genotyping for blood groups

<400> SEQUENCE: 385
gttggccaag atctgaccgt gatggcg 27

<210> SEQ ID NO 386
<211> LENGTH: 27
<212> TYPE: DNA
<213> ORGANISM: Artificial sequence
<220> FEATURE:
<223> OTHER INFORMATION: Synthetic sequence: Probe suitable for detection of genetic variations associated with known erythrocyte antigens, and useful for genotyping for blood groups

<400> SEQUENCE: 386
gttggccaag atccgaccgt gatggcg 27

<210> SEQ ID NO 387
<211> LENGTH: 25
<212> TYPE: DNA
<213> ORGANISM: Artificial sequence
<220> FEATURE:
<223> OTHER INFORMATION: Synthetic sequence: Probe suitable for detection of genetic variations associated with known erythrocyte antigens, and useful for genotyping for blood groups

<400> SEQUENCE: 387
cttgataccg tcggagccgg caatg 25

<210> SEQ ID NO 388
<211> LENGTH: 25
<212> TYPE: DNA
<213> ORGANISM: Artificial sequence
<220> FEATURE:
<223> OTHER INFORMATION: Synthetic sequence: Probe suitable for detection of genetic variations associated with known erythrocyte antigens, and useful for genotyping for blood groups

<400> SEQUENCE: 388
cttgataccg tcagagccgg caatg 25

<210> SEQ ID NO 389
<211> LENGTH: 27
<212> TYPE: DNA
<213> ORGANISM: Artificial sequence
<220> FEATURE:
<223> OTHER INFORMATION: Synthetic sequence: Probe suitable for detection of genetic variations associated with known erythrocyte antigens, and useful for genotyping for blood groups

<400> SEQUENCE: 389
gcttgatacc gtcggagccg gcaatgg 27

<210> SEQ ID NO 390
<211> LENGTH: 27
<212> TYPE: DNA
<213> ORGANISM: Artificial sequence
<220> FEATURE:
<223> OTHER INFORMATION: Synthetic sequence: Probe suitable for detection of genetic variations associated with known erythrocyte antigens, and useful for genotyping for blood groups

<400> SEQUENCE: 390
gcttgatacc gtcagagccg gcaatgg 27

<210> SEQ ID NO 391
<211> LENGTH: 25
<212> TYPE: DNA
<213> ORGANISM: Artificial sequence
<220> FEATURE:
<223> OTHER INFORMATION: Synthetic sequence: Probe suitable for detection of genetic variations associated with known erythrocyte antigens, and useful for genotyping for blood groups

<400> SEQUENCE: 391
ccggcaatgg catgtgggtc actgg 25

<210> SEQ ID NO 392
<211> LENGTH: 25

<212> TYPE: DNA
<213> ORGANISM: Artificial sequence
<220> FEATURE:
<223> OTHER INFORMATION: Synthetic sequence: Probe suitable for detection of genetic variations associated with known erythrocyte antigens, and useful for genotyping for blood groups

<400> SEQUENCE: 392
ccggcaatgg cacgtgggtc actgg 25

<210> SEQ ID NO 393
<211> LENGTH: 23
<212> TYPE: DNA
<213> ORGANISM: Artificial sequence
<220> FEATURE:
<223> OTHER INFORMATION: Synthetic sequence: Probe suitable for detection of genetic variations associated with known erythrocyte antigens, and useful for genotyping for blood groups

<400> SEQUENCE: 393
cggcaatggc atgtgggtca ctg 23

<210> SEQ ID NO 394
<211> LENGTH: 23
<212> TYPE: DNA
<213> ORGANISM: Artificial sequence
<220> FEATURE:
<223> OTHER INFORMATION: Synthetic sequence: Probe suitable for detection of genetic variations associated with known erythrocyte antigens, and useful for genotyping for blood groups

<400> SEQUENCE: 394
cggcaatggc acgtgggtca ctg 23

<210> SEQ ID NO 395
<211> LENGTH: 25
<212> TYPE: DNA
<213> ORGANISM: Artificial sequence
<220> FEATURE:
<223> OTHER INFORMATION: Synthetic sequence: Probe suitable for detection of genetic variations associated with known erythrocyte antigens, and useful for genotyping for blood groups

<400> SEQUENCE: 395
ataccgtcgg agccggcaat ggcat 25

<210> SEQ ID NO 396
<211> LENGTH: 25
<212> TYPE: DNA
<213> ORGANISM: Artificial sequence
<220> FEATURE:
<223> OTHER INFORMATION: Synthetic sequence: Probe suitable for detection of genetic variations associated with known erythrocyte antigens, and useful for genotyping for blood groups

<400> SEQUENCE: 396
ataccgtcgg agacggcaat ggcat 25

<210> SEQ ID NO 397
<211> LENGTH: 27
<212> TYPE: DNA
<213> ORGANISM: Artificial sequence
<220> FEATURE:
<223> OTHER INFORMATION: Synthetic sequence: Probe suitable for detection of genetic variations associated with known erythrocyte antigens, and useful for genotyping for blood groups

<400> SEQUENCE: 397
gccggcaatg gcatgtgggt cactggg 27

<210> SEQ ID NO 398
<211> LENGTH: 27
<212> TYPE: DNA
<213> ORGANISM: Artificial sequence
<220> FEATURE:
<223> OTHER INFORMATION: Synthetic sequence: Probe suitable for detection of genetic variations associated with known erythrocyte antigens, and useful for genotyping for blood groups

<400> SEQUENCE: 398
gccggcaatg gcacgtgggt cactggg 27

<210> SEQ ID NO 399
<211> LENGTH: 25
<212> TYPE: DNA
<213> ORGANISM: Artificial sequence
<220> FEATURE:
<223> OTHER INFORMATION: Synthetic sequence: Probe suitable for detection of genetic variations associated with known erythrocyte antigens, and useful for genotyping for blood groups

<400> SEQUENCE: 399
gcgtggctgt gggtacctcg tgtca 25

<210> SEQ ID NO 400
<211> LENGTH: 25
<212> TYPE: DNA
<213> ORGANISM: Artificial sequence
<220> FEATURE:
<223> OTHER INFORMATION: Synthetic sequence: Probe suitable for detection of genetic variations associated with known erythrocyte antigens, and useful for genotyping for blood groups

<400> SEQUENCE: 400
gcgtggctgt ggatacctcg tgtca 25

<210> SEQ ID NO 401
<211> LENGTH: 27
<212> TYPE: DNA
<213> ORGANISM: Artificial sequence
<220> FEATURE:
<223> OTHER INFORMATION: Synthetic sequence: Probe suitable for detection of genetic variations associated with known erythrocyte antigens, and useful for genotyping for blood groups

<400> SEQUENCE: 401
gataccgtcg gagccggcaa tggcatg 27

<210> SEQ ID NO 402
<211> LENGTH: 27
<212> TYPE: DNA
<213> ORGANISM: Artificial sequence
<220> FEATURE:
<223> OTHER INFORMATION: Synthetic sequence: Probe suitable for detection of genetic variations associated with known erythrocyte antigens, and useful for genotyping for blood groups

<400> SEQUENCE: 402
gataccgtcg gagacggcaa tggcatg 27

<210> SEQ ID NO 403
<211> LENGTH: 25
<212> TYPE: DNA
<213> ORGANISM: Artificial sequence
<220> FEATURE:
<223> OTHER INFORMATION: Synthetic sequence: Probe suitable for detection of genetic variations associated with known erythrocyte antigens, and useful for genotyping for blood groups

<400> SEQUENCE: 403
tgcagactta tgtgcacagt gcggt 25

<210> SEQ ID NO 404
<211> LENGTH: 25
<212> TYPE: DNA
<213> ORGANISM: Artificial sequence
<220> FEATURE:
<223> OTHER INFORMATION: Synthetic sequence: Probe suitable for detection of genetic variations associated with known erythrocyte antigens, and useful for genotyping for blood groups

<400> SEQUENCE: 404
tgcagactta tgggcacagt gcggt 25

<210> SEQ ID NO 405
<211> LENGTH: 23
<212> TYPE: DNA
<213> ORGANISM: Artificial sequence
<220> FEATURE:
<223> OTHER INFORMATION: Synthetic sequence: Probe suitable for detection of genetic variations associated with known erythrocyte antigens, and useful for genotyping for blood groups

<400> SEQUENCE: 405
gcagacttat gtgcacagtg cgg 23

<210> SEQ ID NO 406
<211> LENGTH: 23
<212> TYPE: DNA
<213> ORGANISM: Artificial sequence
<220> FEATURE:
<223> OTHER INFORMATION: Synthetic sequence: Probe suitable for detection of genetic variations associated with known erythrocyte antigens, and useful for genotyping for blood groups

<400> SEQUENCE: 406
gcagacttat gggcacagtg cgg 23

<210> SEQ ID NO 407
<211> LENGTH: 25
<212> TYPE: DNA
<213> ORGANISM: Artificial sequence
<220> FEATURE:
<223> OTHER INFORMATION: Synthetic sequence: Probe suitable for detection of genetic variations associated with known erythrocyte antigens, and useful for genotyping for blood groups

<400> SEQUENCE: 407
gcatttaaac aggtttgctc ctaaa 25

<210> SEQ ID NO 408
<211> LENGTH: 25
<212> TYPE: DNA
<213> ORGANISM: Artificial sequence
<220> FEATURE:
<223> OTHER INFORMATION: Synthetic sequence: Probe suitable for detection of genetic variations associated with known erythrocyte antigens, and useful for genotyping for blood groups

<400> SEQUENCE: 408
gcatttaaac agctttgctc ctaaa 25

<210> SEQ ID NO 409
<211> LENGTH: 27
<212> TYPE: DNA
<213> ORGANISM: Artificial sequence
<220> FEATURE:
<223> OTHER INFORMATION: Synthetic sequence: Probe suitable for detection of genetic variations associated with known erythrocyte antigens, and useful for genotyping for blood groups

<400> SEQUENCE: 409
tgcatttaaa caggtttgct cctaaat 27

<210> SEQ ID NO 410
<211> LENGTH: 27
<212> TYPE: DNA
<213> ORGANISM: Artificial sequence
<220> FEATURE:
<223> OTHER INFORMATION: Synthetic sequence: Probe suitable for detection of genetic variations associated with known erythrocyte antigens, and useful for genotyping for blood groups

<400> SEQUENCE: 410
tgcatttaaa cagctttgct cctaaat 27

<210> SEQ ID NO 411
<211> LENGTH: 25
<212> TYPE: DNA
<213> ORGANISM: Artificial sequence
<220> FEATURE:
<223> OTHER INFORMATION: Synthetic sequence: Probe suitable for detection of genetic variations associated with known erythrocyte antigens, and useful for genotyping for blood groups

<400> SEQUENCE: 411
acaggatgag ctctaagtac ccgcg 25

<210> SEQ ID NO 412
<211> LENGTH: 25
<212> TYPE: DNA
<213> ORGANISM: Artificial sequence
<220> FEATURE:
<223> OTHER INFORMATION: Synthetic sequence: Probe suitable for detection of genetic variations associated with known erythrocyte antigens, and useful for genotyping for blood groups

<400> SEQUENCE: 412
acaggatgag ctgtaagtac ccgcg 25

<210> SEQ ID NO 413
<211> LENGTH: 27
<212> TYPE: DNA
<213> ORGANISM: Artificial sequence
<220> FEATURE:
<223> OTHER INFORMATION: Synthetic sequence: Probe suitable for detection of genetic variations associated with known erythrocyte antigens, and useful for genotyping for blood groups

<400> SEQUENCE: 413
cacaggatga gctctaagta cccgcgg 27

<210> SEQ ID NO 414
<211> LENGTH: 27
<212> TYPE: DNA
<213> ORGANISM: Artificial sequence
<220> FEATURE:
<223> OTHER INFORMATION: Synthetic sequence: Probe suitable for detection of genetic variations associated with known erythrocyte antigens, and useful for genotyping for blood groups

<400> SEQUENCE: 414
cacaggatga gctgtaagta cccgcgg 27

<210> SEQ ID NO 415
<211> LENGTH: 25
<212> TYPE: DNA
<213> ORGANISM: Artificial sequence
<220> FEATURE:
<223> OTHER INFORMATION: Synthetic sequence: Probe suitable for detection of genetic variations associated with known erythrocyte antigens, and useful for genotyping for blood groups

<400> SEQUENCE: 415
tggaggtgac agctttaggc aacct 25

<210> SEQ ID NO 416
<211> LENGTH: 25
<212> TYPE: DNA
<213> ORGANISM: Artificial sequence
<220> FEATURE:
<223> OTHER INFORMATION: Synthetic sequence: Probe suitable for detection of genetic variations associated with known erythrocyte antigens, and useful for genotyping for blood groups

<400> SEQUENCE: 416
tggaggtgac agatttaggc aacct 25

<210> SEQ ID NO 417
<211> LENGTH: 23
<212> TYPE: DNA
<213> ORGANISM: Artificial sequence
<220> FEATURE:
<223> OTHER INFORMATION: Synthetic sequence: Probe suitable for detection of genetic variations associated with known erythrocyte antigens, and useful for genotyping for blood groups

<400> SEQUENCE: 417
ggaggtgaca gctttaggca acc 23

<210> SEQ ID NO 418
<211> LENGTH: 23
<212> TYPE: DNA
<213> ORGANISM: Artificial sequence
<220> FEATURE:
<223> OTHER INFORMATION: Synthetic sequence: Probe suitable for detection of genetic variations associated with known erythrocyte antigens, and useful for genotyping for blood groups

<400> SEQUENCE: 418
ggaggtgaca gatttaggca acc 23

<210> SEQ ID NO 419
<211> LENGTH: 25
<212> TYPE: DNA
<213> ORGANISM: Artificial sequence
<220> FEATURE:
<223> OTHER INFORMATION: Synthetic sequence: Probe suitable for detection of genetic variations associated with known erythrocyte antigens, and useful for genotyping for blood groups

<400> SEQUENCE: 419
tgggtctgct tggagagatc atcta 25

<210> SEQ ID NO 420
<211> LENGTH: 25
<212> TYPE: DNA
<213> ORGANISM: Artificial sequence
<220> FEATURE:
<223> OTHER INFORMATION: Synthetic sequence: Probe suitable for detection of genetic variations associated with known erythrocyte antigens, and useful for genotyping for blood groups

<400> SEQUENCE: 420
tgggtctgct tgaagagatc atcta 25

<210> SEQ ID NO 421
<211> LENGTH: 23
<212> TYPE: DNA
<213> ORGANISM: Artificial sequence
<220> FEATURE:
<223> OTHER INFORMATION: Synthetic sequence: Probe suitable for detection of genetic variations associated with known erythrocyte antigens, and useful for genotyping for blood groups

<400> SEQUENCE: 421
gggtctgctt ggagagatca tct 23

<210> SEQ ID NO 422
<211> LENGTH: 23
<212> TYPE: DNA
<213> ORGANISM: Artificial sequence
<220> FEATURE:
<223> OTHER INFORMATION: Synthetic sequence: Probe suitable for detection of genetic variations associated with known erythrocyte antigens, and useful for genotyping for blood groups

<400> SEQUENCE: 422
gggtctgctt gaagagatca tct 23

<210> SEQ ID NO 423
<211> LENGTH: 25
<212> TYPE: DNA
<213> ORGANISM: Artificial sequence
<220> FEATURE:
<223> OTHER INFORMATION: Synthetic sequence: Probe suitable for detection of genetic variations associated with known erythrocyte antigens, and useful for genotyping for blood groups

<400> SEQUENCE: 423
tcccccagta ttcggctggc cacca 25

<210> SEQ ID NO 424
<211> LENGTH: 25
<212> TYPE: DNA
<213> ORGANISM: Artificial sequence
<220> FEATURE:
<223> OTHER INFORMATION: Synthetic sequence: Probe suitable for detection of genetic variations associated with known erythrocyte antigens, and useful for genotyping for blood groups

<400> SEQUENCE: 424
tcccccagta tttggctggc cacca 25

<210> SEQ ID NO 425
<211> LENGTH: 27
<212> TYPE: DNA
<213> ORGANISM: Artificial sequence
<220> FEATURE:
<223> OTHER INFORMATION: Synthetic sequence: Probe suitable for detection of genetic variations associated with known erythrocyte antigens, and useful for genotyping for blood groups

<400> SEQUENCE: 425
ctcccccagt attcggctgg ccaccat 27

<210> SEQ ID NO 426
<211> LENGTH: 27
<212> TYPE: DNA
<213> ORGANISM: Artificial sequence
<220> FEATURE:
<223> OTHER INFORMATION: Synthetic sequence: Probe suitable for detection of genetic variations associated with known erythrocyte antigens, and useful for genotyping for blood groups

<400> SEQUENCE: 426
ctcccccagt atttggctgg ccaccat 27

<210> SEQ ID NO 427
<211> LENGTH: 25
<212> TYPE: DNA
<213> ORGANISM: Artificial sequence
<220> FEATURE:
<223> OTHER INFORMATION: Synthetic sequence: Probe suitable for detection of genetic variations associated with known erythrocyte antigens, and useful for genotyping for blood groups

<400> SEQUENCE: 427
tttgcagact tatgtgcaca gtgcg 25

<210> SEQ ID NO 428
<211> LENGTH: 25
<212> TYPE: DNA
<213> ORGANISM: Artificial sequence
<220> FEATURE:
<223> OTHER INFORMATION: Synthetic sequence: Probe suitable for detection of genetic variations associated with known erythrocyte antigens, and useful for genotyping for blood groups

<400> SEQUENCE: 428
tttgcagact taggtgcaca gtgcg 25

<210> SEQ ID NO 429
<211> LENGTH: 23
<212> TYPE: DNA
<213> ORGANISM: Artificial sequence
<220> FEATURE:
<223> OTHER INFORMATION: Synthetic sequence: Probe suitable for detection of genetic variations associated with known erythrocyte antigens, and useful for genotyping for blood groups

<400> SEQUENCE: 429
ttgcagactt atgtgcacag tgc 23

<210> SEQ ID NO 430
<211> LENGTH: 23
<212> TYPE: DNA
<213> ORGANISM: Artificial sequence
<220> FEATURE:
<223> OTHER INFORMATION: Synthetic sequence: Probe suitable for detection of genetic variations associated with known erythrocyte antigens, and useful for genotyping for blood groups

<400> SEQUENCE: 430
ttgcagactt aggtgcacag tgc 23

<210> SEQ ID NO 431
<211> LENGTH: 25
<212> TYPE: DNA
<213> ORGANISM: Artificial sequence
<220> FEATURE:
<223> OTHER INFORMATION: Synthetic sequence: Probe suitable for detection of genetic variations associated with known erythrocyte antigens, and useful for genotyping for blood groups

<400> SEQUENCE: 431
agttttctgg aaggtaagat ttttc 25

<210> SEQ ID NO 432
<211> LENGTH: 25

<212> TYPE: DNA
<213> ORGANISM: Artificial sequence
<220> FEATURE:
<223> OTHER INFORMATION: Synthetic sequence: Probe suitable for detection of genetic variations associated with known erythrocyte antigens, and useful for genotyping for blood groups

<400> SEQUENCE: 432
agttttctgg aaagtaagat ttttc 25

<210> SEQ ID NO 433
<211> LENGTH: 27
<212> TYPE: DNA
<213> ORGANISM: Artificial sequence
<220> FEATURE:
<223> OTHER INFORMATION: Synthetic sequence: Probe suitable for detection of genetic variations associated with known erythrocyte antigens, and useful for genotyping for blood groups

<400> SEQUENCE: 433
aagttttctg gaaggtaaga tttttca 27

<210> SEQ ID NO 434
<211> LENGTH: 27
<212> TYPE: DNA
<213> ORGANISM: Artificial sequence
<220> FEATURE:
<223> OTHER INFORMATION: Synthetic sequence: Probe suitable for detection of genetic variations associated with known erythrocyte antigens, and useful for genotyping for blood groups

<400> SEQUENCE: 434
aagttttctg gaaagtaaga tttttca 27

<210> SEQ ID NO 435
<211> LENGTH: 25
<212> TYPE: DNA
<213> ORGANISM: Artificial sequence
<220> FEATURE:
<223> OTHER INFORMATION: Synthetic sequence: Probe suitable for detection of genetic variations associated with known erythrocyte antigens, and useful for genotyping for blood groups

<400> SEQUENCE: 435
cctgcccctc tgggccctaa cactg 25

<210> SEQ ID NO 436
<211> LENGTH: 25
<212> TYPE: DNA
<213> ORGANISM: Artificial sequence
<220> FEATURE:
<223> OTHER INFORMATION: Synthetic sequence: Probe suitable for detection of genetic variations associated with known erythrocyte antigens, and useful for genotyping for blood groups

<400> SEQUENCE: 436
cctgcccctc tgagccctaa cactg 25

<210> SEQ ID NO 437
<211> LENGTH: 23
<212> TYPE: DNA
<213> ORGANISM: Artificial sequence
<220> FEATURE:
<223> OTHER INFORMATION: Synthetic sequence: Probe suitable for detection of genetic variations associated with known erythrocyte antigens, and useful for genotyping for blood groups

<400> SEQUENCE: 437
ctgcccctct gggccctaac act 23

<210> SEQ ID NO 438
<211> LENGTH: 23
<212> TYPE: DNA
<213> ORGANISM: Artificial sequence
<220> FEATURE:
<223> OTHER INFORMATION: Synthetic sequence: Probe suitable for detection of genetic variations associated with known erythrocyte antigens, and useful for genotyping for blood groups

<400> SEQUENCE: 438
ctgcccctct gagccctaac act 23

<210> SEQ ID NO 439
<211> LENGTH: 25
<212> TYPE: DNA
<213> ORGANISM: Artificial sequence
<220> FEATURE:
<223> OTHER INFORMATION: Synthetic sequence: Probe suitable for detection of genetic variations associated with known erythrocyte antigens, and useful for genotyping for blood groups

<400> SEQUENCE: 439
tccttagagg atcaaaaggg gctcg 25

<210> SEQ ID NO 440
<211> LENGTH: 25
<212> TYPE: DNA
<213> ORGANISM: Artificial sequence
<220> FEATURE:
<223> OTHER INFORMATION: Synthetic sequence: Probe suitable for detection of genetic variations associated with known erythrocyte antigens, and useful for genotyping for blood groups

<400> SEQUENCE: 440
tccttagagg attaaaaggg gctcg 25

<210> SEQ ID NO 441
<211> LENGTH: 23
<212> TYPE: DNA
<213> ORGANISM: Artificial sequence
<220> FEATURE:
<223> OTHER INFORMATION: Synthetic sequence: Probe suitable for detection of genetic variations associated with known erythrocyte antigens, and useful for genotyping for blood groups

<400> SEQUENCE: 441
ccttagagga tcaaaagggg ctc 23

<210> SEQ ID NO 442
<211> LENGTH: 23
<212> TYPE: DNA
<213> ORGANISM: Artificial sequence
<220> FEATURE:
<223> OTHER INFORMATION: Synthetic sequence: Probe suitable for detection of genetic variations associated with known erythrocyte antigens, and useful for genotyping for blood groups

<400> SEQUENCE: 442
ccttagagga ttaaaagggg ctc 23

<210> SEQ ID NO 443
<211> LENGTH: 25
<212> TYPE: DNA
<213> ORGANISM: Artificial sequence
<220> FEATURE:
<223> OTHER INFORMATION: Synthetic sequence: Probe suitable for detection of genetic variations associated with known erythrocyte antigens, and useful for genotyping for blood groups

<400> SEQUENCE: 443
tggtgtgcag tgggcaatcc tgctg 25

<210> SEQ ID NO 444
<211> LENGTH: 25
<212> TYPE: DNA
<213> ORGANISM: Artificial sequence
<220> FEATURE:
<223> OTHER INFORMATION: Synthetic sequence: Probe suitable for detection of genetic variations associated with known erythrocyte antigens, and useful for genotyping for blood groups

<400> SEQUENCE: 444
tggtgtgcag tgagcaatcc tgctg 25

<210> SEQ ID NO 445
<211> LENGTH: 23
<212> TYPE: DNA
<213> ORGANISM: Artificial sequence
<220> FEATURE:
<223> OTHER INFORMATION: Synthetic sequence: Probe suitable for detection of genetic variations associated with known erythrocyte antigens, and useful for genotyping for blood groups

<400> SEQUENCE: 445
ggtgtgcagt gggcaatcct gct 23

<210> SEQ ID NO 446
<211> LENGTH: 23
<212> TYPE: DNA
<213> ORGANISM: Artificial sequence
<220> FEATURE:
<223> OTHER INFORMATION: Synthetic sequence: Probe suitable for detection of genetic variations associated with known erythrocyte antigens, and useful for genotyping for blood groups

<400> SEQUENCE: 446
ggtgtgcagt gagcaatcct gct 23

<210> SEQ ID NO 447
<211> LENGTH: 25
<212> TYPE: DNA
<213> ORGANISM: Artificial sequence
<220> FEATURE:
<223> OTHER INFORMATION: Synthetic sequence: Probe suitable for detection of genetic variations associated with known erythrocyte antigens, and useful for genotyping for blood groups

<400> SEQUENCE: 447
aatatcttca acgtgagtca tggtg 25

<210> SEQ ID NO 448
<211> LENGTH: 25
<212> TYPE: DNA
<213> ORGANISM: Artificial sequence
<220> FEATURE:
<223> OTHER INFORMATION: Synthetic sequence: Probe suitable for detection of genetic variations associated with known erythrocyte antigens, and useful for genotyping for blood groups

<400> SEQUENCE: 448
aatatcttca acatgagtca tggtg 25

<210> SEQ ID NO 449
<211> LENGTH: 23
<212> TYPE: DNA
<213> ORGANISM: Artificial sequence
<220> FEATURE:
<223> OTHER INFORMATION: Synthetic sequence: Probe suitable for detection of genetic variations associated with known erythrocyte antigens, and useful for genotyping for blood groups

<400> SEQUENCE: 449
atatcttcaa cgtgagtcat ggt 23

<210> SEQ ID NO 450
<211> LENGTH: 23
<212> TYPE: DNA
<213> ORGANISM: Artificial sequence
<220> FEATURE:
<223> OTHER INFORMATION: Synthetic sequence: Probe suitable for detection of genetic variations associated with known erythrocyte antigens, and useful for genotyping for blood groups

<400> SEQUENCE: 450
atatcttcaa catgagtcat ggt 23

<210> SEQ ID NO 451
<211> LENGTH: 25
<212> TYPE: DNA
<213> ORGANISM: Artificial sequence
<220> FEATURE:
<223> OTHER INFORMATION: Synthetic sequence: Probe suitable for detection of genetic variations associated with known erythrocyte antigens, and useful for genotyping for blood groups

<400> SEQUENCE: 451
tttattgcag acagactacc acatg 25

<210> SEQ ID NO 452
<211> LENGTH: 25
<212> TYPE: DNA
<213> ORGANISM: Artificial sequence
<220> FEATURE:
<223> OTHER INFORMATION: Synthetic sequence: Probe suitable for detection of genetic variations associated with known erythrocyte antigens, and useful for genotyping for blood groups

<400> SEQUENCE: 452
tttattgcag actaccacat gaaca 25

<210> SEQ ID NO 453
<211> LENGTH: 23
<212> TYPE: DNA
<213> ORGANISM: Artificial sequence
<220> FEATURE:
<223> OTHER INFORMATION: Synthetic sequence: Probe suitable for detection of genetic variations associated with known erythrocyte antigens, and useful for genotyping for blood groups

<400> SEQUENCE: 453
ttattgcaga cagactacca cat 23

<210> SEQ ID NO 454
<211> LENGTH: 23
<212> TYPE: DNA
<213> ORGANISM: Artificial sequence
<220> FEATURE:
<223> OTHER INFORMATION: Synthetic sequence: Probe suitable for detection of genetic variations associated with known erythrocyte antigens, and useful for genotyping for blood groups

<400> SEQUENCE: 454
ttattgcaga ctaccacatg aac 23

<210> SEQ ID NO 455
<211> LENGTH: 23
<212> TYPE: DNA
<213> ORGANISM: Artificial sequence
<220> FEATURE:
<223> OTHER INFORMATION: Synthetic sequence: Probe suitable for detection of genetic variations associated with known erythrocyte antigens, and useful for genotyping for blood groups

<400> SEQUENCE: 455
ctggccccca ggcgccctct tct 23

<210> SEQ ID NO 456
<211> LENGTH: 23
<212> TYPE: DNA
<213> ORGANISM: Artificial sequence
<220> FEATURE:
<223> OTHER INFORMATION: Synthetic sequence: Probe suitable for detection of genetic variations associated with known erythrocyte antigens, and useful for genotyping for blood groups

<400> SEQUENCE: 456
ctggccccca gtcgccctct tct 23

<210> SEQ ID NO 457
<211> LENGTH: 21
<212> TYPE: DNA
<213> ORGANISM: Artificial sequence
<220> FEATURE:
<223> OTHER INFORMATION: Synthetic sequence: Probe suitable for detection of genetic variations associated with known erythrocyte antigens, and useful for genotyping for blood groups

<400> SEQUENCE: 457
tggcccccag gcgccctctt c 21

<210> SEQ ID NO 458
<211> LENGTH: 21
<212> TYPE: DNA
<213> ORGANISM: Artificial sequence
<220> FEATURE:
<223> OTHER INFORMATION: Synthetic sequence: Probe suitable for detection of genetic variations associated with known erythrocyte antigens, and useful for genotyping for blood groups

<400> SEQUENCE: 458
tggcccccag tcgccctctt c 21

<210> SEQ ID NO 459
<211> LENGTH: 25
<212> TYPE: DNA
<213> ORGANISM: Artificial sequence
<220> FEATURE:
<223> OTHER INFORMATION: Synthetic sequence: Probe suitable for detection of genetic variations associated with known erythrocyte antigens, and useful for genotyping for blood groups

<400> SEQUENCE: 459
aaggaagaat gccgtgttca acacc 25

<210> SEQ ID NO 460
<211> LENGTH: 25
<212> TYPE: DNA
<213> ORGANISM: Artificial sequence
<220> FEATURE:
<223> OTHER INFORMATION: Synthetic sequence: Probe suitable for detection of genetic variations associated with known erythrocyte antigens, and useful for genotyping for blood groups

<400> SEQUENCE: 460
aaggaagaat gcgtgttcaa cacct 25

<210> SEQ ID NO 461
<211> LENGTH: 23
<212> TYPE: DNA
<213> ORGANISM: Artificial sequence
<220> FEATURE:
<223> OTHER INFORMATION: Synthetic sequence: Probe suitable for detection of genetic variations associated with known erythrocyte antigens, and useful for genotyping for blood groups

<400> SEQUENCE: 461
aggaagaatg ccgtgttcaa cac 23

<210> SEQ ID NO 462
<211> LENGTH: 23
<212> TYPE: DNA
<213> ORGANISM: Artificial sequence
<220> FEATURE:
<223> OTHER INFORMATION: Synthetic sequence: Probe suitable for detection of genetic variations associated with known erythrocyte antigens, and useful for genotyping for blood groups

<400> SEQUENCE: 462
aggaagaatg cgtgttcaac acc 23

<210> SEQ ID NO 463
<211> LENGTH: 19
<212> TYPE: DNA
<213> ORGANISM: Artificial sequence
<220> FEATURE:
<223> OTHER INFORMATION: Synthetic sequence: Probe suitable for detection of genetic variations associated with known erythrocyte antigens, and useful for genotyping for blood groups

<400> SEQUENCE: 463
gcttgccatg gtgctgggt 19

<210> SEQ ID NO 464
<211> LENGTH: 19
<212> TYPE: DNA
<213> ORGANISM: Artificial sequence
<220> FEATURE:
<223> OTHER INFORMATION: Synthetic sequence: Probe suitable for detection of genetic variations associated with known erythrocyte antigens, and useful for genotyping for blood groups

<400> SEQUENCE: 464
gcttgccatt gtgctgggt 19

<210> SEQ ID NO 465
<211> LENGTH: 21
<212> TYPE: DNA
<213> ORGANISM: Artificial sequence
<220> FEATURE:
<223> OTHER INFORMATION: Synthetic sequence: Probe suitable for detection of genetic variations associated with known erythrocyte antigens, and useful for genotyping for blood groups

<400> SEQUENCE: 465
ggcttgccat ggtgctgggt c 21

<210> SEQ ID NO 466
<211> LENGTH: 21
<212> TYPE: DNA
<213> ORGANISM: Artificial sequence
<220> FEATURE:

<223> OTHER INFORMATION: Synthetic sequence: Probe suitable for detection of genetic variations associated with known erythrocyte antigens, and useful for genotyping for blood groups

<400> SEQUENCE: 466
ggcttgccat tgtgctgggt c 21

<210> SEQ ID NO 467
<211> LENGTH: 25
<212> TYPE: DNA
<213> ORGANISM: Artificial sequence
<220> FEATURE:
<223> OTHER INFORMATION: Synthetic sequence: Probe suitable for detection of genetic variations associated with known erythrocyte antigens, and useful for genotyping for blood groups

<400> SEQUENCE: 467
cttgtggctg ggctgatctc cgtcg 25

<210> SEQ ID NO 468
<211> LENGTH: 25
<212> TYPE: DNA
<213> ORGANISM: Artificial sequence
<220> FEATURE:
<223> OTHER INFORMATION: Synthetic sequence: Probe suitable for detection of genetic variations associated with known erythrocyte antigens, and useful for genotyping for blood groups

<400> SEQUENCE: 468
cttgtggctg ggggctctga tctcc 25

<210> SEQ ID NO 469
<211> LENGTH: 23
<212> TYPE: DNA
<213> ORGANISM: Artificial sequence
<220> FEATURE:
<223> OTHER INFORMATION: Synthetic sequence: Probe suitable for detection of genetic variations associated with known erythrocyte antigens, and useful for genotyping for blood groups

<400> SEQUENCE: 469
ttgtggctgg gctgatctcc gtc 23

<210> SEQ ID NO 470
<211> LENGTH: 23
<212> TYPE: DNA
<213> ORGANISM: Artificial sequence
<220> FEATURE:
<223> OTHER INFORMATION: Synthetic sequence: Probe suitable for detection of genetic variations associated with known erythrocyte antigens, and useful for genotyping for blood groups

<400> SEQUENCE: 470
ttgtggctgg gggctctgat ctc 23

<210> SEQ ID NO 471
<211> LENGTH: 25
<212> TYPE: DNA
<213> ORGANISM: Artificial sequence
<220> FEATURE:
<223> OTHER INFORMATION: Synthetic sequence: Probe suitable for detection of genetic variations associated with known erythrocyte antigens, and useful for genotyping for blood groups

<400> SEQUENCE: 471
agtacctgcc ggtaagaaac tagac 25

<210> SEQ ID NO 472

```
<211> LENGTH: 25
<212> TYPE: DNA
<213> ORGANISM: Artificial sequence
<220> FEATURE:
<223> OTHER INFORMATION: Synthetic sequence: Probe suitable for
      detection of genetic variations associated with known erythrocyte
      antigens, and useful for genotyping for blood groups

<400> SEQUENCE: 472

agtacctgcc ggaaactaga caact                                           25


<210> SEQ ID NO 473
<211> LENGTH: 23
<212> TYPE: DNA
<213> ORGANISM: Artificial sequence
<220> FEATURE:
<223> OTHER INFORMATION: Synthetic sequence: Probe suitable for
      detection of genetic variations associated with known erythrocyte
      antigens, and useful for genotyping for blood groups

<400> SEQUENCE: 473

gtacctgccg gtaagaaact aga                                             23


<210> SEQ ID NO 474
<211> LENGTH: 23
<212> TYPE: DNA
<213> ORGANISM: Artificial sequence
<220> FEATURE:
<223> OTHER INFORMATION: Synthetic sequence: Probe suitable for
      detection of genetic variations associated with known erythrocyte
      antigens, and useful for genotyping for blood groups

<400> SEQUENCE: 474

gtacctgccg gaaactagac aac                                             23


<210> SEQ ID NO 475
<211> LENGTH: 25
<212> TYPE: DNA
<213> ORGANISM: Artificial sequence
<220> FEATURE:
<223> OTHER INFORMATION: Synthetic sequence: Probe suitable for
      detection of genetic variations associated with known erythrocyte
      antigens, and useful for genotyping for blood groups

<400> SEQUENCE: 475

cttgtccaca ggggtgttgt aaccg                                           25


<210> SEQ ID NO 476
<211> LENGTH: 25
<212> TYPE: DNA
<213> ORGANISM: Artificial sequence
<220> FEATURE:
<223> OTHER INFORMATION: Synthetic sequence: Probe suitable for
      detection of genetic variations associated with known erythrocyte
      antigens, and useful for genotyping for blood groups

<400> SEQUENCE: 476

cttgtccaca ggtgtgttgt aaccg                                           25


<210> SEQ ID NO 477
<211> LENGTH: 23
<212> TYPE: DNA
<213> ORGANISM: Artificial sequence
<220> FEATURE:
<223> OTHER INFORMATION: Synthetic sequence: Probe suitable for
      detection of genetic variations associated with known erythrocyte
      antigens, and useful for genotyping for blood groups

<400> SEQUENCE: 477
```

ttgtccacag gggtgttgta acc 23

<210> SEQ ID NO 478
<211> LENGTH: 23
<212> TYPE: DNA
<213> ORGANISM: Artificial sequence
<220> FEATURE:
<223> OTHER INFORMATION: Synthetic sequence: Probe suitable for detection of genetic variations associated with known erythrocyte antigens, and useful for genotyping for blood groups

<400> SEQUENCE: 478
ttgtccacag gtgtgttgta acc 23

<210> SEQ ID NO 479
<211> LENGTH: 25
<212> TYPE: DNA
<213> ORGANISM: Artificial sequence
<220> FEATURE:
<223> OTHER INFORMATION: Synthetic sequence: Probe suitable for detection of genetic variations associated with known erythrocyte antigens, and useful for genotyping for blood groups

<400> SEQUENCE: 479
catcatgggc tacaacttca gcttg 25

<210> SEQ ID NO 480
<211> LENGTH: 25
<212> TYPE: DNA
<213> ORGANISM: Artificial sequence
<220> FEATURE:
<223> OTHER INFORMATION: Synthetic sequence: Probe suitable for detection of genetic variations associated with known erythrocyte antigens, and useful for genotyping for blood groups

<400> SEQUENCE: 480
catcatgggc tagaacttca gcttg 25

<210> SEQ ID NO 481
<211> LENGTH: 23
<212> TYPE: DNA
<213> ORGANISM: Artificial sequence
<220> FEATURE:
<223> OTHER INFORMATION: Synthetic sequence: Probe suitable for detection of genetic variations associated with known erythrocyte antigens, and useful for genotyping for blood groups

<400> SEQUENCE: 481
atcatgggct acaacttcag ctt 23

<210> SEQ ID NO 482
<211> LENGTH: 23
<212> TYPE: DNA
<213> ORGANISM: Artificial sequence
<220> FEATURE:
<223> OTHER INFORMATION: Synthetic sequence: Probe suitable for detection of genetic variations associated with known erythrocyte antigens, and useful for genotyping for blood groups

<400> SEQUENCE: 482
atcatgggct agaacttcag ctt 23

<210> SEQ ID NO 483
<211> LENGTH: 25
<212> TYPE: DNA
<213> ORGANISM: Artificial sequence
<220> FEATURE:
<223> OTHER INFORMATION: Synthetic sequence: Probe suitable for detection of genetic variations associated with known erythrocyte antigens, and useful for genotyping for blood groups

<400> SEQUENCE: 483
gtctcctgac aggtcagtgt gaggc 25

<210> SEQ ID NO 484
<211> LENGTH: 25
<212> TYPE: DNA
<213> ORGANISM: Artificial sequence
<220> FEATURE:
<223> OTHER INFORMATION: Synthetic sequence: Probe suitable for detection of genetic variations associated with known erythrocyte antigens, and useful for genotyping for blood groups

<400> SEQUENCE: 484
gtctcctgac agatcagtgt gaggc 25

<210> SEQ ID NO 485
<211> LENGTH: 23
<212> TYPE: DNA
<213> ORGANISM: Artificial sequence
<220> FEATURE:
<223> OTHER INFORMATION: Synthetic sequence: Probe suitable for detection of genetic variations associated with known erythrocyte antigens, and useful for genotyping for blood groups

<400> SEQUENCE: 485
tctcctgaca ggtcagtgtg agg 23

<210> SEQ ID NO 486
<211> LENGTH: 23
<212> TYPE: DNA
<213> ORGANISM: Artificial sequence
<220> FEATURE:
<223> OTHER INFORMATION: Synthetic sequence: Probe suitable for detection of genetic variations associated with known erythrocyte antigens, and useful for genotyping for blood groups

<400> SEQUENCE: 486
tctcctgaca gatcagtgtg agg 23

<210> SEQ ID NO 487
<211> LENGTH: 23
<212> TYPE: DNA
<213> ORGANISM: Artificial sequence
<220> FEATURE:
<223> OTHER INFORMATION: Synthetic sequence: Probe suitable for detection of genetic variations associated with known erythrocyte antigens, and useful for genotyping for blood groups

<400> SEQUENCE: 487
ggtcaacttg gcgcagttgg tgg 23

<210> SEQ ID NO 488
<211> LENGTH: 23
<212> TYPE: DNA
<213> ORGANISM: Artificial sequence
<220> FEATURE:
<223> OTHER INFORMATION: Synthetic sequence: Probe suitable for detection of genetic variations associated with known erythrocyte antigens, and useful for genotyping for blood groups

<400> SEQUENCE: 488
ggtcaacttg gtgcagttgg tgg 23

<210> SEQ ID NO 489
<211> LENGTH: 21
<212> TYPE: DNA

<213> ORGANISM: Artificial sequence
<220> FEATURE:
<223> OTHER INFORMATION: Synthetic sequence: Probe suitable for detection of genetic variations associated with known erythrocyte antigens, and useful for genotyping for blood groups

<400> SEQUENCE: 489
gtcaacttgg cgcagttggt g 21

<210> SEQ ID NO 490
<211> LENGTH: 21
<212> TYPE: DNA
<213> ORGANISM: Artificial sequence
<220> FEATURE:
<223> OTHER INFORMATION: Synthetic sequence: Probe suitable for detection of genetic variations associated with known erythrocyte antigens, and useful for genotyping for blood groups

<400> SEQUENCE: 490
gtcaacttgg tgcagttggt g 21

<210> SEQ ID NO 491
<211> LENGTH: 25
<212> TYPE: DNA
<213> ORGANISM: Artificial sequence
<220> FEATURE:
<223> OTHER INFORMATION: Synthetic sequence: Probe suitable for detection of genetic variations associated with known erythrocyte antigens, and useful for genotyping for blood groups

<400> SEQUENCE: 491
cagctttagg caacctgagg atggt 25

<210> SEQ ID NO 492
<211> LENGTH: 25
<212> TYPE: DNA
<213> ORGANISM: Artificial sequence
<220> FEATURE:
<223> OTHER INFORMATION: Synthetic sequence: Probe suitable for detection of genetic variations associated with known erythrocyte antigens, and useful for genotyping for blood groups

<400> SEQUENCE: 492
cagctttagg caccctgagg atggt 25

<210> SEQ ID NO 493
<211> LENGTH: 27
<212> TYPE: DNA
<213> ORGANISM: Artificial sequence
<220> FEATURE:
<223> OTHER INFORMATION: Synthetic sequence: Probe suitable for detection of genetic variations associated with known erythrocyte antigens, and useful for genotyping for blood groups

<400> SEQUENCE: 493
acagctttag gcaacctgag gatggtc 27

<210> SEQ ID NO 494
<211> LENGTH: 27
<212> TYPE: DNA
<213> ORGANISM: Artificial sequence
<220> FEATURE:
<223> OTHER INFORMATION: Synthetic sequence: Probe suitable for detection of genetic variations associated with known erythrocyte antigens, and useful for genotyping for blood groups

<400> SEQUENCE: 494
acagctttag gcaccctgag gatggtc 27

<210> SEQ ID NO 495
<211> LENGTH: 21
<212> TYPE: DNA
<213> ORGANISM: Artificial sequence
<220> FEATURE:
<223> OTHER INFORMATION: Synthetic sequence: Probe suitable for detection of genetic variations associated with known erythrocyte antigens, and useful for genotyping for blood groups

<400> SEQUENCE: 495
ctggccaagt ttcaactctg c 21

<210> SEQ ID NO 496
<211> LENGTH: 21
<212> TYPE: DNA
<213> ORGANISM: Artificial sequence
<220> FEATURE:
<223> OTHER INFORMATION: Synthetic sequence: Probe suitable for detection of genetic variations associated with known erythrocyte antigens, and useful for genotyping for blood groups

<400> SEQUENCE: 496
ctggccaagt gtcaactctg c 21

<210> SEQ ID NO 497
<211> LENGTH: 19
<212> TYPE: DNA
<213> ORGANISM: Artificial sequence
<220> FEATURE:
<223> OTHER INFORMATION: Synthetic sequence: Probe suitable for detection of genetic variations associated with known erythrocyte antigens, and useful for genotyping for blood groups

<400> SEQUENCE: 497
tggccaagtt tcaactctg 19

<210> SEQ ID NO 498
<211> LENGTH: 19
<212> TYPE: DNA
<213> ORGANISM: Artificial sequence
<220> FEATURE:
<223> OTHER INFORMATION: Synthetic sequence: Probe suitable for detection of genetic variations associated with known erythrocyte antigens, and useful for genotyping for blood groups

<400> SEQUENCE: 498
tggccaagtg tcaactctg 19

<210> SEQ ID NO 499
<211> LENGTH: 23
<212> TYPE: DNA
<213> ORGANISM: Artificial sequence
<220> FEATURE:
<223> OTHER INFORMATION: Synthetic sequence: Probe suitable for detection of genetic variations associated with known erythrocyte antigens, and useful for genotyping for blood groups

<400> SEQUENCE: 499
ggctgatctc cgtcggggga gcc 23

<210> SEQ ID NO 500
<211> LENGTH: 23
<212> TYPE: DNA
<213> ORGANISM: Artificial sequence
<220> FEATURE:
<223> OTHER INFORMATION: Synthetic sequence: Probe suitable for detection of genetic variations associated with known erythrocyte antigens, and useful for genotyping for blood groups

<400> SEQUENCE: 500
ggctgatctc catcggggga gcc 23

<210> SEQ ID NO 501
<211> LENGTH: 21
<212> TYPE: DNA
<213> ORGANISM: Artificial sequence
<220> FEATURE:
<223> OTHER INFORMATION: Synthetic sequence: Probe suitable for detection of genetic variations associated with known erythrocyte antigens, and useful for genotyping for blood groups

<400> SEQUENCE: 501
gctgatctcc gtcgggggag c 21

<210> SEQ ID NO 502
<211> LENGTH: 21
<212> TYPE: DNA
<213> ORGANISM: Artificial sequence
<220> FEATURE:
<223> OTHER INFORMATION: Synthetic sequence: Probe suitable for detection of genetic variations associated with known erythrocyte antigens, and useful for genotyping for blood groups

<400> SEQUENCE: 502
gctgatctcc atcgggggag c 21

<210> SEQ ID NO 503
<211> LENGTH: 25
<212> TYPE: DNA
<213> ORGANISM: Artificial sequence
<220> FEATURE:
<223> OTHER INFORMATION: Synthetic sequence: Probe suitable for detection of genetic variations associated with known erythrocyte antigens, and useful for genotyping for blood groups

<400> SEQUENCE: 503
ggggagccaa gtacctgccg gtaag 25

<210> SEQ ID NO 504
<211> LENGTH: 25
<212> TYPE: DNA
<213> ORGANISM: Artificial sequence
<220> FEATURE:
<223> OTHER INFORMATION: Synthetic sequence: Probe suitable for detection of genetic variations associated with known erythrocyte antigens, and useful for genotyping for blood groups

<400> SEQUENCE: 504
ggggagccaa gtgcctgccg gtaag 25

<210> SEQ ID NO 505
<211> LENGTH: 23
<212> TYPE: DNA
<213> ORGANISM: Artificial sequence
<220> FEATURE:
<223> OTHER INFORMATION: Synthetic sequence: Probe suitable for detection of genetic variations associated with known erythrocyte antigens, and useful for genotyping for blood groups

<400> SEQUENCE: 505
gggagccaag tacctgccgg taa 23

<210> SEQ ID NO 506
<211> LENGTH: 23
<212> TYPE: DNA
<213> ORGANISM: Artificial sequence
<220> FEATURE:

```
<223> OTHER INFORMATION: Synthetic sequence: Probe suitable for
      detection of genetic variations associated with known erythrocyte
      antigens, and useful for genotyping for blood groups

<400> SEQUENCE: 506

gggagccaag tgcctgccgg taa                                          23


<210> SEQ ID NO 507
<211> LENGTH: 21
<212> TYPE: DNA
<213> ORGANISM: Artificial sequence
<220> FEATURE:
<223> OTHER INFORMATION: Synthetic sequence: Probe suitable for
      detection of genetic variations associated with known erythrocyte
      antigens, and useful for genotyping for blood groups

<400> SEQUENCE: 507

gcacctcatg aggctaaata t                                            21


<210> SEQ ID NO 508
<211> LENGTH: 21
<212> TYPE: DNA
<213> ORGANISM: Artificial sequence
<220> FEATURE:
<223> OTHER INFORMATION: Synthetic sequence: Probe suitable for
      detection of genetic variations associated with known erythrocyte
      antigens, and useful for genotyping for blood groups

<400> SEQUENCE: 508

gcacctcatg tggctaaata t                                            21


<210> SEQ ID NO 509
<211> LENGTH: 23
<212> TYPE: DNA
<213> ORGANISM: Artificial sequence
<220> FEATURE:
<223> OTHER INFORMATION: Synthetic sequence: Probe suitable for
      detection of genetic variations associated with known erythrocyte
      antigens, and useful for genotyping for blood groups

<400> SEQUENCE: 509

agcacctcat gaggctaaat att                                          23


<210> SEQ ID NO 510
<211> LENGTH: 23
<212> TYPE: DNA
<213> ORGANISM: Artificial sequence
<220> FEATURE:
<223> OTHER INFORMATION: Synthetic sequence: Probe suitable for
      detection of genetic variations associated with known erythrocyte
      antigens, and useful for genotyping for blood groups

<400> SEQUENCE: 510

agcacctcat gtggctaaat att                                          23


<210> SEQ ID NO 511
<211> LENGTH: 25
<212> TYPE: DNA
<213> ORGANISM: Artificial sequence
<220> FEATURE:
<223> OTHER INFORMATION: Synthetic sequence: Probe suitable for
      detection of genetic variations associated with known erythrocyte
      antigens, and useful for genotyping for blood groups

<400> SEQUENCE: 511

aacatgatgc acatctacgt gttcg                                        25


<210> SEQ ID NO 512
```

<211> LENGTH: 25
<212> TYPE: DNA
<213> ORGANISM: Artificial sequence
<220> FEATURE:
<223> OTHER INFORMATION: Synthetic sequence: Probe suitable for detection of genetic variations associated with known erythrocyte antigens, and useful for genotyping for blood groups

<400> SEQUENCE: 512
aacctgaggc acttctacgt gttcg 25

<210> SEQ ID NO 513
<211> LENGTH: 23
<212> TYPE: DNA
<213> ORGANISM: Artificial sequence
<220> FEATURE:
<223> OTHER INFORMATION: Synthetic sequence: Probe suitable for detection of genetic variations associated with known erythrocyte antigens, and useful for genotyping for blood groups

<400> SEQUENCE: 513
acatgatgca catctacgtg ttc 23

<210> SEQ ID NO 514
<211> LENGTH: 23
<212> TYPE: DNA
<213> ORGANISM: Artificial sequence
<220> FEATURE:
<223> OTHER INFORMATION: Synthetic sequence: Probe suitable for detection of genetic variations associated with known erythrocyte antigens, and useful for genotyping for blood groups

<400> SEQUENCE: 514
acctgaggca cttctacgtg ttc 23

<210> SEQ ID NO 515
<211> LENGTH: 25
<212> TYPE: DNA
<213> ORGANISM: Artificial sequence
<220> FEATURE:
<223> OTHER INFORMATION: Synthetic sequence: Probe suitable for detection of genetic variations associated with known erythrocyte antigens, and useful for genotyping for blood groups

<400> SEQUENCE: 515
agccagttcc cttctgggaa ggtgg 25

<210> SEQ ID NO 516
<211> LENGTH: 25
<212> TYPE: DNA
<213> ORGANISM: Artificial sequence
<220> FEATURE:
<223> OTHER INFORMATION: Synthetic sequence: Probe suitable for detection of genetic variations associated with known erythrocyte antigens, and useful for genotyping for blood groups

<400> SEQUENCE: 516
agccagttcc ctcctgggaa ggtgg 25

<210> SEQ ID NO 517
<211> LENGTH: 27
<212> TYPE: DNA
<213> ORGANISM: Artificial sequence
<220> FEATURE:
<223> OTHER INFORMATION: Synthetic sequence: Probe suitable for detection of genetic variations associated with known erythrocyte antigens, and useful for genotyping for blood groups

<400> SEQUENCE: 517
gagccagttc ccttctggga aggtggt 27

<210> SEQ ID NO 518
<211> LENGTH: 27
<212> TYPE: DNA
<213> ORGANISM: Artificial sequence
<220> FEATURE:
<223> OTHER INFORMATION: Synthetic sequence: Probe suitable for detection of genetic variations associated with known erythrocyte antigens, and useful for genotyping for blood groups

<400> SEQUENCE: 518
gagccagttc cctcctggga aggtggt 27

<210> SEQ ID NO 519
<211> LENGTH: 23
<212> TYPE: DNA
<213> ORGANISM: Artificial sequence
<220> FEATURE:
<223> OTHER INFORMATION: Synthetic sequence: Probe suitable for detection of genetic variations associated with known erythrocyte antigens, and useful for genotyping for blood groups

<400> SEQUENCE: 519
cttagaggat caaaaggggc tcg 23

<210> SEQ ID NO 520
<211> LENGTH: 23
<212> TYPE: DNA
<213> ORGANISM: Artificial sequence
<220> FEATURE:
<223> OTHER INFORMATION: Synthetic sequence: Probe suitable for detection of genetic variations associated with known erythrocyte antigens, and useful for genotyping for blood groups

<400> SEQUENCE: 520
cttagaggat cgaaaggggc tcg 23

<210> SEQ ID NO 521
<211> LENGTH: 21
<212> TYPE: DNA
<213> ORGANISM: Artificial sequence
<220> FEATURE:
<223> OTHER INFORMATION: Synthetic sequence: Probe suitable for detection of genetic variations associated with known erythrocyte antigens, and useful for genotyping for blood groups

<400> SEQUENCE: 521
ttagaggatc aaaaggggct c 21

<210> SEQ ID NO 522
<211> LENGTH: 21
<212> TYPE: DNA
<213> ORGANISM: Artificial sequence
<220> FEATURE:
<223> OTHER INFORMATION: Synthetic sequence: Probe suitable for detection of genetic variations associated with known erythrocyte antigens, and useful for genotyping for blood groups

<400> SEQUENCE: 522
ttagaggatc gaaaggggct c 21

<210> SEQ ID NO 523
<211> LENGTH: 25
<212> TYPE: DNA
<213> ORGANISM: Artificial sequence
<220> FEATURE:
<223> OTHER INFORMATION: Synthetic sequence: Probe suitable for detection of genetic variations associated with known erythrocyte antigens, and useful for genotyping for blood groups

<400> SEQUENCE: 523
acccactatg acgcttcctt agagg 25

<210> SEQ ID NO 524
<211> LENGTH: 25
<212> TYPE: DNA
<213> ORGANISM: Artificial sequence
<220> FEATURE:
<223> OTHER INFORMATION: Synthetic sequence: Probe suitable for detection of genetic variations associated with known erythrocyte antigens, and useful for genotyping for blood groups

<400> SEQUENCE: 524
acccactatg acacttcctt agagg 25

<210> SEQ ID NO 525
<211> LENGTH: 27
<212> TYPE: DNA
<213> ORGANISM: Artificial sequence
<220> FEATURE:
<223> OTHER INFORMATION: Synthetic sequence: Probe suitable for detection of genetic variations associated with known erythrocyte antigens, and useful for genotyping for blood groups

<400> SEQUENCE: 525
tacccactat gacgcttcct tagagga 27

<210> SEQ ID NO 526
<211> LENGTH: 27
<212> TYPE: DNA
<213> ORGANISM: Artificial sequence
<220> FEATURE:
<223> OTHER INFORMATION: Synthetic sequence: Probe suitable for detection of genetic variations associated with known erythrocyte antigens, and useful for genotyping for blood groups

<400> SEQUENCE: 526
tacccactat gacacttcct tagagga 27

<210> SEQ ID NO 527
<211> LENGTH: 25
<212> TYPE: DNA
<213> ORGANISM: Artificial sequence
<220> FEATURE:
<223> OTHER INFORMATION: Synthetic sequence: Probe suitable for detection of genetic variations associated with known erythrocyte antigens, and useful for genotyping for blood groups

<400> SEQUENCE: 527
agtgtcaact ctcctctgct gagaa 25

<210> SEQ ID NO 528
<211> LENGTH: 25
<212> TYPE: DNA
<213> ORGANISM: Artificial sequence
<220> FEATURE:
<223> OTHER INFORMATION: Synthetic sequence: Probe suitable for detection of genetic variations associated with known erythrocyte antigens, and useful for genotyping for blood groups

<400> SEQUENCE: 528
agtgtcaact ctgctctgct gagaa 25

<210> SEQ ID NO 529
<211> LENGTH: 27
<212> TYPE: DNA

<213> ORGANISM: Artificial sequence
<220> FEATURE:
<223> OTHER INFORMATION: Synthetic sequence: Probe suitable for detection of genetic variations associated with known erythrocyte antigens, and useful for genotyping for blood groups

<400> SEQUENCE: 529
aagtgtcaac tctcctctgc tgagaag 27

<210> SEQ ID NO 530
<211> LENGTH: 27
<212> TYPE: DNA
<213> ORGANISM: Artificial sequence
<220> FEATURE:
<223> OTHER INFORMATION: Synthetic sequence: Probe suitable for detection of genetic variations associated with known erythrocyte antigens, and useful for genotyping for blood groups

<400> SEQUENCE: 530
aagtgtcaac tctgctctgc tgagaag 27

<210> SEQ ID NO 531
<211> LENGTH: 25
<212> TYPE: DNA
<213> ORGANISM: Artificial sequence
<220> FEATURE:
<223> OTHER INFORMATION: Synthetic sequence: Probe suitable for detection of genetic variations associated with known erythrocyte antigens, and useful for genotyping for blood groups

<400> SEQUENCE: 531
acctactatg ctctagcagt cagtg 25

<210> SEQ ID NO 532
<211> LENGTH: 25
<212> TYPE: DNA
<213> ORGANISM: Artificial sequence
<220> FEATURE:
<223> OTHER INFORMATION: Synthetic sequence: Probe suitable for detection of genetic variations associated with known erythrocyte antigens, and useful for genotyping for blood groups

<400> SEQUENCE: 532
acctactatg ctgtagcagt cagtg 25

<210> SEQ ID NO 533
<211> LENGTH: 27
<212> TYPE: DNA
<213> ORGANISM: Artificial sequence
<220> FEATURE:
<223> OTHER INFORMATION: Synthetic sequence: Probe suitable for detection of genetic variations associated with known erythrocyte antigens, and useful for genotyping for blood groups

<400> SEQUENCE: 533
cacctactat gctctagcag tcagtgt 27

<210> SEQ ID NO 534
<211> LENGTH: 27
<212> TYPE: DNA
<213> ORGANISM: Artificial sequence
<220> FEATURE:
<223> OTHER INFORMATION: Synthetic sequence: Probe suitable for detection of genetic variations associated with known erythrocyte antigens, and useful for genotyping for blood groups

<400> SEQUENCE: 534
cacctactat gctgtagcag tcagtgt 27

<210> SEQ ID NO 535
<211> LENGTH: 25
<212> TYPE: DNA
<213> ORGANISM: Artificial sequence
<220> FEATURE:
<223> OTHER INFORMATION: Synthetic sequence: Probe suitable for detection of genetic variations associated with known erythrocyte antigens, and useful for genotyping for blood groups

<400> SEQUENCE: 535
ttcagcttgc tgggtcttgc ttgga 25

<210> SEQ ID NO 536
<211> LENGTH: 25
<212> TYPE: DNA
<213> ORGANISM: Artificial sequence
<220> FEATURE:
<223> OTHER INFORMATION: Synthetic sequence: Probe suitable for detection of genetic variations associated with known erythrocyte antigens, and useful for genotyping for blood groups

<400> SEQUENCE: 536
ttcagcttgc tgtgtcttgc ttgga 25

<210> SEQ ID NO 537
<211> LENGTH: 27
<212> TYPE: DNA
<213> ORGANISM: Artificial sequence
<220> FEATURE:
<223> OTHER INFORMATION: Synthetic sequence: Probe suitable for detection of genetic variations associated with known erythrocyte antigens, and useful for genotyping for blood groups

<400> SEQUENCE: 537
cttcagcttg ctgggtcttg cttggag 27

<210> SEQ ID NO 538
<211> LENGTH: 27
<212> TYPE: DNA
<213> ORGANISM: Artificial sequence
<220> FEATURE:
<223> OTHER INFORMATION: Synthetic sequence: Probe suitable for detection of genetic variations associated with known erythrocyte antigens, and useful for genotyping for blood groups

<400> SEQUENCE: 538
cttcagcttg ctgtgtcttg cttggag 27

<210> SEQ ID NO 539
<211> LENGTH: 25
<212> TYPE: DNA
<213> ORGANISM: Artificial sequence
<220> FEATURE:
<223> OTHER INFORMATION: Synthetic sequence: Probe suitable for detection of genetic variations associated with known erythrocyte antigens, and useful for genotyping for blood groups

<400> SEQUENCE: 539
agaagtctca gcattcggtt aaagt 25

<210> SEQ ID NO 540
<211> LENGTH: 25
<212> TYPE: DNA
<213> ORGANISM: Artificial sequence
<220> FEATURE:
<223> OTHER INFORMATION: Synthetic sequence: Probe suitable for detection of genetic variations associated with known erythrocyte antigens, and useful for genotyping for blood groups

<400> SEQUENCE: 540
agaagtctca gcgttcggtt aaagt 25

<210> SEQ ID NO 541
<211> LENGTH: 27
<212> TYPE: DNA
<213> ORGANISM: Artificial sequence
<220> FEATURE:
<223> OTHER INFORMATION: Synthetic sequence: Probe suitable for detection of genetic variations associated with known erythrocyte antigens, and useful for genotyping for blood groups

<400> SEQUENCE: 541
cagaagtctc agcattcggt taaagtt 27

<210> SEQ ID NO 542
<211> LENGTH: 27
<212> TYPE: DNA
<213> ORGANISM: Artificial sequence
<220> FEATURE:
<223> OTHER INFORMATION: Synthetic sequence: Probe suitable for detection of genetic variations associated with known erythrocyte antigens, and useful for genotyping for blood groups

<400> SEQUENCE: 542
cagaagtctc agcgttcggt taaagtt 27

<210> SEQ ID NO 543
<211> LENGTH: 25
<212> TYPE: DNA
<213> ORGANISM: Artificial sequence
<220> FEATURE:
<223> OTHER INFORMATION: Synthetic sequence: Probe suitable for detection of genetic variations associated with known erythrocyte antigens, and useful for genotyping for blood groups

<400> SEQUENCE: 543
aactttaacc gaacgctgag acttc 25

<210> SEQ ID NO 544
<211> LENGTH: 25
<212> TYPE: DNA
<213> ORGANISM: Artificial sequence
<220> FEATURE:
<223> OTHER INFORMATION: Synthetic sequence: Probe suitable for detection of genetic variations associated with known erythrocyte antigens, and useful for genotyping for blood groups

<400> SEQUENCE: 544
aactttaacc gatcgctgag acttc 25

<210> SEQ ID NO 545
<211> LENGTH: 27
<212> TYPE: DNA
<213> ORGANISM: Artificial sequence
<220> FEATURE:
<223> OTHER INFORMATION: Synthetic sequence: Probe suitable for detection of genetic variations associated with known erythrocyte antigens, and useful for genotyping for blood groups

<400> SEQUENCE: 545
aaactttaac cgaacgctga gacttct 27

<210> SEQ ID NO 546
<211> LENGTH: 27
<212> TYPE: DNA
<213> ORGANISM: Artificial sequence
<220> FEATURE:

<223> OTHER INFORMATION: Synthetic sequence: Probe suitable for
      detection of genetic variations associated with known erythrocyte
      antigens, and useful for genotyping for blood groups

<400> SEQUENCE: 546
aaactttaac cgatcgctga gacttct 27

<210> SEQ ID NO 547
<211> LENGTH: 25
<212> TYPE: DNA
<213> ORGANISM: Artificial sequence
<220> FEATURE:
<223> OTHER INFORMATION: Synthetic sequence: Probe suitable for
      detection of genetic variations associated with known erythrocyte
      antigens, and useful for genotyping for blood groups

<400> SEQUENCE: 547
actggaacag ccatgaagtg atgga 25

<210> SEQ ID NO 548
<211> LENGTH: 25
<212> TYPE: DNA
<213> ORGANISM: Artificial sequence
<220> FEATURE:
<223> OTHER INFORMATION: Synthetic sequence: Probe suitable for
      detection of genetic variations associated with known erythrocyte
      antigens, and useful for genotyping for blood groups

<400> SEQUENCE: 548
actggaacag ccgtgaagtg atgga 25

<210> SEQ ID NO 549
<211> LENGTH: 27
<212> TYPE: DNA
<213> ORGANISM: Artificial sequence
<220> FEATURE:
<223> OTHER INFORMATION: Synthetic sequence: Probe suitable for
      detection of genetic variations associated with known erythrocyte
      antigens, and useful for genotyping for blood groups

<400> SEQUENCE: 549
aactggaaca gccatgaagt gatggag 27

<210> SEQ ID NO 550
<211> LENGTH: 27
<212> TYPE: DNA
<213> ORGANISM: Artificial sequence
<220> FEATURE:
<223> OTHER INFORMATION: Synthetic sequence: Probe suitable for
      detection of genetic variations associated with known erythrocyte
      antigens, and useful for genotyping for blood groups

<400> SEQUENCE: 550
aactggaaca gccgtgaagt gatggag 27

<210> SEQ ID NO 551
<211> LENGTH: 25
<212> TYPE: DNA
<213> ORGANISM: Artificial sequence
<220> FEATURE:
<223> OTHER INFORMATION: Synthetic sequence: Probe suitable for
      detection of genetic variations associated with known erythrocyte
      antigens, and useful for genotyping for blood groups

<400> SEQUENCE: 551
aactggaaca gccgtgaagt gatgg 25

<210> SEQ ID NO 552

<211> LENGTH: 25
<212> TYPE: DNA
<213> ORGANISM: Artificial sequence
<220> FEATURE:
<223> OTHER INFORMATION: Synthetic sequence: Probe suitable for detection of genetic variations associated with known erythrocyte antigens, and useful for genotyping for blood groups

<400> SEQUENCE: 552
aactggaaca gctgtgaagt gatgg 25

<210> SEQ ID NO 553
<211> LENGTH: 27
<212> TYPE: DNA
<213> ORGANISM: Artificial sequence
<220> FEATURE:
<223> OTHER INFORMATION: Synthetic sequence: Probe suitable for detection of genetic variations associated with known erythrocyte antigens, and useful for genotyping for blood groups

<400> SEQUENCE: 553
aaactggaac agccgtgaag tgatgga 27

<210> SEQ ID NO 554
<211> LENGTH: 27
<212> TYPE: DNA
<213> ORGANISM: Artificial sequence
<220> FEATURE:
<223> OTHER INFORMATION: Synthetic sequence: Probe suitable for detection of genetic variations associated with known erythrocyte antigens, and useful for genotyping for blood groups

<400> SEQUENCE: 554
aaactggaac agctgtgaag tgatgga 27

<210> SEQ ID NO 555
<211> LENGTH: 23
<212> TYPE: DNA
<213> ORGANISM: Artificial sequence
<220> FEATURE:
<223> OTHER INFORMATION: Synthetic sequence: Probe suitable for detection of genetic variations associated with known erythrocyte antigens, and useful for genotyping for blood groups

<400> SEQUENCE: 555
tgggggctgc cccgcctgtg aca 23

<210> SEQ ID NO 556
<211> LENGTH: 23
<212> TYPE: DNA
<213> ORGANISM: Artificial sequence
<220> FEATURE:
<223> OTHER INFORMATION: Synthetic sequence: Probe suitable for detection of genetic variations associated with known erythrocyte antigens, and useful for genotyping for blood groups

<400> SEQUENCE: 556
tgggggctgc ctcgcctgtg aca 23

<210> SEQ ID NO 557
<211> LENGTH: 21
<212> TYPE: DNA
<213> ORGANISM: Artificial sequence
<220> FEATURE:
<223> OTHER INFORMATION: Synthetic sequence: Probe suitable for detection of genetic variations associated with known erythrocyte antigens, and useful for genotyping for blood groups

<400> SEQUENCE: 557
gggggctgcc ccgcctgtga c 21

<210> SEQ ID NO 558
<211> LENGTH: 21
<212> TYPE: DNA
<213> ORGANISM: Artificial sequence
<220> FEATURE:
<223> OTHER INFORMATION: Synthetic sequence: Probe suitable for detection of genetic variations associated with known erythrocyte antigens, and useful for genotyping for blood groups

<400> SEQUENCE: 558
gggggctgcc tcgcctgtga c 21

<210> SEQ ID NO 559
<211> LENGTH: 25
<212> TYPE: DNA
<213> ORGANISM: Artificial sequence
<220> FEATURE:
<223> OTHER INFORMATION: Synthetic sequence: Probe suitable for detection of genetic variations associated with known erythrocyte antigens, and useful for genotyping for blood groups

<400> SEQUENCE: 559
aagatcatgt ggctctgcag aaagt 25

<210> SEQ ID NO 560
<211> LENGTH: 25
<212> TYPE: DNA
<213> ORGANISM: Artificial sequence
<220> FEATURE:
<223> OTHER INFORMATION: Synthetic sequence: Probe suitable for detection of genetic variations associated with known erythrocyte antigens, and useful for genotyping for blood groups

<400> SEQUENCE: 560
aagatcatgt ggttctgcag aaagt 25

<210> SEQ ID NO 561
<211> LENGTH: 27
<212> TYPE: DNA
<213> ORGANISM: Artificial sequence
<220> FEATURE:
<223> OTHER INFORMATION: Synthetic sequence: Probe suitable for detection of genetic variations associated with known erythrocyte antigens, and useful for genotyping for blood groups

<400> SEQUENCE: 561
taagatcatg tggctctgca gaaagtc 27

<210> SEQ ID NO 562
<211> LENGTH: 27
<212> TYPE: DNA
<213> ORGANISM: Artificial sequence
<220> FEATURE:
<223> OTHER INFORMATION: Synthetic sequence: Probe suitable for detection of genetic variations associated with known erythrocyte antigens, and useful for genotyping for blood groups

<400> SEQUENCE: 562
taagatcatg tggttctgca gaaagtc 27

<210> SEQ ID NO 563
<211> LENGTH: 25
<212> TYPE: DNA
<213> ORGANISM: Artificial sequence
<220> FEATURE:
<223> OTHER INFORMATION: Synthetic sequence: Probe suitable for detection of genetic variations associated with known erythrocyte antigens, and useful for genotyping for blood groups

<400> SEQUENCE: 563
gccccatttg aggacatcta ctttg 25

<210> SEQ ID NO 564
<211> LENGTH: 25
<212> TYPE: DNA
<213> ORGANISM: Artificial sequence
<220> FEATURE:
<223> OTHER INFORMATION: Synthetic sequence: Probe suitable for detection of genetic variations associated with known erythrocyte antigens, and useful for genotyping for blood groups

<400> SEQUENCE: 564
gccccatttg agaacatcta ctttg 25

<210> SEQ ID NO 565
<211> LENGTH: 23
<212> TYPE: DNA
<213> ORGANISM: Artificial sequence
<220> FEATURE:
<223> OTHER INFORMATION: Synthetic sequence: Probe suitable for detection of genetic variations associated with known erythrocyte antigens, and useful for genotyping for blood groups

<400> SEQUENCE: 565
ccccatttga ggacatctac ttt 23

<210> SEQ ID NO 566
<211> LENGTH: 23
<212> TYPE: DNA
<213> ORGANISM: Artificial sequence
<220> FEATURE:
<223> OTHER INFORMATION: Synthetic sequence: Probe suitable for detection of genetic variations associated with known erythrocyte antigens, and useful for genotyping for blood groups

<400> SEQUENCE: 566
ccccatttga gaacatctac ttt 23

<210> SEQ ID NO 567
<211> LENGTH: 25
<212> TYPE: DNA
<213> ORGANISM: Artificial sequence
<220> FEATURE:
<223> OTHER INFORMATION: Synthetic sequence: Probe suitable for detection of genetic variations associated with known erythrocyte antigens, and useful for genotyping for blood groups

<400> SEQUENCE: 567
tcttgcccca caggtcatta atagc 25

<210> SEQ ID NO 568
<211> LENGTH: 25
<212> TYPE: DNA
<213> ORGANISM: Artificial sequence
<220> FEATURE:
<223> OTHER INFORMATION: Synthetic sequence: Probe suitable for detection of genetic variations associated with known erythrocyte antigens, and useful for genotyping for blood groups

<400> SEQUENCE: 568
tcttgcccca caagtcatta atagc 25

<210> SEQ ID NO 569
<211> LENGTH: 25
<212> TYPE: DNA

<213> ORGANISM: Artificial sequence
<220> FEATURE:
<223> OTHER INFORMATION: Synthetic sequence: Probe suitable for detection of genetic variations associated with known erythrocyte antigens, and useful for genotyping for blood groups

<400> SEQUENCE: 569
gctattaatg acctgtgggg caaga 25

<210> SEQ ID NO 570
<211> LENGTH: 25
<212> TYPE: DNA
<213> ORGANISM: Artificial sequence
<220> FEATURE:
<223> OTHER INFORMATION: Synthetic sequence: Probe suitable for detection of genetic variations associated with known erythrocyte antigens, and useful for genotyping for blood groups

<400> SEQUENCE: 570
gctattaatg acttgtgggg caaga 25

<210> SEQ ID NO 571
<211> LENGTH: 25
<212> TYPE: DNA
<213> ORGANISM: Artificial sequence
<220> FEATURE:
<223> OTHER INFORMATION: Synthetic sequence: Probe suitable for detection of genetic variations associated with known erythrocyte antigens, and useful for genotyping for blood groups

<400> SEQUENCE: 571
ggtttcaaca gctctctggc ctgca 25

<210> SEQ ID NO 572
<211> LENGTH: 25
<212> TYPE: DNA
<213> ORGANISM: Artificial sequence
<220> FEATURE:
<223> OTHER INFORMATION: Synthetic sequence: Probe suitable for detection of genetic variations associated with known erythrocyte antigens, and useful for genotyping for blood groups

<400> SEQUENCE: 572
ggtttcaaca gccctctggc ctgca 25

<210> SEQ ID NO 573
<211> LENGTH: 27
<212> TYPE: DNA
<213> ORGANISM: Artificial sequence
<220> FEATURE:
<223> OTHER INFORMATION: Synthetic sequence: Probe suitable for detection of genetic variations associated with known erythrocyte antigens, and useful for genotyping for blood groups

<400> SEQUENCE: 573
gggtttcaac agctctctgg cctgcat 27

<210> SEQ ID NO 574
<211> LENGTH: 27
<212> TYPE: DNA
<213> ORGANISM: Artificial sequence
<220> FEATURE:
<223> OTHER INFORMATION: Synthetic sequence: Probe suitable for detection of genetic variations associated with known erythrocyte antigens, and useful for genotyping for blood groups

<400> SEQUENCE: 574
gggtttcaac agccctctgg cctgcat 27

<210> SEQ ID NO 575
<211> LENGTH: 25
<212> TYPE: DNA
<213> ORGANISM: Artificial sequence
<220> FEATURE:
<223> OTHER INFORMATION: Synthetic sequence: Probe suitable for detection of genetic variations associated with known erythrocyte antigens, and useful for genotyping for blood groups

<400> SEQUENCE: 575
atggagacta tggtgccaac ctgga 25

<210> SEQ ID NO 576
<211> LENGTH: 25
<212> TYPE: DNA
<213> ORGANISM: Artificial sequence
<220> FEATURE:
<223> OTHER INFORMATION: Synthetic sequence: Probe suitable for detection of genetic variations associated with known erythrocyte antigens, and useful for genotyping for blood groups

<400> SEQUENCE: 576
atggagacta tgatgccaac ctgga 25

<210> SEQ ID NO 577
<211> LENGTH: 27
<212> TYPE: DNA
<213> ORGANISM: Artificial sequence
<220> FEATURE:
<223> OTHER INFORMATION: Synthetic sequence: Probe suitable for detection of genetic variations associated with known erythrocyte antigens, and useful for genotyping for blood groups

<400> SEQUENCE: 577
gatggagact atggtgccaa cctggaa 27

<210> SEQ ID NO 578
<211> LENGTH: 27
<212> TYPE: DNA
<213> ORGANISM: Artificial sequence
<220> FEATURE:
<223> OTHER INFORMATION: Synthetic sequence: Probe suitable for detection of genetic variations associated with known erythrocyte antigens, and useful for genotyping for blood groups

<400> SEQUENCE: 578
gatggagact atgatgccaa cctggaa 27

<210> SEQ ID NO 579
<211> LENGTH: 25
<212> TYPE: DNA
<213> ORGANISM: Artificial sequence
<220> FEATURE:
<223> OTHER INFORMATION: Synthetic sequence: Probe suitable for detection of genetic variations associated with known erythrocyte antigens, and useful for genotyping for blood groups

<400> SEQUENCE: 579
ccttggctct tatcttggaa gcaca 25

<210> SEQ ID NO 580
<211> LENGTH: 25
<212> TYPE: DNA
<213> ORGANISM: Artificial sequence
<220> FEATURE:
<223> OTHER INFORMATION: Synthetic sequence: Probe suitable for detection of genetic variations associated with known erythrocyte antigens, and useful for genotyping for blood groups

<400> SEQUENCE: 580
ccttggctct taccttggaa gcaca 25

<210> SEQ ID NO 581
<211> LENGTH: 23
<212> TYPE: DNA
<213> ORGANISM: Artificial sequence
<220> FEATURE:
<223> OTHER INFORMATION: Synthetic sequence: Probe suitable for detection of genetic variations associated with known erythrocyte antigens, and useful for genotyping for blood groups

<400> SEQUENCE: 581
cttggctctt atcttggaag cac 23

<210> SEQ ID NO 582
<211> LENGTH: 23
<212> TYPE: DNA
<213> ORGANISM: Artificial sequence
<220> FEATURE:
<223> OTHER INFORMATION: Synthetic sequence: Probe suitable for detection of genetic variations associated with known erythrocyte antigens, and useful for genotyping for blood groups

<400> SEQUENCE: 582
cttggctctt accttggaag cac 23

<210> SEQ ID NO 583
<211> LENGTH: 19
<212> TYPE: DNA
<213> ORGANISM: Artificial sequence
<220> FEATURE:
<223> OTHER INFORMATION: Synthetic sequence: Probe suitable for detection of genetic variations associated with known erythrocyte antigens, and useful for genotyping for blood groups

<400> SEQUENCE: 583
cctctcttcc gctggcagc 19

<210> SEQ ID NO 584
<211> LENGTH: 19
<212> TYPE: DNA
<213> ORGANISM: Artificial sequence
<220> FEATURE:
<223> OTHER INFORMATION: Synthetic sequence: Probe suitable for detection of genetic variations associated with known erythrocyte antigens, and useful for genotyping for blood groups

<400> SEQUENCE: 584
cctctcttcc gctggcagc 19

<210> SEQ ID NO 585
<211> LENGTH: 21
<212> TYPE: DNA
<213> ORGANISM: Artificial sequence
<220> FEATURE:
<223> OTHER INFORMATION: Synthetic sequence: Probe suitable for detection of genetic variations associated with known erythrocyte antigens, and useful for genotyping for blood groups

<400> SEQUENCE: 585
acctctcttc cgctggcagc t 21

<210> SEQ ID NO 586
<211> LENGTH: 21
<212> TYPE: DNA
<213> ORGANISM: Artificial sequence
<220> FEATURE:

<223> OTHER INFORMATION: Synthetic sequence: Probe suitable for detection of genetic variations associated with known erythrocyte antigens, and useful for genotyping for blood groups

<400> SEQUENCE: 586
acctctcttc cgctggcagc t 21

<210> SEQ ID NO 587
<211> LENGTH: 25
<212> TYPE: DNA
<213> ORGANISM: Artificial sequence
<220> FEATURE:
<223> OTHER INFORMATION: Synthetic sequence: Probe suitable for detection of genetic variations associated with known erythrocyte antigens, and useful for genotyping for blood groups

<400> SEQUENCE: 587
gcatatcagc atcaagtacc actgg 25

<210> SEQ ID NO 588
<211> LENGTH: 25
<212> TYPE: DNA
<213> ORGANISM: Artificial sequence
<220> FEATURE:
<223> OTHER INFORMATION: Synthetic sequence: Probe suitable for detection of genetic variations associated with known erythrocyte antigens, and useful for genotyping for blood groups

<400> SEQUENCE: 588
gcatatcagc attaagtacc actga 25

<210> SEQ ID NO 589
<211> LENGTH: 23
<212> TYPE: DNA
<213> ORGANISM: Artificial sequence
<220> FEATURE:
<223> OTHER INFORMATION: Synthetic sequence: Probe suitable for detection of genetic variations associated with known erythrocyte antigens, and useful for genotyping for blood groups

<400> SEQUENCE: 589
catatcagca tcaagtacca ctg 23

<210> SEQ ID NO 590
<211> LENGTH: 23
<212> TYPE: DNA
<213> ORGANISM: Artificial sequence
<220> FEATURE:
<223> OTHER INFORMATION: Synthetic sequence: Probe suitable for detection of genetic variations associated with known erythrocyte antigens, and useful for genotyping for blood groups

<400> SEQUENCE: 590
catatcagca ttaagtacca ctg 23

<210> SEQ ID NO 591
<211> LENGTH: 25
<212> TYPE: DNA
<213> ORGANISM: Artificial sequence
<220> FEATURE:
<223> OTHER INFORMATION: Synthetic sequence: Probe suitable for detection of genetic variations associated with known erythrocyte antigens, and useful for genotyping for blood groups

<400> SEQUENCE: 591
caagtaccac tggtgtggca atgca 25

<210> SEQ ID NO 592

<211> LENGTH: 25
<212> TYPE: DNA
<213> ORGANISM: Artificial sequence
<220> FEATURE:
<223> OTHER INFORMATION: Synthetic sequence: Probe suitable for detection of genetic variations associated with known erythrocyte antigens, and useful for genotyping for blood groups

<400> SEQUENCE: 592
taagtaccac tgaggtggca atgca 25

<210> SEQ ID NO 593
<211> LENGTH: 27
<212> TYPE: DNA
<213> ORGANISM: Artificial sequence
<220> FEATURE:
<223> OTHER INFORMATION: Synthetic sequence: Probe suitable for detection of genetic variations associated with known erythrocyte antigens, and useful for genotyping for blood groups

<400> SEQUENCE: 593
tcaagtacca ctggtgtggc aatgcac 27

<210> SEQ ID NO 594
<211> LENGTH: 27
<212> TYPE: DNA
<213> ORGANISM: Artificial sequence
<220> FEATURE:
<223> OTHER INFORMATION: Synthetic sequence: Probe suitable for detection of genetic variations associated with known erythrocyte antigens, and useful for genotyping for blood groups

<400> SEQUENCE: 594
ttaagtacca ctgaggtggc aatgcac 27

<210> SEQ ID NO 595
<211> LENGTH: 25
<212> TYPE: DNA
<213> ORGANISM: Artificial sequence
<220> FEATURE:
<223> OTHER INFORMATION: Synthetic sequence: Probe suitable for detection of genetic variations associated with known erythrocyte antigens, and useful for genotyping for blood groups

<400> SEQUENCE: 595
ttataggaga aatgggacaa cttgt 25

<210> SEQ ID NO 596
<211> LENGTH: 25
<212> TYPE: DNA
<213> ORGANISM: Artificial sequence
<220> FEATURE:
<223> OTHER INFORMATION: Synthetic sequence: Probe suitable for detection of genetic variations associated with known erythrocyte antigens, and useful for genotyping for blood groups

<400> SEQUENCE: 596
ttataggaga aacgggacaa cttgt 25

<210> SEQ ID NO 597
<211> LENGTH: 27
<212> TYPE: DNA
<213> ORGANISM: Artificial sequence
<220> FEATURE:
<223> OTHER INFORMATION: Synthetic sequence: Probe suitable for detection of genetic variations associated with known erythrocyte antigens, and useful for genotyping for blood groups

<400> SEQUENCE: 597
tttataggag aaatgggaca acttgtc 27

<210> SEQ ID NO 598
<211> LENGTH: 27
<212> TYPE: DNA
<213> ORGANISM: Artificial sequence
<220> FEATURE:
<223> OTHER INFORMATION: Synthetic sequence: Probe suitable for detection of genetic variations associated with known erythrocyte antigens, and useful for genotyping for blood groups

<400> SEQUENCE: 598
tttataggag aaacgggaca acttgtc 27

<210> SEQ ID NO 599
<211> LENGTH: 25
<212> TYPE: DNA
<213> ORGANISM: Artificial sequence
<220> FEATURE:
<223> OTHER INFORMATION: Synthetic sequence: Probe suitable for detection of genetic variations associated with known erythrocyte antigens, and useful for genotyping for blood groups

<400> SEQUENCE: 599
gtattattgg aacgatcctc ttaat 25

<210> SEQ ID NO 600
<211> LENGTH: 25
<212> TYPE: DNA
<213> ORGANISM: Artificial sequence
<220> FEATURE:
<223> OTHER INFORMATION: Synthetic sequence: Probe suitable for detection of genetic variations associated with known erythrocyte antigens, and useful for genotyping for blood groups

<400> SEQUENCE: 600
gtattattgg aatgatcctc ttaat 25

<210> SEQ ID NO 601
<211> LENGTH: 27
<212> TYPE: DNA
<213> ORGANISM: Artificial sequence
<220> FEATURE:
<223> OTHER INFORMATION: Synthetic sequence: Probe suitable for detection of genetic variations associated with known erythrocyte antigens, and useful for genotyping for blood groups

<400> SEQUENCE: 601
ggtattattg gaacgatcct cttaatt 27

<210> SEQ ID NO 602
<211> LENGTH: 27
<212> TYPE: DNA
<213> ORGANISM: Artificial sequence
<220> FEATURE:
<223> OTHER INFORMATION: Synthetic sequence: Probe suitable for detection of genetic variations associated with known erythrocyte antigens, and useful for genotyping for blood groups

<400> SEQUENCE: 602
ggtattattg gaatgatcct cttaatt 27

<210> SEQ ID NO 603
<211> LENGTH: 25
<212> TYPE: DNA
<213> ORGANISM: Artificial sequence
<220> FEATURE:
<223> OTHER INFORMATION: Synthetic sequence: Probe suitable for detection of genetic variations associated with known erythrocyte antigens, and useful for genotyping for blood groups

<400> SEQUENCE: 603
tgataaaggt gagaattcag ttttt 25

<210> SEQ ID NO 604
<211> LENGTH: 25
<212> TYPE: DNA
<213> ORGANISM: Artificial sequence
<220> FEATURE:
<223> OTHER INFORMATION: Synthetic sequence: Probe suitable for detection of genetic variations associated with known erythrocyte antigens, and useful for genotyping for blood groups

<400> SEQUENCE: 604
tgataaaggt gataattcag ttttt 25

<210> SEQ ID NO 605
<211> LENGTH: 25
<212> TYPE: DNA
<213> ORGANISM: Artificial sequence
<220> FEATURE:
<223> OTHER INFORMATION: Synthetic sequence: Probe suitable for detection of genetic variations associated with known erythrocyte antigens, and useful for genotyping for blood groups

<400> SEQUENCE: 605
aaaaactgaa ttctcacctt tatca 25

<210> SEQ ID NO 606
<211> LENGTH: 25
<212> TYPE: DNA
<213> ORGANISM: Artificial sequence
<220> FEATURE:
<223> OTHER INFORMATION: Synthetic sequence: Probe suitable for detection of genetic variations associated with known erythrocyte antigens, and useful for genotyping for blood groups

<400> SEQUENCE: 606
aaaaactgaa ttatcacctt tatca 25

<210> SEQ ID NO 607
<211> LENGTH: 25
<212> TYPE: DNA
<213> ORGANISM: Artificial sequence
<220> FEATURE:
<223> OTHER INFORMATION: Synthetic sequence: Probe suitable for detection of genetic variations associated with known erythrocyte antigens, and useful for genotyping for blood groups

<400> SEQUENCE: 607
tatatgcaga tacgcacaaa cggga 25

<210> SEQ ID NO 608
<211> LENGTH: 25
<212> TYPE: DNA
<213> ORGANISM: Artificial sequence
<220> FEATURE:
<223> OTHER INFORMATION: Synthetic sequence: Probe suitable for detection of genetic variations associated with known erythrocyte antigens, and useful for genotyping for blood groups

<400> SEQUENCE: 608
tatatgcaga taagcacaaa cggga 25

<210> SEQ ID NO 609
<211> LENGTH: 27
<212> TYPE: DNA

<213> ORGANISM: Artificial sequence
<220> FEATURE:
<223> OTHER INFORMATION: Synthetic sequence: Probe suitable for detection of genetic variations associated with known erythrocyte antigens, and useful for genotyping for blood groups

<400> SEQUENCE: 609
ttatatgcag atacgcacaa acgggac 27

<210> SEQ ID NO 610
<211> LENGTH: 27
<212> TYPE: DNA
<213> ORGANISM: Artificial sequence
<220> FEATURE:
<223> OTHER INFORMATION: Synthetic sequence: Probe suitable for detection of genetic variations associated with known erythrocyte antigens, and useful for genotyping for blood groups

<400> SEQUENCE: 610
ttatatgcag ataagcacaa acgggac 27

<210> SEQ ID NO 611
<211> LENGTH: 25
<212> TYPE: DNA
<213> ORGANISM: Artificial sequence
<220> FEATURE:
<223> OTHER INFORMATION: Synthetic sequence: Probe suitable for detection of genetic variations associated with known erythrocyte antigens, and useful for genotyping for blood groups

<400> SEQUENCE: 611
ggggaaacag ttgtaacaga aattt 25

<210> SEQ ID NO 612
<211> LENGTH: 25
<212> TYPE: DNA
<213> ORGANISM: Artificial sequence
<220> FEATURE:
<223> OTHER INFORMATION: Synthetic sequence: Probe suitable for detection of genetic variations associated with known erythrocyte antigens, and useful for genotyping for blood groups

<400> SEQUENCE: 612
gggcaaacag ttctaacaga aattt 25

<210> SEQ ID NO 613
<211> LENGTH: 27
<212> TYPE: DNA
<213> ORGANISM: Artificial sequence
<220> FEATURE:
<223> OTHER INFORMATION: Synthetic sequence: Probe suitable for detection of genetic variations associated with known erythrocyte antigens, and useful for genotyping for blood groups

<400> SEQUENCE: 613
aggggaaaca gttgtaacag aaatttc 27

<210> SEQ ID NO 614
<211> LENGTH: 27
<212> TYPE: DNA
<213> ORGANISM: Artificial sequence
<220> FEATURE:
<223> OTHER INFORMATION: Synthetic sequence: Probe suitable for detection of genetic variations associated with known erythrocyte antigens, and useful for genotyping for blood groups

<400> SEQUENCE: 614
agggcaaaca gttctaacag aaatttc 27

<210> SEQ ID NO 615
<211> LENGTH: 25
<212> TYPE: DNA
<213> ORGANISM: Artificial sequence
<220> FEATURE:
<223> OTHER INFORMATION: Synthetic sequence: Probe suitable for detection of genetic variations associated with known erythrocyte antigens, and useful for genotyping for blood groups

<400> SEQUENCE: 615
gccagggagg ccagcgtgga cttca 25

<210> SEQ ID NO 616
<211> LENGTH: 25
<212> TYPE: DNA
<213> ORGANISM: Artificial sequence
<220> FEATURE:
<223> OTHER INFORMATION: Synthetic sequence: Probe suitable for detection of genetic variations associated with known erythrocyte antigens, and useful for genotyping for blood groups

<400> SEQUENCE: 616
gccagggagg ccggcgtgga cttca 25

<210> SEQ ID NO 617
<211> LENGTH: 23
<212> TYPE: DNA
<213> ORGANISM: Artificial sequence
<220> FEATURE:
<223> OTHER INFORMATION: Synthetic sequence: Probe suitable for detection of genetic variations associated with known erythrocyte antigens, and useful for genotyping for blood groups

<400> SEQUENCE: 617
ccagggaggc cagcgtggac ttc 23

<210> SEQ ID NO 618
<211> LENGTH: 23
<212> TYPE: DNA
<213> ORGANISM: Artificial sequence
<220> FEATURE:
<223> OTHER INFORMATION: Synthetic sequence: Probe suitable for detection of genetic variations associated with known erythrocyte antigens, and useful for genotyping for blood groups

<400> SEQUENCE: 618
ccagggaggc cggcgtggac ttc 23

<210> SEQ ID NO 619
<211> LENGTH: 25
<212> TYPE: DNA
<213> ORGANISM: Artificial sequence
<220> FEATURE:
<223> OTHER INFORMATION: Synthetic sequence: Probe suitable for detection of genetic variations associated with known erythrocyte antigens, and reactions to pharmaceuticals

<400> SEQUENCE: 619
actgcaacca gtttcctctt gggtg 25

<210> SEQ ID NO 620
<211> LENGTH: 25
<212> TYPE: DNA
<213> ORGANISM: Artificial sequence
<220> FEATURE:
<223> OTHER INFORMATION: Synthetic sequence: Probe suitable for detection of genetic variations associated with known erythrocyte antigens, and useful for genotyping for blood groups

<400> SEQUENCE: 620
actgcaacca gtctcctctt gggtg 25

<210> SEQ ID NO 621
<211> LENGTH: 27
<212> TYPE: DNA
<213> ORGANISM: Artificial sequence
<220> FEATURE:
<223> OTHER INFORMATION: Synthetic sequence: Probe suitable for detection of genetic variations associated with known erythrocyte antigens, and useful for genotyping for blood groups

<400> SEQUENCE: 621
aactgcaacc agtttcctct tgggtgg 27

<210> SEQ ID NO 622
<211> LENGTH: 27
<212> TYPE: DNA
<213> ORGANISM: Artificial sequence
<220> FEATURE:
<223> OTHER INFORMATION: Synthetic sequence: Probe suitable for detection of genetic variations associated with known erythrocyte antigens, and useful for genotyping for blood groups

<400> SEQUENCE: 622
aactgcaacc agtctcctct tgggtgg 27

<210> SEQ ID NO 623
<211> LENGTH: 25
<212> TYPE: DNA
<213> ORGANISM: Artificial sequence
<220> FEATURE:
<223> OTHER INFORMATION: Synthetic sequence: Probe suitable for detection of genetic variations associated with known erythrocyte antigens, and useful for genotyping for blood groups

<400> SEQUENCE: 623
ttgtcctgga ccgccgtctg gttgt 25

<210> SEQ ID NO 624
<211> LENGTH: 25
<212> TYPE: DNA
<213> ORGANISM: Artificial sequence
<220> FEATURE:
<223> OTHER INFORMATION: Synthetic sequence: Probe suitable for detection of genetic variations associated with known erythrocyte antigens, and useful for genotyping for blood groups

<400> SEQUENCE: 624
ttgtcctgga ccaccgtctg gttgt 25

<210> SEQ ID NO 625
<211> LENGTH: 23
<212> TYPE: DNA
<213> ORGANISM: Artificial sequence
<220> FEATURE:
<223> OTHER INFORMATION: Synthetic sequence: Probe suitable for detection of genetic variations associated with known erythrocyte antigens, and useful for genotyping for blood groups

<400> SEQUENCE: 625
tgtcctggac cgccgtctgg ttg 23

<210> SEQ ID NO 626
<211> LENGTH: 23
<212> TYPE: DNA
<213> ORGANISM: Artificial sequence
<220> FEATURE:

<223> OTHER INFORMATION: Synthetic sequence: Probe suitable for detection of genetic variations associated with known erythrocyte antigens, and useful for genotyping for blood groups

<400> SEQUENCE: 626
tgtcctggac caccgtctgg ttg 23

<210> SEQ ID NO 627
<211> LENGTH: 21
<212> TYPE: DNA
<213> ORGANISM: Artificial sequence
<220> FEATURE:
<223> OTHER INFORMATION: Synthetic sequence: Probe suitable for detection of genetic variations associated with known erythrocyte antigens, and useful for genotyping for blood groups

<400> SEQUENCE: 627
gctggtgctt gataccgtcg g 21

<210> SEQ ID NO 628
<211> LENGTH: 21
<212> TYPE: DNA
<213> ORGANISM: Artificial sequence
<220> FEATURE:
<223> OTHER INFORMATION: Synthetic sequence: Probe suitable for detection of genetic variations associated with known erythrocyte antigens, and useful for genotyping for blood groups

<400> SEQUENCE: 628
gctggtgctt cataccgtcg g 21

<210> SEQ ID NO 629
<211> LENGTH: 23
<212> TYPE: DNA
<213> ORGANISM: Artificial sequence
<220> FEATURE:
<223> OTHER INFORMATION: Synthetic sequence: Probe suitable for detection of genetic variations associated with known erythrocyte antigens, and useful for genotyping for blood groups

<400> SEQUENCE: 629
tgctggtgct tgataccgtc gga 23

<210> SEQ ID NO 630
<211> LENGTH: 23
<212> TYPE: DNA
<213> ORGANISM: Artificial sequence
<220> FEATURE:
<223> OTHER INFORMATION: Synthetic sequence: Probe suitable for detection of genetic variations associated with known erythrocyte antigens, and useful for genotyping for blood groups

<400> SEQUENCE: 630
tgctggtgct tcataccgtc gga 23

<210> SEQ ID NO 631
<211> LENGTH: 25
<212> TYPE: DNA
<213> ORGANISM: Artificial sequence
<220> FEATURE:
<223> OTHER INFORMATION: Synthetic sequence: Probe suitable for detection of genetic variations associated with IBD

<400> SEQUENCE: 631
tcaccttccc agcaccttct agttc 25

<210> SEQ ID NO 632
<211> LENGTH: 25

<212> TYPE: DNA
<213> ORGANISM: Artificial sequence
<220> FEATURE:
<223> OTHER INFORMATION: Synthetic sequence: Probe suitable for detection of genetic variations associated with IBD

<400> SEQUENCE: 632
gaactagaag gtgctgggaa ggtga 25

<210> SEQ ID NO 633
<211> LENGTH: 25
<212> TYPE: DNA
<213> ORGANISM: Artificial sequence
<220> FEATURE:
<223> OTHER INFORMATION: Synthetic sequence: Probe suitable for detection of genetic variations associated with IBD

<400> SEQUENCE: 633
tcaccttccc aggaccttct agttc 25

<210> SEQ ID NO 634
<211> LENGTH: 25
<212> TYPE: DNA
<213> ORGANISM: Artificial sequence
<220> FEATURE:
<223> OTHER INFORMATION: Synthetic sequence: Probe suitable for detection of genetic variations associated with IBD

<400> SEQUENCE: 634
gaactagaag gtcctgggaa ggtga 25

<210> SEQ ID NO 635
<211> LENGTH: 25
<212> TYPE: DNA
<213> ORGANISM: Artificial sequence
<220> FEATURE:
<223> OTHER INFORMATION: Synthetic sequence: Probe suitable for detection of genetic variations associated with IBD

<400> SEQUENCE: 635
tcaccttccc agaaccttct agttc 25

<210> SEQ ID NO 636
<211> LENGTH: 25
<212> TYPE: DNA
<213> ORGANISM: Artificial sequence
<220> FEATURE:
<223> OTHER INFORMATION: Synthetic sequence: Probe suitable for detection of genetic variations associated with IBD

<400> SEQUENCE: 636
gaactagaag gttctgggaa ggtga 25

<210> SEQ ID NO 637
<211> LENGTH: 25
<212> TYPE: DNA
<213> ORGANISM: Artificial sequence
<220> FEATURE:
<223> OTHER INFORMATION: Synthetic sequence: Probe suitable for detection of genetic variations associated with IBD

<400> SEQUENCE: 637
tcaccttccc agtaccttct agttc 25

<210> SEQ ID NO 638
<211> LENGTH: 25
<212> TYPE: DNA
<213> ORGANISM: Artificial sequence
<220> FEATURE:
<223> OTHER INFORMATION: Synthetic sequence: Probe suitable for detection of genetic variations associated with IBD

<400> SEQUENCE: 638
gaactagaag gtactgggaa ggtga 25

<210> SEQ ID NO 639
<211> LENGTH: 25
<212> TYPE: DNA
<213> ORGANISM: Artificial sequence
<220> FEATURE:
<223> OTHER INFORMATION: Synthetic sequence: Probe suitable for detection of genetic variations associated with IBD

<400> SEQUENCE: 639
tgctgccctc acaatctctt cctgt 25

<210> SEQ ID NO 640
<211> LENGTH: 25
<212> TYPE: DNA
<213> ORGANISM: Artificial sequence
<220> FEATURE:
<223> OTHER INFORMATION: Synthetic sequence: Probe suitable for detection of genetic variations associated with IBD

<400> SEQUENCE: 640
acaggaagag attgtgaggg cagca 25

<210> SEQ ID NO 641
<211> LENGTH: 25
<212> TYPE: DNA
<213> ORGANISM: Artificial sequence
<220> FEATURE:
<223> OTHER INFORMATION: Synthetic sequence: Probe suitable for detection of genetic variations associated with IBD

<400> SEQUENCE: 641
tgctgccctc acgatctctt cctgt 25

<210> SEQ ID NO 642
<211> LENGTH: 25
<212> TYPE: DNA
<213> ORGANISM: Artificial sequence
<220> FEATURE:
<223> OTHER INFORMATION: Synthetic sequence: Probe suitable for detection of genetic variations associated with IBD

<400> SEQUENCE: 642
acaggaagag atcgtgaggg cagca 25

<210> SEQ ID NO 643
<211> LENGTH: 25
<212> TYPE: DNA
<213> ORGANISM: Artificial sequence
<220> FEATURE:
<223> OTHER INFORMATION: Synthetic sequence: Probe suitable for detection of genetic variations associated with IBD

<400> SEQUENCE: 643
aaggccctgc tccggcgcca ggcct 25

<210> SEQ ID NO 644
<211> LENGTH: 25
<212> TYPE: DNA
<213> ORGANISM: Artificial sequence
<220> FEATURE:
<223> OTHER INFORMATION: Synthetic sequence: Probe suitable for detection of genetic variations associated with IBD

<400> SEQUENCE: 644
aggcctggcg ccggagcagg gcctt 25

<210> SEQ ID NO 645
<211> LENGTH: 25
<212> TYPE: DNA
<213> ORGANISM: Artificial sequence
<220> FEATURE:
<223> OTHER INFORMATION: Synthetic sequence: Probe suitable for detection of genetic variations associated with IBD

<400> SEQUENCE: 645
aaggccctgc tctggcgcca ggcct 25

<210> SEQ ID NO 646
<211> LENGTH: 25
<212> TYPE: DNA
<213> ORGANISM: Artificial sequence
<220> FEATURE:
<223> OTHER INFORMATION: Synthetic sequence: Probe suitable for detection of genetic variations associated with IBD

<400> SEQUENCE: 646
aggcctggcg ccagagcagg gcctt 25

<210> SEQ ID NO 647
<211> LENGTH: 25
<212> TYPE: DNA
<213> ORGANISM: Artificial sequence
<220> FEATURE:
<223> OTHER INFORMATION: Synthetic sequence: Probe suitable for detection of genetic variations associated with IBD

<400> SEQUENCE: 647
ttcagattct ggggcaacag agtgg 25

<210> SEQ ID NO 648
<211> LENGTH: 25
<212> TYPE: DNA
<213> ORGANISM: Artificial sequence
<220> FEATURE:
<223> OTHER INFORMATION: Synthetic sequence: Probe suitable for detection of genetic variations associated with IBD

<400> SEQUENCE: 648
ccactctgtt gccccagaat ctgaa 25

<210> SEQ ID NO 649
<211> LENGTH: 25
<212> TYPE: DNA
<213> ORGANISM: Artificial sequence
<220> FEATURE:
<223> OTHER INFORMATION: Synthetic sequence: Probe suitable for detection of genetic variations associated with IBD

<400> SEQUENCE: 649
ttcagattct ggcgcaacag agtgg 25

<210> SEQ ID NO 650
<211> LENGTH: 25
<212> TYPE: DNA
<213> ORGANISM: Artificial sequence
<220> FEATURE:
<223> OTHER INFORMATION: Synthetic sequence: Probe suitable for detection of genetic variations associated with IBD

<400> SEQUENCE: 650
ccactctgtt gcgccagaat ctgaa 25

<210> SEQ ID NO 651
<211> LENGTH: 25
<212> TYPE: DNA
<213> ORGANISM: Artificial sequence
<220> FEATURE:
<223> OTHER INFORMATION: Synthetic sequence: Probe suitable for detection of genetic variations associated with IBD

<400> SEQUENCE: 651
tcctgcaggc cccttgaaag gaatg 25

<210> SEQ ID NO 652
<211> LENGTH: 25
<212> TYPE: DNA
<213> ORGANISM: Artificial sequence
<220> FEATURE:
<223> OTHER INFORMATION: Synthetic sequence: Probe suitable for detection of genetic variations associated with IBD

<400> SEQUENCE: 652
cattcctttc aaggggcctg cagga 25

<210> SEQ ID NO 653
<211> LENGTH: 25
<212> TYPE: DNA
<213> ORGANISM: Artificial sequence
<220> FEATURE:
<223> OTHER INFORMATION: Synthetic sequence: Probe suitable for detection of genetic variations associated with IBD

<400> SEQUENCE: 653
tcctgcaggc ccttgaaagg aatga 25

<210> SEQ ID NO 654
<211> LENGTH: 25
<212> TYPE: DNA
<213> ORGANISM: Artificial sequence
<220> FEATURE:
<223> OTHER INFORMATION: Synthetic sequence: Probe suitable for detection of genetic variations associated with IBD

<400> SEQUENCE: 654
tcattccttt caagggcctg cagga 25

<210> SEQ ID NO 655
<211> LENGTH: 25
<212> TYPE: DNA
<213> ORGANISM: Artificial sequence
<220> FEATURE:
<223> OTHER INFORMATION: Synthetic sequence: Probe suitable for detection of genetic variations associated with IBD

<400> SEQUENCE: 655
attctcaaca gataccctca cttca 25

<210> SEQ ID NO 656
<211> LENGTH: 25
<212> TYPE: DNA
<213> ORGANISM: Artificial sequence
<220> FEATURE:
<223> OTHER INFORMATION: Synthetic sequence: Probe suitable for detection of genetic variations associated with IBD

<400> SEQUENCE: 656
tgaagtgagg gtatctgttg agaat 25

<210> SEQ ID NO 657
<211> LENGTH: 25
<212> TYPE: DNA
<213> ORGANISM: Artificial sequence
<220> FEATURE:
<223> OTHER INFORMATION: Synthetic sequence: Probe suitable for detection of genetic variations associated with IBD

<400> SEQUENCE: 657
attctcaaca gacaccctca cttca 25

<210> SEQ ID NO 658
<211> LENGTH: 25
<212> TYPE: DNA
<213> ORGANISM: Artificial sequence
<220> FEATURE:
<223> OTHER INFORMATION: Synthetic sequence: Probe suitable for detection of genetic variations associated with IBD

<400> SEQUENCE: 658
tgaagtgagg gtgtctgttg agaat 25

<210> SEQ ID NO 659
<211> LENGTH: 25
<212> TYPE: DNA
<213> ORGANISM: Artificial sequence
<220> FEATURE:
<223> OTHER INFORMATION: Synthetic sequence: Probe suitable for detection of genetic variations associated with IBD

<400> SEQUENCE: 659
aggcagacag ctgtcacttt ccaga 25

<210> SEQ ID NO 660
<211> LENGTH: 25
<212> TYPE: DNA
<213> ORGANISM: Artificial sequence
<220> FEATURE:
<223> OTHER INFORMATION: Synthetic sequence: Probe suitable for detection of genetic variations associated with IBD

<400> SEQUENCE: 660
tctggaaagt gacagctgtc tgcct 25

<210> SEQ ID NO 661
<211> LENGTH: 25
<212> TYPE: DNA
<213> ORGANISM: Artificial sequence
<220> FEATURE:
<223> OTHER INFORMATION: Synthetic sequence: Probe suitable for detection of genetic variations associated with IBD

<400> SEQUENCE: 661
aggcagacag ctatcacttt ccaga 25

<210> SEQ ID NO 662
<211> LENGTH: 25
<212> TYPE: DNA
<213> ORGANISM: Artificial sequence
<220> FEATURE:
<223> OTHER INFORMATION: Synthetic sequence: Probe suitable for detection of genetic variations associated with IBD

<400> SEQUENCE: 662
tctggaaagt gatagctgtc tgcct 25

<210> SEQ ID NO 663
<211> LENGTH: 25
<212> TYPE: DNA
<213> ORGANISM: Artificial sequence
<220> FEATURE:
<223> OTHER INFORMATION: Synthetic sequence: Probe suitable for detection of genetic variations associated with IBD

<400> SEQUENCE: 663
gcttctttgg gaaggggaag taggg 25

<210> SEQ ID NO 664
<211> LENGTH: 25
<212> TYPE: DNA
<213> ORGANISM: Artificial sequence
<220> FEATURE:
<223> OTHER INFORMATION: Synthetic sequence: Probe suitable for detection of genetic variations associated with IBD

<400> SEQUENCE: 664
ccctacttcc ccttcccaaa gaagc 25

<210> SEQ ID NO 665
<211> LENGTH: 25
<212> TYPE: DNA
<213> ORGANISM: Artificial sequence
<220> FEATURE:
<223> OTHER INFORMATION: Synthetic sequence: Probe suitable for detection of genetic variations associated with IBD

<400> SEQUENCE: 665
gcttctttgg gagggggaag taggg 25

<210> SEQ ID NO 666
<211> LENGTH: 25
<212> TYPE: DNA
<213> ORGANISM: Artificial sequence
<220> FEATURE:
<223> OTHER INFORMATION: Synthetic sequence: Probe suitable for detection of genetic variations associated with IBD

<400> SEQUENCE: 666
ccctacttcc ccctcccaaa gaagc 25

<210> SEQ ID NO 667
<211> LENGTH: 25
<212> TYPE: DNA
<213> ORGANISM: Artificial sequence
<220> FEATURE:
<223> OTHER INFORMATION: Synthetic sequence: Probe suitable for detection of genetic variations associated with IBD

<400> SEQUENCE: 667
gtcctcctga ctggggtgag ggcca 25

<210> SEQ ID NO 668
<211> LENGTH: 25
<212> TYPE: DNA
<213> ORGANISM: Artificial sequence
<220> FEATURE:
<223> OTHER INFORMATION: Synthetic sequence: Probe suitable for detection of genetic variations associated with IBD

<400> SEQUENCE: 668
gtcctcctga ctagggtgag ggcca 25

<210> SEQ ID NO 669

<211> LENGTH: 25
<212> TYPE: DNA
<213> ORGANISM: Artificial sequence
<220> FEATURE:
<223> OTHER INFORMATION: Synthetic sequence: Probe suitable for detection of genetic variations associated with IBD

<400> SEQUENCE: 669
tggccctcac cccagtcagg aggac 25

<210> SEQ ID NO 670
<211> LENGTH: 25
<212> TYPE: DNA
<213> ORGANISM: Artificial sequence
<220> FEATURE:
<223> OTHER INFORMATION: Synthetic sequence: Probe suitable for detection of genetic variations associated with IBD

<400> SEQUENCE: 670
tggccctcac cctagtcagg aggac 25

<210> SEQ ID NO 671
<211> LENGTH: 25
<212> TYPE: DNA
<213> ORGANISM: Artificial sequence
<220> FEATURE:
<223> OTHER INFORMATION: Synthetic sequence: Probe suitable for detection of genetic variations associated with IBD

<400> SEQUENCE: 671
ttgttcctat cataaagagt caggg 25

<210> SEQ ID NO 672
<211> LENGTH: 25
<212> TYPE: DNA
<213> ORGANISM: Artificial sequence
<220> FEATURE:
<223> OTHER INFORMATION: Synthetic sequence: Probe suitable for detection of genetic variations associated with IBD

<400> SEQUENCE: 672
ccctgactct ttatgatagg aacaa 25

<210> SEQ ID NO 673
<211> LENGTH: 25
<212> TYPE: DNA
<213> ORGANISM: Artificial sequence
<220> FEATURE:
<223> OTHER INFORMATION: Synthetic sequence: Probe suitable for detection of genetic variations associated with IBD

<400> SEQUENCE: 673
ttgttcctat cacaaagagt caggg 25

<210> SEQ ID NO 674
<211> LENGTH: 25
<212> TYPE: DNA
<213> ORGANISM: Artificial sequence
<220> FEATURE:
<223> OTHER INFORMATION: Synthetic sequence: Probe suitable for detection of genetic variations associated with IBD

<400> SEQUENCE: 674
ccctgactct ttgtgatagg aacaa 25

<210> SEQ ID NO 675
<211> LENGTH: 25
<212> TYPE: DNA

<213> ORGANISM: Artificial sequence
<220> FEATURE:
<223> OTHER INFORMATION: Synthetic sequence: Probe suitable for detection of genetic variations associated with IBD

<400> SEQUENCE: 675
atgaaaacat tgtgaaatac aaagc 25

<210> SEQ ID NO 676
<211> LENGTH: 25
<212> TYPE: DNA
<213> ORGANISM: Artificial sequence
<220> FEATURE:
<223> OTHER INFORMATION: Synthetic sequence: Probe suitable for detection of genetic variations associated with IBD

<400> SEQUENCE: 676
gctttgtatt tcacaatgtt ttcat 25

<210> SEQ ID NO 677
<211> LENGTH: 25
<212> TYPE: DNA
<213> ORGANISM: Artificial sequence
<220> FEATURE:
<223> OTHER INFORMATION: Synthetic sequence: Probe suitable for detection of genetic variations associated with IBD

<400> SEQUENCE: 677
atgaaaacat tgcgaaatac aaagc 25

<210> SEQ ID NO 678
<211> LENGTH: 25
<212> TYPE: DNA
<213> ORGANISM: Artificial sequence
<220> FEATURE:
<223> OTHER INFORMATION: Synthetic sequence: Probe suitable for detection of genetic variations associated with IBD

<400> SEQUENCE: 678
gctttgtatt tcgcaatgtt ttcat 25

<210> SEQ ID NO 679
<211> LENGTH: 25
<212> TYPE: DNA
<213> ORGANISM: Artificial sequence
<220> FEATURE:
<223> OTHER INFORMATION: Synthetic sequence: Probe suitable for detection of genetic variations associated with IBD

<400> SEQUENCE: 679
ccccgaccat tgggcccggc aggcg 25

<210> SEQ ID NO 680
<211> LENGTH: 25
<212> TYPE: DNA
<213> ORGANISM: Artificial sequence
<220> FEATURE:
<223> OTHER INFORMATION: Synthetic sequence: Probe suitable for detection of genetic variations associated with IBD

<400> SEQUENCE: 680
cgcctgccgg gcccaatggt cgggg 25

<210> SEQ ID NO 681
<211> LENGTH: 25
<212> TYPE: DNA
<213> ORGANISM: Artificial sequence
<220> FEATURE:

<223> OTHER INFORMATION: Synthetic sequence: Probe suitable for detection of genetic variations associated with IBD

<400> SEQUENCE: 681
ccccgaccat tgattgggcc cggca 25

<210> SEQ ID NO 682
<211> LENGTH: 25
<212> TYPE: DNA
<213> ORGANISM: Artificial sequence
<220> FEATURE:
<223> OTHER INFORMATION: Synthetic sequence: Probe suitable for detection of genetic variations associated with IBD

<400> SEQUENCE: 682
tgccgggccc aatcaatggt cgggg 25

<210> SEQ ID NO 683
<211> LENGTH: 25
<212> TYPE: DNA
<213> ORGANISM: Artificial sequence
<220> FEATURE:
<223> OTHER INFORMATION: Synthetic sequence: Probe suitable for detection of genetic variations associated with IBD

<400> SEQUENCE: 683
tgcacactgc ctggcccaaa acgtc 25

<210> SEQ ID NO 684
<211> LENGTH: 25
<212> TYPE: DNA
<213> ORGANISM: Artificial sequence
<220> FEATURE:
<223> OTHER INFORMATION: Synthetic sequence: Probe suitable for detection of genetic variations associated with IBD

<400> SEQUENCE: 684
tgcacactgc ctagcccaaa acgtc 25

<210> SEQ ID NO 685
<211> LENGTH: 25
<212> TYPE: DNA
<213> ORGANISM: Artificial sequence
<220> FEATURE:
<223> OTHER INFORMATION: Synthetic sequence: Probe suitable for detection of genetic variations associated with IBD

<400> SEQUENCE: 685
gacgttttgg gccaggcagt gtgca 25

<210> SEQ ID NO 686
<211> LENGTH: 25
<212> TYPE: DNA
<213> ORGANISM: Artificial sequence
<220> FEATURE:
<223> OTHER INFORMATION: Synthetic sequence: Probe suitable for detection of genetic variations associated with IBD

<400> SEQUENCE: 686
gacgttttgg gctaggcagt gtgca 25

<210> SEQ ID NO 687
<211> LENGTH: 25
<212> TYPE: DNA
<213> ORGANISM: Artificial sequence
<220> FEATURE:
<223> OTHER INFORMATION: Synthetic sequence: Probe suitable for detection of genetic variations associated with IBD

<400> SEQUENCE: 687
gctctgagac acgccccaac atgcc 25

<210> SEQ ID NO 688
<211> LENGTH: 25
<212> TYPE: DNA
<213> ORGANISM: Artificial sequence
<220> FEATURE:
<223> OTHER INFORMATION: Synthetic sequence: Probe suitable for detection of genetic variations associated with IBD

<400> SEQUENCE: 688
ggcatgttgg ggcgtgtctc agagc 25

<210> SEQ ID NO 689
<211> LENGTH: 25
<212> TYPE: DNA
<213> ORGANISM: Artificial sequence
<220> FEATURE:
<223> OTHER INFORMATION: Synthetic sequence: Probe suitable for detection of genetic variations associated with IBD

<400> SEQUENCE: 689
gctctgagac acaccccaac atgcc 25

<210> SEQ ID NO 690
<211> LENGTH: 25
<212> TYPE: DNA
<213> ORGANISM: Artificial sequence
<220> FEATURE:
<223> OTHER INFORMATION: Synthetic sequence: Probe suitable for detection of genetic variations associated with IBD

<400> SEQUENCE: 690
ggcatgttgg ggtgtgtctc agagc 25

<210> SEQ ID NO 691
<211> LENGTH: 25
<212> TYPE: DNA
<213> ORGANISM: Artificial sequence
<220> FEATURE:
<223> OTHER INFORMATION: Synthetic sequence: Probe suitable for detection of genetic variations associated with IBD

<400> SEQUENCE: 691
gccaaagtaa tcggattcca ggttt 25

<210> SEQ ID NO 692
<211> LENGTH: 25
<212> TYPE: DNA
<213> ORGANISM: Artificial sequence
<220> FEATURE:
<223> OTHER INFORMATION: Synthetic sequence: Probe suitable for detection of genetic variations associated with IBD

<400> SEQUENCE: 692
aaacctggaa tccgattact ttggc 25

<210> SEQ ID NO 693
<211> LENGTH: 25
<212> TYPE: DNA
<213> ORGANISM: Artificial sequence
<220> FEATURE:
<223> OTHER INFORMATION: Synthetic sequence: Probe suitable for detection of genetic variations associated with IBD

<400> SEQUENCE: 693
gccaaagtaa tctgattcca ggttt 25

<210> SEQ ID NO 694
<211> LENGTH: 25
<212> TYPE: DNA
<213> ORGANISM: Artificial sequence
<220> FEATURE:
<223> OTHER INFORMATION: Synthetic sequence: Probe suitable for detection of genetic variations associated with IBD

<400> SEQUENCE: 694
aaacctggaa tcagattact ttggc 25

<210> SEQ ID NO 695
<211> LENGTH: 25
<212> TYPE: DNA
<213> ORGANISM: Artificial sequence
<220> FEATURE:
<223> OTHER INFORMATION: Synthetic sequence: Probe suitable for detection of genetic variations associated with IBD

<400> SEQUENCE: 695
ctacttcctg gagcagcaag agcat 25

<210> SEQ ID NO 696
<211> LENGTH: 25
<212> TYPE: DNA
<213> ORGANISM: Artificial sequence
<220> FEATURE:
<223> OTHER INFORMATION: Synthetic sequence: Probe suitable for detection of genetic variations associated with IBD

<400> SEQUENCE: 696
atgctcttgc tgctccagga agtag 25

<210> SEQ ID NO 697
<211> LENGTH: 25
<212> TYPE: DNA
<213> ORGANISM: Artificial sequence
<220> FEATURE:
<223> OTHER INFORMATION: Synthetic sequence: Probe suitable for detection of genetic variations associated with IBD

<400> SEQUENCE: 697
ctacttcctg gaacagcaag agcat 25

<210> SEQ ID NO 698
<211> LENGTH: 25
<212> TYPE: DNA
<213> ORGANISM: Artificial sequence
<220> FEATURE:
<223> OTHER INFORMATION: Synthetic sequence: Probe suitable for detection of genetic variations associated with IBD

<400> SEQUENCE: 698
atgctcttgc tgttccagga agtag 25

<210> SEQ ID NO 699
<211> LENGTH: 25
<212> TYPE: DNA
<213> ORGANISM: Artificial sequence
<220> FEATURE:
<223> OTHER INFORMATION: Synthetic sequence: Probe suitable for detection of genetic variations associated with IBD

<400> SEQUENCE: 699
cctggagcag caggagcatt tcttt 25

<210> SEQ ID NO 700
<211> LENGTH: 25
<212> TYPE: DNA
<213> ORGANISM: Artificial sequence
<220> FEATURE:
<223> OTHER INFORMATION: Synthetic sequence: Probe suitable for detection of genetic variations associated with IBD

<400> SEQUENCE: 700
aaagaaatgc tcctgctgct ccagg 25

<210> SEQ ID NO 701
<211> LENGTH: 25
<212> TYPE: DNA
<213> ORGANISM: Artificial sequence
<220> FEATURE:
<223> OTHER INFORMATION: Synthetic sequence: Probe suitable for detection of genetic variations associated with IBD

<400> SEQUENCE: 701
cctggagcag caagagcatt tcttt 25

<210> SEQ ID NO 702
<211> LENGTH: 25
<212> TYPE: DNA
<213> ORGANISM: Artificial sequence
<220> FEATURE:
<223> OTHER INFORMATION: Synthetic sequence: Probe suitable for detection of genetic variations associated with IBD

<400> SEQUENCE: 702
aaagaaatgc tcttgctgct ccagg 25

<210> SEQ ID NO 703
<211> LENGTH: 25
<212> TYPE: DNA
<213> ORGANISM: Artificial sequence
<220> FEATURE:
<223> OTHER INFORMATION: Synthetic sequence: Probe suitable for detection of genetic variations associated with IBD

<400> SEQUENCE: 703
cgccctgctc gacgcgctga ttggg 25

<210> SEQ ID NO 704
<211> LENGTH: 25
<212> TYPE: DNA
<213> ORGANISM: Artificial sequence
<220> FEATURE:
<223> OTHER INFORMATION: Synthetic sequence: Probe suitable for detection of genetic variations associated with IBD

<400> SEQUENCE: 704
cccaatcagc gcgtcgagca gggcg 25

<210> SEQ ID NO 705
<211> LENGTH: 25
<212> TYPE: DNA
<213> ORGANISM: Artificial sequence
<220> FEATURE:
<223> OTHER INFORMATION: Synthetic sequence: Probe suitable for detection of genetic variations associated with IBD

<400> SEQUENCE: 705
cgccctgctc gatgcgctga ttggg 25

<210> SEQ ID NO 706
<211> LENGTH: 25
<212> TYPE: DNA
<213> ORGANISM: Artificial sequence
<220> FEATURE:
<223> OTHER INFORMATION: Synthetic sequence: Probe suitable for detection of genetic variations associated with IBD

<400> SEQUENCE: 706
cccaatcagc gcatcgagca gggcg 25

<210> SEQ ID NO 707
<211> LENGTH: 25
<212> TYPE: DNA
<213> ORGANISM: Artificial sequence
<220> FEATURE:
<223> OTHER INFORMATION: Synthetic sequence: Probe suitable for detection of genetic variations associated with IBD

<400> SEQUENCE: 707
gccaatcagc tccggaacta cggag 25

<210> SEQ ID NO 708
<211> LENGTH: 25
<212> TYPE: DNA
<213> ORGANISM: Artificial sequence
<220> FEATURE:
<223> OTHER INFORMATION: Synthetic sequence: Probe suitable for detection of genetic variations associated with IBD

<400> SEQUENCE: 708
ctccgtagtt ccggagctga ttggc 25

<210> SEQ ID NO 709
<211> LENGTH: 25
<212> TYPE: DNA
<213> ORGANISM: Artificial sequence
<220> FEATURE:
<223> OTHER INFORMATION: Synthetic sequence: Probe suitable for detection of genetic variations associated with IBD

<400> SEQUENCE: 709
gccaatcagc tctggaacta cggag 25

<210> SEQ ID NO 710
<211> LENGTH: 25
<212> TYPE: DNA
<213> ORGANISM: Artificial sequence
<220> FEATURE:
<223> OTHER INFORMATION: Synthetic sequence: Probe suitable for detection of genetic variations associated with IBD

<400> SEQUENCE: 710
ctccgtagtt ccagagctga ttggc 25

<210> SEQ ID NO 711
<211> LENGTH: 25
<212> TYPE: DNA
<213> ORGANISM: Artificial sequence
<220> FEATURE:
<223> OTHER INFORMATION: Synthetic sequence: Probe suitable for detection of genetic variations associated with IBD

<400> SEQUENCE: 711
tcattcactt gccggtcagt gagga 25

<210> SEQ ID NO 712
<211> LENGTH: 25

<212> TYPE: DNA
<213> ORGANISM: Artificial sequence
<220> FEATURE:
<223> OTHER INFORMATION: Synthetic sequence: Probe suitable for detection of genetic variations associated with IBD

<400> SEQUENCE: 712
tcctcactga ccggcaagtg aatga 25

<210> SEQ ID NO 713
<211> LENGTH: 25
<212> TYPE: DNA
<213> ORGANISM: Artificial sequence
<220> FEATURE:
<223> OTHER INFORMATION: Synthetic sequence: Probe suitable for detection of genetic variations associated with IBD

<400> SEQUENCE: 713
tcattcactt gctggtcagt gagga 25

<210> SEQ ID NO 714
<211> LENGTH: 25
<212> TYPE: DNA
<213> ORGANISM: Artificial sequence
<220> FEATURE:
<223> OTHER INFORMATION: Synthetic sequence: Probe suitable for detection of genetic variations associated with IBD

<400> SEQUENCE: 714
tcctcactga ccagcaagtg aatga 25

<210> SEQ ID NO 715
<211> LENGTH: 25
<212> TYPE: DNA
<213> ORGANISM: Artificial sequence
<220> FEATURE:
<223> OTHER INFORMATION: Synthetic sequence: Probe suitable for detection of genetic variations associated with IBD

<400> SEQUENCE: 715
aaacccttat tcacctaatc acagc 25

<210> SEQ ID NO 716
<211> LENGTH: 25
<212> TYPE: DNA
<213> ORGANISM: Artificial sequence
<220> FEATURE:
<223> OTHER INFORMATION: Synthetic sequence: Probe suitable for detection of genetic variations associated with IBD

<400> SEQUENCE: 716
gctgtgatta ggtgaataag ggttt 25

<210> SEQ ID NO 717
<211> LENGTH: 25
<212> TYPE: DNA
<213> ORGANISM: Artificial sequence
<220> FEATURE:
<223> OTHER INFORMATION: Synthetic sequence: Probe suitable for detection of genetic variations associated with IBD

<400> SEQUENCE: 717
aaacccttat tctcctaatc acagc 25

<210> SEQ ID NO 718
<211> LENGTH: 25
<212> TYPE: DNA
<213> ORGANISM: Artificial sequence
<220> FEATURE:
<223> OTHER INFORMATION: Synthetic sequence: Probe suitable for detection of genetic variations associated with IBD

<400> SEQUENCE: 718
gctgtgatta ggagaataag ggttt 25

<210> SEQ ID NO 719
<211> LENGTH: 25
<212> TYPE: DNA
<213> ORGANISM: Artificial sequence
<220> FEATURE:
<223> OTHER INFORMATION: Synthetic sequence: Probe suitable for detection of genetic variations associated with IBD

<400> SEQUENCE: 719
ctgattggaa tcctcaccct ttttt 25

<210> SEQ ID NO 720
<211> LENGTH: 25
<212> TYPE: DNA
<213> ORGANISM: Artificial sequence
<220> FEATURE:
<223> OTHER INFORMATION: Synthetic sequence: Probe suitable for detection of genetic variations associated with IBD

<400> SEQUENCE: 720
aaaaaagggt gaggattcca atcag 25

<210> SEQ ID NO 721
<211> LENGTH: 25
<212> TYPE: DNA
<213> ORGANISM: Artificial sequence
<220> FEATURE:
<223> OTHER INFORMATION: Synthetic sequence: Probe suitable for detection of genetic variations associated with IBD

<400> SEQUENCE: 721
ctgattggaa tcttcaccct ttttt 25

<210> SEQ ID NO 722
<211> LENGTH: 25
<212> TYPE: DNA
<213> ORGANISM: Artificial sequence
<220> FEATURE:
<223> OTHER INFORMATION: Synthetic sequence: Probe suitable for detection of genetic variations associated with IBD

<400> SEQUENCE: 722
aaaaaagggt gaagattcca atcag 25

<210> SEQ ID NO 723
<211> LENGTH: 25
<212> TYPE: DNA
<213> ORGANISM: Artificial sequence
<220> FEATURE:
<223> OTHER INFORMATION: Synthetic sequence: Probe suitable for detection of genetic variations associated with IBD

<400> SEQUENCE: 723
ccagggaagg ttgcgggcct gggcc 25

<210> SEQ ID NO 724
<211> LENGTH: 25
<212> TYPE: DNA
<213> ORGANISM: Artificial sequence
<220> FEATURE:
<223> OTHER INFORMATION: Synthetic sequence: Probe suitable for detection of genetic variations associated with IBD

<400> SEQUENCE: 724
ggcccaggcc cgcaaccttc cctgg 25

<210> SEQ ID NO 725
<211> LENGTH: 25
<212> TYPE: DNA
<213> ORGANISM: Artificial sequence
<220> FEATURE:
<223> OTHER INFORMATION: Synthetic sequence: Probe suitable for detection of genetic variations associated with IBD

<400> SEQUENCE: 725
ccagggaagg ttccgggcct gggcc 25

<210> SEQ ID NO 726
<211> LENGTH: 25
<212> TYPE: DNA
<213> ORGANISM: Artificial sequence
<220> FEATURE:
<223> OTHER INFORMATION: Synthetic sequence: Probe suitable for detection of genetic variations associated with IBD

<400> SEQUENCE: 726
ggcccaggcc cggaaccttc cctgg 25

<210> SEQ ID NO 727
<211> LENGTH: 25
<212> TYPE: DNA
<213> ORGANISM: Artificial sequence
<220> FEATURE:
<223> OTHER INFORMATION: Synthetic sequence: Probe suitable for detection of genetic variations associated with IBD

<400> SEQUENCE: 727
actacctcga tgatattatt gactt 25

<210> SEQ ID NO 728
<211> LENGTH: 25
<212> TYPE: DNA
<213> ORGANISM: Artificial sequence
<220> FEATURE:
<223> OTHER INFORMATION: Synthetic sequence: Probe suitable for detection of genetic variations associated with IBD

<400> SEQUENCE: 728
aagtcaataa tatcatcgag gtagt 25

<210> SEQ ID NO 729
<211> LENGTH: 25
<212> TYPE: DNA
<213> ORGANISM: Artificial sequence
<220> FEATURE:
<223> OTHER INFORMATION: Synthetic sequence: Probe suitable for detection of genetic variations associated with IBD

<400> SEQUENCE: 729
actacctcga tggtattatt gactt 25

<210> SEQ ID NO 730
<211> LENGTH: 25
<212> TYPE: DNA
<213> ORGANISM: Artificial sequence
<220> FEATURE:
<223> OTHER INFORMATION: Synthetic sequence: Probe suitable for detection of genetic variations associated with IBD

<400> SEQUENCE: 730
aagtcaataa taccatcgag gtagt 25

<210> SEQ ID NO 731
<211> LENGTH: 25
<212> TYPE: DNA
<213> ORGANISM: Artificial sequence
<220> FEATURE:
<223> OTHER INFORMATION: Synthetic sequence: Probe suitable for detection of genetic variations associated with IBD

<400> SEQUENCE: 731
attttgggac aaccagccta aagta 25

<210> SEQ ID NO 732
<211> LENGTH: 25
<212> TYPE: DNA
<213> ORGANISM: Artificial sequence
<220> FEATURE:
<223> OTHER INFORMATION: Synthetic sequence: Probe suitable for detection of genetic variations associated with IBD

<400> SEQUENCE: 732
tactttaggc tggttgtccc aaaat 25

<210> SEQ ID NO 733
<211> LENGTH: 25
<212> TYPE: DNA
<213> ORGANISM: Artificial sequence
<220> FEATURE:
<223> OTHER INFORMATION: Synthetic sequence: Probe suitable for detection of genetic variations associated with IBD

<400> SEQUENCE: 733
attttgggac aatcagccta aagta 25

<210> SEQ ID NO 734
<211> LENGTH: 25
<212> TYPE: DNA
<213> ORGANISM: Artificial sequence
<220> FEATURE:
<223> OTHER INFORMATION: Synthetic sequence: Probe suitable for detection of genetic variations associated with IBD

<400> SEQUENCE: 734
tactttaggc tgattgtccc aaaat 25

<210> SEQ ID NO 735
<211> LENGTH: 25
<212> TYPE: DNA
<213> ORGANISM: Artificial sequence
<220> FEATURE:
<223> OTHER INFORMATION: Synthetic sequence: Probe suitable for detection of genetic variations associated with IBD

<400> SEQUENCE: 735
gaagagaatc ccagagcagc ctgtt 25

<210> SEQ ID NO 736
<211> LENGTH: 25
<212> TYPE: DNA
<213> ORGANISM: Artificial sequence
<220> FEATURE:
<223> OTHER INFORMATION: Synthetic sequence: Probe suitable for detection of genetic variations associated with IBD

<400> SEQUENCE: 736
aacaggctgc tctgggattc tcttc 25

<210> SEQ ID NO 737
<211> LENGTH: 25
<212> TYPE: DNA
<213> ORGANISM: Artificial sequence
<220> FEATURE:
<223> OTHER INFORMATION: Synthetic sequence: Probe suitable for detection of genetic variations associated with IBD

<400> SEQUENCE: 737
gaagagaatc cccgagcagc ctgtt 25

<210> SEQ ID NO 738
<211> LENGTH: 25
<212> TYPE: DNA
<213> ORGANISM: Artificial sequence
<220> FEATURE:
<223> OTHER INFORMATION: Synthetic sequence: Probe suitable for detection of genetic variations associated with IBD

<400> SEQUENCE: 738
aacaggctgc tcggggattc tcttc 25

<210> SEQ ID NO 739
<211> LENGTH: 25
<212> TYPE: DNA
<213> ORGANISM: Artificial sequence
<220> FEATURE:
<223> OTHER INFORMATION: Synthetic sequence: Probe suitable for detection of genetic variations associated with IBD

<400> SEQUENCE: 739
agctggctcc ggctttgggg tatct 25

<210> SEQ ID NO 740
<211> LENGTH: 25
<212> TYPE: DNA
<213> ORGANISM: Artificial sequence
<220> FEATURE:
<223> OTHER INFORMATION: Synthetic sequence: Probe suitable for detection of genetic variations associated with IBD

<400> SEQUENCE: 740
agatacccca aagccggagc cagct 25

<210> SEQ ID NO 741
<211> LENGTH: 25
<212> TYPE: DNA
<213> ORGANISM: Artificial sequence
<220> FEATURE:
<223> OTHER INFORMATION: Synthetic sequence: Probe suitable for detection of genetic variations associated with IBD

<400> SEQUENCE: 741
agctggctcc ggttttgggg tatct 25

<210> SEQ ID NO 742
<211> LENGTH: 25
<212> TYPE: DNA
<213> ORGANISM: Artificial sequence
<220> FEATURE:
<223> OTHER INFORMATION: Synthetic sequence: Probe suitable for detection of genetic variations associated with IBD

<400> SEQUENCE: 742
agatacccca aaaccggagc cagct 25

<210> SEQ ID NO 743
<211> LENGTH: 25
<212> TYPE: DNA
<213> ORGANISM: Artificial sequence
<220> FEATURE:
<223> OTHER INFORMATION: Synthetic sequence: Probe suitable for detection of genetic variations associated with IBD

<400> SEQUENCE: 743
tctcctattg acccagaaag cgatt 25

<210> SEQ ID NO 744
<211> LENGTH: 25
<212> TYPE: DNA
<213> ORGANISM: Artificial sequence
<220> FEATURE:
<223> OTHER INFORMATION: Synthetic sequence: Probe suitable for detection of genetic variations associated with IBD

<400> SEQUENCE: 744
aatcgctttc tgggtcaata ggaga 25

<210> SEQ ID NO 745
<211> LENGTH: 25
<212> TYPE: DNA
<213> ORGANISM: Artificial sequence
<220> FEATURE:
<223> OTHER INFORMATION: Synthetic sequence: Probe suitable for detection of genetic variations associated with IBD

<400> SEQUENCE: 745
tctcctattg acgcagaaag cgatt 25

<210> SEQ ID NO 746
<211> LENGTH: 25
<212> TYPE: DNA
<213> ORGANISM: Artificial sequence
<220> FEATURE:
<223> OTHER INFORMATION: Synthetic sequence: Probe suitable for detection of genetic variations associated with IBD

<400> SEQUENCE: 746
aatcgctttc tgcgtcaata ggaga 25

<210> SEQ ID NO 747
<211> LENGTH: 25
<212> TYPE: DNA
<213> ORGANISM: Artificial sequence
<220> FEATURE:
<223> OTHER INFORMATION: Synthetic sequence: Probe suitable for detection of genetic variations associated with IBD

<400> SEQUENCE: 747
gaggtcaccc gcaaggtgac cgtga 25

<210> SEQ ID NO 748
<211> LENGTH: 25
<212> TYPE: DNA
<213> ORGANISM: Artificial sequence
<220> FEATURE:
<223> OTHER INFORMATION: Synthetic sequence: Probe suitable for detection of genetic variations associated with IBD

<400> SEQUENCE: 748
tcacggtcac cttgcgggtg acctc 25

<210> SEQ ID NO 749

<211> LENGTH: 25
<212> TYPE: DNA
<213> ORGANISM: Artificial sequence
<220> FEATURE:
<223> OTHER INFORMATION: Synthetic sequence: Probe suitable for detection of genetic variations associated with IBD

<400> SEQUENCE: 749
gaggtcaccc gcgaggtgac cgtga 25

<210> SEQ ID NO 750
<211> LENGTH: 25
<212> TYPE: DNA
<213> ORGANISM: Artificial sequence
<220> FEATURE:
<223> OTHER INFORMATION: Synthetic sequence: Probe suitable for detection of genetic variations associated with IBD

<400> SEQUENCE: 750
tcacggtcac ctcgcgggtg acctc 25

<210> SEQ ID NO 751
<211> LENGTH: 25
<212> TYPE: DNA
<213> ORGANISM: Artificial sequence
<220> FEATURE:
<223> OTHER INFORMATION: Synthetic sequence: Probe suitable for detection of genetic variations associated with IBD

<400> SEQUENCE: 751
tgttccctgg acaggctgtt cccag 25

<210> SEQ ID NO 752
<211> LENGTH: 25
<212> TYPE: DNA
<213> ORGANISM: Artificial sequence
<220> FEATURE:
<223> OTHER INFORMATION: Synthetic sequence: Probe suitable for detection of genetic variations associated with IBD

<400> SEQUENCE: 752
ctgggaacag cctgtccagg gaaca 25

<210> SEQ ID NO 753
<211> LENGTH: 25
<212> TYPE: DNA
<213> ORGANISM: Artificial sequence
<220> FEATURE:
<223> OTHER INFORMATION: Synthetic sequence: Probe suitable for detection of genetic variations associated with IBD

<400> SEQUENCE: 753
tgttccctgg acgggctgtt cccag 25

<210> SEQ ID NO 754
<211> LENGTH: 25
<212> TYPE: DNA
<213> ORGANISM: Artificial sequence
<220> FEATURE:
<223> OTHER INFORMATION: Synthetic sequence: Probe suitable for detection of genetic variations associated with IBD

<400> SEQUENCE: 754
ctgggaacag cccgtccagg gaaca 25

<210> SEQ ID NO 755
<211> LENGTH: 25
<212> TYPE: DNA

<213> ORGANISM: Artificial sequence
<220> FEATURE:
<223> OTHER INFORMATION: Synthetic sequence: Probe suitable for detection of genetic variations associated with IBD

<400> SEQUENCE: 755
ccttgcaacc ctggcaaagg taatg 25

<210> SEQ ID NO 756
<211> LENGTH: 25
<212> TYPE: DNA
<213> ORGANISM: Artificial sequence
<220> FEATURE:
<223> OTHER INFORMATION: Synthetic sequence: Probe suitable for detection of genetic variations associated with IBD

<400> SEQUENCE: 756
cattaccttt gccagggttg caagg 25

<210> SEQ ID NO 757
<211> LENGTH: 25
<212> TYPE: DNA
<213> ORGANISM: Artificial sequence
<220> FEATURE:
<223> OTHER INFORMATION: Synthetic sequence: Probe suitable for detection of genetic variations associated with IBD

<400> SEQUENCE: 757
ccttgcaacc ctcgcaaagg taatg 25

<210> SEQ ID NO 758
<211> LENGTH: 25
<212> TYPE: DNA
<213> ORGANISM: Artificial sequence
<220> FEATURE:
<223> OTHER INFORMATION: Synthetic sequence: Probe suitable for detection of genetic variations associated with IBD

<400> SEQUENCE: 758
cattaccttt gcgagggttg caagg 25

<210> SEQ ID NO 759
<211> LENGTH: 25
<212> TYPE: DNA
<213> ORGANISM: Artificial sequence
<220> FEATURE:
<223> OTHER INFORMATION: Synthetic sequence: Probe suitable for detection of genetic variations associated with IBD

<400> SEQUENCE: 759
cagtagacga acgatgcaaa atacc 25

<210> SEQ ID NO 760
<211> LENGTH: 25
<212> TYPE: DNA
<213> ORGANISM: Artificial sequence
<220> FEATURE:
<223> OTHER INFORMATION: Synthetic sequence: Probe suitable for detection of genetic variations associated with IBD

<400> SEQUENCE: 760
ggtattttgc atcgttcgtc tactg 25

<210> SEQ ID NO 761
<211> LENGTH: 25
<212> TYPE: DNA
<213> ORGANISM: Artificial sequence
<220> FEATURE:

<223> OTHER INFORMATION: Synthetic sequence: Probe suitable for detection of genetic variations associated with IBD

<400> SEQUENCE: 761
cagtagacga accatgcaaa atacc 25

<210> SEQ ID NO 762
<211> LENGTH: 25
<212> TYPE: DNA
<213> ORGANISM: Artificial sequence
<220> FEATURE:
<223> OTHER INFORMATION: Synthetic sequence: Probe suitable for detection of genetic variations associated with IBD

<400> SEQUENCE: 762
ggtattttgc atggttcgtc tactg 25

<210> SEQ ID NO 763
<211> LENGTH: 25
<212> TYPE: DNA
<213> ORGANISM: Artificial sequence
<220> FEATURE:
<223> OTHER INFORMATION: Synthetic sequence: Probe suitable for detection of genetic variations associated with IBD

<400> SEQUENCE: 763
catcctggag aatagctgag aacct 25

<210> SEQ ID NO 764
<211> LENGTH: 25
<212> TYPE: DNA
<213> ORGANISM: Artificial sequence
<220> FEATURE:
<223> OTHER INFORMATION: Synthetic sequence: Probe suitable for detection of genetic variations associated with IBD

<400> SEQUENCE: 764
aggttctcag ctattctcca ggatg 25

<210> SEQ ID NO 765
<211> LENGTH: 25
<212> TYPE: DNA
<213> ORGANISM: Artificial sequence
<220> FEATURE:
<223> OTHER INFORMATION: Synthetic sequence: Probe suitable for detection of genetic variations associated with IBD

<400> SEQUENCE: 765
catcctggag aacagctgag aacct 25

<210> SEQ ID NO 766
<211> LENGTH: 25
<212> TYPE: DNA
<213> ORGANISM: Artificial sequence
<220> FEATURE:
<223> OTHER INFORMATION: Synthetic sequence: Probe suitable for detection of genetic variations associated with IBD

<400> SEQUENCE: 766
aggttctcag ctgttctcca ggatg 25

<210> SEQ ID NO 767
<211> LENGTH: 25
<212> TYPE: DNA
<213> ORGANISM: Artificial sequence
<220> FEATURE:
<223> OTHER INFORMATION: Synthetic sequence: Probe suitable for detection of genetic variations associated with IBD

<400> SEQUENCE: 767
gaagctgctg caagacttct tcaac 25

<210> SEQ ID NO 768
<211> LENGTH: 25
<212> TYPE: DNA
<213> ORGANISM: Artificial sequence
<220> FEATURE:
<223> OTHER INFORMATION: Synthetic sequence: Probe suitable for detection of genetic variations associated with IBD

<400> SEQUENCE: 768
gttgaagaag tcttgcagca gcttc 25

<210> SEQ ID NO 769
<211> LENGTH: 25
<212> TYPE: DNA
<213> ORGANISM: Artificial sequence
<220> FEATURE:
<223> OTHER INFORMATION: Synthetic sequence: Probe suitable for detection of genetic variations associated with IBD

<400> SEQUENCE: 769
gaagctgctg caggacttct tcaac 25

<210> SEQ ID NO 770
<211> LENGTH: 25
<212> TYPE: DNA
<213> ORGANISM: Artificial sequence
<220> FEATURE:
<223> OTHER INFORMATION: Synthetic sequence: Probe suitable for detection of genetic variations associated with IBD

<400> SEQUENCE: 770
gttgaagaag tcctgcagca gcttc 25

<210> SEQ ID NO 771
<211> LENGTH: 25
<212> TYPE: DNA
<213> ORGANISM: Artificial sequence
<220> FEATURE:
<223> OTHER INFORMATION: Synthetic sequence: Probe suitable for detection of genetic variations associated with IBD

<400> SEQUENCE: 771
tccctctgcc tgaaaactcc cccaa 25

<210> SEQ ID NO 772
<211> LENGTH: 25
<212> TYPE: DNA
<213> ORGANISM: Artificial sequence
<220> FEATURE:
<223> OTHER INFORMATION: Synthetic sequence: Probe suitable for detection of genetic variations associated with IBD

<400> SEQUENCE: 772
ttgggggagt tttcaggcag aggga 25

<210> SEQ ID NO 773
<211> LENGTH: 25
<212> TYPE: DNA
<213> ORGANISM: Artificial sequence
<220> FEATURE:
<223> OTHER INFORMATION: Synthetic sequence: Probe suitable for detection of genetic variations associated with IBD

<400> SEQUENCE: 773
tccctctgcc tggaaactcc cccaa 25

<210> SEQ ID NO 774
<211> LENGTH: 25
<212> TYPE: DNA
<213> ORGANISM: Artificial sequence
<220> FEATURE:
<223> OTHER INFORMATION: Synthetic sequence: Probe suitable for detection of genetic variations associated with IBD

<400> SEQUENCE: 774
ttgggggagt ttccaggcag aggga 25

<210> SEQ ID NO 775
<211> LENGTH: 25
<212> TYPE: DNA
<213> ORGANISM: Artificial sequence
<220> FEATURE:
<223> OTHER INFORMATION: Synthetic sequence: Probe suitable for detection of genetic variations associated with IBD

<400> SEQUENCE: 775
tgtctgcggg agccgatttc atcat 25

<210> SEQ ID NO 776
<211> LENGTH: 25
<212> TYPE: DNA
<213> ORGANISM: Artificial sequence
<220> FEATURE:
<223> OTHER INFORMATION: Synthetic sequence: Probe suitable for detection of genetic variations associated with IBD

<400> SEQUENCE: 776
atgatgaaat cggctcccgc agaca 25

<210> SEQ ID NO 777
<211> LENGTH: 25
<212> TYPE: DNA
<213> ORGANISM: Artificial sequence
<220> FEATURE:
<223> OTHER INFORMATION: Synthetic sequence: Probe suitable for detection of genetic variations associated with IBD

<400> SEQUENCE: 777
tgtctgcggg agtcgatttc atcat 25

<210> SEQ ID NO 778
<211> LENGTH: 25
<212> TYPE: DNA
<213> ORGANISM: Artificial sequence
<220> FEATURE:
<223> OTHER INFORMATION: Synthetic sequence: Probe suitable for detection of genetic variations associated with IBD

<400> SEQUENCE: 778
atgatgaaat cgactcccgc agaca 25

<210> SEQ ID NO 779
<211> LENGTH: 25
<212> TYPE: DNA
<213> ORGANISM: Artificial sequence
<220> FEATURE:
<223> OTHER INFORMATION: Synthetic sequence: Probe suitable for detection of genetic variations associated with IBD

<400> SEQUENCE: 779
ggagaacatt gtcccccagt gctgg 25

<210> SEQ ID NO 780
<211> LENGTH: 25
<212> TYPE: DNA
<213> ORGANISM: Artificial sequence
<220> FEATURE:
<223> OTHER INFORMATION: Synthetic sequence: Probe suitable for detection of genetic variations associated with IBD

<400> SEQUENCE: 780
ccagcactgg gggacaatgt tctcc 25

<210> SEQ ID NO 781
<211> LENGTH: 25
<212> TYPE: DNA
<213> ORGANISM: Artificial sequence
<220> FEATURE:
<223> OTHER INFORMATION: Synthetic sequence: Probe suitable for detection of genetic variations associated with IBD

<400> SEQUENCE: 781
ggagaacatt gttccccagt gctgg 25

<210> SEQ ID NO 782
<211> LENGTH: 25
<212> TYPE: DNA
<213> ORGANISM: Artificial sequence
<220> FEATURE:
<223> OTHER INFORMATION: Synthetic sequence: Probe suitable for detection of genetic variations associated with IBD

<400> SEQUENCE: 782
ccagcactgg ggaacaatgt tctcc 25

<210> SEQ ID NO 783
<211> LENGTH: 25
<212> TYPE: DNA
<213> ORGANISM: Artificial sequence
<220> FEATURE:
<223> OTHER INFORMATION: Synthetic sequence: Probe suitable for detection of genetic variations associated with IBD

<400> SEQUENCE: 783
ataaactaat tgcctcacat tgtca 25

<210> SEQ ID NO 784
<211> LENGTH: 25
<212> TYPE: DNA
<213> ORGANISM: Artificial sequence
<220> FEATURE:
<223> OTHER INFORMATION: Synthetic sequence: Probe suitable for detection of genetic variations associated with IBD

<400> SEQUENCE: 784
tgacaatgtg aggcaattag tttat 25

<210> SEQ ID NO 785
<211> LENGTH: 25
<212> TYPE: DNA
<213> ORGANISM: Artificial sequence
<220> FEATURE:
<223> OTHER INFORMATION: Synthetic sequence: Probe suitable for detection of genetic variations associated with IBD

<400> SEQUENCE: 785
ataaactaat tgtctcacat tgtca 25

<210> SEQ ID NO 786
<211> LENGTH: 25
<212> TYPE: DNA
<213> ORGANISM: Artificial sequence
<220> FEATURE:
<223> OTHER INFORMATION: Synthetic sequence: Probe suitable for detection of genetic variations associated with IBD

<400> SEQUENCE: 786
tgacaatgtg agacaattag tttat 25

<210> SEQ ID NO 787
<211> LENGTH: 25
<212> TYPE: DNA
<213> ORGANISM: Artificial sequence
<220> FEATURE:
<223> OTHER INFORMATION: Synthetic sequence: Probe suitable for detection of genetic variations associated with IBD

<400> SEQUENCE: 787
atgggcgtga tgacaccaag ggaga 25

<210> SEQ ID NO 788
<211> LENGTH: 25
<212> TYPE: DNA
<213> ORGANISM: Artificial sequence
<220> FEATURE:
<223> OTHER INFORMATION: Synthetic sequence: Probe suitable for detection of genetic variations associated with IBD

<400> SEQUENCE: 788
tctcccttgg tgtcatcacg cccat 25

<210> SEQ ID NO 789
<211> LENGTH: 25
<212> TYPE: DNA
<213> ORGANISM: Artificial sequence
<220> FEATURE:
<223> OTHER INFORMATION: Synthetic sequence: Probe suitable for detection of genetic variations associated with IBD

<400> SEQUENCE: 789
atgggcgtga tggcaccaag ggaga 25

<210> SEQ ID NO 790
<211> LENGTH: 25
<212> TYPE: DNA
<213> ORGANISM: Artificial sequence
<220> FEATURE:
<223> OTHER INFORMATION: Synthetic sequence: Probe suitable for detection of genetic variations associated with IBD

<400> SEQUENCE: 790
tctcccttgg tgccatcacg cccat 25

<210> SEQ ID NO 791
<211> LENGTH: 25
<212> TYPE: DNA
<213> ORGANISM: Artificial sequence
<220> FEATURE:
<223> OTHER INFORMATION: Synthetic sequence: Probe suitable for detection of genetic variations associated with IBD

<400> SEQUENCE: 791
atggcaccaa ggaagaaaag gggga 25

<210> SEQ ID NO 792
<211> LENGTH: 25

<212> TYPE: DNA
<213> ORGANISM: Artificial sequence
<220> FEATURE:
<223> OTHER INFORMATION: Synthetic sequence: Probe suitable for detection of genetic variations associated with IBD

<400> SEQUENCE: 792
tccccctttt cttccttggt gccat 25

<210> SEQ ID NO 793
<211> LENGTH: 25
<212> TYPE: DNA
<213> ORGANISM: Artificial sequence
<220> FEATURE:
<223> OTHER INFORMATION: Synthetic sequence: Probe suitable for detection of genetic variations associated with IBD

<400> SEQUENCE: 793
atggcaccaa gggagaaaag gggga 25

<210> SEQ ID NO 794
<211> LENGTH: 25
<212> TYPE: DNA
<213> ORGANISM: Artificial sequence
<220> FEATURE:
<223> OTHER INFORMATION: Synthetic sequence: Probe suitable for detection of genetic variations associated with IBD

<400> SEQUENCE: 794
tccccctttt ctcccttggt gccat 25

<210> SEQ ID NO 795
<211> LENGTH: 25
<212> TYPE: DNA
<213> ORGANISM: Artificial sequence
<220> FEATURE:
<223> OTHER INFORMATION: Synthetic sequence: Probe suitable for detection of genetic variations associated with IBD

<400> SEQUENCE: 795
ggcaaagatg ggcgtgatgg cacca 25

<210> SEQ ID NO 796
<211> LENGTH: 25
<212> TYPE: DNA
<213> ORGANISM: Artificial sequence
<220> FEATURE:
<223> OTHER INFORMATION: Synthetic sequence: Probe suitable for detection of genetic variations associated with IBD

<400> SEQUENCE: 796
tggtgccatc acgcccatct ttgcc 25

<210> SEQ ID NO 797
<211> LENGTH: 25
<212> TYPE: DNA
<213> ORGANISM: Artificial sequence
<220> FEATURE:
<223> OTHER INFORMATION: Synthetic sequence: Probe suitable for detection of genetic variations associated with IBD

<400> SEQUENCE: 797
ggcaaagatg ggtgtgatgg cacca 25

<210> SEQ ID NO 798
<211> LENGTH: 25
<212> TYPE: DNA
<213> ORGANISM: Artificial sequence
<220> FEATURE:
<223> OTHER INFORMATION: Synthetic sequence: Probe suitable for detection of genetic variations associated with IBD

<400> SEQUENCE: 798
tggtgccatc acacccatct ttgcc 25

<210> SEQ ID NO 799
<211> LENGTH: 25
<212> TYPE: DNA
<213> ORGANISM: Artificial sequence
<220> FEATURE:
<223> OTHER INFORMATION: Synthetic sequence: Probe suitable for detection of genetic variations associated with IBD

<400> SEQUENCE: 799
cgtgacccgg ccaggggaag aagct 25

<210> SEQ ID NO 800
<211> LENGTH: 25
<212> TYPE: DNA
<213> ORGANISM: Artificial sequence
<220> FEATURE:
<223> OTHER INFORMATION: Synthetic sequence: Probe suitable for detection of genetic variations associated with IBD

<400> SEQUENCE: 800
cgtgacccgg ccgggggaag aagct 25

<210> SEQ ID NO 801
<211> LENGTH: 25
<212> TYPE: DNA
<213> ORGANISM: Artificial sequence
<220> FEATURE:
<223> OTHER INFORMATION: Synthetic sequence: Probe suitable for detection of genetic variations associated with IBD

<400> SEQUENCE: 801
agcttcttcc cctggccggg tcacg 25

<210> SEQ ID NO 802
<211> LENGTH: 25
<212> TYPE: DNA
<213> ORGANISM: Artificial sequence
<220> FEATURE:
<223> OTHER INFORMATION: Synthetic sequence: Probe suitable for detection of genetic variations associated with IBD

<400> SEQUENCE: 802
agcttcttcc cccggccggg tcacg 25

<210> SEQ ID NO 803
<211> LENGTH: 25
<212> TYPE: DNA
<213> ORGANISM: Artificial sequence
<220> FEATURE:
<223> OTHER INFORMATION: Synthetic sequence: Probe suitable for detection of genetic variations associated with IBD

<400> SEQUENCE: 803
ggacacgtgg gggagtcagc cgtgt 25

<210> SEQ ID NO 804
<211> LENGTH: 25
<212> TYPE: DNA
<213> ORGANISM: Artificial sequence
<220> FEATURE:
<223> OTHER INFORMATION: Synthetic sequence: Probe suitable for detection of genetic variations associated with IBD

<400> SEQUENCE: 804
acacggctga ctcccccacg tgtcc 25

<210> SEQ ID NO 805
<211> LENGTH: 25
<212> TYPE: DNA
<213> ORGANISM: Artificial sequence
<220> FEATURE:
<223> OTHER INFORMATION: Synthetic sequence: Probe suitable for detection of genetic variations associated with IBD

<400> SEQUENCE: 805
ggacacgtgg ggagtcagcc gtgta 25

<210> SEQ ID NO 806
<211> LENGTH: 25
<212> TYPE: DNA
<213> ORGANISM: Artificial sequence
<220> FEATURE:
<223> OTHER INFORMATION: Synthetic sequence: Probe suitable for detection of genetic variations associated with IBD

<400> SEQUENCE: 806
tacacggctg actccccacg tgtcc 25

<210> SEQ ID NO 807
<211> LENGTH: 25
<212> TYPE: DNA
<213> ORGANISM: Artificial sequence
<220> FEATURE:
<223> OTHER INFORMATION: Synthetic sequence: Probe suitable for detection of genetic variations associated with IBD

<400> SEQUENCE: 807 ccccccctt aacgaagaca gggcc 25

<210> SEQ ID NO 808
<211> LENGTH: 25
<212> TYPE: DNA
<213> ORGANISM: Artificial sequence
<220> FEATURE:
<223> OTHER INFORMATION: Synthetic sequence: Probe suitable for detection of genetic variations associated with IBD

<400> SEQUENCE: 808
ggccctgtct tcgttaaggg ggggg 25

<210> SEQ ID NO 809
<211> LENGTH: 25
<212> TYPE: DNA
<213> ORGANISM: Artificial sequence
<220> FEATURE:
<223> OTHER INFORMATION: Synthetic sequence: Probe suitable for detection of genetic variations associated with IBD

<400> SEQUENCE: 809 ccccccctt aatgaagaca gggcc 25

<210> SEQ ID NO 810
<211> LENGTH: 25
<212> TYPE: DNA
<213> ORGANISM: Artificial sequence
<220> FEATURE:
<223> OTHER INFORMATION: Synthetic sequence: Probe suitable for detection of genetic variations associated with IBD

<400> SEQUENCE: 810
ggccctgtct tcattaaggg ggggg 25

<210> SEQ ID NO 811
<211> LENGTH: 25
<212> TYPE: DNA
<213> ORGANISM: Artificial sequence
<220> FEATURE:
<223> OTHER INFORMATION: Synthetic sequence: Probe suitable for detection of genetic variations associated with IBD

<400> SEQUENCE: 811
ttgaggggca tggggacggg gttca 25

<210> SEQ ID NO 812
<211> LENGTH: 25
<212> TYPE: DNA
<213> ORGANISM: Artificial sequence
<220> FEATURE:
<223> OTHER INFORMATION: Synthetic sequence: Probe suitable for detection of genetic variations associated with IBD

<400> SEQUENCE: 812
tgaaccccgt ccccatgccc ctcaa 25

<210> SEQ ID NO 813
<211> LENGTH: 25
<212> TYPE: DNA
<213> ORGANISM: Artificial sequence
<220> FEATURE:
<223> OTHER INFORMATION: Synthetic sequence: Probe suitable for detection of genetic variations associated with IBD

<400> SEQUENCE: 813
ttgaggggca tgaggacggg gttca 25

<210> SEQ ID NO 814
<211> LENGTH: 25
<212> TYPE: DNA
<213> ORGANISM: Artificial sequence
<220> FEATURE:
<223> OTHER INFORMATION: Synthetic sequence: Probe suitable for detection of genetic variations associated with IBD

<400> SEQUENCE: 814
tgaaccccgt cctcatgccc ctcaa 25

<210> SEQ ID NO 815
<211> LENGTH: 25
<212> TYPE: DNA
<213> ORGANISM: Artificial sequence
<220> FEATURE:
<223> OTHER INFORMATION: Synthetic sequence: Probe suitable for detection of genetic variations associated with IBD

<400> SEQUENCE: 815
cccctcggaa tcggagcagg gagga 25

<210> SEQ ID NO 816
<211> LENGTH: 25
<212> TYPE: DNA
<213> ORGANISM: Artificial sequence
<220> FEATURE:
<223> OTHER INFORMATION: Synthetic sequence: Probe suitable for detection of genetic variations associated with IBD

<400> SEQUENCE: 816
tcctccctgc tccgattccg agggg 25

<210> SEQ ID NO 817
<211> LENGTH: 25
<212> TYPE: DNA
<213> ORGANISM: Artificial sequence
<220> FEATURE:
<223> OTHER INFORMATION: Synthetic sequence: Probe suitable for
detection of genetic variations associated with IBD

<400> SEQUENCE: 817
cccctcggaa tcagagcagg gagga 25

<210> SEQ ID NO 818
<211> LENGTH: 25
<212> TYPE: DNA
<213> ORGANISM: Artificial sequence
<220> FEATURE:
<223> OTHER INFORMATION: Synthetic sequence: Probe suitable for
detection of genetic variations associated with IBD

<400> SEQUENCE: 818
tcctccctgc tctgattccg agggg 25

<210> SEQ ID NO 819
<211> LENGTH: 25
<212> TYPE: DNA
<213> ORGANISM: Artificial sequence
<220> FEATURE:
<223> OTHER INFORMATION: Synthetic sequence: Probe suitable for
detection of genetic variations associated with IBD

<400> SEQUENCE: 819
gtccccggtc tgcaaacctg cataa 25

<210> SEQ ID NO 820
<211> LENGTH: 25
<212> TYPE: DNA
<213> ORGANISM: Artificial sequence
<220> FEATURE:
<223> OTHER INFORMATION: Synthetic sequence: Probe suitable for
detection of genetic variations associated with IBD

<400> SEQUENCE: 820
ttatgcaggt ttgcagaccg gggac 25

<210> SEQ ID NO 821
<211> LENGTH: 25
<212> TYPE: DNA
<213> ORGANISM: Artificial sequence
<220> FEATURE:
<223> OTHER INFORMATION: Synthetic sequence: Probe suitable for
detection of genetic variations associated with IBD

<400> SEQUENCE: 821
gtccccggtc tggaaacctg cataa 25

<210> SEQ ID NO 822
<211> LENGTH: 25
<212> TYPE: DNA
<213> ORGANISM: Artificial sequence
<220> FEATURE:
<223> OTHER INFORMATION: Synthetic sequence: Probe suitable for
detection of genetic variations associated with IBD

<400> SEQUENCE: 822
ttatgcaggt ttccagaccg gggac 25

<210> SEQ ID NO 823
<211> LENGTH: 25
<212> TYPE: DNA
<213> ORGANISM: Artificial sequence
<220> FEATURE:
<223> OTHER INFORMATION: Synthetic sequence: Probe suitable for detection of genetic variations associated with IBD

<400> SEQUENCE: 823
tgggatagag gagcattagt tgcca 25

<210> SEQ ID NO 824
<211> LENGTH: 25
<212> TYPE: DNA
<213> ORGANISM: Artificial sequence
<220> FEATURE:
<223> OTHER INFORMATION: Synthetic sequence: Probe suitable for detection of genetic variations associated with IBD

<400> SEQUENCE: 824
tgggatagag gaacattagt tgcca 25

<210> SEQ ID NO 825
<211> LENGTH: 25
<212> TYPE: DNA
<213> ORGANISM: Artificial sequence
<220> FEATURE:
<223> OTHER INFORMATION: Synthetic sequence: Probe suitable for detection of genetic variations associated with IBD

<400> SEQUENCE: 825
tggcaactaa tgctcctcta tccca 25

<210> SEQ ID NO 826
<211> LENGTH: 25
<212> TYPE: DNA
<213> ORGANISM: Artificial sequence
<220> FEATURE:
<223> OTHER INFORMATION: Synthetic sequence: Probe suitable for detection of genetic variations associated with IBD

<400> SEQUENCE: 826
tggcaactaa tgttcctcta tccca 25

<210> SEQ ID NO 827
<211> LENGTH: 25
<212> TYPE: DNA
<213> ORGANISM: Artificial sequence
<220> FEATURE:
<223> OTHER INFORMATION: Synthetic sequence: Probe suitable for detection of genetic variations associated with IBD

<400> SEQUENCE: 827
tctgtaagta gatataactt ttcaa 25

<210> SEQ ID NO 828
<211> LENGTH: 25
<212> TYPE: DNA
<213> ORGANISM: Artificial sequence
<220> FEATURE:
<223> OTHER INFORMATION: Synthetic sequence: Probe suitable for detection of genetic variations associated with IBD

<400> SEQUENCE: 828
ttgaaaagtt atatctactt acaga 25

<210> SEQ ID NO 829

<211> LENGTH: 25
<212> TYPE: DNA
<213> ORGANISM: Artificial sequence
<220> FEATURE:
<223> OTHER INFORMATION: Synthetic sequence: Probe suitable for detection of genetic variations associated with IBD

<400> SEQUENCE: 829
tctgtaagta gacataactt ttcaa 25

<210> SEQ ID NO 830
<211> LENGTH: 25
<212> TYPE: DNA
<213> ORGANISM: Artificial sequence
<220> FEATURE:
<223> OTHER INFORMATION: Synthetic sequence: Probe suitable for detection of genetic variations associated with IBD

<400> SEQUENCE: 830
ttgaaaagtt atgtctactt acaga 25

<210> SEQ ID NO 831
<211> LENGTH: 25
<212> TYPE: DNA
<213> ORGANISM: Artificial sequence
<220> FEATURE:
<223> OTHER INFORMATION: Synthetic sequence: Probe suitable for detection of genetic variations associated with IBD

<400> SEQUENCE: 831
acggtgctgt cctgggatgg atctg 25

<210> SEQ ID NO 832
<211> LENGTH: 25
<212> TYPE: DNA
<213> ORGANISM: Artificial sequence
<220> FEATURE:
<223> OTHER INFORMATION: Synthetic sequence: Probe suitable for detection of genetic variations associated with IBD

<400> SEQUENCE: 832
acggtgctgt ccggggatgg atctg 25

<210> SEQ ID NO 833
<211> LENGTH: 25
<212> TYPE: DNA
<213> ORGANISM: Artificial sequence
<220> FEATURE:
<223> OTHER INFORMATION: Synthetic sequence: Probe suitable for detection of genetic variations associated with IBD

<400> SEQUENCE: 833
cagatccatc ccaggacagc accgt 25

<210> SEQ ID NO 834
<211> LENGTH: 25
<212> TYPE: DNA
<213> ORGANISM: Artificial sequence
<220> FEATURE:
<223> OTHER INFORMATION: Synthetic sequence: Probe suitable for detection of genetic variations associated with IBD

<400> SEQUENCE: 834
cagatccatc cccggacagc accgt 25

<210> SEQ ID NO 835
<211> LENGTH: 25
<212> TYPE: DNA

<213> ORGANISM: Artificial sequence
<220> FEATURE:
<223> OTHER INFORMATION: Synthetic sequence: Probe suitable for detection of genetic variations associated with IBD

<400> SEQUENCE: 835
tcagggtttc tcgctgaggt acatc 25

<210> SEQ ID NO 836
<211> LENGTH: 25
<212> TYPE: DNA
<213> ORGANISM: Artificial sequence
<220> FEATURE:
<223> OTHER INFORMATION: Synthetic sequence: Probe suitable for detection of genetic variations associated with IBD

<400> SEQUENCE: 836
tcagggtttc tcactgaggt acatc 25

<210> SEQ ID NO 837
<211> LENGTH: 25
<212> TYPE: DNA
<213> ORGANISM: Artificial sequence
<220> FEATURE:
<223> OTHER INFORMATION: Synthetic sequence: Probe suitable for detection of genetic variations associated with IBD

<400> SEQUENCE: 837
gatgtacctc agcgagaaac cctga 25

<210> SEQ ID NO 838
<211> LENGTH: 25
<212> TYPE: DNA
<213> ORGANISM: Artificial sequence
<220> FEATURE:
<223> OTHER INFORMATION: Synthetic sequence: Probe suitable for detection of genetic variations associated with IBD

<400> SEQUENCE: 838
gatgtacctc agtgagaaac cctga 25

<210> SEQ ID NO 839
<211> LENGTH: 25
<212> TYPE: DNA
<213> ORGANISM: Artificial sequence
<220> FEATURE:
<223> OTHER INFORMATION: Synthetic sequence: Probe suitable for detection of genetic variations associated with IBD

<400> SEQUENCE: 839
gaggaatgga caatgcccca gtcct 25

<210> SEQ ID NO 840
<211> LENGTH: 25
<212> TYPE: DNA
<213> ORGANISM: Artificial sequence
<220> FEATURE:
<223> OTHER INFORMATION: Synthetic sequence: Probe suitable for detection of genetic variations associated with IBD

<400> SEQUENCE: 840
gaggaatgga cagtgcccca gtcct 25

<210> SEQ ID NO 841
<211> LENGTH: 25
<212> TYPE: DNA
<213> ORGANISM: Artificial sequence
<220> FEATURE:

<223> OTHER INFORMATION: Synthetic sequence: Probe suitable for detection of genetic variations associated with IBD

<400> SEQUENCE: 841
aggactgggg cattgtccat tcctc 25

<210> SEQ ID NO 842
<211> LENGTH: 25
<212> TYPE: DNA
<213> ORGANISM: Artificial sequence
<220> FEATURE:
<223> OTHER INFORMATION: Synthetic sequence: Probe suitable for detection of genetic variations associated with IBD

<400> SEQUENCE: 842
aggactgggg cactgtccat tcctc 25

<210> SEQ ID NO 843
<211> LENGTH: 25
<212> TYPE: DNA
<213> ORGANISM: Artificial sequence
<220> FEATURE:
<223> OTHER INFORMATION: Synthetic sequence: Probe suitable for detection of genetic variations associated with IBD

<400> SEQUENCE: 843
cggcgatatc taaaatccgg cgtag 25

<210> SEQ ID NO 844
<211> LENGTH: 25
<212> TYPE: DNA
<213> ORGANISM: Artificial sequence
<220> FEATURE:
<223> OTHER INFORMATION: Synthetic sequence: Probe suitable for detection of genetic variations associated with IBD

<400> SEQUENCE: 844
cggcgatatc tagaatccgg cgtag 25

<210> SEQ ID NO 845
<211> LENGTH: 25
<212> TYPE: DNA
<213> ORGANISM: Artificial sequence
<220> FEATURE:
<223> OTHER INFORMATION: Synthetic sequence: Probe suitable for detection of genetic variations associated with IBD

<400> SEQUENCE: 845
ctacgccgga ttttagatat cgccg 25

<210> SEQ ID NO 846
<211> LENGTH: 25
<212> TYPE: DNA
<213> ORGANISM: Artificial sequence
<220> FEATURE:
<223> OTHER INFORMATION: Synthetic sequence: Probe suitable for detection of genetic variations associated with IBD

<400> SEQUENCE: 846
ctacgccgga ttctagatat cgccg 25

<210> SEQ ID NO 847
<211> LENGTH: 25
<212> TYPE: DNA
<213> ORGANISM: Artificial sequence
<220> FEATURE:
<223> OTHER INFORMATION: Synthetic sequence: Probe suitable for detection of genetic variations associated with IBD

<400> SEQUENCE: 847
tatctaaaat ccggcgtagt cctga 25

<210> SEQ ID NO 848
<211> LENGTH: 25
<212> TYPE: DNA
<213> ORGANISM: Artificial sequence
<220> FEATURE:
<223> OTHER INFORMATION: Synthetic sequence: Probe suitable for detection of genetic variations associated with IBD

<400> SEQUENCE: 848
tatctaaaat ccagcgtagt cctga 25

<210> SEQ ID NO 849
<211> LENGTH: 25
<212> TYPE: DNA
<213> ORGANISM: Artificial sequence
<220> FEATURE:
<223> OTHER INFORMATION: Synthetic sequence: Probe suitable for detection of genetic variations associated with IBD

<400> SEQUENCE: 849
tcaggactac gccggatttt agata 25

<210> SEQ ID NO 850
<211> LENGTH: 25
<212> TYPE: DNA
<213> ORGANISM: Artificial sequence
<220> FEATURE:
<223> OTHER INFORMATION: Synthetic sequence: Probe suitable for detection of genetic variations associated with IBD

<400> SEQUENCE: 850
tcaggactac gctggatttt agata 25

<210> SEQ ID NO 851
<211> LENGTH: 25
<212> TYPE: DNA
<213> ORGANISM: Artificial sequence
<220> FEATURE:
<223> OTHER INFORMATION: Synthetic sequence: Probe suitable for detection of genetic variations associated with IBD

<400> SEQUENCE: 851
cgtgtgtgtg tatgtgtgtg tgtgt 25

<210> SEQ ID NO 852
<211> LENGTH: 25
<212> TYPE: DNA
<213> ORGANISM: Artificial sequence
<220> FEATURE:
<223> OTHER INFORMATION: Synthetic sequence: Probe suitable for detection of genetic variations associated with IBD

<400> SEQUENCE: 852
cgtgtgtgtg tacgtgtgtg tgtgt 25

<210> SEQ ID NO 853
<211> LENGTH: 25
<212> TYPE: DNA
<213> ORGANISM: Artificial sequence
<220> FEATURE:
<223> OTHER INFORMATION: Synthetic sequence: Probe suitable for detection of genetic variations associated with IBD

<400> SEQUENCE: 853
acacacacac acatacacac acacg 25

<210> SEQ ID NO 854
<211> LENGTH: 25
<212> TYPE: DNA
<213> ORGANISM: Artificial sequence
<220> FEATURE:
<223> OTHER INFORMATION: Synthetic sequence: Probe suitable for detection of genetic variations associated with IBD

<400> SEQUENCE: 854
acacacacac acgtacacac acacg 25

<210> SEQ ID NO 855
<211> LENGTH: 25
<212> TYPE: DNA
<213> ORGANISM: Artificial sequence
<220> FEATURE:
<223> OTHER INFORMATION: Synthetic sequence: Probe suitable for detection of genetic variations associated with IBD

<400> SEQUENCE: 855
ttcctgttac ggtccccctc cctga 25

<210> SEQ ID NO 856
<211> LENGTH: 25
<212> TYPE: DNA
<213> ORGANISM: Artificial sequence
<220> FEATURE:
<223> OTHER INFORMATION: Synthetic sequence: Probe suitable for detection of genetic variations associated with IBD

<400> SEQUENCE: 856
ttcctgttac ggccccctc cctga 25

<210> SEQ ID NO 857
<211> LENGTH: 25
<212> TYPE: DNA
<213> ORGANISM: Artificial sequence
<220> FEATURE:
<223> OTHER INFORMATION: Synthetic sequence: Probe suitable for detection of genetic variations associated with IBD

<400> SEQUENCE: 857
tcagggaggg ggaccgtaac aggaa 25

<210> SEQ ID NO 858
<211> LENGTH: 25
<212> TYPE: DNA
<213> ORGANISM: Artificial sequence
<220> FEATURE:
<223> OTHER INFORMATION: Synthetic sequence: Probe suitable for detection of genetic variations associated with IBD

<400> SEQUENCE: 858
tcagggaggg gggccgtaac aggaa 25

<210> SEQ ID NO 859
<211> LENGTH: 25
<212> TYPE: DNA
<213> ORGANISM: Artificial sequence
<220> FEATURE:
<223> OTHER INFORMATION: Synthetic sequence: Probe suitable for detection of genetic variations associated with IBD

<400> SEQUENCE: 859
tgcagggggc ttgttgggag taaaa 25

<210> SEQ ID NO 860
<211> LENGTH: 25
<212> TYPE: DNA
<213> ORGANISM: Artificial sequence
<220> FEATURE:
<223> OTHER INFORMATION: Synthetic sequence: Probe suitable for detection of genetic variations associated with IBD

<400> SEQUENCE: 860
tgcagggggc tttttgggag taaaa 25

<210> SEQ ID NO 861
<211> LENGTH: 25
<212> TYPE: DNA
<213> ORGANISM: Artificial sequence
<220> FEATURE:
<223> OTHER INFORMATION: Synthetic sequence: Probe suitable for detection of genetic variations associated with IBD

<400> SEQUENCE: 861
ttttactccc aacaagcccc ctgca 25

<210> SEQ ID NO 862
<211> LENGTH: 25
<212> TYPE: DNA
<213> ORGANISM: Artificial sequence
<220> FEATURE:
<223> OTHER INFORMATION: Synthetic sequence: Probe suitable for detection of genetic variations associated with IBD

<400> SEQUENCE: 862
ttttactccc aaaaagcccc ctgca 25

<210> SEQ ID NO 863
<211> LENGTH: 25
<212> TYPE: DNA
<213> ORGANISM: Artificial sequence
<220> FEATURE:
<223> OTHER INFORMATION: Synthetic sequence: Probe suitable for detection of genetic variations associated with IBD

<400> SEQUENCE: 863
caatcccagg ttctcttttc tacct 25

<210> SEQ ID NO 864
<211> LENGTH: 25
<212> TYPE: DNA
<213> ORGANISM: Artificial sequence
<220> FEATURE:
<223> OTHER INFORMATION: Synthetic sequence: Probe suitable for detection of genetic variations associated with IBD

<400> SEQUENCE: 864
caatcccagg ttttcttttc tacct 25

<210> SEQ ID NO 865
<211> LENGTH: 25
<212> TYPE: DNA
<213> ORGANISM: Artificial sequence
<220> FEATURE:
<223> OTHER INFORMATION: Synthetic sequence: Probe suitable for detection of genetic variations associated with IBD

<400> SEQUENCE: 865
aggtagaaaa gagaacctgg gattg 25

<210> SEQ ID NO 866
<211> LENGTH: 25
<212> TYPE: DNA
<213> ORGANISM: Artificial sequence
<220> FEATURE:
<223> OTHER INFORMATION: Synthetic sequence: Probe suitable for
detection of genetic variations associated with IBD

<400> SEQUENCE: 866
aggtagaaaa gaaaacctgg gattg 25

<210> SEQ ID NO 867
<211> LENGTH: 25
<212> TYPE: DNA
<213> ORGANISM: Artificial sequence
<220> FEATURE:
<223> OTHER INFORMATION: Synthetic sequence: Probe suitable for
detection of genetic variations associated with IBD

<400> SEQUENCE: 867
gagccattat tgttccgtgc tgttc 25

<210> SEQ ID NO 868
<211> LENGTH: 25
<212> TYPE: DNA
<213> ORGANISM: Artificial sequence
<220> FEATURE:
<223> OTHER INFORMATION: Synthetic sequence: Probe suitable for
detection of genetic variations associated with IBD

<400> SEQUENCE: 868
gagccattat tgatccgtgc tgttc 25

<210> SEQ ID NO 869
<211> LENGTH: 25
<212> TYPE: DNA
<213> ORGANISM: Artificial sequence
<220> FEATURE:
<223> OTHER INFORMATION: Synthetic sequence: Probe suitable for
detection of genetic variations associated with IBD

<400> SEQUENCE: 869
gaacagcacg gaacaataat ggctc 25

<210> SEQ ID NO 870
<211> LENGTH: 25
<212> TYPE: DNA
<213> ORGANISM: Artificial sequence
<220> FEATURE:
<223> OTHER INFORMATION: Synthetic sequence: Probe suitable for
detection of genetic variations associated with IBD

<400> SEQUENCE: 870
gaacagcacg gatcaataat ggctc 25

<210> SEQ ID NO 871
<211> LENGTH: 25
<212> TYPE: DNA
<213> ORGANISM: Artificial sequence
<220> FEATURE:
<223> OTHER INFORMATION: Synthetic sequence: Probe suitable for
detection of genetic variations associated with IBD

<400> SEQUENCE: 871
gcagagggat cctgtcgacc cccac 25

<210> SEQ ID NO 872
<211> LENGTH: 25

<212> TYPE: DNA
<213> ORGANISM: Artificial sequence
<220> FEATURE:
<223> OTHER INFORMATION: Synthetic sequence: Probe suitable for detection of genetic variations associated with IBD

<400> SEQUENCE: 872
gcagagggat cccgtcgacc cccac 25

<210> SEQ ID NO 873
<211> LENGTH: 25
<212> TYPE: DNA
<213> ORGANISM: Artificial sequence
<220> FEATURE:
<223> OTHER INFORMATION: Synthetic sequence: Probe suitable for detection of genetic variations associated with IBD

<400> SEQUENCE: 873
gtgggggtcg acaggatccc tctgc 25

<210> SEQ ID NO 874
<211> LENGTH: 25
<212> TYPE: DNA
<213> ORGANISM: Artificial sequence
<220> FEATURE:
<223> OTHER INFORMATION: Synthetic sequence: Probe suitable for detection of genetic variations associated with IBD

<400> SEQUENCE: 874
gtgggggtcg acgggatccc tctgc 25

<210> SEQ ID NO 875
<211> LENGTH: 25
<212> TYPE: DNA
<213> ORGANISM: Artificial sequence
<220> FEATURE:
<223> OTHER INFORMATION: Synthetic sequence: Probe suitable for detection of genetic variations associated with IBD

<400> SEQUENCE: 875
gcagaggcag cgggttgtgg aaagc 25

<210> SEQ ID NO 876
<211> LENGTH: 25
<212> TYPE: DNA
<213> ORGANISM: Artificial sequence
<220> FEATURE:
<223> OTHER INFORMATION: Synthetic sequence: Probe suitable for detection of genetic variations associated with IBD

<400> SEQUENCE: 876
gcagaggcag cgagttgtgg aaagc 25

<210> SEQ ID NO 877
<211> LENGTH: 25
<212> TYPE: DNA
<213> ORGANISM: Artificial sequence
<220> FEATURE:
<223> OTHER INFORMATION: Synthetic sequence: Probe suitable for detection of genetic variations associated with IBD

<400> SEQUENCE: 877
gctttccaca acccgctgcc tctgc 25

<210> SEQ ID NO 878
<211> LENGTH: 25
<212> TYPE: DNA
<213> ORGANISM: Artificial sequence
<220> FEATURE:
<223> OTHER INFORMATION: Synthetic sequence: Probe suitable for detection of genetic variations associated with IBD

<400> SEQUENCE: 878
gctttccaca actcgctgcc tctgc 25

<210> SEQ ID NO 879
<211> LENGTH: 25
<212> TYPE: DNA
<213> ORGANISM: Artificial sequence
<220> FEATURE:
<223> OTHER INFORMATION: Synthetic sequence: Probe suitable for detection of genetic variations associated with IBD

<400> SEQUENCE: 879
ctgctgccat ggcgtgtccc tctcg 25

<210> SEQ ID NO 880
<211> LENGTH: 25
<212> TYPE: DNA
<213> ORGANISM: Artificial sequence
<220> FEATURE:
<223> OTHER INFORMATION: Synthetic sequence: Probe suitable for detection of genetic variations associated with IBD

<400> SEQUENCE: 880
ctgctgccat ggtgtgtccc tctcg 25

<210> SEQ ID NO 881
<211> LENGTH: 25
<212> TYPE: DNA
<213> ORGANISM: Artificial sequence
<220> FEATURE:
<223> OTHER INFORMATION: Synthetic sequence: Probe suitable for detection of genetic variations associated with IBD

<400> SEQUENCE: 881
cgagagggac acgccatggc agcag 25

<210> SEQ ID NO 882
<211> LENGTH: 25
<212> TYPE: DNA
<213> ORGANISM: Artificial sequence
<220> FEATURE:
<223> OTHER INFORMATION: Synthetic sequence: Probe suitable for detection of genetic variations associated with IBD

<400> SEQUENCE: 882
cgagagggac acaccatggc agcag 25

<210> SEQ ID NO 883
<211> LENGTH: 25
<212> TYPE: DNA
<213> ORGANISM: Artificial sequence
<220> FEATURE:
<223> OTHER INFORMATION: Synthetic sequence: Probe suitable for detection of genetic variations associated with IBD

<400> SEQUENCE: 883
agtgggaatt atcaatggac tgcaa 25

<210> SEQ ID NO 884
<211> LENGTH: 25
<212> TYPE: DNA
<213> ORGANISM: Artificial sequence
<220> FEATURE:
<223> OTHER INFORMATION: Synthetic sequence: Probe suitable for detection of genetic variations associated with IBD

<400> SEQUENCE: 884
agtgggaatt attaatggac tgcaa 25

<210> SEQ ID NO 885
<211> LENGTH: 25
<212> TYPE: DNA
<213> ORGANISM: Artificial sequence
<220> FEATURE:
<223> OTHER INFORMATION: Synthetic sequence: Probe suitable for detection of genetic variations associated with IBD

<400> SEQUENCE: 885
ttgcagtcca ttgataattc ccact 25

<210> SEQ ID NO 886
<211> LENGTH: 25
<212> TYPE: DNA
<213> ORGANISM: Artificial sequence
<220> FEATURE:
<223> OTHER INFORMATION: Synthetic sequence: Probe suitable for detection of genetic variations associated with IBD

<400> SEQUENCE: 886
ttgcagtcca ttaataattc ccact 25

<210> SEQ ID NO 887
<211> LENGTH: 25
<212> TYPE: DNA
<213> ORGANISM: Artificial sequence
<220> FEATURE:
<223> OTHER INFORMATION: Synthetic sequence: Probe suitable for detection of genetic variations associated with IBD

<400> SEQUENCE: 887
caccaacggg acggagcgcg tgcgg 25

<210> SEQ ID NO 888
<211> LENGTH: 25
<212> TYPE: DNA
<213> ORGANISM: Artificial sequence
<220> FEATURE:
<223> OTHER INFORMATION: Synthetic sequence: Probe suitable for detection of genetic variations associated with IBD

<400> SEQUENCE: 888
caccaacggg acagagcgcg tgcgg 25

<210> SEQ ID NO 889
<211> LENGTH: 25
<212> TYPE: DNA
<213> ORGANISM: Artificial sequence
<220> FEATURE:
<223> OTHER INFORMATION: Synthetic sequence: Probe suitable for detection of genetic variations associated with IBD

<400> SEQUENCE: 889
caccaacggg accgagcgcg tgcgg 25

<210> SEQ ID NO 890
<211> LENGTH: 25
<212> TYPE: DNA
<213> ORGANISM: Artificial sequence
<220> FEATURE:
<223> OTHER INFORMATION: Synthetic sequence: Probe suitable for detection of genetic variations associated with IBD

<400> SEQUENCE: 890
ccgcacgcgc tccgtcccgt tggtg 25

<210> SEQ ID NO 891
<211> LENGTH: 25
<212> TYPE: DNA
<213> ORGANISM: Artificial sequence
<220> FEATURE:
<223> OTHER INFORMATION: Synthetic sequence: Probe suitable for detection of genetic variations associated with IBD

<400> SEQUENCE: 891
ccgcacgcgc tctgtcccgt tggtg 25

<210> SEQ ID NO 892
<211> LENGTH: 25
<212> TYPE: DNA
<213> ORGANISM: Artificial sequence
<220> FEATURE:
<223> OTHER INFORMATION: Synthetic sequence: Probe suitable for detection of genetic variations associated with IBD

<400> SEQUENCE: 892
ccgcacgcgc tcggtcccgt tggtg 25

<210> SEQ ID NO 893
<211> LENGTH: 25
<212> TYPE: DNA
<213> ORGANISM: Artificial sequence
<220> FEATURE:
<223> OTHER INFORMATION: Synthetic sequence: Probe suitable for detection of genetic variations associated with IBD

<400> SEQUENCE: 893
cgagtactgg aacagccaga aggaa 25

<210> SEQ ID NO 894
<211> LENGTH: 25
<212> TYPE: DNA
<213> ORGANISM: Artificial sequence
<220> FEATURE:
<223> OTHER INFORMATION: Synthetic sequence: Probe suitable for detection of genetic variations associated with IBD

<400> SEQUENCE: 894
cgagtactgg aatagccaga aggaa 25

<210> SEQ ID NO 895
<211> LENGTH: 25
<212> TYPE: DNA
<213> ORGANISM: Artificial sequence
<220> FEATURE:
<223> OTHER INFORMATION: Synthetic sequence: Probe suitable for detection of genetic variations associated with IBD

<400> SEQUENCE: 895
ttccttctgg ctgttccagt actcg 25

<210> SEQ ID NO 896
<211> LENGTH: 25
<212> TYPE: DNA
<213> ORGANISM: Artificial sequence
<220> FEATURE:
<223> OTHER INFORMATION: Synthetic sequence: Probe suitable for detection of genetic variations associated with IBD

<400> SEQUENCE: 896
ttccttctgg ctattccagt actcg 25

<210> SEQ ID NO 897
<211> LENGTH: 25
<212> TYPE: DNA
<213> ORGANISM: Artificial sequence
<220> FEATURE:
<223> OTHER INFORMATION: Synthetic sequence: Probe suitable for detection of genetic variations associated with IBD

<400> SEQUENCE: 897
cgaccacgtt tcttgtggca gctta 25

<210> SEQ ID NO 898
<211> LENGTH: 25
<212> TYPE: DNA
<213> ORGANISM: Artificial sequence
<220> FEATURE:
<223> OTHER INFORMATION: Synthetic sequence: Probe suitable for detection of genetic variations associated with IBD

<400> SEQUENCE: 898
taagctgcca caagaaacgt ggtcg 25

<210> SEQ ID NO 899
<211> LENGTH: 25
<212> TYPE: DNA
<213> ORGANISM: Artificial sequence
<220> FEATURE:
<223> OTHER INFORMATION: Synthetic sequence: Probe suitable for detection of genetic variations associated with IBD

<400> SEQUENCE: 899
cgaccacgtt tcctgtggca gctta 25

<210> SEQ ID NO 900
<211> LENGTH: 25
<212> TYPE: DNA
<213> ORGANISM: Artificial sequence
<220> FEATURE:
<223> OTHER INFORMATION: Synthetic sequence: Probe suitable for detection of genetic variations associated with IBD

<400> SEQUENCE: 900
taagctgcca caggaaacgt ggtcg 25

<210> SEQ ID NO 901
<211> LENGTH: 25
<212> TYPE: DNA
<213> ORGANISM: Artificial sequence
<220> FEATURE:
<223> OTHER INFORMATION: Synthetic sequence: Probe suitable for detection of genetic variations associated with IBD

<400> SEQUENCE: 901
tcttgtggca gcttaagttt gaatg 25

<210> SEQ ID NO 902
<211> LENGTH: 25
<212> TYPE: DNA
<213> ORGANISM: Artificial sequence
<220> FEATURE:
<223> OTHER INFORMATION: Synthetic sequence: Probe suitable for detection of genetic variations associated with IBD

<400> SEQUENCE: 902
cattcaaact taagctgcca caaga 25

<210> SEQ ID NO 903
<211> LENGTH: 25
<212> TYPE: DNA
<213> ORGANISM: Artificial sequence
<220> FEATURE:
<223> OTHER INFORMATION: Synthetic sequence: Probe suitable for
detection of genetic variations associated with IBD

<400> SEQUENCE: 903
tcttgtggca gcctaagttt gaatg 25

<210> SEQ ID NO 904
<211> LENGTH: 25
<212> TYPE: DNA
<213> ORGANISM: Artificial sequence
<220> FEATURE:
<223> OTHER INFORMATION: Synthetic sequence: Probe suitable for
detection of genetic variations associated with IBD

<400> SEQUENCE: 904
cattcaaact taggctgcca caaga 25

<210> SEQ ID NO 905
<211> LENGTH: 25
<212> TYPE: DNA
<213> ORGANISM: Artificial sequence
<220> FEATURE:
<223> OTHER INFORMATION: Synthetic sequence: Probe suitable for
detection of genetic variations associated with IBD

<400> SEQUENCE: 905
tcttgtggca gcgtaagttt gaatg 25

<210> SEQ ID NO 906
<211> LENGTH: 25
<212> TYPE: DNA
<213> ORGANISM: Artificial sequence
<220> FEATURE:
<223> OTHER INFORMATION: Synthetic sequence: Probe suitable for
detection of genetic variations associated with IBD

<400> SEQUENCE: 906
cattcaaact tacgctgcca caaga 25

<210> SEQ ID NO 907
<211> LENGTH: 25
<212> TYPE: DNA
<213> ORGANISM: Artificial sequence
<220> FEATURE:
<223> OTHER INFORMATION: Synthetic sequence: Probe suitable for
detection of genetic variations associated with IBD

<400> SEQUENCE: 907
tcttgtggca gcataagttt gaatg 25

<210> SEQ ID NO 908
<211> LENGTH: 25
<212> TYPE: DNA
<213> ORGANISM: Artificial sequence
<220> FEATURE:
<223> OTHER INFORMATION: Synthetic sequence: Probe suitable for
detection of genetic variations associated with IBD

<400> SEQUENCE: 908
cattcaaact tatgctgcca caaga 25

<210> SEQ ID NO 909

<211> LENGTH: 25
<212> TYPE: DNA
<213> ORGANISM: Artificial sequence
<220> FEATURE:
<223> OTHER INFORMATION: Synthetic sequence: Probe suitable for detection of genetic variations associated with IBD

<400> SEQUENCE: 909
tgtggcagct taagtttgaa tgtca 25

<210> SEQ ID NO 910
<211> LENGTH: 25
<212> TYPE: DNA
<213> ORGANISM: Artificial sequence
<220> FEATURE:
<223> OTHER INFORMATION: Synthetic sequence: Probe suitable for detection of genetic variations associated with IBD

<400> SEQUENCE: 910
tgacattcaa acttaagctg ccaca 25

<210> SEQ ID NO 911
<211> LENGTH: 25
<212> TYPE: DNA
<213> ORGANISM: Artificial sequence
<220> FEATURE:
<223> OTHER INFORMATION: Synthetic sequence: Probe suitable for detection of genetic variations associated with IBD

<400> SEQUENCE: 911
tgtggcagct tacgtttgaa tgtca 25

<210> SEQ ID NO 912
<211> LENGTH: 25
<212> TYPE: DNA
<213> ORGANISM: Artificial sequence
<220> FEATURE:
<223> OTHER INFORMATION: Synthetic sequence: Probe suitable for detection of genetic variations associated with IBD

<400> SEQUENCE: 912
tgacattcaa acgtaagctg ccaca 25

<210> SEQ ID NO 913
<211> LENGTH: 25
<212> TYPE: DNA
<213> ORGANISM: Artificial sequence
<220> FEATURE:
<223> OTHER INFORMATION: Synthetic sequence: Probe suitable for detection of genetic variations associated with IBD

<400> SEQUENCE: 913
tgtggcagct taggtttgaa tgtca 25

<210> SEQ ID NO 914
<211> LENGTH: 25
<212> TYPE: DNA
<213> ORGANISM: Artificial sequence
<220> FEATURE:
<223> OTHER INFORMATION: Synthetic sequence: Probe suitable for detection of genetic variations associated with IBD

<400> SEQUENCE: 914
tgacattcaa acctaagctg ccaca 25

<210> SEQ ID NO 915
<211> LENGTH: 25
<212> TYPE: DNA

<213> ORGANISM: Artificial sequence
<220> FEATURE:
<223> OTHER INFORMATION: Synthetic sequence: Probe suitable for detection of genetic variations associated with IBD

<400> SEQUENCE: 915
tgtggcagct tatgtttgaa tgtca 25

<210> SEQ ID NO 916
<211> LENGTH: 25
<212> TYPE: DNA
<213> ORGANISM: Artificial sequence
<220> FEATURE:
<223> OTHER INFORMATION: Synthetic sequence: Probe suitable for detection of genetic variations associated with IBD

<400> SEQUENCE: 916
tgacattcaa acataagctg ccaca 25

<210> SEQ ID NO 917
<211> LENGTH: 25
<212> TYPE: DNA
<213> ORGANISM: Artificial sequence
<220> FEATURE:
<223> OTHER INFORMATION: Synthetic sequence: Probe suitable for detection of genetic variations associated with IBD

<400> SEQUENCE: 917
gcttaagttt gaatgtcatt tcttc 25

<210> SEQ ID NO 918
<211> LENGTH: 25
<212> TYPE: DNA
<213> ORGANISM: Artificial sequence
<220> FEATURE:
<223> OTHER INFORMATION: Synthetic sequence: Probe suitable for detection of genetic variations associated with IBD

<400> SEQUENCE: 918
gaagaaatga cattcaaact taagc 25

<210> SEQ ID NO 919
<211> LENGTH: 25
<212> TYPE: DNA
<213> ORGANISM: Artificial sequence
<220> FEATURE:
<223> OTHER INFORMATION: Synthetic sequence: Probe suitable for detection of genetic variations associated with IBD

<400> SEQUENCE: 919
gcttaagttt gagtgtcatt tcttc 25

<210> SEQ ID NO 920
<211> LENGTH: 25
<212> TYPE: DNA
<213> ORGANISM: Artificial sequence
<220> FEATURE:
<223> OTHER INFORMATION: Synthetic sequence: Probe suitable for detection of genetic variations associated with IBD

<400> SEQUENCE: 920
gaagaaatga cactcaaact taagc 25

<210> SEQ ID NO 921
<211> LENGTH: 25
<212> TYPE: DNA
<213> ORGANISM: Artificial sequence
<220> FEATURE:

<223> OTHER INFORMATION: Synthetic sequence: Probe suitable for detection of genetic variations associated with IBD

<400> SEQUENCE: 921
cggagcgggt gcggttgctg gaaag 25

<210> SEQ ID NO 922
<211> LENGTH: 25
<212> TYPE: DNA
<213> ORGANISM: Artificial sequence
<220> FEATURE:
<223> OTHER INFORMATION: Synthetic sequence: Probe suitable for detection of genetic variations associated with IBD

<400> SEQUENCE: 922
ctttccagca accgcacccg ctccg 25

<210> SEQ ID NO 923
<211> LENGTH: 25
<212> TYPE: DNA
<213> ORGANISM: Artificial sequence
<220> FEATURE:
<223> OTHER INFORMATION: Synthetic sequence: Probe suitable for detection of genetic variations associated with IBD

<400> SEQUENCE: 923
cggagcgggt gcagttgctg gaaag 25

<210> SEQ ID NO 924
<211> LENGTH: 25
<212> TYPE: DNA
<213> ORGANISM: Artificial sequence
<220> FEATURE:
<223> OTHER INFORMATION: Synthetic sequence: Probe suitable for detection of genetic variations associated with IBD

<400> SEQUENCE: 924
ctttccagca actgcacccg ctccg 25

<210> SEQ ID NO 925
<211> LENGTH: 25
<212> TYPE: DNA
<213> ORGANISM: Artificial sequence
<220> FEATURE:
<223> OTHER INFORMATION: Synthetic sequence: Probe suitable for detection of genetic variations associated with IBD

<400> SEQUENCE: 925
cggagcgggt gctgttgctg gaaag 25

<210> SEQ ID NO 926
<211> LENGTH: 25
<212> TYPE: DNA
<213> ORGANISM: Artificial sequence
<220> FEATURE:
<223> OTHER INFORMATION: Synthetic sequence: Probe suitable for detection of genetic variations associated with IBD

<400> SEQUENCE: 926
ctttccagca acagcacccg ctccg 25

<210> SEQ ID NO 927
<211> LENGTH: 25
<212> TYPE: DNA
<213> ORGANISM: Artificial sequence
<220> FEATURE:
<223> OTHER INFORMATION: Synthetic sequence: Probe suitable for detection of genetic variations associated with IBD -continued

<400> SEQUENCE: 927
ttgctggaaa gatgcatcta taacc 25

<210> SEQ ID NO 928
<211> LENGTH: 25
<212> TYPE: DNA
<213> ORGANISM: Artificial sequence
<220> FEATURE:
<223> OTHER INFORMATION: Synthetic sequence: Probe suitable for detection of genetic variations associated with IBD

<400> SEQUENCE: 928
ggttatagat gcatctttcc agcaa 25

<210> SEQ ID NO 929
<211> LENGTH: 25
<212> TYPE: DNA
<213> ORGANISM: Artificial sequence
<220> FEATURE:
<223> OTHER INFORMATION: Synthetic sequence: Probe suitable for detection of genetic variations associated with IBD

<400> SEQUENCE: 929
ttgctggaaa gacgcatcta taacc 25

<210> SEQ ID NO 930
<211> LENGTH: 25
<212> TYPE: DNA
<213> ORGANISM: Artificial sequence
<220> FEATURE:
<223> OTHER INFORMATION: Synthetic sequence: Probe suitable for detection of genetic variations associated with IBD

<400> SEQUENCE: 930
ggttatagat gcgtctttcc agcaa 25

<210> SEQ ID NO 931
<211> LENGTH: 25
<212> TYPE: DNA
<213> ORGANISM: Artificial sequence
<220> FEATURE:
<223> OTHER INFORMATION: Synthetic sequence: Probe suitable for detection of genetic variations associated with IBD

<400> SEQUENCE: 931
ttgctggaaa gaggcatcta taacc 25

<210> SEQ ID NO 932
<211> LENGTH: 25
<212> TYPE: DNA
<213> ORGANISM: Artificial sequence
<220> FEATURE:
<223> OTHER INFORMATION: Synthetic sequence: Probe suitable for detection of genetic variations associated with IBD

<400> SEQUENCE: 932
ggttatagat gcctctttcc agcaa 25

<210> SEQ ID NO 933
<211> LENGTH: 25
<212> TYPE: DNA
<213> ORGANISM: Artificial sequence
<220> FEATURE:
<223> OTHER INFORMATION: Synthetic sequence: Probe suitable for detection of genetic variations associated with IBD

<400> SEQUENCE: 933
agatgcatct ataaccaaga ggagt 25

<210> SEQ ID NO 934
<211> LENGTH: 25
<212> TYPE: DNA
<213> ORGANISM: Artificial sequence
<220> FEATURE:
<223> OTHER INFORMATION: Synthetic sequence: Probe suitable for detection of genetic variations associated with IBD

<400> SEQUENCE: 934
actcctcttg gttatagatg catct 25

<210> SEQ ID NO 935
<211> LENGTH: 25
<212> TYPE: DNA
<213> ORGANISM: Artificial sequence
<220> FEATURE:
<223> OTHER INFORMATION: Synthetic sequence: Probe suitable for detection of genetic variations associated with IBD

<400> SEQUENCE: 935
agatgcatct atcaccaaga ggagt 25

<210> SEQ ID NO 936
<211> LENGTH: 25
<212> TYPE: DNA
<213> ORGANISM: Artificial sequence
<220> FEATURE:
<223> OTHER INFORMATION: Synthetic sequence: Probe suitable for detection of genetic variations associated with IBD

<400> SEQUENCE: 936
actcctcttg gtgatagatg catct 25

<210> SEQ ID NO 937
<211> LENGTH: 25
<212> TYPE: DNA
<213> ORGANISM: Artificial sequence
<220> FEATURE:
<223> OTHER INFORMATION: Synthetic sequence: Probe suitable for detection of genetic variations associated with IBD

<400> SEQUENCE: 937
agatgcatct ataccaagag gagtc 25

<210> SEQ ID NO 938
<211> LENGTH: 25
<212> TYPE: DNA
<213> ORGANISM: Artificial sequence
<220> FEATURE:
<223> OTHER INFORMATION: Synthetic sequence: Probe suitable for detection of genetic variations associated with IBD

<400> SEQUENCE: 938
gactcctctt ggtatagatg catct 25

<210> SEQ ID NO 939
<211> LENGTH: 25
<212> TYPE: DNA
<213> ORGANISM: Artificial sequence
<220> FEATURE:
<223> OTHER INFORMATION: Synthetic sequence: Probe suitable for detection of genetic variations associated with IBD

<400> SEQUENCE: 939
agccagaagg acctcctgga gcaga 25

<210> SEQ ID NO 940
<211> LENGTH: 25
<212> TYPE: DNA
<213> ORGANISM: Artificial sequence
<220> FEATURE:
<223> OTHER INFORMATION: Synthetic sequence: Probe suitable for
detection of genetic variations associated with IBD

<400> SEQUENCE: 940
tctgctccag gaggtccttc tggct 25

<210> SEQ ID NO 941
<211> LENGTH: 25
<212> TYPE: DNA
<213> ORGANISM: Artificial sequence
<220> FEATURE:
<223> OTHER INFORMATION: Synthetic sequence: Probe suitable for
detection of genetic variations associated with IBD

<400> SEQUENCE: 941
agccagaagg acatcctgga gcaga 25

<210> SEQ ID NO 942
<211> LENGTH: 25
<212> TYPE: DNA
<213> ORGANISM: Artificial sequence
<220> FEATURE:
<223> OTHER INFORMATION: Synthetic sequence: Probe suitable for
detection of genetic variations associated with IBD

<400> SEQUENCE: 942
tctgctccag gatgtccttc tggct 25

<210> SEQ ID NO 943
<211> LENGTH: 25
<212> TYPE: DNA
<213> ORGANISM: Artificial sequence
<220> FEATURE:
<223> OTHER INFORMATION: Synthetic sequence: Probe suitable for
detection of genetic variations associated with IBD

<400> SEQUENCE: 943
agccagaagg acttcctgga gcaga 25

<210> SEQ ID NO 944
<211> LENGTH: 25
<212> TYPE: DNA
<213> ORGANISM: Artificial sequence
<220> FEATURE:
<223> OTHER INFORMATION: Synthetic sequence: Probe suitable for
detection of genetic variations associated with IBD

<400> SEQUENCE: 944
tctgctccag gaagtccttc tggct 25

<210> SEQ ID NO 945
<211> LENGTH: 25
<212> TYPE: DNA
<213> ORGANISM: Artificial sequence
<220> FEATURE:
<223> OTHER INFORMATION: Synthetic sequence: Probe suitable for
detection of genetic variations associated with IBD

<400> SEQUENCE: 945
agcagaggcg ggccgcggtg gacac 25

<210> SEQ ID NO 946
<211> LENGTH: 25
<212> TYPE: DNA
<213> ORGANISM: Artificial sequence
<220> FEATURE:
<223> OTHER INFORMATION: Synthetic sequence: Probe suitable for detection of genetic variations associated with IBD

<400> SEQUENCE: 946
gtgtccaccg cggcccgcct ctgct 25

<210> SEQ ID NO 947
<211> LENGTH: 25
<212> TYPE: DNA
<213> ORGANISM: Artificial sequence
<220> FEATURE:
<223> OTHER INFORMATION: Synthetic sequence: Probe suitable for detection of genetic variations associated with IBD

<400> SEQUENCE: 947
agcagaggcg gggcgcggtg gacac 25

<210> SEQ ID NO 948
<211> LENGTH: 25
<212> TYPE: DNA
<213> ORGANISM: Artificial sequence
<220> FEATURE:
<223> OTHER INFORMATION: Synthetic sequence: Probe suitable for detection of genetic variations associated with IBD

<400> SEQUENCE: 948
gtgtccaccg cgccccgcct ctgct 25

<210> SEQ ID NO 949
<211> LENGTH: 25
<212> TYPE: DNA
<213> ORGANISM: Artificial sequence
<220> FEATURE:
<223> OTHER INFORMATION: Synthetic sequence: Probe suitable for detection of genetic variations associated with IBD

<400> SEQUENCE: 949
ccaactagtt gctggatact tgcaa 25

<210> SEQ ID NO 950
<211> LENGTH: 25
<212> TYPE: DNA
<213> ORGANISM: Artificial sequence
<220> FEATURE:
<223> OTHER INFORMATION: Synthetic sequence: Probe suitable for detection of genetic variations associated with IBD

<400> SEQUENCE: 950
ccaactagtt gccggatact tgcaa 25

<210> SEQ ID NO 951
<211> LENGTH: 25
<212> TYPE: DNA
<213> ORGANISM: Artificial sequence
<220> FEATURE:
<223> OTHER INFORMATION: Synthetic sequence: Probe suitable for detection of genetic variations associated with IBD

<400> SEQUENCE: 951
ttgcaagtat ccagcaacta gttgg 25

<210> SEQ ID NO 952
<211> LENGTH: 25

<212> TYPE: DNA
<213> ORGANISM: Artificial sequence
<220> FEATURE:
<223> OTHER INFORMATION: Synthetic sequence: Probe suitable for detection of genetic variations associated with IBD

<400> SEQUENCE: 952
ttgcaagtat ccggcaacta gttgg 25

<210> SEQ ID NO 953
<211> LENGTH: 25
<212> TYPE: DNA
<213> ORGANISM: Artificial sequence
<220> FEATURE:
<223> OTHER INFORMATION: Synthetic sequence: Probe suitable for detection of genetic variations associated with IBD

<400> SEQUENCE: 953
ttgccaggaa agccaatgta tgtgg 25

<210> SEQ ID NO 954
<211> LENGTH: 25
<212> TYPE: DNA
<213> ORGANISM: Artificial sequence
<220> FEATURE:
<223> OTHER INFORMATION: Synthetic sequence: Probe suitable for detection of genetic variations associated with IBD

<400> SEQUENCE: 954
ttgccaggaa agtcaatgta tgtgg 25

<210> SEQ ID NO 955
<211> LENGTH: 25
<212> TYPE: DNA
<213> ORGANISM: Artificial sequence
<220> FEATURE:
<223> OTHER INFORMATION: Synthetic sequence: Probe suitable for detection of genetic variations associated with IBD

<400> SEQUENCE: 955
ccacatacat tggctttcct ggcaa 25

<210> SEQ ID NO 956
<211> LENGTH: 25
<212> TYPE: DNA
<213> ORGANISM: Artificial sequence
<220> FEATURE:
<223> OTHER INFORMATION: Synthetic sequence: Probe suitable for detection of genetic variations associated with IBD

<400> SEQUENCE: 956
ccacatacat tgactttcct ggcaa 25

<210> SEQ ID NO 957
<211> LENGTH: 25
<212> TYPE: DNA
<213> ORGANISM: Artificial sequence
<220> FEATURE:
<223> OTHER INFORMATION: Synthetic sequence: Probe suitable for detection of genetic variations associated with IBD

<400> SEQUENCE: 957
acctatcttc ttcgacacat gggat 25

<210> SEQ ID NO 958
<211> LENGTH: 25
<212> TYPE: DNA
<213> ORGANISM: Artificial sequence
<220> FEATURE:
<223> OTHER INFORMATION: Synthetic sequence: Probe suitable for detection of genetic variations associated with IBD

<400> SEQUENCE: 958
acctatcttc tttgacacat gggat 25

<210> SEQ ID NO 959
<211> LENGTH: 25
<212> TYPE: DNA
<213> ORGANISM: Artificial sequence
<220> FEATURE:
<223> OTHER INFORMATION: Synthetic sequence: Probe suitable for detection of genetic variations associated with IBD

<400> SEQUENCE: 959
atcccatgtg tcgaagaaga taggt 25

<210> SEQ ID NO 960
<211> LENGTH: 25
<212> TYPE: DNA
<213> ORGANISM: Artificial sequence
<220> FEATURE:
<223> OTHER INFORMATION: Synthetic sequence: Probe suitable for detection of genetic variations associated with IBD

<400> SEQUENCE: 960
atcccatgtg tcaaagaaga taggt 25

<210> SEQ ID NO 961
<211> LENGTH: 25
<212> TYPE: DNA
<213> ORGANISM: Artificial sequence
<220> FEATURE:
<223> OTHER INFORMATION: Synthetic sequence: Probe suitable for detection of genetic variations associated with adverse reactions to pharmaceuticals

<400> SEQUENCE: 961
aaggccttcc agcgactgct ctgct 25

<210> SEQ ID NO 962
<211> LENGTH: 25
<212> TYPE: DNA
<213> ORGANISM: Artificial sequence
<220> FEATURE:
<223> OTHER INFORMATION: Synthetic sequence: Probe suitable for detection of genetic variations associated with adverse reactions to pharmaceuticals

<400> SEQUENCE: 962
aaggccttcc agggactgct ctgct 25

<210> SEQ ID NO 963
<211> LENGTH: 25
<212> TYPE: DNA
<213> ORGANISM: Artificial sequence
<220> FEATURE:
<223> OTHER INFORMATION: Synthetic sequence: Probe suitable for detection of genetic variations associated with adverse reactions to pharmaceuticals

<400> SEQUENCE: 963
agcagagcag tcgctggaag gcctt 25

<210> SEQ ID NO 964
<211> LENGTH: 25
<212> TYPE: DNA

<213> ORGANISM: Artificial sequence
<220> FEATURE:
<223> OTHER INFORMATION: Synthetic sequence: Probe suitable for detection of genetic variations associated with adverse reactions to pharmaceuticals

<400> SEQUENCE: 964
agcagagcag tccctggaag gcctt 25

<210> SEQ ID NO 965
<211> LENGTH: 25
<212> TYPE: DNA
<213> ORGANISM: Artificial sequence
<220> FEATURE:
<223> OTHER INFORMATION: Synthetic sequence: Probe suitable for detection of genetic variations associated with adverse reactions to pharmaceuticals

<400> SEQUENCE: 965
ctggcaccca atggaagcca tgcgc 25

<210> SEQ ID NO 966
<211> LENGTH: 25
<212> TYPE: DNA
<213> ORGANISM: Artificial sequence
<220> FEATURE:
<223> OTHER INFORMATION: Synthetic sequence: Probe suitable for detection of genetic variations associated with adverse reactions to pharmaceuticals

<400> SEQUENCE: 966
ctggcaccca atagaagcca tgcgc 25

<210> SEQ ID NO 967
<211> LENGTH: 25
<212> TYPE: DNA
<213> ORGANISM: Artificial sequence
<220> FEATURE:
<223> OTHER INFORMATION: Synthetic sequence: Probe suitable for detection of genetic variations associated with adverse reactions to pharmaceuticals

<400> SEQUENCE: 967
gcgcatggct tccattgggt gccag 25

<210> SEQ ID NO 968
<211> LENGTH: 25
<212> TYPE: DNA
<213> ORGANISM: Artificial sequence
<220> FEATURE:
<223> OTHER INFORMATION: Synthetic sequence: Probe suitable for detection of genetic variations associated with adverse reactions to pharmaceuticals

<400> SEQUENCE: 968
gcgcatggct tctattgggt gccag 25

<210> SEQ ID NO 969
<211> LENGTH: 25
<212> TYPE: DNA
<213> ORGANISM: Artificial sequence
<220> FEATURE:
<223> OTHER INFORMATION: Synthetic sequence: Probe suitable for detection of genetic variations associated with adverse reactions to pharmaceuticals

<400> SEQUENCE: 969
gacgtcacgc agcaaaggga cgagg 25

<210> SEQ ID NO 970
<211> LENGTH: 25
<212> TYPE: DNA
<213> ORGANISM: Artificial sequence
<220> FEATURE:
<223> OTHER INFORMATION: Synthetic sequence: Probe suitable for detection of genetic variations associated with adverse reactions to pharmaceuticals

<400> SEQUENCE: 970
gacgtcacgc aggaaaggga cgagg 25

<210> SEQ ID NO 971
<211> LENGTH: 25
<212> TYPE: DNA
<213> ORGANISM: Artificial sequence
<220> FEATURE:
<223> OTHER INFORMATION: Synthetic sequence: Probe suitable for detection of genetic variations associated with adverse reactions to pharmaceuticals

<400> SEQUENCE: 971
cctcgtccct ttgctgcgtg acgtc 25

<210> SEQ ID NO 972
<211> LENGTH: 25
<212> TYPE: DNA
<213> ORGANISM: Artificial sequence
<220> FEATURE:
<223> OTHER INFORMATION: Synthetic sequence: Probe suitable for detection of genetic variations associated with adverse reactions to pharmaceuticals

<400> SEQUENCE: 972
cctcgtccct ttcctgcgtg acgtc 25

<210> SEQ ID NO 973
<211> LENGTH: 25
<212> TYPE: DNA
<213> ORGANISM: Artificial sequence
<220> FEATURE:
<223> OTHER INFORMATION: Synthetic sequence: Probe suitable for detection of genetic variations associated with adverse reactions to pharmaceuticals

<400> SEQUENCE: 973
agttcaggtg gccactcagc tggct 25

<210> SEQ ID NO 974
<211> LENGTH: 25
<212> TYPE: DNA
<213> ORGANISM: Artificial sequence
<220> FEATURE:
<223> OTHER INFORMATION: Synthetic sequence: Probe suitable for detection of genetic variations associated with adverse reactions to pharmaceuticals

<400> SEQUENCE: 974
agttcaggtg gctactcagc tggct 25

<210> SEQ ID NO 975
<211> LENGTH: 25
<212> TYPE: DNA
<213> ORGANISM: Artificial sequence
<220> FEATURE:
<223> OTHER INFORMATION: Synthetic sequence: Probe suitable for detection of genetic variations associated with adverse reactions to pharmaceuticals

<400> SEQUENCE: 975
agccagctga gtggccacct gaact 25

<210> SEQ ID NO 976
<211> LENGTH: 25
<212> TYPE: DNA
<213> ORGANISM: Artificial sequence
<220> FEATURE:
<223> OTHER INFORMATION: Synthetic sequence: Probe suitable for detection of genetic variations associated with adverse reactions to pharmaceuticals

<400> SEQUENCE: 976
agccagctga gtagccacct gaact 25

<210> SEQ ID NO 977
<211> LENGTH: 25
<212> TYPE: DNA
<213> ORGANISM: Artificial sequence
<220> FEATURE:
<223> OTHER INFORMATION: Synthetic sequence: Probe suitable for detection of genetic variations associated with adverse reactions to pharmaceuticals

<400> SEQUENCE: 977
ctaggaaagc agcattctga agagg 25

<210> SEQ ID NO 978
<211> LENGTH: 25
<212> TYPE: DNA
<213> ORGANISM: Artificial sequence
<220> FEATURE:
<223> OTHER INFORMATION: Synthetic sequence: Probe suitable for detection of genetic variations associated with adverse reactions to pharmaceuticals

<400> SEQUENCE: 978
ctaggaaagc agtattctga agagg 25

<210> SEQ ID NO 979
<211> LENGTH: 25
<212> TYPE: DNA
<213> ORGANISM: Artificial sequence
<220> FEATURE:
<223> OTHER INFORMATION: Synthetic sequence: Probe suitable for detection of genetic variations associated with adverse reactions to pharmaceuticals

<400> SEQUENCE: 979
cctcttcaga atgctgcttt cctag 25

<210> SEQ ID NO 980
<211> LENGTH: 25
<212> TYPE: DNA
<213> ORGANISM: Artificial sequence
<220> FEATURE:
<223> OTHER INFORMATION: Synthetic sequence: Probe suitable for detection of genetic variations associated with adverse reactions to pharmaceuticals

<400> SEQUENCE: 980
cctcttcaga atactgcttt cctag 25

<210> SEQ ID NO 981
<211> LENGTH: 25
<212> TYPE: DNA
<213> ORGANISM: Artificial sequence
<220> FEATURE:

<223> OTHER INFORMATION: Synthetic sequence: Probe suitable for
      detection of genetic variations associated with adverse reactions
      to pharmaceuticals

<400> SEQUENCE: 981
gttagcttct ccggagttaa agtca 25

<210> SEQ ID NO 982
<211> LENGTH: 25
<212> TYPE: DNA
<213> ORGANISM: Artificial sequence
<220> FEATURE:
<223> OTHER INFORMATION: Synthetic sequence: Probe suitable for
      detection of genetic variations associated with adverse reactions
      to pharmaceuticals

<400> SEQUENCE: 982
gttagcttct ccagagttaa agtca 25

<210> SEQ ID NO 983
<211> LENGTH: 25
<212> TYPE: DNA
<213> ORGANISM: Artificial sequence
<220> FEATURE:
<223> OTHER INFORMATION: Synthetic sequence: Probe suitable for
      detection of genetic variations associated with adverse reactions
      to pharmaceuticals

<400> SEQUENCE: 983
tgactttaac tccggagaag ctaac 25

<210> SEQ ID NO 984
<211> LENGTH: 25
<212> TYPE: DNA
<213> ORGANISM: Artificial sequence
<220> FEATURE:
<223> OTHER INFORMATION: Synthetic sequence: Probe suitable for
      detection of genetic variations associated with adverse reactions
      to pharmaceuticals

<400> SEQUENCE: 984
tgactttaac tctggagaag ctaac 25

<210> SEQ ID NO 985
<211> LENGTH: 25
<212> TYPE: DNA
<213> ORGANISM: Artificial sequence
<220> FEATURE:
<223> OTHER INFORMATION: Synthetic sequence: Probe suitable for
      detection of genetic variations associated with adverse reactions
      to pharmaceuticals

<400> SEQUENCE: 985
gatttcgctg gcgtgaagga caagg 25

<210> SEQ ID NO 986
<211> LENGTH: 25
<212> TYPE: DNA
<213> ORGANISM: Artificial sequence
<220> FEATURE:
<223> OTHER INFORMATION: Synthetic sequence: Probe suitable for
      detection of genetic variations associated with adverse reactions
      to pharmaceuticals

<400> SEQUENCE: 986
gatttcgctg gcatgaagga caagg 25

<210> SEQ ID NO 987

<211> LENGTH: 25
<212> TYPE: DNA
<213> ORGANISM: Artificial sequence
<220> FEATURE:
<223> OTHER INFORMATION: Synthetic sequence: Probe suitable for detection of genetic variations associated with adverse reactions to pharmaceuticals

<400> SEQUENCE: 987
ccttgtcctt cacgccagcg aaatc 25

<210> SEQ ID NO 988
<211> LENGTH: 25
<212> TYPE: DNA
<213> ORGANISM: Artificial sequence
<220> FEATURE:
<223> OTHER INFORMATION: Synthetic sequence: Probe suitable for detection of genetic variations associated with adverse reactions to pharmaceuticals

<400> SEQUENCE: 988
ccttgtcctt catgccagcg aaatc 25

<210> SEQ ID NO 989
<211> LENGTH: 25
<212> TYPE: DNA
<213> ORGANISM: Artificial sequence
<220> FEATURE:
<223> OTHER INFORMATION: Synthetic sequence: Probe suitable for detection of genetic variations associated with adverse reactions to pharmaceuticals

<400> SEQUENCE: 989
cgctgcaaat acatctccct catct 25

<210> SEQ ID NO 990
<211> LENGTH: 25
<212> TYPE: DNA
<213> ORGANISM: Artificial sequence
<220> FEATURE:
<223> OTHER INFORMATION: Synthetic sequence: Probe suitable for detection of genetic variations associated with adverse reactions to pharmaceuticals

<400> SEQUENCE: 990
cgctgcaaat acgtctccct catct 25

<210> SEQ ID NO 991
<211> LENGTH: 25
<212> TYPE: DNA
<213> ORGANISM: Artificial sequence
<220> FEATURE:
<223> OTHER INFORMATION: Synthetic sequence: Probe suitable for detection of genetic variations associated with adverse reactions to pharmaceuticals

<400> SEQUENCE: 991
agatgaggga gatgtatttg cagcg 25

<210> SEQ ID NO 992
<211> LENGTH: 25
<212> TYPE: DNA
<213> ORGANISM: Artificial sequence
<220> FEATURE:
<223> OTHER INFORMATION: Synthetic sequence: Probe suitable for detection of genetic variations associated with adverse reactions to pharmaceuticals

<400> SEQUENCE: 992
agatgaggga gacgtatttg cagcg 25

<210> SEQ ID NO 993
<211> LENGTH: 25
<212> TYPE: DNA
<213> ORGANISM: Artificial sequence
<220> FEATURE:
<223> OTHER INFORMATION: Synthetic sequence: Probe suitable for detection of genetic variations associated with adverse reactions to pharmaceuticals

<400> SEQUENCE: 993
gcttccgagg aagggcagaa tggaa 25

<210> SEQ ID NO 994
<211> LENGTH: 25
<212> TYPE: DNA
<213> ORGANISM: Artificial sequence
<220> FEATURE:
<223> OTHER INFORMATION: Synthetic sequence: Probe suitable for detection of genetic variations associated with adverse reactions to pharmaceuticals

<400> SEQUENCE: 994
gcttccgagg aatggcagaa tggaa 25

<210> SEQ ID NO 995
<211> LENGTH: 25
<212> TYPE: DNA
<213> ORGANISM: Artificial sequence
<220> FEATURE:
<223> OTHER INFORMATION: Synthetic sequence: Probe suitable for detection of genetic variations associated with adverse reactions to pharmaceuticals

<400> SEQUENCE: 995
ttccattctg cccttcctcg gaagc 25

<210> SEQ ID NO 996
<211> LENGTH: 25
<212> TYPE: DNA
<213> ORGANISM: Artificial sequence
<220> FEATURE:
<223> OTHER INFORMATION: Synthetic sequence: Probe suitable for detection of genetic variations associated with adverse reactions to pharmaceuticals

<400> SEQUENCE: 996
ttccattctg ccattcctcg gaagc 25

<210> SEQ ID NO 997
<211> LENGTH: 25
<212> TYPE: DNA
<213> ORGANISM: Artificial sequence
<220> FEATURE:
<223> OTHER INFORMATION: Synthetic sequence: Probe suitable for detection of genetic variations associated with adverse reactions to pharmaceuticals

<400> SEQUENCE: 997
ggctgccctc ccggaggtaa ggcct 25

<210> SEQ ID NO 998
<211> LENGTH: 25
<212> TYPE: DNA
<213> ORGANISM: Artificial sequence
<220> FEATURE:
<223> OTHER INFORMATION: Synthetic sequence: Probe suitable for detection of genetic variations associated with adverse reactions to pharmaceuticals

<400> SEQUENCE: 998
ggctgccctc ccagaggtaa ggcct 25

<210> SEQ ID NO 999
<211> LENGTH: 25
<212> TYPE: DNA
<213> ORGANISM: Artificial sequence
<220> FEATURE:
<223> OTHER INFORMATION: Synthetic sequence: Probe suitable for detection of genetic variations associated with adverse reactions to pharmaceuticals

<400> SEQUENCE: 999
aggccttacc tccgggaggg cagcc 25

<210> SEQ ID NO 1000
<211> LENGTH: 25
<212> TYPE: DNA
<213> ORGANISM: Artificial sequence
<220> FEATURE:
<223> OTHER INFORMATION: Synthetic sequence: Probe suitable for detection of genetic variations associated with adverse reactions to pharmaceuticals

<400> SEQUENCE: 1000
aggccttacc tctgggaggg cagcc 25

<210> SEQ ID NO 1001
<211> LENGTH: 25
<212> TYPE: DNA
<213> ORGANISM: Artificial sequence
<220> FEATURE:
<223> OTHER INFORMATION: Synthetic sequence: Probe suitable for detection of genetic variations associated with adverse reactions to pharmaceuticals

<400> SEQUENCE: 1001
atcggtgaga ccattgcccg ctggg 25

<210> SEQ ID NO 1002
<211> LENGTH: 25
<212> TYPE: DNA
<213> ORGANISM: Artificial sequence
<220> FEATURE:
<223> OTHER INFORMATION: Synthetic sequence: Probe suitable for detection of genetic variations associated with adverse reactions to pharmaceuticals

<400> SEQUENCE: 1002
atcggtgaga ccgttgcccg ctggg 25

<210> SEQ ID NO 1003
<211> LENGTH: 25
<212> TYPE: DNA
<213> ORGANISM: Artificial sequence
<220> FEATURE:
<223> OTHER INFORMATION: Synthetic sequence: Probe suitable for detection of genetic variations associated with adverse reactions to pharmaceuticals

<400> SEQUENCE: 1003
cccagcgggc aatggtctca ccgat 25

<210> SEQ ID NO 1004
<211> LENGTH: 25
<212> TYPE: DNA

<213> ORGANISM: Artificial sequence
<220> FEATURE:
<223> OTHER INFORMATION: Synthetic sequence: Probe suitable for detection of genetic variations associated with adverse reactions to pharmaceuticals

<400> SEQUENCE: 1004
cccagcgggc aacggtctca ccgat 25

<210> SEQ ID NO 1005
<211> LENGTH: 25
<212> TYPE: DNA
<213> ORGANISM: Artificial sequence
<220> FEATURE:
<223> OTHER INFORMATION: Synthetic sequence: Probe suitable for detection of genetic variations associated with adverse reactions to pharmaceuticals

<400> SEQUENCE: 1005
taccaaatga gcattagcta ctttt 25

<210> SEQ ID NO 1006
<211> LENGTH: 25
<212> TYPE: DNA
<213> ORGANISM: Artificial sequence
<220> FEATURE:
<223> OTHER INFORMATION: Synthetic sequence: Probe suitable for detection of genetic variations associated with adverse reactions to pharmaceuticals

<400> SEQUENCE: 1006
taccaaatga gccttagcta ctttt 25

<210> SEQ ID NO 1007
<211> LENGTH: 25
<212> TYPE: DNA
<213> ORGANISM: Artificial sequence
<220> FEATURE:
<223> OTHER INFORMATION: Synthetic sequence: Probe suitable for detection of genetic variations associated with adverse reactions to pharmaceuticals

<400> SEQUENCE: 1007
aaaagtagct aatgctcatt tggta 25

<210> SEQ ID NO 1008
<211> LENGTH: 25
<212> TYPE: DNA
<213> ORGANISM: Artificial sequence
<220> FEATURE:
<223> OTHER INFORMATION: Synthetic sequence: Probe suitable for detection of genetic variations associated with adverse reactions to pharmaceuticals

<400> SEQUENCE: 1008
aaaagtagct aaggctcatt tggta 25

<210> SEQ ID NO 1009
<211> LENGTH: 25
<212> TYPE: DNA
<213> ORGANISM: Artificial sequence
<220> FEATURE:
<223> OTHER INFORMATION: Synthetic sequence: Probe suitable for detection of genetic variations associated with adverse reactions to pharmaceuticals

<400> SEQUENCE: 1009
tgccatctaa ccatcttttc ttctc 25

<210> SEQ ID NO 1010
<211> LENGTH: 25
<212> TYPE: DNA
<213> ORGANISM: Artificial sequence
<220> FEATURE:
<223> OTHER INFORMATION: Synthetic sequence: Probe suitable for detection of genetic variations associated with adverse reactions to pharmaceuticals

<400> SEQUENCE: 1010
tgccatctaa ccgtcttttc ttctc 25

<210> SEQ ID NO 1011
<211> LENGTH: 25
<212> TYPE: DNA
<213> ORGANISM: Artificial sequence
<220> FEATURE:
<223> OTHER INFORMATION: Synthetic sequence: Probe suitable for detection of genetic variations associated with adverse reactions to pharmaceuticals

<400> SEQUENCE: 1011
gagaagaaaa gatggttaga tggca 25

<210> SEQ ID NO 1012
<211> LENGTH: 25
<212> TYPE: DNA
<213> ORGANISM: Artificial sequence
<220> FEATURE:
<223> OTHER INFORMATION: Synthetic sequence: Probe suitable for detection of genetic variations associated with adverse reactions to pharmaceuticals

<400> SEQUENCE: 1012
gagaagaaaa gacggttaga tggca 25

<210> SEQ ID NO 1013
<211> LENGTH: 25
<212> TYPE: DNA
<213> ORGANISM: Artificial sequence
<220> FEATURE:
<223> OTHER INFORMATION: Synthetic sequence: Probe suitable for detection of genetic variations associated with adverse reactions to pharmaceuticals

<400> SEQUENCE: 1013
gctgctccct gacgggagcc agtgt 25

<210> SEQ ID NO 1014
<211> LENGTH: 25
<212> TYPE: DNA
<213> ORGANISM: Artificial sequence
<220> FEATURE:
<223> OTHER INFORMATION: Synthetic sequence: Probe suitable for detection of genetic variations associated with adverse reactions to pharmaceuticals

<400> SEQUENCE: 1014
gctgctccct gatgggagcc agtgt 25

<210> SEQ ID NO 1015
<211> LENGTH: 25
<212> TYPE: DNA
<213> ORGANISM: Artificial sequence
<220> FEATURE:
<223> OTHER INFORMATION: Synthetic sequence: Probe suitable for detection of genetic variations associated with adverse reactions to pharmaceuticals

<400> SEQUENCE: 1015
acactggctc ccgtcaggga gcagc 25

<210> SEQ ID NO 1016
<211> LENGTH: 25
<212> TYPE: DNA
<213> ORGANISM: Artificial sequence
<220> FEATURE:
<223> OTHER INFORMATION: Synthetic sequence: Probe suitable for detection of genetic variations associated with adverse reactions to pharmaceuticals

<400> SEQUENCE: 1016
acactggctc ccatcaggga gcagc 25

<210> SEQ ID NO 1017
<211> LENGTH: 25
<212> TYPE: DNA
<213> ORGANISM: Artificial sequence
<220> FEATURE:
<223> OTHER INFORMATION: Synthetic sequence: Probe suitable for detection of genetic variations associated with adverse reactions to pharmaceuticals

<400> SEQUENCE: 1017
agcattgagg accgtgttca agagg 25

<210> SEQ ID NO 1018
<211> LENGTH: 25
<212> TYPE: DNA
<213> ORGANISM: Artificial sequence
<220> FEATURE:
<223> OTHER INFORMATION: Synthetic sequence: Probe suitable for detection of genetic variations associated with adverse reactions to pharmaceuticals

<400> SEQUENCE: 1018
agcattgagg actgtgttca agagg 25

<210> SEQ ID NO 1019
<211> LENGTH: 25
<212> TYPE: DNA
<213> ORGANISM: Artificial sequence
<220> FEATURE:
<223> OTHER INFORMATION: Synthetic sequence: Probe suitable for detection of genetic variations associated with adverse reactions to pharmaceuticals

<400> SEQUENCE: 1019
cctcttgaac acggtcctca atgct 25

<210> SEQ ID NO 1020
<211> LENGTH: 25
<212> TYPE: DNA
<213> ORGANISM: Artificial sequence
<220> FEATURE:
<223> OTHER INFORMATION: Synthetic sequence: Probe suitable for detection of genetic variations associated with adverse reactions to pharmaceuticals

<400> SEQUENCE: 1020
cctcttgaac acagtcctca atgct 25

<210> SEQ ID NO 1021
<211> LENGTH: 25
<212> TYPE: DNA
<213> ORGANISM: Artificial sequence
<220> FEATURE:

<223> OTHER INFORMATION: Synthetic sequence: Probe suitable for
      detection of genetic variations associated with adverse reactions
      to pharmaceuticals

<400> SEQUENCE: 1021
gtccagagat acattgacct tctcc 25

<210> SEQ ID NO 1022
<211> LENGTH: 25
<212> TYPE: DNA
<213> ORGANISM: Artificial sequence
<220> FEATURE:
<223> OTHER INFORMATION: Synthetic sequence: Probe suitable for
      detection of genetic variations associated with adverse reactions
      to pharmaceuticals

<400> SEQUENCE: 1022
gtccagagat accttgacct tctcc 25

<210> SEQ ID NO 1023
<211> LENGTH: 25
<212> TYPE: DNA
<213> ORGANISM: Artificial sequence
<220> FEATURE:
<223> OTHER INFORMATION: Synthetic sequence: Probe suitable for
      detection of genetic variations associated with adverse reactions
      to pharmaceuticals

<400> SEQUENCE: 1023
ggagaaggtc aatgtatctc tggac 25

<210> SEQ ID NO 1024
<211> LENGTH: 25
<212> TYPE: DNA
<213> ORGANISM: Artificial sequence
<220> FEATURE:
<223> OTHER INFORMATION: Synthetic sequence: Probe suitable for
      detection of genetic variations associated with adverse reactions
      to pharmaceuticals

<400> SEQUENCE: 1024
ggagaaggtc aaggtatctc tggac 25

<210> SEQ ID NO 1025
<211> LENGTH: 25
<212> TYPE: DNA
<213> ORGANISM: Artificial sequence
<220> FEATURE:
<223> OTHER INFORMATION: Synthetic sequence: Probe suitable for
      detection of genetic variations associated with adverse reactions
      to pharmaceuticals

<400> SEQUENCE: 1025
tgaaaatgga gaaggtaaaa tgtaa 25

<210> SEQ ID NO 1026
<211> LENGTH: 25
<212> TYPE: DNA
<213> ORGANISM: Artificial sequence
<220> FEATURE:
<223> OTHER INFORMATION: Synthetic sequence: Probe suitable for
      detection of genetic variations associated with adverse reactions
      to pharmaceuticals

<400> SEQUENCE: 1026
tgaaaatgga gaggtaaaat gtaaa 25

<210> SEQ ID NO 1027

<211> LENGTH: 25
<212> TYPE: DNA
<213> ORGANISM: Artificial sequence
<220> FEATURE:
<223> OTHER INFORMATION: Synthetic sequence: Probe suitable for detection of genetic variations associated with adverse reactions to pharmaceuticals

<400> SEQUENCE: 1027
ttacatttta ccttctccat tttca 25

<210> SEQ ID NO 1028
<211> LENGTH: 25
<212> TYPE: DNA
<213> ORGANISM: Artificial sequence
<220> FEATURE:
<223> OTHER INFORMATION: Synthetic sequence: Probe suitable for detection of genetic variations associated with adverse reactions to pharmaceuticals

<400> SEQUENCE: 1028
tttacatttt acctctccat tttca 25

<210> SEQ ID NO 1029
<211> LENGTH: 25
<212> TYPE: DNA
<213> ORGANISM: Artificial sequence
<220> FEATURE:
<223> OTHER INFORMATION: Synthetic sequence: Probe suitable for detection of genetic variations associated with adverse reactions to pharmaceuticals

<400> SEQUENCE: 1029
tccagagata cattgacctt ctccc 25

<210> SEQ ID NO 1030
<211> LENGTH: 25
<212> TYPE: DNA
<213> ORGANISM: Artificial sequence
<220> FEATURE:
<223> OTHER INFORMATION: Synthetic sequence: Probe suitable for detection of genetic variations associated with adverse reactions to pharmaceuticals

<400> SEQUENCE: 1030
tccagagata cactgacctt ctccc 25

<210> SEQ ID NO 1031
<211> LENGTH: 25
<212> TYPE: DNA
<213> ORGANISM: Artificial sequence
<220> FEATURE:
<223> OTHER INFORMATION: Synthetic sequence: Probe suitable for detection of genetic variations associated with adverse reactions to pharmaceuticals

<400> SEQUENCE: 1031
gggagaaggt caatgtatct ctgga 25

<210> SEQ ID NO 1032
<211> LENGTH: 25
<212> TYPE: DNA
<213> ORGANISM: Artificial sequence
<220> FEATURE:
<223> OTHER INFORMATION: Synthetic sequence: Probe suitable for detection of genetic variations associated with adverse reactions to pharmaceuticals

<400> SEQUENCE: 1032
gggagaaggt cagtgtatct ctgga 25

<210> SEQ ID NO 1033
<211> LENGTH: 25
<212> TYPE: DNA
<213> ORGANISM: Artificial sequence
<220> FEATURE:
<223> OTHER INFORMATION: Synthetic sequence: Probe suitable for detection of genetic variations associated with adverse reactions to pharmaceuticals

<400> SEQUENCE: 1033
gagatacatt gaccttctcc ccacc 25

<210> SEQ ID NO 1034
<211> LENGTH: 25
<212> TYPE: DNA
<213> ORGANISM: Artificial sequence
<220> FEATURE:
<223> OTHER INFORMATION: Synthetic sequence: Probe suitable for detection of genetic variations associated with adverse reactions to pharmaceuticals

<400> SEQUENCE: 1034
gagatacatt gagcttctcc ccacc 25

<210> SEQ ID NO 1035
<211> LENGTH: 25
<212> TYPE: DNA
<213> ORGANISM: Artificial sequence
<220> FEATURE:
<223> OTHER INFORMATION: Synthetic sequence: Probe suitable for detection of genetic variations associated with adverse reactions to pharmaceuticals

<400> SEQUENCE: 1035
ggtggggaga aggtcaatgt atctc 25

<210> SEQ ID NO 1036
<211> LENGTH: 25
<212> TYPE: DNA
<213> ORGANISM: Artificial sequence
<220> FEATURE:
<223> OTHER INFORMATION: Synthetic sequence: Probe suitable for detection of genetic variations associated with adverse reactions to pharmaceuticals

<400> SEQUENCE: 1036
ggtggggaga agctcaatgt atctc 25

<210> SEQ ID NO 1037
<211> LENGTH: 25
<212> TYPE: DNA
<213> ORGANISM: Artificial sequence
<220> FEATURE:
<223> OTHER INFORMATION: Synthetic sequence: Probe suitable for detection of genetic variations associated with adverse reactions to pharmaceuticals

<400> SEQUENCE: 1037
tgcacatccg gaggtaggat catga 25

<210> SEQ ID NO 1038
<211> LENGTH: 25
<212> TYPE: DNA
<213> ORGANISM: Artificial sequence
<220> FEATURE:
<223> OTHER INFORMATION: Synthetic sequence: Probe suitable for detection of genetic variations associated with adverse reactions to pharmaceuticals

<400> SEQUENCE: 1038
tgcacatccg gatgtaggat catga 25

<210> SEQ ID NO 1039
<211> LENGTH: 25
<212> TYPE: DNA
<213> ORGANISM: Artificial sequence
<220> FEATURE:
<223> OTHER INFORMATION: Synthetic sequence: Probe suitable for detection of genetic variations associated with adverse reactions to pharmaceuticals

<400> SEQUENCE: 1039
tcatgatcct acctccggat gtgca 25

<210> SEQ ID NO 1040
<211> LENGTH: 25
<212> TYPE: DNA
<213> ORGANISM: Artificial sequence
<220> FEATURE:
<223> OTHER INFORMATION: Synthetic sequence: Probe suitable for detection of genetic variations associated with adverse reactions to pharmaceuticals

<400> SEQUENCE: 1040
tcatgatcct acatccggat gtgca 25

<210> SEQ ID NO 1041
<211> LENGTH: 25
<212> TYPE: DNA
<213> ORGANISM: Artificial sequence
<220> FEATURE:
<223> OTHER INFORMATION: Synthetic sequence: Probe suitable for detection of genetic variations associated with adverse reactions to pharmaceuticals

<400> SEQUENCE: 1041
gcgcttctcc gtgtccacct tgcgc 25

<210> SEQ ID NO 1042
<211> LENGTH: 25
<212> TYPE: DNA
<213> ORGANISM: Artificial sequence
<220> FEATURE:
<223> OTHER INFORMATION: Synthetic sequence: Probe suitable for detection of genetic variations associated with adverse reactions to pharmaceuticals

<400> SEQUENCE: 1042
gcgcttctcc gtctccacct tgcgc 25

<210> SEQ ID NO 1043
<211> LENGTH: 25
<212> TYPE: DNA
<213> ORGANISM: Artificial sequence
<220> FEATURE:
<223> OTHER INFORMATION: Synthetic sequence: Probe suitable for detection of genetic variations associated with adverse reactions to pharmaceuticals

<400> SEQUENCE: 1043
gcgcaaggtg gacacggaga agcgc 25

<210> SEQ ID NO 1044
<211> LENGTH: 25
<212> TYPE: DNA

<213> ORGANISM: Artificial sequence
<220> FEATURE:
<223> OTHER INFORMATION: Synthetic sequence: Probe suitable for detection of genetic variations associated with adverse reactions to pharmaceuticals

<400> SEQUENCE: 1044
gcgcaaggtg gagacggaga agcgc 25

<210> SEQ ID NO 1045
<211> LENGTH: 25
<212> TYPE: DNA
<213> ORGANISM: Artificial sequence
<220> FEATURE:
<223> OTHER INFORMATION: Synthetic sequence: Probe suitable for detection of genetic variations associated with adverse reactions to pharmaceuticals

<400> SEQUENCE: 1045
gtgcccctgg ccgtgatagt ggcca 25

<210> SEQ ID NO 1046
<211> LENGTH: 25
<212> TYPE: DNA
<213> ORGANISM: Artificial sequence
<220> FEATURE:
<223> OTHER INFORMATION: Synthetic sequence: Probe suitable for detection of genetic variations associated with adverse reactions to pharmaceuticals

<400> SEQUENCE: 1046
gtgcccctgg ccatgatagt ggcca 25

<210> SEQ ID NO 1047
<211> LENGTH: 25
<212> TYPE: DNA
<213> ORGANISM: Artificial sequence
<220> FEATURE:
<223> OTHER INFORMATION: Synthetic sequence: Probe suitable for detection of genetic variations associated with adverse reactions to pharmaceuticals

<400> SEQUENCE: 1047
tggccactat cacggccagg ggcac 25

<210> SEQ ID NO 1048
<211> LENGTH: 25
<212> TYPE: DNA
<213> ORGANISM: Artificial sequence
<220> FEATURE:
<223> OTHER INFORMATION: Synthetic sequence: Probe suitable for detection of genetic variations associated with adverse reactions to pharmaceuticals

<400> SEQUENCE: 1048
tggccactat catggccagg ggcac 25

<210> SEQ ID NO 1049
<211> LENGTH: 25
<212> TYPE: DNA
<213> ORGANISM: Artificial sequence
<220> FEATURE:
<223> OTHER INFORMATION: Synthetic sequence: Probe suitable for detection of genetic variations associated with adverse reactions to pharmaceuticals

<400> SEQUENCE: 1049
gcggcgccgc aactgcagag ggagg 25

<210> SEQ ID NO 1050
<211> LENGTH: 25
<212> TYPE: DNA
<213> ORGANISM: Artificial sequence
<220> FEATURE:
<223> OTHER INFORMATION: Synthetic sequence: Probe suitable for detection of genetic variations associated with adverse reactions to pharmaceuticals

<400> SEQUENCE: 1050
gcggcgccgc aagtgcagag ggagg 25

<210> SEQ ID NO 1051
<211> LENGTH: 25
<212> TYPE: DNA
<213> ORGANISM: Artificial sequence
<220> FEATURE:
<223> OTHER INFORMATION: Synthetic sequence: Probe suitable for detection of genetic variations associated with adverse reactions to pharmaceuticals

<400> SEQUENCE: 1051
cctccctctg cagttgcggc gccgc 25

<210> SEQ ID NO 1052
<211> LENGTH: 25
<212> TYPE: DNA
<213> ORGANISM: Artificial sequence
<220> FEATURE:
<223> OTHER INFORMATION: Synthetic sequence: Probe suitable for detection of genetic variations associated with adverse reactions to pharmaceuticals

<400> SEQUENCE: 1052
cctccctctg cacttgcggc gccgc 25

<210> SEQ ID NO 1053
<211> LENGTH: 25
<212> TYPE: DNA
<213> ORGANISM: Artificial sequence
<220> FEATURE:
<223> OTHER INFORMATION: Synthetic sequence: Probe suitable for detection of genetic variations associated with adverse reactions to pharmaceuticals

<400> SEQUENCE: 1053
gatcctgggt ttcgggccgc gttcc 25

<210> SEQ ID NO 1054
<211> LENGTH: 25
<212> TYPE: DNA
<213> ORGANISM: Artificial sequence
<220> FEATURE:
<223> OTHER INFORMATION: Synthetic sequence: Probe suitable for detection of genetic variations associated with adverse reactions to pharmaceuticals

<400> SEQUENCE: 1054
gatcctgggt tttgggccgc gttcc 25

<210> SEQ ID NO 1055
<211> LENGTH: 25
<212> TYPE: DNA
<213> ORGANISM: Artificial sequence
<220> FEATURE:
<223> OTHER INFORMATION: Synthetic sequence: Probe suitable for detection of genetic variations associated with adverse reactions to pharmaceuticals

<400> SEQUENCE: 1055
ggaacgcggc ccgaaaccca ggatc 25

<210> SEQ ID NO 1056
<211> LENGTH: 25
<212> TYPE: DNA
<213> ORGANISM: Artificial sequence
<220> FEATURE:
<223> OTHER INFORMATION: Synthetic sequence: Probe suitable for detection of genetic variations associated with adverse reactions to pharmaceuticals

<400> SEQUENCE: 1056
ggaacgcggc ccaaaaccca ggatc 25

<210> SEQ ID NO 1057
<211> LENGTH: 25
<212> TYPE: DNA
<213> ORGANISM: Artificial sequence
<220> FEATURE:
<223> OTHER INFORMATION: Synthetic sequence: Probe suitable for detection of genetic variations associated with adverse reactions to pharmaceuticals

<400> SEQUENCE: 1057
ctttcctggt gagcccatcc cccta 25

<210> SEQ ID NO 1058
<211> LENGTH: 25
<212> TYPE: DNA
<213> ORGANISM: Artificial sequence
<220> FEATURE:
<223> OTHER INFORMATION: Synthetic sequence: Probe suitable for detection of genetic variations associated with adverse reactions to pharmaceuticals

<400> SEQUENCE: 1058
ctttcctggt gaccccatcc cccta 25

<210> SEQ ID NO 1059
<211> LENGTH: 25
<212> TYPE: DNA
<213> ORGANISM: Artificial sequence
<220> FEATURE:
<223> OTHER INFORMATION: Synthetic sequence: Probe suitable for detection of genetic variations associated with adverse reactions to pharmaceuticals

<400> SEQUENCE: 1059
tagggggatg ggctcaccag gaaag 25

<210> SEQ ID NO 1060
<211> LENGTH: 25
<212> TYPE: DNA
<213> ORGANISM: Artificial sequence
<220> FEATURE:
<223> OTHER INFORMATION: Synthetic sequence: Probe suitable for detection of genetic variations associated with adverse reactions to pharmaceuticals

<400> SEQUENCE: 1060
tagggggatg gggtcaccag gaaag 25

<210> SEQ ID NO 1061
<211> LENGTH: 25
<212> TYPE: DNA
<213> ORGANISM: Artificial sequence
<220> FEATURE:

<223> OTHER INFORMATION: Synthetic sequence: Probe suitable for detection of genetic variations associated with adverse reactions to pharmaceuticals

<400> SEQUENCE: 1061
ctcccacccc caggacgccc ctttc 25

<210> SEQ ID NO 1062
<211> LENGTH: 25
<212> TYPE: DNA
<213> ORGANISM: Artificial sequence
<220> FEATURE:
<223> OTHER INFORMATION: Synthetic sequence: Probe suitable for detection of genetic variations associated with adverse reactions to pharmaceuticals

<400> SEQUENCE: 1062
ctcccacccc caagacgccc ctttc 25

<210> SEQ ID NO 1063
<211> LENGTH: 25
<212> TYPE: DNA
<213> ORGANISM: Artificial sequence
<220> FEATURE:
<223> OTHER INFORMATION: Synthetic sequence: Probe suitable for detection of genetic variations associated with adverse reactions to pharmaceuticals

<400> SEQUENCE: 1063
gaaaggggcg tcctgggggt gggag 25

<210> SEQ ID NO 1064
<211> LENGTH: 25
<212> TYPE: DNA
<213> ORGANISM: Artificial sequence
<220> FEATURE:
<223> OTHER INFORMATION: Synthetic sequence: Probe suitable for detection of genetic variations associated with adverse reactions to pharmaceuticals

<400> SEQUENCE: 1064
gaaaggggcg tcttgggggt gggag 25

<210> SEQ ID NO 1065
<211> LENGTH: 25
<212> TYPE: DNA
<213> ORGANISM: Artificial sequence
<220> FEATURE:
<223> OTHER INFORMATION: Synthetic sequence: Probe suitable for detection of genetic variations associated with adverse reactions to pharmaceuticals

<400> SEQUENCE: 1065
cttggaagaa cccggtctct acaaa 25

<210> SEQ ID NO 1066
<211> LENGTH: 25
<212> TYPE: DNA
<213> ORGANISM: Artificial sequence
<220> FEATURE:
<223> OTHER INFORMATION: Synthetic sequence: Probe suitable for detection of genetic variations associated with adverse reactions to pharmaceuticals

<400> SEQUENCE: 1066
cttggaagaa ccgggtctct acaaa 25

<210> SEQ ID NO 1067

-continued

<211> LENGTH: 25
<212> TYPE: DNA
<213> ORGANISM: Artificial sequence
<220> FEATURE:
<223> OTHER INFORMATION: Synthetic sequence: Probe suitable for detection of genetic variations associated with adverse reactions to pharmaceuticals

<400> SEQUENCE: 1067
tttgtagaga ccgggttctt ccaag 25

<210> SEQ ID NO 1068
<211> LENGTH: 25
<212> TYPE: DNA
<213> ORGANISM: Artificial sequence
<220> FEATURE:
<223> OTHER INFORMATION: Synthetic sequence: Probe suitable for detection of genetic variations associated with adverse reactions to pharmaceuticals

<400> SEQUENCE: 1068
tttgtagaga cccggttctt ccaag 25

<210> SEQ ID NO 1069
<211> LENGTH: 25
<212> TYPE: DNA
<213> ORGANISM: Artificial sequence
<220> FEATURE:
<223> OTHER INFORMATION: Synthetic sequence: Probe suitable for detection of genetic variations associated with adverse reactions to pharmaceuticals

<400> SEQUENCE: 1069
gctgcacgct acccaccagg ccccc 25

<210> SEQ ID NO 1070
<211> LENGTH: 25
<212> TYPE: DNA
<213> ORGANISM: Artificial sequence
<220> FEATURE:
<223> OTHER INFORMATION: Synthetic sequence: Probe suitable for detection of genetic variations associated with adverse reactions to pharmaceuticals

<400> SEQUENCE: 1070
gctgcacgct actcaccagg ccccc 25

<210> SEQ ID NO 1071
<211> LENGTH: 25
<212> TYPE: DNA
<213> ORGANISM: Artificial sequence
<220> FEATURE:
<223> OTHER INFORMATION: Synthetic sequence: Probe suitable for detection of genetic variations associated with adverse reactions to pharmaceuticals

<400> SEQUENCE: 1071
gggggcctgg tgggtagcgt gcagc 25

<210> SEQ ID NO 1072
<211> LENGTH: 25
<212> TYPE: DNA
<213> ORGANISM: Artificial sequence
<220> FEATURE:
<223> OTHER INFORMATION: Synthetic sequence: Probe suitable for detection of genetic variations associated with adverse reactions to pharmaceuticals

<400> SEQUENCE: 1072
gggggcctgg tgagtagcgt gcagc 25

<210> SEQ ID NO 1073
<211> LENGTH: 25
<212> TYPE: DNA
<213> ORGANISM: Artificial sequence
<220> FEATURE:
<223> OTHER INFORMATION: Synthetic sequence: Probe suitable for detection of genetic variations associated with adverse reactions to pharmaceuticals

<400> SEQUENCE: 1073
gctgggcaac ctgctgcatg tggac 25

<210> SEQ ID NO 1074
<211> LENGTH: 25
<212> TYPE: DNA
<213> ORGANISM: Artificial sequence
<220> FEATURE:
<223> OTHER INFORMATION: Synthetic sequence: Probe suitable for detection of genetic variations associated with adverse reactions to pharmaceuticals

<400> SEQUENCE: 1074
gctgggcaac cttgctgcat gtgga 25

<210> SEQ ID NO 1075
<211> LENGTH: 25
<212> TYPE: DNA
<213> ORGANISM: Artificial sequence
<220> FEATURE:
<223> OTHER INFORMATION: Synthetic sequence: Probe suitable for detection of genetic variations associated with adverse reactions to pharmaceuticals

<400> SEQUENCE: 1075
gtccacatgc agcaggttgc ccagc 25

<210> SEQ ID NO 1076
<211> LENGTH: 25
<212> TYPE: DNA
<213> ORGANISM: Artificial sequence
<220> FEATURE:
<223> OTHER INFORMATION: Synthetic sequence: Probe suitable for detection of genetic variations associated with adverse reactions to pharmaceuticals

<400> SEQUENCE: 1076
tccacatgca gcaaggttgc ccagc 25

<210> SEQ ID NO 1077
<211> LENGTH: 25
<212> TYPE: DNA
<213> ORGANISM: Artificial sequence
<220> FEATURE:
<223> OTHER INFORMATION: Synthetic sequence: Probe suitable for detection of genetic variations associated with adverse reactions to pharmaceuticals

<400> SEQUENCE: 1077
ctgtgcccat cacccagatc ctggg 25

<210> SEQ ID NO 1078
<211> LENGTH: 25
<212> TYPE: DNA
<213> ORGANISM: Artificial sequence
<220> FEATURE:
<223> OTHER INFORMATION: Synthetic sequence: Probe suitable for detection of genetic variations associated with adverse reactions to pharmaceuticals

<400> SEQUENCE: 1078
ctgtgcccat catccagatc ctggg 25

<210> SEQ ID NO 1079
<211> LENGTH: 25
<212> TYPE: DNA
<213> ORGANISM: Artificial sequence
<220> FEATURE:
<223> OTHER INFORMATION: Synthetic sequence: Probe suitable for detection of genetic variations associated with adverse reactions to pharmaceuticals

<400> SEQUENCE: 1079
cccaggatct gggtgatggg cacag 25

<210> SEQ ID NO 1080
<211> LENGTH: 25
<212> TYPE: DNA
<213> ORGANISM: Artificial sequence
<220> FEATURE:
<223> OTHER INFORMATION: Synthetic sequence: Probe suitable for detection of genetic variations associated with adverse reactions to pharmaceuticals

<400> SEQUENCE: 1080
cccaggatct ggatgatggg cacag 25

<210> SEQ ID NO 1081
<211> LENGTH: 25
<212> TYPE: DNA
<213> ORGANISM: Artificial sequence
<220> FEATURE:
<223> OTHER INFORMATION: Synthetic sequence: Probe suitable for detection of genetic variations associated with adverse reactions to pharmaceuticals

<400> SEQUENCE: 1081
aggcgcttct ccgtgtccac cttgc 25

<210> SEQ ID NO 1082
<211> LENGTH: 25
<212> TYPE: DNA
<213> ORGANISM: Artificial sequence
<220> FEATURE:
<223> OTHER INFORMATION: Synthetic sequence: Probe suitable for detection of genetic variations associated with adverse reactions to pharmaceuticals

<400> SEQUENCE: 1082
aggcgcttct ccatgtccac cttgc 25

<210> SEQ ID NO 1083
<211> LENGTH: 25
<212> TYPE: DNA
<213> ORGANISM: Artificial sequence
<220> FEATURE:
<223> OTHER INFORMATION: Synthetic sequence: Probe suitable for detection of genetic variations associated with adverse reactions to pharmaceuticals

<400> SEQUENCE: 1083
gcaaggtgga cacggagaag cgcct 25

<210> SEQ ID NO 1084
<211> LENGTH: 25
<212> TYPE: DNA

<213> ORGANISM: Artificial sequence
<220> FEATURE:
<223> OTHER INFORMATION: Synthetic sequence: Probe suitable for detection of genetic variations associated with adverse reactions to pharmaceuticals

<400> SEQUENCE: 1084
gcaaggtgga catggagaag cgcct 25

<210> SEQ ID NO 1085
<211> LENGTH: 25
<212> TYPE: DNA
<213> ORGANISM: Artificial sequence
<220> FEATURE:
<223> OTHER INFORMATION: Synthetic sequence: Probe suitable for detection of genetic variations associated with adverse reactions to pharmaceuticals

<400> SEQUENCE: 1085
tcgctggagc agtgggtgac cgagg 25

<210> SEQ ID NO 1086
<211> LENGTH: 25
<212> TYPE: DNA
<213> ORGANISM: Artificial sequence
<220> FEATURE:
<223> OTHER INFORMATION: Synthetic sequence: Probe suitable for detection of genetic variations associated with adverse reactions to pharmaceuticals

<400> SEQUENCE: 1086
tcgctggagc aggggtgacc gagga 25

<210> SEQ ID NO 1087
<211> LENGTH: 25
<212> TYPE: DNA
<213> ORGANISM: Artificial sequence
<220> FEATURE:
<223> OTHER INFORMATION: Synthetic sequence: Probe suitable for detection of genetic variations associated with adverse reactions to pharmaceuticals

<400> SEQUENCE: 1087
cctcggtcac ccactgctcc agcga 25

<210> SEQ ID NO 1088
<211> LENGTH: 25
<212> TYPE: DNA
<213> ORGANISM: Artificial sequence
<220> FEATURE:
<223> OTHER INFORMATION: Synthetic sequence: Probe suitable for detection of genetic variations associated with adverse reactions to pharmaceuticals

<400> SEQUENCE: 1088
tcctcggtca cccctgctcc agcga 25

<210> SEQ ID NO 1089
<211> LENGTH: 25
<212> TYPE: DNA
<213> ORGANISM: Artificial sequence
<220> FEATURE:
<223> OTHER INFORMATION: Synthetic sequence: Probe suitable for detection of genetic variations associated with adverse reactions to pharmaceuticals

<400> SEQUENCE: 1089
gccaaccact ccggtgggtg atggg 25

<210> SEQ ID NO 1090
<211> LENGTH: 25
<212> TYPE: DNA
<213> ORGANISM: Artificial sequence
<220> FEATURE:
<223> OTHER INFORMATION: Synthetic sequence: Probe suitable for detection of genetic variations associated with adverse reactions to pharmaceuticals

<400> SEQUENCE: 1090
gccaaccact ccagtgggtg atggg 25

<210> SEQ ID NO 1091
<211> LENGTH: 25
<212> TYPE: DNA
<213> ORGANISM: Artificial sequence
<220> FEATURE:
<223> OTHER INFORMATION: Synthetic sequence: Probe suitable for detection of genetic variations associated with adverse reactions to pharmaceuticals

<400> SEQUENCE: 1091
cccatcaccc accggagtgg ttggc 25

<210> SEQ ID NO 1092
<211> LENGTH: 25
<212> TYPE: DNA
<213> ORGANISM: Artificial sequence
<220> FEATURE:
<223> OTHER INFORMATION: Synthetic sequence: Probe suitable for detection of genetic variations associated with adverse reactions to pharmaceuticals

<400> SEQUENCE: 1092
cccatcaccc actggagtgg ttggc 25

<210> SEQ ID NO 1093
<211> LENGTH: 25
<212> TYPE: DNA
<213> ORGANISM: Artificial sequence
<220> FEATURE:
<223> OTHER INFORMATION: Synthetic sequence: Probe suitable for detection of genetic variations associated with adverse reactions to pharmaceuticals

<400> SEQUENCE: 1093
gccaaccact ccggtgggtg atggg 25

<210> SEQ ID NO 1094
<211> LENGTH: 25
<212> TYPE: DNA
<213> ORGANISM: Artificial sequence
<220> FEATURE:
<223> OTHER INFORMATION: Synthetic sequence: Probe suitable for detection of genetic variations associated with adverse reactions to pharmaceuticals

<400> SEQUENCE: 1094
gccaaccact cctgtgggtg atggg 25

<210> SEQ ID NO 1095
<211> LENGTH: 25
<212> TYPE: DNA
<213> ORGANISM: Artificial sequence
<220> FEATURE:
<223> OTHER INFORMATION: Synthetic sequence: Probe suitable for detection of genetic variations associated with adverse reactions to pharmaceuticals

<400> SEQUENCE: 1095
cccatcaccc accggagtgg ttggc 25

<210> SEQ ID NO 1096
<211> LENGTH: 25
<212> TYPE: DNA
<213> ORGANISM: Artificial sequence
<220> FEATURE:
<223> OTHER INFORMATION: Synthetic sequence: Probe suitable for detection of genetic variations associated with adverse reactions to pharmaceuticals

<400> SEQUENCE: 1096
cccatcaccc acaggagtgg ttggc 25

<210> SEQ ID NO 1097
<211> LENGTH: 25
<212> TYPE: DNA
<213> ORGANISM: Artificial sequence
<220> FEATURE:
<223> OTHER INFORMATION: Synthetic sequence: Probe suitable for detection of genetic variations associated with adverse reactions to pharmaceuticals

<400> SEQUENCE: 1097
ccctttcgcc ccaacggtct cttgg 25

<210> SEQ ID NO 1098
<211> LENGTH: 25
<212> TYPE: DNA
<213> ORGANISM: Artificial sequence
<220> FEATURE:
<223> OTHER INFORMATION: Synthetic sequence: Probe suitable for detection of genetic variations associated with adverse reactions to pharmaceuticals

<400> SEQUENCE: 1098
ccctttcgcc cctttcgccc caacg 25

<210> SEQ ID NO 1099
<211> LENGTH: 25
<212> TYPE: DNA
<213> ORGANISM: Artificial sequence
<220> FEATURE:
<223> OTHER INFORMATION: Synthetic sequence: Probe suitable for detection of genetic variations associated with adverse reactions to pharmaceuticals

<400> SEQUENCE: 1099
ccaagagacc gttggggcga aaggg 25

<210> SEQ ID NO 1100
<211> LENGTH: 25
<212> TYPE: DNA
<213> ORGANISM: Artificial sequence
<220> FEATURE:
<223> OTHER INFORMATION: Synthetic sequence: Probe suitable for detection of genetic variations associated with adverse reactions to pharmaceuticals

<400> SEQUENCE: 1100
cgttggggcg aaaggggcga aaggg 25

<210> SEQ ID NO 1101
<211> LENGTH: 25
<212> TYPE: DNA
<213> ORGANISM: Artificial sequence
<220> FEATURE:

<223> OTHER INFORMATION: Synthetic sequence: Probe suitable for detection of genetic variations associated with adverse reactions to pharmaceuticals

<400> SEQUENCE: 1101
acctagctca ggagggactg aagga 25

<210> SEQ ID NO 1102
<211> LENGTH: 25
<212> TYPE: DNA
<213> ORGANISM: Artificial sequence
<220> FEATURE:
<223> OTHER INFORMATION: Synthetic sequence: Probe suitable for detection of genetic variations associated with adverse reactions to pharmaceuticals

<400> SEQUENCE: 1102
acctagctca gggagggact gaagg 25

<210> SEQ ID NO 1103
<211> LENGTH: 25
<212> TYPE: DNA
<213> ORGANISM: Artificial sequence
<220> FEATURE:
<223> OTHER INFORMATION: Synthetic sequence: Probe suitable for detection of genetic variations associated with adverse reactions to pharmaceuticals

<400> SEQUENCE: 1103
tccttcagtc cctcctgagc taggt 25

<210> SEQ ID NO 1104
<211> LENGTH: 25
<212> TYPE: DNA
<213> ORGANISM: Artificial sequence
<220> FEATURE:
<223> OTHER INFORMATION: Synthetic sequence: Probe suitable for detection of genetic variations associated with adverse reactions to pharmaceuticals

<400> SEQUENCE: 1104
ccttcagtcc ctccctgagc taggt 25

<210> SEQ ID NO 1105
<211> LENGTH: 25
<212> TYPE: DNA
<213> ORGANISM: Artificial sequence
<220> FEATURE:
<223> OTHER INFORMATION: Synthetic sequence: Probe suitable for detection of genetic variations associated with adverse reactions to pharmaceuticals

<400> SEQUENCE: 1105
ggatgagctg ctaactgagc acagg 25

<210> SEQ ID NO 1106
<211> LENGTH: 25
<212> TYPE: DNA
<213> ORGANISM: Artificial sequence
<220> FEATURE:
<223> OTHER INFORMATION: Synthetic sequence: Probe suitable for detection of genetic variations associated with adverse reactions to pharmaceuticals

<400> SEQUENCE: 1106
ggatgagctg ctgagcacag gatga 25

<210> SEQ ID NO 1107

<211> LENGTH: 25
<212> TYPE: DNA
<213> ORGANISM: Artificial sequence
<220> FEATURE:
<223> OTHER INFORMATION: Synthetic sequence: Probe suitable for detection of genetic variations associated with adverse reactions to pharmaceuticals

<400> SEQUENCE: 1107
cctgtgctca gttagcagct catcc 25

<210> SEQ ID NO 1108
<211> LENGTH: 25
<212> TYPE: DNA
<213> ORGANISM: Artificial sequence
<220> FEATURE:
<223> OTHER INFORMATION: Synthetic sequence: Probe suitable for detection of genetic variations associated with adverse reactions to pharmaceuticals

<400> SEQUENCE: 1108
tcatcctgtg ctcagcagct catcc 25

<210> SEQ ID NO 1109
<211> LENGTH: 25
<212> TYPE: DNA
<213> ORGANISM: Artificial sequence
<220> FEATURE:
<223> OTHER INFORMATION: Synthetic sequence: Probe suitable for detection of genetic variations associated with adverse reactions to pharmaceuticals

<400> SEQUENCE: 1109
ctaactgagc acaggatgac ctggg 25

<210> SEQ ID NO 1110
<211> LENGTH: 25
<212> TYPE: DNA
<213> ORGANISM: Artificial sequence
<220> FEATURE:
<223> OTHER INFORMATION: Synthetic sequence: Probe suitable for detection of genetic variations associated with adverse reactions to pharmaceuticals

<400> SEQUENCE: 1110
ctaactgagc acggatgacc tggga 25

<210> SEQ ID NO 1111
<211> LENGTH: 25
<212> TYPE: DNA
<213> ORGANISM: Artificial sequence
<220> FEATURE:
<223> OTHER INFORMATION: Synthetic sequence: Probe suitable for detection of genetic variations associated with adverse reactions to pharmaceuticals

<400> SEQUENCE: 1111
cccaggtcat cctgtgctca gttag 25

<210> SEQ ID NO 1112
<211> LENGTH: 25
<212> TYPE: DNA
<213> ORGANISM: Artificial sequence
<220> FEATURE:
<223> OTHER INFORMATION: Synthetic sequence: Probe suitable for detection of genetic variations associated with adverse reactions to pharmaceuticals

<400> SEQUENCE: 1112
tcccaggtca tccgtgctca gttag 25

<210> SEQ ID NO 1113
<211> LENGTH: 25
<212> TYPE: DNA
<213> ORGANISM: Artificial sequence
<220> FEATURE:
<223> OTHER INFORMATION: Synthetic sequence: Probe suitable for detection of genetic variations associated with adverse reactions to pharmaceuticals

<400> SEQUENCE: 1113
tggcagagat ggagaaggtg agagt 25

<210> SEQ ID NO 1114
<211> LENGTH: 25
<212> TYPE: DNA
<213> ORGANISM: Artificial sequence
<220> FEATURE:
<223> OTHER INFORMATION: Synthetic sequence: Probe suitable for detection of genetic variations associated with adverse reactions to pharmaceuticals

<400> SEQUENCE: 1114
tggcagagat ggaggtgaga gtggc 25

<210> SEQ ID NO 1115
<211> LENGTH: 25
<212> TYPE: DNA
<213> ORGANISM: Artificial sequence
<220> FEATURE:
<223> OTHER INFORMATION: Synthetic sequence: Probe suitable for detection of genetic variations associated with adverse reactions to pharmaceuticals

<400> SEQUENCE: 1115
actctcacct tctccatctc tgcca 25

<210> SEQ ID NO 1116
<211> LENGTH: 25
<212> TYPE: DNA
<213> ORGANISM: Artificial sequence
<220> FEATURE:
<223> OTHER INFORMATION: Synthetic sequence: Probe suitable for detection of genetic variations associated with adverse reactions to pharmaceuticals

<400> SEQUENCE: 1116
gccactctca cctccatctc tgcca 25

<210> SEQ ID NO 1117
<211> LENGTH: 25
<212> TYPE: DNA
<213> ORGANISM: Artificial sequence
<220> FEATURE:
<223> OTHER INFORMATION: Synthetic sequence: Probe suitable for detection of genetic variations associated with adverse reactions to pharmaceuticals

<400> SEQUENCE: 1117
gatgagaacc tgcgcatagt ggtgg 25

<210> SEQ ID NO 1118
<211> LENGTH: 25
<212> TYPE: DNA
<213> ORGANISM: Artificial sequence
<220> FEATURE:
<223> OTHER INFORMATION: Synthetic sequence: Probe suitable for detection of genetic variations associated with adverse reactions to pharmaceuticals

<400> SEQUENCE: 1118
gatgagaacc tgtgcatagt ggtgg 25

<210> SEQ ID NO 1119
<211> LENGTH: 25
<212> TYPE: DNA
<213> ORGANISM: Artificial sequence
<220> FEATURE:
<223> OTHER INFORMATION: Synthetic sequence: Probe suitable for detection of genetic variations associated with adverse reactions to pharmaceuticals

<400> SEQUENCE: 1119
ccaccactat gcgcaggttc tcatc 25

<210> SEQ ID NO 1120
<211> LENGTH: 25
<212> TYPE: DNA
<213> ORGANISM: Artificial sequence
<220> FEATURE:
<223> OTHER INFORMATION: Synthetic sequence: Probe suitable for detection of genetic variations associated with adverse reactions to pharmaceuticals

<400> SEQUENCE: 1120
ccaccactat gcacaggttc tcatc 25

<210> SEQ ID NO 1121
<211> LENGTH: 25
<212> TYPE: DNA
<213> ORGANISM: Artificial sequence
<220> FEATURE:
<223> OTHER INFORMATION: Synthetic sequence: Probe suitable for detection of genetic variations associated with adverse reactions to pharmaceuticals

<400> SEQUENCE: 1121
gagatcgacg acgtgatagg gcagg 25

<210> SEQ ID NO 1122
<211> LENGTH: 25
<212> TYPE: DNA
<213> ORGANISM: Artificial sequence
<220> FEATURE:
<223> OTHER INFORMATION: Synthetic sequence: Probe suitable for detection of genetic variations associated with adverse reactions to pharmaceuticals

<400> SEQUENCE: 1122
gagatcgacg acatgatagg gcagg 25

<210> SEQ ID NO 1123
<211> LENGTH: 25
<212> TYPE: DNA
<213> ORGANISM: Artificial sequence
<220> FEATURE:
<223> OTHER INFORMATION: Synthetic sequence: Probe suitable for detection of genetic variations associated with adverse reactions to pharmaceuticals

<400> SEQUENCE: 1123
cctgccctat cacgtcgtcg atctc 25

<210> SEQ ID NO 1124
<211> LENGTH: 25
<212> TYPE: DNA

<213> ORGANISM: Artificial sequence
<220> FEATURE:
<223> OTHER INFORMATION: Synthetic sequence: Probe suitable for detection of genetic variations associated with adverse reactions to pharmaceuticals

<400> SEQUENCE: 1124
cctgccctat catgtcgtcg atctc 25

<210> SEQ ID NO 1125
<211> LENGTH: 25
<212> TYPE: DNA
<213> ORGANISM: Artificial sequence
<220> FEATURE:
<223> OTHER INFORMATION: Synthetic sequence: Probe suitable for detection of genetic variations associated with adverse reactions to pharmaceuticals

<400> SEQUENCE: 1125
atagggcagg tgcggcgacc agaga 25

<210> SEQ ID NO 1126
<211> LENGTH: 25
<212> TYPE: DNA
<213> ORGANISM: Artificial sequence
<220> FEATURE:
<223> OTHER INFORMATION: Synthetic sequence: Probe suitable for detection of genetic variations associated with adverse reactions to pharmaceuticals

<400> SEQUENCE: 1126
atagggcagg tggggcgacc agaga 25

<210> SEQ ID NO 1127
<211> LENGTH: 25
<212> TYPE: DNA
<213> ORGANISM: Artificial sequence
<220> FEATURE:
<223> OTHER INFORMATION: Synthetic sequence: Probe suitable for detection of genetic variations associated with adverse reactions to pharmaceuticals

<400> SEQUENCE: 1127
tctctggtcg ccgcacctgc cctat 25

<210> SEQ ID NO 1128
<211> LENGTH: 25
<212> TYPE: DNA
<213> ORGANISM: Artificial sequence
<220> FEATURE:
<223> OTHER INFORMATION: Synthetic sequence: Probe suitable for detection of genetic variations associated with adverse reactions to pharmaceuticals

<400> SEQUENCE: 1128
tctctggtcg ccccacctgc cctat 25

<210> SEQ ID NO 1129
<211> LENGTH: 25
<212> TYPE: DNA
<213> ORGANISM: Artificial sequence
<220> FEATURE:
<223> OTHER INFORMATION: Synthetic sequence: Probe suitable for detection of genetic variations associated with adverse reactions to pharmaceuticals

<400> SEQUENCE: 1129
gctttgggga catcgtcccc ctggg 25

<210> SEQ ID NO 1130
<211> LENGTH: 25
<212> TYPE: DNA
<213> ORGANISM: Artificial sequence
<220> FEATURE:
<223> OTHER INFORMATION: Synthetic sequence: Probe suitable for detection of genetic variations associated with adverse reactions to pharmaceuticals

<400> SEQUENCE: 1130
gctttgggga caccgtcccc ctggg 25

<210> SEQ ID NO 1131
<211> LENGTH: 25
<212> TYPE: DNA
<213> ORGANISM: Artificial sequence
<220> FEATURE:
<223> OTHER INFORMATION: Synthetic sequence: Probe suitable for detection of genetic variations associated with adverse reactions to pharmaceuticals

<400> SEQUENCE: 1131
cccaggggga cgatgtcccc aaagc 25

<210> SEQ ID NO 1132
<211> LENGTH: 25
<212> TYPE: DNA
<213> ORGANISM: Artificial sequence
<220> FEATURE:
<223> OTHER INFORMATION: Synthetic sequence: Probe suitable for detection of genetic variations associated with adverse reactions to pharmaceuticals

<400> SEQUENCE: 1132
cccaggggga cggtgtcccc aaagc 25

<210> SEQ ID NO 1133
<211> LENGTH: 25
<212> TYPE: DNA
<213> ORGANISM: Artificial sequence
<220> FEATURE:
<223> OTHER INFORMATION: Synthetic sequence: Probe suitable for detection of genetic variations associated with adverse reactions to pharmaceuticals

<400> SEQUENCE: 1133
tccccacagg ccgccgtgca tgcct 25

<210> SEQ ID NO 1134
<211> LENGTH: 25
<212> TYPE: DNA
<213> ORGANISM: Artificial sequence
<220> FEATURE:
<223> OTHER INFORMATION: Synthetic sequence: Probe suitable for detection of genetic variations associated with adverse reactions to pharmaceuticals

<400> SEQUENCE: 1134
tccccacagg ccaccgtgca tgcct 25

<210> SEQ ID NO 1135
<211> LENGTH: 25
<212> TYPE: DNA
<213> ORGANISM: Artificial sequence
<220> FEATURE:
<223> OTHER INFORMATION: Synthetic sequence: Probe suitable for detection of genetic variations associated with adverse reactions to pharmaceuticals

<400> SEQUENCE: 1135
aggcatgcac ggcggcctgt gggga 25

<210> SEQ ID NO 1136
<211> LENGTH: 25
<212> TYPE: DNA
<213> ORGANISM: Artificial sequence
<220> FEATURE:
<223> OTHER INFORMATION: Synthetic sequence: Probe suitable for detection of genetic variations associated with adverse reactions to pharmaceuticals

<400> SEQUENCE: 1136
aggcatgcac ggtggcctgt gggga 25

<210> SEQ ID NO 1137
<211> LENGTH: 25
<212> TYPE: DNA
<213> ORGANISM: Artificial sequence
<220> FEATURE:
<223> OTHER INFORMATION: Synthetic sequence: Probe suitable for detection of genetic variations associated with adverse reactions to pharmaceuticals

<400> SEQUENCE: 1137
tcggtgccca ctggacagcc ccggc 25

<210> SEQ ID NO 1138
<211> LENGTH: 25
<212> TYPE: DNA
<213> ORGANISM: Artificial sequence
<220> FEATURE:
<223> OTHER INFORMATION: Synthetic sequence: Probe suitable for detection of genetic variations associated with adverse reactions to pharmaceuticals

<400> SEQUENCE: 1138
tcggtgccca ctgtgcccac tggac 25

<210> SEQ ID NO 1139
<211> LENGTH: 25
<212> TYPE: DNA
<213> ORGANISM: Artificial sequence
<220> FEATURE:
<223> OTHER INFORMATION: Synthetic sequence: Probe suitable for detection of genetic variations associated with adverse reactions to pharmaceuticals

<400> SEQUENCE: 1139
gccggggctg tccagtgggc accga 25

<210> SEQ ID NO 1140
<211> LENGTH: 25
<212> TYPE: DNA
<213> ORGANISM: Artificial sequence
<220> FEATURE:
<223> OTHER INFORMATION: Synthetic sequence: Probe suitable for detection of genetic variations associated with adverse reactions to pharmaceuticals

<400> SEQUENCE: 1140
gtccagtggg cacagtgggc accga 25

<210> SEQ ID NO 1141
<211> LENGTH: 25
<212> TYPE: DNA
<213> ORGANISM: Artificial sequence
<220> FEATURE:

<223> OTHER INFORMATION: Synthetic sequence: Probe suitable for detection of genetic variations associated with adverse reactions to pharmaceuticals

<400> SEQUENCE: 1141
gattgcttcc tgatcaaaat ggagc 25

<210> SEQ ID NO 1142
<211> LENGTH: 25
<212> TYPE: DNA
<213> ORGANISM: Artificial sequence
<220> FEATURE:
<223> OTHER INFORMATION: Synthetic sequence: Probe suitable for detection of genetic variations associated with adverse reactions to pharmaceuticals

<400> SEQUENCE: 1142
gattgcttcc tgttcaaaat ggagc 25

<210> SEQ ID NO 1143
<211> LENGTH: 25
<212> TYPE: DNA
<213> ORGANISM: Artificial sequence
<220> FEATURE:
<223> OTHER INFORMATION: Synthetic sequence: Probe suitable for detection of genetic variations associated with adverse reactions to pharmaceuticals

<400> SEQUENCE: 1143
gctccatttt gatcaggaag caatc 25

<210> SEQ ID NO 1144
<211> LENGTH: 25
<212> TYPE: DNA
<213> ORGANISM: Artificial sequence
<220> FEATURE:
<223> OTHER INFORMATION: Synthetic sequence: Probe suitable for detection of genetic variations associated with adverse reactions to pharmaceuticals

<400> SEQUENCE: 1144
gctccatttt gaacaggaag caatc 25

<210> SEQ ID NO 1145
<211> LENGTH: 25
<212> TYPE: DNA
<213> ORGANISM: Artificial sequence
<220> FEATURE:
<223> OTHER INFORMATION: Synthetic sequence: Probe suitable for detection of genetic variations associated with adverse reactions to pharmaceuticals

<400> SEQUENCE: 1145
ggatggggaa gaggagcatt gagga 25

<210> SEQ ID NO 1146
<211> LENGTH: 25
<212> TYPE: DNA
<213> ORGANISM: Artificial sequence
<220> FEATURE:
<223> OTHER INFORMATION: Synthetic sequence: Probe suitable for detection of genetic variations associated with adverse reactions to pharmaceuticals

<400> SEQUENCE: 1146
ggatggggaa gaagagcatt gagga 25

<210> SEQ ID NO 1147

<211> LENGTH: 25
<212> TYPE: DNA
<213> ORGANISM: Artificial sequence
<220> FEATURE:
<223> OTHER INFORMATION: Synthetic sequence: Probe suitable for detection of genetic variations associated with adverse reactions to pharmaceuticals

<400> SEQUENCE: 1147
tcctcaatgc tcctcttccc catcc 25

<210> SEQ ID NO 1148
<211> LENGTH: 25
<212> TYPE: DNA
<213> ORGANISM: Artificial sequence
<220> FEATURE:
<223> OTHER INFORMATION: Synthetic sequence: Probe suitable for detection of genetic variations associated with adverse reactions to pharmaceuticals

<400> SEQUENCE: 1148
tcctcaatgc tcttcttccc catcc 25

<210> SEQ ID NO 1149
<211> LENGTH: 25
<212> TYPE: DNA
<213> ORGANISM: Artificial sequence
<220> FEATURE:
<223> OTHER INFORMATION: Synthetic sequence: Probe suitable for detection of genetic variations associated with adverse reactions to pharmaceuticals

<400> SEQUENCE: 1149
ttaggaaatt ctttgtcatc atgta 25

<210> SEQ ID NO 1150
<211> LENGTH: 25
<212> TYPE: DNA
<213> ORGANISM: Artificial sequence
<220> FEATURE:
<223> OTHER INFORMATION: Synthetic sequence: Probe suitable for detection of genetic variations associated with adverse reactions to pharmaceuticals

<400> SEQUENCE: 1150
ttaggaaatt ctctgtcatc atgta 25

<210> SEQ ID NO 1151
<211> LENGTH: 25
<212> TYPE: DNA
<213> ORGANISM: Artificial sequence
<220> FEATURE:
<223> OTHER INFORMATION: Synthetic sequence: Probe suitable for detection of genetic variations associated with adverse reactions to pharmaceuticals

<400> SEQUENCE: 1151
tacatgatga caaagaattt cctaa 25

<210> SEQ ID NO 1152
<211> LENGTH: 25
<212> TYPE: DNA
<213> ORGANISM: Artificial sequence
<220> FEATURE:
<223> OTHER INFORMATION: Synthetic sequence: Probe suitable for detection of genetic variations associated with adverse reactions to pharmaceuticals

<400> SEQUENCE: 1152
tacatgatga cagagaattt cctaa 25

<210> SEQ ID NO 1153
<211> LENGTH: 25
<212> TYPE: DNA
<213> ORGANISM: Artificial sequence
<220> FEATURE:
<223> OTHER INFORMATION: Synthetic sequence: Probe suitable for detection of genetic variations associated with adverse reactions to pharmaceuticals

<400> SEQUENCE: 1153
tcgggacttt atcgattgct tcctg 25

<210> SEQ ID NO 1154
<211> LENGTH: 25
<212> TYPE: DNA
<213> ORGANISM: Artificial sequence
<220> FEATURE:
<223> OTHER INFORMATION: Synthetic sequence: Probe suitable for detection of genetic variations associated with adverse reactions to pharmaceuticals

<400> SEQUENCE: 1154
tcgggacttt atggattgct tcctg 25

<210> SEQ ID NO 1155
<211> LENGTH: 25
<212> TYPE: DNA
<213> ORGANISM: Artificial sequence
<220> FEATURE:
<223> OTHER INFORMATION: Synthetic sequence: Probe suitable for detection of genetic variations associated with adverse reactions to pharmaceuticals

<400> SEQUENCE: 1155
caggaagcaa tcgataaagt cccga 25

<210> SEQ ID NO 1156
<211> LENGTH: 25
<212> TYPE: DNA
<213> ORGANISM: Artificial sequence
<220> FEATURE:
<223> OTHER INFORMATION: Synthetic sequence: Probe suitable for detection of genetic variations associated with adverse reactions to pharmaceuticals

<400> SEQUENCE: 1156
caggaagcaa tccataaagt cccga 25

<210> SEQ ID NO 1157
<211> LENGTH: 25
<212> TYPE: DNA
<213> ORGANISM: Artificial sequence
<220> FEATURE:
<223> OTHER INFORMATION: Synthetic sequence: Probe suitable for detection of genetic variations associated with adverse reactions to pharmaceuticals

<400> SEQUENCE: 1157
tgcaggtgac cattgacggc aggaa 25

<210> SEQ ID NO 1158
<211> LENGTH: 25
<212> TYPE: DNA
<213> ORGANISM: Artificial sequence
<220> FEATURE:
<223> OTHER INFORMATION: Synthetic sequence: Probe suitable for detection of genetic variations associated with adverse reactions to pharmaceuticals

<400> SEQUENCE: 1158
tgcaggtgac cactgacggc aggaa 25

<210> SEQ ID NO 1159
<211> LENGTH: 25
<212> TYPE: DNA
<213> ORGANISM: Artificial sequence
<220> FEATURE:
<223> OTHER INFORMATION: Synthetic sequence: Probe suitable for detection of genetic variations associated with adverse reactions to pharmaceuticals

<400> SEQUENCE: 1159
ttcctgccgt caatggtcac ctgca 25

<210> SEQ ID NO 1160
<211> LENGTH: 25
<212> TYPE: DNA
<213> ORGANISM: Artificial sequence
<220> FEATURE:
<223> OTHER INFORMATION: Synthetic sequence: Probe suitable for detection of genetic variations associated with adverse reactions to pharmaceuticals

<400> SEQUENCE: 1160
ttcctgccgt cagtggtcac ctgca 25

<210> SEQ ID NO 1161
<211> LENGTH: 25
<212> TYPE: DNA
<213> ORGANISM: Artificial sequence
<220> FEATURE:
<223> OTHER INFORMATION: Synthetic sequence: Probe suitable for detection of genetic variations associated with adverse reactions to pharmaceuticals

<400> SEQUENCE: 1161
ggaatctggt acctggacca aatca 25

<210> SEQ ID NO 1162
<211> LENGTH: 25
<212> TYPE: DNA
<213> ORGANISM: Artificial sequence
<220> FEATURE:
<223> OTHER INFORMATION: Synthetic sequence: Probe suitable for detection of genetic variations associated with adverse reactions to pharmaceuticals

<400> SEQUENCE: 1162
ggaatctggt acttggacca aatca 25

<210> SEQ ID NO 1163
<211> LENGTH: 25
<212> TYPE: DNA
<213> ORGANISM: Artificial sequence
<220> FEATURE:
<223> OTHER INFORMATION: Synthetic sequence: Probe suitable for detection of genetic variations associated with adverse reactions to pharmaceuticals

<400> SEQUENCE: 1163
tgatttggtc caggtaccag attcc 25

<210> SEQ ID NO 1164
<211> LENGTH: 25
<212> TYPE: DNA

<213> ORGANISM: Artificial sequence
<220> FEATURE:
<223> OTHER INFORMATION: Synthetic sequence: Probe suitable for detection of genetic variations associated with adverse reactions to pharmaceuticals

<400> SEQUENCE: 1164
tgatttggtc caagtaccag attcc 25

<210> SEQ ID NO 1165
<211> LENGTH: 25
<212> TYPE: DNA
<213> ORGANISM: Artificial sequence
<220> FEATURE:
<223> OTHER INFORMATION: Synthetic sequence: Probe suitable for detection of genetic variations associated with adverse reactions to pharmaceuticals

<400> SEQUENCE: 1165
aagaagtgct gaaaaatata tttaa 25

<210> SEQ ID NO 1166
<211> LENGTH: 25
<212> TYPE: DNA
<213> ORGANISM: Artificial sequence
<220> FEATURE:
<223> OTHER INFORMATION: Synthetic sequence: Probe suitable for detection of genetic variations associated with adverse reactions to pharmaceuticals

<400> SEQUENCE: 1166
aagaagtgct gagaaatata tttaa 25

<210> SEQ ID NO 1167
<211> LENGTH: 25
<212> TYPE: DNA
<213> ORGANISM: Artificial sequence
<220> FEATURE:
<223> OTHER INFORMATION: Synthetic sequence: Probe suitable for detection of genetic variations associated with adverse reactions to pharmaceuticals

<400> SEQUENCE: 1167
ttaaatatat ttttcagcac ttctt 25

<210> SEQ ID NO 1168
<211> LENGTH: 25
<212> TYPE: DNA
<213> ORGANISM: Artificial sequence
<220> FEATURE:
<223> OTHER INFORMATION: Synthetic sequence: Probe suitable for detection of genetic variations associated with adverse reactions to pharmaceuticals

<400> SEQUENCE: 1168
ttaaatatat ttctcagcac ttctt 25

<210> SEQ ID NO 1169
<211> LENGTH: 25
<212> TYPE: DNA
<213> ORGANISM: Artificial sequence
<220> FEATURE:
<223> OTHER INFORMATION: Synthetic sequence: Probe suitable for detection of genetic variations associated with adverse reactions to pharmaceuticals

<400> SEQUENCE: 1169
agggtatttt tacatccctc cagtt 25

<210> SEQ ID NO 1170
<211> LENGTH: 25
<212> TYPE: DNA
<213> ORGANISM: Artificial sequence
<220> FEATURE:
<223> OTHER INFORMATION: Synthetic sequence: Probe suitable for detection of genetic variations associated with adverse reactions to pharmaceuticals

<400> SEQUENCE: 1170
agggtatttt tatatccctc cagtt 25

<210> SEQ ID NO 1171
<211> LENGTH: 25
<212> TYPE: DNA
<213> ORGANISM: Artificial sequence
<220> FEATURE:
<223> OTHER INFORMATION: Synthetic sequence: Probe suitable for detection of genetic variations associated with adverse reactions to pharmaceuticals

<400> SEQUENCE: 1171
aactggaggg atgtaaaaat accct 25

<210> SEQ ID NO 1172
<211> LENGTH: 25
<212> TYPE: DNA
<213> ORGANISM: Artificial sequence
<220> FEATURE:
<223> OTHER INFORMATION: Synthetic sequence: Probe suitable for detection of genetic variations associated with adverse reactions to pharmaceuticals

<400> SEQUENCE: 1172
aactggaggg atataaaaat accct 25

<210> SEQ ID NO 1173
<211> LENGTH: 25
<212> TYPE: DNA
<213> ORGANISM: Artificial sequence
<220> FEATURE:
<223> OTHER INFORMATION: Synthetic sequence: Probe suitable for detection of genetic variations associated with adverse reactions to pharmaceuticals

<400> SEQUENCE: 1173
cgcttgaacc tcgaacaatt gaaga 25

<210> SEQ ID NO 1174
<211> LENGTH: 25
<212> TYPE: DNA
<213> ORGANISM: Artificial sequence
<220> FEATURE:
<223> OTHER INFORMATION: Synthetic sequence: Probe suitable for detection of genetic variations associated with adverse reactions to pharmaceuticals

<400> SEQUENCE: 1174
cgcttgaacc tcaaacaatt gaaga 25

<210> SEQ ID NO 1175
<211> LENGTH: 25
<212> TYPE: DNA
<213> ORGANISM: Artificial sequence
<220> FEATURE:
<223> OTHER INFORMATION: Synthetic sequence: Probe suitable for detection of genetic variations associated with adverse reactions to pharmaceuticals

<400> SEQUENCE: 1175
tcttcaattg ttcgaggttc aagcg 25

<210> SEQ ID NO 1176
<211> LENGTH: 25
<212> TYPE: DNA
<213> ORGANISM: Artificial sequence
<220> FEATURE:
<223> OTHER INFORMATION: Synthetic sequence: Probe suitable for detection of genetic variations associated with adverse reactions to pharmaceuticals

<400> SEQUENCE: 1176
tcttcaattg tttgaggttc aagcg 25

<210> SEQ ID NO 1177
<211> LENGTH: 25
<212> TYPE: DNA
<213> ORGANISM: Artificial sequence
<220> FEATURE:
<223> OTHER INFORMATION: Synthetic sequence: Probe suitable for detection of genetic variations associated with adverse reactions to pharmaceuticals

<400> SEQUENCE: 1177
aacctggtga tggatccctt actat 25

<210> SEQ ID NO 1178
<211> LENGTH: 25
<212> TYPE: DNA
<213> ORGANISM: Artificial sequence
<220> FEATURE:
<223> OTHER INFORMATION: Synthetic sequence: Probe suitable for detection of genetic variations associated with adverse reactions to pharmaceuticals

<400> SEQUENCE: 1178
aacctggtga tgaatccctt actat 25

<210> SEQ ID NO 1179
<211> LENGTH: 25
<212> TYPE: DNA
<213> ORGANISM: Artificial sequence
<220> FEATURE:
<223> OTHER INFORMATION: Synthetic sequence: Probe suitable for detection of genetic variations associated with adverse reactions to pharmaceuticals

<400> SEQUENCE: 1179
atagtaaggg atccatcacc aggtt 25

<210> SEQ ID NO 1180
<211> LENGTH: 25
<212> TYPE: DNA
<213> ORGANISM: Artificial sequence
<220> FEATURE:
<223> OTHER INFORMATION: Synthetic sequence: Probe suitable for detection of genetic variations associated with adverse reactions to pharmaceuticals

<400> SEQUENCE: 1180
atagtaaggg attcatcacc aggtt 25

<210> SEQ ID NO 1181
<211> LENGTH: 25
<212> TYPE: DNA
<213> ORGANISM: Artificial sequence
<220> FEATURE:

<223> OTHER INFORMATION: Synthetic sequence: Probe suitable for detection of genetic variations associated with adverse reactions to pharmaceuticals

<400> SEQUENCE: 1181
taagaagaaa ccggggtggg tggtg 25

<210> SEQ ID NO 1182
<211> LENGTH: 25
<212> TYPE: DNA
<213> ORGANISM: Artificial sequence
<220> FEATURE:
<223> OTHER INFORMATION: Synthetic sequence: Probe suitable for detection of genetic variations associated with adverse reactions to pharmaceuticals

<400> SEQUENCE: 1182
taagaagaaa ccagggtggg tggtg 25

<210> SEQ ID NO 1183
<211> LENGTH: 25
<212> TYPE: DNA
<213> ORGANISM: Artificial sequence
<220> FEATURE:
<223> OTHER INFORMATION: Synthetic sequence: Probe suitable for detection of genetic variations associated with adverse reactions to pharmaceuticals

<400> SEQUENCE: 1183
caccacccac cccggtttct tctta 25

<210> SEQ ID NO 1184
<211> LENGTH: 25
<212> TYPE: DNA
<213> ORGANISM: Artificial sequence
<220> FEATURE:
<223> OTHER INFORMATION: Synthetic sequence: Probe suitable for detection of genetic variations associated with adverse reactions to pharmaceuticals

<400> SEQUENCE: 1184
caccacccac cctggtttct tctta 25

<210> SEQ ID NO 1185
<211> LENGTH: 25
<212> TYPE: DNA
<213> ORGANISM: Artificial sequence
<220> FEATURE:
<223> OTHER INFORMATION: Synthetic sequence: Probe suitable for detection of genetic variations associated with adverse reactions to pharmaceuticals

<400> SEQUENCE: 1185
aagcaccccc tggatccagg taagg 25

<210> SEQ ID NO 1186
<211> LENGTH: 25
<212> TYPE: DNA
<213> ORGANISM: Artificial sequence
<220> FEATURE:
<223> OTHER INFORMATION: Synthetic sequence: Probe suitable for detection of genetic variations associated with adverse reactions to pharmaceuticals

<400> SEQUENCE: 1186
aagcaccccc tgaatccagg taagg 25

<210> SEQ ID NO 1187

<211> LENGTH: 25
<212> TYPE: DNA
<213> ORGANISM: Artificial sequence
<220> FEATURE:
<223> OTHER INFORMATION: Synthetic sequence: Probe suitable for detection of genetic variations associated with adverse reactions to pharmaceuticals

<400> SEQUENCE: 1187
ccttacctgg atccaggggg tgctt 25

<210> SEQ ID NO 1188
<211> LENGTH: 25
<212> TYPE: DNA
<213> ORGANISM: Artificial sequence
<220> FEATURE:
<223> OTHER INFORMATION: Synthetic sequence: Probe suitable for detection of genetic variations associated with adverse reactions to pharmaceuticals

<400> SEQUENCE: 1188
ccttacctgg attcaggggg tgctt 25

<210> SEQ ID NO 1189
<211> LENGTH: 25
<212> TYPE: DNA
<213> ORGANISM: Artificial sequence
<220> FEATURE:
<223> OTHER INFORMATION: Synthetic sequence: Probe suitable for detection of genetic variations associated with adverse reactions to pharmaceuticals

<400> SEQUENCE: 1189
tgattatttc ccgggaaccc ataac 25

<210> SEQ ID NO 1190
<211> LENGTH: 25
<212> TYPE: DNA
<213> ORGANISM: Artificial sequence
<220> FEATURE:
<223> OTHER INFORMATION: Synthetic sequence: Probe suitable for detection of genetic variations associated with adverse reactions to pharmaceuticals

<400> SEQUENCE: 1190
tgattatttc ccaggaaccc ataac 25

<210> SEQ ID NO 1191
<211> LENGTH: 25
<212> TYPE: DNA
<213> ORGANISM: Artificial sequence
<220> FEATURE:
<223> OTHER INFORMATION: Synthetic sequence: Probe suitable for detection of genetic variations associated with adverse reactions to pharmaceuticals

<400> SEQUENCE: 1191
gttatgggtt cccgggaaat aatca 25

<210> SEQ ID NO 1192
<211> LENGTH: 25
<212> TYPE: DNA
<213> ORGANISM: Artificial sequence
<220> FEATURE:
<223> OTHER INFORMATION: Synthetic sequence: Probe suitable for detection of genetic variations associated with adverse reactions to pharmaceuticals

<400> SEQUENCE: 1192

-continued gttatgggtt cctgggaaat aatca 25

<210> SEQ ID NO 1193
<211> LENGTH: 25
<212> TYPE: DNA
<213> ORGANISM: Artificial sequence
<220> FEATURE:
<223> OTHER INFORMATION: Synthetic sequence: Probe suitable for detection of genetic variations associated with adverse reactions to pharmaceuticals

<400> SEQUENCE: 1193
ttgattattt cccgggaacc cataa 25

<210> SEQ ID NO 1194
<211> LENGTH: 25
<212> TYPE: DNA
<213> ORGANISM: Artificial sequence
<220> FEATURE:
<223> OTHER INFORMATION: Synthetic sequence: Probe suitable for detection of genetic variations associated with adverse reactions to pharmaceuticals

<400> SEQUENCE: 1194
ttgattattt cctgggaacc cataa 25

<210> SEQ ID NO 1195
<211> LENGTH: 25
<212> TYPE: DNA
<213> ORGANISM: Artificial sequence
<220> FEATURE:
<223> OTHER INFORMATION: Synthetic sequence: Probe suitable for detection of genetic variations associated with adverse reactions to pharmaceuticals

<400> SEQUENCE: 1195
ttatgggttc ccgggaaata atcaa 25

<210> SEQ ID NO 1196
<211> LENGTH: 25
<212> TYPE: DNA
<213> ORGANISM: Artificial sequence
<220> FEATURE:
<223> OTHER INFORMATION: Synthetic sequence: Probe suitable for detection of genetic variations associated with adverse reactions to pharmaceuticals

<400> SEQUENCE: 1196
ttatgggttc ccaggaaata atcaa 25

<210> SEQ ID NO 1197
<211> LENGTH: 25
<212> TYPE: DNA
<213> ORGANISM: Artificial sequence
<220> FEATURE:
<223> OTHER INFORMATION: Synthetic sequence: Probe suitable for detection of genetic variations associated with adverse reactions to pharmaceuticals

<400> SEQUENCE: 1197
gagaaggctt caatggatcc ttttg 25

<210> SEQ ID NO 1198
<211> LENGTH: 25
<212> TYPE: DNA
<213> ORGANISM: Artificial sequence
<220> FEATURE:
<223> OTHER INFORMATION: Synthetic sequence: Probe suitable for detection of genetic variations associated with adverse reactions to pharmaceuticals

<400> SEQUENCE: 1198
gagaaggctt cagtggatcc ttttg 25

<210> SEQ ID NO 1199
<211> LENGTH: 25
<212> TYPE: DNA
<213> ORGANISM: Artificial sequence
<220> FEATURE:
<223> OTHER INFORMATION: Synthetic sequence: Probe suitable for detection of genetic variations associated with adverse reactions to pharmaceuticals

<400> SEQUENCE: 1199
caaaaggatc cattgaagcc ttctc 25

<210> SEQ ID NO 1200
<211> LENGTH: 25
<212> TYPE: DNA
<213> ORGANISM: Artificial sequence
<220> FEATURE:
<223> OTHER INFORMATION: Synthetic sequence: Probe suitable for detection of genetic variations associated with adverse reactions to pharmaceuticals

<400> SEQUENCE: 1200
caaaaggatc cactgaagcc ttctc 25

<210> SEQ ID NO 1201
<211> LENGTH: 25
<212> TYPE: DNA
<213> ORGANISM: Artificial sequence
<220> FEATURE:
<223> OTHER INFORMATION: Synthetic sequence: Probe suitable for detection of genetic variations associated with adverse reactions to pharmaceuticals

<400> SEQUENCE: 1201
aaatggagaa ggtaaaatgt taaca 25

<210> SEQ ID NO 1202
<211> LENGTH: 25
<212> TYPE: DNA
<213> ORGANISM: Artificial sequence
<220> FEATURE:
<223> OTHER INFORMATION: Synthetic sequence: Probe suitable for detection of genetic variations associated with adverse reactions to pharmaceuticals

<400> SEQUENCE: 1202
aaatggagaa ggaaaaatgt taaca 25

<210> SEQ ID NO 1203
<211> LENGTH: 25
<212> TYPE: DNA
<213> ORGANISM: Artificial sequence
<220> FEATURE:
<223> OTHER INFORMATION: Synthetic sequence: Probe suitable for detection of genetic variations associated with adverse reactions to pharmaceuticals

<400> SEQUENCE: 1203
tgttaacatt ttaccttctc cattt 25

<210> SEQ ID NO 1204
<211> LENGTH: 25
<212> TYPE: DNA

<213> ORGANISM: Artificial sequence
<220> FEATURE:
<223> OTHER INFORMATION: Synthetic sequence: Probe suitable for detection of genetic variations associated with adverse reactions to pharmaceuticals

<400> SEQUENCE: 1204
tgttaacatt tttccttctc cattt 25

<210> SEQ ID NO 1205
<211> LENGTH: 25
<212> TYPE: DNA
<213> ORGANISM: Artificial sequence
<220> FEATURE:
<223> OTHER INFORMATION: Synthetic sequence: Probe suitable for detection of genetic variations associated with adverse reactions to pharmaceuticals

<400> SEQUENCE: 1205
aatggaaaga gatggaagga gatcc 25

<210> SEQ ID NO 1206
<211> LENGTH: 25
<212> TYPE: DNA
<213> ORGANISM: Artificial sequence
<220> FEATURE:
<223> OTHER INFORMATION: Synthetic sequence: Probe suitable for detection of genetic variations associated with adverse reactions to pharmaceuticals

<400> SEQUENCE: 1206
aatggaaaga gacggaagga gatcc 25

<210> SEQ ID NO 1207
<211> LENGTH: 25
<212> TYPE: DNA
<213> ORGANISM: Artificial sequence
<220> FEATURE:
<223> OTHER INFORMATION: Synthetic sequence: Probe suitable for detection of genetic variations associated with adverse reactions to pharmaceuticals

<400> SEQUENCE: 1207
ggatctcctt ccatctcttt ccatt 25

<210> SEQ ID NO 1208
<211> LENGTH: 25
<212> TYPE: DNA
<213> ORGANISM: Artificial sequence
<220> FEATURE:
<223> OTHER INFORMATION: Synthetic sequence: Probe suitable for detection of genetic variations associated with adverse reactions to pharmaceuticals

<400> SEQUENCE: 1208
ggatctcctt ccgtctcttt ccatt 25

<210> SEQ ID NO 1209
<211> LENGTH: 25
<212> TYPE: DNA
<213> ORGANISM: Artificial sequence
<220> FEATURE:
<223> OTHER INFORMATION: Synthetic sequence: Probe suitable for detection of genetic variations associated with adverse reactions to pharmaceuticals

<400> SEQUENCE: 1209
gcattgagga ccgtgttcaa gagga 25

<210> SEQ ID NO 1210
<211> LENGTH: 25
<212> TYPE: DNA
<213> ORGANISM: Artificial sequence
<220> FEATURE:
<223> OTHER INFORMATION: Synthetic sequence: Probe suitable for detection of genetic variations associated with adverse reactions to pharmaceuticals

<400> SEQUENCE: 1210
gcattgagga ccatgttcaa gagga 25

<210> SEQ ID NO 1211
<211> LENGTH: 25
<212> TYPE: DNA
<213> ORGANISM: Artificial sequence
<220> FEATURE:
<223> OTHER INFORMATION: Synthetic sequence: Probe suitable for detection of genetic variations associated with adverse reactions to pharmaceuticals

<400> SEQUENCE: 1211
tcctcttgaa cacggtcctc aatgc 25

<210> SEQ ID NO 1212
<211> LENGTH: 25
<212> TYPE: DNA
<213> ORGANISM: Artificial sequence
<220> FEATURE:
<223> OTHER INFORMATION: Synthetic sequence: Probe suitable for detection of genetic variations associated with adverse reactions to pharmaceuticals

<400> SEQUENCE: 1212
tcctcttgaa catggtcctc aatgc 25

<210> SEQ ID NO 1213
<211> LENGTH: 25
<212> TYPE: DNA
<213> ORGANISM: Artificial sequence
<220> FEATURE:
<223> OTHER INFORMATION: Synthetic sequence: Probe suitable for detection of genetic variations associated with adverse reactions to pharmaceuticals

<400> SEQUENCE: 1213
ttttcaggaa aacggatttg tgtgg 25

<210> SEQ ID NO 1214
<211> LENGTH: 25
<212> TYPE: DNA
<213> ORGANISM: Artificial sequence
<220> FEATURE:
<223> OTHER INFORMATION: Synthetic sequence: Probe suitable for detection of genetic variations associated with adverse reactions to pharmaceuticals

<400> SEQUENCE: 1214
ttttcaggaa aatggatttg tgtgg 25

<210> SEQ ID NO 1215
<211> LENGTH: 25
<212> TYPE: DNA
<213> ORGANISM: Artificial sequence
<220> FEATURE:
<223> OTHER INFORMATION: Synthetic sequence: Probe suitable for detection of genetic variations associated with adverse reactions to pharmaceuticals

<400> SEQUENCE: 1215
ccacacaaat ccgttttcct gaaaa 25

<210> SEQ ID NO 1216
<211> LENGTH: 25
<212> TYPE: DNA
<213> ORGANISM: Artificial sequence
<220> FEATURE:
<223> OTHER INFORMATION: Synthetic sequence: Probe suitable for detection of genetic variations associated with adverse reactions to pharmaceuticals

<400> SEQUENCE: 1216
ccacacaaat ccattttcct gaaaa 25

<210> SEQ ID NO 1217
<211> LENGTH: 25
<212> TYPE: DNA
<213> ORGANISM: Artificial sequence
<220> FEATURE:
<223> OTHER INFORMATION: Synthetic sequence: Probe suitable for detection of genetic variations associated with adverse reactions to pharmaceuticals

<400> SEQUENCE: 1217
gttcatggtt gcggtggggg agttc 25

<210> SEQ ID NO 1218
<211> LENGTH: 25
<212> TYPE: DNA
<213> ORGANISM: Artificial sequence
<220> FEATURE:
<223> OTHER INFORMATION: Synthetic sequence: Probe suitable for detection of genetic variations associated with adverse reactions to pharmaceuticals

<400> SEQUENCE: 1218
gttcatggtt gcagtggggg agttc 25

<210> SEQ ID NO 1219
<211> LENGTH: 25
<212> TYPE: DNA
<213> ORGANISM: Artificial sequence
<220> FEATURE:
<223> OTHER INFORMATION: Synthetic sequence: Probe suitable for detection of genetic variations associated with adverse reactions to pharmaceuticals

<400> SEQUENCE: 1219
gaactccccc accgcaacca tgaac 25

<210> SEQ ID NO 1220
<211> LENGTH: 25
<212> TYPE: DNA
<213> ORGANISM: Artificial sequence
<220> FEATURE:
<223> OTHER INFORMATION: Synthetic sequence: Probe suitable for detection of genetic variations associated with adverse reactions to pharmaceuticals

<400> SEQUENCE: 1220
gaactccccc actgcaacca tgaac 25

<210> SEQ ID NO 1221
<211> LENGTH: 25
<212> TYPE: DNA
<213> ORGANISM: Artificial sequence
<220> FEATURE:

<223> OTHER INFORMATION: Synthetic sequence: Probe suitable for detection of genetic variations associated with adverse reactions to pharmaceuticals

<400> SEQUENCE: 1221
tgctgccctc acaatctctt cctgt 25

<210> SEQ ID NO 1222
<211> LENGTH: 25
<212> TYPE: DNA
<213> ORGANISM: Artificial sequence
<220> FEATURE:
<223> OTHER INFORMATION: Synthetic sequence: Probe suitable for detection of genetic variations associated with adverse reactions to pharmaceuticals

<400> SEQUENCE: 1222
tgctgccctc acgatctctt cctgt 25

<210> SEQ ID NO 1223
<211> LENGTH: 25
<212> TYPE: DNA
<213> ORGANISM: Artificial sequence
<220> FEATURE:
<223> OTHER INFORMATION: Synthetic sequence: Probe suitable for detection of genetic variations associated with adverse reactions to pharmaceuticals

<400> SEQUENCE: 1223
acaggaagag attgtgaggg cagca 25

<210> SEQ ID NO 1224
<211> LENGTH: 25
<212> TYPE: DNA
<213> ORGANISM: Artificial sequence
<220> FEATURE:
<223> OTHER INFORMATION: Synthetic sequence: Probe suitable for detection of genetic variations associated with adverse reactions to pharmaceuticals

<400> SEQUENCE: 1224
acaggaagag atcgtgaggg cagca 25

<210> SEQ ID NO 1225
<211> LENGTH: 25
<212> TYPE: DNA
<213> ORGANISM: Artificial sequence
<220> FEATURE:
<223> OTHER INFORMATION: Synthetic sequence: Probe suitable for detection of genetic variations associated with adverse reactions to pharmaceuticals

<400> SEQUENCE: 1225
ttgaaaagtt atatctactt acaga 25

<210> SEQ ID NO 1226
<211> LENGTH: 25
<212> TYPE: DNA
<213> ORGANISM: Artificial sequence
<220> FEATURE:
<223> OTHER INFORMATION: Synthetic sequence: Probe suitable for detection of genetic variations associated with adverse reactions to pharmaceuticals

<400> SEQUENCE: 1226
ttgaaaagtt atgtctactt acaga 25

<210> SEQ ID NO 1227

<211> LENGTH: 25
<212> TYPE: DNA
<213> ORGANISM: Artificial sequence
<220> FEATURE:
<223> OTHER INFORMATION: Synthetic sequence: Probe suitable for detection of genetic variations associated with adverse reactions to pharmaceuticals

<400> SEQUENCE: 1227
tctgtaagta gatataactt ttcaa 25

<210> SEQ ID NO 1228
<211> LENGTH: 25
<212> TYPE: DNA
<213> ORGANISM: Artificial sequence
<220> FEATURE:
<223> OTHER INFORMATION: Synthetic sequence: Probe suitable for detection of genetic variations associated with adverse reactions to pharmaceuticals

<400> SEQUENCE: 1228
tctgtaagta gacataactt ttcaa 25

<210> SEQ ID NO 1229
<211> LENGTH: 25
<212> TYPE: DNA
<213> ORGANISM: Artificial sequence
<220> FEATURE:
<223> OTHER INFORMATION: Synthetic sequence: Probe suitable for detection of genetic variations associated with adverse reactions to pharmaceuticals

<400> SEQUENCE: 1229
gtccccggtc tggaaacctg cataa 25

<210> SEQ ID NO 1230
<211> LENGTH: 25
<212> TYPE: DNA
<213> ORGANISM: Artificial sequence
<220> FEATURE:
<223> OTHER INFORMATION: Synthetic sequence: Probe suitable for detection of genetic variations associated with adverse reactions to pharmaceuticals

<400> SEQUENCE: 1230
gtccccggtc tgcaaacctg cataa 25

<210> SEQ ID NO 1231
<211> LENGTH: 25
<212> TYPE: DNA
<213> ORGANISM: Artificial sequence
<220> FEATURE:
<223> OTHER INFORMATION: Synthetic sequence: Probe suitable for detection of genetic variations associated with adverse reactions to pharmaceuticals

<400> SEQUENCE: 1231
ttatgcaggt ttccagaccg gggac 25

<210> SEQ ID NO 1232
<211> LENGTH: 25
<212> TYPE: DNA
<213> ORGANISM: Artificial sequence
<220> FEATURE:
<223> OTHER INFORMATION: Synthetic sequence: Probe suitable for detection of genetic variations associated with adverse reactions to pharmaceuticals

<400> SEQUENCE: 1232

```
ttatgcaggt ttgcagaccg gggac                                        25


<210> SEQ ID NO 1233
<211> LENGTH: 25
<212> TYPE: DNA
<213> ORGANISM: Artificial sequence
<220> FEATURE:
<223> OTHER INFORMATION: Synthetic sequence: Probe suitable for
      detection of genetic variations associated with adverse reactions
      to pharmaceuticals

<400> SEQUENCE: 1233

tgtctgcggg agccgatttc atcat                                        25


<210> SEQ ID NO 1234
<211> LENGTH: 25
<212> TYPE: DNA
<213> ORGANISM: Artificial sequence
<220> FEATURE:
<223> OTHER INFORMATION: Synthetic sequence: Probe suitable for
      detection of genetic variations associated with adverse reactions
      to pharmaceuticals

<400> SEQUENCE: 1234

tgtctgcggg agtcgatttc atcat                                        25


<210> SEQ ID NO 1235
<211> LENGTH: 25
<212> TYPE: DNA
<213> ORGANISM: Artificial sequence
<220> FEATURE:
<223> OTHER INFORMATION: Synthetic sequence: Probe suitable for
      detection of genetic variations associated with adverse reactions
      to pharmaceuticals

<400> SEQUENCE: 1235

atgatgaaat cggctcccgc agaca                                        25


<210> SEQ ID NO 1236
<211> LENGTH: 25
<212> TYPE: DNA
<213> ORGANISM: Artificial sequence
<220> FEATURE:
<223> OTHER INFORMATION: Synthetic sequence: Probe suitable for
      detection of genetic variations associated with adverse reactions
      to pharmaceuticals

<400> SEQUENCE: 1236

atgatgaaat cgactcccgc agaca                                        25


<210> SEQ ID NO 1237
<211> LENGTH: 25
<212> TYPE: DNA
<213> ORGANISM: Artificial sequence
<220> FEATURE:
<223> OTHER INFORMATION: Synthetic sequence: Probe suitable for
      detection of genetic variations associated with adverse reactions
      to pharmaceuticals

<400> SEQUENCE: 1237

gtcagaacat agatcaaagt tttcc                                        25


<210> SEQ ID NO 1238
<211> LENGTH: 25
<212> TYPE: DNA
<213> ORGANISM: Artificial sequence
<220> FEATURE:
<223> OTHER INFORMATION: Synthetic sequence: Probe suitable for
      detection of genetic variations associated with adverse reactions
```

to pharmaceuticals

<400> SEQUENCE: 1238
gtcagaacat aggtcaaagt tttcc 25

<210> SEQ ID NO 1239
<211> LENGTH: 25
<212> TYPE: DNA
<213> ORGANISM: Artificial sequence
<220> FEATURE:
<223> OTHER INFORMATION: Synthetic sequence: Probe suitable for detection of genetic variations associated with adverse reactions to pharmaceuticals

<400> SEQUENCE: 1239
ggaaaacttt gatctatgtt ctgac 25

<210> SEQ ID NO 1240
<211> LENGTH: 25
<212> TYPE: DNA
<213> ORGANISM: Artificial sequence
<220> FEATURE:
<223> OTHER INFORMATION: Synthetic sequence: Probe suitable for detection of genetic variations associated with adverse reactions to pharmaceuticals

<400> SEQUENCE: 1240
ggaaaacttt gacctatgtt ctgac 25

<210> SEQ ID NO 1241
<211> LENGTH: 25
<212> TYPE: DNA
<213> ORGANISM: Artificial sequence
<220> FEATURE:
<223> OTHER INFORMATION: Synthetic sequence: Probe suitable for detection of genetic variations associated with adverse reactions to pharmaceuticals

<400> SEQUENCE: 1241
aatattgatg aagcagaatg ggagt 25

<210> SEQ ID NO 1242
<211> LENGTH: 25
<212> TYPE: DNA
<213> ORGANISM: Artificial sequence
<220> FEATURE:
<223> OTHER INFORMATION: Synthetic sequence: Probe suitable for detection of genetic variations associated with adverse reactions to pharmaceuticals

<400> SEQUENCE: 1242
aatattgatg aaacagaatg ggagt 25

<210> SEQ ID NO 1243
<211> LENGTH: 25
<212> TYPE: DNA
<213> ORGANISM: Artificial sequence
<220> FEATURE:
<223> OTHER INFORMATION: Synthetic sequence: Probe suitable for detection of genetic variations associated with adverse reactions to pharmaceuticals

<400> SEQUENCE: 1243
actcccattc tgcttcatca atatt 25

<210> SEQ ID NO 1244
<211> LENGTH: 25
<212> TYPE: DNA

<213> ORGANISM: Artificial sequence
<220> FEATURE:
<223> OTHER INFORMATION: Synthetic sequence: Probe suitable for detection of genetic variations associated with adverse reactions to pharmaceuticals

<400> SEQUENCE: 1244
actcccattc tgtttcatca atatt 25

<210> SEQ ID NO 1245
<211> LENGTH: 25
<212> TYPE: DNA
<213> ORGANISM: Artificial sequence
<220> FEATURE:
<223> OTHER INFORMATION: Synthetic sequence: Probe suitable for detection of genetic variations associated with adverse reactions to pharmaceuticals

<400> SEQUENCE: 1245
gagacaaggg caagagagag gcgat 25

<210> SEQ ID NO 1246
<211> LENGTH: 25
<212> TYPE: DNA
<213> ORGANISM: Artificial sequence
<220> FEATURE:
<223> OTHER INFORMATION: Synthetic sequence: Probe suitable for detection of genetic variations associated with adverse reactions to pharmaceuticals

<400> SEQUENCE: 1246
gagacaaggg caggagagag gcgat 25

<210> SEQ ID NO 1247
<211> LENGTH: 25
<212> TYPE: DNA
<213> ORGANISM: Artificial sequence
<220> FEATURE:
<223> OTHER INFORMATION: Synthetic sequence: Probe suitable for detection of genetic variations associated with adverse reactions to pharmaceuticals

<400> SEQUENCE: 1247
atcgcctctc tcttgccctt gtctc 25

<210> SEQ ID NO 1248
<211> LENGTH: 25
<212> TYPE: DNA
<213> ORGANISM: Artificial sequence
<220> FEATURE:
<223> OTHER INFORMATION: Synthetic sequence: Probe suitable for detection of genetic variations associated with adverse reactions to pharmaceuticals

<400> SEQUENCE: 1248
atcgcctctc tcctgccctt gtctc 25

<210> SEQ ID NO 1249
<211> LENGTH: 25
<212> TYPE: DNA
<213> ORGANISM: Artificial sequence
<220> FEATURE:
<223> OTHER INFORMATION: Synthetic sequence: Probe suitable for detection of genetic variations associated with adverse reactions to pharmaceuticals

<400> SEQUENCE: 1249
agctctgtgg gcacaggacg catgg 25

<210> SEQ ID NO 1250
<211> LENGTH: 25
<212> TYPE: DNA
<213> ORGANISM: Artificial sequence
<220> FEATURE:
<223> OTHER INFORMATION: Synthetic sequence: Probe suitable for detection of genetic variations associated with adverse reactions to pharmaceuticals

<400> SEQUENCE: 1250
agctctgtgg gcccaggacg catgg 25

<210> SEQ ID NO 1251
<211> LENGTH: 25
<212> TYPE: DNA
<213> ORGANISM: Artificial sequence
<220> FEATURE:
<223> OTHER INFORMATION: Synthetic sequence: Probe suitable for detection of genetic variations associated with adverse reactions to pharmaceuticals

<400> SEQUENCE: 1251
ccatgcgtcc tgtgcccaca gagct 25

<210> SEQ ID NO 1252
<211> LENGTH: 25
<212> TYPE: DNA
<213> ORGANISM: Artificial sequence
<220> FEATURE:
<223> OTHER INFORMATION: Synthetic sequence: Probe suitable for detection of genetic variations associated with adverse reactions to pharmaceuticals

<400> SEQUENCE: 1252
ccatgcgtcc tgggcccaca gagct 25

<210> SEQ ID NO 1253
<211> LENGTH: 25
<212> TYPE: DNA
<213> ORGANISM: Artificial sequence
<220> FEATURE:
<223> OTHER INFORMATION: Synthetic sequence: Probe suitable for detection of genetic variations associated with adverse reactions to pharmaceuticals

<400> SEQUENCE: 1253
cctccgcctc tcggattcaa gcaat 25

<210> SEQ ID NO 1254
<211> LENGTH: 25
<212> TYPE: DNA
<213> ORGANISM: Artificial sequence
<220> FEATURE:
<223> OTHER INFORMATION: Synthetic sequence: Probe suitable for detection of genetic variations associated with adverse reactions to pharmaceuticals

<400> SEQUENCE: 1254
cctccgcctc tcagattcaa gcaat 25

<210> SEQ ID NO 1255
<211> LENGTH: 25
<212> TYPE: DNA
<213> ORGANISM: Artificial sequence
<220> FEATURE:
<223> OTHER INFORMATION: Synthetic sequence: Probe suitable for detection of genetic variations associated with adverse reactions to pharmaceuticals

<400> SEQUENCE: 1255
attgcttgaa tccgagaggc ggagg 25

<210> SEQ ID NO 1256
<211> LENGTH: 25
<212> TYPE: DNA
<213> ORGANISM: Artificial sequence
<220> FEATURE:
<223> OTHER INFORMATION: Synthetic sequence: Probe suitable for detection of genetic variations associated with adverse reactions to pharmaceuticals

<400> SEQUENCE: 1256
attgcttgaa tctgagaggc ggagg 25

<210> SEQ ID NO 1257
<211> LENGTH: 25
<212> TYPE: DNA
<213> ORGANISM: Artificial sequence
<220> FEATURE:
<223> OTHER INFORMATION: Synthetic sequence: Probe suitable for detection of genetic variations associated with adverse reactions to pharmaceuticals

<400> SEQUENCE: 1257
caaccatgac ccgtgagtac atacc 25

<210> SEQ ID NO 1258
<211> LENGTH: 25
<212> TYPE: DNA
<213> ORGANISM: Artificial sequence
<220> FEATURE:
<223> OTHER INFORMATION: Synthetic sequence: Probe suitable for detection of genetic variations associated with adverse reactions to pharmaceuticals

<400> SEQUENCE: 1258
caaccatgac ccatgagtac atacc 25

<210> SEQ ID NO 1259
<211> LENGTH: 25
<212> TYPE: DNA
<213> ORGANISM: Artificial sequence
<220> FEATURE:
<223> OTHER INFORMATION: Synthetic sequence: Probe suitable for detection of genetic variations associated with adverse reactions to pharmaceuticals

<400> SEQUENCE: 1259
ggtatgtact cacgggtcat ggttg 25

<210> SEQ ID NO 1260
<211> LENGTH: 25
<212> TYPE: DNA
<213> ORGANISM: Artificial sequence
<220> FEATURE:
<223> OTHER INFORMATION: Synthetic sequence: Probe suitable for detection of genetic variations associated with adverse reactions to pharmaceuticals

<400> SEQUENCE: 1260
ggtatgtact catgggtcat ggttg 25

<210> SEQ ID NO 1261
<211> LENGTH: 25
<212> TYPE: DNA
<213> ORGANISM: Artificial sequence
<220> FEATURE:

<223> OTHER INFORMATION: Synthetic sequence: Probe suitable for detection of genetic variations associated with adverse reactions to pharmaceuticals

<400> SEQUENCE: 1261
gcctgggcac ttcgaccctt acaat 25

<210> SEQ ID NO 1262
<211> LENGTH: 25
<212> TYPE: DNA
<213> ORGANISM: Artificial sequence
<220> FEATURE:
<223> OTHER INFORMATION: Synthetic sequence: Probe suitable for detection of genetic variations associated with adverse reactions to pharmaceuticals

<400> SEQUENCE: 1262
gcctgggcac ttagaccctt acaat 25

<210> SEQ ID NO 1263
<211> LENGTH: 25
<212> TYPE: DNA
<213> ORGANISM: Artificial sequence
<220> FEATURE:
<223> OTHER INFORMATION: Synthetic sequence: Probe suitable for detection of genetic variations associated with adverse reactions to pharmaceuticals

<400> SEQUENCE: 1263
attgtaaggg tcgaagtgcc caggc 25

<210> SEQ ID NO 1264
<211> LENGTH: 25
<212> TYPE: DNA
<213> ORGANISM: Artificial sequence
<220> FEATURE:
<223> OTHER INFORMATION: Synthetic sequence: Probe suitable for detection of genetic variations associated with adverse reactions to pharmaceuticals

<400> SEQUENCE: 1264
attgtaaggg tctaagtgcc caggc 25

<210> SEQ ID NO 1265
<211> LENGTH: 25
<212> TYPE: DNA
<213> ORGANISM: Artificial sequence
<220> FEATURE:
<223> OTHER INFORMATION: Synthetic sequence: Probe suitable for detection of genetic variations associated with adverse reactions to pharmaceuticals

<400> SEQUENCE: 1265
ggagagcact aagaagttcc taaaa 25

<210> SEQ ID NO 1266
<211> LENGTH: 25
<212> TYPE: DNA
<213> ORGANISM: Artificial sequence
<220> FEATURE:
<223> OTHER INFORMATION: Synthetic sequence: Probe suitable for detection of genetic variations associated with adverse reactions to pharmaceuticals

<400> SEQUENCE: 1266
ggagagcact aaaaagttcc taaaa 25

<210> SEQ ID NO 1267

<211> LENGTH: 25
<212> TYPE: DNA
<213> ORGANISM: Artificial sequence
<220> FEATURE:
<223> OTHER INFORMATION: Synthetic sequence: Probe suitable for detection of genetic variations associated with adverse reactions to pharmaceuticals

<400> SEQUENCE: 1267
ttttaggaac ttcttagtgc tctcc 25

<210> SEQ ID NO 1268
<211> LENGTH: 25
<212> TYPE: DNA
<213> ORGANISM: Artificial sequence
<220> FEATURE:
<223> OTHER INFORMATION: Synthetic sequence: Probe suitable for detection of genetic variations associated with adverse reactions to pharmaceuticals

<400> SEQUENCE: 1268
ttttaggaac tttttagtgc tctcc 25

<210> SEQ ID NO 1269
<211> LENGTH: 25
<212> TYPE: DNA
<213> ORGANISM: Artificial sequence
<220> FEATURE:
<223> OTHER INFORMATION: Synthetic sequence: Probe suitable for detection of genetic variations associated with adverse reactions to pharmaceuticals

<400> SEQUENCE: 1269
agatatggga cccgtacaca tggac 25

<210> SEQ ID NO 1270
<211> LENGTH: 25
<212> TYPE: DNA
<213> ORGANISM: Artificial sequence
<220> FEATURE:
<223> OTHER INFORMATION: Synthetic sequence: Probe suitable for detection of genetic variations associated with adverse reactions to pharmaceuticals

<400> SEQUENCE: 1270
agatatggga cctgtacaca tggac 25

<210> SEQ ID NO 1271
<211> LENGTH: 25
<212> TYPE: DNA
<213> ORGANISM: Artificial sequence
<220> FEATURE:
<223> OTHER INFORMATION: Synthetic sequence: Probe suitable for detection of genetic variations associated with adverse reactions to pharmaceuticals

<400> SEQUENCE: 1271
gtccatgtgt acgggtccca tatct 25

<210> SEQ ID NO 1272
<211> LENGTH: 25
<212> TYPE: DNA
<213> ORGANISM: Artificial sequence
<220> FEATURE:
<223> OTHER INFORMATION: Synthetic sequence: Probe suitable for detection of genetic variations associated with adverse reactions to pharmaceuticals

<400> SEQUENCE: 1272
gtccatgtgt acaggtccca tatct 25

<210> SEQ ID NO 1273
<211> LENGTH: 25
<212> TYPE: DNA
<213> ORGANISM: Artificial sequence
<220> FEATURE:
<223> OTHER INFORMATION: Synthetic sequence: Probe suitable for detection of genetic variations associated with adverse reactions to pharmaceuticals

<400> SEQUENCE: 1273
aaggagattg atgcagtttt gccca 25

<210> SEQ ID NO 1274
<211> LENGTH: 25
<212> TYPE: DNA
<213> ORGANISM: Artificial sequence
<220> FEATURE:
<223> OTHER INFORMATION: Synthetic sequence: Probe suitable for detection of genetic variations associated with adverse reactions to pharmaceuticals

<400> SEQUENCE: 1274
aaggagattg atacagtttt gccca 25

<210> SEQ ID NO 1275
<211> LENGTH: 25
<212> TYPE: DNA
<213> ORGANISM: Artificial sequence
<220> FEATURE:
<223> OTHER INFORMATION: Synthetic sequence: Probe suitable for detection of genetic variations associated with adverse reactions to pharmaceuticals

<400> SEQUENCE: 1275
tgggcaaaac tgcatcaatc tcctt 25

<210> SEQ ID NO 1276
<211> LENGTH: 25
<212> TYPE: DNA
<213> ORGANISM: Artificial sequence
<220> FEATURE:
<223> OTHER INFORMATION: Synthetic sequence: Probe suitable for detection of genetic variations associated with adverse reactions to pharmaceuticals

<400> SEQUENCE: 1276
tgggcaaaac tgtatcaatc tcctt 25

<210> SEQ ID NO 1277
<211> LENGTH: 25
<212> TYPE: DNA
<213> ORGANISM: Artificial sequence
<220> FEATURE:
<223> OTHER INFORMATION: Synthetic sequence: Probe suitable for detection of genetic variations associated with adverse reactions to pharmaceuticals

<400> SEQUENCE: 1277
ttggcatgag gtttgctctc atgaa 25

<210> SEQ ID NO 1278
<211> LENGTH: 25
<212> TYPE: DNA
<213> ORGANISM: Artificial sequence
<220> FEATURE:
<223> OTHER INFORMATION: Synthetic sequence: Probe suitable for detection of genetic variations associated with adverse reactions to pharmaceuticals

<400> SEQUENCE: 1278
ttggcatgag gtctgctctc atgaa 25

<210> SEQ ID NO 1279
<211> LENGTH: 25
<212> TYPE: DNA
<213> ORGANISM: Artificial sequence
<220> FEATURE:
<223> OTHER INFORMATION: Synthetic sequence: Probe suitable for detection of genetic variations associated with adverse reactions to pharmaceuticals

<400> SEQUENCE: 1279
ttcatgagag caaacctcat gccaa 25

<210> SEQ ID NO 1280
<211> LENGTH: 25
<212> TYPE: DNA
<213> ORGANISM: Artificial sequence
<220> FEATURE:
<223> OTHER INFORMATION: Synthetic sequence: Probe suitable for detection of genetic variations associated with adverse reactions to pharmaceuticals

<400> SEQUENCE: 1280
ttcatgagag cagacctcat gccaa 25

<210> SEQ ID NO 1281
<211> LENGTH: 25
<212> TYPE: DNA
<213> ORGANISM: Artificial sequence
<220> FEATURE:
<223> OTHER INFORMATION: Synthetic sequence: Probe suitable for detection of genetic variations associated with adverse reactions to pharmaceuticals

<400> SEQUENCE: 1281
ttttgtcttt cagtatctct tccct 25

<210> SEQ ID NO 1282
<211> LENGTH: 25
<212> TYPE: DNA
<213> ORGANISM: Artificial sequence
<220> FEATURE:
<223> OTHER INFORMATION: Synthetic sequence: Probe suitable for detection of genetic variations associated with adverse reactions to pharmaceuticals

<400> SEQUENCE: 1282
ttttgtcttt caatatctct tccct 25

<210> SEQ ID NO 1283
<211> LENGTH: 25
<212> TYPE: DNA
<213> ORGANISM: Artificial sequence
<220> FEATURE:
<223> OTHER INFORMATION: Synthetic sequence: Probe suitable for detection of genetic variations associated with adverse reactions to pharmaceuticals

<400> SEQUENCE: 1283
agggaagaga tactgaaaga caaaa 25

<210> SEQ ID NO 1284
<211> LENGTH: 25
<212> TYPE: DNA

<213> ORGANISM: Artificial sequence
<220> FEATURE:
<223> OTHER INFORMATION: Synthetic sequence: Probe suitable for detection of genetic variations associated with adverse reactions to pharmaceuticals

<400> SEQUENCE: 1284
agggaagaga tattgaaaga caaaa 25

<210> SEQ ID NO 1285
<211> LENGTH: 25
<212> TYPE: DNA
<213> ORGANISM: Artificial sequence
<220> FEATURE:
<223> OTHER INFORMATION: Synthetic sequence: Probe suitable for detection of genetic variations associated with adverse reactions to pharmaceuticals

<400> SEQUENCE: 1285
atcccccctg caccccccag catcc 25

<210> SEQ ID NO 1286
<211> LENGTH: 25
<212> TYPE: DNA
<213> ORGANISM: Artificial sequence
<220> FEATURE:
<223> OTHER INFORMATION: Synthetic sequence: Probe suitable for detection of genetic variations associated with adverse reactions to pharmaceuticals

<400> SEQUENCE: 1286 atccccctg cacccccagc atccc 25

<210> SEQ ID NO 1287
<211> LENGTH: 25
<212> TYPE: DNA
<213> ORGANISM: Artificial sequence
<220> FEATURE:
<223> OTHER INFORMATION: Synthetic sequence: Probe suitable for detection of genetic variations associated with adverse reactions to pharmaceuticals

<400> SEQUENCE: 1287
ggatgctggg gggtgcaggg gggat 25

<210> SEQ ID NO 1288
<211> LENGTH: 25
<212> TYPE: DNA
<213> ORGANISM: Artificial sequence
<220> FEATURE:
<223> OTHER INFORMATION: Synthetic sequence: Probe suitable for detection of genetic variations associated with adverse reactions to pharmaceuticals

<400> SEQUENCE: 1288
gggatgctgg gggtgcaggg gggat 25

<210> SEQ ID NO 1289
<211> LENGTH: 25
<212> TYPE: DNA
<213> ORGANISM: Artificial sequence
<220> FEATURE:
<223> OTHER INFORMATION: Synthetic sequence: Probe suitable for detection of genetic variations associated with adverse reactions to pharmaceuticals

<400> SEQUENCE: 1289
agggaaaaga agaggatact tctct 25

<210> SEQ ID NO 1290
<211> LENGTH: 25
<212> TYPE: DNA
<213> ORGANISM: Artificial sequence
<220> FEATURE:
<223> OTHER INFORMATION: Synthetic sequence: Probe suitable for detection of genetic variations associated with adverse reactions to pharmaceuticals

<400> SEQUENCE: 1290
agggaaaaga agatacttct ctatc 25

<210> SEQ ID NO 1291
<211> LENGTH: 25
<212> TYPE: DNA
<213> ORGANISM: Artificial sequence
<220> FEATURE:
<223> OTHER INFORMATION: Synthetic sequence: Probe suitable for detection of genetic variations associated with adverse reactions to pharmaceuticals

<400> SEQUENCE: 1291
agagaagtat cctcttcttt tccct 25

<210> SEQ ID NO 1292
<211> LENGTH: 25
<212> TYPE: DNA
<213> ORGANISM: Artificial sequence
<220> FEATURE:
<223> OTHER INFORMATION: Synthetic sequence: Probe suitable for detection of genetic variations associated with adverse reactions to pharmaceuticals

<400> SEQUENCE: 1292
gatagagaag tatcttcttt tccct 25

<210> SEQ ID NO 1293
<211> LENGTH: 25
<212> TYPE: DNA
<213> ORGANISM: Artificial sequence
<220> FEATURE:
<223> OTHER INFORMATION: Synthetic sequence: Probe suitable for detection of genetic variations associated with adverse reactions to pharmaceuticals

<400> SEQUENCE: 1293
cacacattct tggccttctg cagat 25

<210> SEQ ID NO 1294
<211> LENGTH: 25
<212> TYPE: DNA
<213> ORGANISM: Artificial sequence
<220> FEATURE:
<223> OTHER INFORMATION: Synthetic sequence: Probe suitable for detection of genetic variations associated with adverse reactions to pharmaceuticals

<400> SEQUENCE: 1294
cacacattct tgaccttctg cagat 25

<210> SEQ ID NO 1295
<211> LENGTH: 25
<212> TYPE: DNA
<213> ORGANISM: Artificial sequence
<220> FEATURE:
<223> OTHER INFORMATION: Synthetic sequence: Probe suitable for detection of genetic variations associated with adverse reactions to pharmaceuticals

<400> SEQUENCE: 1295
atctgcagaa ggccaagaat gtgtg 25

<210> SEQ ID NO 1296
<211> LENGTH: 25
<212> TYPE: DNA
<213> ORGANISM: Artificial sequence
<220> FEATURE:
<223> OTHER INFORMATION: Synthetic sequence: Probe suitable for detection of genetic variations associated with adverse reactions to pharmaceuticals

<400> SEQUENCE: 1296
atctgcagaa ggtcaagaat gtgtg 25

<210> SEQ ID NO 1297
<211> LENGTH: 25
<212> TYPE: DNA
<213> ORGANISM: Artificial sequence
<220> FEATURE:
<223> OTHER INFORMATION: Synthetic sequence: Probe suitable for detection of genetic variations associated with adverse reactions to pharmaceuticals

<400> SEQUENCE: 1297
ctgcctagtg ggttcacctg cccac 25

<210> SEQ ID NO 1298
<211> LENGTH: 25
<212> TYPE: DNA
<213> ORGANISM: Artificial sequence
<220> FEATURE:
<223> OTHER INFORMATION: Synthetic sequence: Probe suitable for detection of genetic variations associated with adverse reactions to pharmaceuticals

<400> SEQUENCE: 1298
ctgcctagtg gggtcacctg cccac 25

<210> SEQ ID NO 1299
<211> LENGTH: 25
<212> TYPE: DNA
<213> ORGANISM: Artificial sequence
<220> FEATURE:
<223> OTHER INFORMATION: Synthetic sequence: Probe suitable for detection of genetic variations associated with adverse reactions to pharmaceuticals

<400> SEQUENCE: 1299
gtgggcaggt gaacccacta ggcag 25

<210> SEQ ID NO 1300
<211> LENGTH: 25
<212> TYPE: DNA
<213> ORGANISM: Artificial sequence
<220> FEATURE:
<223> OTHER INFORMATION: Synthetic sequence: Probe suitable for detection of genetic variations associated with adverse reactions to pharmaceuticals

<400> SEQUENCE: 1300
gtgggcaggt gaccccacta ggcag 25

<210> SEQ ID NO 1301
<211> LENGTH: 25
<212> TYPE: DNA
<213> ORGANISM: Artificial sequence
<220> FEATURE:

<223> OTHER INFORMATION: Synthetic sequence: Probe suitable for detection of genetic variations associated with adverse reactions to pharmaceuticals

<400> SEQUENCE: 1301
gacctgcaga agcgcctggc agtgt 25

<210> SEQ ID NO 1302
<211> LENGTH: 25
<212> TYPE: DNA
<213> ORGANISM: Artificial sequence
<220> FEATURE:
<223> OTHER INFORMATION: Synthetic sequence: Probe suitable for detection of genetic variations associated with adverse reactions to pharmaceuticals

<400> SEQUENCE: 1302
acactgccag gcgcttctgc aggtc 25

<210> SEQ ID NO 1303
<211> LENGTH: 25
<212> TYPE: DNA
<213> ORGANISM: Artificial sequence
<220> FEATURE:
<223> OTHER INFORMATION: Synthetic sequence: Probe suitable for detection of genetic variations associated with adverse reactions to pharmaceuticals

<400> SEQUENCE: 1303
gacctgcaga agtgcctggc agtgt 25

<210> SEQ ID NO 1304
<211> LENGTH: 25
<212> TYPE: DNA
<213> ORGANISM: Artificial sequence
<220> FEATURE:
<223> OTHER INFORMATION: Synthetic sequence: Probe suitable for detection of genetic variations associated with adverse reactions to pharmaceuticals

<400> SEQUENCE: 1304
acactgccag gcacttctgc aggtc 25

<210> SEQ ID NO 1305
<211> LENGTH: 25
<212> TYPE: DNA
<213> ORGANISM: Artificial sequence
<220> FEATURE:
<223> OTHER INFORMATION: Synthetic sequence: Probe suitable for detection of genetic variations associated with adverse reactions to pharmaceuticals

<400> SEQUENCE: 1305
atggaggacg tgtgcggccg cctgg 25

<210> SEQ ID NO 1306
<211> LENGTH: 25
<212> TYPE: DNA
<213> ORGANISM: Artificial sequence
<220> FEATURE:
<223> OTHER INFORMATION: Synthetic sequence: Probe suitable for detection of genetic variations associated with adverse reactions to pharmaceuticals

<400> SEQUENCE: 1306
ccaggcggcc gcacacgtcc tccat 25

<210> SEQ ID NO 1307

<211> LENGTH: 25
<212> TYPE: DNA
<213> ORGANISM: Artificial sequence
<220> FEATURE:
<223> OTHER INFORMATION: Synthetic sequence: Probe suitable for detection of genetic variations associated with adverse reactions to pharmaceuticals

<400> SEQUENCE: 1307
atggaggacg tgcgcggccg cctgg 25

<210> SEQ ID NO 1308
<211> LENGTH: 25
<212> TYPE: DNA
<213> ORGANISM: Artificial sequence
<220> FEATURE:
<223> OTHER INFORMATION: Synthetic sequence: Probe suitable for detection of genetic variations associated with adverse reactions to pharmaceuticals

<400> SEQUENCE: 1308
ccaggcggcc gcgcacgtcc tccat 25

<210> SEQ ID NO 1309
<211> LENGTH: 25
<212> TYPE: DNA
<213> ORGANISM: Artificial sequence
<220> FEATURE:
<223> OTHER INFORMATION: Synthetic sequence: Probe suitable for detection of genetic variations associated with adverse reactions to pharmaceuticals

<400> SEQUENCE: 1309
ttgaggggca tggggacggg gttca 25

<210> SEQ ID NO 1310
<211> LENGTH: 25
<212> TYPE: DNA
<213> ORGANISM: Artificial sequence
<220> FEATURE:
<223> OTHER INFORMATION: Synthetic sequence: Probe suitable for detection of genetic variations associated with adverse reactions to pharmaceuticals

<400> SEQUENCE: 1310
ttgaggggca tgaggacggg gttca 25

<210> SEQ ID NO 1311
<211> LENGTH: 25
<212> TYPE: DNA
<213> ORGANISM: Artificial sequence
<220> FEATURE:
<223> OTHER INFORMATION: Synthetic sequence: Probe suitable for detection of genetic variations associated with adverse reactions to pharmaceuticals

<400> SEQUENCE: 1311
tgaaccccgt ccccatgccc ctcaa 25

<210> SEQ ID NO 1312
<211> LENGTH: 25
<212> TYPE: DNA
<213> ORGANISM: Artificial sequence
<220> FEATURE:
<223> OTHER INFORMATION: Synthetic sequence: Probe suitable for detection of genetic variations associated with adverse reactions to pharmaceuticals

<400> SEQUENCE: 1312
tgaaccccgt cctcatgccc ctcaa 25

<210> SEQ ID NO 1313
<211> LENGTH: 25
<212> TYPE: DNA
<213> ORGANISM: Artificial sequence
<220> FEATURE:
<223> OTHER INFORMATION: Synthetic sequence: Probe suitable for detection of genetic variations associated with adverse reactions to pharmaceuticals

<400> SEQUENCE: 1313
gcttctttgg gaaggggaag taggg 25

<210> SEQ ID NO 1314
<211> LENGTH: 25
<212> TYPE: DNA
<213> ORGANISM: Artificial sequence
<220> FEATURE:
<223> OTHER INFORMATION: Synthetic sequence: Probe suitable for detection of genetic variations associated with adverse reactions to pharmaceuticals

<400> SEQUENCE: 1314
gcttctttgg gagggggaag taggg 25

<210> SEQ ID NO 1315
<211> LENGTH: 25
<212> TYPE: DNA
<213> ORGANISM: Artificial sequence
<220> FEATURE:
<223> OTHER INFORMATION: Synthetic sequence: Probe suitable for detection of genetic variations associated with adverse reactions to pharmaceuticals

<400> SEQUENCE: 1315
ccctacttcc ccttcccaaa gaagc 25

<210> SEQ ID NO 1316
<211> LENGTH: 25
<212> TYPE: DNA
<213> ORGANISM: Artificial sequence
<220> FEATURE:
<223> OTHER INFORMATION: Synthetic sequence: Probe suitable for detection of genetic variations associated with adverse reactions to pharmaceuticals

<400> SEQUENCE: 1316
ccctacttcc ccctcccaaa gaagc 25

<210> SEQ ID NO 1317
<211> LENGTH: 20
<212> TYPE: DNA
<213> ORGANISM: Artificial Sequence
<220> FEATURE:
<223> OTHER INFORMATION: Synthetic sequence: PCR primer suitable for amplifying target DNA regions comprising genetic variations associated with IBD

<400> SEQUENCE: 1317
agttggggag gtcttgaagg 20

<210> SEQ ID NO 1318
<211> LENGTH: 20
<212> TYPE: DNA
<213> ORGANISM: Artificial Sequence
<220> FEATURE:
<223> OTHER INFORMATION: Synthetic sequence: PCR primer suitable for amplifying target DNA regions comprising genetic variations associated with IBD

<400> SEQUENCE: 1318
cctatggcgc aacatctgta 20

<210> SEQ ID NO 1319
<211> LENGTH: 19
<212> TYPE: DNA
<213> ORGANISM: Artificial Sequence
<220> FEATURE:
<223> OTHER INFORMATION: Synthetic sequence: PCR primer suitable for amplifying target DNA regions comprising genetic variations associated with IBD

<400> SEQUENCE: 1319
ggaagagctg caggtggac 19

<210> SEQ ID NO 1320
<211> LENGTH: 20
<212> TYPE: DNA
<213> ORGANISM: Artificial Sequence
<220> FEATURE:
<223> OTHER INFORMATION: Synthetic sequence: PCR primer suitable for amplifying target DNA regions comprising genetic variations associated with IBD

<400> SEQUENCE: 1320
gaatcgcttt agcgaacacc 20

<210> SEQ ID NO 1321
<211> LENGTH: 22
<212> TYPE: DNA
<213> ORGANISM: Artificial Sequence
<220> FEATURE:
<223> OTHER INFORMATION: Synthetic sequence: PCR primer suitable for amplifying target DNA regions comprising genetic variations associated with IBD

<400> SEQUENCE: 1321
tctgagcttt ggacttctga ca 22

<210> SEQ ID NO 1322
<211> LENGTH: 20
<212> TYPE: DNA
<213> ORGANISM: Artificial Sequence
<220> FEATURE:
<223> OTHER INFORMATION: Synthetic sequence: PCR primer suitable for amplifying target DNA regions comprising genetic variations associated with IBD

<400> SEQUENCE: 1322
agggtggcaa gaaatcttca 20

<210> SEQ ID NO 1323
<211> LENGTH: 20
<212> TYPE: DNA
<213> ORGANISM: Artificial Sequence
<220> FEATURE:
<223> OTHER INFORMATION: Synthetic sequence: PCR primer suitable for amplifying target DNA regions comprising genetic variations associated with IBD

<400> SEQUENCE: 1323
tcccatttcc gtctttttga 20

<210> SEQ ID NO 1324
<211> LENGTH: 19
<212> TYPE: DNA

<213> ORGANISM: Artificial Sequence
<220> FEATURE:
<223> OTHER INFORMATION: Synthetic sequence: PCR primer suitable for amplifying target DNA regions comprising genetic variations associated with IBD

<400> SEQUENCE: 1324
caaaatcctt cccgctgag 19

<210> SEQ ID NO 1325
<211> LENGTH: 24
<212> TYPE: DNA
<213> ORGANISM: Artificial Sequence
<220> FEATURE:
<223> OTHER INFORMATION: Synthetic sequence: PCR primer suitable for amplifying target DNA regions comprising genetic variations associated with IBD

<400> SEQUENCE: 1325
actttagggt gcttacaact gact 24

<210> SEQ ID NO 1326
<211> LENGTH: 20
<212> TYPE: DNA
<213> ORGANISM: Artificial Sequence
<220> FEATURE:
<223> OTHER INFORMATION: Synthetic sequence: PCR primer suitable for amplifying target DNA regions comprising genetic variations associated with IBD

<400> SEQUENCE: 1326
gactctgacc aggcatttcc 20

<210> SEQ ID NO 1327
<211> LENGTH: 20
<212> TYPE: DNA
<213> ORGANISM: Artificial Sequence
<220> FEATURE:
<223> OTHER INFORMATION: Synthetic sequence: PCR primer suitable for amplifying target DNA regions comprising genetic variations associated with IBD

<400> SEQUENCE: 1327
gcctcaacct ctcaaagtgc 20

<210> SEQ ID NO 1328
<211> LENGTH: 20
<212> TYPE: DNA
<213> ORGANISM: Artificial Sequence
<220> FEATURE:
<223> OTHER INFORMATION: Synthetic sequence: PCR primer suitable for amplifying target DNA regions comprising genetic variations associated with IBD

<400> SEQUENCE: 1328
aattcacatc actgccacca 20

<210> SEQ ID NO 1329
<211> LENGTH: 20
<212> TYPE: DNA
<213> ORGANISM: Artificial Sequence
<220> FEATURE:
<223> OTHER INFORMATION: Synthetic sequence: PCR primer suitable for amplifying target DNA regions comprising genetic variations associated with IBD

<400> SEQUENCE: 1329
cactatctct ccccgacagc 20

<210> SEQ ID NO 1330
<211> LENGTH: 20
<212> TYPE: DNA
<213> ORGANISM: Artificial Sequence
<220> FEATURE:
<223> OTHER INFORMATION: Synthetic sequence: PCR primer suitable for amplifying target DNA regions comprising genetic variations associated with IBD

<400> SEQUENCE: 1330
tggctgtgaa gaacagcaaa 20

<210> SEQ ID NO 1331
<211> LENGTH: 20
<212> TYPE: DNA
<213> ORGANISM: Artificial Sequence
<220> FEATURE:
<223> OTHER INFORMATION: Synthetic sequence: PCR primer suitable for amplifying target DNA regions comprising genetic variations associated with IBD

<400> SEQUENCE: 1331
gagaatgccc agaagatcca 20

<210> SEQ ID NO 1332
<211> LENGTH: 20
<212> TYPE: DNA
<213> ORGANISM: Artificial Sequence
<220> FEATURE:
<223> OTHER INFORMATION: Synthetic sequence: PCR primer suitable for amplifying target DNA regions comprising genetic variations associated with IBD

<400> SEQUENCE: 1332
aagcagaatc cctcctccag 20

<210> SEQ ID NO 1333
<211> LENGTH: 20
<212> TYPE: DNA
<213> ORGANISM: Artificial Sequence
<220> FEATURE:
<223> OTHER INFORMATION: Synthetic sequence: PCR primer suitable for amplifying target DNA regions comprising genetic variations associated with IBD

<400> SEQUENCE: 1333
ggctgcgaag tctgtaaacc 20

<210> SEQ ID NO 1334
<211> LENGTH: 20
<212> TYPE: DNA
<213> ORGANISM: Artificial Sequence
<220> FEATURE:
<223> OTHER INFORMATION: Synthetic sequence: PCR primer suitable for amplifying target DNA regions comprising genetic variations associated with IBD

<400> SEQUENCE: 1334
cgctacatgc ttcaaactcg 20

<210> SEQ ID NO 1335
<211> LENGTH: 20
<212> TYPE: DNA
<213> ORGANISM: Artificial Sequence
<220> FEATURE:
<223> OTHER INFORMATION: Synthetic sequence: PCR primer suitable for amplifying target DNA regions comprising genetic variations associated with IBD

<400> SEQUENCE: 1335
gcggcgatta cagaaaacat 20

<210> SEQ ID NO 1336
<211> LENGTH: 20
<212> TYPE: DNA
<213> ORGANISM: Artificial Sequence
<220> FEATURE:
<223> OTHER INFORMATION: Synthetic sequence: PCR primer suitable for amplifying target DNA regions comprising genetic variations associated with IBD

<400> SEQUENCE: 1336
aatgccatgc tccattcttt 20

<210> SEQ ID NO 1337
<211> LENGTH: 20
<212> TYPE: DNA
<213> ORGANISM: Artificial Sequence
<220> FEATURE:
<223> OTHER INFORMATION: Synthetic sequence: PCR primer suitable for amplifying target DNA regions comprising genetic variations associated with IBD

<400> SEQUENCE: 1337
gagaaacccc acaaccagtg 20

<210> SEQ ID NO 1338
<211> LENGTH: 20
<212> TYPE: DNA
<213> ORGANISM: Artificial Sequence
<220> FEATURE:
<223> OTHER INFORMATION: Synthetic sequence: PCR primer suitable for amplifying target DNA regions comprising genetic variations associated with IBD

<400> SEQUENCE: 1338
agcggctact tttcccaaat 20

<210> SEQ ID NO 1339
<211> LENGTH: 20
<212> TYPE: DNA
<213> ORGANISM: Artificial Sequence
<220> FEATURE:
<223> OTHER INFORMATION: Synthetic sequence: PCR primer suitable for amplifying target DNA regions comprising genetic variations associated with IBD

<400> SEQUENCE: 1339
cagagtctca cccccacatt 20

<210> SEQ ID NO 1340
<211> LENGTH: 20
<212> TYPE: DNA
<213> ORGANISM: Artificial Sequence
<220> FEATURE:
<223> OTHER INFORMATION: Synthetic sequence: PCR primer suitable for amplifying target DNA regions comprising genetic variations associated with IBD

<400> SEQUENCE: 1340
ctcagatcag cagggagagg 20

<210> SEQ ID NO 1341
<211> LENGTH: 20
<212> TYPE: DNA
<213> ORGANISM: Artificial Sequence
<220> FEATURE:

<223> OTHER INFORMATION: Synthetic sequence: PCR primer suitable for amplifying target DNA regions comprising genetic variations associated with IBD

<400> SEQUENCE: 1341
tccctccagt gagcaggtat 20

<210> SEQ ID NO 1342
<211> LENGTH: 20
<212> TYPE: DNA
<213> ORGANISM: Artificial Sequence
<220> FEATURE:
<223> OTHER INFORMATION: Synthetic sequence: PCR primer suitable for amplifying target DNA regions comprising genetic variations associated with IBD

<400> SEQUENCE: 1342
gcatcaccca ggatgaagat 20

<210> SEQ ID NO 1343
<211> LENGTH: 20
<212> TYPE: DNA
<213> ORGANISM: Artificial Sequence
<220> FEATURE:
<223> OTHER INFORMATION: Synthetic sequence: PCR primer suitable for amplifying target DNA regions comprising genetic variations associated with IBD

<400> SEQUENCE: 1343
tcaggttctt ccaggagtgg 20

<210> SEQ ID NO 1344
<211> LENGTH: 20
<212> TYPE: DNA
<213> ORGANISM: Artificial Sequence
<220> FEATURE:
<223> OTHER INFORMATION: Synthetic sequence: PCR primer suitable for amplifying target DNA regions comprising genetic variations associated with IBD

<400> SEQUENCE: 1344
ctgtttggct ttggacaaca 20

<210> SEQ ID NO 1345
<211> LENGTH: 19
<212> TYPE: DNA
<213> ORGANISM: Artificial Sequence
<220> FEATURE:
<223> OTHER INFORMATION: Synthetic sequence: PCR primer suitable for amplifying target DNA regions comprising genetic variations associated with IBD

<400> SEQUENCE: 1345
cgcctcactg ttctcaggt 19

<210> SEQ ID NO 1346
<211> LENGTH: 20
<212> TYPE: DNA
<213> ORGANISM: Artificial Sequence
<220> FEATURE:
<223> OTHER INFORMATION: Synthetic sequence: PCR primer suitable for amplifying target DNA regions comprising genetic variations associated with IBD

<400> SEQUENCE: 1346
aagctttgca ccttgacctc 20

<210> SEQ ID NO 1347

<211> LENGTH: 20
<212> TYPE: DNA
<213> ORGANISM: Artificial Sequence
<220> FEATURE:
<223> OTHER INFORMATION: Synthetic sequence: PCR primer suitable for amplifying target DNA regions comprising genetic variations associated with IBD

<400> SEQUENCE: 1347
tcacttgctg agaacccaga 20

<210> SEQ ID NO 1348
<211> LENGTH: 20
<212> TYPE: DNA
<213> ORGANISM: Artificial Sequence
<220> FEATURE:
<223> OTHER INFORMATION: Synthetic sequence: PCR primer suitable for amplifying target DNA regions comprising genetic variations associated with IBD

<400> SEQUENCE: 1348
ggaccctggg actagaggag 20

<210> SEQ ID NO 1349
<211> LENGTH: 20
<212> TYPE: DNA
<213> ORGANISM: Artificial Sequence
<220> FEATURE:
<223> OTHER INFORMATION: Synthetic sequence: PCR primer suitable for amplifying target DNA regions comprising genetic variations associated with IBD

<400> SEQUENCE: 1349
acttaattgc ctgggtgacg 20

<210> SEQ ID NO 1350
<211> LENGTH: 20
<212> TYPE: DNA
<213> ORGANISM: Artificial Sequence
<220> FEATURE:
<223> OTHER INFORMATION: Synthetic sequence: PCR primer suitable for amplifying target DNA regions comprising genetic variations associated with IBD

<400> SEQUENCE: 1350
gcaattcacc aaactgatcg 20

<210> SEQ ID NO 1351
<211> LENGTH: 20
<212> TYPE: DNA
<213> ORGANISM: Artificial Sequence
<220> FEATURE:
<223> OTHER INFORMATION: Synthetic sequence: PCR primer suitable for amplifying target DNA regions comprising genetic variations associated with IBD

<400> SEQUENCE: 1351
ccacctttgc ttttctcacc 20

<210> SEQ ID NO 1352
<211> LENGTH: 20
<212> TYPE: DNA
<213> ORGANISM: Artificial Sequence
<220> FEATURE:
<223> OTHER INFORMATION: Synthetic sequence: PCR primer suitable for amplifying target DNA regions comprising genetic variations associated with IBD

<400> SEQUENCE: 1352
ctgcgtttgt gcttgtgttt 20

<210> SEQ ID NO 1353
<211> LENGTH: 20
<212> TYPE: DNA
<213> ORGANISM: Artificial Sequence
<220> FEATURE:
<223> OTHER INFORMATION: Synthetic sequence: PCR primer suitable for amplifying target DNA regions comprising genetic variations associated with IBD

<400> SEQUENCE: 1353
tttggggagc tgaaggacta 20

<210> SEQ ID NO 1354
<211> LENGTH: 20
<212> TYPE: DNA
<213> ORGANISM: Artificial Sequence
<220> FEATURE:
<223> OTHER INFORMATION: Synthetic sequence: PCR primer suitable for amplifying target DNA regions comprising genetic variations associated with IBD

<400> SEQUENCE: 1354
ctttgtgacc attccggttt 20

<210> SEQ ID NO 1355
<211> LENGTH: 20
<212> TYPE: DNA
<213> ORGANISM: Artificial Sequence
<220> FEATURE:
<223> OTHER INFORMATION: Synthetic sequence: PCR primer suitable for amplifying target DNA regions comprising genetic variations associated with IBD

<400> SEQUENCE: 1355
tggtgtctcc aggtcaatca 20

<210> SEQ ID NO 1356
<211> LENGTH: 20
<212> TYPE: DNA
<213> ORGANISM: Artificial Sequence
<220> FEATURE:
<223> OTHER INFORMATION: Synthetic sequence: PCR primer suitable for amplifying target DNA regions comprising genetic variations associated with IBD

<400> SEQUENCE: 1356
ggctgatcct tcccagaaat 20

<210> SEQ ID NO 1357
<211> LENGTH: 20
<212> TYPE: DNA
<213> ORGANISM: Artificial Sequence
<220> FEATURE:
<223> OTHER INFORMATION: Synthetic sequence: PCR primer suitable for amplifying target DNA regions comprising genetic variations associated with IBD

<400> SEQUENCE: 1357
actgtttggt gggcttcatc 20

<210> SEQ ID NO 1358
<211> LENGTH: 20
<212> TYPE: DNA
<213> ORGANISM: Artificial Sequence
<220> FEATURE:
<223> OTHER INFORMATION: Synthetic sequence: PCR primer suitable for amplifying target DNA regions comprising genetic variations associated with IBD

<400> SEQUENCE: 1358
agggatccat caccaggttt 20

<210> SEQ ID NO 1359
<211> LENGTH: 20
<212> TYPE: DNA
<213> ORGANISM: Artificial Sequence
<220> FEATURE:
<223> OTHER INFORMATION: Synthetic sequence: PCR primer suitable for amplifying target DNA regions comprising genetic variations associated with IBD

<400> SEQUENCE: 1359
agggttatgt ggcaatgacg 20

<210> SEQ ID NO 1360
<211> LENGTH: 20
<212> TYPE: DNA
<213> ORGANISM: Artificial Sequence
<220> FEATURE:
<223> OTHER INFORMATION: Synthetic sequence: PCR primer suitable for amplifying target DNA regions comprising genetic variations associated with IBD

<400> SEQUENCE: 1360
accaatgctc atcccaactc 20

<210> SEQ ID NO 1361
<211> LENGTH: 20
<212> TYPE: DNA
<213> ORGANISM: Artificial Sequence
<220> FEATURE:
<223> OTHER INFORMATION: Synthetic sequence: PCR primer suitable for amplifying target DNA regions comprising genetic variations associated with IBD

<400> SEQUENCE: 1361
catgaaccac catgctcagt 20

<210> SEQ ID NO 1362
<211> LENGTH: 20
<212> TYPE: DNA
<213> ORGANISM: Artificial Sequence
<220> FEATURE:
<223> OTHER INFORMATION: Synthetic sequence: PCR primer suitable for amplifying target DNA regions comprising genetic variations associated with IBD

<400> SEQUENCE: 1362
accacactca gggtctctgg 20

<210> SEQ ID NO 1363
<211> LENGTH: 20
<212> TYPE: DNA
<213> ORGANISM: Artificial Sequence
<220> FEATURE:
<223> OTHER INFORMATION: Synthetic sequence: PCR primer suitable for amplifying target DNA regions comprising genetic variations associated with IBD

<400> SEQUENCE: 1363
agaatggcta ctgggtggtg 20

<210> SEQ ID NO 1364
<211> LENGTH: 20
<212> TYPE: DNA

<213> ORGANISM: Artificial Sequence
<220> FEATURE:
<223> OTHER INFORMATION: Synthetic sequence: PCR primer suitable for amplifying target DNA regions comprising genetic variations associated with IBD

<400> SEQUENCE: 1364
agagcagctg gcgaatgtat 20

<210> SEQ ID NO 1365
<211> LENGTH: 20
<212> TYPE: DNA
<213> ORGANISM: Artificial Sequence
<220> FEATURE:
<223> OTHER INFORMATION: Synthetic sequence: PCR primer suitable for amplifying target DNA regions comprising genetic variations associated with IBD

<400> SEQUENCE: 1365
tcaaagtctc cagggtcagg 20

<210> SEQ ID NO 1366
<211> LENGTH: 20
<212> TYPE: DNA
<213> ORGANISM: Artificial Sequence
<220> FEATURE:
<223> OTHER INFORMATION: Synthetic sequence: PCR primer suitable for amplifying target DNA regions comprising genetic variations associated with IBD

<400> SEQUENCE: 1366
agggcgaatc atgtatgagg 20

<210> SEQ ID NO 1367
<211> LENGTH: 20
<212> TYPE: DNA
<213> ORGANISM: Artificial Sequence
<220> FEATURE:
<223> OTHER INFORMATION: Synthetic sequence: PCR primer suitable for amplifying target DNA regions comprising genetic variations associated with IBD

<400> SEQUENCE: 1367
catccccatt tgctcacttt 20

<210> SEQ ID NO 1368
<211> LENGTH: 20
<212> TYPE: DNA
<213> ORGANISM: Artificial Sequence
<220> FEATURE:
<223> OTHER INFORMATION: Synthetic sequence: PCR primer suitable for amplifying target DNA regions comprising genetic variations associated with IBD

<400> SEQUENCE: 1368
gcctggtcac tctcagttcc 20

<210> SEQ ID NO 1369
<211> LENGTH: 20
<212> TYPE: DNA
<213> ORGANISM: Artificial Sequence
<220> FEATURE:
<223> OTHER INFORMATION: Synthetic sequence: PCR primer suitable for amplifying target DNA regions comprising genetic variations associated with IBD

<400> SEQUENCE: 1369
cgaggagttc ccaacaggta 20

<210> SEQ ID NO 1370
<211> LENGTH: 20
<212> TYPE: DNA
<213> ORGANISM: Artificial Sequence
<220> FEATURE:
<223> OTHER INFORMATION: Synthetic sequence: PCR primer suitable for amplifying target DNA regions comprising genetic variations associated with IBD

<400> SEQUENCE: 1370
ggcttttgtc tcctttgtgg 20

<210> SEQ ID NO 1371
<211> LENGTH: 20
<212> TYPE: DNA
<213> ORGANISM: Artificial Sequence
<220> FEATURE:
<223> OTHER INFORMATION: Synthetic sequence: PCR primer suitable for amplifying target DNA regions comprising genetic variations associated with IBD

<400> SEQUENCE: 1371
tccagtgttt gtccatgctg 20

<210> SEQ ID NO 1372
<211> LENGTH: 23
<212> TYPE: DNA
<213> ORGANISM: Artificial Sequence
<220> FEATURE:
<223> OTHER INFORMATION: Synthetic sequence: PCR primer suitable for amplifying target DNA regions comprising genetic variations associated with IBD

<400> SEQUENCE: 1372
ttcccctgat gttaaaagaa aca 23

<210> SEQ ID NO 1373
<211> LENGTH: 20
<212> TYPE: DNA
<213> ORGANISM: Artificial Sequence
<220> FEATURE:
<223> OTHER INFORMATION: Synthetic sequence: PCR primer suitable for amplifying target DNA regions comprising genetic variations associated with IBD

<400> SEQUENCE: 1373
gtcaacagtt cccctttgga 20

<210> SEQ ID NO 1374
<211> LENGTH: 20
<212> TYPE: DNA
<213> ORGANISM: Artificial Sequence
<220> FEATURE:
<223> OTHER INFORMATION: Synthetic sequence: PCR primer suitable for amplifying target DNA regions comprising genetic variations associated with IBD

<400> SEQUENCE: 1374
tggcagggga taagtaccag 20

<210> SEQ ID NO 1375
<211> LENGTH: 20
<212> TYPE: DNA
<213> ORGANISM: Artificial Sequence
<220> FEATURE:
<223> OTHER INFORMATION: Synthetic sequence: PCR primer suitable for amplifying target DNA regions comprising genetic variations associated with IBD

<400> SEQUENCE: 1375
actgtttggt gggcttcatc 20

<210> SEQ ID NO 1376
<211> LENGTH: 23
<212> TYPE: DNA
<213> ORGANISM: Artificial Sequence
<220> FEATURE:
<223> OTHER INFORMATION: Synthetic sequence: PCR primer suitable for amplifying target DNA regions comprising genetic variations associated with IBD

<400> SEQUENCE: 1376
gggtgataca tacacaaggg ttt 23

<210> SEQ ID NO 1377
<211> LENGTH: 20
<212> TYPE: DNA
<213> ORGANISM: Artificial Sequence
<220> FEATURE:
<223> OTHER INFORMATION: Synthetic sequence: PCR primer suitable for amplifying target DNA regions comprising genetic variations associated with IBD

<400> SEQUENCE: 1377
cctgccaaag aagaaacacc 20

<210> SEQ ID NO 1378
<211> LENGTH: 20
<212> TYPE: DNA
<213> ORGANISM: Artificial Sequence
<220> FEATURE:
<223> OTHER INFORMATION: Synthetic sequence: PCR primer suitable for amplifying target DNA regions comprising genetic variations associated with IBD

<400> SEQUENCE: 1378
gatgaagccc accaaacagt 20

<210> SEQ ID NO 1379
<211> LENGTH: 20
<212> TYPE: DNA
<213> ORGANISM: Artificial Sequence
<220> FEATURE:
<223> OTHER INFORMATION: Synthetic sequence: PCR primer suitable for amplifying target DNA regions comprising genetic variations associated with IBD

<400> SEQUENCE: 1379
ggggatcatg gacattgaag 20

<210> SEQ ID NO 1380
<211> LENGTH: 20
<212> TYPE: DNA
<213> ORGANISM: Artificial Sequence
<220> FEATURE:
<223> OTHER INFORMATION: Synthetic sequence: PCR primer suitable for amplifying target DNA regions comprising genetic variations associated with IBD

<400> SEQUENCE: 1380
tgtggtcaga gcccagtaca 20

<210> SEQ ID NO 1381
<211> LENGTH: 20
<212> TYPE: DNA
<213> ORGANISM: Artificial Sequence
<220> FEATURE:

<223> OTHER INFORMATION: Synthetic sequence: PCR primer suitable for amplifying target DNA regions comprising genetic variations associated with IBD

<400> SEQUENCE: 1381
ccttctgggg gaactttaca 20

<210> SEQ ID NO 1382
<211> LENGTH: 21
<212> TYPE: DNA
<213> ORGANISM: Artificial Sequence
<220> FEATURE:
<223> OTHER INFORMATION: Synthetic sequence: PCR primer suitable for amplifying target DNA regions comprising genetic variations associated with IBD

<400> SEQUENCE: 1382
cgctgtaagg ttgatctttg g 21

<210> SEQ ID NO 1383
<211> LENGTH: 20
<212> TYPE: DNA
<213> ORGANISM: Artificial Sequence
<220> FEATURE:
<223> OTHER INFORMATION: Synthetic sequence: PCR primer suitable for amplifying target DNA regions comprising genetic variations associated with IBD

<400> SEQUENCE: 1383
ctgaacaccg ctcccataaa 20

<210> SEQ ID NO 1384
<211> LENGTH: 20
<212> TYPE: DNA
<213> ORGANISM: Artificial Sequence
<220> FEATURE:
<223> OTHER INFORMATION: Synthetic sequence: PCR primer suitable for amplifying target DNA regions comprising genetic variations associated with IBD

<400> SEQUENCE: 1384
cctcctccat cttcatgctc 20

<210> SEQ ID NO 1385
<211> LENGTH: 20
<212> TYPE: DNA
<213> ORGANISM: Artificial Sequence
<220> FEATURE:
<223> OTHER INFORMATION: Synthetic sequence: PCR primer suitable for amplifying target DNA regions comprising genetic variations associated with IBD

<400> SEQUENCE: 1385
ccgggatcag gaaagaagat 20

<210> SEQ ID NO 1386
<211> LENGTH: 20
<212> TYPE: DNA
<213> ORGANISM: Artificial Sequence
<220> FEATURE:
<223> OTHER INFORMATION: Synthetic sequence: PCR primer suitable for amplifying target DNA regions comprising genetic variations associated with IBD

<400> SEQUENCE: 1386
aggggctttc agttttccat 20

<210> SEQ ID NO 1387

<211> LENGTH: 21
<212> TYPE: DNA
<213> ORGANISM: Artificial Sequence
<220> FEATURE:
<223> OTHER INFORMATION: Synthetic sequence: PCR primer suitable for amplifying target DNA regions comprising genetic variations associated with IBD

<400> SEQUENCE: 1387
tgtgtgggta ttgttgcatt g 21

<210> SEQ ID NO 1388
<211> LENGTH: 20
<212> TYPE: DNA
<213> ORGANISM: Artificial Sequence
<220> FEATURE:
<223> OTHER INFORMATION: Synthetic sequence: PCR primer suitable for amplifying target DNA regions comprising genetic variations associated with IBD

<400> SEQUENCE: 1388
ccatgtacca cagcttgctc 20

<210> SEQ ID NO 1389
<211> LENGTH: 20
<212> TYPE: DNA
<213> ORGANISM: Artificial Sequence
<220> FEATURE:
<223> OTHER INFORMATION: Synthetic sequence: PCR primer suitable for amplifying target DNA regions comprising genetic variations associated with IBD

<400> SEQUENCE: 1389
ctcattggtg gggaagaaga 20

<210> SEQ ID NO 1390
<211> LENGTH: 20
<212> TYPE: DNA
<213> ORGANISM: Artificial Sequence
<220> FEATURE:
<223> OTHER INFORMATION: Synthetic sequence: PCR primer suitable for amplifying target DNA regions comprising genetic variations associated with IBD

<400> SEQUENCE: 1390
cgaactgcct cctgacattt 20

<210> SEQ ID NO 1391
<211> LENGTH: 18
<212> TYPE: DNA
<213> ORGANISM: Artificial Sequence
<220> FEATURE:
<223> OTHER INFORMATION: Synthetic sequence: PCR primer suitable for amplifying target DNA regions comprising genetic variations associated with IBD

<400> SEQUENCE: 1391
gcccaggagc ctgaagac 18

<210> SEQ ID NO 1392
<211> LENGTH: 20
<212> TYPE: DNA
<213> ORGANISM: Artificial Sequence
<220> FEATURE:
<223> OTHER INFORMATION: Synthetic sequence: PCR primer suitable for amplifying target DNA regions comprising genetic variations associated with IBD

<400> SEQUENCE: 1392
ccttctctct gcgtttgctc 20

<210> SEQ ID NO 1393
<211> LENGTH: 20
<212> TYPE: DNA
<213> ORGANISM: Artificial Sequence
<220> FEATURE:
<223> OTHER INFORMATION: Synthetic sequence: PCR primer suitable for amplifying target DNA regions comprising genetic variations associated with IBD

<400> SEQUENCE: 1393
ggcctcaatg aactcctcaa 20

<210> SEQ ID NO 1394
<211> LENGTH: 20
<212> TYPE: DNA
<213> ORGANISM: Artificial Sequence
<220> FEATURE:
<223> OTHER INFORMATION: Synthetic sequence: PCR primer suitable for amplifying target DNA regions comprising genetic variations associated with IBD

<400> SEQUENCE: 1394
ggatagcaac tgctccaagg 20

<210> SEQ ID NO 1395
<211> LENGTH: 20
<212> TYPE: DNA
<213> ORGANISM: Artificial Sequence
<220> FEATURE:
<223> OTHER INFORMATION: Synthetic sequence: PCR primer suitable for amplifying target DNA regions comprising genetic variations associated with IBD

<400> SEQUENCE: 1395
acttcaccaa catgcaggac 20

<210> SEQ ID NO 1396
<211> LENGTH: 20
<212> TYPE: DNA
<213> ORGANISM: Artificial Sequence
<220> FEATURE:
<223> OTHER INFORMATION: Synthetic sequence: PCR primer suitable for amplifying target DNA regions comprising genetic variations associated with IBD

<400> SEQUENCE: 1396
caggtcacag ctctcaatgc 20

<210> SEQ ID NO 1397
<211> LENGTH: 20
<212> TYPE: DNA
<213> ORGANISM: Artificial Sequence
<220> FEATURE:
<223> OTHER INFORMATION: Synthetic sequence: PCR primer suitable for amplifying target DNA regions comprising genetic variations associated with IBD

<400> SEQUENCE: 1397
tggttaagga tgcccagaag 20

<210> SEQ ID NO 1398
<211> LENGTH: 21
<212> TYPE: DNA
<213> ORGANISM: Artificial Sequence
<220> FEATURE:
<223> OTHER INFORMATION: Synthetic sequence: PCR primer suitable for amplifying target DNA regions comprising genetic variations associated with IBD

<400> SEQUENCE: 1398
cgaaaagaca acctcaagca c 21

<210> SEQ ID NO 1399
<211> LENGTH: 20
<212> TYPE: DNA
<213> ORGANISM: Artificial Sequence
<220> FEATURE:
<223> OTHER INFORMATION: Synthetic sequence: PCR primer suitable for amplifying target DNA regions comprising genetic variations associated with IBD

<400> SEQUENCE: 1399
ctgtcgtcca tgctgtgttt 20

<210> SEQ ID NO 1400
<211> LENGTH: 20
<212> TYPE: DNA
<213> ORGANISM: Artificial Sequence
<220> FEATURE:
<223> OTHER INFORMATION: Synthetic sequence: PCR primer suitable for amplifying target DNA regions comprising genetic variations associated with IBD

<400> SEQUENCE: 1400
gaccagcccc aagatgacta 20

<210> SEQ ID NO 1401
<211> LENGTH: 20
<212> TYPE: DNA
<213> ORGANISM: Artificial Sequence
<220> FEATURE:
<223> OTHER INFORMATION: Synthetic sequence: PCR primer suitable for amplifying target DNA regions comprising genetic variations associated with IBD

<400> SEQUENCE: 1401
gcctcaatga cgacctaagc 20

<210> SEQ ID NO 1402
<211> LENGTH: 20
<212> TYPE: DNA
<213> ORGANISM: Artificial Sequence
<220> FEATURE:
<223> OTHER INFORMATION: Synthetic sequence: PCR primer suitable for amplifying target DNA regions comprising genetic variations associated with IBD

<400> SEQUENCE: 1402
tcatgggaaa atcccacatt 20

<210> SEQ ID NO 1403
<211> LENGTH: 20
<212> TYPE: DNA
<213> ORGANISM: Artificial Sequence
<220> FEATURE:
<223> OTHER INFORMATION: Synthetic sequence: PCR primer suitable for amplifying target DNA regions comprising genetic variations associated with IBD

<400> SEQUENCE: 1403
aagaaaaccc cagcagtgtg 20

<210> SEQ ID NO 1404
<211> LENGTH: 20
<212> TYPE: DNA

<213> ORGANISM: Artificial Sequence
<220> FEATURE:
<223> OTHER INFORMATION: Synthetic sequence: PCR primer suitable for amplifying target DNA regions comprising genetic variations associated with IBD

<400> SEQUENCE: 1404
gccttttgga aaatcaacca 20

<210> SEQ ID NO 1405
<211> LENGTH: 20
<212> TYPE: DNA
<213> ORGANISM: Artificial Sequence
<220> FEATURE:
<223> OTHER INFORMATION: Synthetic sequence: PCR primer suitable for amplifying target DNA regions comprising genetic variations associated with IBD

<400> SEQUENCE: 1405
gaagacccag gtccagatga 20

<210> SEQ ID NO 1406
<211> LENGTH: 20
<212> TYPE: DNA
<213> ORGANISM: Artificial Sequence
<220> FEATURE:
<223> OTHER INFORMATION: Synthetic sequence: PCR primer suitable for amplifying target DNA regions comprising genetic variations associated with IBD

<400> SEQUENCE: 1406
actgaccgtg caagtcacag 20

<210> SEQ ID NO 1407
<211> LENGTH: 20
<212> TYPE: DNA
<213> ORGANISM: Artificial Sequence
<220> FEATURE:
<223> OTHER INFORMATION: Synthetic sequence: PCR primer suitable for amplifying target DNA regions comprising genetic variations associated with IBD

<400> SEQUENCE: 1407
ctgtcatcga cccactgatg 20

<210> SEQ ID NO 1408
<211> LENGTH: 19
<212> TYPE: DNA
<213> ORGANISM: Artificial Sequence
<220> FEATURE:
<223> OTHER INFORMATION: Synthetic sequence: PCR primer suitable for amplifying target DNA regions comprising genetic variations associated with IBD

<400> SEQUENCE: 1408
gacacaggga aggctcaca 19

<210> SEQ ID NO 1409
<211> LENGTH: 20
<212> TYPE: DNA
<213> ORGANISM: Artificial Sequence
<220> FEATURE:
<223> OTHER INFORMATION: Synthetic sequence: PCR primer suitable for amplifying target DNA regions comprising genetic variations associated with IBD

<400> SEQUENCE: 1409
aagaaaaccc cagcagtgtg 20

<210> SEQ ID NO 1410
<211> LENGTH: 20
<212> TYPE: DNA
<213> ORGANISM: Artificial Sequence
<220> FEATURE:
<223> OTHER INFORMATION: Synthetic sequence: PCR primer suitable for amplifying target DNA regions comprising genetic variations associated with IBD

<400> SEQUENCE: 1410
gccttttgga aaatcaacca 20

<210> SEQ ID NO 1411
<211> LENGTH: 20
<212> TYPE: DNA
<213> ORGANISM: Artificial Sequence
<220> FEATURE:
<223> OTHER INFORMATION: Synthetic sequence: PCR primer suitable for amplifying target DNA regions comprising genetic variations associated with IBD

<400> SEQUENCE: 1411
aagaaaaccc cagcagtgtg 20

<210> SEQ ID NO 1412
<211> LENGTH: 20
<212> TYPE: DNA
<213> ORGANISM: Artificial Sequence
<220> FEATURE:
<223> OTHER INFORMATION: Synthetic sequence: PCR primer suitable for amplifying target DNA regions comprising genetic variations associated with IBD

<400> SEQUENCE: 1412
gccttttgga aaatcaacca 20

<210> SEQ ID NO 1413
<211> LENGTH: 20
<212> TYPE: DNA
<213> ORGANISM: Artificial Sequence
<220> FEATURE:
<223> OTHER INFORMATION: Synthetic sequence: PCR primer suitable for amplifying target DNA regions comprising genetic variations associated with IBD

<400> SEQUENCE: 1413
gtagatgaag tcccccagca 20

<210> SEQ ID NO 1414
<211> LENGTH: 20
<212> TYPE: DNA
<213> ORGANISM: Artificial Sequence
<220> FEATURE:
<223> OTHER INFORMATION: Synthetic sequence: PCR primer suitable for amplifying target DNA regions comprising genetic variations associated with IBD

<400> SEQUENCE: 1414
gcattgaacc cgtcttgttt 20

<210> SEQ ID NO 1415
<211> LENGTH: 21
<212> TYPE: DNA
<213> ORGANISM: Artificial Sequence
<220> FEATURE:
<223> OTHER INFORMATION: Synthetic sequence: PCR primer suitable for amplifying target DNA regions comprising genetic variations associated with IBD

<400> SEQUENCE: 1415
gcaccgacat ttactgacac c 21

<210> SEQ ID NO 1416
<211> LENGTH: 20
<212> TYPE: DNA
<213> ORGANISM: Artificial Sequence
<220> FEATURE:
<223> OTHER INFORMATION: Synthetic sequence: PCR primer suitable for amplifying target DNA regions comprising genetic variations associated with IBD

<400> SEQUENCE: 1416
atgaggctgg agaagaagca 20

<210> SEQ ID NO 1417
<211> LENGTH: 19
<212> TYPE: DNA
<213> ORGANISM: Artificial Sequence
<220> FEATURE:
<223> OTHER INFORMATION: Synthetic sequence: PCR primer suitable for amplifying target DNA regions comprising genetic variations associated with IBD

<400> SEQUENCE: 1417
gagcacgtgg tggagtttg 19

<210> SEQ ID NO 1418
<211> LENGTH: 20
<212> TYPE: DNA
<213> ORGANISM: Artificial Sequence
<220> FEATURE:
<223> OTHER INFORMATION: Synthetic sequence: PCR primer suitable for amplifying target DNA regions comprising genetic variations associated with IBD

<400> SEQUENCE: 1418
ttgtccaagt ccctccacac 20

<210> SEQ ID NO 1419
<211> LENGTH: 20
<212> TYPE: DNA
<213> ORGANISM: Artificial Sequence
<220> FEATURE:
<223> OTHER INFORMATION: Synthetic sequence: PCR primer suitable for amplifying target DNA regions comprising genetic variations associated with IBD

<400> SEQUENCE: 1419
atggccacgt cgttgttatt 20

<210> SEQ ID NO 1420
<211> LENGTH: 20
<212> TYPE: DNA
<213> ORGANISM: Artificial Sequence
<220> FEATURE:
<223> OTHER INFORMATION: Synthetic sequence: PCR primer suitable for amplifying target DNA regions comprising genetic variations associated with IBD

<400> SEQUENCE: 1420
agccacctgt gcttcttcac 20

<210> SEQ ID NO 1421
<211> LENGTH: 20
<212> TYPE: DNA
<213> ORGANISM: Artificial Sequence
<220> FEATURE:

<223> OTHER INFORMATION: Synthetic sequence: PCR primer suitable for amplifying target DNA regions comprising genetic variations associated with IBD

<400> SEQUENCE: 1421
gtgttcagag gatgggcatt 20

<210> SEQ ID NO 1422
<211> LENGTH: 20
<212> TYPE: DNA
<213> ORGANISM: Artificial Sequence
<220> FEATURE:
<223> OTHER INFORMATION: Synthetic sequence: PCR primer suitable for amplifying target DNA regions comprising genetic variations associated with IBD

<400> SEQUENCE: 1422
ggggctgaat aaagggttgt 20

<210> SEQ ID NO 1423
<211> LENGTH: 20
<212> TYPE: DNA
<213> ORGANISM: Artificial Sequence
<220> FEATURE:
<223> OTHER INFORMATION: Synthetic sequence: PCR primer suitable for amplifying target DNA regions comprising genetic variations associated with IBD

<400> SEQUENCE: 1423
gagctacgca catcaccaaa 20

<210> SEQ ID NO 1424
<211> LENGTH: 20
<212> TYPE: DNA
<213> ORGANISM: Artificial Sequence
<220> FEATURE:
<223> OTHER INFORMATION: Synthetic sequence: PCR primer suitable for amplifying target DNA regions comprising genetic variations associated with IBD

<400> SEQUENCE: 1424
ggtcctcttt gcaatccaga 20

<210> SEQ ID NO 1425
<211> LENGTH: 20
<212> TYPE: DNA
<213> ORGANISM: Artificial Sequence
<220> FEATURE:
<223> OTHER INFORMATION: Synthetic sequence: PCR primer suitable for amplifying target DNA regions comprising genetic variations associated with IBD

<400> SEQUENCE: 1425
cagacgacac aggaagcaga 20

<210> SEQ ID NO 1426
<211> LENGTH: 20
<212> TYPE: DNA
<213> ORGANISM: Artificial Sequence
<220> FEATURE:
<223> OTHER INFORMATION: Synthetic sequence: PCR primer suitable for amplifying target DNA regions comprising genetic variations associated with IBD

<400> SEQUENCE: 1426
tgtctgagca ccacttttgg 20

<210> SEQ ID NO 1427

<211> LENGTH: 20
<212> TYPE: DNA
<213> ORGANISM: Artificial Sequence
<220> FEATURE:
<223> OTHER INFORMATION: Synthetic sequence: PCR primer suitable for amplifying target DNA regions comprising genetic variations associated with IBD

<400> SEQUENCE: 1427
gggaaagagt gagtgggaca 20

<210> SEQ ID NO 1428
<211> LENGTH: 20
<212> TYPE: DNA
<213> ORGANISM: Artificial Sequence
<220> FEATURE:
<223> OTHER INFORMATION: Synthetic sequence: PCR primer suitable for amplifying target DNA regions comprising genetic variations associated with IBD

<400> SEQUENCE: 1428
cccctgggtc tgtgttttta 20

<210> SEQ ID NO 1429
<211> LENGTH: 23
<212> TYPE: DNA
<213> ORGANISM: Artificial sequence
<220> FEATURE:
<223> OTHER INFORMATION: Synthetic sequence: Probe suitable for detection of genetic variations associated with IBD

<400> SEQUENCE: 1429
tcacagacgt tcctggaatg gac 23

<210> SEQ ID NO 1430
<211> LENGTH: 23
<212> TYPE: DNA
<213> ORGANISM: Artificial sequence
<220> FEATURE:
<223> OTHER INFORMATION: Synthetic sequence: Probe suitable for detection of genetic variations associated with IBD

<400> SEQUENCE: 1430
tcacagacgt ttctggaatg gac 23

<210> SEQ ID NO 1431
<211> LENGTH: 23
<212> TYPE: DNA
<213> ORGANISM: Artificial sequence
<220> FEATURE:
<223> OTHER INFORMATION: Synthetic sequence: Probe suitable for detection of genetic variations associated with IBD

<400> SEQUENCE: 1431
gtccattcca ggaacgtctg tga 23

<210> SEQ ID NO 1432
<211> LENGTH: 23
<212> TYPE: DNA
<213> ORGANISM: Artificial sequence
<220> FEATURE:
<223> OTHER INFORMATION: Synthetic sequence: Probe suitable for detection of genetic variations associated with IBD

<400> SEQUENCE: 1432
gtccattcca gaaacgtctg tga 23

<210> SEQ ID NO 1433

<211> LENGTH: 23
<212> TYPE: DNA
<213> ORGANISM: Artificial sequence
<220> FEATURE:
<223> OTHER INFORMATION: Synthetic sequence: Probe suitable for detection of genetic variations associated with IBD

<400> SEQUENCE: 1433
gtcctgctga gccgcgagct gtt 23

<210> SEQ ID NO 1434
<211> LENGTH: 23
<212> TYPE: DNA
<213> ORGANISM: Artificial sequence
<220> FEATURE:
<223> OTHER INFORMATION: Synthetic sequence: Probe suitable for detection of genetic variations associated with IBD

<400> SEQUENCE: 1434
gtcctgctga gtcgcgagct gtt 23

<210> SEQ ID NO 1435
<211> LENGTH: 23
<212> TYPE: DNA
<213> ORGANISM: Artificial sequence
<220> FEATURE:
<223> OTHER INFORMATION: Synthetic sequence: Probe suitable for detection of genetic variations associated with IBD

<400> SEQUENCE: 1435
aacagctcgc ggctcagcag gac 23

<210> SEQ ID NO 1436
<211> LENGTH: 23
<212> TYPE: DNA
<213> ORGANISM: Artificial sequence
<220> FEATURE:
<223> OTHER INFORMATION: Synthetic sequence: Probe suitable for detection of genetic variations associated with IBD

<400> SEQUENCE: 1436
aacagctcgc gactcagcag gac 23

<210> SEQ ID NO 1437
<211> LENGTH: 23
<212> TYPE: DNA
<213> ORGANISM: Artificial sequence
<220> FEATURE:
<223> OTHER INFORMATION: Synthetic sequence: Probe suitable for detection of genetic variations associated with IBD

<400> SEQUENCE: 1437
ttctcataat agaatccagt atc 23

<210> SEQ ID NO 1438
<211> LENGTH: 23
<212> TYPE: DNA
<213> ORGANISM: Artificial sequence
<220> FEATURE:
<223> OTHER INFORMATION: Synthetic sequence: Probe suitable for detection of genetic variations associated with IBD

<400> SEQUENCE: 1438
ttctcataat acaatccagt atc 23

<210> SEQ ID NO 1439
<211> LENGTH: 23
<212> TYPE: DNA

<213> ORGANISM: Artificial sequence
<220> FEATURE:
<223> OTHER INFORMATION: Synthetic sequence: Probe suitable for detection of genetic variations associated with IBD

<400> SEQUENCE: 1439
gatactggat tctattatga gaa 23

<210> SEQ ID NO 1440
<211> LENGTH: 23
<212> TYPE: DNA
<213> ORGANISM: Artificial sequence
<220> FEATURE:
<223> OTHER INFORMATION: Synthetic sequence: Probe suitable for detection of genetic variations associated with IBD

<400> SEQUENCE: 1440
gatactggat tgtattatga gaa 23

<210> SEQ ID NO 1441
<211> LENGTH: 23
<212> TYPE: DNA
<213> ORGANISM: Artificial sequence
<220> FEATURE:
<223> OTHER INFORMATION: Synthetic sequence: Probe suitable for detection of genetic variations associated with IBD

<400> SEQUENCE: 1441
ctgcaagctg cggaagataa tga 23

<210> SEQ ID NO 1442
<211> LENGTH: 23
<212> TYPE: DNA
<213> ORGANISM: Artificial sequence
<220> FEATURE:
<223> OTHER INFORMATION: Synthetic sequence: Probe suitable for detection of genetic variations associated with IBD

<400> SEQUENCE: 1442
ctgcaagctg cagaagataa tga 23

<210> SEQ ID NO 1443
<211> LENGTH: 23
<212> TYPE: DNA
<213> ORGANISM: Artificial sequence
<220> FEATURE:
<223> OTHER INFORMATION: Synthetic sequence: Probe suitable for detection of genetic variations associated with IBD

<400> SEQUENCE: 1443
tcattatctt ccgcagcttg cag 23

<210> SEQ ID NO 1444
<211> LENGTH: 23
<212> TYPE: DNA
<213> ORGANISM: Artificial sequence
<220> FEATURE:
<223> OTHER INFORMATION: Synthetic sequence: Probe suitable for detection of genetic variations associated with IBD

<400> SEQUENCE: 1444
tcattatctt ctgcagcttg cag 23

<210> SEQ ID NO 1445
<211> LENGTH: 23
<212> TYPE: DNA
<213> ORGANISM: Artificial sequence
<220> FEATURE:

<223> OTHER INFORMATION: Synthetic sequence: Probe suitable for detection of genetic variations associated with IBD

<400> SEQUENCE: 1445
tcaccagagg tccaacctta ctg 23

<210> SEQ ID NO 1446
<211> LENGTH: 23
<212> TYPE: DNA
<213> ORGANISM: Artificial sequence
<220> FEATURE:
<223> OTHER INFORMATION: Synthetic sequence: Probe suitable for detection of genetic variations associated with IBD

<400> SEQUENCE: 1446
tcaccagagg ttcaacctta ctg 23

<210> SEQ ID NO 1447
<211> LENGTH: 23
<212> TYPE: DNA
<213> ORGANISM: Artificial sequence
<220> FEATURE:
<223> OTHER INFORMATION: Synthetic sequence: Probe suitable for detection of genetic variations associated with IBD

<400> SEQUENCE: 1447
cagtaaggtt ggacctctgg tga 23

<210> SEQ ID NO 1448
<211> LENGTH: 23
<212> TYPE: DNA
<213> ORGANISM: Artificial sequence
<220> FEATURE:
<223> OTHER INFORMATION: Synthetic sequence: Probe suitable for detection of genetic variations associated with IBD

<400> SEQUENCE: 1448
cagtaaggtt gaacctctgg tga 23

<210> SEQ ID NO 1449
<211> LENGTH: 23
<212> TYPE: DNA
<213> ORGANISM: Artificial sequence
<220> FEATURE:
<223> OTHER INFORMATION: Synthetic sequence: Probe suitable for detection of genetic variations associated with IBD

<400> SEQUENCE: 1449
gatgggggga aaaaccatgt ctt 23

<210> SEQ ID NO 1450
<211> LENGTH: 23
<212> TYPE: DNA
<213> ORGANISM: Artificial sequence
<220> FEATURE:
<223> OTHER INFORMATION: Synthetic sequence: Probe suitable for detection of genetic variations associated with IBD

<400> SEQUENCE: 1450
gatgggggga aaaaaccatg tct 23

<210> SEQ ID NO 1451
<211> LENGTH: 23
<212> TYPE: DNA
<213> ORGANISM: Artificial sequence
<220> FEATURE:
<223> OTHER INFORMATION: Synthetic sequence: Probe suitable for detection of genetic variations associated with IBD

<400> SEQUENCE: 1451
aagacatggt ttttcccccc atc 23

<210> SEQ ID NO 1452
<211> LENGTH: 23
<212> TYPE: DNA
<213> ORGANISM: Artificial sequence
<220> FEATURE:
<223> OTHER INFORMATION: Synthetic sequence: Probe suitable for detection of genetic variations associated with IBD

<400> SEQUENCE: 1452
agacatggtt ttttcccccc atc 23

<210> SEQ ID NO 1453
<211> LENGTH: 23
<212> TYPE: DNA
<213> ORGANISM: Artificial sequence
<220> FEATURE:
<223> OTHER INFORMATION: Synthetic sequence: Probe suitable for detection of genetic variations associated with IBD

<400> SEQUENCE: 1453
gcccgccccc ccccacacac agc 23

<210> SEQ ID NO 1454
<211> LENGTH: 23
<212> TYPE: DNA
<213> ORGANISM: Artificial sequence
<220> FEATURE:
<223> OTHER INFORMATION: Synthetic sequence: Probe suitable for detection of genetic variations associated with IBD

<400> SEQUENCE: 1454
gcccgccccc cacacacaca gca 23

<210> SEQ ID NO 1455
<211> LENGTH: 23
<212> TYPE: DNA
<213> ORGANISM: Artificial sequence
<220> FEATURE:
<223> OTHER INFORMATION: Synthetic sequence: Probe suitable for detection of genetic variations associated with IBD

<400> SEQUENCE: 1455
gctgtgtgtg gggggggcg ggc 23

<210> SEQ ID NO 1456
<211> LENGTH: 23
<212> TYPE: DNA
<213> ORGANISM: Artificial sequence
<220> FEATURE:
<223> OTHER INFORMATION: Synthetic sequence: Probe suitable for detection of genetic variations associated with IBD

<400> SEQUENCE: 1456
tgctgtgtgt gtgggggcg ggc 23

<210> SEQ ID NO 1457
<211> LENGTH: 23
<212> TYPE: DNA
<213> ORGANISM: Artificial sequence
<220> FEATURE:
<223> OTHER INFORMATION: Synthetic sequence: Probe suitable for detection of genetic variations associated with IBD

<400> SEQUENCE: 1457
tggggtgggg caggggtcgc cga 23

<210> SEQ ID NO 1458
<211> LENGTH: 23
<212> TYPE: DNA
<213> ORGANISM: Artificial sequence
<220> FEATURE:
<223> OTHER INFORMATION: Synthetic sequence: Probe suitable for detection of genetic variations associated with IBD

<400> SEQUENCE: 1458
tggggtgggg cggggtcgcc gag 23

<210> SEQ ID NO 1459
<211> LENGTH: 23
<212> TYPE: DNA
<213> ORGANISM: Artificial sequence
<220> FEATURE:
<223> OTHER INFORMATION: Synthetic sequence: Probe suitable for detection of genetic variations associated with IBD

<400> SEQUENCE: 1459
tcggcgaccc ctgccccacc cca 23

<210> SEQ ID NO 1460
<211> LENGTH: 23
<212> TYPE: DNA
<213> ORGANISM: Artificial sequence
<220> FEATURE:
<223> OTHER INFORMATION: Synthetic sequence: Probe suitable for detection of genetic variations associated with IBD

<400> SEQUENCE: 1460
ctcggcgacc ccgccccacc cca 23

<210> SEQ ID NO 1461
<211> LENGTH: 23
<212> TYPE: DNA
<213> ORGANISM: Artificial sequence
<220> FEATURE:
<223> OTHER INFORMATION: Synthetic sequence: Probe suitable for detection of genetic variations associated with IBD

<400> SEQUENCE: 1461
ggaggcggga tctgcgtgcg ggc 23

<210> SEQ ID NO 1462
<211> LENGTH: 23
<212> TYPE: DNA
<213> ORGANISM: Artificial sequence
<220> FEATURE:
<223> OTHER INFORMATION: Synthetic sequence: Probe suitable for detection of genetic variations associated with IBD

<400> SEQUENCE: 1462
ggaggcggga tttgcgtgcg ggc 23

<210> SEQ ID NO 1463
<211> LENGTH: 23
<212> TYPE: DNA
<213> ORGANISM: Artificial sequence
<220> FEATURE:
<223> OTHER INFORMATION: Synthetic sequence: Probe suitable for detection of genetic variations associated with IBD

<400> SEQUENCE: 1463
gcccgcacgc agatcccgcc tcc 23

<210> SEQ ID NO 1464
<211> LENGTH: 23
<212> TYPE: DNA
<213> ORGANISM: Artificial sequence
<220> FEATURE:
<223> OTHER INFORMATION: Synthetic sequence: Probe suitable for detection of genetic variations associated with IBD

<400> SEQUENCE: 1464
gcccgcacgc aaatcccgcc tcc 23

<210> SEQ ID NO 1465
<211> LENGTH: 23
<212> TYPE: DNA
<213> ORGANISM: Artificial sequence
<220> FEATURE:
<223> OTHER INFORMATION: Synthetic sequence: Probe suitable for detection of genetic variations associated with IBD

<400> SEQUENCE: 1465
gaaggaagct gcgcaacacc cct 23

<210> SEQ ID NO 1466
<211> LENGTH: 23
<212> TYPE: DNA
<213> ORGANISM: Artificial sequence
<220> FEATURE:
<223> OTHER INFORMATION: Synthetic sequence: Probe suitable for detection of genetic variations associated with IBD

<400> SEQUENCE: 1466
gaaggaagct gtgcaacacc cct 23

<210> SEQ ID NO 1467
<211> LENGTH: 23
<212> TYPE: DNA
<213> ORGANISM: Artificial sequence
<220> FEATURE:
<223> OTHER INFORMATION: Synthetic sequence: Probe suitable for detection of genetic variations associated with IBD

<400> SEQUENCE: 1467
aggggtgttg cgcagcttcc ttc 23

<210> SEQ ID NO 1468
<211> LENGTH: 23
<212> TYPE: DNA
<213> ORGANISM: Artificial sequence
<220> FEATURE:
<223> OTHER INFORMATION: Synthetic sequence: Probe suitable for detection of genetic variations associated with IBD

<400> SEQUENCE: 1468
aggggtgttg cacagcttcc ttc 23

<210> SEQ ID NO 1469
<211> LENGTH: 23
<212> TYPE: DNA
<213> ORGANISM: Artificial sequence
<220> FEATURE:
<223> OTHER INFORMATION: Synthetic sequence: Probe suitable for detection of genetic variations associated with IBD

<400> SEQUENCE: 1469
gaggtggggt gagctctttc tgt 23

<210> SEQ ID NO 1470
<211> LENGTH: 23
<212> TYPE: DNA
<213> ORGANISM: Artificial sequence
<220> FEATURE:
<223> OTHER INFORMATION: Synthetic sequence: Probe suitable for detection of genetic variations associated with IBD

<400> SEQUENCE: 1470
gaggtggggt gggctctttc tgt 23

<210> SEQ ID NO 1471
<211> LENGTH: 23
<212> TYPE: DNA
<213> ORGANISM: Artificial sequence
<220> FEATURE:
<223> OTHER INFORMATION: Synthetic sequence: Probe suitable for detection of genetic variations associated with IBD

<400> SEQUENCE: 1471
acagaaagag ctcaccccac ctc 23

<210> SEQ ID NO 1472
<211> LENGTH: 23
<212> TYPE: DNA
<213> ORGANISM: Artificial sequence
<220> FEATURE:
<223> OTHER INFORMATION: Synthetic sequence: Probe suitable for detection of genetic variations associated with IBD

<400> SEQUENCE: 1472
acagaaagag cccaccccac ctc 23

<210> SEQ ID NO 1473
<211> LENGTH: 23
<212> TYPE: DNA
<213> ORGANISM: Artificial sequence
<220> FEATURE:
<223> OTHER INFORMATION: Synthetic sequence: Probe suitable for detection of genetic variations associated with IBD

<400> SEQUENCE: 1473
tacttctcgg cggaagatgc gga 23

<210> SEQ ID NO 1474
<211> LENGTH: 23
<212> TYPE: DNA
<213> ORGANISM: Artificial sequence
<220> FEATURE:
<223> OTHER INFORMATION: Synthetic sequence: Probe suitable for detection of genetic variations associated with IBD

<400> SEQUENCE: 1474
tacttctcgg ccgaagatgc gga 23

<210> SEQ ID NO 1475
<211> LENGTH: 23
<212> TYPE: DNA
<213> ORGANISM: Artificial sequence
<220> FEATURE:
<223> OTHER INFORMATION: Synthetic sequence: Probe suitable for detection of genetic variations associated with IBD

<400> SEQUENCE: 1475
tccgcatctt ccgccgagaa gta 23

<210> SEQ ID NO 1476
<211> LENGTH: 23

<212> TYPE: DNA
<213> ORGANISM: Artificial sequence
<220> FEATURE:
<223> OTHER INFORMATION: Synthetic sequence: Probe suitable for detection of genetic variations associated with IBD

<400> SEQUENCE: 1476
tccgcatctt cggccgagaa gta 23

<210> SEQ ID NO 1477
<211> LENGTH: 23
<212> TYPE: DNA
<213> ORGANISM: Artificial sequence
<220> FEATURE:
<223> OTHER INFORMATION: Synthetic sequence: Probe suitable for detection of genetic variations associated with IBD

<400> SEQUENCE: 1477
atctacatgg acaccatcat gga 23

<210> SEQ ID NO 1478
<211> LENGTH: 23
<212> TYPE: DNA
<213> ORGANISM: Artificial sequence
<220> FEATURE:
<223> OTHER INFORMATION: Synthetic sequence: Probe suitable for detection of genetic variations associated with IBD

<400> SEQUENCE: 1478
atctacatgg ataccatcat gga 23

<210> SEQ ID NO 1479
<211> LENGTH: 23
<212> TYPE: DNA
<213> ORGANISM: Artificial sequence
<220> FEATURE:
<223> OTHER INFORMATION: Synthetic sequence: Probe suitable for detection of genetic variations associated with IBD

<400> SEQUENCE: 1479
tccatgatgg tgtccatgta gat 23

<210> SEQ ID NO 1480
<211> LENGTH: 23
<212> TYPE: DNA
<213> ORGANISM: Artificial sequence
<220> FEATURE:
<223> OTHER INFORMATION: Synthetic sequence: Probe suitable for detection of genetic variations associated with IBD

<400> SEQUENCE: 1480
tccatgatgg tatccatgta gat 23

<210> SEQ ID NO 1481
<211> LENGTH: 23
<212> TYPE: DNA
<213> ORGANISM: Artificial sequence
<220> FEATURE:
<223> OTHER INFORMATION: Synthetic sequence: Probe suitable for detection of genetic variations associated with IBD

<400> SEQUENCE: 1481
agtggtccgg cacgggaaga cct 23

<210> SEQ ID NO 1482
<211> LENGTH: 23
<212> TYPE: DNA
<213> ORGANISM: Artificial sequence
<220> FEATURE:
<223> OTHER INFORMATION: Synthetic sequence: Probe suitable for detection of genetic variations associated with IBD

<400> SEQUENCE: 1482
agtggtccgg cgcgggaaga cct 23

<210> SEQ ID NO 1483
<211> LENGTH: 23
<212> TYPE: DNA
<213> ORGANISM: Artificial sequence
<220> FEATURE:
<223> OTHER INFORMATION: Synthetic sequence: Probe suitable for detection of genetic variations associated with IBD

<400> SEQUENCE: 1483
aggtcttccc gtgccggacc act 23

<210> SEQ ID NO 1484
<211> LENGTH: 23
<212> TYPE: DNA
<213> ORGANISM: Artificial sequence
<220> FEATURE:
<223> OTHER INFORMATION: Synthetic sequence: Probe suitable for detection of genetic variations associated with IBD

<400> SEQUENCE: 1484
aggtcttccc gcgccggacc act 23

<210> SEQ ID NO 1485
<211> LENGTH: 23
<212> TYPE: DNA
<213> ORGANISM: Artificial sequence
<220> FEATURE:
<223> OTHER INFORMATION: Synthetic sequence: Probe suitable for detection of genetic variations associated with IBD

<400> SEQUENCE: 1485
cgggaatggc accatggacc agg 23

<210> SEQ ID NO 1486
<211> LENGTH: 23
<212> TYPE: DNA
<213> ORGANISM: Artificial sequence
<220> FEATURE:
<223> OTHER INFORMATION: Synthetic sequence: Probe suitable for detection of genetic variations associated with IBD

<400> SEQUENCE: 1486
cgggaatggc atcatggacc agg 23

<210> SEQ ID NO 1487
<211> LENGTH: 23
<212> TYPE: DNA
<213> ORGANISM: Artificial sequence
<220> FEATURE:
<223> OTHER INFORMATION: Synthetic sequence: Probe suitable for detection of genetic variations associated with IBD

<400> SEQUENCE: 1487
cctggtccat ggtgccattc ccg 23

<210> SEQ ID NO 1488
<211> LENGTH: 23
<212> TYPE: DNA
<213> ORGANISM: Artificial sequence
<220> FEATURE:
<223> OTHER INFORMATION: Synthetic sequence: Probe suitable for detection of genetic variations associated with IBD

<400> SEQUENCE: 1488
cctggtccat gatgccattc ccg 23

<210> SEQ ID NO 1489
<211> LENGTH: 23
<212> TYPE: DNA
<213> ORGANISM: Artificial sequence
<220> FEATURE:
<223> OTHER INFORMATION: Synthetic sequence: Probe suitable for detection of genetic variations associated with IBD

<400> SEQUENCE: 1489
atttcttagc ccagctacct gta 23

<210> SEQ ID NO 1490
<211> LENGTH: 23
<212> TYPE: DNA
<213> ORGANISM: Artificial sequence
<220> FEATURE:
<223> OTHER INFORMATION: Synthetic sequence: Probe suitable for detection of genetic variations associated with IBD

<400> SEQUENCE: 1490
atttcttagc ctagctacct gta 23

<210> SEQ ID NO 1491
<211> LENGTH: 23
<212> TYPE: DNA
<213> ORGANISM: Artificial sequence
<220> FEATURE:
<223> OTHER INFORMATION: Synthetic sequence: Probe suitable for detection of genetic variations associated with IBD

<400> SEQUENCE: 1491
tacaggtagc tgggctaaga aat 23

<210> SEQ ID NO 1492
<211> LENGTH: 23
<212> TYPE: DNA
<213> ORGANISM: Artificial sequence
<220> FEATURE:
<223> OTHER INFORMATION: Synthetic sequence: Probe suitable for detection of genetic variations associated with IBD

<400> SEQUENCE: 1492
tacaggtagc taggctaaga aat 23

<210> SEQ ID NO 1493
<211> LENGTH: 23
<212> TYPE: DNA
<213> ORGANISM: Artificial sequence
<220> FEATURE:
<223> OTHER INFORMATION: Synthetic sequence: Probe suitable for detection of genetic variations associated with IBD

<400> SEQUENCE: 1493
agaacttgtt tagaacttgt cat 23

<210> SEQ ID NO 1494
<211> LENGTH: 23
<212> TYPE: DNA
<213> ORGANISM: Artificial sequence
<220> FEATURE:
<223> OTHER INFORMATION: Synthetic sequence: Probe suitable for detection of genetic variations associated with IBD

<400> SEQUENCE: 1494
agaacttgtt tggaacttgt cat 23

<210> SEQ ID NO 1495
<211> LENGTH: 23
<212> TYPE: DNA
<213> ORGANISM: Artificial sequence
<220> FEATURE:
<223> OTHER INFORMATION: Synthetic sequence: Probe suitable for detection of genetic variations associated with IBD

<400> SEQUENCE: 1495
atgacaagtt ctaaacaagt tct 23

<210> SEQ ID NO 1496
<211> LENGTH: 23
<212> TYPE: DNA
<213> ORGANISM: Artificial sequence
<220> FEATURE:
<223> OTHER INFORMATION: Synthetic sequence: Probe suitable for detection of genetic variations associated with IBD

<400> SEQUENCE: 1496
atgacaagtt ccaaacaagt tct 23

<210> SEQ ID NO 1497
<211> LENGTH: 23
<212> TYPE: DNA
<213> ORGANISM: Artificial sequence
<220> FEATURE:
<223> OTHER INFORMATION: Synthetic sequence: Probe suitable for detection of genetic variations associated with IBD

<400> SEQUENCE: 1497
cagcagggtc tcgatggccc tgc 23

<210> SEQ ID NO 1498
<211> LENGTH: 23
<212> TYPE: DNA
<213> ORGANISM: Artificial sequence
<220> FEATURE:
<223> OTHER INFORMATION: Synthetic sequence: Probe suitable for detection of genetic variations associated with IBD

<400> SEQUENCE: 1498
cagcagggtc ttgatggccc tgc 23

<210> SEQ ID NO 1499
<211> LENGTH: 23
<212> TYPE: DNA
<213> ORGANISM: Artificial sequence
<220> FEATURE:
<223> OTHER INFORMATION: Synthetic sequence: Probe suitable for detection of genetic variations associated with IBD

<400> SEQUENCE: 1499
gcagggccat cgagaccctg ctg 23

<210> SEQ ID NO 1500
<211> LENGTH: 23
<212> TYPE: DNA
<213> ORGANISM: Artificial sequence
<220> FEATURE:
<223> OTHER INFORMATION: Synthetic sequence: Probe suitable for detection of genetic variations associated with IBD

<400> SEQUENCE: 1500
gcagggccat caagaccctg ctg 23

<210> SEQ ID NO 1501
<211> LENGTH: 23
<212> TYPE: DNA
<213> ORGANISM: Artificial sequence
<220> FEATURE:
<223> OTHER INFORMATION: Synthetic sequence: Probe suitable for detection of genetic variations associated with IBD

<400> SEQUENCE: 1501
gaccagtgaa gaaagtgtct ttg 23

<210> SEQ ID NO 1502
<211> LENGTH: 23
<212> TYPE: DNA
<213> ORGANISM: Artificial sequence
<220> FEATURE:
<223> OTHER INFORMATION: Synthetic sequence: Probe suitable for detection of genetic variations associated with IBD

<400> SEQUENCE: 1502
gaccagtgaa gcaagtgtct ttg 23

<210> SEQ ID NO 1503
<211> LENGTH: 23
<212> TYPE: DNA
<213> ORGANISM: Artificial sequence
<220> FEATURE:
<223> OTHER INFORMATION: Synthetic sequence: Probe suitable for detection of genetic variations associated with IBD

<400> SEQUENCE: 1503
caaagacact ttcttcactg gtc 23

<210> SEQ ID NO 1504
<211> LENGTH: 23
<212> TYPE: DNA
<213> ORGANISM: Artificial sequence
<220> FEATURE:
<223> OTHER INFORMATION: Synthetic sequence: Probe suitable for detection of genetic variations associated with IBD

<400> SEQUENCE: 1504
caaagacact tgcttcactg gtc 23

<210> SEQ ID NO 1505
<211> LENGTH: 23
<212> TYPE: DNA
<213> ORGANISM: Artificial sequence
<220> FEATURE:
<223> OTHER INFORMATION: Synthetic sequence: Probe suitable for detection of genetic variations associated with IBD

<400> SEQUENCE: 1505
gcaggtgacc actgacggca gga 23

<210> SEQ ID NO 1506
<211> LENGTH: 23
<212> TYPE: DNA
<213> ORGANISM: Artificial sequence
<220> FEATURE:
<223> OTHER INFORMATION: Synthetic sequence: Probe suitable for detection of genetic variations associated with IBD

<400> SEQUENCE: 1506
gcaggtgacc attgacggca gga 23

<210> SEQ ID NO 1507
<211> LENGTH: 23
<212> TYPE: DNA
<213> ORGANISM: Artificial sequence
<220> FEATURE:
<223> OTHER INFORMATION: Synthetic sequence: Probe suitable for detection of genetic variations associated with IBD

<400> SEQUENCE: 1507
tcctgccgtc agtggtcacc tgc 23

<210> SEQ ID NO 1508
<211> LENGTH: 23
<212> TYPE: DNA
<213> ORGANISM: Artificial sequence
<220> FEATURE:
<223> OTHER INFORMATION: Synthetic sequence: Probe suitable for detection of genetic variations associated with IBD

<400> SEQUENCE: 1508
tcctgccgtc aatggtcacc tgc 23

<210> SEQ ID NO 1509
<211> LENGTH: 23
<212> TYPE: DNA
<213> ORGANISM: Artificial sequence
<220> FEATURE:
<223> OTHER INFORMATION: Synthetic sequence: Probe suitable for detection of genetic variations associated with IBD

<400> SEQUENCE: 1509
agaagtgctg aaaaatatat tta 23

<210> SEQ ID NO 1510
<211> LENGTH: 23
<212> TYPE: DNA
<213> ORGANISM: Artificial sequence
<220> FEATURE:
<223> OTHER INFORMATION: Synthetic sequence: Probe suitable for detection of genetic variations associated with IBD

<400> SEQUENCE: 1510
agaagtgctg agaaatatat tta 23

<210> SEQ ID NO 1511
<211> LENGTH: 23
<212> TYPE: DNA
<213> ORGANISM: Artificial sequence
<220> FEATURE:
<223> OTHER INFORMATION: Synthetic sequence: Probe suitable for detection of genetic variations associated with IBD

<400> SEQUENCE: 1511
taaatatatt tttcagcact tct 23

<210> SEQ ID NO 1512
<211> LENGTH: 23
<212> TYPE: DNA
<213> ORGANISM: Artificial sequence
<220> FEATURE:
<223> OTHER INFORMATION: Synthetic sequence: Probe suitable for detection of genetic variations associated with IBD

<400> SEQUENCE: 1512
taaatatatt tctcagcact tct 23

<210> SEQ ID NO 1513

<211> LENGTH: 23
<212> TYPE: DNA
<213> ORGANISM: Artificial sequence
<220> FEATURE:
<223> OTHER INFORMATION: Synthetic sequence: Probe suitable for detection of genetic variations associated with IBD

<400> SEQUENCE: 1513
gagtgtggtc tagagttggg atg 23

<210> SEQ ID NO 1514
<211> LENGTH: 23
<212> TYPE: DNA
<213> ORGANISM: Artificial sequence
<220> FEATURE:
<223> OTHER INFORMATION: Synthetic sequence: Probe suitable for detection of genetic variations associated with IBD

<400> SEQUENCE: 1514
gagtgtggtc tggagttggg atg 23

<210> SEQ ID NO 1515
<211> LENGTH: 23
<212> TYPE: DNA
<213> ORGANISM: Artificial sequence
<220> FEATURE:
<223> OTHER INFORMATION: Synthetic sequence: Probe suitable for detection of genetic variations associated with IBD

<400> SEQUENCE: 1515
catcccaact ctagaccaca ctc 23

<210> SEQ ID NO 1516
<211> LENGTH: 23
<212> TYPE: DNA
<213> ORGANISM: Artificial sequence
<220> FEATURE:
<223> OTHER INFORMATION: Synthetic sequence: Probe suitable for detection of genetic variations associated with IBD

<400> SEQUENCE: 1516
catcccaact ccagaccaca ctc 23

<210> SEQ ID NO 1517
<211> LENGTH: 23
<212> TYPE: DNA
<213> ORGANISM: Artificial sequence
<220> FEATURE:
<223> OTHER INFORMATION: Synthetic sequence: Probe suitable for detection of genetic variations associated with IBD

<400> SEQUENCE: 1517
aatgtcccag ccgttttatg ctt 23

<210> SEQ ID NO 1518
<211> LENGTH: 23
<212> TYPE: DNA
<213> ORGANISM: Artificial sequence
<220> FEATURE:
<223> OTHER INFORMATION: Synthetic sequence: Probe suitable for detection of genetic variations associated with IBD

<400> SEQUENCE: 1518
aatgtcccag ctgttttatg ctt 23

<210> SEQ ID NO 1519
<211> LENGTH: 23
<212> TYPE: DNA

<213> ORGANISM: Artificial sequence
<220> FEATURE:
<223> OTHER INFORMATION: Synthetic sequence: Probe suitable for detection of genetic variations associated with IBD

<400> SEQUENCE: 1519
aagcataaaa cggctgggac att 23

<210> SEQ ID NO 1520
<211> LENGTH: 23
<212> TYPE: DNA
<213> ORGANISM: Artificial sequence
<220> FEATURE:
<223> OTHER INFORMATION: Synthetic sequence: Probe suitable for detection of genetic variations associated with IBD

<400> SEQUENCE: 1520
aagcataaaa cagctgggac att 23

<210> SEQ ID NO 1521
<211> LENGTH: 23
<212> TYPE: DNA
<213> ORGANISM: Artificial sequence
<220> FEATURE:
<223> OTHER INFORMATION: Synthetic sequence: Probe suitable for detection of genetic variations associated with IBD

<400> SEQUENCE: 1521
ggactacaga gctggaagca tct 23

<210> SEQ ID NO 1522
<211> LENGTH: 23
<212> TYPE: DNA
<213> ORGANISM: Artificial sequence
<220> FEATURE:
<223> OTHER INFORMATION: Synthetic sequence: Probe suitable for detection of genetic variations associated with IBD

<400> SEQUENCE: 1522
ggactacaga gttggaagca tct 23

<210> SEQ ID NO 1523
<211> LENGTH: 23
<212> TYPE: DNA
<213> ORGANISM: Artificial sequence
<220> FEATURE:
<223> OTHER INFORMATION: Synthetic sequence: Probe suitable for detection of genetic variations associated with IBD

<400> SEQUENCE: 1523
agatgcttcc agctctgtag tcc 23

<210> SEQ ID NO 1524
<211> LENGTH: 23
<212> TYPE: DNA
<213> ORGANISM: Artificial sequence
<220> FEATURE:
<223> OTHER INFORMATION: Synthetic sequence: Probe suitable for detection of genetic variations associated with IBD

<400> SEQUENCE: 1524
agatgcttcc aactctgtag tcc 23

<210> SEQ ID NO 1525
<211> LENGTH: 23
<212> TYPE: DNA
<213> ORGANISM: Artificial sequence
<220> FEATURE:

<223> OTHER INFORMATION: Synthetic sequence: Probe suitable for detection of genetic variations associated with IBD

<400> SEQUENCE: 1525
ccattgcctc catccctgta aga 23

<210> SEQ ID NO 1526
<211> LENGTH: 23
<212> TYPE: DNA
<213> ORGANISM: Artificial sequence
<220> FEATURE:
<223> OTHER INFORMATION: Synthetic sequence: Probe suitable for detection of genetic variations associated with IBD

<400> SEQUENCE: 1526
ccattgcctc cgtccctgta aga 23

<210> SEQ ID NO 1527
<211> LENGTH: 23
<212> TYPE: DNA
<213> ORGANISM: Artificial sequence
<220> FEATURE:
<223> OTHER INFORMATION: Synthetic sequence: Probe suitable for detection of genetic variations associated with IBD

<400> SEQUENCE: 1527
tcttacaggg atggaggcaa tgg 23

<210> SEQ ID NO 1528
<211> LENGTH: 23
<212> TYPE: DNA
<213> ORGANISM: Artificial sequence
<220> FEATURE:
<223> OTHER INFORMATION: Synthetic sequence: Probe suitable for detection of genetic variations associated with IBD

<400> SEQUENCE: 1528
tcttacaggg acggaggcaa tgg 23

<210> SEQ ID NO 1529
<211> LENGTH: 23
<212> TYPE: DNA
<213> ORGANISM: Artificial sequence
<220> FEATURE:
<223> OTHER INFORMATION: Synthetic sequence: Probe suitable for detection of genetic variations associated with IBD

<400> SEQUENCE: 1529
tttcctgccc tcggttgtct ttg 23

<210> SEQ ID NO 1530
<211> LENGTH: 23
<212> TYPE: DNA
<213> ORGANISM: Artificial sequence
<220> FEATURE:
<223> OTHER INFORMATION: Synthetic sequence: Probe suitable for detection of genetic variations associated with IBD

<400> SEQUENCE: 1530
tttcctgccc tgggttgtct ttg 23

<210> SEQ ID NO 1531
<211> LENGTH: 23
<212> TYPE: DNA
<213> ORGANISM: Artificial sequence
<220> FEATURE:
<223> OTHER INFORMATION: Synthetic sequence: Probe suitable for detection of genetic variations associated with IBD

<400> SEQUENCE: 1531
caaagacaac cgagggcagg aaa 23

<210> SEQ ID NO 1532
<211> LENGTH: 23
<212> TYPE: DNA
<213> ORGANISM: Artificial sequence
<220> FEATURE:
<223> OTHER INFORMATION: Synthetic sequence: Probe suitable for detection of genetic variations associated with IBD

<400> SEQUENCE: 1532
caaagacaac ccagggcagg aaa 23

<210> SEQ ID NO 1533
<211> LENGTH: 23
<212> TYPE: DNA
<213> ORGANISM: Artificial sequence
<220> FEATURE:
<223> OTHER INFORMATION: Synthetic sequence: Probe suitable for detection of genetic variations associated with IBD

<400> SEQUENCE: 1533
ctggtggtct tggaagaagc gct 23

<210> SEQ ID NO 1534
<211> LENGTH: 23
<212> TYPE: DNA
<213> ORGANISM: Artificial sequence
<220> FEATURE:
<223> OTHER INFORMATION: Synthetic sequence: Probe suitable for detection of genetic variations associated with IBD

<400> SEQUENCE: 1534
ctggtggtct ttgaagaagc gct 23

<210> SEQ ID NO 1535
<211> LENGTH: 23
<212> TYPE: DNA
<213> ORGANISM: Artificial sequence
<220> FEATURE:
<223> OTHER INFORMATION: Synthetic sequence: Probe suitable for detection of genetic variations associated with IBD

<400> SEQUENCE: 1535
agcgcttctt ccaagaccac cag 23

<210> SEQ ID NO 1536
<211> LENGTH: 23
<212> TYPE: DNA
<213> ORGANISM: Artificial sequence
<220> FEATURE:
<223> OTHER INFORMATION: Synthetic sequence: Probe suitable for detection of genetic variations associated with IBD

<400> SEQUENCE: 1536
agcgcttctt caaagaccac cag 23

<210> SEQ ID NO 1537
<211> LENGTH: 23
<212> TYPE: DNA
<213> ORGANISM: Artificial sequence
<220> FEATURE:
<223> OTHER INFORMATION: Synthetic sequence: Probe suitable for detection of genetic variations associated with IBD

<400> SEQUENCE: 1537
cattgcagac cagatcgcac tca 23

<210> SEQ ID NO 1538
<211> LENGTH: 23
<212> TYPE: DNA
<213> ORGANISM: Artificial sequence
<220> FEATURE:
<223> OTHER INFORMATION: Synthetic sequence: Probe suitable for detection of genetic variations associated with IBD

<400> SEQUENCE: 1538
cattgcagac cggatcgcac tca 23

<210> SEQ ID NO 1539
<211> LENGTH: 23
<212> TYPE: DNA
<213> ORGANISM: Artificial sequence
<220> FEATURE:
<223> OTHER INFORMATION: Synthetic sequence: Probe suitable for detection of genetic variations associated with IBD

<400> SEQUENCE: 1539
tgagtgcgat ctggtctgca atg 23

<210> SEQ ID NO 1540
<211> LENGTH: 23
<212> TYPE: DNA
<213> ORGANISM: Artificial sequence
<220> FEATURE:
<223> OTHER INFORMATION: Synthetic sequence: Probe suitable for detection of genetic variations associated with IBD

<400> SEQUENCE: 1540
tgagtgcgat ccggtctgca atg 23

<210> SEQ ID NO 1541
<211> LENGTH: 23
<212> TYPE: DNA
<213> ORGANISM: Artificial sequence
<220> FEATURE:
<223> OTHER INFORMATION: Synthetic sequence: Probe suitable for detection of genetic variations associated with IBD

<400> SEQUENCE: 1541
cagagggaag aaagaggcga agc 23

<210> SEQ ID NO 1542
<211> LENGTH: 23
<212> TYPE: DNA
<213> ORGANISM: Artificial sequence
<220> FEATURE:
<223> OTHER INFORMATION: Synthetic sequence: Probe suitable for detection of genetic variations associated with IBD

<400> SEQUENCE: 1542
cagagggaag agagaggcga agc 23

<210> SEQ ID NO 1543
<211> LENGTH: 23
<212> TYPE: DNA
<213> ORGANISM: Artificial sequence
<220> FEATURE:
<223> OTHER INFORMATION: Synthetic sequence: Probe suitable for detection of genetic variations associated with IBD

<400> SEQUENCE: 1543
gcttcgcctc tttcttccct ctg 23

<210> SEQ ID NO 1544
<211> LENGTH: 23
<212> TYPE: DNA
<213> ORGANISM: Artificial sequence
<220> FEATURE:
<223> OTHER INFORMATION: Synthetic sequence: Probe suitable for detection of genetic variations associated with IBD

<400> SEQUENCE: 1544
gcttcgcctc tctcttccct ctg 23

<210> SEQ ID NO 1545
<211> LENGTH: 23
<212> TYPE: DNA
<213> ORGANISM: Artificial sequence
<220> FEATURE:
<223> OTHER INFORMATION: Synthetic sequence: Probe suitable for detection of genetic variations associated with IBD

<400> SEQUENCE: 1545
acctggtgat gaatccctta cta 23

<210> SEQ ID NO 1546
<211> LENGTH: 23
<212> TYPE: DNA
<213> ORGANISM: Artificial sequence
<220> FEATURE:
<223> OTHER INFORMATION: Synthetic sequence: Probe suitable for detection of genetic variations associated with IBD

<400> SEQUENCE: 1546
acctggtgat ggatccctta cta 23

<210> SEQ ID NO 1547
<211> LENGTH: 23
<212> TYPE: DNA
<213> ORGANISM: Artificial sequence
<220> FEATURE:
<223> OTHER INFORMATION: Synthetic sequence: Probe suitable for detection of genetic variations associated with IBD

<400> SEQUENCE: 1547
tagtaaggga ttcatcacca ggt 23

<210> SEQ ID NO 1548
<211> LENGTH: 23
<212> TYPE: DNA
<213> ORGANISM: Artificial sequence
<220> FEATURE:
<223> OTHER INFORMATION: Synthetic sequence: Probe suitable for detection of genetic variations associated with IBD

<400> SEQUENCE: 1548
tagtaaggga tccatcacca ggt 23

<210> SEQ ID NO 1549
<211> LENGTH: 23
<212> TYPE: DNA
<213> ORGANISM: Artificial sequence
<220> FEATURE:
<223> OTHER INFORMATION: Synthetic sequence: Probe suitable for detection of genetic variations associated with IBD

<400> SEQUENCE: 1549
gcttgaacct caaacaattg aag 23

<210> SEQ ID NO 1550
<211> LENGTH: 23
<212> TYPE: DNA
<213> ORGANISM: Artificial sequence
<220> FEATURE:
<223> OTHER INFORMATION: Synthetic sequence: Probe suitable for detection of genetic variations associated with IBD

<400> SEQUENCE: 1550
gcttgaacct cgaacaattg aag 23

<210> SEQ ID NO 1551
<211> LENGTH: 23
<212> TYPE: DNA
<213> ORGANISM: Artificial sequence
<220> FEATURE:
<223> OTHER INFORMATION: Synthetic sequence: Probe suitable for detection of genetic variations associated with IBD

<400> SEQUENCE: 1551
cttcaattgt ttgaggttca agc 23

<210> SEQ ID NO 1552
<211> LENGTH: 23
<212> TYPE: DNA
<213> ORGANISM: Artificial sequence
<220> FEATURE:
<223> OTHER INFORMATION: Synthetic sequence: Probe suitable for detection of genetic variations associated with IBD

<400> SEQUENCE: 1552
cttcaattgt tcgaggttca agc 23

<210> SEQ ID NO 1553
<211> LENGTH: 23
<212> TYPE: DNA
<213> ORGANISM: Artificial sequence
<220> FEATURE:
<223> OTHER INFORMATION: Synthetic sequence: Probe suitable for detection of genetic variations associated with IBD

<400> SEQUENCE: 1553
aagaagaaac cagggtgggt ggt 23

<210> SEQ ID NO 1554
<211> LENGTH: 23
<212> TYPE: DNA
<213> ORGANISM: Artificial sequence
<220> FEATURE:
<223> OTHER INFORMATION: Synthetic sequence: Probe suitable for detection of genetic variations associated with IBD

<400> SEQUENCE: 1554
aagaagaaac cggggtgggt ggt 23

<210> SEQ ID NO 1555
<211> LENGTH: 23
<212> TYPE: DNA
<213> ORGANISM: Artificial sequence
<220> FEATURE:
<223> OTHER INFORMATION: Synthetic sequence: Probe suitable for detection of genetic variations associated with IBD

<400> SEQUENCE: 1555
accacccacc ctggtttctt ctt 23

<210> SEQ ID NO 1556
<211> LENGTH: 23

<212> TYPE: DNA
<213> ORGANISM: Artificial sequence
<220> FEATURE:
<223> OTHER INFORMATION: Synthetic sequence: Probe suitable for detection of genetic variations associated with IBD

<400> SEQUENCE: 1556
accacccacc ccggtttctt ctt 23

<210> SEQ ID NO 1557
<211> LENGTH: 23
<212> TYPE: DNA
<213> ORGANISM: Artificial sequence
<220> FEATURE:
<223> OTHER INFORMATION: Synthetic sequence: Probe suitable for detection of genetic variations associated with IBD

<400> SEQUENCE: 1557
ccttggatct ccgagacaat gct 23

<210> SEQ ID NO 1558
<211> LENGTH: 23
<212> TYPE: DNA
<213> ORGANISM: Artificial sequence
<220> FEATURE:
<223> OTHER INFORMATION: Synthetic sequence: Probe suitable for detection of genetic variations associated with IBD

<400> SEQUENCE: 1558
ccttggatct ctgagacaat gct 23

<210> SEQ ID NO 1559
<211> LENGTH: 23
<212> TYPE: DNA
<213> ORGANISM: Artificial sequence
<220> FEATURE:
<223> OTHER INFORMATION: Synthetic sequence: Probe suitable for detection of genetic variations associated with IBD

<400> SEQUENCE: 1559
agcattgtct cggagatcca agg 23

<210> SEQ ID NO 1560
<211> LENGTH: 23
<212> TYPE: DNA
<213> ORGANISM: Artificial sequence
<220> FEATURE:
<223> OTHER INFORMATION: Synthetic sequence: Probe suitable for detection of genetic variations associated with IBD

<400> SEQUENCE: 1560
agcattgtct cagagatcca agg 23

<210> SEQ ID NO 1561
<211> LENGTH: 23
<212> TYPE: DNA
<213> ORGANISM: Artificial sequence
<220> FEATURE:
<223> OTHER INFORMATION: Synthetic sequence: Probe suitable for detection of genetic variations associated with IBD

<400> SEQUENCE: 1561
tgaacctggc taccaggacc tgg 23

<210> SEQ ID NO 1562
<211> LENGTH: 23
<212> TYPE: DNA
<213> ORGANISM: Artificial sequence
<220> FEATURE:
<223> OTHER INFORMATION: Synthetic sequence: Probe suitable for
      detection of genetic variations associated with IBD

<400> SEQUENCE: 1562
tgaacctggc tgccaggacc tgg 23

<210> SEQ ID NO 1563
<211> LENGTH: 23
<212> TYPE: DNA
<213> ORGANISM: Artificial sequence
<220> FEATURE:
<223> OTHER INFORMATION: Synthetic sequence: Probe suitable for
      detection of genetic variations associated with IBD

<400> SEQUENCE: 1563
ccaggtcctg gtagccaggt tca 23

<210> SEQ ID NO 1564
<211> LENGTH: 23
<212> TYPE: DNA
<213> ORGANISM: Artificial sequence
<220> FEATURE:
<223> OTHER INFORMATION: Synthetic sequence: Probe suitable for
      detection of genetic variations associated with IBD

<400> SEQUENCE: 1564
ccaggtcctg gcagccaggt tca 23

<210> SEQ ID NO 1565
<211> LENGTH: 23
<212> TYPE: DNA
<213> ORGANISM: Artificial sequence
<220> FEATURE:
<223> OTHER INFORMATION: Synthetic sequence: Probe suitable for
      detection of genetic variations associated with IBD

<400> SEQUENCE: 1565
caagttactc acatggaaaa ctg 23

<210> SEQ ID NO 1566
<211> LENGTH: 23
<212> TYPE: DNA
<213> ORGANISM: Artificial sequence
<220> FEATURE:
<223> OTHER INFORMATION: Synthetic sequence: Probe suitable for
      detection of genetic variations associated with IBD

<400> SEQUENCE: 1566
caagttactc agatggaaaa ctg 23

<210> SEQ ID NO 1567
<211> LENGTH: 23
<212> TYPE: DNA
<213> ORGANISM: Artificial sequence
<220> FEATURE:
<223> OTHER INFORMATION: Synthetic sequence: Probe suitable for
      detection of genetic variations associated with IBD

<400> SEQUENCE: 1567
cagttttcca tgtgagtaac ttg 23

<210> SEQ ID NO 1568
<211> LENGTH: 23
<212> TYPE: DNA
<213> ORGANISM: Artificial sequence
<220> FEATURE:
<223> OTHER INFORMATION: Synthetic sequence: Probe suitable for detection of genetic variations associated with IBD

<400> SEQUENCE: 1568
cagttttcca tctgagtaac ttg 23

<210> SEQ ID NO 1569
<211> LENGTH: 23
<212> TYPE: DNA
<213> ORGANISM: Artificial sequence
<220> FEATURE:
<223> OTHER INFORMATION: Synthetic sequence: Probe suitable for detection of genetic variations associated with IBD

<400> SEQUENCE: 1569
gcagaagaaa tatgtgagca agc 23

<210> SEQ ID NO 1570
<211> LENGTH: 23
<212> TYPE: DNA
<213> ORGANISM: Artificial sequence
<220> FEATURE:
<223> OTHER INFORMATION: Synthetic sequence: Probe suitable for detection of genetic variations associated with IBD

<400> SEQUENCE: 1570
gcagaagaaa tgtgtgagca agc 23

<210> SEQ ID NO 1571
<211> LENGTH: 23
<212> TYPE: DNA
<213> ORGANISM: Artificial sequence
<220> FEATURE:
<223> OTHER INFORMATION: Synthetic sequence: Probe suitable for detection of genetic variations associated with IBD

<400> SEQUENCE: 1571
gcttgctcac atatttcttc tgc 23

<210> SEQ ID NO 1572
<211> LENGTH: 23
<212> TYPE: DNA
<213> ORGANISM: Artificial sequence
<220> FEATURE:
<223> OTHER INFORMATION: Synthetic sequence: Probe suitable for detection of genetic variations associated with IBD

<400> SEQUENCE: 1572
gcttgctcac acatttcttc tgc 23

<210> SEQ ID NO 1573
<211> LENGTH: 23
<212> TYPE: DNA
<213> ORGANISM: Artificial sequence
<220> FEATURE:
<223> OTHER INFORMATION: Synthetic sequence: Probe suitable for detection of genetic variations associated with IBD

<400> SEQUENCE: 1573
gagataagtt tacatgcact ttg 23

<210> SEQ ID NO 1574
<211> LENGTH: 23
<212> TYPE: DNA
<213> ORGANISM: Artificial sequence
<220> FEATURE:
<223> OTHER INFORMATION: Synthetic sequence: Probe suitable for detection of genetic variations associated with IBD

<400> SEQUENCE: 1574
gagataagtt tccatgcact ttg 23

<210> SEQ ID NO 1575
<211> LENGTH: 23
<212> TYPE: DNA
<213> ORGANISM: Artificial sequence
<220> FEATURE:
<223> OTHER INFORMATION: Synthetic sequence: Probe suitable for detection of genetic variations associated with IBD

<400> SEQUENCE: 1575
caaagtgcat gtaaacttat ctc 23

<210> SEQ ID NO 1576
<211> LENGTH: 23
<212> TYPE: DNA
<213> ORGANISM: Artificial sequence
<220> FEATURE:
<223> OTHER INFORMATION: Synthetic sequence: Probe suitable for detection of genetic variations associated with IBD

<400> SEQUENCE: 1576
caaagtgcat ggaaacttat ctc 23

<210> SEQ ID NO 1577
<211> LENGTH: 23
<212> TYPE: DNA
<213> ORGANISM: Artificial sequence
<220> FEATURE:
<223> OTHER INFORMATION: Synthetic sequence: Probe suitable for detection of genetic variations associated with IBD

<400> SEQUENCE: 1577
gcagccagcc ccaggccggg agg 23

<210> SEQ ID NO 1578
<211> LENGTH: 23
<212> TYPE: DNA
<213> ORGANISM: Artificial sequence
<220> FEATURE:
<223> OTHER INFORMATION: Synthetic sequence: Probe suitable for detection of genetic variations associated with IBD

<400> SEQUENCE: 1578
gcagccagcc cgaggccggg agg 23

<210> SEQ ID NO 1579
<211> LENGTH: 23
<212> TYPE: DNA
<213> ORGANISM: Artificial sequence
<220> FEATURE:
<223> OTHER INFORMATION: Synthetic sequence: Probe suitable for detection of genetic variations associated with IBD

<400> SEQUENCE: 1579
cctcccggcc tggggctggc tgc 23

<210> SEQ ID NO 1580
<211> LENGTH: 23
<212> TYPE: DNA
<213> ORGANISM: Artificial sequence
<220> FEATURE:
<223> OTHER INFORMATION: Synthetic sequence: Probe suitable for detection of genetic variations associated with IBD

<400> SEQUENCE: 1580
cctcccggcc tcgggctggc tgc 23

<210> SEQ ID NO 1581
<211> LENGTH: 23
<212> TYPE: DNA
<213> ORGANISM: Artificial sequence
<220> FEATURE:
<223> OTHER INFORMATION: Synthetic sequence: Probe suitable for detection of genetic variations associated with IBD

<400> SEQUENCE: 1581
ttcaggtgtc catacaggaa gtg 23

<210> SEQ ID NO 1582
<211> LENGTH: 23
<212> TYPE: DNA
<213> ORGANISM: Artificial sequence
<220> FEATURE:
<223> OTHER INFORMATION: Synthetic sequence: Probe suitable for detection of genetic variations associated with IBD

<400> SEQUENCE: 1582
ttcaggtgtc cgtacaggaa gtg 23

<210> SEQ ID NO 1583
<211> LENGTH: 23
<212> TYPE: DNA
<213> ORGANISM: Artificial sequence
<220> FEATURE:
<223> OTHER INFORMATION: Synthetic sequence: Probe suitable for detection of genetic variations associated with IBD

<400> SEQUENCE: 1583
cacttcctgt atggacacct gaa 23

<210> SEQ ID NO 1584
<211> LENGTH: 23
<212> TYPE: DNA
<213> ORGANISM: Artificial sequence
<220> FEATURE:
<223> OTHER INFORMATION: Synthetic sequence: Probe suitable for detection of genetic variations associated with IBD

<400> SEQUENCE: 1584
cacttcctgt acggacacct gaa 23

<210> SEQ ID NO 1585
<211> LENGTH: 23
<212> TYPE: DNA
<213> ORGANISM: Artificial sequence
<220> FEATURE:
<223> OTHER INFORMATION: Synthetic sequence: Probe suitable for detection of genetic variations associated with IBD

<400> SEQUENCE: 1585
gccctggtgg tagacaacac act 23

<210> SEQ ID NO 1586
<211> LENGTH: 23
<212> TYPE: DNA
<213> ORGANISM: Artificial sequence
<220> FEATURE:
<223> OTHER INFORMATION: Synthetic sequence: Probe suitable for detection of genetic variations associated with IBD

<400> SEQUENCE: 1586
gccctggtgg tggacaacac act 23

<210> SEQ ID NO 1587
<211> LENGTH: 23
<212> TYPE: DNA
<213> ORGANISM: Artificial sequence
<220> FEATURE:
<223> OTHER INFORMATION: Synthetic sequence: Probe suitable for detection of genetic variations associated with IBD

<400> SEQUENCE: 1587
agtgtgttgt ctaccaccag ggc 23

<210> SEQ ID NO 1588
<211> LENGTH: 23
<212> TYPE: DNA
<213> ORGANISM: Artificial sequence
<220> FEATURE:
<223> OTHER INFORMATION: Synthetic sequence: Probe suitable for detection of genetic variations associated with IBD

<400> SEQUENCE: 1588
agtgtgttgt ccaccaccag ggc 23

<210> SEQ ID NO 1589
<211> LENGTH: 23
<212> TYPE: DNA
<213> ORGANISM: Artificial sequence
<220> FEATURE:
<223> OTHER INFORMATION: Synthetic sequence: Probe suitable for detection of genetic variations associated with IBD

<400> SEQUENCE: 1589
atccagatcc tcaaagtgaa cat 23

<210> SEQ ID NO 1590
<211> LENGTH: 23
<212> TYPE: DNA
<213> ORGANISM: Artificial sequence
<220> FEATURE:
<223> OTHER INFORMATION: Synthetic sequence: Probe suitable for detection of genetic variations associated with IBD

<400> SEQUENCE: 1590
atccagatcc ttaaagtgaa cat 23

<210> SEQ ID NO 1591
<211> LENGTH: 23
<212> TYPE: DNA
<213> ORGANISM: Artificial sequence
<220> FEATURE:
<223> OTHER INFORMATION: Synthetic sequence: Probe suitable for detection of genetic variations associated with IBD

<400> SEQUENCE: 1591
atgttcactt tgaggatctg gat 23

<210> SEQ ID NO 1592
<211> LENGTH: 23
<212> TYPE: DNA
<213> ORGANISM: Artificial sequence
<220> FEATURE:
<223> OTHER INFORMATION: Synthetic sequence: Probe suitable for detection of genetic variations associated with IBD

<400> SEQUENCE: 1592
atgttcactt taaggatctg gat 23

<210> SEQ ID NO 1593

<211> LENGTH: 23
<212> TYPE: DNA
<213> ORGANISM: Artificial sequence
<220> FEATURE:
<223> OTHER INFORMATION: Synthetic sequence: Probe suitable for detection of genetic variations associated with IBD

<400> SEQUENCE: 1593
ttttccatac attaaagata gtc 23

<210> SEQ ID NO 1594
<211> LENGTH: 23
<212> TYPE: DNA
<213> ORGANISM: Artificial sequence
<220> FEATURE:
<223> OTHER INFORMATION: Synthetic sequence: Probe suitable for detection of genetic variations associated with IBD

<400> SEQUENCE: 1594
ttttccatac atggtcctgc cgc 23

<210> SEQ ID NO 1595
<211> LENGTH: 23
<212> TYPE: DNA
<213> ORGANISM: Artificial sequence
<220> FEATURE:
<223> OTHER INFORMATION: Synthetic sequence: Probe suitable for detection of genetic variations associated with IBD

<400> SEQUENCE: 1595
gactatcttt aatgtatgga aaa 23

<210> SEQ ID NO 1596
<211> LENGTH: 23
<212> TYPE: DNA
<213> ORGANISM: Artificial sequence
<220> FEATURE:
<223> OTHER INFORMATION: Synthetic sequence: Probe suitable for detection of genetic variations associated with IBD

<400> SEQUENCE: 1596
gcggcaggac catgtatgga aaa 23

<210> SEQ ID NO 1597
<211> LENGTH: 23
<212> TYPE: DNA
<213> ORGANISM: Artificial sequence
<220> FEATURE:
<223> OTHER INFORMATION: Synthetic sequence: Probe suitable for detection of genetic variations associated with IBD

<400> SEQUENCE: 1597
ttgtgtcttg ccatgctaaa gga 23

<210> SEQ ID NO 1598
<211> LENGTH: 23
<212> TYPE: DNA
<213> ORGANISM: Artificial sequence
<220> FEATURE:
<223> OTHER INFORMATION: Synthetic sequence: Probe suitable for detection of genetic variations associated with IBD

<400> SEQUENCE: 1598
ttgtgtcttg cgatgctaaa gga 23

<210> SEQ ID NO 1599
<211> LENGTH: 23
<212> TYPE: DNA

<213> ORGANISM: Artificial sequence
<220> FEATURE:
<223> OTHER INFORMATION: Synthetic sequence: Probe suitable for detection of genetic variations associated with IBD

<400> SEQUENCE: 1599
tcctttagca tggcaagaca caa 23

<210> SEQ ID NO 1600
<211> LENGTH: 23
<212> TYPE: DNA
<213> ORGANISM: Artificial sequence
<220> FEATURE:
<223> OTHER INFORMATION: Synthetic sequence: Probe suitable for detection of genetic variations associated with IBD

<400> SEQUENCE: 1600
tcctttagca tcgcaagaca caa 23

<210> SEQ ID NO 1601
<211> LENGTH: 23
<212> TYPE: DNA
<213> ORGANISM: Artificial sequence
<220> FEATURE:
<223> OTHER INFORMATION: Synthetic sequence: Probe suitable for detection of genetic variations associated with IBD

<400> SEQUENCE: 1601
tgctcaggag aagggagatg tga 23

<210> SEQ ID NO 1602
<211> LENGTH: 23
<212> TYPE: DNA
<213> ORGANISM: Artificial sequence
<220> FEATURE:
<223> OTHER INFORMATION: Synthetic sequence: Probe suitable for detection of genetic variations associated with IBD

<400> SEQUENCE: 1602
tgctcaggag aggggagatg tga 23

<210> SEQ ID NO 1603
<211> LENGTH: 23
<212> TYPE: DNA
<213> ORGANISM: Artificial sequence
<220> FEATURE:
<223> OTHER INFORMATION: Synthetic sequence: Probe suitable for detection of genetic variations associated with IBD

<400> SEQUENCE: 1603
tcacatctcc cttctcctga gca 23

<210> SEQ ID NO 1604
<211> LENGTH: 23
<212> TYPE: DNA
<213> ORGANISM: Artificial sequence
<220> FEATURE:
<223> OTHER INFORMATION: Synthetic sequence: Probe suitable for detection of genetic variations associated with IBD

<400> SEQUENCE: 1604
tcacatctcc cctctcctga gca 23

<210> SEQ ID NO 1605
<211> LENGTH: 23
<212> TYPE: DNA
<213> ORGANISM: Artificial sequence
<220> FEATURE:

<223> OTHER INFORMATION: Synthetic sequence: Probe suitable for detection of genetic variations associated with IBD

<400> SEQUENCE: 1605
ggctgctccc cccgtggccc ctg 23

<210> SEQ ID NO 1606
<211> LENGTH: 23
<212> TYPE: DNA
<213> ORGANISM: Artificial sequence
<220> FEATURE:
<223> OTHER INFORMATION: Synthetic sequence: Probe suitable for detection of genetic variations associated with IBD

<400> SEQUENCE: 1606
ggctgctccc cgcgtggccc ctg 23

<210> SEQ ID NO 1607
<211> LENGTH: 23
<212> TYPE: DNA
<213> ORGANISM: Artificial sequence
<220> FEATURE:
<223> OTHER INFORMATION: Synthetic sequence: Probe suitable for detection of genetic variations associated with IBD

<400> SEQUENCE: 1607
caggggccac gggggagca gcc 23

<210> SEQ ID NO 1608
<211> LENGTH: 23
<212> TYPE: DNA
<213> ORGANISM: Artificial sequence
<220> FEATURE:
<223> OTHER INFORMATION: Synthetic sequence: Probe suitable for detection of genetic variations associated with IBD

<400> SEQUENCE: 1608
caggggccac gggggagca gcc 23

<210> SEQ ID NO 1609
<211> LENGTH: 23
<212> TYPE: DNA
<213> ORGANISM: Artificial sequence
<220> FEATURE:
<223> OTHER INFORMATION: Synthetic sequence: Probe suitable for detection of genetic variations associated with IBD

<400> SEQUENCE: 1609
tagcaccccc caagccaagc aga 23

<210> SEQ ID NO 1610
<211> LENGTH: 23
<212> TYPE: DNA
<213> ORGANISM: Artificial sequence
<220> FEATURE:
<223> OTHER INFORMATION: Synthetic sequence: Probe suitable for detection of genetic variations associated with IBD

<400> SEQUENCE: 1610
tagcaccccc ccagccaagc aga 23

<210> SEQ ID NO 1611
<211> LENGTH: 23
<212> TYPE: DNA
<213> ORGANISM: Artificial sequence
<220> FEATURE:
<223> OTHER INFORMATION: Synthetic sequence: Probe suitable for detection of genetic variations associated with IBD

<400> SEQUENCE: 1611
tctgcttggc ttggggggtg cta 23

<210> SEQ ID NO 1612
<211> LENGTH: 23
<212> TYPE: DNA
<213> ORGANISM: Artificial sequence
<220> FEATURE:
<223> OTHER INFORMATION: Synthetic sequence: Probe suitable for detection of genetic variations associated with IBD

<400> SEQUENCE: 1612
tctgcttggc tgggggggtg cta 23

<210> SEQ ID NO 1613
<211> LENGTH: 23
<212> TYPE: DNA
<213> ORGANISM: Artificial sequence
<220> FEATURE:
<223> OTHER INFORMATION: Synthetic sequence: Probe suitable for detection of genetic variations associated with IBD

<400> SEQUENCE: 1613
cttgctcagg aaaggggaga tgt 23

<210> SEQ ID NO 1614
<211> LENGTH: 23
<212> TYPE: DNA
<213> ORGANISM: Artificial sequence
<220> FEATURE:
<223> OTHER INFORMATION: Synthetic sequence: Probe suitable for detection of genetic variations associated with IBD

<400> SEQUENCE: 1614
cttgctcagg agaggggaga tgt 23

<210> SEQ ID NO 1615
<211> LENGTH: 23
<212> TYPE: DNA
<213> ORGANISM: Artificial sequence
<220> FEATURE:
<223> OTHER INFORMATION: Synthetic sequence: Probe suitable for detection of genetic variations associated with IBD

<400> SEQUENCE: 1615
acatctcccc tttcctgagc aag 23

<210> SEQ ID NO 1616
<211> LENGTH: 23
<212> TYPE: DNA
<213> ORGANISM: Artificial sequence
<220> FEATURE:
<223> OTHER INFORMATION: Synthetic sequence: Probe suitable for detection of genetic variations associated with IBD

<400> SEQUENCE: 1616
acatctcccc tctcctgagc aag 23

<210> SEQ ID NO 1617
<211> LENGTH: 23
<212> TYPE: DNA
<213> ORGANISM: Artificial sequence
<220> FEATURE:
<223> OTHER INFORMATION: Synthetic sequence: Probe suitable for detection of genetic variations associated with IBD

<400> SEQUENCE: 1617
tgctcaggag aagggagatg tga 23

<210> SEQ ID NO 1618
<211> LENGTH: 23
<212> TYPE: DNA
<213> ORGANISM: Artificial sequence
<220> FEATURE:
<223> OTHER INFORMATION: Synthetic sequence: Probe suitable for detection of genetic variations associated with IBD

<400> SEQUENCE: 1618
tgctcaggag aggggagatg tga 23

<210> SEQ ID NO 1619
<211> LENGTH: 23
<212> TYPE: DNA
<213> ORGANISM: Artificial sequence
<220> FEATURE:
<223> OTHER INFORMATION: Synthetic sequence: Probe suitable for detection of genetic variations associated with IBD

<400> SEQUENCE: 1619
tcacatctcc cttctcctga gca 23

<210> SEQ ID NO 1620
<211> LENGTH: 23
<212> TYPE: DNA
<213> ORGANISM: Artificial sequence
<220> FEATURE:
<223> OTHER INFORMATION: Synthetic sequence: Probe suitable for detection of genetic variations associated with IBD

<400> SEQUENCE: 1620
tcacatctcc cctctcctga gca 23

<210> SEQ ID NO 1621
<211> LENGTH: 23
<212> TYPE: DNA
<213> ORGANISM: Artificial sequence
<220> FEATURE:
<223> OTHER INFORMATION: Synthetic sequence: Probe suitable for detection of genetic variations associated with IBD

<400> SEQUENCE: 1621
agcgtgaacc caaaaatgtg cgg 23

<210> SEQ ID NO 1622
<211> LENGTH: 23
<212> TYPE: DNA
<213> ORGANISM: Artificial sequence
<220> FEATURE:
<223> OTHER INFORMATION: Synthetic sequence: Probe suitable for detection of genetic variations associated with IBD

<400> SEQUENCE: 1622
agcgtgaacc cgaaaatgtg cgg 23

<210> SEQ ID NO 1623
<211> LENGTH: 23
<212> TYPE: DNA
<213> ORGANISM: Artificial sequence
<220> FEATURE:
<223> OTHER INFORMATION: Synthetic sequence: Probe suitable for detection of genetic variations associated with IBD

<400> SEQUENCE: 1623
ccgcacattt ttgggttcac gct 23

<210> SEQ ID NO 1624
<211> LENGTH: 23
<212> TYPE: DNA
<213> ORGANISM: Artificial sequence
<220> FEATURE:
<223> OTHER INFORMATION: Synthetic sequence: Probe suitable for detection of genetic variations associated with IBD

<400> SEQUENCE: 1624
ccgcacattt tcgggttcac gct 23

<210> SEQ ID NO 1625
<211> LENGTH: 23
<212> TYPE: DNA
<213> ORGANISM: Artificial sequence
<220> FEATURE:
<223> OTHER INFORMATION: Synthetic sequence: Probe suitable for detection of genetic variations associated with IBD

<400> SEQUENCE: 1625
ctggggatgc tacagagacc aga 23

<210> SEQ ID NO 1626
<211> LENGTH: 23
<212> TYPE: DNA
<213> ORGANISM: Artificial sequence
<220> FEATURE:
<223> OTHER INFORMATION: Synthetic sequence: Probe suitable for detection of genetic variations associated with IBD

<400> SEQUENCE: 1626
ctggggatgc tgcagagacc aga 23

<210> SEQ ID NO 1627
<211> LENGTH: 23
<212> TYPE: DNA
<213> ORGANISM: Artificial sequence
<220> FEATURE:
<223> OTHER INFORMATION: Synthetic sequence: Probe suitable for detection of genetic variations associated with IBD

<400> SEQUENCE: 1627
tctggtctct gtagcatccc cag 23

<210> SEQ ID NO 1628
<211> LENGTH: 23
<212> TYPE: DNA
<213> ORGANISM: Artificial sequence
<220> FEATURE:
<223> OTHER INFORMATION: Synthetic sequence: Probe suitable for detection of genetic variations associated with IBD

<400> SEQUENCE: 1628
tctggtctct gcagcatccc cag 23

<210> SEQ ID NO 1629
<211> LENGTH: 23
<212> TYPE: DNA
<213> ORGANISM: Artificial sequence
<220> FEATURE:
<223> OTHER INFORMATION: Synthetic sequence: Probe suitable for detection of genetic variations associated with IBD

<400> SEQUENCE: 1629
actgggacca acagaatcga agt 23

<210> SEQ ID NO 1630
<211> LENGTH: 23
<212> TYPE: DNA
<213> ORGANISM: Artificial sequence
<220> FEATURE:
<223> OTHER INFORMATION: Synthetic sequence: Probe suitable for detection of genetic variations associated with IBD

<400> SEQUENCE: 1630
actgggacca atagaatcga agt 23

<210> SEQ ID NO 1631
<211> LENGTH: 23
<212> TYPE: DNA
<213> ORGANISM: Artificial sequence
<220> FEATURE:
<223> OTHER INFORMATION: Synthetic sequence: Probe suitable for detection of genetic variations associated with IBD

<400> SEQUENCE: 1631
acttcgattc tgttggtccc agt 23

<210> SEQ ID NO 1632
<211> LENGTH: 23
<212> TYPE: DNA
<213> ORGANISM: Artificial sequence
<220> FEATURE:
<223> OTHER INFORMATION: Synthetic sequence: Probe suitable for detection of genetic variations associated with IBD

<400> SEQUENCE: 1632
acttcgattc tattggtccc agt 23

<210> SEQ ID NO 1633
<211> LENGTH: 23
<212> TYPE: DNA
<213> ORGANISM: Artificial sequence
<220> FEATURE:
<223> OTHER INFORMATION: Synthetic sequence: Probe suitable for detection of genetic variations associated with IBD

<400> SEQUENCE: 1633
accaagaagg cctcaggcac gat 23

<210> SEQ ID NO 1634
<211> LENGTH: 23
<212> TYPE: DNA
<213> ORGANISM: Artificial sequence
<220> FEATURE:
<223> OTHER INFORMATION: Synthetic sequence: Probe suitable for detection of genetic variations associated with IBD

<400> SEQUENCE: 1634
accaagaagg cttcaggcac gat 23

<210> SEQ ID NO 1635
<211> LENGTH: 23
<212> TYPE: DNA
<213> ORGANISM: Artificial sequence
<220> FEATURE:
<223> OTHER INFORMATION: Synthetic sequence: Probe suitable for detection of genetic variations associated with IBD

<400> SEQUENCE: 1635
atcgtgcctg aggccttctt ggt 23

<210> SEQ ID NO 1636
<211> LENGTH: 23

<212> TYPE: DNA
<213> ORGANISM: Artificial sequence
<220> FEATURE:
<223> OTHER INFORMATION: Synthetic sequence: Probe suitable for detection of genetic variations associated with IBD

<400> SEQUENCE: 1636
atcgtgcctg aagccttctt ggt 23

<210> SEQ ID NO 1637
<211> LENGTH: 23
<212> TYPE: DNA
<213> ORGANISM: Artificial sequence
<220> FEATURE:
<223> OTHER INFORMATION: Synthetic sequence: Probe suitable for detection of genetic variations associated with IBD

<400> SEQUENCE: 1637
atgggcattt tcagaattct ccc 23

<210> SEQ ID NO 1638
<211> LENGTH: 23
<212> TYPE: DNA
<213> ORGANISM: Artificial sequence
<220> FEATURE:
<223> OTHER INFORMATION: Synthetic sequence: Probe suitable for detection of genetic variations associated with IBD

<400> SEQUENCE: 1638
atgggcattt ttagaattct ccc 23

<210> SEQ ID NO 1639
<211> LENGTH: 23
<212> TYPE: DNA
<213> ORGANISM: Artificial sequence
<220> FEATURE:
<223> OTHER INFORMATION: Synthetic sequence: Probe suitable for detection of genetic variations associated with IBD

<400> SEQUENCE: 1639
gggagaattc tgaaaatgcc cat 23

<210> SEQ ID NO 1640
<211> LENGTH: 23
<212> TYPE: DNA
<213> ORGANISM: Artificial sequence
<220> FEATURE:
<223> OTHER INFORMATION: Synthetic sequence: Probe suitable for detection of genetic variations associated with IBD

<400> SEQUENCE: 1640
gggagaattc taaaaatgcc cat 23

<210> SEQ ID NO 1641
<211> LENGTH: 23
<212> TYPE: DNA
<213> ORGANISM: Artificial sequence
<220> FEATURE:
<223> OTHER INFORMATION: Synthetic sequence: Probe suitable for detection of genetic variations associated with IBD

<400> SEQUENCE: 1641
acagcaattt agtataggat tcc 23

<210> SEQ ID NO 1642
<211> LENGTH: 23
<212> TYPE: DNA
<213> ORGANISM: Artificial sequence
<220> FEATURE:
<223> OTHER INFORMATION: Synthetic sequence: Probe suitable for detection of genetic variations associated with IBD

<400> SEQUENCE: 1642
acagcaattt attataggat tcc 23

<210> SEQ ID NO 1643
<211> LENGTH: 23
<212> TYPE: DNA
<213> ORGANISM: Artificial sequence
<220> FEATURE:
<223> OTHER INFORMATION: Synthetic sequence: Probe suitable for detection of genetic variations associated with IBD

<400> SEQUENCE: 1643
ggaatcctat actaaattgc tgt 23

<210> SEQ ID NO 1644
<211> LENGTH: 23
<212> TYPE: DNA
<213> ORGANISM: Artificial sequence
<220> FEATURE:
<223> OTHER INFORMATION: Synthetic sequence: Probe suitable for detection of genetic variations associated with IBD

<400> SEQUENCE: 1644
ggaatcctat aataaattgc tgt 23

<210> SEQ ID NO 1645
<211> LENGTH: 23
<212> TYPE: DNA
<213> ORGANISM: Artificial sequence
<220> FEATURE:
<223> OTHER INFORMATION: Synthetic sequence: Probe suitable for detection of genetic variations associated with IBD

<400> SEQUENCE: 1645
ctaggtcagc tcaagatcct gtg 23

<210> SEQ ID NO 1646
<211> LENGTH: 23
<212> TYPE: DNA
<213> ORGANISM: Artificial sequence
<220> FEATURE:
<223> OTHER INFORMATION: Synthetic sequence: Probe suitable for detection of genetic variations associated with IBD

<400> SEQUENCE: 1646
ctaggtcagc tgaagatcct gtg 23

<210> SEQ ID NO 1647
<211> LENGTH: 23
<212> TYPE: DNA
<213> ORGANISM: Artificial sequence
<220> FEATURE:
<223> OTHER INFORMATION: Synthetic sequence: Probe suitable for detection of genetic variations associated with IBD

<400> SEQUENCE: 1647
cacaggatct tgagctgacc tag 23

<210> SEQ ID NO 1648
<211> LENGTH: 23
<212> TYPE: DNA
<213> ORGANISM: Artificial sequence
<220> FEATURE:
<223> OTHER INFORMATION: Synthetic sequence: Probe suitable for detection of genetic variations associated with IBD

<400> SEQUENCE: 1648
cacaggatct tcagctgacc tag 23

<210> SEQ ID NO 1649
<211> LENGTH: 23
<212> TYPE: DNA
<213> ORGANISM: Artificial sequence
<220> FEATURE:
<223> OTHER INFORMATION: Synthetic sequence: Probe suitable for detection of genetic variations associated with IBD

<400> SEQUENCE: 1649
gtcccgtctc cacaggctag gca 23

<210> SEQ ID NO 1650
<211> LENGTH: 23
<212> TYPE: DNA
<213> ORGANISM: Artificial sequence
<220> FEATURE:
<223> OTHER INFORMATION: Synthetic sequence: Probe suitable for detection of genetic variations associated with IBD

<400> SEQUENCE: 1650
gtcccgtctc cgcaggctag gca 23

<210> SEQ ID NO 1651
<211> LENGTH: 23
<212> TYPE: DNA
<213> ORGANISM: Artificial sequence
<220> FEATURE:
<223> OTHER INFORMATION: Synthetic sequence: Probe suitable for detection of genetic variations associated with IBD

<400> SEQUENCE: 1651
tgcctagcct gtggagacgg gac 23

<210> SEQ ID NO 1652
<211> LENGTH: 23
<212> TYPE: DNA
<213> ORGANISM: Artificial sequence
<220> FEATURE:
<223> OTHER INFORMATION: Synthetic sequence: Probe suitable for detection of genetic variations associated with IBD

<400> SEQUENCE: 1652
tgcctagcct gcggagacgg gac 23

<210> SEQ ID NO 1653
<211> LENGTH: 50
<212> TYPE: DNA
<213> ORGANISM: Artificial sequence
<220> FEATURE:
<223> OTHER INFORMATION: Synthetic sequence: External control DNA CEH

<400> SEQUENCE: 1653
gtcgtcaaga tgctaccgtt caggagtcgt caagatgcta ccgttcagga 50

<210> SEQ ID NO 1654
<211> LENGTH: 19
<212> TYPE: DNA
<213> ORGANISM: Artificial sequence
<220> FEATURE:
<223> OTHER INFORMATION: Synthetic sequence: Probe ON1 suitable for the detection of the external control nucleic acid of SEQ ID NO: 1653

-continued

```
<400> SEQUENCE: 1654

cttgacgact cctgaacgg                                                19


<210> SEQ ID NO 1655
<211> LENGTH: 19
<212> TYPE: DNA
<213> ORGANISM: Artificial sequence
<220> FEATURE:
<223> OTHER INFORMATION: Synthetic sequence: Probe ON2 suitable
      for the detection of the external control nucleic acid of
      SEQ ID NO: 1653

<400> SEQUENCE: 1655

cttgacgaca cctgaacgg                                                19
```